(12) United States Patent
Zhang et al.

(10) Patent No.: US 7,456,195 B2
(45) Date of Patent: Nov. 25, 2008

(54) PHENYLGLYCINAMIDE AND PYRIDYLGLYCINAMIDE DERIVATIVES USEFUL AS ANTICOAGULANTS

(75) Inventors: Xiaojun Zhang, Furlong, PA (US); Alexandra A. Nirschl, Yardley, PA (US); Yan Zou, Levittown, PA (US); Eldon Scott Priestley, Yardley, PA (US)

(73) Assignee: Bristol-Myers Squibb Company, Princton, NJ (US)

( * ) Notice: Subject to any disclaimer, the term of this patent is extended or adjusted under 35 U.S.C. 154(b) by 64 days.

(21) Appl. No.: 11/472,845

(22) Filed: Jun. 22, 2006

(65) Prior Publication Data
US 2007/0003539 A1 Jan. 4, 2007

Related U.S. Application Data

(60) Provisional application No. 60/694,074, filed on Jun. 24, 2005, provisional application No. 60/694,076, filed on Jun. 24, 2005.

(51) Int. Cl.
| | |
|---|---|
| *A61K 31/472* | (2006.01) |
| *A61K 31/4725* | (2006.01) |
| *C07D 217/14* | (2006.01) |
| *C07D 217/24* | (2006.01) |
| *A61P 7/02* | (2006.01) |
| *A61K 31/444* | (2006.01) |
| *A61K 31/502* | (2006.01) |
| *A61K 31/5025* | (2006.01) |
| *C07D 401/12* | (2006.01) |
| *C07D 237/34* | (2006.01) |
| *C07F 5/02* | (2006.01) |
| *C07F 5/04* | (2006.01) |
| *C07F 7/04* | (2006.01) |
| *A61P 9/10* | (2006.01) |

(52) U.S. Cl. ............ 514/310; 546/143; 546/122; 514/300; 514/248; 514/235.2; 514/217.07; 544/229; 544/237; 544/236; 544/128; 544/166; 540/597; 540/604

(58) Field of Classification Search ............ 514/313, 514/301, 310, 217.07, 235.2; 546/13, 143; 544/128; 540/597
See application file for complete search history.

(56) References Cited

U.S. PATENT DOCUMENTS

| | | | |
|---|---|---|---|
| 5,475,106 A | 12/1995 | Bourzat et al. | |
| 6,140,353 A | 10/2000 | Ackermann et al. | |
| 6,194,409 B1 | 2/2001 | van Boeckel et al. | |
| 6,242,644 B1 | 6/2001 | Ackermann et al. | |
| 6,358,960 B1 | 3/2002 | Senokuchi et al. | |
| 6,472,393 B1 | 10/2002 | Aliagas-Martin et al. | |
| 6,500,803 B1 | 12/2002 | Klingler et al. | |
| 6,548,694 B2 | 4/2003 | Alig et al. | |
| 6,642,252 B2 | 11/2003 | Bisacchi et al. | |
| 6,642,386 B2 | 11/2003 | Alig et al. | |
| 6,699,994 B1 | 3/2004 | Babu et al. | |
| 7,144,895 B2* | 12/2006 | Bisacchi et al. | 514/310 |
| 2004/0176375 A1 | 9/2004 | Bisacchi et al. | |
| 2004/0204412 A1 | 10/2004 | Glunz et al. | |
| 2004/0235828 A1 | 11/2004 | Dorsch et al. | |
| 2005/0130975 A1* | 6/2005 | Barbeau | 514/248 |
| 2005/0176760 A1 | 8/2005 | Cezanne et al. | |
| 2006/0166997 A1 | 7/2006 | Zhang et al. | |
| 2006/0211720 A1 | 9/2006 | Glunz et al. | |
| 2007/0078155 A1* | 4/2007 | Jaeschke et al. | 514/300 |
| 2007/0135479 A1* | 6/2007 | Ray | 514/309 |

FOREIGN PATENT DOCUMENTS

| | | | |
|---|---|---|---|
| WO | WO02/057236 | | 7/2002 |
| WO | WO 03/013531 | * | 2/2003 |
| WO | WO03/013531 | | 2/2003 |
| WO | WO 03/084533 | | 10/2003 |
| WO | WO2004/072101 | | 8/2004 |
| WO | WO 2004/072102 | * | 8/2004 |
| WO | WO2004/072102 | | 8/2004 |

OTHER PUBLICATIONS

U.S. Appl. No. 11/328,479, Zhang et al.
Carson, S.D. et al., "The role of tissue factor in the production of thrombin", *Blood Coagulation and Fibrinolysis*, vol. 4, pp. 281-292 (1993).
Colman, R.W., Chapter 6: "Contact Activation Pathway: Imflammatory, Fibrinolytic, Anticoagulant, Antiadhesive, and Antiangiogenic Activities", *Hemostasis and Thrombosis: Basic Principles and Clinical Practice*, 4th Ed., Lippincott Williams & Wilkins, publ., Colman, R.W. et al., eds., pp. 103-121 (2001).
Morrissey, J.H., "Quantitation of activated Factor VII Levels in Plasma Using a Tissue Factor Mutant Selectively Deficient in Promoting Factor VII Activation", *Blood*, vol. 81, No. 3, 1993: pp. 734-744.

(Continued)

*Primary Examiner*—Mark L. Berch
*Assistant Examiner*—Cecilia M Jaisle
(74) *Attorney, Agent, or Firm*—Jing G. Sun

(57) ABSTRACT

The present invention provides novel phenylglycinamide derivatives of Formula (I) or (IV):

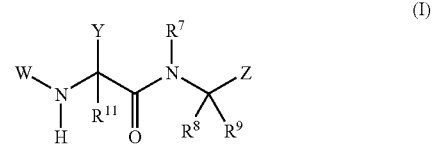

or a stereoisomer, tautomer, pharmaceutically acceptable salt, solvate, or prodrug thereof, wherein the variables W, $W_1$, Y, Z, $R^7$, $R^8$, $R^9$, and $R^{11}$ are as defined herein. These compounds are selective inhibitors of factor VIIa which can be used as medicaments.

11 Claims, No Drawings

OTHER PUBLICATIONS

Goodnight, S.H. et al., Chapter 4: "Screening Tests of Hemostasis", *Disorders of Hemostasis and Thrombosis: A Clinical Guide*, The McGraw-Hill Companies, publ., pp. 41-51 (2001).

Schmaier, A.H., Chapter 5: "Contact Activation", *Hemostasis and Thrombosis: Basic Principles and Clinical Practice*, 4th Ed., Lippincott Williams & Wilkins, publ., Colman, R.W. et al., eds., pp. 105-127 (2001).

Hoffman, M., "A cell-based model of coagulation and the role of factor Vlla", *Blood Reviews* (2003) 17, S1-S5.

Himber, J. et al., "Inhibition of tissue factor limits the growth of venous thrombus in the rabbit", *Journal of Thrombosis and Haemostasis*, 1: 889-895 (2003).

Morrissey, J.H., "Tissue factor: in at the start . . . and the finish?", *Journal of Thrombosis and Haemostatis*, 1: 878-880 (2003).

Hirsh, J. et al., "New anticoagulants", *Blood*, vol. 105, No. 2, 453-463 (2005).

Girard, T.J. et al., "The role of tissue factor/factor Vlla in the pathophysiology of acute thrombotic formation", *Curr. Opin. Pharmacol.*, 2001, 1, 159-163.

Lazarus, R.A. et al., Inhibitors of Tissue Factor*Factor Vlla for Anticoagulant Therapy, *Current Medicinal Chemistry*, 2004, 11, 2275-2290.

Szalony, J.A. et al., "Pharmacological Intervention at Disparate Sites in the Coagulation Cascade: Comparison of Anti-thrombotic Efficacy vs. Bleeding Propensity in a Rat Model of Acute Arterial Thrombosis", *Journal of Thrombosis and Thrombolysis* 14(2), 113-121, (2002).

Suleymanov, O.D., "Pharmacological Interruption of Acute Thrombus Formation with Minimal Hemorrhagic Complications by a Small Molecule Tissue Factor/Factor Vlla Inhibitor: Comparison to Factor Xa and Thrombin Inhibition in a Nonhuman Primate Thrombosis Model", *The Journal of Pharmacology and Experimental Therapeutics*, vol. 306, pp. 1115-1121 (2003).

Young, W.B. et al. "Factor Vlla inhibitors: Chemical optimization, preclinical pharmacokinetics, pharmacodynamics, and efficacy in an arterial baboon thrombosis model", *Bioorganic & Medicinal Chemistry Letters* 16 (2006) 2037-2041.

Szalony, J.A. et al., "Administration of a small molecule tissue factor/Factor Vlla inhibitor in a non-human primate thrombosis model of venous thrombosis: effects on thrombus formation and bleeding time", *Thrombosis Research* 112 (2003) 167-174.

Moons, A.M. et al., "Recombinant Nematode Anticoagulant Protein c2, an Inhibitor of the Tissue Factor/Factor Vlla Complex, in Patients Undergoing Elective Coronary Angioplasty", *Journal of the American College of Cardiology*, vol. 41, No. 12, 2147-2153i (2003).

Lee, A. et al., "Dos-Response Study of Recombinant Factor Vlla/Tissue Factor Inhibitor Recombinant Nematode Anticoagulant Protein c2 in Prevention of Postoperative Venous Thromboembolism in Patients Undergoing Total Knee Replacement", *Circulation*, 104, 74-78 (2001).

Frederick, R. et al., "Modulators of the Coagulation Cascade: Focus and Recent Advances in Inhibitors of Tissue Factor, Factor Vlla and their Complex", *Current Medicinal Chemistry*, 12, 397-417 (2005).

Arnold, C.S., "The antithrombotic and anti-inflammatory effects of BCX-3607, a small molecule tissue factor/factor Vlla inhibitor", *Thrombosis Research* 117, 343-349, (2006).

Zbinden et al., *Design of selective phenylglycine amide tissue factor/factor Vlla inhibitors* Bioorganic Medicinal Chemistry Letters, vol. 15, Feb. 1, 2005, pp. 817-822.

* cited by examiner

PHENYLGLYCINAMIDE AND PYRIDYLGLYCINAMIDE DERIVATIVES USEFUL AS ANTICOAGULANTS

CROSS-REFERENCE TO RELATED APPLICATIONS

The present application claims the priority benefit of U.S. Provisional Application Ser. No. 60/694,074, filed Jun. 24, 2005 and U.S. Provisional Application Ser. No. 60/694,076, filed Jun. 24, 2005. The entire disclosure of each of the foregoing applications is herein incorporated by reference in its entirety.

FIELD OF THE INVENTION

The present invention provides novel phenylglycinamide and pyridylglycinamide derivatives and analogues thereof, which are selective inhibitors of serine protease enzymes of the coagulation cascade and/or contact activation system; for example factor VIIa, factor Xa, factor XIa, factor IXa, thrombin, and/or plasma kallikrein. In particular, it relates to compounds that are factor VIIa inhibitors. This invention also relates to pharmaceutical compositions comprising these compounds and methods of using the same.

BACKGROUND OF THE INVENTION

Factor VIIa is a plasma serine protease involved in the initiation of the coagulation cascade. It is present in human blood at a concentration of approximately 500 ng/mL, with about 1% of the total amount in the proteolytically active form factor VIIa (Morrissey, J. H. et al. *Blood* 1993, 81, 734-744). Factor VIIa binds with high affinity to its cofactor, tissue factor, in the presence of calcium ions to form a complex with enhanced proteolytic activity (Carson, S. D. and Brozna, J. P. *Blood Coag. Fibrinol.* 1993, 4, 281-292). Tissue factor is normally expressed in cells surrounding the vasculature and within the vessel wall, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin coverts fibrinogen to fibrin, which polymerizes to form the structural framework of a blood clot, and activates platelets, which are a key cellular component of coagulation (Hoffman, M. *Blood Reviews* 2003, 17, S1-S5). In addition, there is evidence that tissue factor is present in blood, likely in an encrypted form that is de-encrypted during clot formation. (Giesen, P. L. A. et al. *Proc. Natl. Acad. Sci.* 1999, 96, 2311-2315; Himber, J. et al. *J. Thromb. Haemost.* 2003, 1, 889-895). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H. *J. Thromb. Haemost.* 2003, 1, 878-880).

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsch, J. et al. *Blood* 2005, 105, 453-463).

Because of its key role in the coagulation cascade, researchers have postulated that inhibition of factor VIIa could be used to treat or prevent thrombotic or thromboembolic disease. (Girard, T. J.; Nicholson, N. S. *Curr. Opin. Pharmacol.* 2001, 1, 159-163; Lazarus, R. A., et al. *Curr. Med. Chem.* 2004, 11, 2275-2290; Frederick, R. et al. *Curr. Med. Chem.* 2005, 12, 397-417.) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al. *J. Thrombosis and Thrombolysis* 2002, 14, 113-121). In addition, small molecule active site directed factor VIIa inhibitors have demonstrated antithrombotic efficacy in animal models of arterial thrombosis (Suleymanov, O., et al. *J Pharmacology and Experimental Therapeutics* 2003, 306, 1115-1121; Young, W. B., et al. *Bioorg. Med. Chem. Lett.* 2006, 16, 2037-2041) and venous thrombosis (Szalony, J. A., et al. Thrombosis Research 2003, 112, 167-174; Arnold, C. S., et al. *Thrombosis Research* 2006, 117, 343-349), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 reduces systemic thrombin generation in patients undergoing coronary angioplasty (Moons, A. H. M. *J. Am. Coll. Cardiol.* 2003, 41, 2147-2153) and that it prevents deep vein thrombosis in patients undergoing total knee replacement (Lee, A., et al. *Circulation* 2001, 104, 74-78).

Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytically active factor XII (factor XIIa and factor XIIf). Factor XIIa (or XIIf) has a number of target proteins, including plasma prekallikrein and factor XI. Active plasma kallikrein further activates factor XII, leading to an amplification of contact activation. Activated FXI acts on FIX, which acts through the coagulation cascade to produce thrombin. Thus, inhibitors of plasma kallikrein would be expected to exert an antithrombotic effect under conditions of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Plasma kallikrein is a zymogen of a trypsin-like serine protease and is present in plasma at 35 to 50 µg/mL. The gene structure is similar to that of factor XI; overall, the amino acid sequence of plasma kallikrein has 58% homology to factor XI. Proteolytic activation by factor XIIa at an internal 1389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998). Inhibitors of plasma kallikrein would be expected to reduce potential for bradykinin release and thus to exert an anti-inflammatory effect.

While a number of factor VIIa inhibitors have been discussed in the art, improved inhibitors, especially non-peptide inhibitors, of serine proteases for the treatment of thromboembolic disorders are always desirable. The present invention discloses phenylglycinamide and pyridylglycinamide derivatives and analogues thereof, as inhibitors of coagulation Factor VIIa and, as such, their utility in the treatment of thromboembolic disorders.

In addition, it is also desirable to find new compounds with improved pharmacological characteristics compared with known serine protease inhibitors. For example, it is preferred to find new compounds with improved factor VIIa inhibitory activity and selectivity for factor VIIa versus other serine proteases. Also, it is preferred to find new compounds with improved plasma kallikrein inhibitory activity and selectivity for plasma kallikrein versus other serine proteases. Also, it is preferred to find new compounds with improved activity in in vitro clotting assays, such as the prothrombin time (PT) assay or activated partial thromboplastin time assay (APTT) (for a description of the PT and APTT assays see, Goodnight, S. H.; Hathaway, W. E. Screening Tests of Hemostasis. *Disorders of Thrombosis and Hemostasis: a clinical guide*, 2$^{nd}$ edition, McGraw-Hill: New York, 2001 pp. 41-51). It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and, (h) factors that improve manufacturing costs or feasibility.

SUMMARY OF THE INVENTION

The present invention provides novel phenylglycinamide and pyridylglycinamide derivatives, and analogues thereof, which are useful as selective inhibitors of serine protease enzymes, especially factor VIIa, including stereoisomers, tautomers, pharmaceutically acceptable salts, solvates, or prodrugs thereof.

The present invention also provides processes and intermediates for making one of the compounds of the present invention or a stereoisomer, tautomer, pharmaceutically acceptable salt, solvate, or prodrug thereof.

The present invention also provides pharmaceutical compositions comprising a pharmaceutically acceptable carrier and at least one of the compounds of the present invention or a stereoisomer, tautomer, pharmaceutically acceptable salt, solvate, or prodrug thereof.

The present invention also provides a method for modulation of the coagulation cascade and/or the contact activation system comprising administering to a patient in need of such treatment a therapeutically effective amount of at least one of the compounds of the present invention or a stereoisomer, tautomer, pharmaceutically acceptable salt, solvate, or prodrug thereof.

The present invention also provides a method for treating a thrombotic or thromboembolic disorder comprising administering to a patient in need of such treatment a therapeutically effective amount of at least one of the compounds of the present invention or a stereoisomer, tautomer, pharmaceutically acceptable salt, solvate, or prodrug thereof.

The present invention also provides a method for treating inflammatory disorders comprising administering to a host in need of such treatment a therapeutically effective amount of at least one of the compounds of the present invention or a stereoisomer, tautomer, pharmaceutically acceptable salt or prodrug thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thrombotic or thromboembolic disorder.

The present invention also provides the use of the compounds of the present invention or stereoisomers, tautomers, pharmaceutically acceptable salts, solvates, or prodrugs thereof, for the manufacture of a medicament for the treatment of an inflammatory disorder.

These and other features of the invention will be set forth in the expanded form as the disclosure continues.

DETAILED DESCRIPTION OF THE INVENTION

In a first embodiment, the present invention provides, inter alia, compounds of Formula (I):

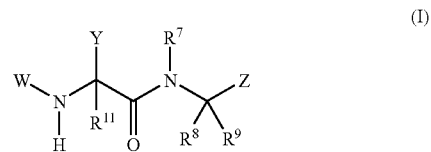

or a stereoisomer or pharmaceutically acceptable salt, solvate, or prodrug thereof, wherein:

W is substituted with 0-2 $R^6$ and selected from:

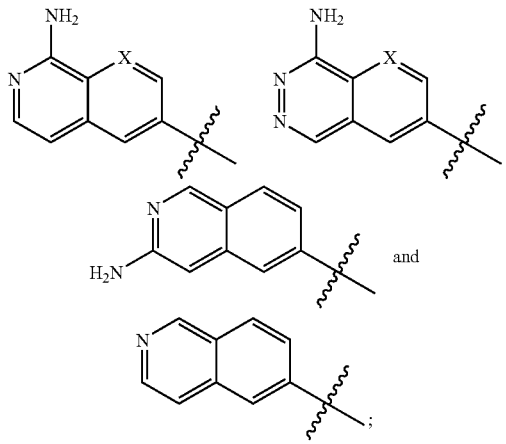

X is CH, $CR^6$ or N;
Y is selected from:

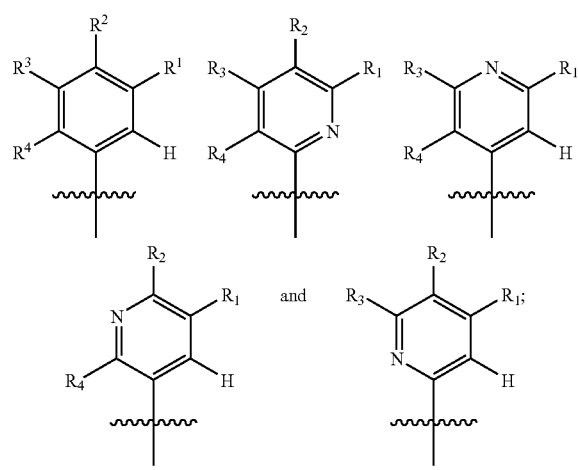

$R^1$ is independently at each occurrence, H, F, Cl, Br, I, $C_{1-4}$ alkyl substituted with 0-1 OH, $C_{2-4}$ alkenyl, $C_{2-4}$ alkynyl, $C_{1-4}$ alkoxy, $C_{1-4}$ alkylthio, $C_{1-4}$ haloalkyl, —O—$C_{1-4}$ haloalkyl, or $C_{3-6}$ cycloalkyl;

$R^2$ and $R^3$ are, independently at each occurrence, selected from: H, F, Cl, Br, I, $OR^a$, $SR^e$, $OCF_3$, $OCHF_2$, $OCH_2F$, CN, $NO_2$, —$NR^cR^d$, —$C(O)R^a$, —$CO_2R^a$, —$NR^cC(O)R^a$, —$C(O)NR^cR^d$, —$NR^cC(O)OR^e$, —$NR^cC(O)NR^cR^d$, —$OC(O)NR^cR^d$, —$SO_2NR^cR^d$, —$NR^cSO_2NR^cR^d$, —$NR^cSO_2R^e$, —$NR^cSO_2CF_3$, —$SO_2CF_3$, —$S(O)_2R^e$, $C_{1-4}$ alkyl substituted with 0-2 $R^f$, $C_{2-4}$ alkenyl substituted with 0-2 $R^f$, and $C_{2-4}$ alkynyl substituted with 0-2 $R^f$;

$R^4$ is, independently at each occurrence, H, F, Cl, Br, I, $OR^a$, $SR^e$, $OCF_3$, $OCHF_2$, $OCH_2F$, CN, $NO_2$, —$NR^cR^d$, —$C(O)R^a$, —$CO_2R^a$, —$NR^cC(O)R^a$, —$C(O)NR^cR^d$, —$NR^cC(O)OR^e$, —$NR^cC(O)NR^cR^d$, —$OC(O)NR^cR^d$, —$SO_2NR^cR^d$, —$NR^cSO_2NR^cR^d$, —$NR^cSO_2R^e$, —$NR^cSO_2CF_3$, —$SO_2CF_3$, —$S(O)_2R^e$, —$OCH_2CO_2R^a$, —O(benzyl substituted with $CO_2R^a$), tetrazolyl, —$SO_2NHCOR^a$, —$CONHSO_2R^e$, $C_{1-4}$ alkyl substituted with 0-2 $R^f$, $C_{2-4}$ alkenyl substituted with 0-2 $R^f$, or $C_{2-4}$ alkynyl substituted with 0-2 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, Br, $C_{1-3}$ alkyl, or $C_{1-3}$ alkoxy;

$R^7$ is H, $C_{1-4}$ alkyl, —$CH_2CO_2R^a$, —$CH_2CH_2CO_2R^a$, —$CH_2CH_2OH$, —$CH_2CH_2CH_2OH$, tetrazolyl, —$CH_2CONHSO_2R^e$, or —$CH_2CH_2CONHSO_2R^e$;

$R^8$ is H, $C_{1-4}$ alkyl, $CO_2R^a$, —$CH_2CO_2R^a$, —$CH_2OH$, —$CH_2CH_2OH$, tetrazolyl, —$CONHSO_2R^e$, or —$CH_2CONHSO_2R^e$;

$R^9$ is H or $C_{1-4}$ alkyl;

alternatively, $R^8$ and $R^9$ can be taken together with the carbon atom to which they are attached to form a 3- to 5-membered carbocycle;

Z is phenyl substituted with 0-3 $R^{10}$ or pyridyl substituted with 0-3 $R^{10}$;

$R^{10}$ is, independently at each occurrence, F, Cl, Br, CN, $CH_2F$, $CHF_2$, $CF_3$, $OCF_3$, $SCF_3$, $NO_2$, $C_{1-6}$ alkyl, $C_{2-6}$ alkenyl, —$(CH_2)_n$—$OR^a$, $SR^e$, —$(CH_2)_n$—$NR^cR^d$, $CO_2R^a$, $CONR^cR^d$, —$SO_2R^e$, —$SO_2NR^cR^d$, —$NR^hCOR^a$, —$NR^hCO_2R^a$, —$NR^hCONR^cR^d$, —$OC(O)NR^cR^d$, —$SO_2NR^cR^d$, —$OSO_2NR^cR^d$, —$NR^hSO_2NR^cR^d$, —$NR^hSO_2R^e$, —$B(OH)_2$, —$(CH_2)_n$-phenyl, —NH-phenyl, —NH(-5- to 6-membered heteroaryl comprising: carbon atoms and 1-3 heteroatoms selected from N, O, and $S(O)_p$), or —$(CH_2)_n$-5- to 10-membered heterocycle comprising: carbon atoms and 1-4 heteroatoms selected from N, O, and $S(O)_p$, wherein said phenyl, heteroaryl and heterocycle are substituted with 0-3 $R^i$;

alternatively, when two $R^{10}$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^i$;

$R^{11}$ is H or $C_{1-3}$ alkyl;

$R^a$ is, independently at each occurrence, H, $C_{1-4}$ alkyl, $C_{3-6}$ cycloalkyl, phenyl, or benzyl; wherein said alkyl, cycloalkyl, phenyl and benzyl are optionally substituted with 0-2 $R^f$;

$R^c$ and $R^d$ are, independently at each occurrence, H, $C_{1-4}$ alkyl, $C_{3-6}$ cycloalkyl, phenyl, or benzyl;

alternatively, $R^c$ and $R^d$, when attached to the same nitrogen atom, combine to form a 3- to 7-membered heterocycle comprising: carbon atoms and 0-2 additional heteroatoms selected from N, O, and $S(O)_p$; wherein said heterocycle is substituted with 0-2 $R^g$;

$R^e$ is, independently at each occurrence, $C_{1-4}$ alkyl, $C_{3-6}$ cycloalkyl, phenyl, or benzyl;

$R^f$ is, independently at each occurrence, F, $CF_3$, OH, $C_{1-3}$ alkoxy, or $C_{3-6}$ cycloalkyl;

$R^g$ is, independently at each occurrence, =O, F, Cl, Br, $CF_3$, OH, or $C_{1-4}$ alkyl;

$R^h$ is, independently at each occurrence, H or $C_{1-3}$ alkyl;

$R^i$ is, independently at each occurrence, F, Cl, Br, $CF_3$, OH, or $C_{1-4}$ alkyl;

n, at each occurrence, is selected from 0, 1, 2, 3, and 4; and p, at each occurrence, is selected from 0, 1, and 2;

provided that when $R^8$ and $R^9$ are both H, then Z is other than unsubstituted phenyl.

In a second embodiment, the present invention includes the compounds of Formula (I), within the scope of the first embodiment wherein:

$R^1$ is F, Cl, Br, $C_{1-4}$ alkyl, $C_{2-4}$ alkenyl, $C_{1-4}$ alkoxy, $C_{1-4}$ alkylthio, $C_{3-6}$ cycloalkyl, $OCF_3$, $OCHF_2$, or $OCH_2F$;

$R^2$ and $R^3$ are, independently at each occurrence, selected from: H, F, Cl, Br, $C_{1-4}$ alkyl, $C_{1-4}$ alkoxy, $OCF_3$, $OCHF_2$, or $OCH_2F$;

$R^4$ is, independently at each occurrence, H, F, Cl, Br, $C_{1-4}$ alkyl, or $C_{1-4}$ alkoxy;

$R^6$ is, independently at each occurrence, F, Cl, Me or OMe;

$R^7$ is H, $C_{1-4}$ alkyl, or $—CH_2CO_2R^a$; and $R^8$ is H, $C_{1-4}$ alkyl, $CO_2R^a$, or $—CH_2CO_2R^a$;

provided that when $R^8$ and $R^9$ are both H, then Z is other than unsubstituted phenyl.

In some embodiments, the present invention includes compounds of Formula (I) wherein: W is substituted with 0-2 $R^6$ and selected from:

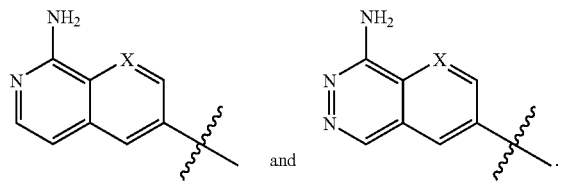

In other embodiments, the present invention includes compounds of Formula (I) wherein: W is

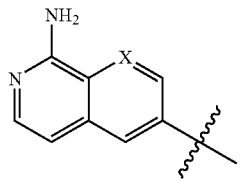

substituted with 0-2 $R^6$.

In some embodiments, the present invention includes compounds of Formula (I) wherein: X is CH.

In some embodiments, the present invention includes compounds of Formula (I) wherein: Y is:

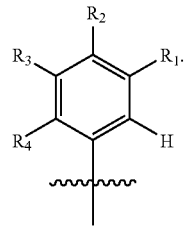

In some embodiments, the present invention includes compounds of Formula (I) wherein: Y is selected from:

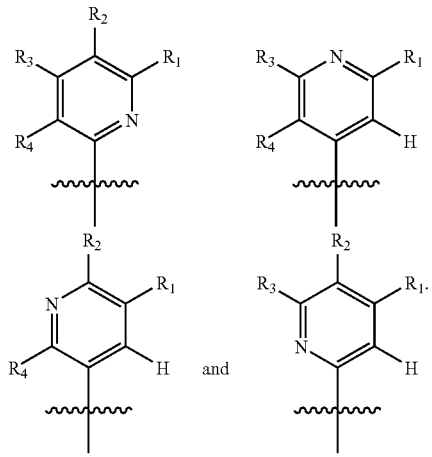

In some embodiments, the present invention includes compounds of Formula (I) wherein: $R^1$ is F, Cl, Br, $C_{1-4}$ alkyl, $C_{1-4}$ alkoxy, $OCHF_2$, or cyclopropyl. In other embodiments, the present invention includes compounds of Formula (I) wherein: $R^1$ is F, Cl, Br, Me, Et, Pr, i-Pr, vinyl, 2-propenyl, allyl, OMe, OEt, OPr, $OCHF_2$, SMe, SEt, or cyclopropyl. In other embodiments, the present invention includes compounds of Formula (I) wherein: $R^1$ is Cl, Br, Me, Et, Pr, i-Pr, vinyl, 2-propenyl, OMe, OEt, OPr, $OCHF_2$, or cyclopropyl. In other embodiments, the present invention includes compounds of Formula (I) wherein: $R^1$ is Cl, Br, Me, Et, OMe, OEt, OPr, $OCHF_2$, or cyclopropyl. In other embodiments, the present invention includes compounds of Formula (I) wherein: $R^1$ is OMe or OEt.

In some embodiments, the present invention includes compounds of Formula (I) wherein: $R^2$ is H, F, Cl, Br, $C_{1-4}$ alkyl, $C_{1-4}$ alkoxy, or $OCHF_2$. In other embodiments, the present invention includes compounds of Formula (I) wherein: $R^2$ is H, F, Cl, Br, $C_{1-4}$ alkoxy, or $OCHF_2$. In other embodiments, the present invention includes compounds of Formula (I) wherein: $R^2$ is H, F, Cl, OMe, O(i-Pr), or $OCHF_2$. In other embodiments, the present invention includes compounds of Formula (I) wherein: $R^2$ is H, OMe, or O(i-Pr).

In some embodiments, the present invention includes compounds of Formula (I) wherein: $R^3$ is H, F, Cl, Br, $C_{1-4}$ alkyl, $C_{1-4}$ alkoxy, or $OCHF_2$. In other embodiments, the present invention includes compounds of Formula (I) wherein: $R^{3-}$ is H or $C_{1-4}$ alkoxy. In other embodiments, the present invention includes compounds of Formula (I) wherein: $R^3$ is H.

In some embodiments, the present invention includes compounds of Formula (I) wherein: $R^4$ is H, F, Cl, Br, $C_{1-4}$ alkyl, or $C_{1-4}$ alkoxy. In other embodiments, the present invention includes compounds of Formula (I) wherein: $R^4$ is H, F, Cl, or $C_{1-3}$ alkoxy. In other embodiments, the present invention includes compounds of Formula (I) wherein: $R^4$ is H, F, Cl, or OMe.

In some embodiments, the present invention includes compounds of Formula (I) wherein: $R^6$ is, independently at each occurrence, F, Cl, Me or OMe. In other embodiments, the present invention includes compounds of Formula (I) wherein: $R^6$ is, independently at each occurrence, F, Cl, or Me.

In some embodiments, the present invention includes compounds of Formula (I) wherein: $R^7$ is H, Me, $—CH_2CO_2H$, —CH$_2$CO$_2$Me, or —CH$_2$CO$_2$Et. In other embodiments, the present invention includes compounds of Formula (I) wherein: R$^7$ is H or Me.

In some embodiments, the present invention includes compounds of Formula (I) wherein: R$^8$ is H, Me, CO$_2$H, CO$_2$Me, CO$_2$Et, —CH$_2$CO$_2$H, —CH$_2$CO$_2$Me, or —CH$_2$CO$_2$Et. In other embodiments, the present invention includes compounds of Formula (I) wherein: R$^8$ is H or Me.

In some embodiments, the present invention includes compounds of Formula (I) wherein: R$^9$ is H.

In some embodiments, the present invention includes compounds of Formula (I) wherein: R$^{10}$ is, independently at each occurrence, F, Cl, Br, CF$_3$, NO$_2$, C$_{1-6}$ alkyl, C$_{2-6}$ alkenyl, OR$^a$, SR$^e$, NR$^c$R$^d$, —CH$_2$NR$^c$R$^d$, CONR$^c$R$^d$, —SO$_2$R$^e$, —SO$_2$NR$^c$R$^d$, —NHCOR$^a$, —NHCO$_2$R$^a$, —NHCONR$^c$R$^d$, —OSO$_2$NR$^c$R$^d$, —NHSO$_2$NR$^c$R$^d$, —NHSO$_2$R$^e$, —B(OH)$_2$, phenyl substituted with 0-2 R$^i$, or a 5- to 6-membered heterocycle substituted with 0-2 R$^i$ and selected from: morpholinyl, piperidyl, pyrazolyl, and triazolyl. In other embodiments, the present invention includes compounds of Formula (I) wherein: R$^{10}$ is, independently at each occurrence, F, Cl, Br, C$_{1-4}$ alkyl, C$_{2-4}$ alkenyl, OR$^a$, SR$^e$, NR$^c$R$^d$, —CH$_2$NR$^c$R$^d$, CONR$^c$R$^d$, —SO$_2$R$^e$, —SO$_2$NR$^c$R$^d$, —NHCOR$^a$, —NHCO$_2$R$^a$, —NHCONR$^c$R$^d$, —OSO$_2$NR$^c$R$^d$, —NHSO$_2$NR$^c$R$^d$, —NHSO$_2$R$^e$, morpholin-4-yl, piperid-1-yl, 3,5-dimethyl-pyrazol-1-yl, or 3,5-diethyl-pyrazol-1-yl. In other embodiments, the present invention includes compounds of Formula (I) wherein: R$^{10}$ is, independently at each occurrence, CONR$^c$R$^d$, —SO$_2$R$^e$, —SO$_2$NR$^c$R$^d$, —NHCOR$^a$, —NHCO$_2$R$^a$, —NHCONR$^c$R$^d$, —OSO$_2$NR$^c$R$^d$, —NHSO$_2$NR$^c$R$^d$, or —NHSO$_2$R$^e$.

In some embodiments, the present invention includes compounds of Formula (I) wherein: R$^{11}$ is H.

In some embodiments, the present invention includes compounds of Formula (I) wherein: Z is phenyl substituted with 0-3 R$^{10}$.

In a third embodiment, the present invention includes the compounds of Formula (II):

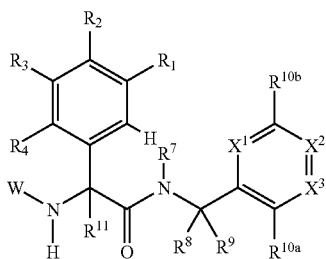

or a stereoisomer or pharmaceutically acceptable salt, solvate, or prodrug thereof, wherein:

W is substituted with 0-1 R$^6$ and selected from:

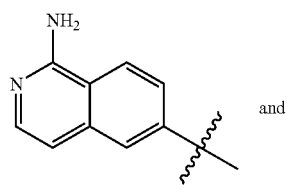

and

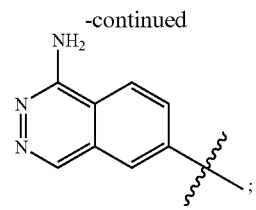

X$^1$ is CH or N;
X$^2$ is CH or N;
X$^3$ is CR$^{10c}$ or N;
provided that only one of X$^1$, X$^2$ and X$^3$ may be N;
R$^1$ is H, F, Cl, Br, C$_{1-4}$ alkyl, C$_{2-4}$ alkenyl, C$_{1-4}$ alkoxy, C$_{1-4}$ alkylthio, C$_{3-6}$ cycloalkyl, OCF$_3$, OCHF$_2$, or OCH$_2$F;
R$^2$ and R$^3$ are independently selected from: H, F, Cl, Br, I, OR$^a$, SR$^e$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^e$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^e$, —NR$^c$SO$_2$CF$_3$, —SO$_2$CF$_3$, —S(O)$_2$R$^e$, C$_{1-4}$ alkyl substituted with 0-2 R$^f$, C$_{2-4}$ alkenyl substituted with 0-2 R$^f$, and C$_{2-4}$ alkynyl substituted with 0-2 R$^f$;
R$^4$ is H, F, Cl, Br, I, OR$^a$, SR$^e$, OCF$_3$, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^e$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^e$, —NR$^c$SO$_2$CF$_3$, —SO$_2$CF$_3$, —S(O)$_2$R$^e$, —OCH$_2$CO$_2$R$^a$, —O(benzyl substituted with CO$_2$R$^a$), tetrazolyl, SO$_2$NHCOR$^a$, —CONHSO$_2$R$^e$, C$_{1-4}$ alkyl substituted with 0-2 R$^f$, C$_{2-4}$ alkenyl substituted with 0-2 R$^f$, C$_{2-4}$ alkynyl substituted with 0-2 R$^f$;
alternatively, R$^2$ and R$^3$ may combine to form a 5- to 6-membered carbocycle or heterocycle comprising: carbon atoms and 0-3 heteroatoms selected from N, NR$^c$, O, and S(O)$_p$, wherein said carbocycle and heterocycle are substituted with 0-3 R$^f$;
R$^6$ is, independently at each occurrence, F, Cl, Br, C$_{1-3}$ alkoxy or C$_{1-3}$ alkyl;
R$^7$ is H, C$_{1-4}$ alkyl, —CH$_2$CO$_2$R$^a$, —CH$_2$CH$_2$CO$_2$R$^a$, —CH$_2$CH$_2$OH, —CH$_2$CH$_2$CH$_2$OH, tetrazolyl, —CH$_2$CONHSO$_2$R$^e$, or —CH$_2$CH$_2$CONHSO$_2$R$^e$;
R$^8$ is H, C$_{1-4}$ alkyl, CO$_2$R$^a$, —CH$_2$CO$_2$R$^a$, —CH$_2$OH, —CH$_2$CH$_2$OH, tetrazolyl, —CONHSO$_2$R$^e$, or —CH$_2$CONHSO$_2$R$^e$;
R$^9$ is H or Me;
alternatively, R$^8$ and R$^9$ can be taken together with the carbon atom to which they are attached to form a 3- to 5-membered carbocycle;
R$^{10a}$ is H, F, Cl, Br, CF$_3$, C$_{1-6}$ alkyl, C$_{2-6}$ alkenyl, OR$^a$, SR$^e$, NR$^c$R$^d$, CONR$^c$R$^d$, —SO$_2$R$^e$, —SO$_2$NR$^c$R$^d$, phenyl substituted with 0-2 R$^i$, or a 5- to 6-membered heterocycle substituted with 0-2 R$^i$ and selected from: morpholinyl, piperidyl, pyrazolyl, and triazolyl;
R$^{10b}$ is H, OR$^a$, NR$^c$R$^d$, —NHCOR$^a$, —NHCO$_2$R$^a$, —NHCONR$^c$R$^d$, —SO$_2$NR$^c$R$^d$, —OSO$_2$NR$^c$R$^d$, —NHSO$_2$NR$^c$R$^d$, —NHSO$_2$R$^e$, —B(OH)$_2$, —NH(-5 to 6-membered heteroaryl comprising: carbon atoms and 1-3 heteroatoms selected from N, O, and S(O)$_p$ and substituted with 0-2 R$^i$), —NH-phenyl substituted with 0-2 R$^i$, or a 5-membered heterocycle substituted with 0-2 R$^i$ and selected from: tetrazolyl, pyrazolyl, pyrrolyl, and triazolyl;
R$^{10c}$ is H, F, Cl, Br, CF$_3$, C$_{1-6}$ alkyl, OR$^a$, SR$^e$, or NR$^c$R$^d$;
R$^{11}$ is H;

R$^a$ is, independently at each occurrence, H, C$_{1-4}$ alkyl, C$_{3-6}$ cycloalkyl, phenyl, or benzyl; wherein said alkyl, cycloalkyl, phenyl and benzyl are optionally substituted with 0-2 R$^f$;

R$^c$ and R$^d$ are, independently at each occurrence, H, C$_{1-4}$ alkyl, C$_{3-6}$ cycloalkyl, phenyl, or benzyl;

alternatively, R$^c$ and R$^d$, when attached to the same nitrogen atom, combine to form a 4- to 7-membered heterocycle comprising: carbon atoms and 0-2 additional heteroatoms selected from N, O, and S(O)$_p$; wherein said heterocycle is substituted with 0-2 R$^g$;

R$^e$ is, independently at each occurrence, C$_{1-4}$ alkyl, C$_{3-6}$ cycloalkyl, phenyl, or benzyl;

R$^f$ is, independently at each occurrence, F, CF$_3$, OH, C$_{1-3}$ alkoxy, or C$_{3-6}$ cycloalkyl;

R$^g$ is, independently at each occurrence, =O, F, Cl, Br, CF$_3$, OH, or C$_{1-4}$ alkyl;

R$^i$ is, independently at each occurrence, F, Cl, Br, CF$_3$, OH, or C$_{1-4}$ alkyl;

n, at each occurrence, is selected from 0, 1, 2, 3, and 4; and p, at each occurrence, is selected from 0, 1, and 2;

provided that when R$^8$ and R$^9$ are both H, X$^1$, X$^2$, and X$^3$ are CH, and R$^{10a}$ is H, then R$^{10b}$ is other than H.

In a fourth embodiment, the present invention includes the compounds of Formula (II), within the scope of the third embodiment wherein:

R$^1$ is F, Cl, Br, Me, Et, Pr, i-Pr, vinyl, 2-propenyl, allyl, OMe, OEt, OPr, OCHF$_2$, SMe, SEt, or cyclopropyl;

R$^2$ and R$^3$ are independently selected from: H, F, Cl, Br, C$_{1-4}$ alkyl, C$_{1-4}$ alkoxy, or OCHF$_2$;

alternatively, R$^2$ and R$^3$ may combine to form a 5- to 6-membered carbocycle or heterocycle comprising: carbon atoms and 0-3 heteroatoms selected from N, NR$^c$, O, and S(O)$_p$, wherein said carbocycle and heterocycle are substituted with 0-3 R$^f$;

R$^4$ is H, F, Cl, Br, C$_{1-4}$ alkyl, or C$_{1-4}$ alkoxy;

R$^6$ is, independently at each occurrence, F, Cl, Me or OMe;

R$^7$ is H, C$_{1-4}$ alkyl, or —CH$_2$CO$_2$R$^a$;

R$^8$ is H, C$_{1-4}$ alkyl, CO$_2$R$^a$, or —CH$_2$CO$_2$R$^a$;

R$^9$ is H; and

R$^{10c}$ is H, F, Cl, Br, C$_{1-4}$ alkyl, or NR$^c$R$^d$;

provided that when R$^8$ is H, X$^1$, X$^2$, and X$^3$ are CH, and R$^{10a}$ is H, then R$^{10b}$ is other than H.

In a fifth embodiment, the present invention includes the compounds of Formula (II), within the scope of the third embodiment wherein:

R$^1$ is Cl, Br, Me, Et, vinyl, 2-propenyl, OMe, OEt, OPr, OCHF$_2$, or cyclopropyl;

R$^2$ is H, F, Cl, Br, C$_{1-4}$ alkoxy, or OCHF$_2$;

R$^3$ is H or C$_{1-4}$ alkoxy;

alternatively, R$^2$ and R$^3$ may combine to form a 5- to 6-membered carbocycle or heterocycle comprising: carbon atoms and 0-3 heteroatoms selected from N, NR$^c$, O, and S(O)$_p$, wherein said carbocycle and heterocycle are substituted with 0-3 R$^f$;

R$^4$ is H, F, Cl, or C$_{1-3}$ alkoxy;

R$^6$ is, independently at each occurrence, F, Cl, or Me;

R$^7$ is H, C$_{1-4}$ alkyl, or —CH$_2$CO$_2$R$^a$;

R$^8$ is H, C$_{1-4}$ alkyl, CO$_2$R$^a$, or —CH$_2$CO$_2$R$^a$;

R$^9$ is H;

R$^{10a}$ is H, F, Cl, Br, C$_{1-4}$ alkyl, C$_{2-4}$ alkenyl, OR$^a$, SR$^e$, CONR$^c$R$^d$, —SO$_2$R$^e$, —SO$_2$NR$^c$R$^d$, morpholin-4-yl, piperid-1-yl, 3,5-dimethyl-pyrazol-1-yl, or 3,5-diethyl-pyrazol-1-yl;

R$^{10b}$ is H, OH, NHR$^c$, —NHCOR$^a$, —NHCO$_2$R$^a$, —NHCONR$^c$R$^d$, —SO$_2$NHR$^c$, —OSO$_2$NHR$^c$, —NHSO$_2$NR$^c$R$^d$, or —NHSO$_2$R$^e$;

R$^{10c}$ is H, Cl, or Me;

R$^a$ is, independently at each occurrence, H, C$_{1-4}$ alkyl, or C$_{3-6}$ cycloalkyl;

R$^c$ and R$^d$ are, independently at each occurrence, H, C$_{1-4}$ alkyl or C$_{3-6}$ cycloalkyl;

alternatively, R$^c$ and R$^d$, when attached to the same nitrogen atom, combine to form a 4- to 7-membered heterocycle comprising: carbon atoms and 0-2 additional heteroatoms selected from N, O, and S(O)$_p$; wherein said heterocycle is substituted with 0-2 R$^g$; and R$^e$ is C$_{1-4}$ alkyl or C$_{3-6}$ cycloalkyl;

provided that when R$^8$ is H, X$^1$, X$^2$, and X$^3$ are CH, and R$^{10a}$ is H, then R$^{10b}$ is other than H; additionally, provided that any two of R$^2$, R$^8$, R$^{10a}$, and R$^{10b}$ are other than H.

In a sixth embodiment, the present invention includes the compounds of Formula (II), within the scope of the third embodiment wherein:

W is selected from:

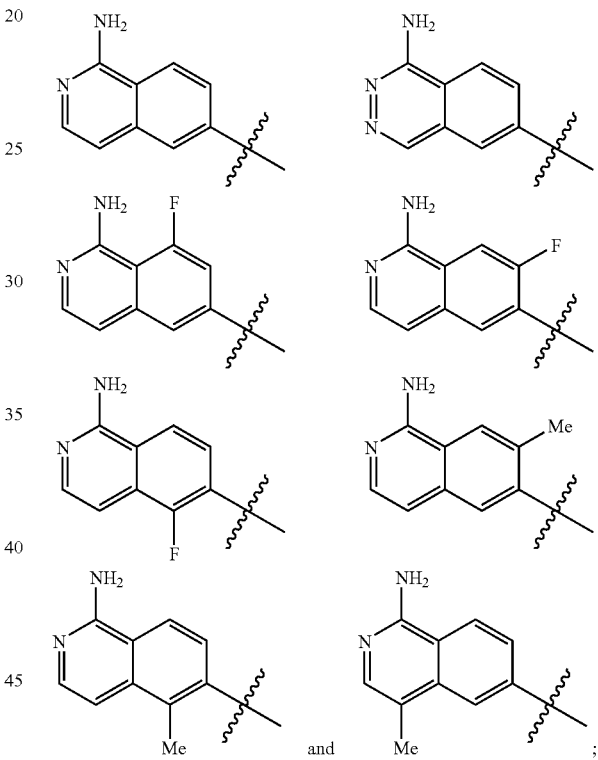

R$^1$ is Cl, Br, Me, Et, OMe, OEt, OPr, OCHF$_2$, or cyclopropyl;

R$^2$ is H, F, Cl, OMe, O(i-Pr), or OCHF$_2$;

R$^3$ is H or OMe;

alternatively, R$^2$ and R$^3$ may combine to form a 5-membered heterocycle comprising: carbon atoms and 1-3 heteroatoms selected from N, NR$^c$, O, and S(O)$_p$, wherein said heterocycle is substituted with 0-3 R$^f$;

R$^4$ is H, F, Cl, or OMe;

R$^7$ is H, Me, —CH$_2$CO$_2$H, or —CH$_2$CO$_2$(C$_{1-4}$ alkyl);

R$^8$ is H, Me, CO$_2$H, CO$_2$(C$_{1-4}$ alkyl), —CH$_2$CO$_2$H, or —CH$_2$CO$_2$(C$_{1-4}$ alkyl);

R$^9$ is H;

R$^{10a}$ is H, F, O(C$_{1-4}$ alkyl), CONR$^c$R$^d$, —S(C$_{1-4}$ alkyl), —SO$_2$(C$_{1-4}$ alkyl), —SO$_2$-cyclopropyl, —SO$_2$-cyclobutyl, —SO$_2$-cyclopentyl, —SO$_2$— (pyrrolidin-1-yl), —SO$_2$— (piperid-1-yl), —SO$_2$-(azepan-1-yl), —SO$_2$NR$^c$R$^d$, —SO₂NH-cyclopropyl, morpholin-4-yl, 3,5-dimethyl-pyrazol-1-yl, or 3,5-diethyl-pyrazol-1-yl;

$R^{10b}$ is H, OH, NH$_2$, —NHCO(C$_{1-4}$ alkyl), —NHCO$_2$(C$_{1-4}$ alkyl), —NHSO$_2$NH$_2$, —SO$_2$NH$_2$, or —NHCONR$^c$R$^d$;

$R^{10c}$ is H, F, Cl, or Me;

$R^c$ and $R^d$ are, independently at each occurrence, H or C$_{1-4}$ alkyl;

alternatively, $R^c$ and $R^d$, when attached to the same nitrogen atom, combine to form a 4- to 5-membered heterocycle comprising: carbon atoms and 0-2 additional heteroatoms selected from N, O, and S(O)$_p$; wherein said heterocycle is substituted with 0-2 R$^g$; and R$^g$ is, independently at each occurrence, =O, F, Cl, Br, CF$_3$, OH, or C$_{1-4}$ alkyl;

provided that when R$^8$ is H, X$^1$, X$^2$, and X$^3$ are CH, and R$^{10a}$ is H, then R$^{10b}$ is other than H; additionally, provided that any two of R$^2$, R$^8$, R$^{10a}$, and R$^{10b}$ are other than H.

In some embodiments, the present invention includes compounds of Formula (I) wherein: W is

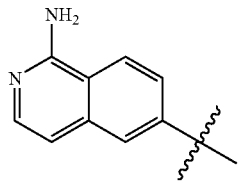

substituted with 0-1 R$^6$.

In some embodiments, the present invention includes compounds of Formula (II) wherein: X$^1$ is CH.

In some embodiments, the present invention includes compounds of Formula (II) wherein: X$^2$ is CH.

In some embodiments, the present invention includes compounds of Formula (II) wherein: X$^3$ is CR$^{10c}$. In other embodiments, the present invention includes compounds of Formula (II) wherein: X$^3$ is CH.

In some embodiments, the present invention includes compounds of Formula (II) wherein: R$^1$ is F, Cl, Br, C$_{1-4}$ alkyl, C$_{1-4}$ alkoxy, OCHF$_2$, or cyclopropyl. In other embodiments, the present invention includes compounds of Formula (II) wherein: R$^1$ is F, Cl, Br, Me, Et, Pr, i-Pr, vinyl, 2-propenyl, allyl, OMe, OEt, OPr, OCHF$_2$, SMe, SEt, or cyclopropyl. In other embodiments, the present invention includes compounds of Formula (II) wherein: R$^1$ is Cl, Br, Me, Et, Pr, i-Pr, vinyl, 2-propenyl, OMe, OEt, OPr, OCHF$_2$, or cyclopropyl. In other embodiments, the present invention includes compounds of Formula (II) wherein: R$^1$ is Cl, Br, Me, Et, OMe, OEt, OPr, OCHF$_2$, or cyclopropyl. In other embodiments, the present invention includes compounds of Formula (II) wherein: R$^1$ is OMe or OEt.

In some embodiments, the present invention includes compounds of Formula (II) wherein: R$^2$ is H, F, Cl, Br, C$_{1-4}$ alkyl, C$_{1-4}$ alkoxy, or OCHF$_2$. In other embodiments, the present invention includes compounds of Formula (II) wherein: R$^2$ is H, F, Cl, Br, C$_{1-4}$ alkoxy, or OCHF$_2$. In other embodiments, the present invention includes compounds of Formula (II) wherein: R$^2$ is H, F, Cl, OMe, O(i-Pr), or OCHF$_2$. In other embodiments, the present invention includes compounds of Formula (II) wherein: R$^2$ is H, OMe, or O(i-Pr).

In some embodiments, the present invention includes compounds of Formula (II) wherein: R$^3$ is H, F, Cl, Br, C$_{1-4}$ alkyl, C$_{1-4}$ alkoxy, or OCHF$_2$. In other embodiments, the present invention includes compounds of Formula (II) wherein: R$^3$ is H or C$_{1-4}$ alkoxy. In other embodiments, the present invention includes compounds of Formula (II) wherein: R$^3$ is H.

In some embodiments, the present invention includes compounds of Formula (II) wherein: R$^4$ is H, F, Cl, Br, C$_{1-4}$ alkyl, or C$_{1-4}$ alkoxy. In other embodiments, the present invention includes compounds of Formula (II) wherein: R$^4$ is H, F, Cl, or C$_{1-3}$ alkoxy. In other embodiments, the present invention includes compounds of Formula (II) wherein: R$^4$ is H, F, Cl, or OMe.

In some embodiments, the present invention includes compounds of Formula (II) wherein: R$^6$ is, independently at each occurrence, F, Cl, Me or OMe. In other embodiments, the present invention includes compounds of Formula (II) wherein: R$^6$ is, independently at each occurrence, F, Cl, or Me. In other embodiments, the present invention includes compounds of Formula (II) wherein: R$^6$ is, independently at each occurrence, F or Me.

In some embodiments, the present invention includes compounds of Formula (II) wherein: R$^7$ is H, Me, —CH$_2$CO$_2$H, —CH$_2$CO$_2$Me, or —CH$_2$CO$_2$Et. In other embodiments, the present invention includes compounds of Formula (II) wherein: R$^7$ is H or Me.

In some embodiments, the present invention includes compounds of Formula (II) wherein: R$^8$ is H, Me, CO$_2$H, CO$_2$Me, CO$_2$Et, —CH$_2$CO$_2$H, —CH$_2$CO$_2$Me, or —CH$_2$CO$_2$Et. In other embodiments, the present invention includes compounds of Formula (II) wherein: R$^8$ is H or Me.

In some embodiments, the present invention includes compounds of Formula (II) wherein: R$^9$ is H.

In some embodiments, the present invention includes compounds of Formula (II) wherein: R$^{10a}$ is H, F, Cl, Br, C$_{1-4}$ alkyl, C$_{2-4}$ alkenyl, OR$^a$, SR$^e$, CONR$^c$R$^d$, —SO$_2$R$^e$, —SO$_2$NR$^c$R$^d$, morpholin-4-yl, piperid-1-yl, 3,5-dimethyl-pyrazol-1-yl, or 3,5-diethyl-pyrazol-1-yl. In other embodiments, the present invention includes compounds of Formula (II) wherein: R$^{10a}$ is H, F, i-Bu, —CH=C(Me)$_2$, O(C$_{1-4}$ alkyl), CONR$^c$R$^d$, —S(C$_{1-4}$ alkyl), —SO$_2$(C$_{1-4}$ alkyl), —SO$_2$-cyclopropyl, —SO$_2$-cyclobutyl, —SO$_2$-cyclopentyl, —SO$_2$—(pyrrolidin-1-yl), —SO$_2$—(piperid-1-yl), —SO$_2$-(azepan-1-yl), —SO$_2$NR$^c$R$^d$, —SO$_2$NH-cyclopropyl, morpholin-4-yl, 3,5-dimethyl-pyrazol-1-yl, or 3,5-diethyl-pyrazol-1-yl. In other embodiments, the present invention includes compounds of Formula (II) wherein:

R$^{10a}$ is H, F, O(i-Pr), CONMe$_2$, CONEt$_2$, CON(Me)Et, —CO-(pyrrolidin-1-yl), —CO-(piperid-1-yl), —S(i-Pr), —SO$_2$Et, —SO$_2$Pr, —SO$_2$(i-Pr), —SO$_2$(t-Bu), —SO$_2$-cyclopropyl, —SO$_2$-cyclobutyl, —SO$_2$-cyclopentyl, —SO$_2$-(pyrrolidin-1-yl), —SO$_2$—(piperid-1-yl), —SO$_2$-(azepan-1-yl), —SO$_2$NHMe, —SO$_2$NMe$_2$, —SO$_2$NHEt, —SO$_2$NH(i-Pr), —SO$_2$NH-cyclopropyl, morpholin-4-yl, 3,5-dimethyl-pyrazol-1-yl, or 3,5-diethyl-pyrazol-1-yl. In other embodiments, the present invention includes compounds of Formula (II) wherein: R$^{10a}$ is —SO$_2$Et, —SO$_2$Pr, —SO$_2$(i-Pr), —SO$_2$(t-Bu), —SO$_2$-cyclopropyl, —SO$_2$-cyclobutyl, —SO$_2$-cyclopentyl, —SO$_2$—(pyrrolidin-1-yl), —SO$_2$—(piperid-1-yl), —SO$_2$-(azepan-1-yl), —SO$_2$NHMe, —SO$_2$NMe$_2$, —SO$_2$NHEt, —SO$_2$NH(i-Pr), or —SO$_2$NH-cyclopropyl. In other embodiments, the present invention includes compounds of Formula (II) wherein: R$^{10a}$ is —SO$_2$Et, —SO$_2$Pr, or —SO$_2$(i-Pr).

In some embodiments, the present invention includes compounds of Formula (II) wherein: R$^{10b}$ is H, OH, NHR$^c$, —NHCOR$^a$, —NHCO$_2$R$^a$, —NHCONR$^c$R$^d$, —SO$_2$NHR$^c$, —OSO$_2$NHR$^c$, —NHSO$_2$NR$^c$R$^d$, or —NHSO$_2$R$^e$. In other embodiments, the present invention includes compounds of Formula (II) wherein: R$^{10b}$ is H, OH, NH$_2$, —NHCO(C$_{1-4}$ alkyl), —NHCO₂(C₁₋₄ alkyl), —NHSO₂NH₂, —SO₂NH₂, —NHCONR^cR^d, or —OSO₂NH₂. In other embodiments, the present invention includes compounds of Formula (II) wherein: $R^{10b}$ is H, OH, NH₂, —NHCOMe, —NHCO₂Me, —NHCO₂Et, —NHCO₂(i-Pr), —NHSO₂NH₂, or —SO₂NH₂. In other embodiments, the present invention includes compounds of Formula (II) wherein: $R^{10b}$ is H, OH, NH₂, —NHCOMe, —NHCO₂Me, —NHSO₂NH₂, or —SO₂NH₂. In other embodiments, the present invention includes compounds of Formula (II) wherein: $R^{10b}$ is —NHCOMe or —NHCO₂Me.

In some embodiments, the present invention includes compounds of Formula (II) wherein: $R^{10c}$ is H, F, Cl, or Me. In other embodiments, the present invention includes compounds of Formula (II) wherein: $R^{10c}$ is H.

In a seventh embodiment, the present invention includes the compounds of Formula (III):

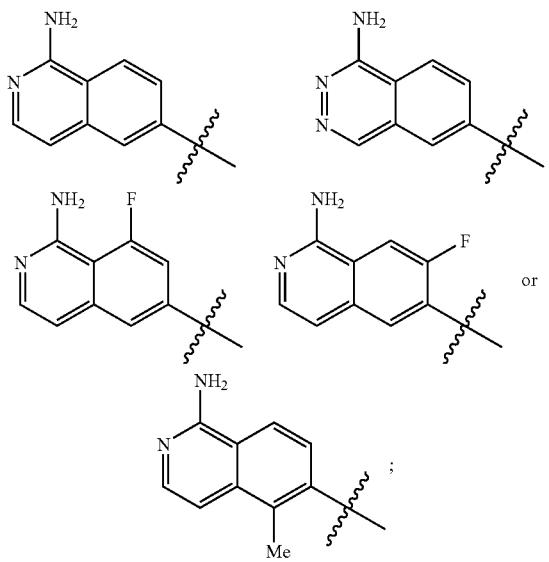

(III)

or a stereoisomer or pharmaceutically acceptable salt, solvate, or prodrug thereof, wherein:
W is

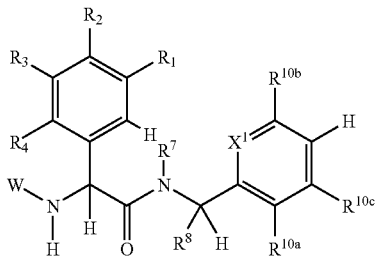

X¹ is CH or N;
$R^1$ is Cl, Br, Me, Et, OMe, OEt, OCHF₂, or cyclopropyl;
$R^2$ is H, F, Cl, OMe, O(i-Pr), or OCHF₂;
$R^3$ is H or OMe;
$R^4$ is H, F, Cl, or OMe;
$R^7$ is H, Me, —CH₂CO₂H, or —CH₂CO₂(C₁₋₄ alkyl);
$R^8$ is H, Me, CO₂H, CO₂(C₁₋₄ alkyl), —CH₂CO₂H, or —CH₂CO₂(C₁₋₄ alkyl);

$R^{10a}$ is H, F, O(C₁₋₄ alkyl), CONR^cR^d, —S(C₁₋₄ alkyl), —SO₂(C₁₋₄ alkyl), —SO₂-cyclopropyl, —SO₂-cyclobutyl, —SO₂-cyclopentyl, —SO₂-(pyrrolidin-1-yl), —SO₂—(piperid-1-yl), —SO₂-(azepan-1-yl), —SO₂NR^cR^d, —SO₂NH-cyclopropyl, morpholin-4-yl, 3,5-dimethyl-pyrazol-1-yl, or 3,5-diethyl-pyrazol-1-yl;

$R^{10b}$ is H, OH, NH₂, —NHCO(C₁₋₄ alkyl), —NHCO₂(C₁₋₄ alkyl), —NHSO₂NH₂, —SO₂NH₂, or —NHCONR^cR^d;

$R^{10c}$ is H, Cl, or Me;

$R^c$ and $R^d$ are, independently at each occurrence, H or C₁₋₄ alkyl;

alternatively, $R^c$ and $R^d$, when attached to the same nitrogen atom, combine to form a 4- to 5-membered heterocycle comprising: carbon atoms and 0-2 additional heteroatoms selected from N, O, and S(O)ₚ; wherein said heterocycle is substituted with 0-2 $R^g$; and $R^g$ is, independently at each occurrence, =O, F, Cl, Br, CF₃, OH, or C₁₋₄ alkyl;

provided that when $R^8$ is H, $X^1$ is CH, and $R^{10a}$ and $R^{10c}$ are H, then $R^{10b}$ is other than H; additionally, provided that any two of $R^2$, $R^8$, $R^{10a}$, and $R^{10b}$ are other than H.

In an eighth embodiment, the present invention includes the compounds of Formula (III), within the scope of the seventh embodiment wherein:
W is

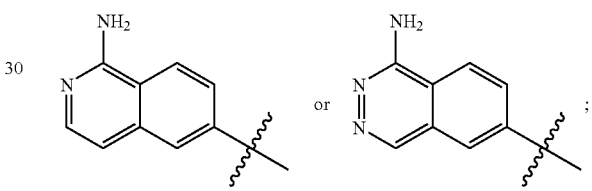

X¹ is CH;
$R^7$ is H, Me, or —CH₂CO₂H;
$R^8$ is H, Me, CO₂H, —CH₂CO₂H, or —CH₂CO₂Me;
$R^{10a}$ is H, F, O(i-Pr), —CONMe₂, —CO-(pyrrolidin-1-yl), —CO-(piperid-1-yl), —S(i-Pr), —SO₂Et, —SO₂Pr, —SO₂(i-Pr), —SO₂(t-Bu), —SO₂-cyclopropyl, —SO₂-cyclobutyl, —SO₂-cyclopentyl, —SO₂— (pyrrolidin-1-yl), —SO₂—(piperid-1-yl), —SO₂-(azepan-1-yl), —SO₂NHMe, —SO₂NMe₂, —SO₂NHEt, —SO₂NH(i-Pr), —SO₂NH-cyclopropyl, morpholin-4-yl, 3,5-dimethyl-pyrazol-1-yl, or 3,5-diethyl-pyrazol-1-yl;

$R^{10b}$ is H, OH, NH₂, —NHCOMe, —NHCOPr, —NHCO₂Me, —NHCO₂Et, —NHCO₂(i-Pr), —NHCO₂(i-Bu), —NHSO₂NH₂, —SO₂NH₂, —NHCON(Me)₂, —NHCON(Me)(Et), —NHCON(Me)(i-Pr),

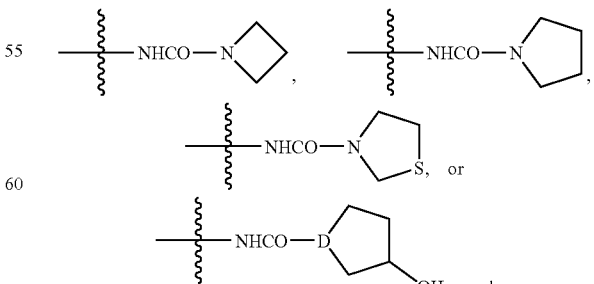

$R^{10c}$ is H;

provided that when $R^8$ is H, $X^1$ is CH, and $R^{10a}$ and $R^{10c}$ are H, then $R^{10b}$ is other than H; additionally, provided that any two of $R^2$, $R^8$, $R^{10a}$, and $R^{10b}$ are other than H.

In some embodiments, the present invention includes compounds of Formula (III) wherein: W is

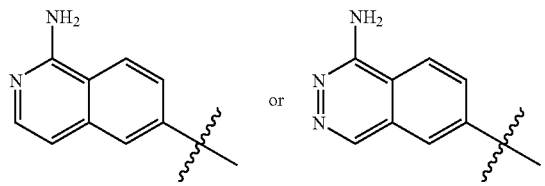

In other embodiments, the present invention includes compounds of Formula (III) wherein: W is

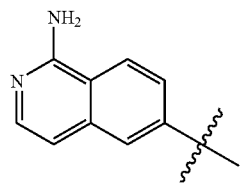

In some embodiments, the present invention includes compounds of Formula (III) wherein: $X^1$ is CH.

In some embodiments, the present invention includes compounds of Formula (III) wherein: $R^1$ is OMe or OEt. In other embodiments, the present invention includes compounds of Formula (III) wherein: $R^1$ is OMe. In other embodiments, the present invention includes compounds of Formula (III) wherein: $R^1$ is OEt.

In some embodiments, the present invention includes compounds of Formula (III) wherein: $R^2$ is H, OMe, or O(i-Pr). In other embodiments, the present invention includes compounds of Formula (III) wherein: $R^2$ is OMe, or O(i-Pr). In other embodiments, the present invention includes compounds of Formula (III) wherein: $R^2$ is O(i-Pr).

In some embodiments, the present invention includes compounds of Formula (III) wherein: $R^4$ is H.

In some embodiments, the present invention includes compounds of Formula (III) wherein: $R^7$ is H or Me. In other embodiments, the present invention includes compounds of Formula (III) wherein: $R^7$ is H.

In some embodiments, the present invention includes compounds of Formula (III) wherein: $R^8$ is H or Me. In other embodiments, the present invention includes compounds of Formula (III) wherein: $R^8$ is H.

In some embodiments, the present invention includes compounds of Formula (III) wherein: $R^{10a}$ is CONMe$_2$, —CO-(pyrrolidin-1-yl), —CO-(piperid-1-yl), —S(i-Pr), —SO$_2$Et, —SO$_2$Pr, —SO$_2$(i-Pr), —SO$_2$(t-Bu), —SO$_2$-cyclopropyl, —SO$_2$-cyclobutyl, —SO$_2$-cyclopentyl, —SO$_2$-(pyrrolidin-1-yl), —SO$_2$— (piperid-1-yl), —SO$_2$-(azepan-1-yl), —SO$_2$NHMe, —SO$_2$NMe$_2$, —SO$_2$NHEt, —SO$_2$NH(i-Pr), or —SO$_2$NH-cyclopropyl. In other embodiments, the present invention includes compounds of Formula (III) wherein: $R^{10a}$ is —SO$_2$Et, —SO$_2$Pr, —SO$_2$(i-Pr), —SO$_2$(t-Bu), —SO$_2$-cyclopropyl, —SO$_2$-cyclobutyl, —SO$_2$-cyclopentyl, —SO$_2$—(pyrrolidin-1-yl), —SO$_2$— (piperid-1-yl), —SO$_2$-(azepan-1-yl), —SO$_2$NHMe, —SO$_2$NMe$_2$, —SO$_2$NHEt, —SO$_2$NH(i-Pr), or —SO$_2$NH-cyclopropyl. In other embodiments, the present invention includes compounds of Formula (III) wherein: $R^{10a}$ is —SO$_2$Et, —SO$_2$Pr, or —SO$_2$(i-Pr).

In some embodiments, the present invention includes compounds of Formula (III) wherein: $R^{10b}$ is H, —NHCOMe, —NHCO$_2$Me, —NHSO$_2$NH$_2$, or —SO$_2$NH$_2$. In other embodiments, the present invention includes compounds of Formula (III) wherein: $R^{10b}$ is —NHCOMe or —NHCO$_2$Me.

In some embodiments, the present invention includes compounds of Formula (III) wherein: $R^{10c}$ is H.

In a ninth embodiment, the present invention provides, inter alia, compounds of Formula (IV):

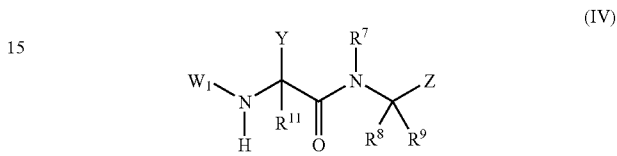

or a stereoisomer or pharmaceutically acceptable salt, solvate, or prodrug thereof, wherein:

$W_1$ is substituted with 0-2 $R^6$ and selected from:

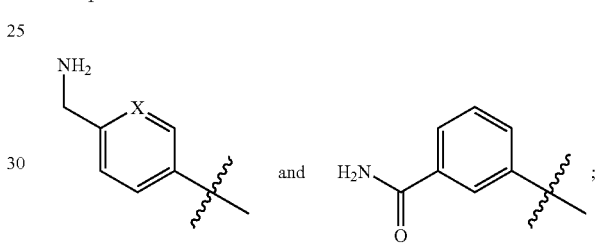

X is CH, $CR^6$, or N;
Y is selected from:

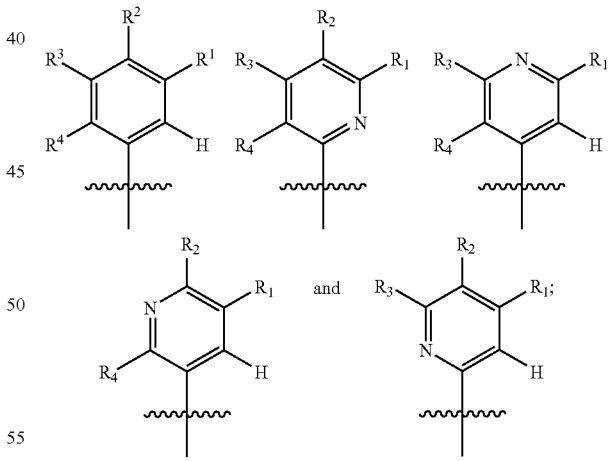

$R^1$ is independently at each occurrence, H, F, Cl, Br, I, $C_{1-4}$ alkyl substituted with 0-1OH, $C_{2-4}$ alkenyl, $C_{2-4}$ alkynyl, $C_{1-4}$ alkoxy, $C_{1-4}$ alkylthio, $C_{1-4}$ haloalkyl, —O—$C_{1-4}$ haloalkyl, or $C_{3-6}$ cycloalkyl;

$R^2$ and $R^3$ are, independently at each occurrence, selected from: H, F, Cl, Br, I, $OR^a$, $SR^e$, $OCF_3$, $OCHF_2$, $OCH_2F$, CN, $NO_2$, —$NR^cR^d$, —$C(O)R^a$, —$CO_2R^a$, —$NR^cC(O)R^a$, —$C(O)NR^cR^d$, —$NR^cC(O)OR^e$, —$NR^cC(O)NR^cR^d$, —OC(O)$NR^cR^d$, —$SO_2NR^cR^d$, —$NR^cSO_2NR^cR^d$, —$NR^cSO_2R^e$, —$NR^cSO_2CF_3$, —$SO_2CF_3$, —$S(O)_2R^e$, $C_{1-4}$ alkyl substituted with 0-2 $R^f$, $C_{2-4}$ alkenyl substituted with 0-2 $R^f$, and $C_{2-4}$ alkynyl substituted with 0-2 $R^f$;

$R^4$ is, independently at each occurrence, H, F, Cl, Br, I, $OR^a$, $SR^e$, $OCF_3$, $OCHF_2$, $OCH_2F$, CN, $NO_2$, $-NR^cR^d$, $-C(O)R^a$, $-CO_2R^a$, $-NR^cC(O)R^a$, $-C(O)NR^cR^d$, $-NR^cC(O)OR^e$, $-NR^cC(O)NR^cR^d$, $-OC(O)NR^cR^d$, $-SO_2NR^cR^d$, $-NR^cSO_2NR^cR^d$, $-NR^cSO_2R^e$, $-NR^cSO_2CF_3$, $-SO_2CF_3$, $-S(O)_2R^e$, $-OCH_2CO_2R^a$, $-O$(benzyl substituted with $CO_2R^a$), tetrazolyl, $-SO_2NHCOR^a$, $-CONHSO_2R^e$, $C_{1-4}$ alkyl substituted with 0-2 $R^f$, $C_{2-4}$ alkenyl substituted with 0-2 $R^f$, or $C_{2-4}$ alkynyl substituted with 0-2 $R^f$;

alternatively, $R^2$ and $R^3$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

alternatively, $R^3$ and $R^4$ may combine to form a 5- to 7-membered carbocycle or heterocycle comprising: carbon atoms and 0-4 heteroatoms selected from N, $NR^c$, O, and $S(O)_p$, wherein said carbocycle and heterocycle are substituted with 0-3 $R^f$;

$R^6$ is, independently at each occurrence, F, Cl, Br, $C_{1-3}$ alkyl, or $C_{1-3}$ alkoxy;

$R^7$ is H, $C_{1-4}$ alkyl, $-CH_2CO_2R^a$, $-CH_2CH_2CO_2R^a$, $-CH_2CH_2OH$, $-CH_2CH_2CH_2OH$, tetrazolyl, $-CH_2CONHSO_2R^e$, or $-CH_2CH_2CONHSO_2R^e$;

$R^8$ is H, $C_{1-4}$ alkyl, $CO_2R^a$, $-CH_2CO_2R^a$, $-CH_2OH$, $-CH_2CH_2OH$, tetrazolyl, $-CONHSO_2R^e$, or $-CH_2CONHSO_2R^e$;

$R^9$ is H or $C_{1-4}$ alkyl;

alternatively, $R^8$ and $R^9$ can be taken together with the carbon atom to which they are attached to form a 3- to 5-membered carbocycle;

Z is phenyl substituted with 0-3 $R^{10}$ or pyridyl substituted with 0-3 $R^{10}$;

$R^{10}$ is, independently at each occurrence, F, Cl, Br, CN, $CH_2F$, $CHF_2$, $CF_3$, $OCF_3$, $SCF_3$, $NO_2$, $C_{1-6}$ alkyl, $C_{2-6}$ alkenyl, $-(CH_2)_n-OR^a$, $SR^e$, $-(CH_2)_n-NR^cR^d$, $CO_2R^a$, $CONR^cR^d$, $-SO_2R^e$, $-SO_2NR^cR^d$, $-NR^hCOR^a$, $-NR^hCO_2R^a$, $-NR^hCONR^cR^d$, $-OC(O)NR^cR^d$, $-SO_2NR^cR^d$, $-OSO_2NR^cR^d$, $-NR^hSO_2NR^cR^d$, $-NR^hSO_2R^e$, $-B(OH)_2$, $-(CH_2)_n$-phenyl, $-NH$-phenyl, $-NH$(-5- to 6-membered heteroaryl comprising: carbon atoms and 1-3 heteroatoms selected from N, O, and $S(O)_p$), or $-(CH_2)_n$-5- to 10-membered heterocycle comprising: carbon atoms and 1-4 heteroatoms selected from N, O, and $S(O)_p$, wherein said phenyl, heteroaryl and heterocycle are substituted with 0-3 $R^i$;

alternatively, when two $R^{10}$ groups are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^i$;

$R^{11}$ is H or $C_{1-3}$ alkyl;

$R^a$ is, independently at each occurrence, H, $C_{1-4}$ alkyl, $C_{3-6}$ cycloalkyl, phenyl, or benzyl; wherein said alkyl, cycloalkyl, phenyl and benzyl are optionally substituted with 0-2 $R^f$;

$R^c$ and $R^d$ are, independently at each occurrence, H, $C_{1-4}$ alkyl, $C_{3-6}$ cycloalkyl, phenyl, or benzyl;

alternatively, $R^c$ and $R^d$, when attached to the same nitrogen atom, combine to form a 3- to 7-membered heterocycle comprising: carbon atoms and 0-2 additional heteroatoms selected from N, O, and $S(O)_p$; wherein said heterocycle is substituted with 0-2 $R^g$;

$R^e$ is, independently at each occurrence, $C_{1-4}$ alkyl, $C_{3-6}$ cycloalkyl, phenyl, or benzyl;

$R^f$ is, independently at each occurrence, F, $CF_3$, OH, $C_{1-3}$ alkoxy, or $C_{3-6}$ cycloalkyl;

$R^g$ is, independently at each occurrence, =O, F, Cl, Br, $CF_3$, OH, or $C_{1-4}$ alkyl;

$R^h$ is, independently at each occurrence, H or $C_{1-3}$ alkyl;

$R^i$ is, independently at each occurrence, F, Cl, Br, $CF_3$, OH, or $C_{1-4}$ alkyl; n, at each occurrence, is selected from 0, 1, 2, 3, and 4; and p, at each occurrence, is selected from 0, 1, and 2;

provided that when $R^8$ and $R^9$ are both H, then Z is other than unsubstituted phenyl.

In a tenth embodiment, the present invention includes the compounds of Formula (IV), within the scope of the ninth embodiment wherein:

$R^1$ is F, Cl, Br, $C_{1-4}$ alkyl, $C_{2-4}$ alkenyl, $C_{1-4}$ alkoxy, $C_{1-4}$ alkylthio, $C_{3-6}$ cycloalkyl, $OCF_3$, $OCHF_2$, or $OCH_2F$;

$R^2$ and $R^3$ are, independently at each occurrence, selected from: H, F, Cl, Br, $C_{1-4}$ alkyl, $C_{1-4}$ alkoxy, $OCF_3$, $OCHF_2$, or $OCH_2F$;

$R^4$ is, independently at each occurrence, H, F, Cl, Br, $C_{1-4}$ alkyl, or $C_{1-4}$ alkoxy;

$R^6$ is, independently at each occurrence, F, Cl, Me or OMe;

$R^7$ is H, $C_{1-4}$ alkyl, or $-CH_2CO_2R^a$; and $R^8$ is H, $C_{1-4}$ alkyl, $CO_2R^a$, or $-CH_2CO_2R^a$;

provided that when $R^8$ and $R^9$ are both H, then Z is other than unsubstituted phenyl.

In some embodiments, the present invention includes compounds of Formula (IV) wherein: $W_1$ is

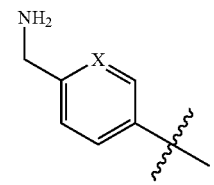

substituted with 0-2 $R^6$.

In some embodiments, the present invention includes compounds of Formula (IV) wherein: X is CH.

In some embodiments, the present invention includes compounds of Formula (IV) wherein: Y is:

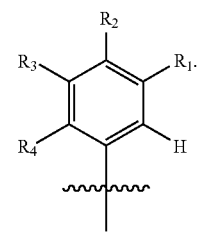

In some embodiments, the present invention includes compounds of Formula (IV) wherein: Y is selected from:

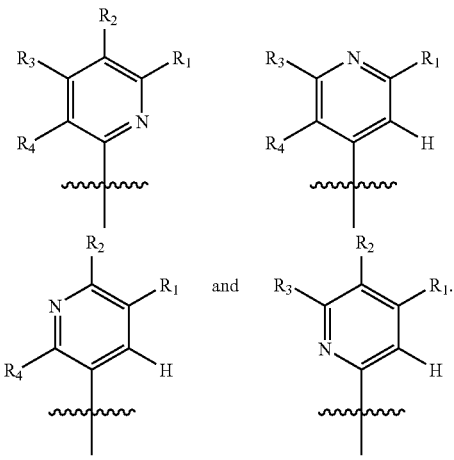

In some embodiments, the present invention includes compounds of Formula (IV) wherein: F, Cl, Br, $C_{1-4}$ alkyl, $C_{1-4}$ alkoxy, $OCHF_2$, or cyclopropyl. In other embodiments, the present invention includes compounds of Formula (IV) wherein: $R^1$ is F, Cl, Br, Me, Et, Pr, i-Pr, vinyl, 2-propenyl, allyl, OMe, OEt, OPr, $OCHF_2$, SMe, SEt, or cyclopropyl. In other embodiments, the present invention includes compounds of Formula (IV) wherein: $R^1$ is Cl, Br, Me, Et, Pr, i-Pr, vinyl, 2-propenyl, OMe, OEt, OPr, $OCHF_2$, or cyclopropyl. In other embodiments, the present invention includes compounds of Formula (IV) wherein: $R^1$ is Cl, Br, Me, Et, OMe, OEt, OPr, $OCHF_2$, or cyclopropyl. In other embodiments, the present invention includes compounds of Formula (IV) wherein: $R^1$ is OMe or OEt.

In some embodiments, the present invention includes compounds of Formula (IV) wherein: $R^2$ is H, F, Cl, Br, $C_{1-4}$ alkyl, $C_{1-4}$ alkoxy, or $OCHF_2$. In other embodiments, the present invention includes compounds of Formula (IV) wherein: $R^2$ is H, F, Cl, Br, $C_{1-4}$ alkoxy, or $OCHF_2$. In other embodiments, the present invention includes compounds of Formula (IV) wherein: $R^2$ is H, F, Cl, OMe, O(i-Pr), or $OCHF_2$. In other embodiments, the present invention includes compounds of Formula (IV) wherein: $R^2$ is H, OMe, or O(i-Pr).

In some embodiments, the present invention includes compounds of Formula (IV) wherein: $R^3$ is H, F, Cl, Br, $C_{1-4}$ alkyl, $C_{1-4}$ alkoxy, or $OCHF_2$. In other embodiments, the present invention includes compounds of Formula (IV) wherein: $R^3$ is H or $C_{1-4}$ alkoxy. In other embodiments, the present invention includes compounds of Formula (IV) wherein: $R^3$ is H.

In some embodiments, the present invention includes compounds of Formula (IV) wherein: $R^4$ is H, F, Cl, Br, $C_{1-4}$ alkyl, or $C_{1-4}$ alkoxy. In other embodiments, the present invention includes compounds of Formula (IV) wherein: $R^4$ is H, F, Cl, or $C_{1-3}$ alkoxy. In other embodiments, the present invention includes compounds of Formula (IV) wherein: $R^4$ is H, F, Cl, or OMe.

In some embodiments, the present invention includes compounds of Formula (IV) wherein: $R^6$ is, independently at each occurrence, F, Cl, Me or OMe. In other embodiments, the present invention includes compounds of Formula (IV) wherein: $R^6$ is, independently at each occurrence, F, Cl, or Me.

In some embodiments, the present invention includes compounds of Formula (IV) wherein: $R^7$ is H, Me, —$CH_2CO_2H$, —$CH_2CO_2Me$, or —$CH_2CO_2Et$. In other embodiments, the present invention includes compounds of Formula (IV) wherein: $R^7$ is H or Me.

In some embodiments, the present invention includes compounds of Formula (IV) wherein: $R^8$ is H, Me, $CO_2H$, $CO_2Me$, $CO_2Et$, —$CH_2CO_2H$, —$CH_2CO_2Me$, or —$CH_2CO_2Et$. In other embodiments, the present invention includes compounds of Formula (IV) wherein: $R^8$ is H or Me.

In some embodiments, the present invention includes compounds of Formula (IV) wherein: $R^9$ is H.

In some embodiments, the present invention includes compounds of Formula (IV) wherein: $R^{10}$ is, independently at each occurrence, F, Cl, Br, $CF_3$, $NO_2$, $C_{1-6}$ alkyl, $C_{2-6}$ alkenyl, $OR^a$, $SR^e$, $NR^cR^d$, —$CH_2NR^cR^d$, $CONR^cR^d$, —$SO_2R^e$, —$SO_2NR^cR^d$, —$NHCOR^a$, —$NHCO_2R^a$, —$NHCONR^cR^d$, —$OSO_2NR^cR^d$, —$NHSO_2NR^cR^d$, —$NHSO_2R^e$, —$B(OH)_2$, phenyl substituted with 0-2 $R^i$, or a 5- to 6-membered heterocycle substituted with 0-2 $R^i$ and selected from: morpholinyl, piperidyl, pyrazolyl, and triazolyl. In other embodiments, the present invention includes compounds of Formula (IV) wherein: $R^{10}$ is, independently at each occurrence, F, Cl, Br, $C_{1-4}$ alkyl, $C_{2-4}$ alkenyl, $OR^a$, $SR^e$, $NR^cR^d$, —$CH_2NR^cR^d$, $CONR^cR^d$, —$SO_2R^e$, —$SO_2NR^cR^d$, —$NHCOR^a$, —$NHCO_2R^a$, —$NHCONR^cR^d$, —$OSO_2NR^cR^d$, —$NHSO_2NR^cR^d$, —$NHSO_2R^e$, morpholin-4-yl, piperid-1-yl, 3,5-dimethyl-pyrazol-1-yl, or 3,5-diethyl-pyrazol-1-yl. In other embodiments, the present invention includes compounds of Formula (IV) wherein: $R^{10}$ is, independently at each occurrence, $CONR^cR^d$, —$SO_2R^e$, —$SO_2NR^cR^d$, —$NHCOR^a$, —$NHCO_2R^a$, —$NHCONR^cR^d$, —$OSO_2NR^cR^d$, —$NHSO_2NR^cR^d$, or —$NHSO_2R^e$.

In some embodiments, the present invention includes compounds of Formula (IV) wherein: $R^{11}$ is H.

In some embodiments, the present invention includes compounds of Formula (IV) wherein: Z is phenyl substituted with 0-3 $R^{10}$.

In an eleventh embodiment, the present invention includes the compounds of Formula (V):

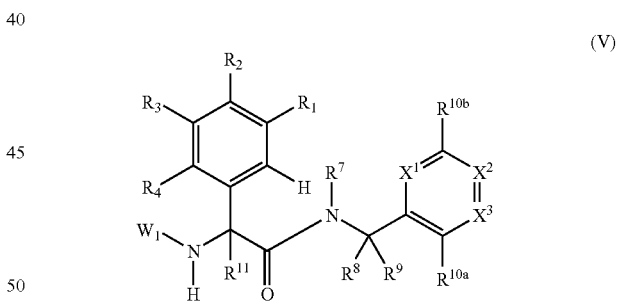

(V)

or a stereoisomer or pharmaceutically acceptable salt, solvate, or prodrug thereof, wherein:

$W_1$ is substituted with 0-2 $R^6$ and selected from:

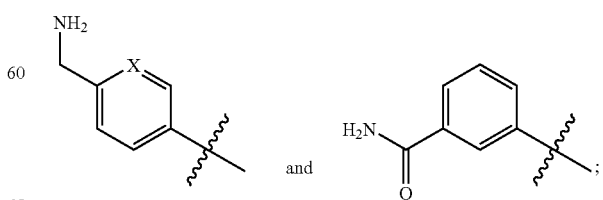

X is CH or N;

$X^1$ is CH or N;
$X^2$ is CH or N;
$X^3$ is $CR^{10c}$ or N;
provided that only one of $X^1$, $X^2$ and $X^3$ may be N;
$R^1$ is H, F, Cl, Br, $C_{1-4}$ alkyl, $C_{2-4}$ alkenyl, $C_{1-4}$ alkoxy, $C_{1-4}$ alkylthio, $C_{3-6}$ cycloalkyl, $OCF_3$, $OCHF_2$, or $OCH_2F$;

$R^2$ and $R^3$ are independently selected from: H, F, Cl, Br, I, $OR^a$, $SR^e$, $OCF_3$, $OCHF_2$, $OCH_2F$, CN, $NO_2$, $—NR^cR^d$, $—C(O)R^a$, $—CO_2R^a$, $—NR^cC(O)R^a$, $—C(O)NR^cR^d$, $—NR^cC(O)OR^e$, $—NR^cC(O)NR^cR^d$, $—OC(O)NR^cR^d$, $—SO_2NR^cR^d$, $—NR^cSO_2NR^cR^d$, $—NR^cSO_2R^e$, $—NR^cSO_2CF_3$, $—SO_2CF_3$, $—S(O)_2R^e$, $C_{1-4}$ alkyl substituted with 0-2 $R^f$, $C_{2-4}$ alkenyl substituted with 0-2 $R^f$, and $C_{2-4}$ alkynyl substituted with 0-2 $R^f$;

$R^4$ is H, F, Cl, Br, I, $OR^a$, $SR^e$, $OCF_3$, CN, $NO_2$, $—NR^cR^d$, $—C(O)R^a$, $—CO_2R^a$, $—NR^cC(O)R^a$, $—C(O)NR^cR^d$, $—NR^cC(O)OR^e$, $—NR^cC(O)NR^cR^d$, $—OC(O)NR^cR^d$, $—SO_2NR^cR^d$, $—NR^cSO_2NR^cR^d$, $—NR^cSO_2R^e$, $—NR^cSO_2CF_3$, $—SO_2CF_3$, $—S(O)_2R^e$, $—OCH_2CO_2R^a$, —O(benzyl substituted with $CO_2R^a$), tetrazolyl, $SO_2NHCOR^a$, $—CONHSO_2R^e$, $C_{1-4}$ alkyl substituted with 0-2 $R^f$, $C_{2-4}$ alkenyl substituted with 0-2 $R^f$, $C_{2-4}$ alkynyl substituted with 0-2 $R^f$;

alternatively, $R^2$ and $R^3$ may combine to form a 5- to 6-membered carbocycle or heterocycle comprising: carbon atoms and 0-3 heteroatoms selected from N, $NR^c$, O, and $S(O)_p$, wherein said carbocycle and heterocycle are substituted with 0-3 $R^f$;

$R^6$ is, independently at each occurrence, F, Cl, Br, $C_{1-3}$ alkoxy or $C_{1-3}$ alkyl;

$R^7$ is H, $C_{1-4}$ alkyl, $—CH_2CO_2R^a$, $—CH_2CH_2CO_2R^a$, $—CH_2CH_2OH$, $—CH_2CH_2CH_2OH$, tetrazolyl, $—CH_2CONHSO_2R^e$, or $—CH_2CH_2CONHSO_2R^e$;

$R^8$ is H, $C_{1-4}$ alkyl, $CO_2R^a$, $—CH_2CO_2R^a$, $—CH_2OH$, $—CH_2CH_2OH$, tetrazolyl, $CONHSO_2R^e$, or $—CH_2CONHSO_2R^e$;

$R^9$ is H or Me;

alternatively, $R^8$ and $R^9$ can be taken together with the carbon atom to which they are attached to form a 3- to 5-membered carbocycle;

$R^{10a}$ is H, F, Cl, Br, $CF_3$, $C_{1-6}$ alkyl, $C_{2-6}$ alkenyl, $OR^a$, $SR^e$, $NR^cR^d$, $CONR^cR^d$, $—SO_2R^e$, $—SO_2NR^cR^d$, phenyl substituted with 0-2 $R^i$, or a 5- to 6-membered heterocycle substituted with 0-2 $R^i$ and selected from: morpholinyl, piperidyl, pyrazolyl, and triazolyl;

$R^{10b}$ is H, $OR^a$, $NR^cR^d$, $—NHCOR^a$, $—NHCO_2R^a$, $—NH-CONR^cR^d$, $—SO_2NR^cR^d$, $—OSO_2NR^cR^d$, $—NHSO_2NR^cR^d$, $—NHSO_2R^e$, $—B(OH)_2$, $—NH$-(5 to 6-membered heteroaryl comprising: carbon atoms and 1-3 heteroatoms selected from N, O, and $S(O)_p$ and substituted with 0-2 $R^i$), —NH-phenyl substituted with 0-2 $R^i$, or a 5-membered heterocycle substituted with 0-2 $R^i$ and selected from: tetrazolyl, pyrazolyl, pyrrolyl, and triazolyl;

$R^{10c}$ is H, F, Cl, Br, $CF_3$, $C_{1-6}$ alkyl, $OR^a$, $SR^e$, or $NR^cR^d$;

$R^{11}$ is H;

$R^a$ is, independently at each occurrence, H, $C_{1-4}$ alkyl, $C_{3-6}$ cycloalkyl, phenyl, or benzyl; wherein said alkyl, cycloalkyl, phenyl and benzyl are optionally substituted with 0-2 $R^f$;

$R^c$ and $R^d$ are, independently at each occurrence, H, $C_{1-4}$ alkyl, $C_{3-6}$ cycloalkyl, phenyl, or benzyl;

alternatively, $R^c$ and $R^d$, when attached to the same nitrogen atom, combine to form a 4- to 7-membered heterocycle comprising: carbon atoms and 0-2 additional heteroatoms selected from N, O, and $S(O)_p$; wherein said heterocycle is substituted with 0-2 $R^g$;

$R^e$ is, independently at each occurrence, $C_{1-4}$ alkyl, $C_{3-6}$ cycloalkyl, phenyl, or benzyl;

$R^f$ is, independently at each occurrence, F, $CF_3$, OH, $C_{1-3}$ alkoxy, or $C_{3-6}$ cycloalkyl;

$R^g$ is, independently at each occurrence, =O, F, Cl, Br, $CF_3$, OH, or $C_{1-4}$ alkyl;

$R^i$ is, independently at each occurrence, F, Cl, Br, $CF_3$, OH, or $C_{1-4}$ alkyl; n, at each occurrence, is selected from 0, 1, 2, 3, and 4; and p, at each occurrence, is selected from 0, 1, and 2;

provided that when $R^8$ and $R^9$ are both H, $X^1$, $X^2$, and $X^3$ are CH, and $R^{10a}$ is H, then $R^{10b}$ is other than H.

In a twelfth embodiment, the present invention includes the compounds of Formula (V), within the scope of the eleventh embodiment wherein:

$W_1$ is

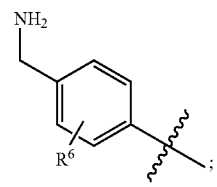

$R^1$ is F, Cl, Br, Me, Et, Pr, i-Pr, vinyl, 2-propenyl, allyl, OMe, OEt, OPr, $OCHF_2$, SMe, SEt, or cyclopropyl;

$R^2$ and $R^3$ are independently selected from: H, F, Cl, Br, $C_{1-4}$ alkyl, $C_{1-4}$ alkoxy, or $OCHF_2$;

alternatively, $R^2$ and $R^3$ may combine to form a 5- to 6-membered carbocycle or heterocycle comprising: carbon atoms and 0-3 heteroatoms selected from N, $NR^c$, O, and $S(O)_p$, wherein said carbocycle and heterocycle are substituted with 0-3 $R^f$;

$R^4$ is H, F, Cl, Br, $C_{1-4}$ alkyl, or $C_{1-4}$ alkoxy;

$R^6$ is, independently at each occurrence, F, Cl, $C_{1-3}$ alkoxy or $C_{1-3}$ alkyl;

$R^7$ is H, $C_{1-4}$ alkyl, or $—CH_2CO_2R^a$;

$R^8$ is H, $C_{1-4}$ alkyl, $CO_2R^a$, or $—CH_2CO_2R^a$;

$R^{10a}$ is H, F, Cl, Br, $C_{1-4}$ alkyl, $C_{2-4}$ alkenyl, $OR^a$, $SR^e$, $CONR^cR^d$, $—SO_2R^e$, $—SO_2NR^cR^d$, morpholin-4-yl, piperid-1-yl, 3,5-dimethyl-pyrazol-1-yl, or 3,5-diethyl-pyrazol-1-yl;

$R^{10b}$ is H, OH, $NHR^c$, $—NHCOR^a$, $—NHCO_2R^a$, $—NH-CONR^cR^d$, $—SO_2NHR^c$, $—OSO_2NHR^c$, $—NHSO_2NR^cR^d$, or $—NHSO_2R^e$; and $R^{10c}$ is H, F, Cl, Br, $C_{1-4}$ alkyl, or $NR^cR^d$;

provided that when $R^8$ is H, $X^1$, $X^2$, and $X^3$ are CH, and $R^{10a}$ is H, then $R^{10b}$ is other than H.

In a thirteenth embodiment, the present invention includes the compounds of Formula (V), within the scope of the twelfth embodiment wherein:

$R^1$ is Cl, Br, Me, Et, OMe, OEt, $OCHF_2$, or cyclopropyl;

$R^2$ is H, F, Cl, OMe, O(i-Pr), or $OCHF_2$;

$R^3$ is H or OMe;

alternatively, $R^2$ and $R^3$ may combine to form a 5-membered heterocycle comprising: carbon atoms and 1-3 heteroatoms selected from N, $NR^c$, O, and $S(O)_p$, wherein said heterocycle is substituted with 0-3 $R^f$;

$R^4$ is H, F, Cl, or OMe;

$R^6$ is, independently at each occurrence, F, Cl, or Me;

$R^7$ is H, Me, $—CH_2CO_2H$, or $—CH_2CO_2(C_{1-4}$ alkyl);

$R^8$ is H, Me, $CO_2H$, $CO_2(C_{1-4}$ alkyl), $—CH_2CO_2H$, or $—CH_2CO_2(C_{1-4}$ alkyl);

$R^9$ is H;

$R^{10a}$ is H, F, O($C_{1-4}$ alkyl), $CONR^cR^d$, $—S(C_{1-4}$ alkyl), $—SO_2(C_{1-4}$ alkyl), $—SO_2$-cyclopropyl, $—SO_2$-cyclobutyl, $—SO_2$-cyclopentyl, $—SO_2$-(pyrrolidin-1-yl), $—SO_2—$ (piperid-1-yl), —SO$_2$-(azepan-1-yl), —SO$_2$NR$^c$R$^d$, —SO$_2$NH-cyclopropyl, morpholin-4-yl, 3,5-dimethyl-pyrazol-1-yl, or 3,5-diethyl-pyrazol-1-yl;

R$^{10b}$ is H, OH, NH$_2$, —NHCO(C$_{1-4}$ alkyl), —NHCO$_2$(C$_{1-4}$ alkyl), —NHSO$_2$NH$_2$, —SO$_2$NH$_2$, or —NHCONR$^c$R$^d$;

R$^{10c}$ is H, F, Cl, or Me; R$^c$ and R$^d$ are, independently at each occurrence, H or C$_{1-4}$ alkyl;

alternatively, R$^c$ and R$^d$, when attached to the same nitrogen atom, combine to form a 4- to 5-membered heterocycle comprising: carbon atoms and 0-2 additional heteroatoms selected from N, O, and S(O)$_p$; wherein said heterocycle is substituted with 0-2 R$^g$; and R$^g$ is, independently at each occurrence, =O, F, Cl, Br, CF$_3$, OH, or C$_{1-4}$ alkyl;

provided that when R$^8$ is H, X$^1$, X$^2$, and X$^3$ are CH, and R$^{10a}$ is H, then R$^{10b}$ is other than H; additionally, provided that any two of R$^2$, R$^8$, R$^{10a}$, and R$^{10b}$ are other than H.

In a fourteenth embodiment, the present invention includes the compounds of Formula (V), within the scope of the thirteenth embodiment wherein:

W$_1$ is:

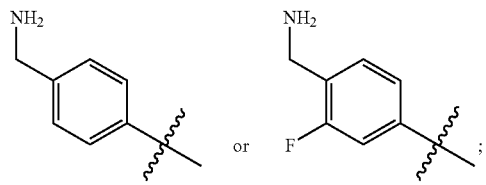

or

X$^1$ is CH;

R$^7$ is H, Me, or —CH$_2$CO$_2$H;

R$^8$ is H, Me, CO$_2$H, —CH$_2$CO$_2$H, or —CH$_2$CO$_2$Me;

R$^{10a}$ is H, F, O(i-Pr), CONMe$_2$, —CO-(pyrrolidin-1-yl), —CO-(piperid-1-yl), —S(i-Pr), —SO$_2$Et, —SO$_2$Pr, —SO$_2$(i-Pr), —SO$_2$(t-Bu), —SO$_2$-cyclopropyl, —SO$_2$-cyclobutyl, —SO$_2$-cyclopentyl, —SO$_2$-(pyrrolidin-1-yl), —SO$_2$— (piperid-1-yl), —SO$_2$-(azepan-1-yl), —SO$_2$NHMe, —SO$_2$NMe$_2$, —SO$_2$NHEt, —SO$_2$NH(i-Pr), —SO$_2$NH-cyclopropyl, morpholin-4-yl, 3,5-dimethyl-pyrazol-1-yl, or 3,5-diethyl-pyrazol-1-yl;

R$^{10b}$ is H, OH, NH$_2$, —NHCOMe, —NHCOPr, —NHCO$_2$Me, —NHCO$_2$Et, —NHCO$_2$(i-Pr), —NHCO$_2$(i-Bu), —NHSO$_2$NH$_2$, —SO$_2$NH$_2$, —NHCON(Me)$_2$, —NHCON(Me)(Et), —NHCON(Me)(i-Pr),

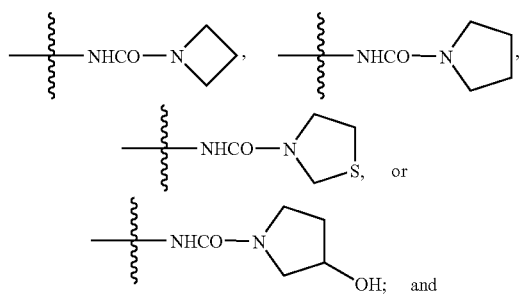

R$^{10c}$ is H;

provided that when R$^8$ is H, R$^{10a}$ is H, then R$^{10b}$ is other than H; additionally, provided that any two of R$^2$, R$^8$, R$^{10a}$, and R$^{10b}$ are other than H.

In a fifteenth embodiment, the present invention includes the compounds of Formula (V), within the scope of the fourteenth embodiment wherein:

R$^1$ is OEt;
R$^2$ is, H, F, Cl, OMe, or O(i-Pr);
R$^4$ is H or F;
R$^7$ is H or Me;
R$^8$ is H or Me;
R$^{10a}$ is —SO$_2$Et;
R$^{10b}$ is —NHCOMe.

In a sixteenth aspect, the present invention provides a compound selected from the exemplified compounds or a stereoisomer or pharmaceutically acceptable salt, solvate, or prodrug thereof.

In a seventeenth embodiment, the present invention includes a compound of Formula (IIa):

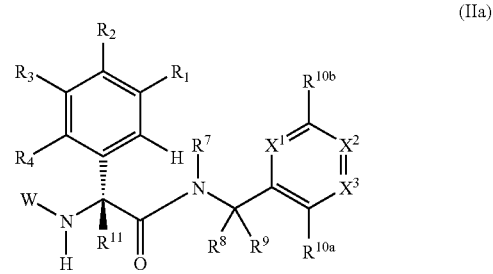

wherein: W, R$^1$, R$^2$, R$^3$, R$^4$, R$^7$, R$^8$, R$^9$, R$^{10a}$, R$^{10b}$, X$^1$, X$^2$, and X$^3$ are the same as defined in the third embodiment.

In an eighteen embodiment, the present invention includes a compound of Formula (Va):

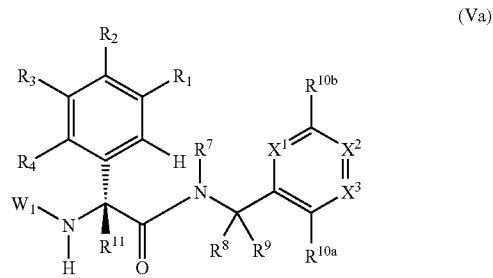

wherein: W$_1$, R$^1$, R$^2$, R$^3$, R$^4$, R$^7$, R$^8$, R$^9$, R$^{10a}$, R$^{10b}$, X$^1$, X$^2$, and X$^3$ are the same as defined in the eleventh embodiment.

In another embodiment, the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a novel process for making one of the compounds of the present invention or a stereoisomer, tautomer, pharmaceutically acceptable salt, solvate or prodrug thereof.

In another embodiment, the present invention provides a novel intermediate for making one of the compounds of the present invention or a stereoisomer, tautomer, pharmaceutically acceptable salt, solvate or prodrug thereof.

In another embodiment the present invention provides a method for modulation of the coagulation cascade and/or contact activation system comprising administering to a patient in need of such treatment a therapeutically effective amount of at least one of the compounds of the present invention or a stereoisomer, tautomer, pharmaceutically acceptable salt, solvate, or prodrug thereof.

In another embodiment the present invention provides a method for treating thrombotic or thromboembolic disorders comprising: administering to a patient in need of such treatment a therapeutically effective amount of at least one of the compounds of the present invention or a stereoisomer, tautomer, pharmaceutically acceptable salt, solvate, or prodrug thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer, tautomer, pharmaceutically acceptable salt, solvate, or prodrug thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug thereof in an amount effective to treat a thromboembolic disorder.

In another embodiment, the present invention provides a method of treating a patient in need of inflammatory disorder treatment, comprising: administering a compound of the present invention or a stereoisomer, tautomer, pharmaceutically acceptable salt, solvate, or prodrug thereof in an amount effective to treat an inflammatory disorder.

In another embodiment, the present invention provides a method, comprising: administering a compound of the present invention or a stereoisomer, tautomer, pharmaceutically acceptable salt form thereof in an amount effective to treat a thrombotic or thromboembolic and/or inflammatory disorder.

In another embodiment, the present invention provides a pharmaceutical composition further comprising at least one additional therapeutic agent selected from one or more of potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In a preferred embodiment, the present invention provides a pharmaceutical composition wherein the additional therapeutic agent(s) is an antihypertensive agent selected from ACE inhibitors, AT-1 receptor antagonists, beta-adrenergic receptor antagonists, ETA receptor antagonists, dual ETA/AT-1 receptor antagonists, and vasopeptidase inhibitors, an antiarrythmic agent selected from IKur inhibitors, an anticoagulant agent selected from thrombin inhibitors, antithrombin-III activators, heparin co-factor II activators, other factor VIIa inhibitors, other plasma kallikrein inhibitors, plasminogen activator inhibitor (PAI-1) antagonists, thrombin activatable fibrinolysis inhibitor (TAFI) inhibitors, factor IXa inhibitors, factor Xa inhibitors, and factor XIa inhibitors, or an antiplatelet agent selected from GPIIb/IIIa blockers, protease activated receptor (PAR-1) antagonists, phosphodiesterase-III inhibitors, $P2Y_1$ receptor antagonists, $P2Y_{12}$ receptor antagonists, thromboxane receptor antagonists, cyclooxygense-1 inhibitors, and aspirin, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a compound of the present invention for use in therapy.

In another embodiment, the present invention provides a compound of the present invention for use in therapy for treating a thrombotic and thromboembolic disorder.

In another embodiment, the present invention also provides the use of a compound of the present invention for the manufacture of a medicament for the treatment of a thrombotic or thromboembolic disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a thrombotic or thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative. In cases wherein there are quarternary carbon atoms on compounds of the present invention, these may be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^{10}$, then said group may optionally be substituted with up to three $R^{10}$ groups and $R^{2b}$ at each occurrence is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. Branched cycloalkyl groups such as 1-methylcyclopropyl and 2-methylcyclopropyl are included in the definition of "cycloalkyl".

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "heterocycle" or "heterocyclic group" is intended to mean a stable 5, 6, or 7-membered monocyclic or polycyclic or 7, 8, 9, 10, 11, 12, 13, or 14-membered polycyclic heterocyclic ring which is saturated, partially unsaturated or fully unsaturated, and which consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

When a dotted ring is used within a ring structure, this indicates that the ring structure may be saturated, partially saturated or unsaturated.

The term "counterion" is used to represent a small, negatively charged species such as chloride, bromide, hydroxide, acetate, and sulfate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Isotopically labeled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "*Design and Application of Prodrugs*," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

As used herein, the term "patient" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination with other active ingredients to inhibit factor VIIa and/or plasma kallikrein or to treat the disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22:27-55, occurs when the effect (in this case, e.g., prevention of thrombosis) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The term "pharmaceutical composition" means a composition comprising a compound of the invention in combination with at least one additional pharmaceutical carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th ed., 1990, which is incorporated herein by reference in its entirety.

Abbreviations used in the Examples are defined as follows: "1×" for once, "2×" for twice, "3×" for thrice, "°C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "atm" for atmosphere, "psi" for pounds per square inch, "RT" for retention time, "sat" or "sat'd" for saturated, "MW" for molecular weight, "MS" for mass spectrometry, "ESI" for electrospray ionization mass spectroscopy, "HR" for high resolution, "LC-MS" for liquid chromatography mass spectrometry, "HPLC" for high pressure liquid chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" or "TLC" for thin layer chromatography, and "α", "β", "R", "S", "E", and "Z" are stereochemical designations familiar to one skilled in the art.

AcOH or HOAc is acetic acid,
AIBN is azo-bis-isobutyrlnitrile,
$BH_3 \cdot SMe_2$ is borane-dimethyl sulfide complex,
$BH_3 \cdot THF$ is borane-tetrahydrofuran complex,
BINAP is 2,2'-bis(diphenylphosphino)-1,1'-binaphthyl,
Bn is benzyl,
Boc is tert-butyl oxycarbonyl,
BOP is benzotriazol-1-yloxy-tris(dimethylamino)phosphonium hexafluorophosphate,
Bu is butyl,
iBu or i-Bu is isobutyl,
t-Bu is tert-butyl,
Cbz is carbonylbenzyloxy,
CbzSerOtBu is (S)-2-tert-butoxycarbonylamino-3-hydroxy-propionic acid tert-butyl ester,
CDI is 1,1'-carbonyldiimidazole,
$CH_2Cl_2$ is dichloromethane,
$CH_3CN$ is acetonitrile,
Davis oxaziridine is 2-benzenesulfonyl-3-phenyl-oxaziridine,
DBU is 1,8-diazabicyclo[5.4.0]undec-7-ene,
DCE is 1,2-dichloroethane,
DIBAH is diisobutylaluminum hydride,
DIC is 1,3-diisopropylcarbodiimde,
DIEA is diethylpropyl amine,
DMAP is dimethylaminopyridine,
DMF is dimethylformamide,
DMSO is dimethyl sulfoxide,
DMPU is 1,3-dimethyl-3,4,5,6-tetrahydro-2(1H)-pyrimidone,
DPPA is diphenylphosphoryl azide,
EDCI is 1-(3-dimethylaminopropyl)-3-ethylcarbodiimide hydrochloride,
Et is ethyl,
EtOAc is ethyl acetate,
HATU is O-(7-azabenzotriazol-1-yl)-N,N,N',N'-tetramethyluronium,
HBTU is O-benzotriazol-1-yl-N,N,N',N'-tetramethyluronium hexafluorophosphate,
HCl is hydrochloric acid,
HOAt or HOAT is 1-hydroxy-7-azabenzotriazole,
HOBt or HOBT is 1-hydroxybenzotriaole,
$H_3PO_4$ is phosphoric acid,
$K_2CO_3$ is potassium carbonate,
LAH is lithium aluminum hydride,
LDA is lithium diisopropylamide,
LiHMDS is bis(trimethylsilyl)amide,
mCPBA or MCPBA is meta-chloroperbenzoic acid,
Me is methyl,
MeOH is methanol,
$MgSO_4$ is magnesium sulfate,
MoOPH is oxodiperoxymolybdenum(pyridine)(hexamethylphosphoric triamide),
MsCl is methanesulfonyl chloride,
Na is sodium,
NaH is sodium hydride,
$NaHCO_3$ is sodium bicarbonate,
$NaHSO_3$ is sodium thiosulfite,
NaOAc is sodium actetate,
NBS is N-bromosuccinimide,
NCS is N-chlorosuccinimide,
OAc is acetate,
Pd/C is palladium on carbon,
$Pd(PPh_3)_4$ is tetraks (triphenylphosphine) palladium,
Ph is phenyl,
Pr is propyl,
iPr or i-Pr is isopropyl,
i-PrOH or IPA is isopropanol,
PyBroP or Py-BroP is bromotripyrrolidinophosphonium hexafluorophosphate,
Selectfluor™ is [1(chloromethy)-4-fluoro-1,4-diazoniabicyclo[2,2,2]octanebis(tetrafluoroborate)],
TBAI is tetrabutylammonium iodide,
tBME is tert-butyl methyl ether,
TEA is triethylamine,
TFA is trifluoroacetic acid, TFAA is trifluoroacetic anhydride,
THF is tetrahydrofuran.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds having the general Formula (I):

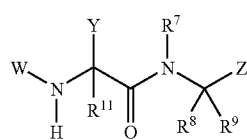

(I)

wherein W, Y, $R^7$-$R^9$, $R^{11}$ and Z are each as defined above, can be prepared by coupling an acid of Formula (Ia):

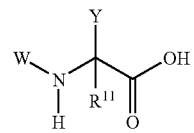

(Ia)

with an amine of Formula (Ib):

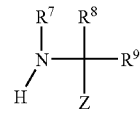

(Ib)

under conditions suitable for forming an amide bond between the acid and the amine. Coupling conditions can be found in Bodanszky, "Principles of Peptide Synthesis, Second Edition" Springer Verlag Ed, Berlin (1993). Coupling reagents include CDI, DIC, and EDCI. Optionally, an intermediate activated ester can be prepared by adding one equivalent of 1-hydroxybenzotriazole or 1-hydroxy-7-azabenzotriazole. Other coupling reagents include HATU, HBTU, and Py-Brop which are usually reacted in the presence of one equivalent of a tertiary base such as DIEA or TEA. Protection and deprotection of functional groups may be required before or after the amide formation step to afford a compound of Formula (I).

The intermediate acids of Formula (Ia) can be prepared in several different ways. For example, they can be prepared according to the steps described in Scheme 1, where amines 1 (prepared following the methods shown in later Schemes and in the Examples) react with phenyl acetate derivatives 2 (for preparation, see WO2004072101) under basic conditions to give 3. LG is a leaving group such as Cl, Br, OMs (methylsulfonate) or OTf (trifluoromethylsulfonate) and P and P' are protecting groups. Pyridyl acetate derivatives 2 can be prepared by methods known to one skilled in the art. Deprotection of P in 3 by hydrolysis or hydrogenation gives acid intermediates Iaa containing a substituted 1-aminoisoquinoline or 1-aminophthalazine group.

Scheme 1

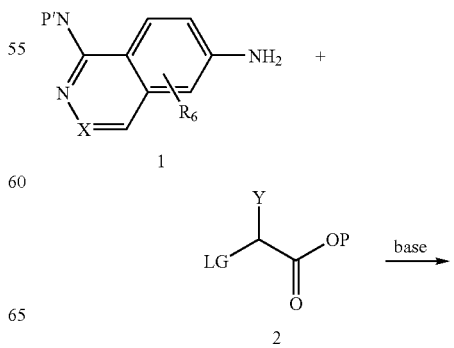

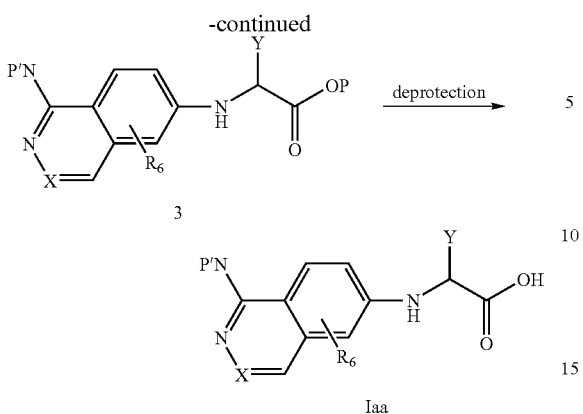
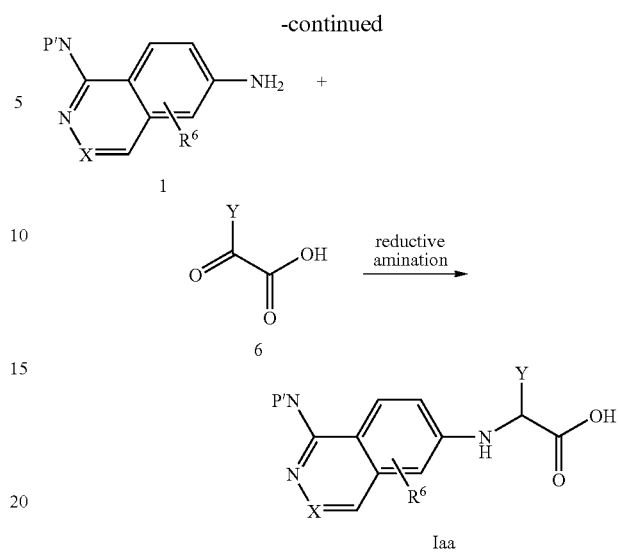

Acids Iaa wherein Y is a phenyl group can also be prepared by a Petasis boronic acid Mannich reaction (*J. Am. Chem. Soc.* 1997, 119, 445-446) shown in Scheme 2a. Amines 1 react with phenyl boronic acid derivatives 4 and glyoxaldehyde 5 in a suitable solvent to give the acids Iaa directly. This three component condensation reaction can be carried out thermally or under micro-wave irradiation. Preparation of boronic acids 4 is well known to those skilled in the art (see *Tetrahedron* 2002, 58, 9633-9695; *Synthesis* 2003, 4, 469-483). Acids Iaa wherein Y is a pyridyl group can be prepared by reductive amination (*Tetrahedron*, 1996, 52, 9777-9784) of pyridyl α-keto acids 6 with amines 1 as shown in Scheme 2b. Pyridyl α-keto acids 6 can be prepared by methods known to one skilled in the art.

Acids Iaa wherein Y is a phenyl group can also be prepared by reductive amination (*Tetrahedron*, 1996, 52, 9777-9784) of α-keto acids 6 with amines 1 as shown in Scheme 3.

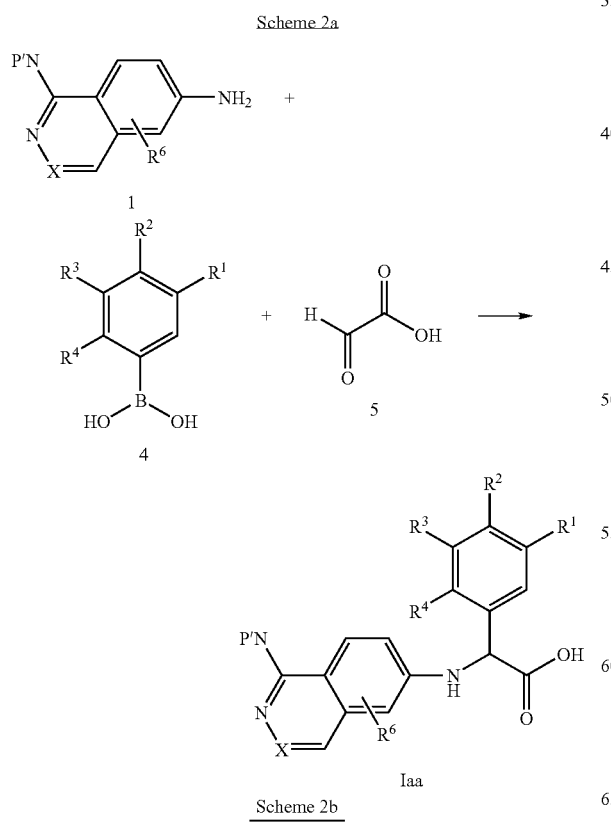

Scheme 2a

Scheme 2b

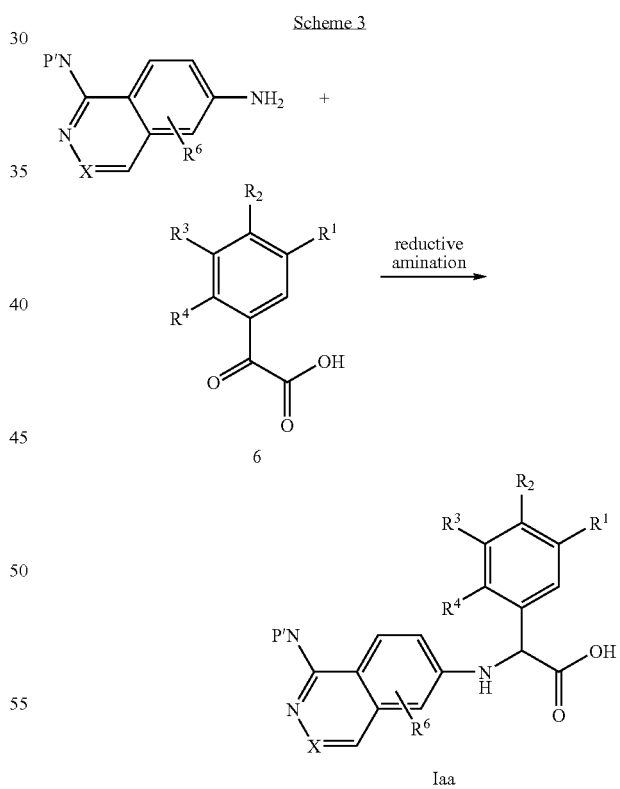

Scheme 3

Alternatively to Schemes 1, 2a, 2b, and 3, as exemplified in Scheme 4a, acids Ia where W=isoquinolin-6-yl can be prepared from amino-esters 8. Amino-esters 8 can be accessed through a Strecker type synthesis, by condensation of aldehydes 7 with trimethylsilylcyanide in presence of ammonia, followed by treatment with hydrochloric acid in MeOH. Compounds 8 can be converted to 10 via coupling with aryl halides or sulfonates 9 by methods known in the art. For example, amino-esters 8 may be coupled with aryl halides 9 in the presence of a palladium catalyst, an appropriate ligand, for example, BINAP, and a base such as cesium carbonate to provide esters 10. Hydrolysis of 10 gives Iab.

Scheme 4a

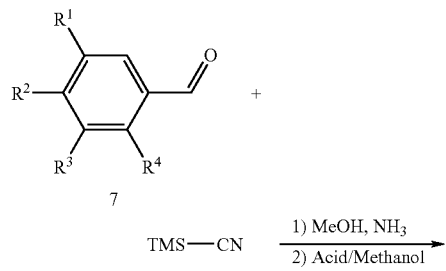

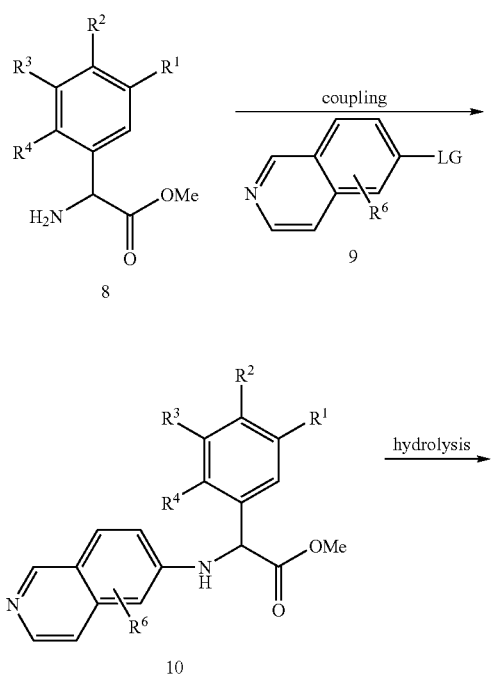

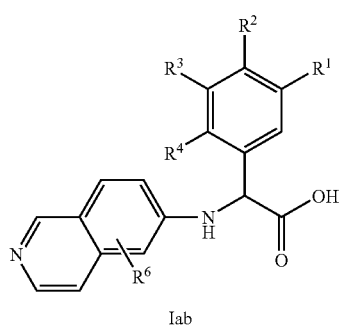

synthesis, by condensation of pyridyl aldehydes 7 with trimethylsilylcyanide in presence of ammonia, followed by treatment with hydrochloric acid in MeOH. Pyridyl aldehydes 7 are commercially available or can be synthesized by methods known to one skilled in the art. Compounds 8 can be converted to 10 via coupling with aryl halides or sulfonates 9 by methods known in the art. For example, amino esters 8 may be coupled to aryl halides 9 in the presence of a palladium catalyst, an appropriate ligand, for example, BINAP, and a base such as cesium carbonate to provide esters 10. Hydrolysis of 10 gives Iab.

Scheme 4b

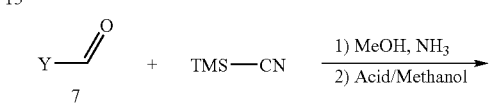

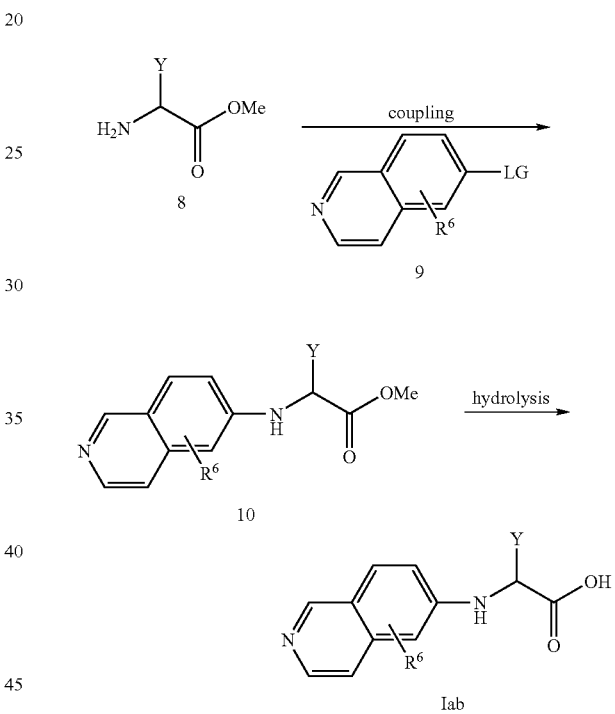

Substituted isoquinoline amines 1 can be obtained from 11 as shown in Scheme 5. Anilines 11 can be treated with an electrophilic source of halogens (Hal+), such as, for example, NCS, NBS or Selectfluor™. Bromides 12 can further be manipulated to provide anilines 1 wherein $R^6$=alkyl, for example, via reaction with tetra-alkyltins in the presence of a palladium catalyst such as $PdCl_2(PPh_3)_3$.

Scheme 5

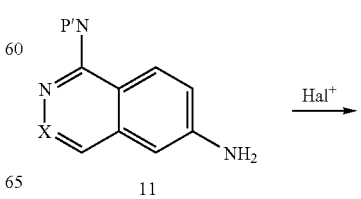

Alternatively to Schemes 1 and 2, as exemplified in Scheme 4b, acids Ia where W=isoquinolin-6-yl can be prepared from amino-esters 8. Amino esters 8 can be accessed by several methods known in the art, including a Strecker type

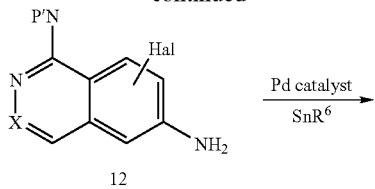

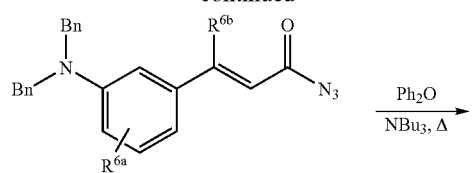

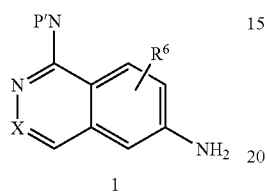

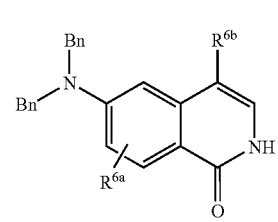

Substituted aminoisoquinoline amines 20 can be obtained from phenyl halides 13 as shown in Scheme 6. Phenyl halide anilines can be protected with appropriate protecting groups by methods known to those in the art to provide halides 13. These can be advanced by heating with an alkyl crotonates or alkyl acrylates 14 in the presence of a palladium catalyst such as palladium (II) acetate and a ligand such as tri(o-tolyl) phosphine and a base such as triethylamine to give esters 15. Hydrolysis, followed by activation of the resulting acid as, for example, a mixed anhydride, and treatment with an azide source, such as sodium azide, yields acyl azides 16. Heating azides 16 at high temperature in a solvent such as diphenyl ether, in the presence of an appropriate base such as tributylamine, provides isoquinolin-1(2H)-ones 17. Treatment with phosphorous (III) oxychloride at reflux gives chlorides 18 which can be converted to the desired aminoisoquinolines 19 by heating in a solution of ammonia in a solvent such as ethylene glycol in the presence of a catalyst such as copper (I) oxide. Appropriate protection with, for example, excess di-tert-butyl dicarbonate, and deprotection of the C-6 aniline in ways known in the art yields aminoisoquinolines 20.

Scheme 6a

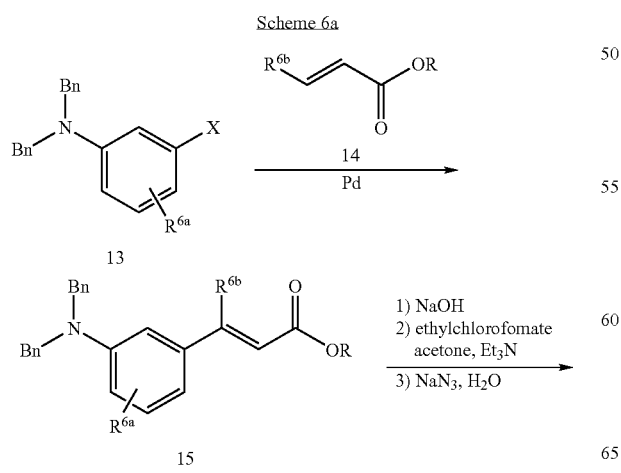

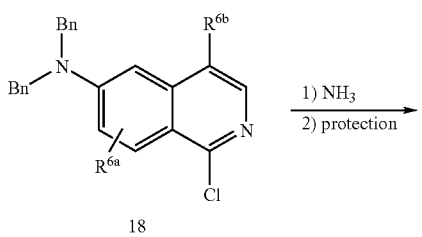

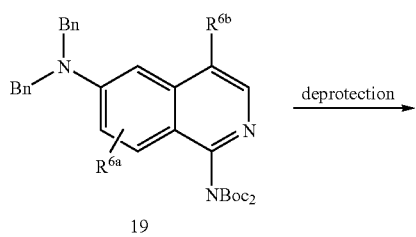

These can be advanced to acids 22 by coupling with chlorides 21 in the presence of a base such as DIPEA and heating, followed by deprotection of the benzyl ester as shown in Scheme 6b.

Acid Ia wherein W is aminophthalazine-6-yl may be prepared according to Scheme 7. 4-Bromobenzoic acid 23 is converted to the acid chloride and reacted with diethylamine. The resulting diethylbenzamide 24 is formylated by treatment with lithium tetramethylpiperidide at −78° C., followed by quenching with DMF. Subsequent cyclization in refluxing hydrochloric acid provides the hydroxyphthalide 25. The hydroxyphthalide 25 is refluxed with hydrazine in ethanol to afford 6-bromophthalazin-1 (2H)-one 26. Treatment with phosphorous oxychloride gives 6-bromo-1-chlorophthalazine 27, which is converted to 1-amino-6-bromophthalazine 28 by reaction with ammonia saturated ethylene glycol at 130° C. The amine is protected by reaction with di-tert-butyl dicarbonate and 4-dimethylaminopyridine in acetonitrile. The resulting bromide 29 can then by coupled with a phenylglycine ester 30 with palladium-BINAP complex. Subsequent ester hydrolysis of ester 31 gives acid 32.

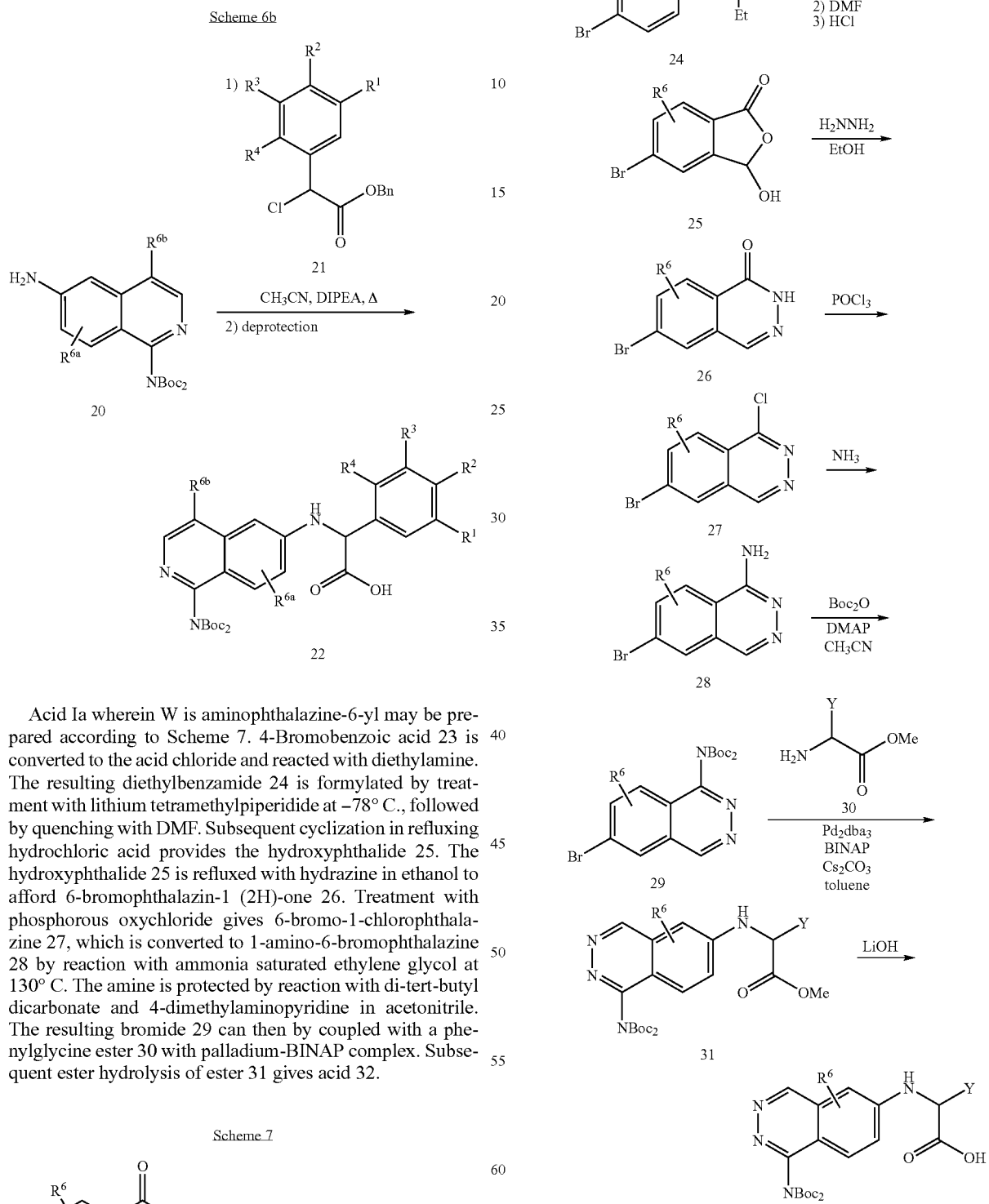

Amines of Formula (Ib) are either commercially available or prepared according to the procedures given in the Schemes and Examples below.

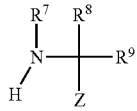
(Ib)

In general, functionalized benzylamines 34, wherein $R^7$=H, and Z is a functionalized phenyl group, are prepared as exemplified in Scheme 8 via reduction of commercially available or prepared benzonitriles 33 (as shown in the Schemes and Examples below) via, for example, hydrogenation in the presence of a catalyst such as Pd/C or Raney Nickel, or using a hydride source, such as $BH_3$ or LAH in THF. Alternatively, as shown in Scheme 9, benzylamines 34 can be prepared from esters 35 or aldehydes 36 via reduction to benzyl alcohols 37 using, for example, LAH, followed by conversion to azides 38 with an appropriate reagent such as diphenylphosphoryl azide in a solvent such as THF or toluene. Reduction of azides 38 with, for example, hydrogenation, LAH or triphenylphosphine, provides benzylamines 34. Finally, as shown in Scheme 10, benzylamines 34 can also be prepared from esters 35 via hydrolysis, treatment with ammonium hydroxide in the presence of appropriate coupling reagents, such as EDC and HOBT or HOAT, followed by reduction of the derived primary amide with a hydride source, such as $BH_3$.

Scheme 8

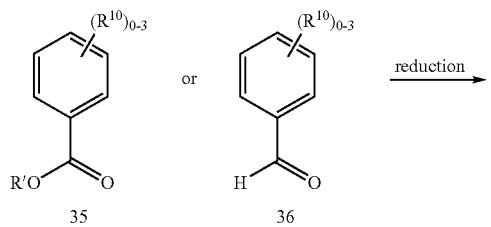

Scheme 9

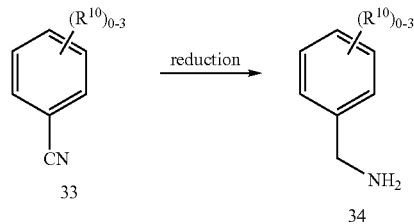

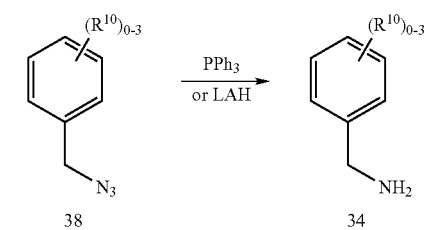

Scheme 10

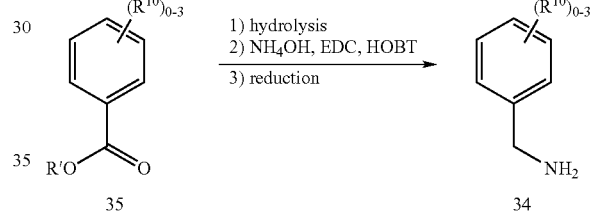

Amines of Formula (Ib), in which $R^7$=alkyl and Z is a functionalized phenyl group, can be prepared from benzylamines 34 as exemplified in Scheme 11 via protection with, for example, trifluoroacetic anhydride to give 39, followed by alkylation with an alkyl halide, for example, methyl iodide. Deprotection with a base such as potassium carbonate yields the desired N-methyl benzylamines 41.

Scheme 11

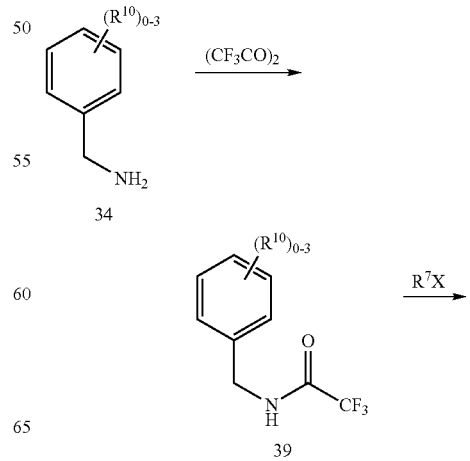

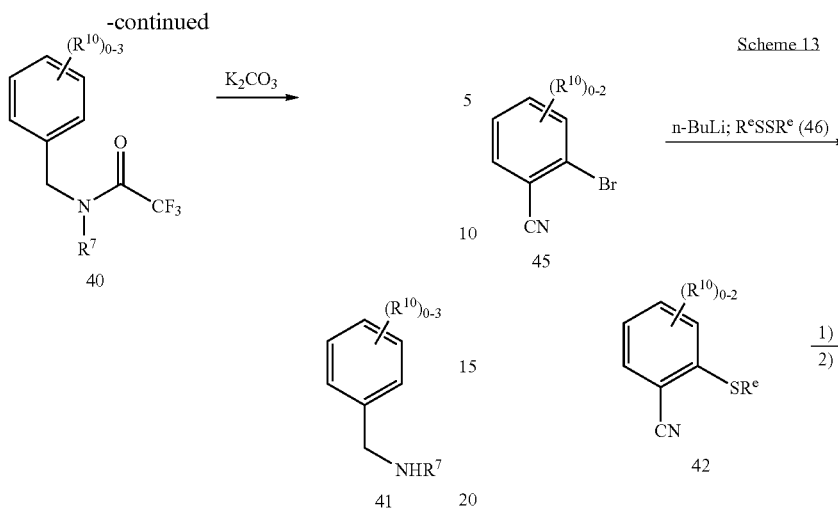

Benzylamines 44 containing an ortho-sulfone substituent can be prepared, as shown in Scheme 12, from sulfides 42, via oxidation to benzonitrile sulfones 43 with an appropriate oxidizing agent, such as MCPBA. Benzonitriles 43 can then be converted to the corresponding benzylamines 44 as was previously shown in Scheme 8.

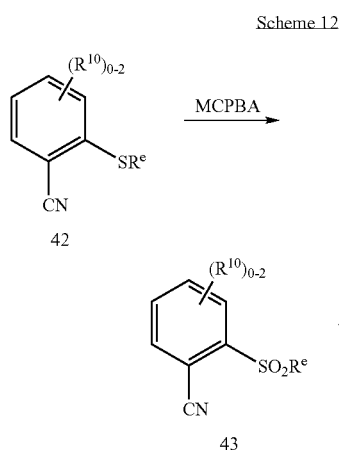

Sulfides 42 can be prepared in several different ways. As shown in Scheme 13, one method involves advancing commercially available o-bromobenzonitriles 45 via lithium-halogen exchange using, for example n-butyl lithium at cold temperatures in a solvent such as THF followed by reaction with disulfides 46. Sulfides 42 can then be converted to the corresponding benzylamines 44 by oxidation to the sulfones then reduction to the benzylamines as was previously shown in Schemes 8 and 12.

In addition, as shown in Scheme 14, sulfides 42 can also be prepared from o-cyanophenyldisulfides 47 by reaction with organometallic nucleophiles 48, for example, Grignard reagents. Sulfides 42 can then be converted to the corresponding benzylamines 44 by oxidation to the sulfones then reduction benzylamines as was previously shown in Schemes 8 and 12.

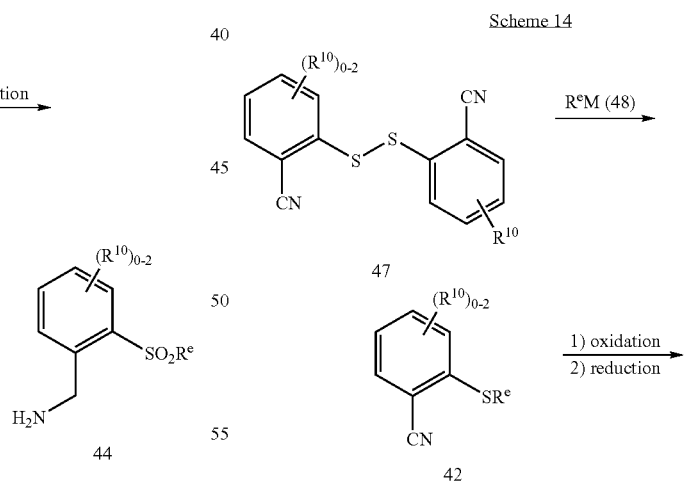

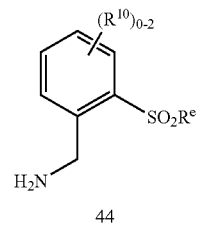

As shown in Scheme 15, sulfides 42 can also be prepared from o-fluorobenzonitriles 49 via reaction with thiols 50 in a solvent such as DMF in the presence of a base such as sodium carbonate. Sulfides 42 can then be converted to the corresponding benzylamines 44 by oxidation to the sulfones then reduction benzylamines as was previously shown in Schemes 8 and 12. Also, sulfides 42 can be converted to benzylamines 51 by treatment with a reducing agent, such as BH$_3$.

Scheme 15

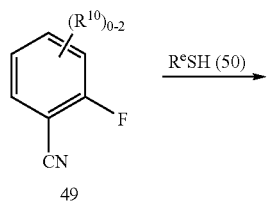

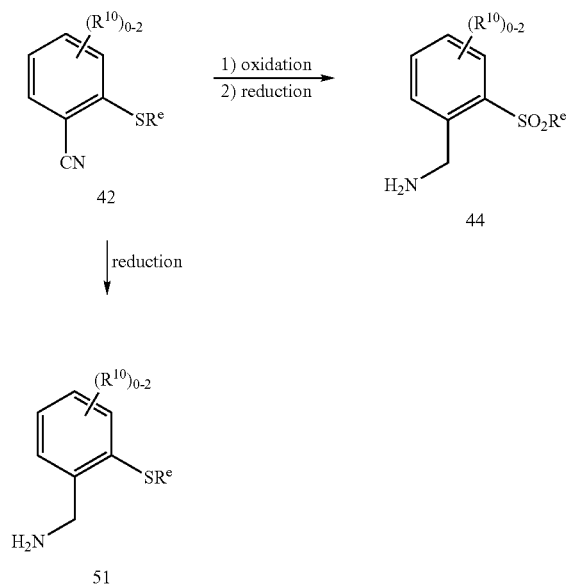

Finally, as shown in Scheme 16, sulfides 54 can be prepared from thiosalicylates 52 via alkylation with alkyl halides 53, followed by oxidation to the sulfones 55 as was previously shown in Scheme 12. The esters 55 can be converted to benzylamines 44 as was previously shown in Scheme 9 or Scheme 10.

Scheme 16

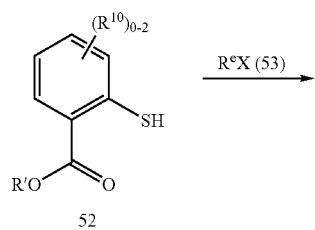

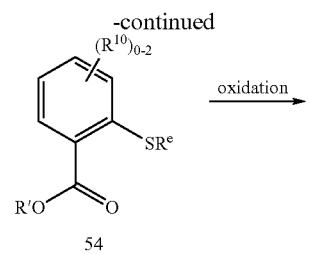

Benzylamines 58 containing a heterocyclic substituent can be prepared as shown in Scheme 17. Fluorobenzonitriles 49 are treated with amines 56 in a solvent such as acetonitrile. The resulting benzonitriles 57 are then converted to the benzylamines 58 as was previously shown in Scheme 8.

Scheme 17

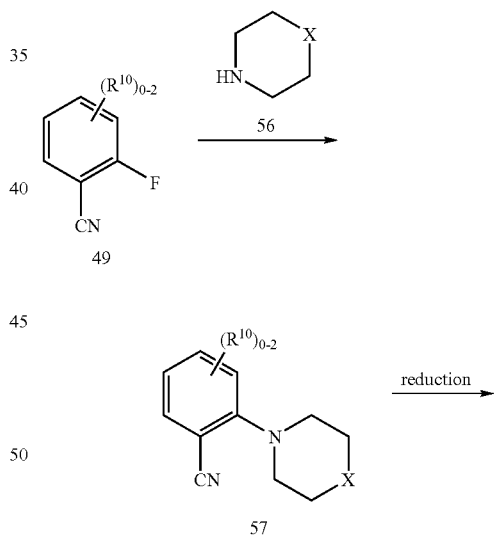

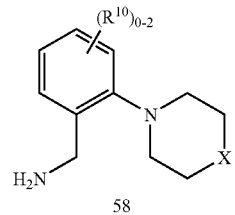

As shown in Scheme 18, benzylamines 62 containing an ortho-sulfonamide substituent can be prepared from o-cyano sulfonyl chlorides 59 via reaction with amines 60 (or amine hydrochloride salts) in the presence of a base, for example, TEA, in a solvent such as THF or water. Benzonitriles 61 can then be converted to the corresponding benzylamines 62 as was previously shown in Scheme 8.

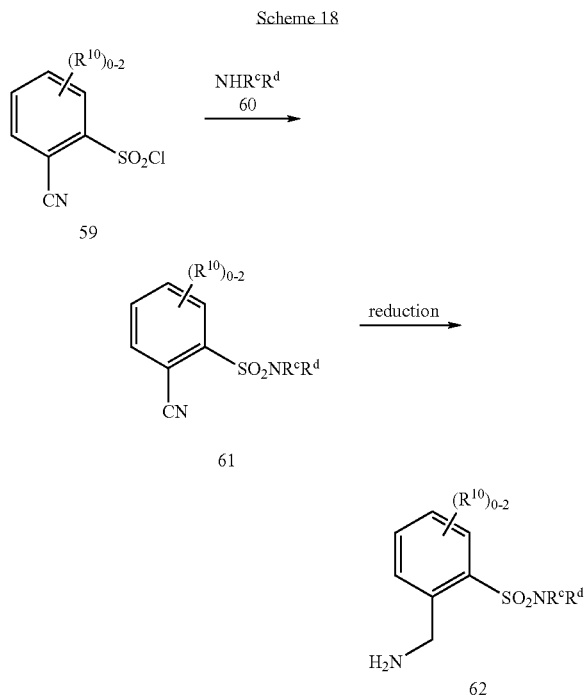

Scheme 18

Benzylamines 65 containing an amide substituent can be derived from cyanobenzoic acids 63 as shown in Scheme 19, by treatment of acids 63 with amines 60 (or amine hydrochloride salts) in the presence of appropriate coupling reagents such as EDC, HOAT and a base such as DIEA. The derived benzonitriles 64 can then be converted to the benzylamines 65 as was previously shown in Scheme 8. Alternatively, amides 65 can be prepared as shown in Scheme 20 from isobenzofuran-1(3H)-ones 66 by treatment with amines 60 in the presence of trimethylaluminum. The derived benzyl alcohols 67 can then be converted to the corresponding benzylamines as was previously shown in Scheme 9.

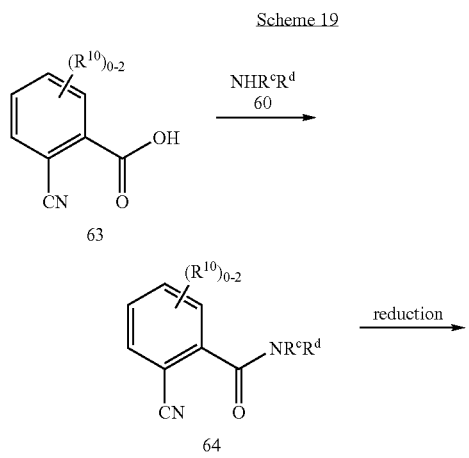

Scheme 19

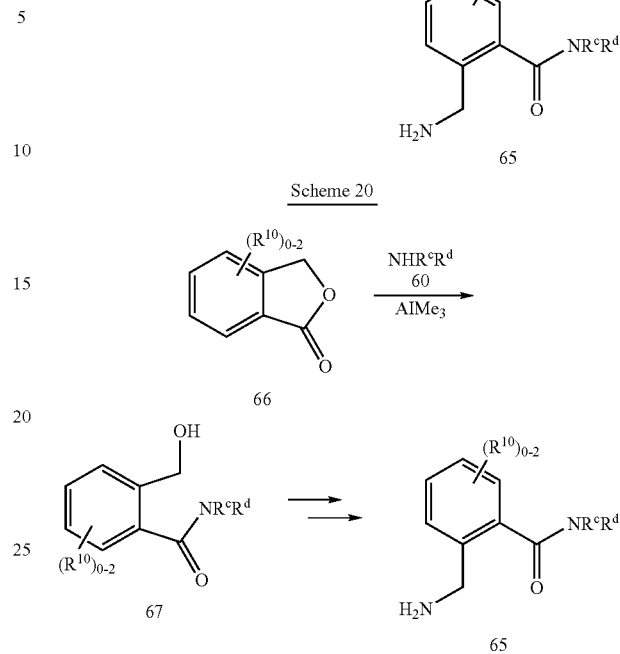

Scheme 20

Benzylamines 71 containing an ortho-ether substituent can be prepared, as shown in Scheme 21, from phenols 68, via alkylation with alkyl halides 69. The derived benzonitriles 70 can then be converted to the corresponding benzylamines 71 as was previously shown in Scheme 8.

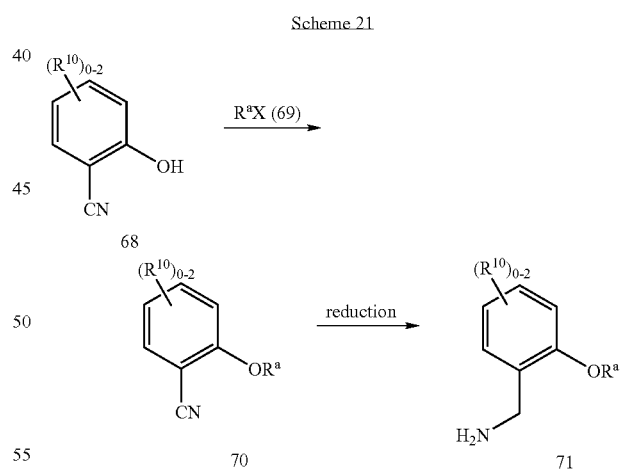

Scheme 21

Functionalized benzylamines 76 containing an alkyl substituent can be prepared, as shown in Scheme 22, from benzaldehydes 72, via Wittig reaction with alkyltriphenylphosphonium halides 73 in the presence of a base, such as potassium tert-butoxide. The derived olefins 74 can then be converted to the corresponding unsaturated benzylamines 75 using a hydride source such as $BH_3$, or to the saturated benzylamines 76 via hydrogenation in the presence of a catalyst, such as Pd/C.

Scheme 22

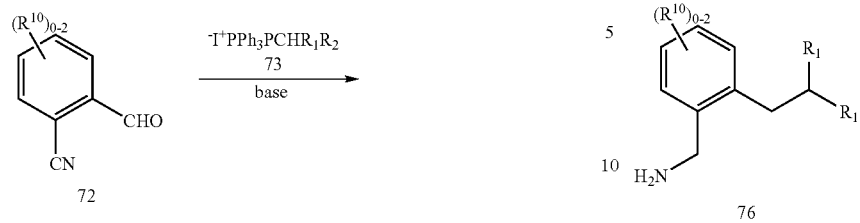

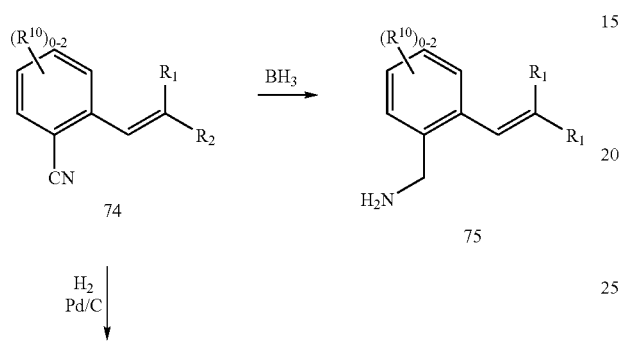

As exemplified in Scheme 23, functionalized benzylamines 81 and 83 containing acetamide or carbamate substituents can be prepared from nitro compounds 77 via reduction to the anilines 78 with, for example, iron. Anilines 78 can be treated with anhydrides 79 to provide acetamides 80, or with alkyl chloroformates 82 to give carbamates 83. These benzonitrile products 80 and 83 can then be converted to the desired benzylamines 81 and 84 as was previously shown in Scheme 8.

Scheme 23

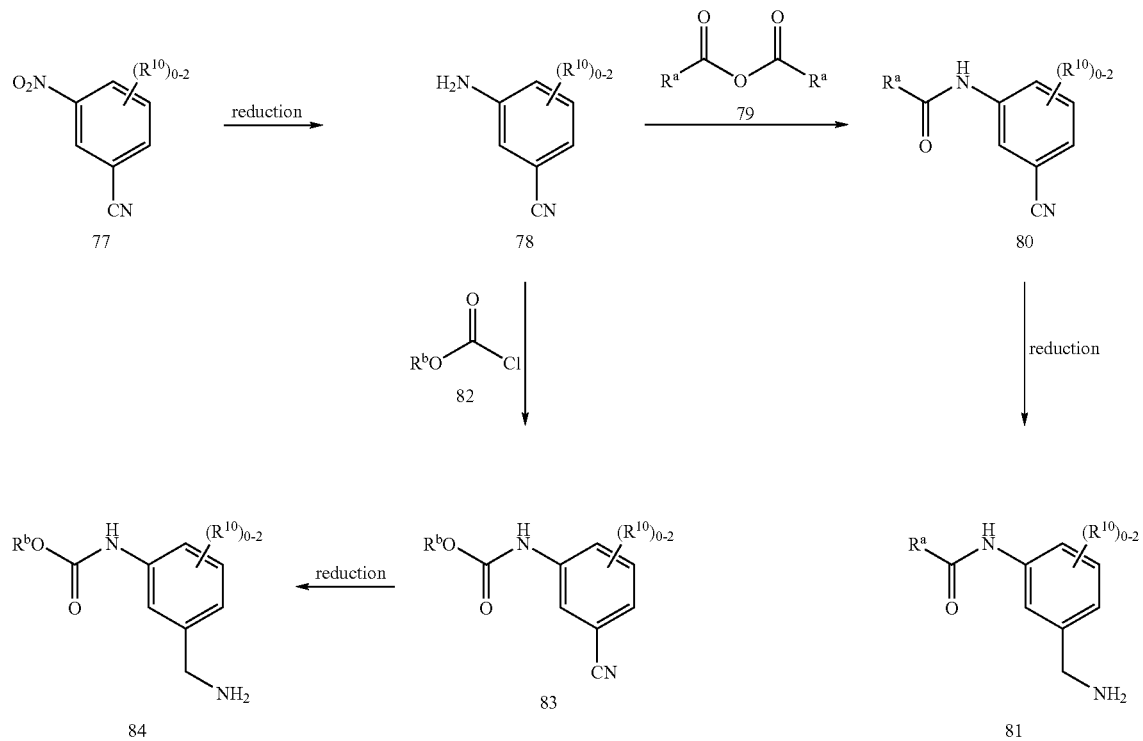

As shown in Scheme 24, chiral β-aminoesters 89 can be prepared by a conjugate addition of lithium (S)-(−)—N-benzy-N-α-methylbenzamides to α,β-unsaturated esters 87 which in turn can be prepared by condensation of the aldehydes 85 and diethylphosphonate esters 86. The conjugated adduct 88 can be hydrogenated with a catalyst such as Pd(OH)$_2$/C to give enantiomerically enriched β-aminoesters 89.

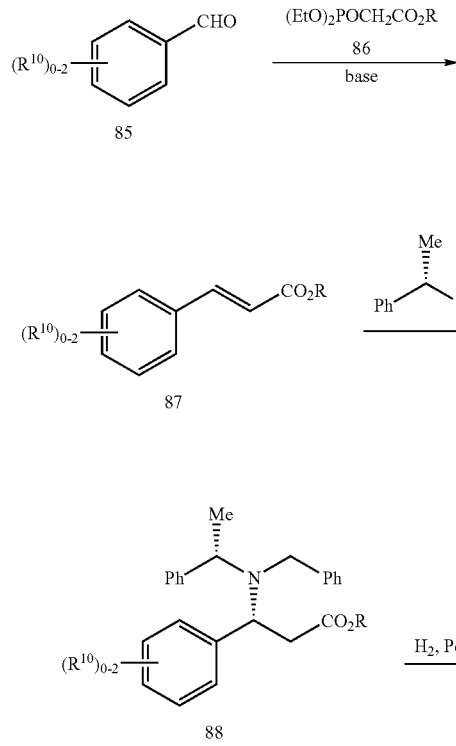

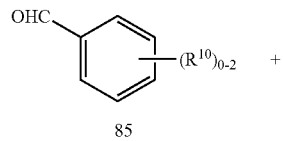

Alternatively, aldehydes 85 (Scheme 25) can be condensed with (S)-(+)-toluene sulfinamide 90 in the presence of catalyst such as Ti(OEt)$_4$ to the sulfinylimines 91. Addition of metal enolates 92 to the sulfinylimine 91 should proceed stereoselectively to give the sulfinamides 93 which can be deprotected under acidic conditions to β-aminoesters 89.

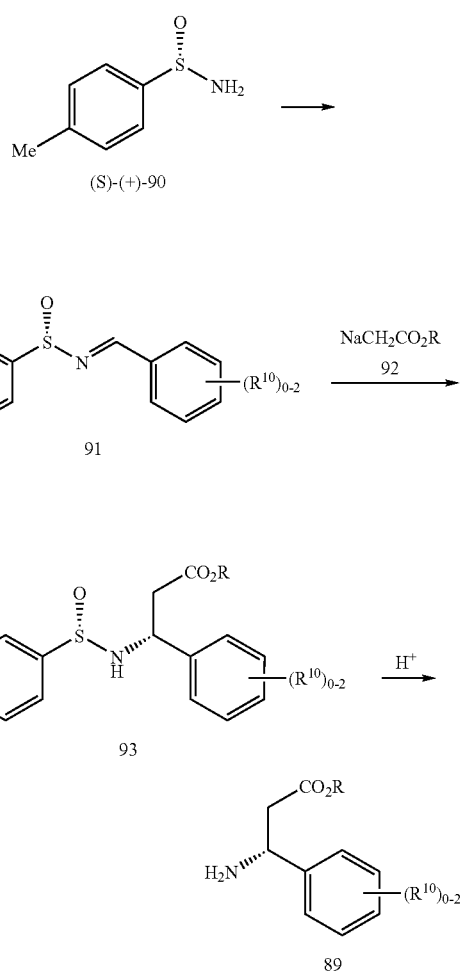

The compound of the instant invention herein described may have asymmetric centers. For example, the chiral carbon atom in Formula (I) or (IV) as indicated below, exists in either S or R configuration.

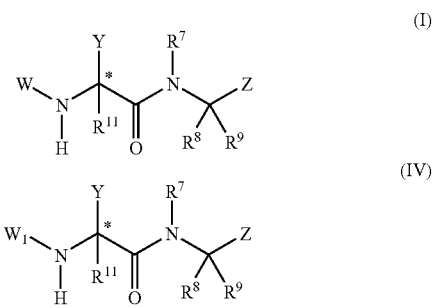

Possibly, a second chiral carbon atom exists when $R^8$ and $R^9$ are different. Thus, the stereoisomeric configurations of each compound of the present invention are considered part of the invention. For example, but not limited to therein, in compounds of Formula (II), the following two stereoisomeric configurations are possible:

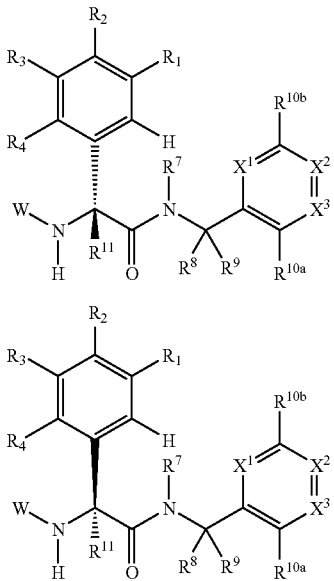

For example, but not limited to therein, in compounds of Formula (V), the following two stereoisomeric configurations are possible:

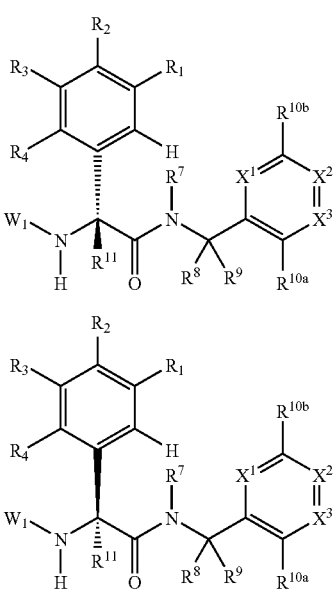

They are collectively, as well as individually, considered part of the invention. In a preferred stereoisomeric embodiment, the present invention provides for a stereoisomeric configuration of isomer-1 for all embodiments of Formula (I), (II) or (III); a stereoisomeric configuration of isomer-3 for all embodiments of Formula (IV), (V) or (VI); or tautomer, pharmaceutically acceptable salt, solvate, or prodrug form thereof.

In the following experimental procedures, solution ratios express a volume relationship, unless stated otherwise. NMR chemical shifts (δ) are reported in parts per million.

Products were analyzed by reverse phase analytical HPLC carried out on a Shimadzu Analytical HPLC system running DiscoveryVP software using Method A: Phenomenex Luna C18 column (4.6×50 mm or 4.6×75 mm) eluted at 4 mL/min with a 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 mm). Purification of intermediates and final products was carried out via either normal or reverse phase chromatography. Normal phase chromatography was carried out on an ISCO CombiFlash™ System using pre-packed $SiO_2$ cartridges eluted with gradients of hexanes and ethyl acetate. Reverse phase preparative HPLC was carried out using a Shimadzu Preparative HPLC system running DiscoveryVP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

EXAMPLES

The following examples have been prepared, isolated and characterized using the methods disclosed herein. The following examples demonstrate a partial scope of the invention and are not meant to be limiting of the scope of the invention.

Synthesis of Common Intermediates

Intermediate 1

6-Amino-1-di-tert-butoxycarbonylaminoisoquinoline

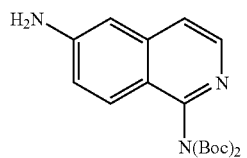

Intermediate 1A (E)-2-(2-(Dimethylamino)vinyl)-4-nitrobenzonitrile

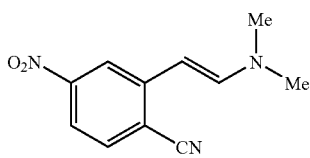

A mixture of compound 2-methyl-4-nitrobenzonitrile (Aldrich, 5.0 g, 31 mmol) and 1-(1,1-dimethylethoxy)-N,N,N',N'-tetramethyl-methanediamine (Aldrich, 12.2 mL, 59 mmol) in dry DMF (8 mL) was stirred at 70° C. for 2 h under $N_2$. After cooling to rt, DMF was removed in vacuo and the crude product was triturated with hexanes/ethyl acetate (5:1). The solid was collected by filtration and washed with hexane to give Intermediate 1A (6.5 g, 97% yield) as black solid. $^1$H NMR (400 MHz, CDCl$_3$) δ ppm 2.97 (s, 6H) 5.36 (d, J=13.18 Hz, 1H) 7.16 (d, J=13.62 Hz, 1H) 7.52 (d, J=8.79 Hz, 1H) 7.60 (m, 1H) 8.11 (d, J=1.76 Hz, 1H).

Intermediate 1B 2-(2,4-Dimethoxybenzyl)-6-nitroisoquinolin-1(2H)-imine

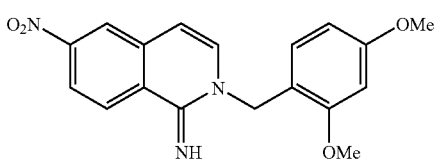

Intermediate 1A (4.6 g, 21.2 mmol) and 2,4-dimethoxylbenzylamine (4.0 mL, 1.25 equiv) in DMPU (10 mL) was heated at 140° C. for 3 h. The solvent was removed by vacuum distillation and residue treated with hexanes/ethyl acetate (1:1). The solid was collected by filtration and washed with hexane to give Intermediate 1B (4.6 g). $^1$H NMR (400 MHz, DMSO-d$_6$) δ ppm 3.72 (s, 3H) 3.81 (s, 3H) 4.96 (s, 1H) 6.28 (d, J=6.59 Hz, 1H) 6.46 (d, J=7.47 Hz, 1H) 6.58 (d, J=1.76 Hz, 1H) 7.03 (d, J=8.79 Hz, 1H) 7.27 (d, J=6.15 Hz, 1H) 8.02 (dd, J=9.01, 2.42 Hz, 1H) 8.31 (d, J=2.20 Hz, 1H) 8.43 (d, J=8.35 Hz, 1H).

Intermediate 1C

6-Nitroisoquinolin-1-amine

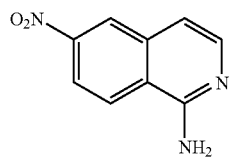

To a solution of Intermediate 1B (11.9 g, 35 mmol) in anisole (24 mL) was added TFA (24 mL). The reaction mixture was stirred at 90° C. for 6 h and the solvent removed under reduced pressure. The residue was suspended in MeOH (50 mL) and then treated with NaHCO$_3$ (3.3 g, 39 mmol) in water (200 mL). The mixture was stirred at rt for 15 min and pH was checked to be ca 8.0. Most of the methanol was removed in vacuo. The precipitate was collected by filtration and washed with water to afford Intermediate 1C (6.0 g). $^1$H NMR (400 MHz, DMSO-d$_6$) δ ppm 7.20 (d, J=5.72 1H) 7.36 (s, 2H) 7.95 (d, J=5.72 Hz, 1H) 8.15 (dd, J=9.24, 2.64 Hz, 1H) 8.43 (d, J=9.24 Hz, 1H) 8.67 (d, J=2.64 Hz, 1H).

Intermediate 1D

6-Nitro-1-di-tert-butoxycarbonylaminoisoquinoline

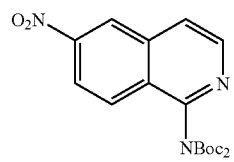

A mixture of Intermediate 1C (50 mg) and di-tert-butyl dicarbonate (200 mg) was heated at 120° C. for 1.0 h. The crude residue was purified by flash chromatography (25% EtOAc/hexanes) to afford 78 mg (78% yield) of Intermediate 1D as a solid. $^1$H NMR (400 MHz, CDCl$_3$) δ ppm 1.33 (s, 18H) 7.86 (d, J=5.27 Hz, 1H) 8.15 (d, J=9.23 Hz, 1H) 8.39 (dd, J=9.23, 2.20 Hz, 1H) 8.62 (d, J=5.71 Hz, 1H) 8.82 (d, J=2.20 Hz, 1H). LC-MS: 801 (2M+Na).

Intermediate 1

6-Amino-1-di-tert-butoxycarbonylaminoisoquinoline

Intermediate 1D (55 mg) in methanol (2.5 mL) was hydrogenated with a hydrogen balloon in the presence of Pd/C (10%, 35 mg) for 2.0 h. Filtration of the Pd/C and concentration gave Intermediate 1 as a white solid (47 mg, 92%). $^1$H NMR (400 MHz, CDCl$_3$) δ ppm 1.33 (m, 18H) 4.18 (s, 2H) 6.89 (d, J=2.20 Hz, 1H) 6.99 (dd, J=9.01, 2.42 Hz, 1H) 7.35 (d, J=6.59 Hz, 1H) 7.75 (d, J=8.79 Hz, 1H) 8.22 (d, J=5.71 Hz, 1H). LC-MS: 741 (2M+Na).

Intermediate 2

2-(1-Di-tert-butoxycarbonylaminoisoquinolin-6-ylamino)-2-(3-ethoxy-4-isopropoxyphenyl)acetic acid

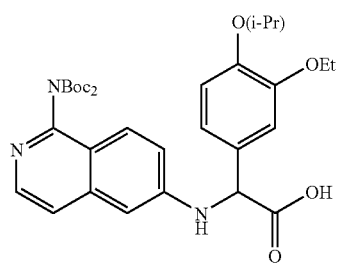

Intermediate 2A

2-Isopropoxyphenyl acetate

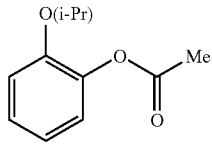

To a solution of 2-isopropoxyphenol (1.53 g, 10 mmol) in CH$_2$Cl$_2$ at 0° C., pyridine (1.76 mL, 22 mmol) was added and followed by acetyl chloride (0.79 mL, 1.1 eq). The mixture was stirred at 0° C. for 1.0 h, diluted with diethyl ether, washed with 5% citric acid and brine. The organic extract was dried over Na$_2$SO$_4$, evaporated to give Intermediate 2A as an oil. It was used for next step without further purification.

Intermediate 2B

5-Iodo-2-isopropoxyphenyl acetate

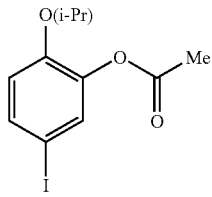

To a solution of Intermediate 2A (10 mmol) in CH$_2$Cl$_2$ at 0° C., iodine monochloride (1.0 M in CH$_2$Cl$_2$, 11.0 mL) was added dropwise in 20 min. The mixture was stirred at 0° C. for 2.0 h, diluted with ether, washed with saturated Na$_2$S$_2$O$_3$ and brine. The organic extract was dried over MgSO$_4$, evaporated to give Intermediate 2B as an oil. It was used for next step without further purification.

Intermediate 2C

5-Iodo-2-isopropoxyphenol

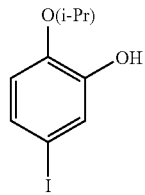

To a solution of Intermediate 2B (10 mmol) in MeOH (5 mL) and THF (15 mL), LiOH (1.0 M, 15 mL) was added at 0° C. After the mixture was stirred at rt for 3.0 h, 5% citric acid (30 mL) and diethyl ether (150 mL) was added. The organic extract was washed with brine, dried over Na$_2$SO$_4$ and evaporated to give Intermediate 2C (2.3 g) as an oil.

Intermediate 2D

2-Ethoxy-4-iodo-1-isopropoxybenzene

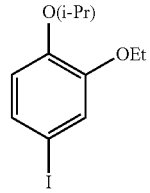

To a solution of Intermediate 2C (2.3 g, 8.3 mmol) in DMF (20 mL) K$_2$CO$_3$ (2.3 g, 16.5 mmol) and ethyl iodide (0.86 mL, 10.8 mmol) were added. The mixture was stirred at 40° C. for 2.0 h. It was diluted with diethyl ether, washed with brine, dried over MgSO$_4$. The crude was purified by chromatography (5:1 EtOAc/hexanes) to give Intermediate 2D (2.5 g, 96% yield) as an oil.

Intermediate 2E

3-Ethoxy-4-isopropoxyphenylboronic acid

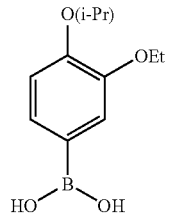

To a solution of Intermediate 2D (2.39 g, 7.8 mmol) in THF (25 mL) at −78° C., n-BuLi (1.6 M in hexanes, 6.83 mL, 1.4 eq) was slowly added. The reaction mixture was stirred at −78° C. for 20 min, followed by addition of triisopropyl borate (4.95 mL, 21.5 mmol). The mixture was stirred at −78° C. for 3.0 h and then warm up to rt over 1.0 h. It was quenched by addition of 5% citric acid (20 mL), followed by a solution of Na$_2$S$_2$O$_3$. After extraction with EtOAc, drying over Na$_2$SO$_4$, the crude was purified by chromatography to give Intermediate 2E (1.2 g, 67% yield) as a white solid. $^1$H NMR (400 MHz, CDCl$_3$) δ ppm 1.41 (d, J=6.15 Hz, 6H) 1.49 (t, J=7.03 Hz, 3H) 4.21 (q, J=7.03 Hz, 2H) 4.64 (m, 1H) 7.02 (d, J=8.35 Hz, 1H) 7.70 (s, 1H) 7.79 (m, 1H).

Intermediate 2

2-(1-Di-tert-butoxycarbonylaminoisoquinolin-6-ylamino)-2-(3-ethoxy-4-isopropoxyphenyl)acetic acid A mixture of Intermediate 2E (308 mg, 1.38 mmol), Intermediate 1 (494 mg, 1.38 mmol) and glyoxylic acid monohydrate (127.1 mg, 1.38 mmol) in toluene (12 mL) and methanol (2.5 mL) was heated at 60° C. for 6.0 h and then stirred at rt over night. After removing solvent, the crude was purified by chromatography eluting with CH$_2$Cl$_2$/MeOH to give Intermediate 2 (0.65 g, 78% yield) as a yellow solid. $^1$H NMR (400 MHz, Methanol-d$_4$) δ ppm 1.29 (m, 24H) 1.35 (t, J=7.03 Hz, 3H) 4.05 (dd, J=7.03, 5.27 Hz, 2H) 4.49 (m, 1H) 5.11 (s, 1H)

6.68 (d, J=1.76 Hz, 1H) 6.93 (d, J=8.35 Hz, 1H) 7.10 (dd, J=8.35, 2.20 Hz, 1H) 7.17 (d, J=1.76 Hz, 1H) 7.27 (dd, J=9.23, 2.20 Hz, 1H) 7.42 (d, J=5.71 Hz, 1H) 7.62 (d, J=9.23 Hz, 1H) 8.01 (d, J=6.15 Hz, 1H).

Intermediate 3

2-(1-Aminoisoquinolin-6-ylamino)-2-(3-ethoxy-4-isopropoxyphenyl)acetic acid hydrochloride

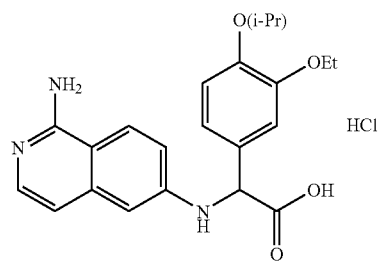

Intermediate 2 (1.04 g, 1.75 mmol) was dissolved in ethyl acetate (26 mL) and was treated with a 4N HCl solution in 1,4-dioxane (26 mL, 105 mmol). After stirring at rt overnight, the reaction was concentrated, diluted with diethyl ether and filtered to provide Intermediate 3 (747 mg) as a yellow solid. $^1$H NMR (400 MHz, d6-DMSO) δ ppm 1.22 (d, J=7.03 Hz, 6H), 1.30 (t, J=7.03 Hz, 3H), 4.00 (q, J=7.03 Hz, 2H), 4.37-4.53 (m, 2H), 5.19-5.33 (m, 1H), 6.75 (s, 1H), 6.81 (d, J=7.03 Hz, 1H), 6.90-7.04 (m, 2H), 7.13 (d, J=2.20 Hz, 1H), 7.24 (d, J=8.79 Hz, 1H), 7.43 (dd, 1H), 7.43 (dd, J=7.03, 5.71 Hz, 1H), 7.63 (s, 1H), 8.20 (d, J=9.23 Hz, 1H), 8.50 (s, 2H), 12.52 (d, J=5.27 Hz, 1H). LC-MS: 396.30 (M+H)$^+$.

Intermediate 4

2-(1-Di-tert-butoxycarbonylaminoisoquinolin-6-ylamino)-2-(3,4-dimethoxyphenyl)acetic acid

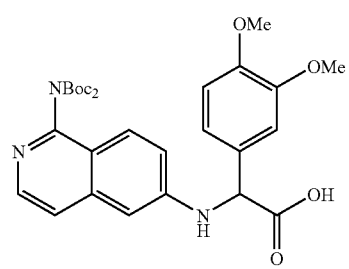

A mixture of 3,4-dimethoxyphenyl boronic acid (457 mg, 2.5 mmol), Intermediate 1 (900 mg, 2.5 mmol) and glyoxylic acid monohydrate (231 mg, 2.5 mmol) in toluene (20 mL) and methanol (2.5 mL) was heated at 50° C. for 3.0 h and then stirred at rt over night. After removing solvent, the crude was purified by chromatography eluting with CH$_2$Cl$_2$/MeOH. Intermediate 4 (1.18 g, 85%) was obtained as a yellow solid. $^1$H NMR (400 MHz, Methanol-d$_4$) δ ppm 1.27 (s, 18H) 3.79 (s, 3H) 3.81 (s, 3H) 5.07 (s, 1H) 6.67 (d, J=2.20 Hz, 1H) 6.92 (d, J=8.35 Hz, 1H) 7.13 (m, 1H) 7.18 (d, J=1.76 Hz, 1H) 7.26 (dd, J=9.23, 2.20 Hz, 1H) 7.41 (d, J=6.15 Hz, 1H) 7.62 (d, J=9.23 Hz, 1H) 8.00 (d, J=5.71 Hz, 1H).

Intermediate 5

3-(Aminomethyl)benzenesulfonamide

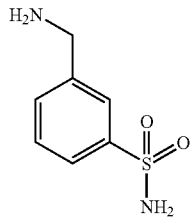

Intermediate 5A

3-Cyanobenzenesulfonamide

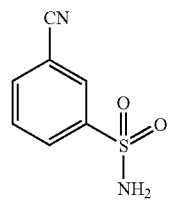

To 3-cyanobenzene sulfonyl chloride (0.37 g, 1.81 mmol) in THF (3 mL), ammonium hydroxide (28% in water, 0.13 g, 3.62 mmol) was added. The reaction was stirred at rt for 30 min. Water was added and the product was extracted with EtOAc. After drying over Na$_2$SO$_4$, the solvent was evaporated to give 0.3 g of Intermediate 5A a white solid.

Intermediate 5

3-(Aminomethyl)benzenesulfonamide

To Intermediate 5A (0.3 g, 1.65 mmol) in methanol (8 mL) under nitrogen, 10% Pd/C (0.1 g) was added and then a balloon filled with hydrogen gas was introduced. The reaction was stirred for 3.0 h at rt. The catalyst was filtered off and the solvent was removed to give Intermediate 5 (0.29 g). $^1$H NMR (400 MHz, DMSO-d$_6$) δ ppm 3.79 (m, 2H) 7.47 (t, J=7.58 Hz, 1H) 7.53 (m, 1H) 7.65 (d, J=7.58 Hz, 1H) 7.81 (s, 1H).

Intermediate 6

(2-(Methylsulfonyl)phenyl)methanamine

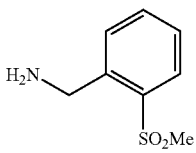

Intermediate 6A 2-(Methylsulfonyl)benzonitrile

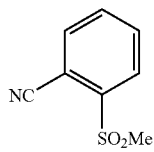

To a solution of MCPBA (75%, 7.8 g, 31.6 mmol) and NaHCO$_3$ (3.0 g, 35.8 mmol) in CH$_2$Cl$_2$ (150 mL), 2-methylthiobenzonitrile (2.14 g, 14.3 mmol) in CH$_2$Cl$_2$ (50 mL) was added at 0° C. The mixture was stirred at 0° C. for 30 min, then at rt over night. After filtration, the organic phase was washed with brine, dried over Na$_2$SO$_4$. Intermediate 6A was obtained as a slightly yellow solid after removal of solvent. $^1$H NMR (400 MHz, Methanol-d$_4$) δ ppm 3.22 (s, 3H) 7.83 (m, 2H) 7.96 (m, 1H) 8.11 (d, J=7.91 Hz, 1H).

Intermediate 6

(2-(Methylsulfonyl)phenyl)methanamine

To a solution of Intermediate 6A (181 mg, 1.0 mmol) in MeOH (10 mL), Pd/C (10% by weight, 50 mg) and 4.0 N HCl in dioxane (0.5 mL, 2.0 mmol) were added. This mixture was hydrogenated with a H$_2$ balloon for 4.0 h. After filtration and concentration, Intermediate 6 was obtained as HCl salt. $^1$H NMR (400 MHz, DMSO-d$_6$) δ ppm 3.33 (s, 3H) 4.42 (s, 2H) 7.69 (m, 1H) 7.81 (m, 2H) 8.00 (d, J=7.47 Hz, 1H) 8.56 (s, 3H).

Intermediate 7

(2-(Cyclopropylsulfonyl)phenyl)methanamine Hydrochloride Salt

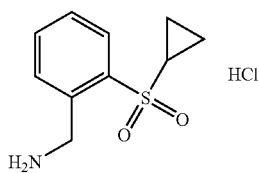

Intermediate 7A 2-(Cyclopropylsulfonyl)benzonitrile

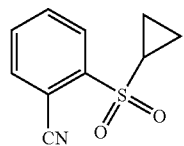

To 2,2'-dithio-bis(benzonitrile) (obtained from Sumitomo Seika) (2.00 g, 7.46 mmol) in THF (37 mL) at −78° C., a 0.5 M THF solution of cyclopropyl magnesium bromide (149 mL, 74.6 mmol) was added via addition funnel. After 10 min, the reaction was quenched with saturated aqueous ammonium chloride (200 mL). After warming to rt, the reaction product was diluted with water and ethyl acetate and the layers were separated. The organic layer was washed with water and brine, dried (MgSO$_4$), filtered and concentrated. The resulting residue was purified via silica gel chromatography eluting with 15% ethyl acetate/hexane to provide 2-(cyclopropylthio)benzonitrile as a yellow oil (1.36 g). The oil was dissolved in CH$_2$Cl$_2$, ~75% MCPBA (6.00 g, 26.1 mmol) was added and the reaction was stirred at rt for 2 h. 1N NaOH was added and the layers were separated. The organic layer was washed with 1N NaOH (3×) and brine (1×) then dried (MgSO$_4$), filtered and concentrated to provide Intermediate 7A (1.50 g, 97% yield, 2 steps) as a white solid.

Intermediate 7

(2-(Cyclopropylsulfonyl)phenyl)methanamine Hydrochloride Salt

To Intermediate 7A (1.50 g, 7.25 mmol) in refluxing THF (72 mL), a 2M THF solution of BH$_3$.SMe$_2$ (10.8 mL, 21.7 mmol) was added. After heating at reflux for 2 h, the reaction was cooled to rt and 6M HCl (4.32 mL) was slowly added. The reaction was heated to reflux for 30 min, then cooled to rt, concentrated and azeotroped (3×) with THF/MeOH on a rotary evaporator. The resulting residue was taken up in THF and filtered to provide Intermediate 7 (1.40 g, 79%) as a white solid. $^1$H NMR (400 MHz, CD$_3$OD) δ ppm 1.15 (m, 2H) 1.29 (m, 2H) 2.91 (m, 1H) 4.52 (s, 2H) 7.72 (m, J=7.69, 7.69 Hz, 2H) 7.80 (t, J=6.81 Hz, 1H) 8.04 (d, J=7.91 Hz, 1H).

Intermediate 8

(2-(Cyclopropylsulfonyl)phenyl)-N-methylmethanamine hydrochloride

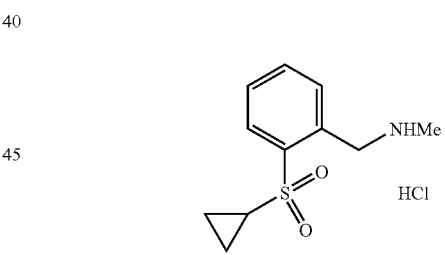

Intermediate 8A

N-(2-(Cyclopropylsulfonyl)benzyl)-2,2,2-trifluoroacetamide

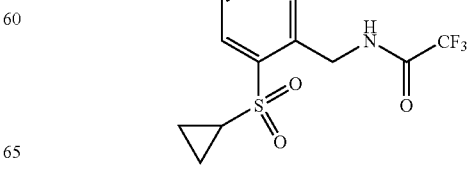

To Intermediate 7 (1.16 g, 4.70 mmol) in CH$_2$Cl$_2$ (47 mL) at 0° C. was added DIPEA (1.60 mL, 9.40 mmol) followed by trifluoroacetic anhydride (3.30 mL, 23.5 mmol). After stirring (0° C. to rt) for 1.5 h, the reaction was concentrated. The resulting residue was dissolved in ethyl acetate, washed with water and brine, dried (MgSO$_4$), filtered and concentrated to provide Intermediate 8A (1.68 g) as a yellow oil. LC-MS: 307.93 (M+H)$^+$

8B

N-(2-(Cyclopropylsulfonyl)benzyl)-2,2,2-trifluoro-N-methylacetamide

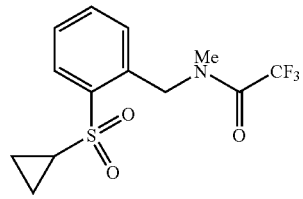

To Intermediate 8A (1.68 g, 5.47 mmol) in CH$_3$CN (55 mL) was added potassium carbonate (1.13 g, 8.20 mmol), tetrabutylammonium bromide (88 mg, 0.27 mmol) and methyl iodide (3.40 mL, 54.7 mmol) and the reaction was heated to reflux overnight. After cooling to rt and concentrating, the remaining residue was dissolved in ethyl acetate and washed with water (3×) and brine. The organic layer was dried (MgSO$_4$), filtered and concentrated to provide Intermediate 8B (1.50 g) as a yellow oil. LC-MS: 321.95 (M+H)$^+$.

Intermediate 8

(2-(Cyclopropylsulfonyl)phenyl)-N-methylmethanamine hydrochloride

To Intermediate 8B (1.50 g, 4.67 mmol) in MeOH (23 mL) and water (5 mL) was added potassium carbonate (3.20 g, 23.4 mmol) and the reaction was refluxed for 45 min. After cooling to rt, the mixture was filtered and the filtrate was concentrated. The resulting residue was dissolved in ethyl acetate and washed with water and brine. The aqueous layer was back-extracted with ethyl acetate (5×). The combined organic layers were dried (MgSO$_4$), filtered and concentrated to provide a yellow oil. The oil was dissolved in THF and 4N HCl in 1,4-dioxane (2.2 mL) was added. The resulting white solid was filtered to provide Intermediate 8 (1.00 g). $^1$H NMR (400 MHz, CD$_3$OD) δ ppm 1.03-1.21 (m, 2H), 1.30 (ddd, J=7.14, 4.50, 4.17 Hz, 2H), 2.80 (s, 3H), 2.84-3.03 (m, 1H), 2.86-3.05 (m, 1H), 4.41-4.65 (m, 2H), 7.59-7.93 (m, 3H), 8.06 (d, J=7.91 Hz, 1H). LC-MS: 226.10 (M+H)$^+$.

Intermediate 9

N-(3-(Aminomethyl)-4-(ethylsulfonyl)phenyl)acetamide

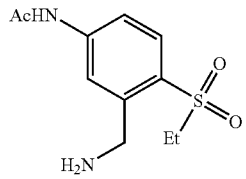

Intermediate 9A 2-(Ethylthio)-5-nitrobenzonitrile

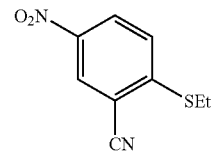

To 2-fluoro-5-nitrobenzonitrile (5.00 g, 30.1 mmol) in DMF (100 mL), triethylamine (9.30 mL, 66.7 mmol) was added and followed by ethanethiol (2.80 mL, 37.9 mmol). After stirring at rt for 1 h, the reaction mixture was poured into water (500 mL). The resulting precipitate was filtered and dried on high vacuum overnight to provide Intermediate 9A (6.08 g, 97%).

Intermediate 9B 2-(Ethylsulfonyl)-5-nitrobenzonitrile

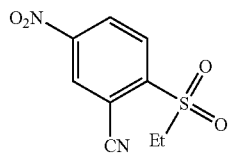

To Intermediate 9A (6.08 g, 29.2 mmol) in CH$_2$Cl$_2$ (100 mL), 75% MCPBA (16.0 g, 69.5 mmol) was added. After stirring at rt overnight, the reaction product was washed with saturated aqueous NaHCO$_3$, 1M H$_3$PO$_4$ and brine then dried (Na$_2$SO$_4$), filtered and concentrated. The resulting residue was purified via silica gel chromatography eluting with 10-35% ethyl acetate/hexane to provide Intermediate 9B (6.20 g, 88%). LC-MS: 209.20 (M+H)$^+$.

Intermediate 9C

N-(3-Cyano-4-(ethylsulfonyl)phenyl)acetamide

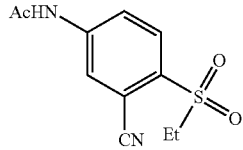

To Intermediate 9B (3.60 g, 15.0 mmol) in 1:1 acetic acid/acetic anhydride (150 mL), Fe (4.20 g, 75.2 mmol) was added. The reaction mixture was heated to 100° C. for 2 h then poured into ice. After the ice melted, the product was extracted with ethyl acetate, and the organic layer was washed with saturated aqueous $NaHCO_3$ and brine. The organic layer was dried ($Na_2SO_4$), filtered and concentrated to provide Intermediate 9C (3.14 g, 83%). LC-MS: 241.18 $(M+H)^+$.

Intermediate 9

N-(3-(Aminomethyl)-4-(ethylsulfonyl)phenyl)acetamide

To Intermediate 9C (423 mg, 1.65 mmol) in MeOH (17 mL), Raney Ni (cat) was added. The whole mixture was stirred under hydrogen (60 psi) for 8 h. The reaction product was filtered and concentrated to provide Intermediate 9 (397 mg, 92%). LC-MS: 253.23 $(M+H)^+$.

Intermediate 10

N-(4-(Ethylsulfonyl)-3-((methylamino)methyl)phenyl)acetamide trifluoroacetic acid salt

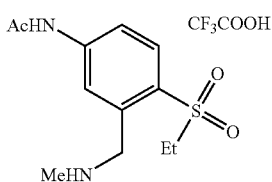

Intermediate 10A

N-(4-(Ethylsulfonyl)-3-((methylamino)-2,2,2-trifluoroacetamide)-phenyl)acetamide

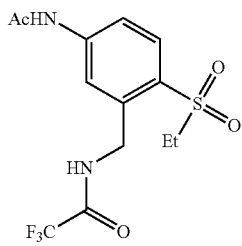

A solution of Intermediate 9 (100 mg, 0.39 mmol) in trifluoroacetic anhydride (5 mL) was stirred at rt for 30 min. The reaction was poured into ice, and after the ice melted, the product was extracted with ethyl acetate. The organic layer was washed with brine, dried ($Na_2SO_4$), filtered and concentrated. The resulting residue was purified via silica gel chromatography eluting with 10-60% ethyl acetate/hexanes to provide Intermediate 10A (45 mg). LC-MS: 353.11 $(M+H)^+$.

Intermediate 10B

N-(4-(Ethylsulfonyl)-3-((methylamino-2,2,2-trifluoroacetamide-N-methyl)-phenyl)acetamide

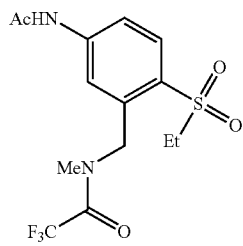

To a mixture of 60% NaH (4.8 mg, 0.12 mmol) in DMF (1 mL) was added a solution of Intermediate 10A (41 mg, 0.12 mmol) in DMF (1.5 mL). After stirring at rt for 1 h, a solution of methyl iodide (17 mg, 0.12 mmol) in DMF (0.5 mL) was added and the reaction was heated to 80° C. overnight. The reaction was cooled to rt and concentrated. The resulting residue was purified via preparative HPLC eluting with MeOH/water/TFA to provide Intermediate 10B (38 mg).

Intermediate 10

N-(4-(Ethylsulfonyl)-3-((methylamino)methyl)phenyl)acetamide trifluoroacetic acid salt To Intermediate 10B (38 mg, 0.10 mmol) in MeOH (3 mL) was added potassium carbonate (42 mg, 0.30 mmol) in water (0.5 mL). The reaction was heated to reflux for 1 h, then was cooled to rt and concentrated. The resulting residue was purified via preparative HPLC eluting with $CH_3CN$/water/TFA to provide Intermediate 10 (31 mg). $^1$H NMR (400 MHz, $CD_3OD$) δ ppm 1.26 (t, J=7.25 Hz, 3H), 2.18 (s, 3H), 2.78 (s, 3H), 3.23-3.36 (m, 3H), 4.43 (s, 2H), 7.80 (dd, J=8.79, 2.20 Hz, 1H), 7.99 (d, J=8.79 Hz, 1H), 8.11 (d, J=2.20 Hz, 1H). LC-MS: 271.16 $(M+H)^+$.

Intermediate 11

(2-(Cyclobutylsulfonyl)phenyl)methanamine hydrochloride

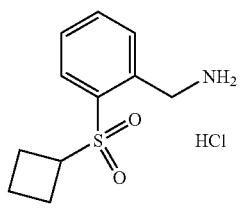

Intermediate 11A

Methyl 2-(cyclobutylsulfonyl)benzoate

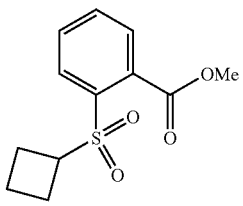

To methylthiosalicylate (3.92 mL, 28.5 mmol) in DMF at 0° C. was added triethylamine (3.97 mL, 28.5 mmol) then cyclobutyl bromide (5.00 g, 37.0 mmol). The ice bath was removed and the reaction was stirred at rt for 1 h then heated to 50° C. overnight. After cooling to rt, diethyl ether was added and the mixture was filtered. The filtrate was diluted with ethyl acetate, then washed with water (6×) and brine (1×). The organic layer was dried (MgSO$_4$), filtered and concentrated to provide a yellow oil. The yellow oil was dissolved in CH$_2$Cl$_2$ (143 mL) and MCPBA (~75%, 19.7 g, ca. 85.5 mmol) was added. The reaction was stirred for 2.5 h, then was cooled to 0° C. 1 N NaOH was added, and the whole was stirred for 5 min. The layers were separated, and the organic layer was washed with 1 N NaOH (2×). The aqueous layer was back-extracted with CH$_2$Cl$_2$. The combined organic layers were washed with brine, dried (MgSO$_4$), filtered and concentrated to provide Intermediate 11A as a clear oil (7.20 g). LC-MS: 255.01 (M+H)$^+$.

Intermediate 11B 2-(Cyclobutylsulfonyl)benzoic acid

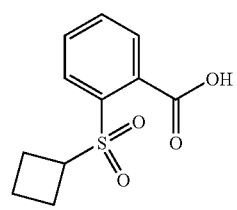

To Intermediate 11A (7.20 g, 28.3 mmol) in THF (190 mL) was added 1 N LiOH (94 mL). The reaction was stirred for 1 h at rt, then was heated gradually to 65° C. After cooling to rt, the THF was removed under reduced pressure. The remaining solution was cooled to 0° C. and acidified to pH 1 with 1N HCl. The product was extracted with CH$_2$Cl$_2$, and the organic layer was washed with brine, dried (MgSO$_4$), filtered and concentrated to provide Intermediate 11B as a clear oil (6.30 g). LC-MS: 241.08 (M+H)$^+$.

Intermediate 11C 2-(Cyclobutylsulfonyl)benzamide

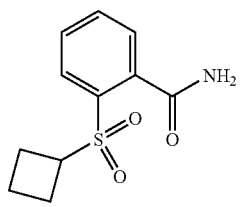

To Intermediate 11B (6.30 g, 26.2 mmol) in DMF (52.5 mL) was added HOBT.H$_2$O (4.9 g, 32.0 mmol) and EDC (5.98 g, 31.3 mmol). After stirring 1 h at rt, the reaction was cooled to 0° C. and 25% ammonium hydroxide was added. The reaction was stirred for 1.5 h and was then diluted with ethyl acetate/THF and washed with 1N HCl (2×) and 1 N NaOH (2×). The aqueous layer was back-extracted with ethyl acetate. The combined organic layers were washed with brine, dried (MgSO$_4$), filtered and concentrated to provide Intermediate 11C (5 g) as a yellow solid. LC-MS: 240.08 (M+H)$^+$.

Intermediate 11

(2-(Cyclobutylsulfonyl)phenyl)methanamine hydrochloride

To Intermediate 11C (5.00 g, 20.9 mmol) in THF (80 mL) at reflux was added a 1M THF solution of BH$_3$.THF (63 mL, 62.7 mmol) via an addition funnel, dropwise over 20 min. After refluxing for 6 h, additional BH$_3$.THF solution was added (20 mL) and refluxing continued overnight. After cooling to rt, 6N HCl (12.5 mL) was added and the reaction was heated again to reflux for 1 h. The reaction was cooled to rt, concentrated then azeotroped (3×) with MeOH/THF. After drying under vacuum for 1 h, the resulting residue was taken up in THF and filtered to provide Intermediate 11 as a white solid. $^1$H NMR (400 MHz, CD$_3$OD) δ ppm 1.94-2.11 (m, 2H), 2.13-2.26 (m, 2H), 2.43-2.61 (m, 2H), 4.11-4.23 (m, 1H), 4.43 (s, 2H), 7.66-7.76 (m, 2H), 7.81 (t, J=6.81 Hz, 1H), 8.03 (d, J=6.15 Hz, 1H). LC-MS: 226.11 (M+H)$^+$.

Intermediate 12

(2-(Cyclobutylsulfonyl)phenyl)-N-methylmethanamine hydrochloride

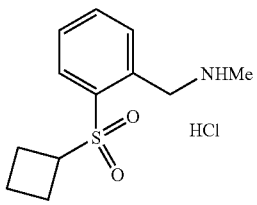

Intermediate 12A

N-(2-(Cyclobutylsulfonyl)benzyl)-2,2,2-trifluoroacetamide

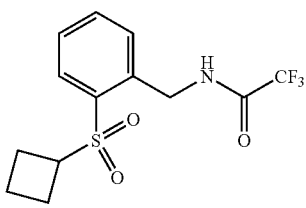

To Intermediate 11 (3.20 g, 12.3 mmol) in CH$_2$Cl$_2$ (61.5 mL) at 0° C. was added DIPEA (4.70 mL, 27.0 mmol) followed by trifluoroacetic anhydride (8.70 mL, 61.5 mmol). After stirring (0° C. to rt) for 30 min, the reaction was concentrated. The resulting residue was diluted with ethyl acetate, washed with water (2×) and brine, dried (MgSO$_4$), filtered and concentrated to provide Intermediate 12A (4.70 g) as an oily solid. LC-MS: 343.95 (M+23)$^+$.

Intermediate 12B

N-(2-(Cyclobutylsulfonyl)benzyl)-2,2,2-trifluoro-N-methylacetamide

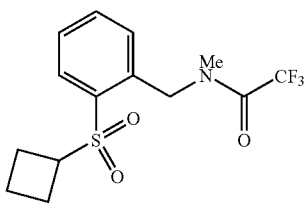

To Intermediate 12A (4.70 g, 14.6 mmol) in CH$_3$CN (73 mL) was added potassium carbonate (3.03 g, 21.9 mmol), tetrabutylammonium bromide (470 mg, 1.46 mmol) and methyl iodide (9.09 mL, 146 mmol) and the reaction was heated to 80° C. overnight. After cooling to rt and concentrating, the remaining residue was dissolved in ethyl acetate and washed with water (2×) and brine. The aqueous layer was back-extracted with ethyl acetate and the combined organic layers were dried (MgSO$_4$), filtered and concentrated to provide Intermediate 12B (4.70 g) as a yellow oil. LC-MS: 335.96 (M+H)$^+$.

Intermediate 12

(2-(Cyclobutylsulfonyl)phenyl)-N-methylmethanamine hydrochloride

To Intermediate 12B (4.70 g, 14.0 mmol) in MeOH (70 mL) and water (5 mL) was added potassium carbonate (9.70 g, 70.0 mmol) and the reaction was refluxed for 45 min. After cooling to rt, the reaction was filtered and the filtrate was concentrated. The resulting residue was dissolved in ethyl acetate and washed with water (2×). The aqueous layer was back-extracted with ethyl acetate. The combined organic layers were dried (MgSO$_4$), filtered and concentrated to provide a yellow solid (3.20 g). The solid was dissolved in THF and conc. HCl was added (1.1 mL). Intermediate 12 (3.20 g) was obtained after concentrating and drying under vacuum. $^1$H NMR (400 MHz, CD$_3$OD) δ ppm 1.93-2.12 (m, 2H), 2.13-2.27 (m, 2 H), 2.43-2.59 (m, 2H), 4.11-4.24 (m, 1H), 4.49 (s, 2H), 7.70-7.86 (m, 3H), 8.05 (d, J=7.91 Hz, 1H). LC-MS: 240.12 (M+H)$^+$.

Intermediate 13

2-(3-Ethoxy-4-isopropoxyphenyl)-2-(isoquinolin-6-ylamino)acetic Acid Hydrochloric Acid Salt

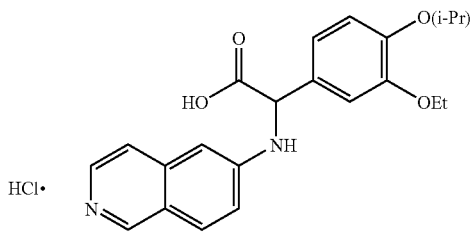

Intermediate 13A

2-Amino-2-(3-ethoxy-4-isopropoxyphenyl)acetonitrile Hydrochloric Acid Salt

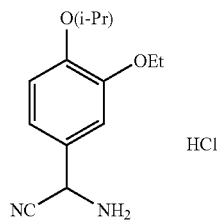

3-Ethoxy-4-isopropoxybenzaldehyde (WO 2004072101) (24 g, 115 mmol) was dissolved in a 7N MeOH solution of ammonia (200 mL) and the whole was cooled to 0° C. Trimethylsilyl cyanide (24 mL, 180 mmol) was added and the reaction mixture was stirred overnight with gradual warming to rt. The reaction product was concentrated to provide 2-amino-2-(3-ethoxy-4-isopropoxyphenyl)acetonitrile (29 g, 100%) as a yellow oil. The oil (23 g) was dissolved in ethyl ether (460 mL), cooled to 0° C., and HCl (g) was bubbled through the solution for 5 min. The resulting precipitate was filtered and dried on the high vac to provide Intermediate 13A (19 g, 72%) as a yellow solid.

Intermediate 13B

Methyl 2-amino-2-(3-ethoxy-4-isopropoxyphenyl)acetate

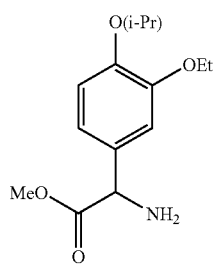

Intermediate 13A (4.00 g, 14.8) was dissolved in MeOH (74 mL) and cooled to 0° C. HCl (g) was bubbled through the system for 20 min which caused a solid to precipitate. The ice bath was removed and the reaction mixture was warmed to rt for 45 min. Water (300 μL) was added and the reaction was heated to reflux. After 5 h, the reaction product was cooled to rt and concentrated. Water and ethyl acetate were added and the layers were separated. The organic layer was washed with saturated aqueous sodium bicarbonate and brine, dried (MgSO$_4$), filtered and concentrated and purified via silica gel chromatography (eluting with 50-75% ethyl acetate in hexane, then 100% ethyl acetate, then 2% MeOH/ethyl acetate) to provide Intermediate 13B (4.00 g, 82%) as a brown oil. LC-MS: 268.2 (M+H)$^+$.

Intermediate 13C

Methyl 2-(3-ethoxy-4-isopropoxyphenyl)-2-(isoquinolin-6-ylamino)acetate

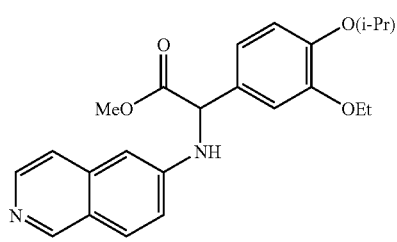

Intermediate 13B (172 mg, 0.640 mmol), 6-bromoisoquinoline (140 mg, 0.670 mmol), cesium carbonate (626 mg, 1.92 mmol), racemic BINAP (20.0 mg, 0.0321 mmol) and Pd$_2$(dba)$_3$ (10 mg, 0.0109 mmol) were combined in a tube and the whole was degassed for 5 min with nitrogen. Toluene (3 mL) was added and the reaction was sealed and heated to 100° C. for 20 h. After cooling to rt, the reaction product was diluted with ethyl acetate and was washed with brine. The organic layer was dried (Na$_2$SO$_4$), filtered and concentrated. The resulting residue was purified via silica gel chromatography (eluting with 10-90% ethyl acetate in hexane) to provide Intermediate 13C (182 mg). LC-MS: 395.20 (M+H)$^+$.

Intermediate 13

2-(3-Ethoxy-4-isopropoxyphenyl)-2-(isoquinolin-6-ylamino)acetic Acid Hydrochloric Acid Salt Intermediate 13C (406 mg, 1.03 mmol) was dissolved in THF (10 mL) and a 1 M aqueous LiOH solution (3 mL) was added. The reaction was stirred at rt for 1 h and was then concentrated. The residue was dissolved in water (20 mL) and was washed with ethyl acetate (2×10 mL). The aqueous layer was acidified with 1 N HCl to provide a yellow precipitate. The whole was cooled in an ice bath then filtered and dried to provide Intermediate 13 (230 mg). LC-MS: 381.18 (M+H)$^+$.

Intermediate 14

(2-(Isopropylsulfonyl)benzylamine Hydrochloride Salt

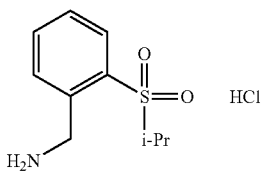

Intermediate 14A 2-(Isopropylsulfonyl)benzonitrile

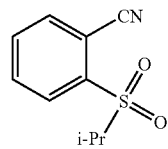

To 2-bromobenzonitrile (728 mg, 4.00 mmol) in THF (20 mL) at −78° C. was added a 1.9M solution of n-BuLi in hexanes (2.31 mL, 4.4 mmol). After stirring at the same temperature for 1 h, diisopropyl disulfide (782 mg, 5.20 mmol) in THF (10 mL) was added and the reaction was stirred at −78° C. for 1 h, then at rt overnight. The reaction was quenched with saturated aqueous ammonium chloride and was allowed to warm to rt. Ethyl acetate and water were added and the layers were separated. The organic layer was washed with brine, then was dried (Na$_2$SO$_4$), filtered and concentrated to provide a yellow oil (1.04 g). The oil (354 mg, 2.00 mmol) was dissolved in CH$_2$Cl$_2$ and ~75% MCPBA (2.20 g) was added. After stirring at rt for 30 min, the reaction was diluted with ethyl acetate and washed with saturated aqueous NaHCO$_3$ and brine, dried (Na$_2$SO$_4$), filtered then concentrated to provide Intermediate 14A (150 mg). LC-MS: 210.19 (M+H)$^+$.

Intermediate 14

(2-(Isopropylsulfonyl)benzylamine Hydrochloride Salt

To Intermediate 14A (116 mg, 0.554 mmol) in methanol (10 mL), conc. HCl (146 mg) was added and followed by 10%

Pd/C (15 mg). The mixture was hydrogenated at 30 psi for 2 h. The reaction product was filtered and concentrated to provide Intermediate 14 (135 mg, 98%). LC-MS: 214.1 (M+H)⁺.

Intermediate 15

2-(1-Di-tert-butoxycarbonylaminoisoquinolin-6-ylamino)-2-(4-chloro-3-ethoxyphenyl)acetic acid

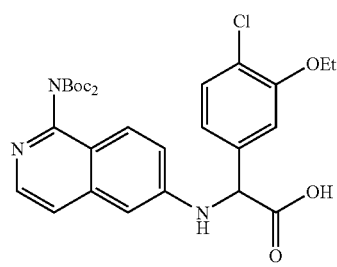

Intermediate 15A

4-Bromo-1-chloro-2-ethoxybenzene

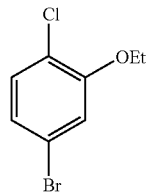

To a solution of 2-chloro-5-bromophenol (WO98/03464, 3.43 g, 16.5 mmol) and $K_2CO_3$ (4.57 g, 33.0 mmol) in DMF (20 mL) was added ethyl iodide (1.78 mL, 22.3 mmol) at rt. The mixture was heated at 55° C. for 3.0 h. After cooled to rt, it was diluted with ether, washed with water and brine, dried over $MgSO_4$. The crude residue was purified by flash column chromatography to give 3.85 g (99%) of Intermediate 15A as viscous oil. ¹H NMR (400 MHz, CDCl₃) δ ppm 1.48 (t, J=7.03 Hz, 3H) 4.08 (d, J=7.03 Hz, 2H) 7.03 (m, 2H) 7.22 (d, J=6.15 Hz, 2H).

Intermediate 15B

4-Chloro-3-ethoxyphenylboronic acid

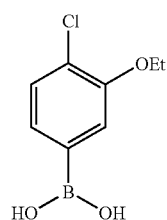

To a solution of Intermediate 15A (3.8 g, 16 mmol) in THF (20 mL) at −78° C. was added n-BuLi (1.6 M in hexanes, 13.6 mL, 21.8 mmol). The mixture was stirred at −78° C. for 40 min before triisopropyl borate (7.43 mL, 32 mmol) was added. The reaction was left stirring from −78° C. to rt over 18 h. It was quenched with 1.0 N HCl (50 mL), extracted with EtOAc, washed with brine and dried over $Na_2SO_4$. The crude residue was purified by flash column chromatography ($CH_2Cl_2$:EtOAc:MeOH=50:50:1) to give 1.85 g (57%) of Intermediate 15B as a white solid. ¹H NMR (400 MHz, CDCl₃) δ ppm 1.53 (t, J=7.03 Hz, 3H) 4.23 (d, J=7.03 Hz, 2H) 7.48 (d, J=7.91 Hz, 1H) 7.66 (d, J=6.15 Hz, 2H).

Intermediate 15

2-(1-Di-tert-butoxycarbonylaminoisoquinolin-6-ylamino)-2-(4-chloro-3-ethoxyphenyl)acetic acid A mixture of Intermediate 15B (46 mg, 0.23 mmol), Intermediate 1 (72 mg, 0.2 mmol) and glyoxylic acid monohydrate (21 mg, 0.23 mmol) in 1,2-dichloroethane (0.8 mL) was heated at 100° C. for 5 min. in a Microwave Reactor. The crude product was purified by flash column chromatography ($CH_2Cl_2$:MeOH=100:15) to give 57 mg (50%) of Intermediate 15 as a solid. ¹H NMR (400 MHz, Methanol-d₄) δ ppm 1.29 (s, 18H) 1.32 (t, J=7.03 Hz, 3H) 4.10 (m, 2H) 5.52 (s, 1H) 6.81 (s, 1H), 7.21 (d, J=7.91 Hz, 1H) 7.21 (s, 1H), 7.37 (d, J=7.91 Hz, 1H) 7.50 (m, 1H), 7.69 (d, J=7.91 Hz, 1H) 7.96 (d, J=7.91 Hz, 1H) 8.00 (d, J=7.91 Hz, 1H) LC MS 572 (M+H).

Intermediate 16

(1-Di-tert-butoxycarbonylamino-isoquinolin-6-ylamino)-(3-ethoxy-phenyl)-acetic acid

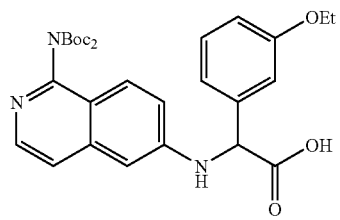

A mixture of 3-ethoxyphenylboronic acid (45 mg, 0.27 mmol), Intermediate 1 (72 mg, 0.20 mmol) and glyoxylic acid monohydrate (26 mg, 0.28 mmol) in 1,2-dichloroethane (2 mL) was heated at 100° C. for 12.5 min. in a microwave reactor. The crude product was purified by flash column chromatography (gradient from 0-20% methanol in dichloromethane) to give 60 mg (56%) of Intermediate 16 as a solid. LC-MS m/z: 538.3 (M+H)⁺.

General Coupling-Deprotection Procedure:

Most of the final compounds described in the following examples were made according to the following general coupling-deprotection scheme:

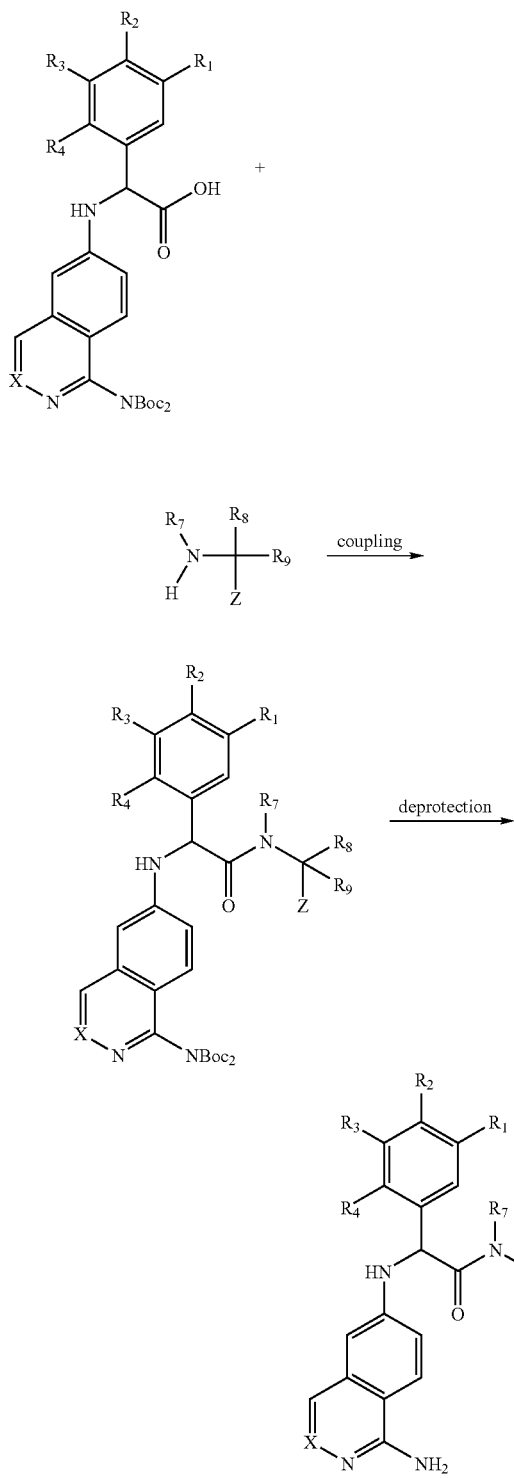

A mixture of intermediate acid (1 eq, preparation given in examples), amine (1.5-8 eq, commercial available or otherwise noted with preparation), EDCI (2-4 eq), HOAT (0.4-3 eq), DIEA (0-8 eq) in CH$_2$Cl$_2$ (0.01M) or CH$_2$Cl$_2$/DMF (0.03 M, 10:1) was stirred at rt for 4 h to overnight. The reaction product was concentrated and purified via preparative HPLC (MeOH/H$_2$O/TFA or CH$_3$CN/H$_2$O/TFA) to provide the desired di-Boc-protected amide. To a solution of the amide (1 eq) in EtOAc (~0.04 M) was added a 4 M solution of HCl in dioxane (~100 eq) and the reaction was stirred at rt for 4 h to overnight. The reaction product was then concentrated and purified via preparative HPLC (MeOH/H$_2$O/TFA or CH$_3$CN/H$_2$O/TFA) then lyophilized (CH$_3$CN, H$_2$O) to provide the desired final compound as a solid TFA salt. The yields of the final TFA salts were in the range of 15-85%.

Example 1

N-(3-Acetylamino-benzyl)-2-(1-amino-isoquinolin-6-ylamino)-2-(3-ethoxy-4-isopropoxy-phenyl)-acetamide trifluoroacetic acid salt

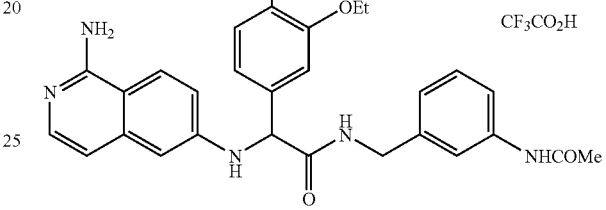

Example 1 was prepared according to the general coupling-deprotection using Intermediate 2 and commercial N-(3-(aminomethyl)phenyl)acetamide HCl salt. $^1$H NMR (400 MHz, Methanol-d$_4$) δ ppm 1.21 (d, J=6.15 Hz, 6H) 1.28 (t, J=7.03 Hz, 3H) 2.00 (s, 3H) 3.90 (q, J=7.03 Hz, 2H) 4.29 (m, 2H) 4.44 (m, 1H) 4.97 (s, 1H) 6.56 (s, 1H) 6.70 (d, J=7.03 Hz, 1H) 6.81 (d, J=7.03 Hz, 1H) 6.87 (d, J=8.35 Hz, 1H) 6.99 (m, 2H) 7.08 (m, 2H) 7.25 (m, 2H) 7.36 (s, 1H) 7.99 (d, J=9.23 Hz, 1H) 8.73 (t, J=5.71 Hz, 1H). LC-MS 542 (M+H).

Example 2

(R)-N-(3-Acetylamino-benzyl)-2-(1-amino-isoquinolin-6-ylamino)-2-(3-ethoxy-4-isopropoxy-phenyl)-acetamide

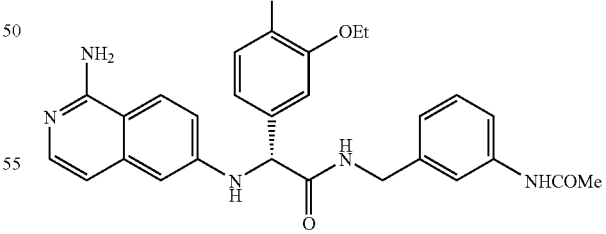

Example 2 (41 mg) was separated from the racemic mixture (120 mg) of Example 1 using a semi-preparative HPLC equipped with a Chiralpak®OJ-H column (2 cm×25m, 5 g). The separation was performed using an isocratic method of 20% ethanol/methanol (1:1) in heptane with 0.1% diethylamine and a flow rate of 20 mL/min. Retention time for Example 2 was 22 min. The retention time for the other isomer (43 mg) was 28 min. LC-MS 542 (M+H).

Example 3

N-(3-Acetylamino-benzyl)-2-(1-amino-isoquinolin-6-ylamino)-2-(3,4-dimethoxy-phenyl)-acetamide trifluoroacetic acid salt

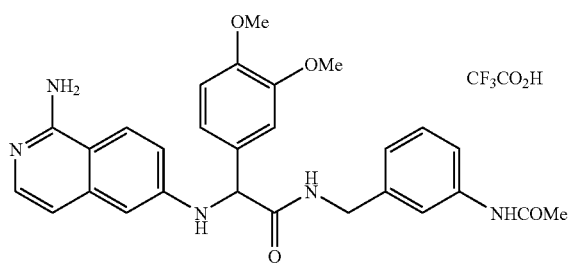

Example 3 was prepared according to the general coupling-deprotection using Intermediate 4 and commercial N-(3-(aminomethyl)phenyl)acetamide HCl salt. $^1$H NMR (400 MHz, Methanol-d$_4$) δ ppm 2.00 (s, 3H) 3.70 (s, 3H) 3.74 (s, 3H) 4.28 (dd, J=5.93, 2.42 Hz, 1H) 4.98 (s, 1H) 6.56 (d, J=1.76 Hz, 1H) 6.70 (d, J=7.47 Hz, 1H) 6.82 (d, J=7.47 Hz, 1H) 6.87 (m, 1H) 7.07 (m, 3H) 7.26 (m, 3H) 7.99 (d, J=8.79 Hz, 1H) 8.73 (t, J=5.93 Hz, 1H). LC-MS 500 (M+H).

Example 4

(R)-N-(3-Acetylamino-benzyl)-2-(1-amino-isoquinolin-6-ylamino)-2-(3,4-dimethoxy-phenyl)-acetamide

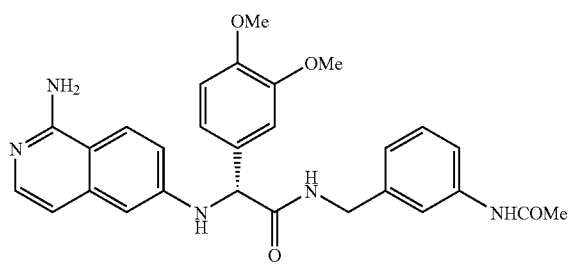

Example 4 (34 mg) was separated from the racemic mixture (100 mg) of Example 3 using a semi-preparative HPLC equipped with a Chiralpak®OJ-H column (2 cm×25 m, 5 g). The separation was performed using an isocratic method of 35% ethanol/heptane with 0.1% diethylamine and a flow rate of 20 mL/min. Retention time of Example 4 was 24 min. Retention time of the other isomer (41 mg) was 38 min. LC-MS 500 (M+H).

Example 5

[2-(1-Amino-isoquinolin-6-ylamino)-2-(3-ethoxy-4-isopropoxy-phenyl)-acetylamino]-(3-sulfamoyl-phenyl)-acetic acid trifluoroacetic acid salt

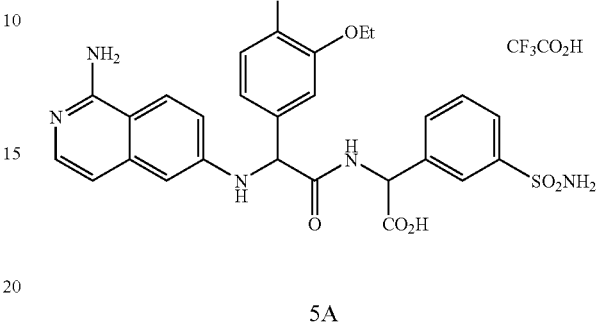

5A

N-tert-Butyl-3-(hydroxymethyl)benzenesulfonamide

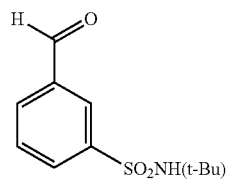

To a solution of 3-tert-butylsulfamoyl-benzoic acid (5.15 g, 20 mmol, *J. Med. Chem.* 1999, 42, 515-525) in THF (100 mL) at −20° C. was added N-methyl morpholine (2.97 mL, 1.35 eq) and ethyl chloroformate (2.11 mL, 1.1 eq). The mixture was stirred between −20 to −10° C. for 30 min. Then NaBH$_4$ (1.13 g, 1.5 eq) was added, followed by slow addition of MeOH (20 mL). After stirring at −20° C. for 40 min, the reaction was quenched by addition of 5% citric acid. After removal of solvent, the crude was diluted with EtOAc, washed with 5% NaHCO$_3$ and dried over Na$_2$SO$_4$. Evaporation of solvent gave 5A as a white solid.

5B

N-tert-Butyl-3-formylbenzenesulfonamide

To a solution of 5A (4.4 g, 18 mmol) in CH$_2$Cl$_2$ (80 mL) at 0° C., NaHCO$_3$ (1.8 g, 1.2 eq) and Dess-Martin periodinane (7.64 g, 18 mmol) were added. The mixture was stirred at rt for 2.0 h before it was diluted with EtOAc and washed with water and brine. The extract was dried over Na$_2$SO$_4$ and the crude was purified by chromatography eluting with 1:3 EtOAc/hexanes to give 5B (3.9 g, 89% yield).

5C

Amino-(3-tert-butylsulfamoyl-phenyl)-acetic acid methyl ester

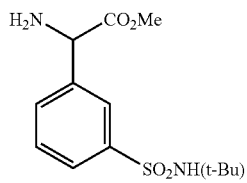

To a solution of 5B (190 mg, 0.79 mmol) in 7.0 N NH$_3$ in MeOH (4.0 mL), trimethylsilyl cyanide (0.28 mL, 2.1 mmol) was added at 0° C. The mixture was stirred at rt over night. Solvent was removed in vacuo to give the corresponding amino nitrile. The amino nitrile was dissolved in MeOH (5.0 mL) and treated with 4.0 N HCl/dioxane (5.18 mL, 10 eq) at rt for 3.0 h, reflux for 8.0 h. After removal of solvent, 5C was obtained with sufficient purity for next step.

5D

Amino-(3-sulfamoyl-phenyl)-acetic acid methyl ester

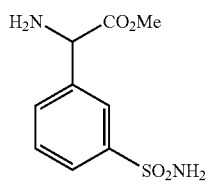

5C (150 mg, 0.5 mmol) was treated with anisole (0.16 mL, 3.0 eq) and TFA (2.5 mL) at rt over night. After removal of solvent in vacuo, the crude was dissolved in MeOH (3.0 mL) and treated with basic resin (WA215 from Supelco) at rt for 1.0 h until pH>7. Filtration and evaporation of solvent gave 5D as an oil. $^1$H NMR (400 MHz, Methanol-d$_4$) δ ppm 1.21 (m, 6H) 1.28 (m, 3H) 3.94 (m, 2H) 4.44 (m, 1H) 5.14 (d, J=15.38 Hz, 1H) 5.51 (d, J=12.30 Hz, 1H) 6.60 (dd, J=41.74, 2.20 Hz, 1H) 6.74 (dd, J=38.67, 7.03 Hz, 1H) 6.87 (m, 1H) 7.02 (m, 3H) 7.22 (t, J=7.47 Hz, 1H) 7.32 (d, J=5.71 Hz, 1H) 7.51 (m, 1H) 7.76 (m, 2H) 7.98 (t, J=9.01 Hz, 1H).

5E

Example 5 (5 mg) was prepared according to the general coupling-deprotection using Intermediate 2 (25 mg) and 5D (20 mg) followed by saponification of the methyl ester (13 mg) using 4.0 equivalents of LiOH (1.0 M in H$_2$O) in THF for 5.0 h. $^1$H NMR (400 MHz, Methanol-d$_4$) δ ppm 1.21 (m, 6H) 1.28 (m, 3H) 3.94 (m, 2H) 4.44 (m, 1H) 5.14 (d, J=15.38 Hz, 1H) 5.51 (d, J=12.30 Hz, 1H) 6.60 (dd, J=41.74, 2.20 Hz, 1H) 6.74 (dd, J=38.67, 7.03 Hz, 1H) 6.87 (m, 1H) 7.02 (m, 3H) 7.22 (t, J=7.47 Hz, 1H) 7.32 (d, J=5.71 Hz, 1H) 7.51 (m, 1H) 7.76 (m, 2H) 7.98 (t, J=9.01 Hz, 1H). LC-MS 608 (M+H).

Example 6

2-(2-(1-Aminoisoquinolin-6-ylamino)-2-(3-ethoxy-4-isopropoxyphenyl)acetamido)-2-phenylacetic acid trifluoroacetic acid salt

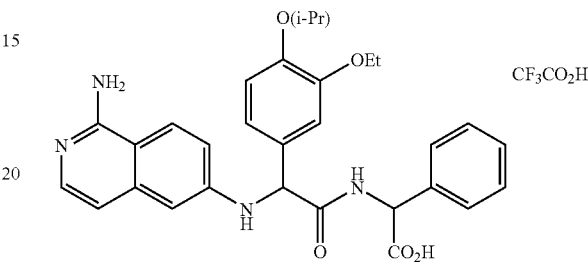

Example 6 was prepared according to the general coupling-deprotection using Intermediate 2 and phenylglycine methyl ester followed by saponification of the methyl ester as in procedure 5E. $^1$H NMR (400 MHz, Methanol-d$_4$) δ ppm 1.21 (dd, J=5.93, 2.86 Hz, 6H) 1.28 (m, 3H) 3.90 (q, J=6.88 Hz, 1H) 3.96 (q, J=7.03 Hz, 1H) 4.43 (m, 1H) 5.14 (m, 1H) 5.42 (m, 1H) 6.76 (m, 3H) 7.03 (m, 3H) 7.17 (m, 3H) 7.27 (m, 3H) 7.98 (dd, J=9.01, 5.05 Hz, 1H) 8.81 (m, 1H). LC-MS 529(M+H).

Example 7

2-(1-Amino-isoquinolin-6-ylamino)-2-(3-ethoxy-4-isopropoxy-phenyl)-N-(3-sulfamoyl-benzyl)-acetamide trifluoroacetic acid salt

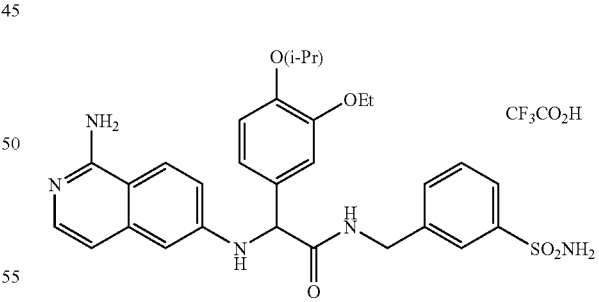

Example 7 was prepared according to the general coupling-deprotection using Intermediate 2 and Intermediate 5. $^1$H NMR (400 MHz, Methanol-d$_4$) δ ppm 1.30 (d, J=6.15 Hz, 6H) 1.37 (t, J=7.03 Hz, 3H) 4.02 (m, 2H) 4.47 (d, J=2.64 Hz, 2H) 4.54 (m, 1H) 5.07 (s, 1H) 6.65 (d, J=2.20 Hz, 1H) 6.81 (d, J=7.03 Hz, 1H) 6.98 (d, J=8.35 Hz, 1H) 7.08 (m, 2H) 7.18 (dd, J=9.01, 2.42 Hz, 1H) 7.32 (d, J=7.03 Hz, 1H) 7.38 (m, 2H) 7.75 (m, 1H) 7.78 (s, 1H) 8.08 (d, J=9.23 Hz, 1H). LC-MS 564 (M+H).

Example 8

(R)-2-(1-Amino-isoquinolin-6-ylamino)-2-(3-ethoxy-4-isopropoxy-phenyl)-N-(3-sulfamoyl-benzyl)-acetamide trifluoroacetic acid salt

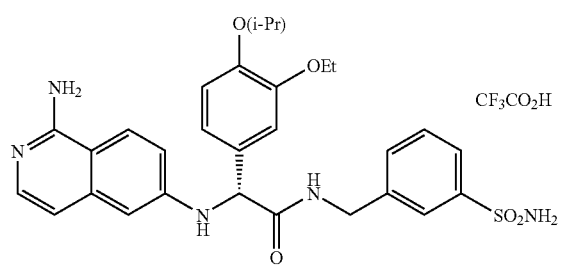

Example 8 (48 mg) was separated from the racemic mixture (100 mg) of Example 7 using a preparative HPLC equipped with a Chiralpak® AD column (5 cm×50 cm, 20μ). The separation was performed using an isocratic method of 30% ethanol/isopropanol (1:1) in heptane with 0.1% trifluoroacetic acid and a flow rate of 50 mL/min. Retention time for Example 8 was 70 min. LC-MS 564 (M+H).

Example 9

2-(1-Amino-isoquinolin-6-ylamino)-2-(3-ethoxy-4-isopropoxy-phenyl)-N-(2-sulfamoyl-benzyl)-acetamide trifluoroacetic acid salt

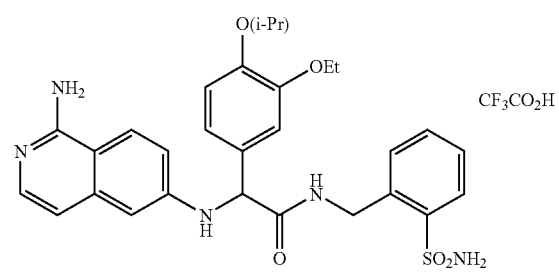

9A 2-(Aminomethyl)benzenesulfonamide

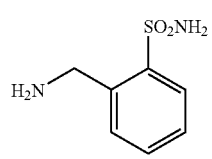

To 2-cyanobenzenesulfonamide (213 mg, 1.2 mmol) in methanol (5.0 mL) was added 10% Pd/C (50 mg) and 4.0 M HCl in dioxane (0.6 mL, 2.4 mmol). The mixture was stirred under a hydrogen balloon at rt overnight and filtrated. The filtrate was concentrated to a colorless oil of 9A as HCl salt (200 mg, 80% yield). $^1$H NMR (400 MHz, Methanol-d$_4$) δ ppm 4.34 (s, 2H) 7.43-7.57 (m, 3H) 7.91 (d, J=7.91 Hz, 1H).

9B

Example 9 was prepared according to the general coupling-deprotection using Intermediate 2 and 9A. $^1$H NMR (400 MHz, Methanol-d$_4$) δ ppm 1.21 (d, J=6.15 Hz, 6H) 1.28 (t, J=7.03 Hz, 3H) 3.89 (m, 2H) 4.45 (m, 1H) 4.78 (m, 2H) 5.01 (s, 1H) 6.58 (d, J=2.20 Hz, 1H) 6.74 (d, J=7.03 Hz, 1H) 6.88 (d, J=7.91 Hz, 1H) 6.97 (m, 2H) 7.10 (dd, J=9.23, 2.20 Hz, 1H) 7.20 (m, 1H) 7.28 (m, 2H) 7.82 (m, 1H) 7.99 (d, J=9.23 Hz, 1H) 8.54 (m, 1H). LC-MS 564 (M+H).

Example 10

N-(3-Hydroxybenzyl)-2-(1-aminoisoquinolin-6-ylamino)-2-(3-ethoxy-4-isopropoxyphenyl)acetamide trifluoroacetic acid salt

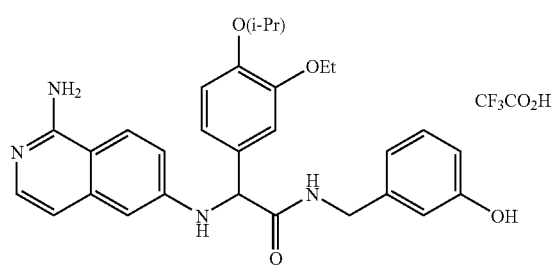

Example 10 was prepared according to the general coupling-deprotection using Intermediate 2 and 3-(aminomethyl)phenol. $^1$H NMR (400 MHz, Methanol-d$_4$) ppm 1.20 (t, J=5.49 Hz, 6H) 1.28 (t, J=7.03 Hz, 3H) 3.91 (q, J=7.03 Hz, 2H) 4.23 (d, J=3.08 Hz, 2H) 4.44 (m, 1H) 4.97 (s, 1H) 6.55 (m, 4H) 6.73 (d, J=7.47 Hz, 1H) 6.87 (d, J=8.35 Hz, 1H) 6.95 (m, 2H) 7.01 (d, J=1.76 Hz, 1H) 7.10 (dd, J=9.01, 2.42 Hz, 1H) 7.23 (d, J=7.47 Hz, 1H) 7.99 (d, J=9.23 Hz, 1H). LC-MS 501 (M+H).

Example 11

N-(3-Aminobenzyl)-2-(1-aminoisoquinolin-6-ylamino)-2-(3-ethoxy-4-isopropoxyphenyl)acetamide trifluoroacetic acid salt

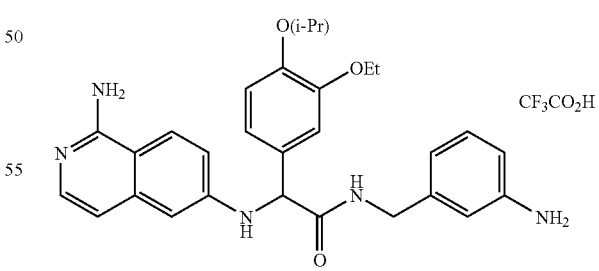

Example 11 was prepared according to the general coupling-deprotection using Intermediate 2 and 3-(aminomethyl)benzenamine. $^1$H NMR (400 MHz, Methanol-d$_4$) (ppm 1.29 (d, J=6.15 Hz, 6H) 1.36 (t, J=7.03 Hz, 3H) 4.00 (q, J=7.03 Hz, 2H) 4.40 (d, J=5.71 Hz, 2H) 4.52 (m, 1H) 5.09 (s, 1H) 6.67 (d, J=2.20 Hz, 1H) 6.82 (d, J=7.03 Hz, 1H) 6.96 (d, J=8.35 Hz, 1H) 7.06 (m, 5H) 7.19 (dd, J=9.23, 2.64 Hz, 1H)

7.26 (t, J=7.91 Hz, 1H) 7.33 (d, J=7.03 Hz, 1H) 8.09 (d, J=9.23 Hz, 1H) 8.89 (m, 1H). LC-MS 500 (M+H).

Example 12

3-((2-(1-Aminoisoquinolin-6-ylamino)-2-(3-ethoxy-4-isopropoxyphenyl)acetamido)methyl)phenylboronic acid trifluoroacetic acid salt

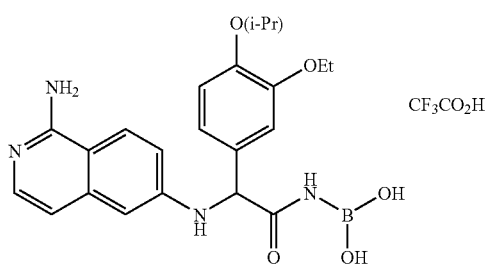

Example 12 was prepared according to the general coupling-deprotection using Intermediate 2 and 3-(aminomethyl)phenylboronic acid. $^1$H NMR (400 MHz, Methanol-$d_4$) δ ppm 1.22 (d, J=6.15 Hz, 6H) 1.28 (t, J=6.81 Hz, 3H) 3.90 (m, J=5.71 Hz, 2H) 4.33 (m, 2H) 4.44 (dd, J=12.30, 6.15 Hz, 1H) 4.97 (s, 1H) 6.57 (s, 1H) 6.70 (d, J=7.03 Hz, 1H) 6.87 (d, J=7.91 Hz, 1H) 6.99 (m, 2H) 7.12 (m, 3H) 7.24 (d, J=7.03 Hz, 1H) 7.39 (m, 2H) 7.99 (d, J=9.23 Hz, 1H) 8.75 (d, J=6.15 Hz, 1H); LC-MS 529 (M+H).

Example 13

3-((2-(1-Aminoisoquinolin-6-ylamino)-2-(3-ethoxy-4-isopropoxyphenyl)acetamido)methyl)benzamide trifluoroacetic acid salt

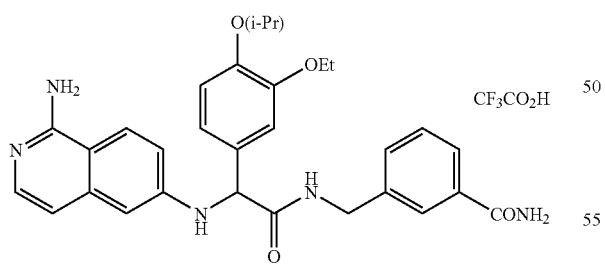

Example 13 was prepared according to the general coupling-deprotection using Intermediate 2 and 3-(aminomethyl)benzamide. $^1$H NMR (400 MHz, Methanol-$d_4$) δ ppm 1.21 (d, J=6.15 Hz, 6H) 1.28 (t, J=6.81 Hz, 3H) 3.92 (m, 2H) 4.37 (d, J=5.71 Hz, 2H) 4.44 (m, 1H) 6.57 (d, J=1.76 Hz, 1H) 6.70 (d, J=7.03 Hz, 1H) 6.88 (d, J=8.35 Hz, 1H) 6.98 (m, 2H) 7.09 (dd, J=9.23, 2.20 Hz, 1H) 7.24 (m, 3H) 7.64 (m, 2H) 7.99 (d, J=8.79 Hz, 1H) 8.81 (t, J=5.93 Hz, 1H). LC-MS 528 (M+H).

Example 14

N-(3-(Methylsulfonyl)benzyl)-2-(1-aminoisoquinolin-6-ylamino)-2-(3-ethoxy-4-isopropoxyphenyl)acetamide trifluoroacetic acid salt

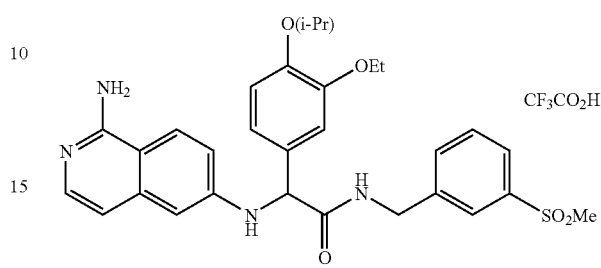

Example 14 was prepared according to the general coupling-deprotection using Intermediate 2 and (3-(methylsulfonyl)phenyl)methanamine. $^1$H NMR (400 MHz, Methanol-$d_4$) δ ppm 1.22 (d, J=6.15 Hz, 6H) 1.29 (t, J=6.81 Hz, 3H) 3.93 (q, J=6.74 Hz, 2H) 4.36 (dd, J=15.16, 5.49 Hz, 1H) 4.47 (m, 2H) 5.00 (s, 1H) 6.57 (d, J=1.76 Hz, 1H) 6.73 (d, J=7.03 Hz, 1H) 6.89 (d, J=8.35 Hz, 1H) 7.00 (m, 2H) 7.10 (dd, J=9.23, 2.20 Hz, 1H) 7.24 (d, J=7.03 Hz, 1H) 7.41 (m, 2H) 7.69 (m, 2H) 8.00 (d, J=9.23 Hz, 1H) 8.88 (t, J=5.93 Hz, 1H). LC-MS 563 (M+H).

Example 17

2-(1-Aminoisoquinolin-6-ylamino)-2-(3-ethoxy-4-isopropoxyphenyl)-N-(indolin-4-ylmethyl)acetamide trifluoroacetic acid salt

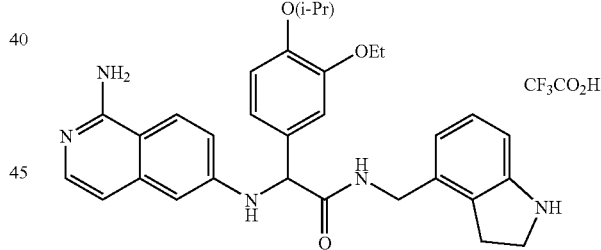

17A

Indolin-4-ylmethanamine

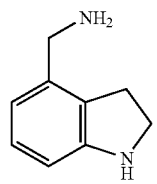

To 1H-indole-4-carbonitrile (284 mg, 2.0 mmol) in MeOH (10 mL), 4.0 N HCl/dioxane (1.25 mL, 2.5 eq) and 10% Pd/C (200 mg) were added. The mixture was hydrogenated with a H₂ balloon for 48 h. Filtration and evaporation of solvent gave 17A as HCl salt. ¹H NMR (400 MHz, Methanol-d₄) δ ppm 3.45 (t, J=7.69 Hz, 2H) 3.92 (t, J=7.69 Hz, 2H) 4.22 (s, 2H) 7.57 (m, 5H).

17B

Example 17 was prepared according to the general coupling-deprotection using Intermediate 2 and 17A. ¹H NMR (400 MHz, Methanol-d₄) δ ppm 1.21 (d, J=6.15 Hz, 6H) 1.28 (t, J=7.03 Hz, 3H) 2.81 (s, 1H) 3.00 (m, 1H) 3.56 (t, J=8.13 Hz, 2H) 3.93 (q, J=6.88 Hz, 2H) 4.36 (m, 3H) 5.01 (m, 1H) 6.74 (d, J=7.03 Hz, 1H) 6.90 (m, 2H) 6.98 (m, 1H) 7.08 (m, 4H) 7.25 (d, J=7.03 Hz, 1H) 8.00 (d, J=9.23 Hz, 1H) 8.75 (t, J=5.93 Hz, 1H). LC-MS 526 (M+H).

Example 18

(2S)-tert-Butyl 2-(2-(1-aminoisoquinolin-6-ylamino)-2-(3-ethoxy-4-isopropoxyphenyl)acetamido)-2-phenylacetate trifluoroacetic acid salt

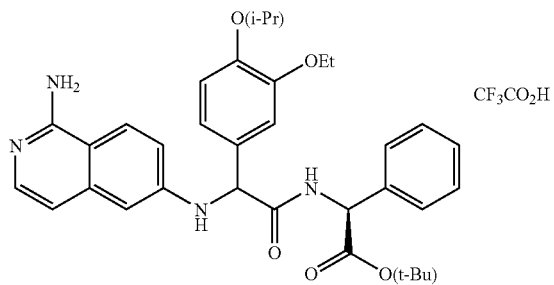

Example 18 was prepared according to the general coupling-deprotection using Intermediate 2 and (S)-tert-butyl 2-amino-2-phenylacetate. ¹H NMR (400 MHz, Methanol-d₄) δ ppm 1.25 (m, 18H) 3.91 (q, J=7.03 Hz, 1H) 3.97 (q, J=7.03 Hz, 1H) 4.43 (dd, J=11.21, 5.05 Hz, 1H) 5.13 (d, J=4.83 Hz, 1H) 5.30 (t, J=3.74 Hz, 1H) 6.65 (m, 2H) 6.93 (m, 3H) 7.18 (m, 7H) 7.99 (dd, J=9.23, 4.39 Hz, 1H) 8.79 (m, 1H). LC-MS 585 (M+H).

Example 19

2-(1-Amino-isoquinolin-6-ylamino)-N-(3,5-disulfamoyl-benzyl)-2-(3-ethoxy-4-isopropoxy-phenyl)-acetamide trifluoroacetic acid salt

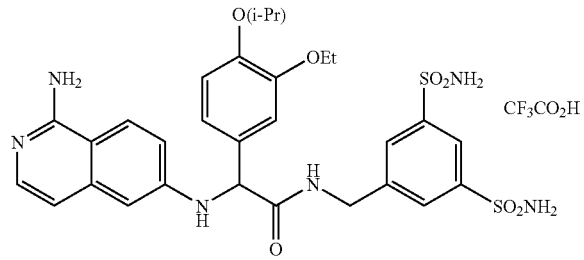

19A

Methyl 3,5-bis(chlorosulfonyl)benzoate

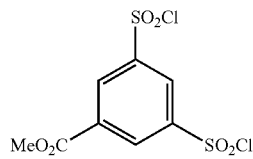

To a solution of 3,5-bis(chlorosulfonyl)benzoyl chloride (100 mg, 0.3 mmol, WO2001010838) in CH₂Cl₂ (1.5 mL) at 0° C. was added MeOH (0.026 mL, 2.2 eq). The mixture was stirred at rt for 3.0 h. After removal of solvent in vacuo, 19A was obtained as a white solid.

19B 3,5-Bis-tert-butylsulfamoyl-benzoic acid methyl ester

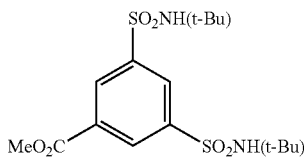

To a solution of 19A (0.3 mmol) in CH₂Cl₂ (2.0 mL) was added tert-butylamine (0.095 mL, 0.9 mmol) and diisopropyl ethylamine (0.21 mL, 4.0 eq). The mixture was stirred at rt over night. It was diluted with EtOAc, washed with 5% citric acid, brine and dried over MgSO₄. After removal of solvent, the crude was purified by chromatography eluting with 2:3 EtOAc/hexanes to give 19B (98 mg, 81% yield).

19C

N1,N3-di-tert-Butyl-5-(hydroxymethyl)benzene-1,3-disulfonamide

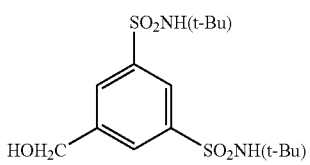

To a solution of 19B (98 mg, 0.24 mmol) in THF (1.5 mL), LiBH₄ (2.0 M in THF, 0.21 mL, 1.75 eq) was added. The mixture was stirred at rt over night, diluted with EtOAc, quenched with 5% citric acid. The organic-extract was washed with brine, dried over Na₂SO₄. After removal of solvent in vacuo, 19C (90 mg, 94% yield) was obtained as an oil.

19D 5-(Azidomethyl)-N1,N3-di-tert-butylbenzene-1,3-disulfonamide

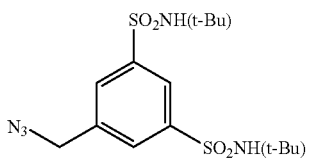

To a solution of 19C (90 mg, 0.23 mmol) in THF (1.5 mL), diphenyl phosphoryl azide (0.062 mL, 1.25 eq) and DBU (0.043 mL, 1.25 eq) were added. The mixture was stirred at rt over night. The product was directly purified by chromatography eluting with 1:2 EtOAc/hexanes to give 19D (80 mg, 85% yield) as a solid.

19E 5-(Aminomethyl)-N1,N3-di-tert-butylbenzene-1,3-disulfonamide

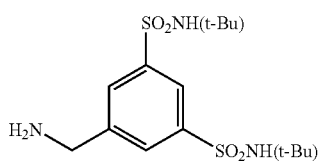

A mixture of 19D (538 mg) and 10% Pd/C (650 mg) in MeOH (10 mL) was hydrogenated with a $H_2$ balloon for 3.0 h at rt. Filtration and evaporation of solvent gave 19E.

19F 5-(Aminomethyl)benzene-1,3-disulfonamide

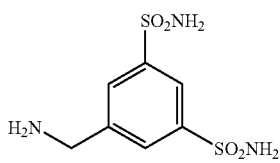

19E was treat with trifluoroacetic acid over night. After removal of trifluoroacetic acid in vacuo, the residue was suspended in DMF and treated with basic resin (WA215 from Supelco, 2.5 g) for 1.0 h until pH>7. Filtration and evaporation of solvent gave 19F contaminated with ca 8% of the mono-deprotection product 5-aminomethyl-benzene-1,3-disulfonic acid 1-amide 3-tert-butylamide (19F'). $^1$H NMR (400 MHz, Methanol-$d_4$) (ppm 4.21 (m, 2H) 7.98 (m, 1H) 8.15 (d, J=1.76 Hz, 2H).

19G

Example 19 was prepared according to the general coupling-deprotection using Intermediate 2 and 19F. $^1$H NMR (400 MHz, Methanol-$d_4$) δ ppm 1.21 (d, J=6.15 Hz, 6H) 1.29 (t, J=7.03 Hz, 3H) 3.94 (q, J=7.03 Hz, 2H) 4.45 (m, 3H) 4.97 (s, 1H) 6.50 (d, J=1.76 Hz, 1H) 6.69 (d, J=7.03 Hz, 1H) 6.89 (d, J=8.35 Hz, 1H) 6.98 (m, 2H) 7.08 (dd, J=9.23, 2.20 Hz, 1H) 7.20 (d, J=7.03 Hz, 1H) 7.86 (d, J=1.76 Hz, 2H) 7.98 (d, J=9.23 Hz, 1H) 8.16 (s, 1H) 8.93 (m, 1H). LC-MS 643 (M+H).

Example 20

2-(1-Amino-isoquinolin-6-ylamino)-N-(3-tert-butyl-sulfamoyl-5-sulfamoyl-benzyl)-2-(3-ethoxy-4-isopropoxy-phenyl)-acetamide trifluoroacetic acid salt

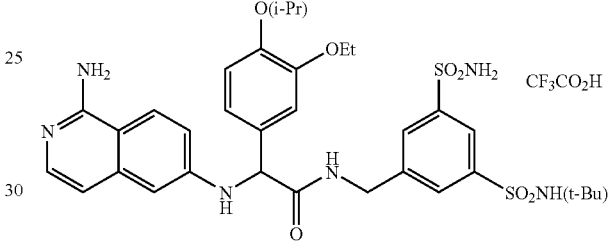

Example 20 was prepared according to the general coupling-deprotection using Intermediate 2 and 19F'. $^1$H NMR (400 MHz, Methanol-$d_4$) δ ppm 1.02 (s, 9H) 1.21 (d, J=6.15 Hz, 6H) 1.29 (t, J=7.03 Hz, 3H) 3.95 (m, 2H) 4.45 (m, 3H) 4.96 (s, 1H) 6.50 (d, J=2.20 Hz, 1H) 6.70 (d, J=7.47 Hz, 1H) 6.89 (d, J=8.35 Hz, 1H) 6.98 (m, 2H) 7.07 (dd, J=9.23, 2.64 Hz, 1H) 7.20 (d, J=7.03 Hz, 1H) 7.86 (d, J=12.74 Hz, 2H) 7.98 (d, J=9.23 Hz, 1H) 8.13 (s, 1H) 8.95 (s, 1H). LC-MS 699 (M+H).

Example 21

N-(3-(Methylsulfonamido)benzyl)-2-(1-aminoisoquinolin-6-ylamino)-2-(3-ethoxy-4-isopropoxyphenyl)acetamide trifluoroacetic acid salt

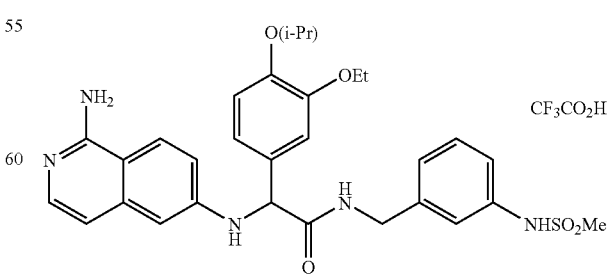

21A

N-(3-(Aminomethyl)phenyl)methanesulfonamide

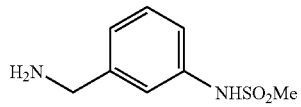

21A was prepared according to the procedure given in *J. Med. Chem.* 2003, 46, 3116-3126.

21B

Example 21 was prepared according to the general coupling-deprotection using Intermediate 2 and 21A. LC-MS 578 (M+H).

Example 22

N-(2-(Methylsulfonyl)benzyl)-2-(1-aminoisoquinolin-6-ylamino)-2-(3-ethoxy-4-isopropoxyphenyl)acetamide trifluoroacetic acid salt

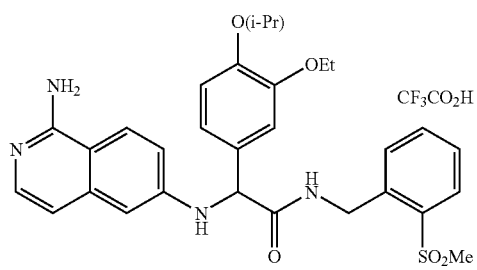

Example 22 was prepared according to the general coupling-deprotection using Intermediate 2 and Intermediate 6. $^1$H NMR (400 MHz, Methanol-$d_4$) δ ppm 1.29 (d, J=6.15 Hz, 6H) 1.36 (t, J=7.03 Hz, 3H) 3.15 (s, 3H) 3.99 (m, 2H) 4.53 (m, 1H) 4.71 (dd, J=15.82, 5.71 Hz, 1H) 4.82 (d, J=6.15 Hz, 1H) 5.10 (s, 1H) 6.65 (d, J=2.20 Hz, 1H) 6.80 (d, J=7.03 Hz, 1H) 6.96 (d, J=8.35 Hz, 1H) 7.06 (m, 2H) 7.18 (dd, J=9.23, 2.20 Hz, 1H) 7.33 (m, 2H) 7.47 (m, 2H) 7.91 (m, 1H) 8.07 (d, J=9.23 Hz, 1H) 8.68 (t, J=6.15 Hz, 1H). LC-MS 563 (M+H).

Example 23

Methyl 2-((2-(1-aminoisoquinolin-6-ylamino)-2-(3-ethoxy-4-isopropoxyphenyl)acetamido)methyl)benzoate trifluoroacetic acid salt

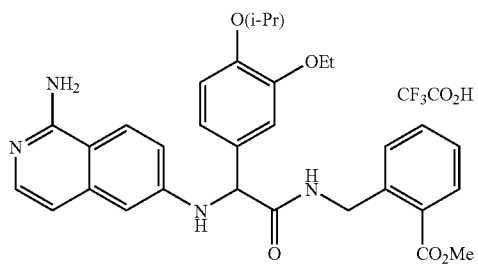

23A

Methyl 2-(aminomethyl)benzoate

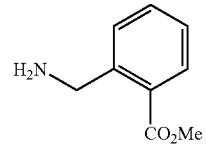

To a solution of methyl 2-cyanobenzoate (322 mg, 2.0 mmol)) in MeOH (6 mL), Pd/C (10% by weight, 61 mg) and 4.0 N HCl in dioxane (0.875 mL, 1.75 eq) were added. This mixture was hydrogenated with a H$_2$ balloon for 2.0 h. After filtration and concentration, 23A was obtained as HCl salt. $^1$H NMR (400 MHz, DMSO-$d_6$) δ ppm 3.86 (s, 3H) 4.30 (d, J=5.71 Hz, 2H) 7.55 (m, 1H) 7.65 (m, 2H) 7.99 (d, J=7.91 Hz, 1H) 8.49 (s, 3H).

23B

Example 23 was prepared according to the general coupling-deprotection using Intermediate 2 and 23A. $^1$H NMR (400 MHz, Methanol-$d_4$) δ ppm 1.28 (t, J=6.81 Hz, 6H) 1.36 (t, J=7.03 Hz, 3H) 3.75 (s, 3H) 3.98 (m, 2H) 4.52 (m, 1H) 4.64 (m, 1H) 4.73 (m, 1H) 5.06 (s, 1H) 6.58 (d, J=2.20 Hz, 1H) 6.72 (d, J=7.03 Hz, 1H) 6.95 (d, J=8.35 Hz, 1H) 7.04 (m, 2H) 7.14 (dd, J=9.23, 2.20 Hz, 1H) 7.30 (m, 3H) 7.39 (t, J=6.81 Hz, 1H) 7.83 (d, J=6.15 Hz, 1H) 8.05 (d, J=9.23 Hz, 1H) 8.53 (t, J=6.15 Hz, 1H). MS 543 (M+H).

Example 24

2-(1-Amino-isoquinolin-6-ylamino)-2-(3-ethoxy-4-isopropoxy-phenyl)-N-(2-methoxy-5-sulfamoyl-benzyl)-acetamide trifluoroacetic acid salt

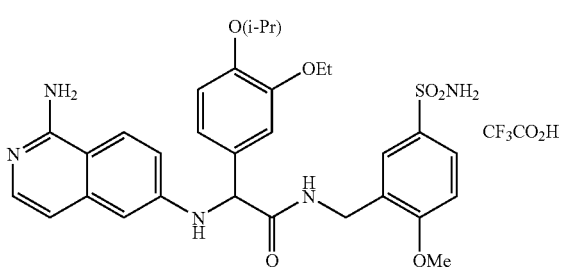

24A 3-(Hydroxymethyl)-4-methoxybenzenesulfonamide

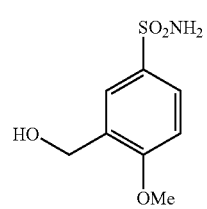

To a solution of methyl 2-methoxy-5-sulfamoylbenzoate (245 mg, 1.0 mmol) in THF (5.0 mL), LiBH$_4$ (2.0 M in THF, 1.0 mL) was added. After stirring at rt for 5.0 h, another portion of LiBH$_4$ (1.0 mL) was added followed by 1.0 ml of MeOH. The mixture was stirred for 3 h, diluted with EtOAc and quenched with 5% citric acid. Extraction with EtOAc, drying with Na$_2$SO$_4$ and evaporation of solvent gave 24A (240 mg) as a white solid. $^1$H NMR (400 MHz, CDCl$_3$) δ ppm 3.86 (s, 3H) 4.66 (d, J=6.15 Hz, 2H) 4.75 (s, 2H) 6.88 (d, J=8.79 Hz, 1H) 7.80 (dd, J=8.79, 2.20 Hz, 1H) 7.85 (d, J=2.20 Hz, 1H).

24B 3-(Azidomethyl)-4-methoxybenzenesulfonamide

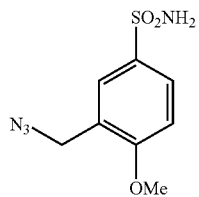

To a solution of 24A (230 mg, 1.0 mmol) in THF (4.0 mL), DPPA (0.5 mL, 2.0 eq) and DBU (0.34 mL, 2.0 eq) were added. The mixture was stirred at rt over night. It was diluted with EtOAc, quenched with 5% citric acid. The organic layer was washed with brine, dried with Na$_2$SO$_4$. The product was purified by chromatography eluting with hexanes/EtOAc (1:1) to give 120 mg of 24B as white solid. $^1$H NMR (400 MHz, CDCl$_3$) δ ppm 3.90 (s, 3H) 4.35 (s, 2H) 5.23 (s, 2H) 6.95 (d, J=8.35 Hz, 1H) 7.81 (d, J=2.20 Hz, 1H) 7.87 (dd, J=8.79, 2.20 Hz, 1H).

24C 3-(Aminomethyl)-4-methoxybenzenesulfonamide

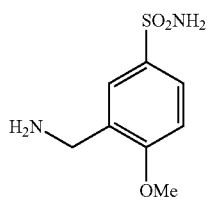

To a solution of 24B (116 mg) in MeOH (10 mL), Pd/C (10% by weight, 30 mg) was added. This mixture was hydrogenated with a H$_2$ balloon for 4.0 h. After filtration and concentration, 24C was obtained as a white solid. $^1$H NMR (400 MHz, CD$_3$CN) δ ppm 3.75 (s, 2H) 3.86 (s, 3H) 7.00 (d, J=8.35 Hz, 1H) 7.70 (dd, J=8.57, 2.42 Hz, 1H) 7.81 (d, J=2.20 Hz, 1H).

24D

Example 24 was prepared according to the general coupling-deprotection using Intermediate 2 and 24C. $^1$H NMR (400 MHz, Methanol-d$_4$) δ ppm 1.29 (d, J=6.15 Hz, 6H) 1.36 (t, J=7.03 Hz, 3H) 3.74 (s, 3H) 3.99 (q, J=7.03 Hz, 2H) 4.47 (m, 3H) 5.07 (s, 1H) 6.61 (d, J=2.20 Hz, 1H) 6.77 (d, J=7.03 Hz, 1H) 6.97 (t, J=8.13 Hz, 2H) 7.06 (m, 2H) 7.15 (dd, J=9.23, 2.20 Hz, 1H) 7.30 (d, J=7.03 Hz, 1H) 7.75 (m, 2H) 8.06 (d, J=9.23 Hz, 1H) 8.61 (t, J=5.93 Hz, 1H). LS-MS 594 (M+H).

Example 25

N-(3-(Aminosulfonyl)aminobenzyl)-2-(1-aminoisoquinolin-6-ylamino)-2-(3-ethoxy-4-isopropoxyphenyl)acetamide trifluoroacetic acid salt

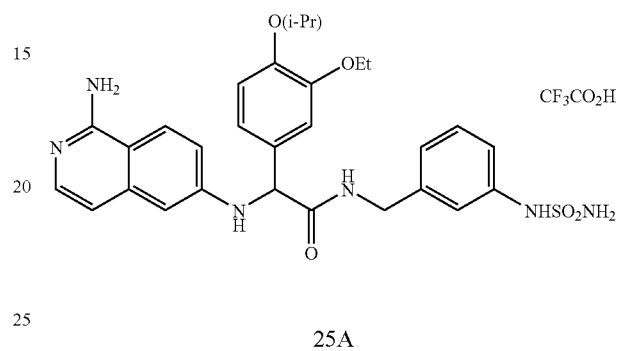

25A

Benzyl chlorosulfonylcarbamate

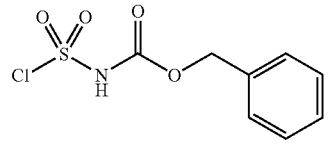

To a solution of chlorosulfonyl isocynate (5.0 mL, 57.4 mmol) in CH$_2$Cl$_2$ (20 mL) at 0° C., benzyl alcohol (5.94 mL, 57.4 mmol) was added slowly. After completion of addition, the cooling bath was removed and stirred at rt for 30 min. Evaporation of the volatile and trituration with petroleum ether gave 25A as white solid product.

25B

[(3-Cyanophenylamino)sulfonyl] carbamic acid phenylmethyl ester

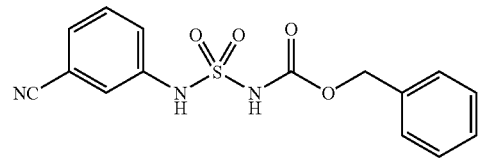

A mixture of 3-aminobenzonitrile (119 mg, 1.0 mmol), 25A (287 mg, 1.15 mmol) and Et$_3$N (0.174 mL, 1.2 mmol) in CH$_2$Cl$_2$ (5.0 mL) was stirred at rt over night. It was diluted with EtOAc, washed with 1.0 N HCl, sat. NaHCO$_3$ and brine. After drying over Na$_2$SO$_4$ and evaporation of solvent, 25B was obtained as a solid with sufficient purity for next step. $^1$H NMR (400 MHz, DMSO-d$_6$) δ ppm 5.05 (s, 2H) 7.20 (m, 2H) 7.29 (m, 3H) 7.41 (m, 1H) 7.49 (m, 3H).

25C 3-(Aminosulfonyl)amino benzylamine

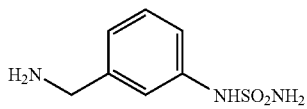

To a solution of 25B (200 mg) in MeOH (8 mL), Pd/C (10% by weight, 61 mg) and 4.0 N HCl in dioxane (2.0 eq) were added. This mixture was hydrogenated with a H$_2$ balloon for 4 h. After filtration and concentration, the product 25C was obtained as HCl salt. $^1$H NMR (400 MHz, DMSO-d$_6$) δ ppm 3.93 (d, J=5.71 Hz, 2H) 7.08 (d, J=8.35 Hz, 2H) 7.19 (s, 2H) 7.28 (m, 2H) 8.47 (s, 3H) 9.69 (s, 1H).

25D

Example 25 was prepared according to the general coupling-deprotection using Intermediate 2 and 25C. $^1$H NMR (400 MHz, Methanol-d$_4$) δ ppm 1.29 (d, J=6.15 Hz, 6H) 1.36 (t, J=7.03 Hz, 3H) 3.99 (t, J=7.03 Hz, 2H) 4.37 (d, J=4.39 Hz, 2H) 4.52 (m, 1H) 5.07 (s, 1H) 6.65 (d, J=2.20 Hz, 1H) 6.82 (m, 2H) 6.96 (d, J=8.35 Hz, 1H) 7.11 (m, 6H) 7.31 (d, J=7.03 Hz, 1H) 8.07 (d, J=9.23 Hz, 1H). LC-MS 579 (M+H).

Example 26

(R)-N-(3-(Aminosulfonyl)aminobenzyl)-2-(1-aminoisoquinolin-6-ylamino)-2-(3-ethoxy-4-isopropoxyphenyl)acetamide

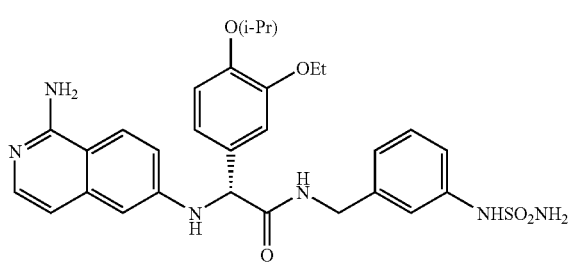

Example 26 (30 mg) was separated from the racemic mixture (110 mg) of Example 25 using a semi-preparative HPLC equipped with a Chiralpak® AD-H column (2 cm×25 m, 5µ). The separation was performed using an isocratic method of 40% ethanol/isopropanol (1:1) in heptane with 0.06% diethylamine and a flow rate of 12 mL/min. Retention time for Example 26 was 28 min. Retention time for the other isomer (33 mg) was 18 min. LC-MS 579 (M+H).

Example 27

3-((2-(1-Aminoisoquinolin-6-ylamino)-2-(3-ethoxy-4-isopropoxyphenyl)acetamido)methyl)phenyl sulfamate trifluoroacetic acid salt

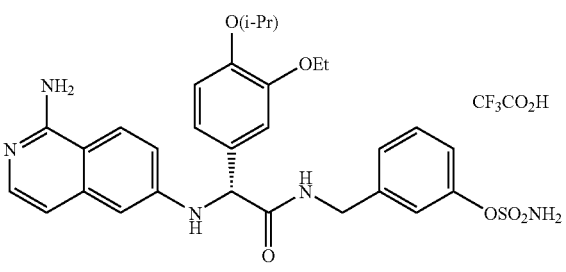

27A

Sulfamoyl chloride

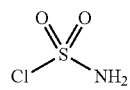

Formic acid (1.0 mL, 26.5 mmol) was added dropwise to chlorosulfonyl isocyanate (2.31 mL, 26.5 mmol) at 0° C. At the end of addition, stirring continued at rt for 3.0 h. Anhydrous toluene (20 mL) was added. The insoluble was filtered. The filtrate was condensed (<30° C.) to give 27A as a slightly yellow solid.

27B

3-Cyanophenyl sulfamate

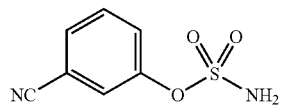

To a solution of 3-hydroxybenzonitrile (120 mg, 1.0 mmol) in DMA (2.0 mL) at 0° C., 27A (232 mg, 2.0 mmol) was added. Cooling bath was removed and the reaction was stirred at rt for 2 h. It was diluted with EtOAc, washed with sat. NaHCO$_3$ and brine, dried with Na$_2$SO$_4$. After evaporation of solvent, 27B was obtained as viscous oil that was sufficient pure for next step. $^1$H NMR (400 MHz, CDCl$_3$) δ ppm 5.79 (s, 2H) 7.52 (m, 1H) 7.59 (m, 2H) 7.64 (s, 1H).

27C 3-(Aminomethyl)phenyl sulfamate

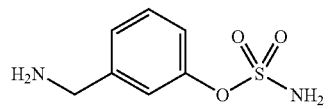

To a solution of 27B (200 mg) in MeOH (8 mL), Pd/C (10% by weight, 50 mg) and 4.0 N HCl in dioxane (2.0 eq) were added. This mixture was hydrogenated with a H₂ balloon over night. After filtration and concentration, 27C was obtained as HCl salt. ¹H NMR (400 MHz, DMSO-d₆) δ ppm 4.03 (q, J=5.71 Hz, 2H) 6.29 (s, 3H) 7.28 (d, J=7.47 Hz, 1H) 7.46 (m, 3H) 8.11 (s, 2H) 8.56 (s, 3H).

27D

Example 27 was prepared according to the general coupling-deprotection using Intermediate 2 and 27C. ¹H NMR (400 MHz, Methanol-d₄) δ ppm 1.29 (d, J=6.15 Hz, 6H) 1.37 (t, J=7.03 Hz, 3H) 4.02 (q, J=7.03 Hz, 2H) 4.46 (m, 3H) 5.08 (s, 1H) 6.67 (d, J=2.20 Hz, 1H) 6.82 (d, J=7.03 Hz, 1H) 6.97 (d, J=7.91 Hz, 1H) 7.09 (m, 4H) 7.17 (m, 2H) 7.26 (t, J=7.91 Hz, 1H) 7.32 (m, 1H) 8.08 (d, J=9.23 Hz, 1H) 8.89 (t, J=6.15 Hz, 1H). LC-MS 580 (M+H).

Example 28

2-(1-Amino-isoquinolin-6-ylamino)-N-(3,5-bis-acetylamino-benzyl)-2-(3-ethoxy-4-isopropoxy-phenyl)-acetamide trifluoroacetic acid salt

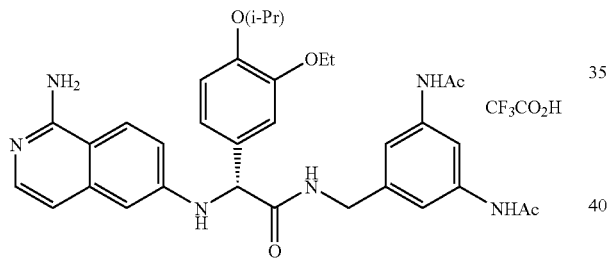

28A 3,5-Diaminobenzonitrile

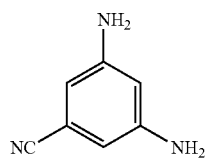

A solution of 3,5-dinitrobenzonitrile (194 mg), Pd/C (10% by weight, 40 mg) in EtOAc (8.0 mL) was hydrogenated with a H₂ balloon for 2.0 h at rt. After filtration and evaporation of solvent, 28A was obtained as sufficient pure for next step. ¹H NMR (400 MHz, CDCl₃) δ ppm 6.13 (s, 1H), 6.32 (s, 2H).

28B

N-(3-Acetylamino-5-cyano-phenyl)-acetamide

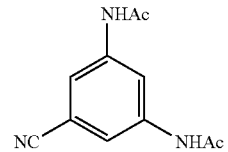

28A was stirred with acetic anhydride (0.57 mL, 6.0 eq) and pyridine (1.0 mL, 12 eq) in CH₂Cl₂ (2.0 mL) for 2.0 h. It was diluted with EtOAc, washed with 1.0 N HCl and brine. After drying over Na₂SO₄ and evaporation of solvent, 28B (110 mg) was obtained as solid. ¹H NMR (400 MHz, CDCl₃) δ ppm 9.58 (s, 2H), 7.85 (s, 1H), 7.44 (s, 2H), 1.87 (s, 6H).

28C

N-(3-Acetylamino-5-aminomethyl-phenyl)-acetamide

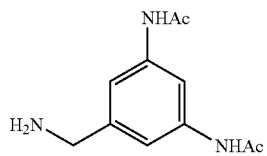

To a solution of 28B (110 mg) in MeOH (8 mL), Pd/C (10% by weight, 80 mg) and 4.0 N HCl in dioxane (0.25 mL, 2.0 eq) were added. This mixture was hydrogenated with a H₂ balloon for 3.0 h. After filtration and concentration, 28C, contaminated with N-(3-amino-5-aminomethyl-phenyl)-acetamide (ca 30%), was obtained as HCl salt.

28D

Example 28 was prepared according to the general coupling-deprotection using Intermediate 2 and 28C. ¹H NMR (400 MHz, Methanol-d₄) δ ppm 1.28 (d, J=6.15 Hz, 6H) 1.35 (m, 3H) 2.07 (s, 6H) 3.97 (m, 3H) 4.27 (m, 1H) 4.38 (m, 1H) 4.51 (m, 1H) 5.03 (s, 1H) 6.61 (d, J=1.76 Hz, 1H) 6.75 (d, J=7.03 Hz, 1H) 6.94 (m, 1H) 7.05 (m, 2H) 7.17 (m, 3H) 7.29 (d, J=7.47 Hz, 1H) 7.68 (s, 1H) 8.05 (m, 1H) 8.83 (t, J=5.71 Hz, 1H). LS-MS 599 (M+H).

Example 29

N-(3-Acetylamino-5-amino-benzyl)-2-(1-amino-isoquinolin-6-ylamino)-2-(3-ethoxy-4-isopropoxy-phenyl)-acetamide trifluoroacetic acid salt

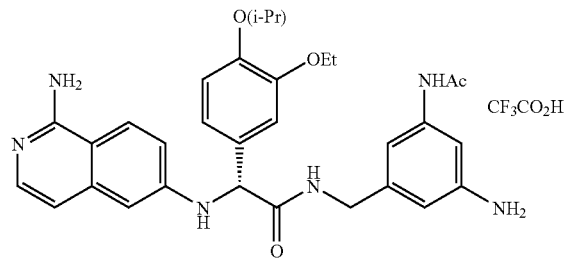

Example 29 was isolated as a minor product from Example 28 from hydrolysis of one acetamide. $^1$H NMR (400 MHz, Methanol-$d_4$) δ ppm 1.28 (d, J=6.15 Hz, 6H) 1.35 (t, J=7.03 Hz, 3H) 2.10 (s, 3H) 3.98 (m, 2H) 4.42 (m, 2H) 5.06 (s, 1H) 6.62 (d, J=1.76 Hz, 1H) 6.77 (d, J=7.03 Hz, 1H) 6.91 (s, 1H) 6.95 (d, J=8.35 Hz, 1H) 7.05 (m, 2H) 7.18 (dd, J=9.23, 2.20 Hz, 1H) 7.24 (s, 1H) 7.30 (d, J=7.03 Hz, 1H) 7.69 (s, 1H) 8.08 (d, J=9.23 Hz, 1H) 8.94 (t, J=5.93 Hz, 1H). LC-MS 557(M+H).

Example 30

N-(3-(Aminosulfonyl)aminobenzyl)-2-(1-aminoiso-quinolin-6-ylamino)-2-(3,4-dimethoxyphenyl)aceta-mide trifluoroacetic acid salt

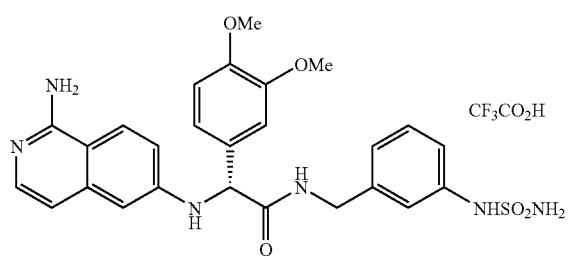

Example 30 was prepared according to the general coupling-deprotection using Intermediate 4 and 25C. $^1$H NMR (400 MHz, Methanol-$d_4$) δ ppm 3.78 (s, 3H) 3.81 (s, 3H) 4.36 (m, 2H) 5.09 (s, 1H) 6.65 (d, J=2.20 Hz, 1H) 6.79 (d, J=7.03 Hz, 1H) 6.84 (d, J=7.91 Hz, 1H) 6.95 (d, J=9.23 Hz, 1H) 7.11 (m, 6H) 7.30 (d, J=7.03 Hz, 1H) 8.06 (d, J=9.23 Hz, 1H) 8.82 (t, J=6.15 Hz, 1H). LC-MS 537 (M+H).

Example 31

N-[3-(Acetyl-methyl-amino)-benzyl]-2-(1-amino-isoquinolin-6-ylamino)-2-(3-ethoxy-4-isopropoxy-phenyl)-acetamide trifluoroacetic acid salt

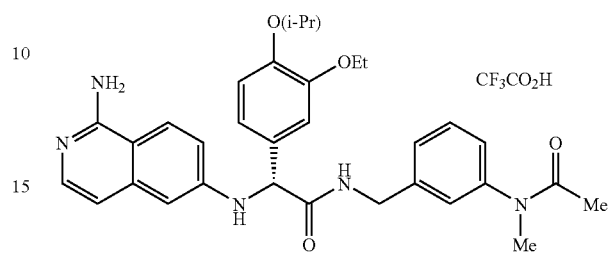

Example 31 was prepared according to the general coupling-deprotection using Intermediate 2 and N-(3-(aminomethyl)phenyl)-N-methylacetamide. $^1$H NMR (400 MHz, DMSO-$d$) δ ppm 1.23 (dd J=5.99, 1.83 Hz, 6H) 1.30 (t, J=6.97 Hz, 3H) 1.61 (s, 3H) 2.99 (s, 3H) 3.97 (q, J=7.09 Hz, 3H) 4.31 (m, 2H) 4.47 (m, 1H) 5.16 (d, J=6.85 Hz, 1H) 6.67 (s, 1H) 6.78 (d, J=7.09 Hz, 1H) 6.91 (d, J=8.56 Hz, 1H) 6.98 (s, 1H) 7.02 (m, 1H) 7.12 (m, 2H) 7.17 (d, J=2.20 Hz, 1H) 7.27 (m, 2H) 7.41 (m, 1H) 7.61 (d, J=6.85 Hz, 1H) 8.15 (d, J=9.29 Hz, 1H) 8.35 (s, 2H) 8.88 (t, J=5.99 Hz, 1H) 12.20 (s, 1H). LC-MS 556 (M+H).

Example 32

5-((2-(1-Aminoisoquinolin-6-ylamino)-2-(3-ethoxy-4-isopropoxyphenyl)acetamido)methyl)isophthala-mide trifluoroacetic acid salt

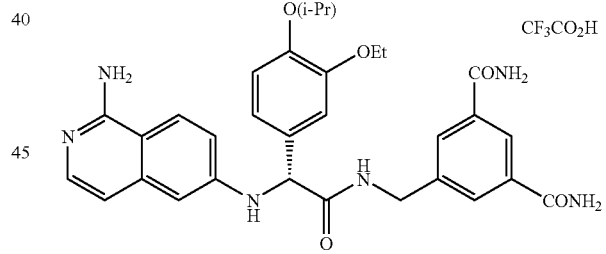

32A

Diethyl 5-(azidomethyl)isophthalate

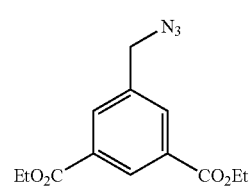

To a solution of diethyl 5-(hydroxymethyl)isophthalate (1.0 g, 3.96 mmol) and diiphenylphosphoryl azide (1.30 g, 4.75 mmol) in toluene (10 mL) at 0° C., 1,8-diazabicyclo[5.4.0]undec-7-ene (0.66 g, 4.35 mmol) was added. The reaction mixture was warmed to rt and stirred overnight. It was then washed with water and then 10% citric acid. The organic layer was dried over sodium sulfate, filtered and concentrated in vacuo. The crude product was purified by flash column chromatography (1:4 ethyl acetate/hexanes) to yield 1.1 g of white crystalline 32A.

32B 5-(Azidomethyl)isophthalic acid

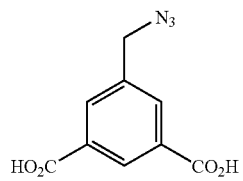

To a solution of 32A (0.5 g, 1.8 mmol) in THF (15 mL) and ethanol (2 mL) 1N LiOH (9 mL) was added. The reaction mixture was stirred overnight at rt and then neutralized and acidified with 1N HCl to pH 3-4. The aqueous layer was extracted with ethyl acetate and then the organic layer was dried over sodium sulfate, filtered and concentrated in vacuo to give 0.33 g (89%) of white solid 32B.

32C 5-(Azidomethyl)isophthalamide

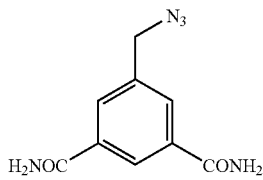

To a solution of 32B (0.3 g, 1.44 mmol) in DMF (5 mL) pyridine (0.23 mL, 2.88 mmol) was added and followed by di-t-butyl dicarbonate (0.95 g, 4.34 mmol) and ammonium bicarbonate 0.34 g, 4.34 mmol). The reaction was stirred overnight at rt and then poured into cold water. The product precipitated and filtered to give 0.19 g (97%) of white solid 32C.

32D 5-(Aminomethyl)isophthalamide

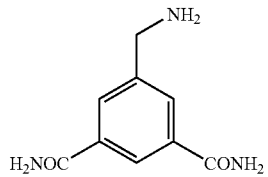

To a solution of 32C (0.05 g, 0.24 mmol) in methanol (30 mL), 10% Pd/C (20 mg) was added under nitrogen and then a balloon filled with hydrogen gas was introduced. The reaction was stirred for 1 h at rt. The catalyst was filtered off and the solvent was removed to give 0.034 g (72%) of white solid 32D. $^1$H NMR (400 MHz, DMSO-d$_6$) (ppm 1.96 (s, 2H) 3.78 (s, 2H) 7.39 (s, 2H) 7.95 (d, J=1.71 Hz, 4H) 8.17 (s, 1H).

32E

Example 32 was prepared according to the general coupling-deprotection using Intermediate 2 and 32D. $^1$H NMR (400 MHz, DMSO-d$_6$) δ ppm 1.22 (d, J=6.11 Hz, 6H) 1.29 (t, J=6.97 Hz, 3H) 3.94 (q, J=6.77 Hz, 2H) 4.26 (m, 2H) 4.44 (m, 2H) 5.17 (d, J=7.09 Hz, 1H) 6.59 (m, 1H) 6.79 (d, J=7.34 Hz, 1H) 6.90 (d, J=8.56 Hz, 1H) 6.99 (d, J=10.27 Hz, 1H) 7.10 (d, J=1.96 Hz, 1H) 7.24 (m, 1H) 7.38 (m, 1H) 7.43 (s, 2H) 7.59 (d, J=7.34 Hz, 1H) 7.91 (d, J=1.22 Hz, 2H) 7.93 (s, 2H) 8.13 (d, J=9.05 Hz, 1H) 8.21 (s, 1H) 8.28 (s, 2H) 8.91 (t, J=5.99 Hz, 1H) 12.07 (s, 1H). LS-MS 571 (M+H).

Example 33

1-(3-((2-(1-Aminoisoquinolin-6-ylamino)-2-(3-ethoxy-4-isopropoxyphenyl)acetamido)methyl)phenyl)-3-methylurea trifluoroacetic acid salt

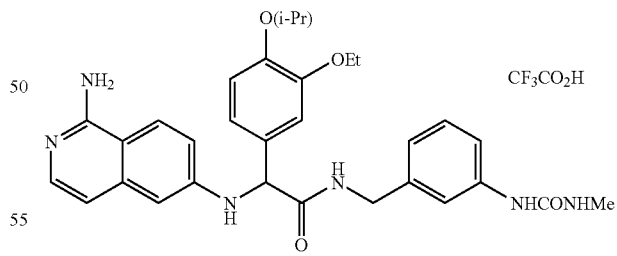

Example 33 was prepared according to the general coupling-deprotection using Intermediate 2 and 1-(3-(aminomethyl)phenyl)-3-methylurea. $^1$H NMR (400 MHz, DMSO-d$_6$) δ ppm 1.29 (t, J=6.97 Hz, 3H) 2.62 (d, J=4.40 Hz, 3H) 3.96 (q, J=6.93 Hz, 2H) 4.21 (m, 2H) 4.45 (m, 2H) 5.15 (d, J=6.85 Hz, 1H) 5.96 (q, J=4.40 Hz, 1H) 6.61 (s, 1H) 6.66 (d, J=7.34 Hz, 1H) 6.79 (d, J=7.09 Hz, 1H) 6.92 (d, J=8.31 Hz, 1H) 7.00 (d, J=1.96 Hz, 1H) 7.06 (t, J=7.70 Hz, 1H) 7.13 (d, J=1.96 Hz, 1H) 7.22 (d, J=9.54 Hz, 1H) 7.26 (s, 1H) 7.31 (s, 1H) 7.40 (m, 1H) 7.58 (d, J=6.85 Hz, 1H) 8.15 (d, J=9.29 Hz, 1H) 8.32 (s, 2H) 8.44 (s, 1H) 8.80 (t, J=5.99 Hz, 1H) 12.14 (d, J=3.18 Hz, 1H). LC-MS 557 (M+H).

Example 34

Methyl 3-((2-(1-aminoisoquinolin-6-ylamino)-2-(3-ethoxy-4-isopropoxyphenyl)acetamido)methyl)phenylcarbamate trifluoroacetic acid salt

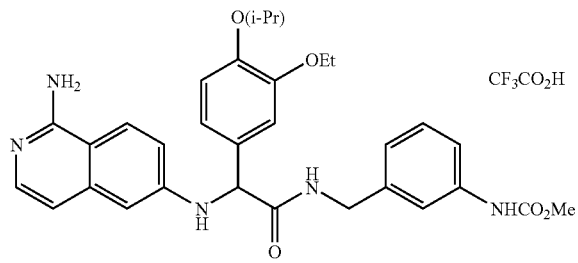

34A

Methyl 3-cyanophenylcarbamate

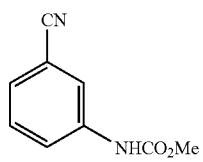

To 3-aminobenzonitrile (1.0 g, 8.46 mmol) in $CH_2Cl_2$ and $Et_3N$ (1.77 mL, 12.7 mmol), methyl chloroformate (0.98 mL, 12.7 mmol) was added. The reaction was stirred at rt overnight and then the solvent was evaporated and dried under vacuo. The crude residue was purified by flash column chromatography (1:1 ethyl acetate/hexanes) to give 34A (0.31 g, 21% yield).

34B methyl 3-(aminomethyl)phenylcarbamate

To 34A (0.31 g, 1.75 mmol) in methanol (30 mL) under nitrogen, 10% Pd/C (0.10 g) and conc. HCl (0.1 mL) were added and then a balloon filled with hydrogen gas was introduced. The reaction was stirred for 3 h at rt. The catalyst was filtered off and the solvent was removed to give 0.37 g of 34B as HCl salt. $^1$H NMR (400 MHz, DMSO-$d_6$) δ ppm 3.65 (s, 3H) 3.92 (q, J=5.79 Hz, 2H) 4.89 (m, 1H) 7.15 (d, J=7.58 Hz, 1H) 7.30 (t, J=7.95 Hz, 1H) 7.41 (d, J=8.31 Hz, 1H) 7.54 (s, 1H) 8.48 (s, 1H) 9.78 (s, 1H).

34C

Example 34 was prepared according to the general coupling-deprotection using Intermediate 2 and 34B. $^1$H NMR (400 MHz, DMSO-$d_6$) δ ppm 1.22 (d, J=6.11 Hz, 6H) 1.29 (t, J=6.97 Hz, 3H) 3.63 (s, 3H) 3.96 (q, J=7.09 Hz, 2H) 4.23 (m, 2H) 4.45 (m, 1H) 5.14 (d, J=6.85 Hz, 1H) 6.62 (s, 1H) 6.77 (m, 2H) 6.91 (d, J=8.31 Hz, 1H) 7.01 (m, 1H) 7.13 (m, 2H) 7.26 (m, 2H) 7.37 (s, 1H) 7.41 (m, J=6.85 Hz, 1H) 7.58 (d, J=7.09 Hz, 1H) 8.15 (d, J=9.29 Hz, 1H) 8.34 (d, J=6.85 Hz, 2H) 8.83 (t, J=5.87 Hz, 1H) 9.58 (s, 1H) 12.21 (s, 1H). LC-MS 558 (M+H).

Example 35

N-(3-((2-(1-Aminoisoquinolin-6-ylamino)-2-(3-ethoxy-4-isopropoxyphenyl)acetamido)methyl)phenyl)propionamide trifluoroacetic acid salt

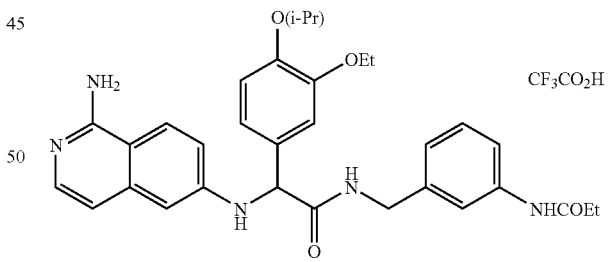

Example 35 was prepared according to the general coupling-deprotection using Intermediate 2 and N-(3-(aminomethyl)phenyl)propionamide. $^1$H NMR (400 MHz, Methanol-$d_4$) δ ppm 1.17 (t, J=7.58 Hz, 3H) 1.29 (d, J=6.11 Hz, 6H) 1.35 (t, J=6.97 Hz, 3H) 2.35 (q, J=7.74 Hz, 2H) 3.98 (m, 2H) 4.37 (t, J=6.11 Hz, 2H) 4.52 (m, 1H) 5.05 (s, 1H) 6.64 (d, J=2.20 Hz, 1H) 6.78 (d, J=7.09 Hz, 1H) 6.88 (d, J=7.58 Hz, 1H) 6.95 (d, J=8.07 Hz, 1H) 7.07 (m, 2H) 7.16 (m, 2H) 7.30 (d, J=7.09 Hz, 1H) 7.36 (d, J=8.56 Hz, 1H) 7.46 (d, J=1.71 Hz, 1H) 8.07 (d, J=9.05 Hz, 1H) 8.79 (t, J=5.99 Hz, 1H) 9.64 (s, 1H). LC-MS 556 (M+H).

Example 36

2-(1-Amino-isoquinolin-6-ylamino)-2-(3-ethoxy-4-isopropoxy-phenyl)-N-[1-(3-sulfamoyl-phenyl)-ethyl]-acetamide trifluoroacetic acid salt

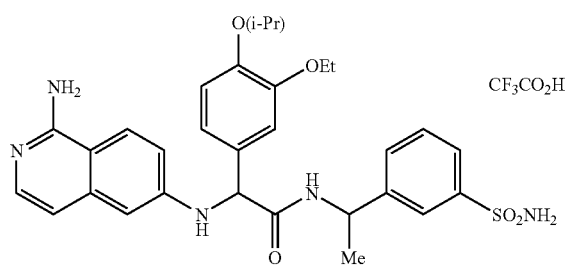

36A 3-tert-Butylsulfamoyl-N-methoxy-N-methyl-benzamide

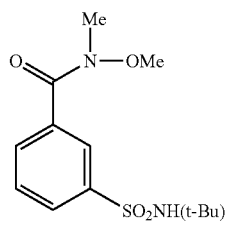

To 3-(t-butylsulfonamide)benzoic acid (2.0 g, 7.8 mmol) in CH$_2$Cl$_2$ (50 mL), HOAt (2.1 g, 15.5 mmol) and N-methoxymethanamine hydrochloride (1.3 g, 13.6 mmol) were added, followed by N-methylmorpholine (2.5 mL, 23.2 mmol) and EDC (2.97 g, 15.5 mmol). The reaction mixture was stirred overnight at rt and then washed with water and brine. The organic layer was dried over Na$_2$SO$_4$ and solvent was evaporated. The crude residue was purified by flash column chromatography to yield 36A (1.5 g, 64%) as a white solid.

36B

3-Acetyl-N-tert-butylbenzenesulfonamide

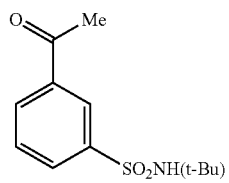

To 36A (1.11 g, 3.69 mmol) in THF (20 mL) at −78° C., MeMgBr (3 M in ether, 3.7 mL, 11.1 mmol) was added dropwise. The reaction mixture was stirred at −78° C. for 20 min and then warmed to rt. Stirring was continued for 24 h at rt before saturated NH$_4$Cl was added at −78° C. The product was extracted with ether and the organic layer was washed with water, brine and dried over Na$_2$SO$_4$. The solvent was evaporated to yield 36B (0.86 g, 90%) as a colorless semi-solid.

36C 3-(1-Aminoethyl)-N-tert-butylbenzenesulfonamide

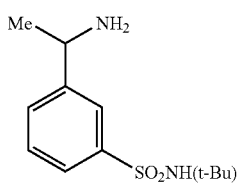

To a solution of 36B (0.3 g, 1.17 mmol) in methanol (3 mL), a solution of ammonium acetate (0.9 g, 11.7 mmol) and NaCNBH$_3$ (0.1 g, 1.64 mmol) in methanol (4 mL) was added. The resulting reaction mixture was stirred at rt for 48 h. The reaction was acidified to pH 2 using 1 N HCl and then the solvent evaporated. The residue was redissolved in water and then extracted with ether. The aqueous layer was basified to pH 10 using solid NaOH and then extracted with EtOAc. The organic extracts were dried over Na$_2$SO$_4$ and concentrated. Purification was performed by prep HPLC to give 36C (0.19 g) as a colorless semi-solid.

36D 3-(1-Aminoethyl)benzenesulfonamide

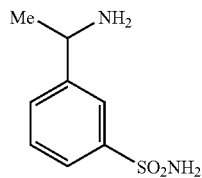

To 36C (0.12 g, 0.49 mmol), trifluoracetic acid (5 mL) was added and stirred at rt overnight. The reaction product was concentrated and placed under vacuo for 1 h. The residue was dissolved in methanol and A base resin (Supelco Diaion WA21J resin, 0.2 g) was added. The mixture was stirred for 30 min and then filtered and concentrated to give 36D (0.08 g, 82%). $^1$H NMR (400 MHz, Methanol-d$_4$) δ ppm 1.37 (d, J=6.60 Hz, 3H) 4.28 (q, J=6.60 Hz, 1H) 5.64 (m, 2H) 7.32 (m, 2H) 7.55 (t, J=7.70 Hz, 1H) 7.63 (m, 1H) 7.74 (m, 1H) 7.90 (t, J=1.71 Hz, 1H).

36E

Example 36 was prepared according to the general coupling-deprotection using Intermediate 2 and 36D. $^1$H NMR (400 MHz, Methanol-d$_4$) δ ppm 1.28 (m, 6H) 1.32 (m, 3H) 1.47 (m, 3H) 3.97 (m, 2H) 4.52 (m, 1H) 5.08 (m, 2H) 6.60 (dd, J=20.17, 2.08 Hz, 1H) 6.78 (m, 1H) 6.95 (m, 1H) 7.14 (m, 5H) 7.69 (m, 3H) 8.05 (t, J=9.29 Hz, 1H). LC-MS 578 (M+H).

Example 37

2-(1-Amino-isoquinolin-6-ylamino)-N-[1-(3-tert-butylsulfamoyl-phenyl)-ethyl]-2-(3-ethoxy-4-isopropoxy-phenyl)-acetamide trifluoroacetic acid salt

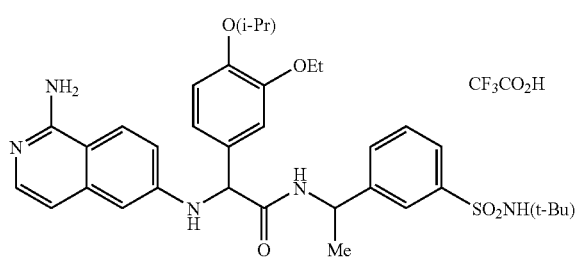

Example 37 was prepared according to the general coupling-deprotection using Intermediate 2 and 36C. ¹H NMR (400 MHz, Methanol-d₄) δ ppm 1.09 (m, 9H) 1.29 (m, 6H) 1.38 (m, 3H) 1.44 (m, 3H) 4.00 (m, 2H) 4.52 (m, 1H) 5.09 (m, 2H) 7.05 (m, 9H) 7.64 (m, 3H) 8.06 (t, J=9.66 Hz, 1H) 8.85 (dd, J=45.97, 7.58 Hz, 1H). LC-MS 634 (M+H).

Example 38

N-(3-((2-(1-Aminoisoquinolin-6-ylamino)-2-(3-ethoxy-4-isopropoxyphenyl)acetamido)methyl)phenyl)butyramide trifluoroacetic acid salt

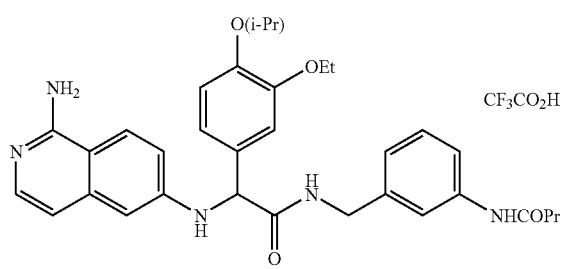

38A

N-(3-(Aminomethyl)phenyl)butyramide

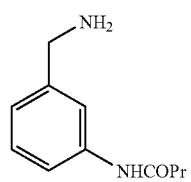

38A was prepared by hydrogenation of N-(3-cyanophenyl)butyramide in MeOH/HCl with 10% Pd/C and a hydrogen balloon. ¹H NMR (400 MHz, DMSO-d₆) δ ppm 0.90 (m, 3H) 1.59 (m, 2H) 2.27 (m, 2H) 3.89 (s, 2H) 7.12 (dd, J=7.95, 1.59 Hz, 1H) 7.29 (t, J=7.83 Hz, 1H) 7.49 (m, 1H) 7.73 (s, 1H) 10.03 (s, 1H).

38B

Example 38 was prepared according to the general coupling-deprotection using Intermediate 2 and 38A. ¹H NMR (400 MHz, DMSO-d₆) δ ppm 0.89 (t, J=7.34 Hz, 3H) 1.22 (d, J=6.11 Hz, 6H) 1.29 (t, J=6.97 Hz, 3H) 1.58 (m, 2H) 2.24 (t, J=7.34 Hz, 2H) 3.95 (q, J=6.85 Hz, 2H) 4.24 (m, 2H) 4.45 (m, 1H) 5.15 (d, J=7.09 Hz, 1H) 6.62 (s, 1H) 6.79 (t, J=7.21 Hz, 3H) 6.92 (d, J=8.31 Hz, 1H) 7.01 (m, 1H) 7.13 (m, 3H) 7.25 (d, J=11.00 Hz, 1H) 7.40 (m, 3H) 7.54 (s, 1H) 7.58 (d, J=7.09 Hz, 1H) 8.15 (d, J=9.29 Hz, 1H) 8.35 (s, 3H) 8.83 (t, J=5.87 Hz, 1H) 9.81 (s, 1H) 12.21 (s, 1H). LC-MS 570 (M+H).

Example 39

N-(3-(Dimethylamino)benzyl)-2-(1-aminoisoquinolin-6-ylamino)-2-(3-ethoxy-4-isopropoxyphenyl)acetamide trifluoroacetic acid salt

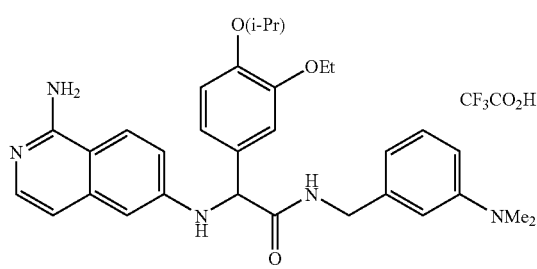

Example 39 was prepared according to the general coupling-deprotection using Intermediate 2 and 3-dimethylaminobenzylamine. ¹H NMR (400 MHz, DMSO-d₆) (ppm 1.22 (d, J=5.87 Hz, 6H) 1.29 (t, J=6.97 Hz, 3H) 2.78 (m, 6H) 3.96 (q, J=7.09 Hz, 2H) 4.23 (m, 2H) 4.46 (m, 1H) 5.16 (d, J=6.85 Hz, 1H) 6.46 (d, J=7.34 Hz, 1H) 6.57 (d, J=9.29 Hz, 1H) 6.64 (s, 1H) 6.77 (d, J=7.09 Hz, 1H) 6.92 (d, J=8.31 Hz, 1H) 7.03 (m, 2H) 7.16 (d, J=1.96 Hz, 1H) 7.25 (d, J=8.31 Hz, 1H) 7.41 (dd, J=6.60, 5.62 Hz, 1H) 7.60 (d, J=7.09 Hz, 1H) 8.15 (d, J=9.05 Hz, 1H) 8.35 (s, 2H) 8.78 (t, J=5.75 Hz, 1H) 12.21 (s, 1H). LC-MS 528 (M+H).

Example 40

N-(3-((2-(1-Aminoisoquinolin-6-ylamino)-2-(3-ethoxy-4-isopropoxyphenyl)acetamido)methyl)phenyl)cyclopropanecarboxamide butyramide trifluoroacetic acid salt

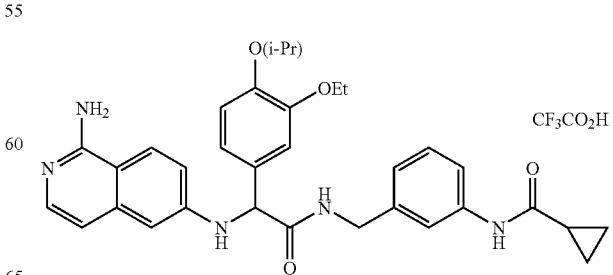

40A

N-(3-(Aminomethyl)phenyl)cyclopropanecarboxamide

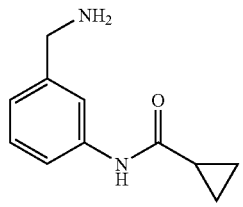

40A was prepared by hydrogenation of N-(3-cyanophenyl)cyclopropanecarboxamide in MeOH/HCl with 10% Pd/C and a hydrogen balloon. $^1$H NMR (400 MHz, DMSO-$d_6$) δ ppm 0.78 (d, J=6.11 Hz, 4H) 1.83 (m, 1H) 3.95 (d, J=5.62 Hz, 2H) 7.13 (d, J=7.83 Hz, 1H) 7.32 (t, J=7.83 Hz, 1H) 7.49 (d, J=9.05 Hz, 1H) 7.78 (s, 1H) 8.29 (s, 2H) 10.39 (s, 1H).

40B

Example 40 was prepared according to the general coupling-deprotection using Intermediate 2 and 40A. $^1$H NMR (400 MHz, DMSO-$d_6$) (ppm 0.77 (d, J=6.11 Hz, 4H) 1.22 (d, J=6.11 Hz, 6H) 1.29 (t, J=6.97 Hz, 3H) 1.75 (m, 1H) 3.96 (q, J=7.09 Hz, 2H) 4.24 (m, 2H) 4.45 (m, 1H) 5.14 (d, J=6.85 Hz, 1H) 6.62 (s, 1H) 6.79 (t, J=7.34 Hz, 2H) 6.91 (d, J=8.31 Hz, 1H) 7.01 (m, 1H) 7.13 (m, 2H) 7.24 (d, J=8.31 Hz, 1H) 7.39 (d, J=7.09 Hz, 2H) 7.54 (s, 1H) 7.58 (d, J=7.09 Hz, 1H) 8.15 (d, J=9.29 Hz, 1H) 8.35 (s, 2H) 8.83 (t, J=5.75 Hz, 1H) 10.13 (s, 1H) 12.20 (s, 1H). LC-MS 568 (M+H).

Example 41

1-(3-((2-(1-Aminoisoquinolin-6-ylamino)-2-(3-ethoxy-4-isopropoxyphenyl)acetamido)methyl)phenyl)urea trifluoroacetic acid salt

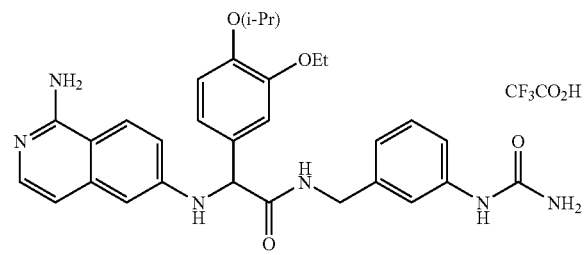

41A

1-(3-Cyanophenyl)urea

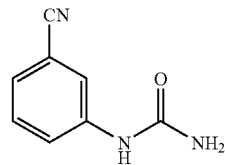

To 3-cyanophenyl isocyanate (1.0 g, 6.90 mmol) in THF (5 mL), ammonium hydroxide (1.7 mL, 13.8 mmol) was added. The reaction was stirred for 2 h at rt. The solvent was evaporated and the crude residue was redissolved in ethyl acetate. The organic layer was washed with water and brine and dried over sodium sulfate. The solvent was evaporated and the crude residue was purified by flash column chromatography to 41A (0.37 g).

41B 1-(3-(Aminomethyl)phenyl)urea

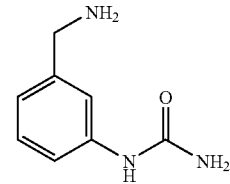

To 41A (0.37 g, 2.29 mmol) in methanol (15 mL) under nitrogen, 10% Pd/C (45 mg) and conc HCl (0.1 mL) were added and then a balloon filled with hydrogen gas was introduced. The reaction was stirred overnight at rt. The catalyst was filtered off and the solvent was removed to give 41B (0.36 g, 78%) as HCl salt. $^1$H NMR (400 MHz, DMSO-$d_6$) δ ppm 3.91 (q, J=5.79 Hz, 2H) 5.64 (s, 2H) 7.00 (d, J=7.58 Hz, 1H) 7.23 (t, J=7.83 Hz, 1H) 7.37 (d, J=8.31 Hz, 1H) 7.51 (s, 1H) 8.33 (s, 2H) 8.96 (s, 1H).

41C

Example 41 was prepared according to the general coupling-deprotection using Intermediate 2 and 41B. $^1$H NMR (400 MHz, DMSO-$d_6$) δ ppm 1.22 (d, J=6.11 Hz, 6H) 1.30 (t, J=6.97 Hz, 3H) 3.96 (q, J=6.85 Hz, 2H) 4.22 (m, 2H) 4.46 (m, 1H) 5.15 (d, J=7.58 Hz, 1H) 5.80 (s, 2H) 6.62 (s, 1H) 6.67 (d, J=7.83 Hz, 1H) 6.80 (d, J=7.09 Hz, 1H) 6.92 (d, J=8.56 Hz, 1H) 7.00 (m, 1H) 7.06 (t, J=7.83 Hz, 1H) 7.13 (d, J=1.96 Hz, 1H) 7.21 (d, J=8.07 Hz, 1H) 7.25 (m, 1H) 7.32 (s, 1H) 7.41 (d, J=6.36 Hz, 1H) 7.58 (d, J=7.09 Hz, 1H) 8.15 (d, J=9.29 Hz, 1H) 8.30 (s, 2H) 8.46 (s, 1H) 8.80 (t, J=5.87 Hz, 1H) 12.08 (s, 1H). LC-MS 543 (M+H).

Example 42

N-(3-(Ethylamino)benzyl)-2-(1-aminoisoquinolin-6-ylamino)-2-(3-ethoxy-4-isopropoxyphenyl)acetamide trifluoroacetic acid salt

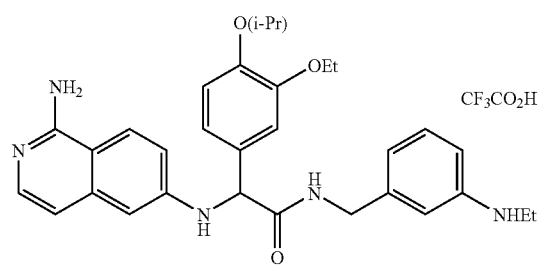

42A

N-(3-Cyanophenyl)-2,2,2-trifluoroacetamide

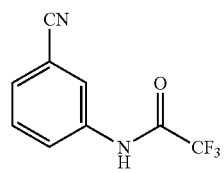

To 3-aminobenzonitrile (1.0 g, 8.46 mmol) in CH$_2$Cl$_2$ (15 mL) and pyridine (1.86 mL, 23.0 mmol) at 0° C., trifluoroacetic anhydride (1.8 mL, 12.7 mmol) was added. The reaction was allowed to warm to rt and stirred for 24 h. The solvent was evaporated and the crude residue was redissolved in ethyl acetate. The organic layer was washed with water and brine and dried over Na$_2$SO$_4$. The solvent was evaporated to give 42A (1.8 g) as an orange solid.

42B 3-(Ethylamino)benzonitrile

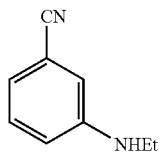

To 42A (0.50 g, 2.33 mmol) and K$_2$CO$_3$ (1.6 g, 11.65 mmol) in DMF (8 mL), ethyl iodide (0.37 mL, 4.66 mmol) was added. The reaction mixture was stirred at 50° C. for 3 h. Methanol and water added to the reaction and stirred further 24 h. The reaction mixture was extracted with ethyl acetate and washed with water and dried over Na$_2$SO$_4$. The solvent was evaporated and the crude residue was purified by flash column chromatography to give 42B (0.22 g, 65% yield) as a colorless oil.

42C 3-(Aminomethyl)-N-ethylbenzenamine

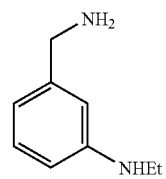

To 42B (0.22 g, 1.50 mmol) in methanol (8 mL) under nitrogen, 10% Pd/C (44 mg) and conc HCl (0.1 mL) were added and then a balloon filled with hydrogen gas was introduced. The reaction was stirred overnight at rt. The catalyst was filtered off and the solvent was removed to give 42C (0.246 g, 86%) as a white solid. $^1$H NMR (400 MHz, DMSO-d$_6$) δ ppm 1.14 (t, J=7.09 Hz, 3H) 3.02 (dd, J=7.09, 5.38 Hz, 2H) 3.74 (s, 2H) 5.54 (t, J=5.50 Hz, 1H) 6.06 (m, 2H) 6.47 (dd, J=7.70, 1.83 Hz, 1H) 6.54 (m, 2H) 7.03 (t, J=7.70 Hz, 1H).

42D

Example 42 was prepared according to the general coupling-deprotection using Intermediate 2 and 42C. $^1$H NMR (400 MHz, DMSO-d$_6$) δ ppm 1.28 (m, 9H) 1.36 (t, J=6.97 Hz, 3H) 3.28 (m, 2H) 4.48 (m, 3H) 5.11 (s, 2H) 6.68 (d, J=2.20 Hz, 1H) 6.82 (d, J=6.85 Hz, 1H) 6.96 (d, J=8.31 Hz, 1H) 7.07 (m, 1H) 7.12 (d, J=2.20 Hz, 1H) 7.19 (dd, J=9.17, 2.32 Hz, 1H) 7.28 (m, 3H) 7.33 (d, J=7.09 Hz, 1H) 7.41 (t, J=7.95 Hz, 1H) 8.09 (d, J=9.29 Hz, 1H) 8.98 (t, J=6.11 Hz, 1H). LC-MS 528 (M+H).

Example 43

N-(3-((2-(1-Aminoisoquinolin-6-ylamino)-2-(3-ethoxy-4-isopropoxyphenyl)acetamido)methyl)phenyl)isobutyramide trifluoroacetic acid salt

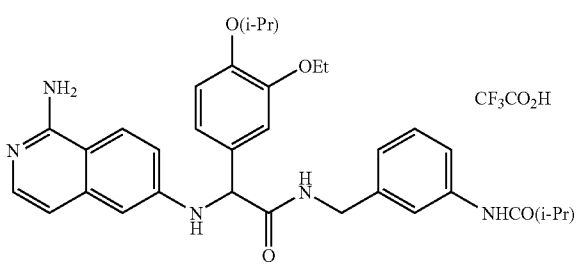

43A

N-(3-(Aminomethyl)phenyl)isobutyramide

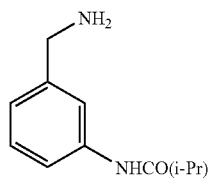

43A was prepared by hydrogenation of N-(3-cyanophenyl) isobutyramide in MeOH/HCl with 10% Pd/C and a hydrogen balloon. $^1$H NMR (400 MHz, Methanol-$d_4$) δ ppm 1.08 (d, J=6.85 Hz, 6H) 2.63 (m, 1H) 3.94 (s, 2H) 7.15 (d, J=7.83 Hz, 1H) 7.32 (t, J=7.83 Hz, 1H) 7.51 (dd, J=8.07, 0.98 Hz, 1H) 7.80 (s, 1H) 8.37 (s, 2H) 10.04 (s, 1H).

43B

Example 43 was prepared according to the general coupling-deprotection using Intermediate 2 and 43A. $^1$H NMR (400 MHz, Methanol-$d_4$) (ppm 1.17 (d, J=7.03 Hz, 6H) 1.29 (d, J=6.15 Hz, 6H) 1.35 (t, J=7.03 Hz, 3H) 2.58 (m, 1H) 3.98 (m, 2H) 4.37 (m, 2H) 4.52 (m, 1H) 5.06 (s, 1H) 6.64 (d, J=1.76 Hz, 1H) 6.78 (d, J=7.03 Hz, 1H) 6.89 (d, J=7.91 Hz, 1H) 6.95 (d, J=8.35 Hz, 1H) 7.06 (m, 2H) 7.16 (m, 2H) 7.30 (d, J=7.03 Hz, 1H) 7.38 (d, J=7.47 Hz, 1H) 7.49 (s, 1H) 8.07 (d, J=9.23 Hz, 1H) 8.81 (t, J=5.93 Hz, 1H) 9.63 (s, 1H). LC-MS 570 (M+H).

Example 44

N-(3-((2-(1-Aminoisoquinolin-6-ylamino)-2-(3-ethoxy-4-isopropoxyphenyl)acetamido)methyl)phenyl)-3-methylbutanamide trifluoroacetic acid salt

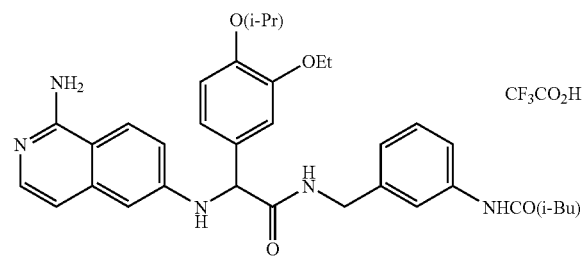

Example 44 was prepared according to the general coupling-deprotection using Intermediate 2 and N-(3-(aminomethyl)phenyl)-3-methylbutanamide. $^1$H NMR (400 MHz, Methanol-$d_4$) δ ppm 1.35 (t, J=7.03 Hz, 3H) 2.15 (m, 3H) 3.98 (m, 2H) 4.37 (m, 2H) 4.52 (m, 1H) 5.05 (s, 1H) 6.64 (d, J=1.76 Hz, 1H) 6.78 (d, J=7.03 Hz, 1H) 6.89 (d, J=7.47 Hz, 1H) 6.95 (d, J=8.35 Hz, 1H) 7.06 (m, 2H) 7.16 (m, 2H) 7.30 (d, J=7.03 Hz, 1H) 7.36 (d, J=7.91 Hz, 1H) 7.49 (s, 1H) 8.07 (d, J=9.23 Hz, 1H) 8.81 (t, J=5.93 Hz, 1H) 9.70 (s, 1H). LC-MS 584 (M+H).

Example 45

N-(3-Formamidobenzyl)-2-(1-aminoisoquinolin-6-ylamino)-2-(3-ethoxy-4-isopropoxyphenyl)acetamide trifluoroacetic acid salt

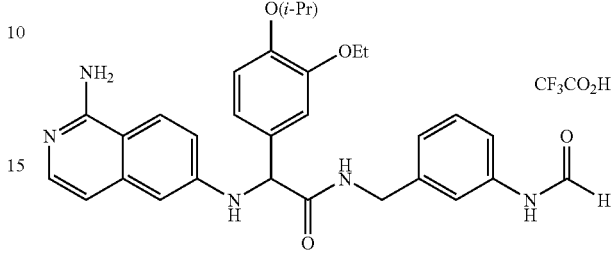

45A

Benzyl 3-formamidobenzylcarbamate

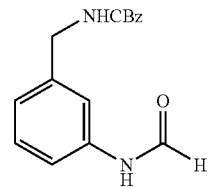

To acetic anhydride (7.96 g, 78.0 mmol), formic acid (5.88 mL, 156 mmol) was added over 10 min at rt. Benzy 3-aminoobenzylcarbamate (1.0 g, 3.9 mmol) in THF (10 mL) was then added to the reaction. The reaction was stirred at rt for 24 h. The solvent was evaporated and the crude residue was purified by flash column chromatography to yield 1.0 g of white solid 45A.

45B

N-(3-(Aminomethyl)phenyl)formamide

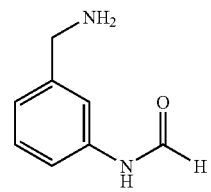

To 45A (0.21 g, 0.74 mmol) in methanol (15 mL) under nitrogen, 10% Pd/C (40 mg) was added and then a balloon filled with hydrogen gas was introduced. The reaction was stirred for 30 min at rt. The catalyst was filtered off and the solvent was removed to give 0.11 g of white solid 45B. $^1$H NMR (400 MHz, Methanol-$d_4$) δ ppm 1.86 (s, 2H) 3.68 (d, J=3.52 Hz, 2H) 7.04 (d, J=7.47 Hz, 1H) 7.23 (t, J=7.69 Hz, 1H) 7.41 (m, 1H) 7.51 (s, 1H) 8.24 (d, J=1.76 Hz, 1H) 10.12 (s, 1H).

45C

Example 45 was prepared according to the general coupling-deprotection using Intermediate 2 and 45B. $^1$H NMR (400 MHz, Methanol-$d_4$) δ ppm 1.30 (t, J=6.36 Hz, 6H) 1.36 (m, 3H) 3.99 (m, 2H) 4.37 (d, J=5.87 Hz, 2H) 4.52 (m, 1H) 5.05 (s, 1H) 6.64 (d, J=2.20 Hz, 1H) 6.77 (m, 1H) 6.95 (m, 2H) 7.07 (m, 2H) 7.17 (m, 2H) 7.31 (m, 1H) 7.37 (m, 1H) 7.48 (s, 1H) 8.07 (m, 1H) 8.33 (m, 1H) 8.83 (m, 1H). LC-MS 528 (M+H).

Example 46

N-(3-(Methylamino)benzyl)-2-(1-aminoisoquinolin-6-ylamino)-2-(3-ethoxy-4-isopropoxyphenyl)acetamide trifluoroacetic acid salt

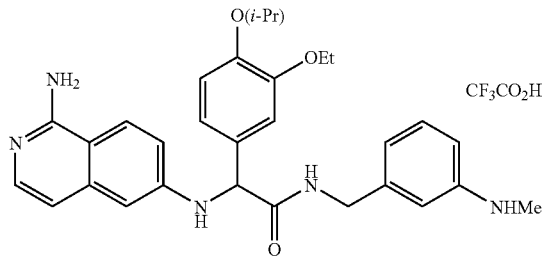

Example 46 was prepared according to the general coupling-deprotection using Intermediate 2 and 3-methylaminobenzylamine. $^1$H NMR (400 MHz, Methanol-$d_4$) δ ppm 1.29 (d, J=6.11 Hz, 6H) 1.35 (t, J=6.97 Hz, 3H) 2.94 (s, 3H) 4.00 (m, 2H) 4.47 (m, 3H) 5.10 (s, 1H) 6.68 (d, J=2.20 Hz, 1H) 6.81 (d, J=7.09 Hz, 2H) 6.96 (d, J=8.31 Hz, 1H) 7.15 (m, 6H) 7.36 (m, 2H) 8.08 (d, J=9.05 Hz, 1H) 8.95 (t, J=6.11 Hz, 1H). LC-MS 514 (M+H).

Example 47

N-[1-(3-Acetylamino-phenyl)-ethyl]-2-(1-amino-isoquinolin-6-ylamino)-2-(3-ethoxy-4-isopropoxy-phenyl)-acetamide trifluoroacetic acid salt

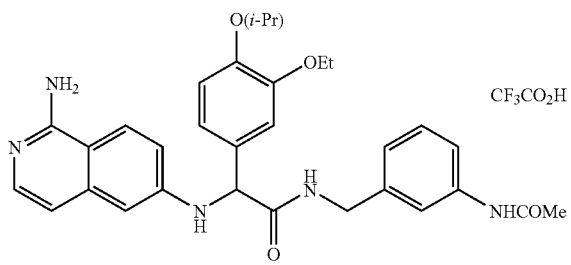

47A

N-(3-(1-Aminoethyl)phenyl)acetamide

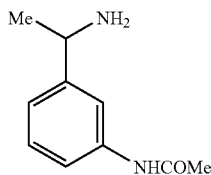

To a solution of N-(3-acetylphenyl)acetamide (1.0 g, 5.6 mmol) in methanol (10 mL), a solution of ammonium acetate (4.34 g, 56.4 mmol) and NaCNBH$_3$ (1.05 g, 16.8 mmol) in methanol (15 mL) was added. The resulting reaction mixture was stirred at rt for 48 h. The reaction was acidified to pH 2 using 1N HCl and then the solvent was evaporated. The residue was redissolved in water and then extracted with ether. The aqueous layer was basified to pH 10 using solid NaOH and then extracted with ethyl acetate. The organic extract was washed with brine and dried over sodium sulfate and concentrated to give 47A. $^1$H NMR (400 MHz, Methanol-$d_4$) (ppm 1.40 (d, J=6.85 Hz, 3H) 2.04 (s, 3H) 4.24 (q, J=6.85 Hz, 1H) 6.85 (s, 2H) 7.11 (d, J=7.83 Hz, 1H) 7.31 (t, J=7.83 Hz, 1H) 7.45 (d, J=8.07 Hz, 1H) 7.70 (s, 1H) 9.98 (s, 1H).

47B

Example 47 was prepared according to the general coupling-deprotection using Intermediate 2 and 47A. $^1$H NMR (400 MHz, Methanol-$d_4$) (ppm 1.28 (d, J=6.11 Hz, 6H) 1.34 (m, 3H) 1.48 (d, J=7.09 Hz, 3H) 2.00 (d, J=58.44 Hz, 3H) 3.94 (m, 2H) 4.51 (m, 1H) 5.01 (m, 1H) 5.08 (s, 1H) 6.64 (d, J=1.96 Hz, 1H) 6.76 (d, J=7.58 Hz, 1H) 6.80 (d, J=7.09 Hz, 1H) 6.93 (d, J=8.80 Hz, 1H) 7.04 (m, 3H) 7.16 (dd, J=9.17, 2.32 Hz, 1H) 7.27 (m, 1H) 7.31 (d, J=7.09 Hz, 1H) 7.36 (s, 1H) 8.06 (d, J=9.29 Hz, 1H) 8.64 (d, J=8.07 Hz, 1H). LC-MS 556 (M+H).

Example 48

Diastereoisomer of Example 47 N-[1-(3-Acetylamino-phenyl)-ethyl]-2-(1-amino-isoquinolin-6-ylamino)-2-(3-ethoxy-4-isopropoxy-phenyl)-acetamide trifluoroacetic acid salt

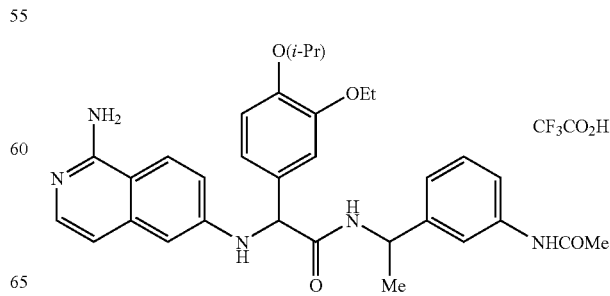

Example 48, a diastereoisomer of Example 47, was separated by prep HPLC (YMC ODSS5 30×100 mm, 40 mL/min from 10% CH$_3$CN to 90% CH$_3$CN). Retention time for Example 47 is 7.5 min. and for Example 48 is 8.5 min. $^1$H NMR (400 MHz, Methanol-d$_4$) δ ppm 1.29 (d, J=5.87 Hz, 6H) 1.37 (t, J=6.85 Hz, 6H) 2.10 (s, 3H) 4.00 (m, 2H) 4.52 (m, 1H) 5.03 (d, J=13.45 Hz, 2H) 6.59 (d, J=2.20 Hz, 1H) 6.72 (d, J=7.09 Hz, 1H) 6.95 (d, J=8.31 Hz, 1H) 7.10 (m, 4H) 7.27 (m, 2H) 7.38 (m, 1H) 7.62 (s, 1H) 8.04 (d, J=9.29 Hz, 1H) 8.74 (d, J=7.83 Hz, 1H).). LC-MS 556 (M+H).

Example 49

2-(1-Aminoisoquinolin-6-ylamino)-2-(3-ethoxy-4-isopropoxyphenyl)-N—((S)-1-phenylethyl)acetamide trifluoroacetic acid salt

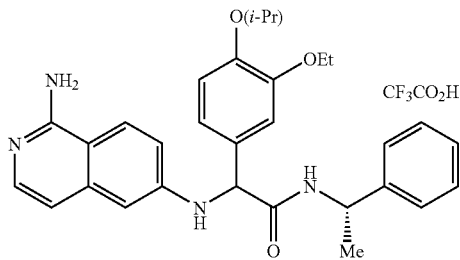

Example 49 was prepared according to the general coupling-deprotection using Intermediate 2 and (S)-1-phenylethanamine. $^1$H NMR (400 MHz, Methanol-d$_4$) δ ppm 1.27 (m, 12H) 3.98 (m, 2H) 4.53 (d, J=26.65 Hz, 1H) 5.05 (m, 2H) 6.72 (m, 2H) 7.08 (m, 7H) 7.36 (m, 3H) 8.07 (t, J=8.56 Hz, 1H) 8.68 (m, J=39.00, 7.95 Hz, 1H). LC-MS 499 (M+H).

Example 50

2-(1-Aminoisoquinolin-6-ylamino)-2-(3-ethoxy-4-isopropoxyphenyl)-N—((R)-1-phenylethyl)acetamide trifluoroacetic acid salt

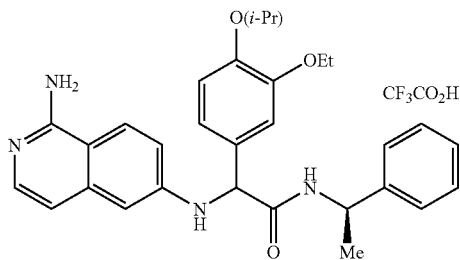

Example 50 was prepared according to the general coupling-deprotection using Intermediate 2 and (R)-1-phenylethanamine. $^1$H NMR (400 MHz, Methanol-d$_4$) δ ppm 1.36 (m, 12H) 3.97 (m, 2H) 4.53 (m, 1H) 5.04 (m, 3H) 6.73 (m, 2H) 6.95 (dd, J=8.56, 4.89 Hz, 1H) 7.13 (m, 6H) 7.33 (m, 3H) 8.07 (t, J=8.68 Hz, 1H) 8.68 (dd, J=39.13, 8.07 Hz, 1H). LC-MS 499 (M+H).

Example 51

2-(1-Aminoisoquinolin-6-ylamino)-N-benzyl-2-(3-ethoxy-4-isopropoxyphenyl)-N-methylacetamide trifluoroacetic acid salt

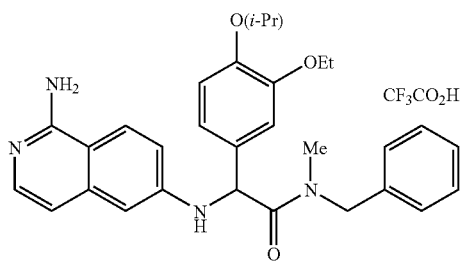

Example 51 was prepared according to the general coupling-deprotection using Intermediate 2 and N-methyl(phenyl)methanamine. $^1$H NMR (400 MHz, Methanol-d$_4$) δ ppm 1.29 (d, J=6.11 Hz, 6H) 1.35 (m, 3H) 3.00 (d, J=39.13 Hz, 3H) 4.01 (m, 2H) 4.59 (m, 3H) 5.64 (d, J=10.03 Hz, 1H) 6.84 (m, 4H) 7.09 (m, 2H) 7.17 (m, 2H) 7.27 (m, 4H) 8.04 (m, 1H). LC-MS 499 (M+H).

Example 52

(R)-2-(1-aminoisoquinolin-6-ylamino)-N-benzyl-2-(3-ethoxy-4-isopropoxyphenyl)-N-methylacetamide trifluoroacetic acid salt

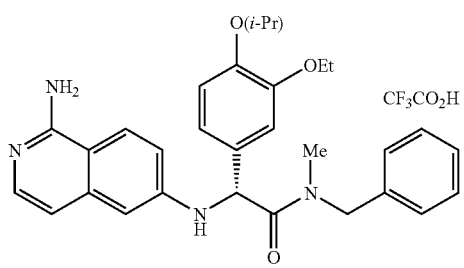

Example 52 (34 mg) was separated from the racemic mixture (80 mg) of Example 51 using a preparative HPLC equipped with a Chiralpak® AD column (5 cm×50 cm, 20μ). The separations were performed using an isocratic method of 95% 1:1 ethanol/methanol, 5% heptane with 0.1% diethylamine for 120 min with a flow rate of 50 mL/min. Retention time for Example 52 was 26 min. Retention time for the other isomer (32 mg) was 90 min. $^1$H NMR (400 MHz, Methanol-d$_4$) δ ppm 1.33 (m, 9H) 3.01 (m, 3H) 3.98 (m, 2H) 4.59 (m, 3H) 5.61 (d, J=9.54 Hz, 1H) 6.70 (m, 2H) 7.05 (m, 6H) 7.25 (m, 3H) 7.39 (dd, J=12.96, 6.60 Hz, 1H) 7.95 (m, 1H). LC-MS 499 (M+H).

Example 53

N-(2-(Isopropylsulfonyl)benzyl)-2-(1-aminoisoquinolin-6-ylamino)-2-(3,4-dimethoxyphenyl)acetamide trifluoroacetic acid salt

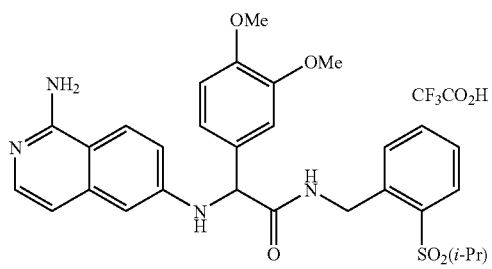

Example 53 was prepared according to the general coupling-deprotection using Intermediate 4 and Intermediate 14. $^1$H NMR (400 MHz, Methanol-d$_4$) δ ppm 1.24 (m, 6H) 3.44 (m, 1H) 3.81 (d, J=17.61 Hz, 6H) 4.73 (m, 3H) 5.10 (s, 1H) 6.64 (d, J=2.20 Hz, 1H) 6.80 (d, J=7.09 Hz, 1H) 6.97 (d, J=8.80 Hz, 1H) 7.09 (m, 2H) 7.18 (dd, J=9.17, 2.32 Hz, 1H) 7.35 (m, 2H) 7.48 (m, 2H) 7.84 (dd, J=7.70, 1.59 Hz, 1H) 8.07 (d, J=9.29 Hz, 1H) 8.61 (m, 1H). LC-MS 535 (M+H).

Example 54

N-[1-(3-Acetylamino-phenyl)-ethyl]-2-(1-amino-isoquinolin-6-ylamino)-2-(3,4-dimethoxy-phenyl)-acetamide trifluoroacetic acid salt

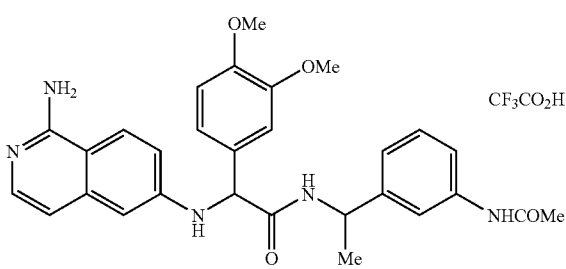

Example 54 was prepared according to the general coupling-deprotection using Intermediate 4 and 47A. $^1$H NMR (400 MHz, Methanol-d$_4$) δ ppm 1.48 (d, J=6.85 Hz, 3H) 2.07 (s, 3H) 3.73 (s, 3H) 3.82 (s, 3H) 5.00 (m, 1H) 5.09 (s, 1H) 6.64 (d, J=2.20 Hz, 1H) 6.79 (m, 2H) 6.93 (d, J=8.31 Hz, 1H) 7.05 (m, 3H) 7.16 (dd, J=9.17, 2.32 Hz, 1H) 7.24 (m, 1H) 7.31 (m, 2H) 8.06 (d, J=9.29 Hz, 1H) 8.65 (d, J=8.07 Hz, 1H). LC-MS 514 (M+H).

Example 55

Diastereoisomer of Example 54 N-[1-(3-Acetylamino-phenyl)-ethyl]-2-(1-amino-isoquinolin-6-ylamino)-2-(3,4-dimethoxy-phenyl)-acetamide trifluoroacetic acid salt

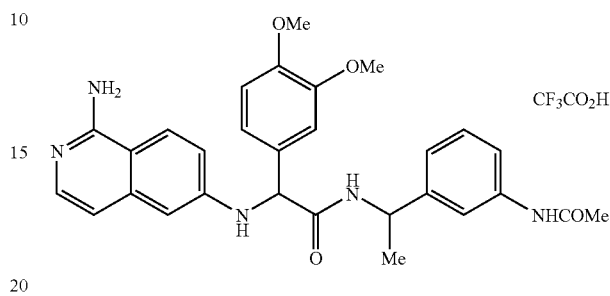

Example 55, a diastereoisomer of Example 54, was separated by prep HPLC (YMC ODSS5 30×100 mm, 40 mL/min from 5% CH$_3$CN to 42% CH$_3$CN). Retention time for Example 55 was 8.0 min and for Example 54 was 7.3 min. $^1$H NMR (400 MHz, Methanol-d$_4$) δ ppm 1.38 (d, J=7.09 Hz, 3H) 2.11 (s, 3H) 3.81 (s, 3H) 3.83 (s, 3H) 5.01 (m, 1H) 5.06 (s, 1H) 6.60 (d, J=1.96 Hz, 1H) 6.73 (d, J=7.09 Hz, 1H) 6.97 (d, J=8.31 Hz, 1H) 7.13 (m, 4H) 7.28 (m, 2H) 7.38 (m, 1H) 7.62 (d, J=1.96 Hz, 1H) 8.05 (d, J=9.29 Hz, 1H) 8.76 (d, J=8.07 Hz, 1H). LC-MS 514 (M+H).

Example 56

3-(2-(1-Aminoisoquinolin-6-ylamino)-2-(3-ethoxy-4-isopropoxyphenyl)acetamido)-3-phenylpropanoic acid trifluoroacetic acid salt

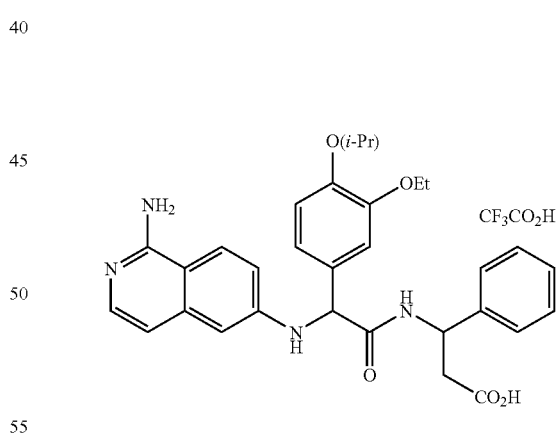

Example 56 was prepared according to the general coupling-deprotection using Intermediate 2 and methyl 3-amino-3-phenylpropanoate followed by hydrolysis of the methyl ester as in procedure 5E. $^1$H NMR (400 MHz, Methanol-d$_4$) δ ppm 1.28 (m, 6H) 1.34 (t, J=6.97 Hz, 3H) 2.83 (m, 2H) 3.94 (m, 2H) 4.52 (m, 1H) 5.06 (s, 1H) 5.38 (m, 1H) 6.66 (d, J=1.96 Hz, 1H) 6.92 (m, 2H) 7.04 (m, 4H) 7.14 (m, 4H) 7.31 (d, J=7.09 Hz, 1H) 8.07 (d, J=9.05 Hz, 1H) 8.81 (d, J=8.31 Hz, 1H). LC-MS 543 (M+H).

Example 57

(3R)-Methyl 3-(2-(1-Aminoisoquinolin-6-ylamino)-2-(3-ethoxy-4-isopropoxyphenyl)acetamido)-3-phenylpropanoate trifluoroacetic acid salt

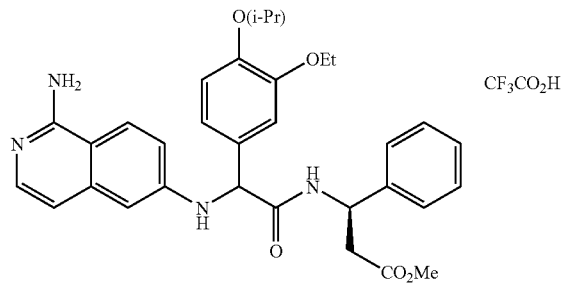

Example 57 was prepared according to the general coupling-deprotection using Intermediate 2 and (R)-methyl 3-amino-3-phenylpropanoate. $^1$H NMR (400 MHz, Methanol-$d_4$) δ ppm 1.05 (m, 3H) 1.29 (d, J=6.11 Hz, 6H) 1.35 (m, 3H) 2.81 (m, 2H) 3.75 (m, J=7.21, 7.21 Hz, 1H) 4.00 (m, 3H) 4.51 (m, 1H) 5.03 (d, J=11.98 Hz, 1H) 5.41 (s, 1H) 6.73 (m, 2H) 6.94 (d, J=8.07 Hz, 1H) 7.11 (m, 5H) 7.32 (m, 4H) 8.06 (t, J=9.17 Hz, 1H). LC-MS 557 (M+H).

Example 58

(3R)-3-(2-(1-Aminoisoquinolin-6-ylamino)-2-(3-ethoxy-4-isopropoxyphenyl)acetamido)-3-phenylpropanoic acid trifluoroacetic acid salt

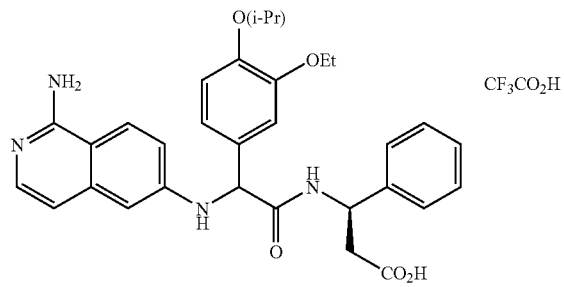

Example 58 was prepared by saponification of Example 57 as in procedure 5E. $^1$H NMR (400 MHz, Methanol-$d_4$) δ ppm 1.26 (m, 6H) 1.33 (t, J=6.97 Hz, 3H) 2.82 (m, 2H) 3.94 (d, J=0.98 Hz, 2H) 4.51 (m, 1H) 5.05 (s, 1H) 5.37 (dd, J=8.80, 5.62 Hz, 1H) 6.66 (d, J=2.20 Hz, 1H) 6.91 (m, 2H) 7.03 (m, 4H) 7.13 (m, 4H) 7.31 (d, J=7.09 Hz, 1H) 8.06 (d, J=9.29 Hz, 1H). LC-MS 543 (M+H).

Example 59

(3S)-3-(2-(1-Aminoisoquinolin-6-ylamino)-2-(3-ethoxy-4-isopropoxyphenyl)acetamido)-3-phenylpropanoic acid trifluoroacetic acid salt

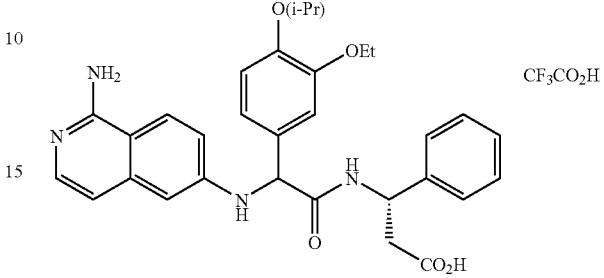

Example 59 was prepared according to the general coupling-deprotection using Intermediate 2 and (S)-methyl 3-amino-3-phenylpropanoate followed by hydrolysis of the methyl ester as in procedure 5E. $^1$H NMR (400 MHz, Methanol-$d_4$) δ ppm 1.27 (m, 6H) 1.35 (m, 3H) 2.76 (m, 2H) 3.99 (m, 2H) 4.50 (dd, J=12.10, 5.99 Hz, 1H) 5.06 (s, 1H) 5.38 (m, 1H) 6.60 (s, 1H) 6.74 (d, J=7.09 Hz, 1H) 6.94 (d, J=8.07 Hz, 1H) 7.03 (m, 2H) 7.14 (dd, J=9.17, 2.08 Hz, 1H) 7.32 (m, 6H) 8.05 (d, J=9.29 Hz, 1H) 8.91 (m, J=8.31 Hz, 1H). LC-MS 543 (M+H).

Example 60

(3R)-Ethyl 3-(3-acetamidophenyl)-3-(2-(1-aminoisoquinolin-6-ylamino)-2-(3-ethoxy-4-isopropoxyphenyl)acetamido)propanoate trifluoroacetic acid salt

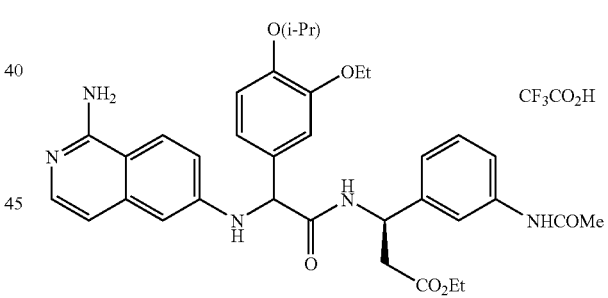

60A (R)-Ethyl 3-(benzyl((S)-1-phenylethyl)amino)-3-(3-nitrophenyl)propanoate

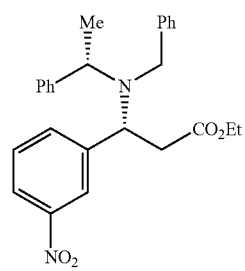

To a solution of (S)-N-benzyl-α-methyl-benzylamine (1.52 g, 7.2 mmol) in THF (20 mL), n-BuLi in hexanes (4.5 mL, 1.6 M) was added dropwise at −78° C. The reaction mixture was stirred for 30 min. at −78° C. To the solution was added ethyl-m-nitrocinnamate (1.0 g, 4.52 mmol) in THF (15 mL). After stirring for 30 min at −78° C., saturated NH₄Cl was added and then the reaction product was extracted with ethyl acetate. The organic extracts were washed with brine and dried over Na₂SO₄. The solvent was evaporated and crude residue was purified by flash column chromatography to give 60A (1.26 g, 65%) as a yellow oil.

60B (R)-Ethyl-3-amino-3-(3-aminophenyl)propanoate

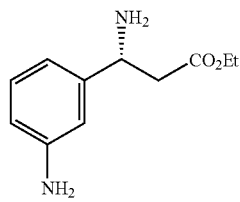

To 60A (0.62 g, 1.42 mmol) in methanol (10 mL), water (0.075 mL) and acetic acid (0.0375 mL) under nitrogen, 20% Pd(OH)₂/C (0.15 g) was added and then a balloon filled with hydrogen gas was introduced. The reaction was stirred for 2 h at rt. The catalyst was filtered off and the solvent evaporated. The crude residue was purified by flash column chromatography to give 60B (0.27 g).

60C (R)-3-(3-Amino-phenyl)-3-tert-butoxycarbony-lamino-propionic acid ethyl ester

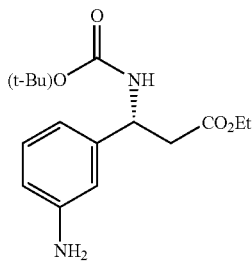

To 60B (0.058 g, 0.28 mmol) in methanol (4 mL), di-t-butyl dicarbonate Et₃N (0.077 mL, 0.55 mmol) was added. The reaction was stirred at rt for 45 min. The solvent was evaporated and the crude residue was purified by flash column chromatography to give 0.59 g (69%) of 60C. ¹H NMR (400 MHz, Methanol-d₄) δ ppm 1.18 (t, J=7.21 Hz, 3H) 1.40 (s, 9H) 2.71 (m, 2H) 4.08 (m, 2H) 4.93 (m, J=6.85 Hz, 1H) 6.60 (m, 2H) 6.66 (s, 1H) 7.03 (t, J=7.83 Hz, 1H) 7.09 (d, J=7.83 Hz, 1H).

60D (R)-3-(3-Acetylamino-phenyl)-3-tert-butoxycarbony-lamino-propionic acid ethyl ester

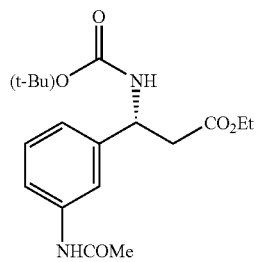

To 60C, acetic anhydride (0.3 mL) was added. The reaction was stirred at room temp for 20 min. The solvent was removed and placed under high vacuo for 24 h to give 60D (0.056 g, 85%) as a white solid.

60E (R)-3-(3-Acetylamino-phenyl)-3-amino-propionic acid ethyl ester

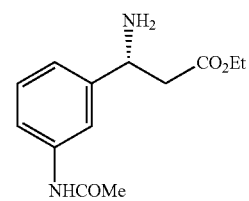

To 60D (0.056 g, 0.16 mmol), 4 N HCl in dioxane (2.5 mL), was added. The reaction was stirred for 2 h at rt. The solvent was removed and dried over high vacuo to give 60E (0.043 g) as the HCl salt. ¹H NMR (400 MHz, Methanol-d₄) δ ppm 1.21 (t, J=7.09 Hz, 3H) 2.14 (s, 3H) 3.02 (m, 2H) 3.66 (m, 2H) 4.15 (q, J=7.09 Hz, 2H) 4.68 (t, J=7.21 Hz, 1H) 7.18 (m, 1H) 7.40 (m, 2H) 7.86 (s, 1H).

60F

Example 60 was prepared according to the general coupling-deprotection using Intermediate 2 and 60E. ¹H NMR (400 MHz, Methanol-d₄) δ ppm 1.06 (m, 3H) 1.32 (m, 9H) 2.09 (m, 3H) 2.84 (m, 2H) 3.94 (m, 4H) 4.49 (dd, J=12.23, 6.11 Hz, 1H) 5.02 (d, J=1.96 Hz, 1H) 5.37 (m, 1H) 6.57 (d, J=18.34 Hz, 1H) 6.84 (m, 3H) 7.04 (m, 3H) 7.12 (m, 1H) 7.40 (m, 3H) 8.03 (t, J=8.80 Hz, 1H) 8.88 (m, 1H). LC-MS 826 (M+H).

Example 61

(3R)-3-(3-Acetamidophenyl)-3-(2-(1-aminoisoquinolin-6-ylamino)-2-(3-ethoxy-4-isopropoxyphenyl)acetamido)propanoic acid trifluoroacetic acid salt

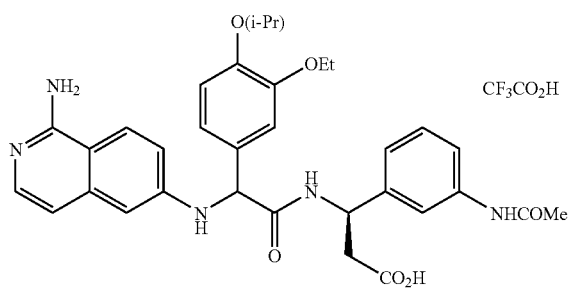

Example 61 was prepared by saponification of Example 60 as in procedure 5E. $^1$H NMR (400 MHz, Methanol-$d_4$) δ ppm 1.33 (m, 9H) 2.08 (m, 3H) 2.83 (m, 2H) 3.94 (m, 2H) 4.50 (m, 1H) 5.04 (m, 1H) 5.36 (dd, J=9.29, 4.65 Hz, 1H) 6.58 (d, J=12.72 Hz, 1H) 6.83 (m, 3H) 7.08 (m, 4H) 7.35 (m, 3H) 8.03 (m, 1H) 8.87 (m, 1H). LC-MS 600 (M+H).

Example 62

2-(1-Amino-isoquinolin-6-ylamino)-2-(4-chloro-3-ethoxy-phenyl)-N-(3-methanesulfonylamino-benzyl)-acetamide trifluoroacetic acid salt

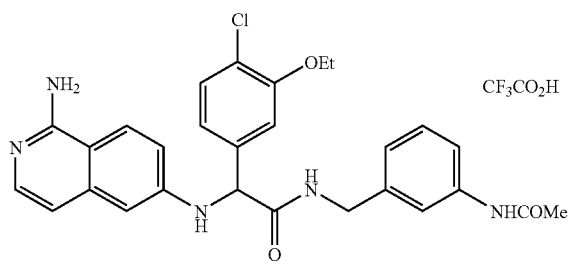

Example 62 was prepared according to the general coupling-deprotection using Intermediate 15 and commercial N-(3-(aminomethyl)phenyl)acetamide HCl salt. $^1$H NMR (400 MHz, Methanol-$d_4$) δ ppm 1.38 (t, J=7.03 Hz, 3H) 2.09 (s, 3H) 4.02 (q, J=6.88 Hz, 2H) 4.37 (d, J=5.71 Hz, 2H) 5.13 (s, 1H) 6.65 (d, J=2.20 Hz, 1H) 6.79 (d, J=7.03 Hz, 1H) 6.90 (d, J=7.91 Hz, 1H) 7.08 (dd, J=8.35, 1.76 Hz, 1H) 7.14-7.20 (m, 3H) 7.31 (d, J=7.03 Hz, 2H) 7.33-7.37 (m, 2H) 7.44 (s, 1H) 8.08 (d, J=9.23 Hz, 1H) 8.87 (b, 1H); LC MS (518 (M+H).

Example 63

N-(5-Acetylamino-2-ethanesulfonyl-benzyl)-2-(1-amino-isoquinolin-6-ylamino)-2-(4-chloro-3-ethoxy-phenyl)-acetamide trifluoroacetic acid salt

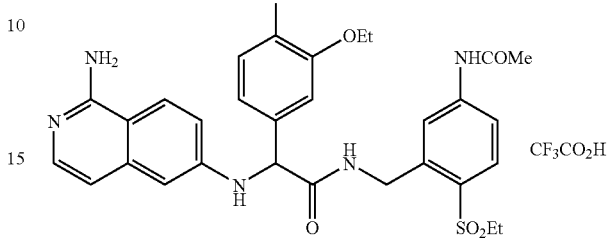

Example 63 was prepared according to the general coupling-deprotection using Intermediate 15 and Intermediate 9. $^1$H NMR (400 MHz, Methanol-$d_4$) δ ppm 1.16 (t, J=7.25 Hz, 3H) 1.35-1.40 (m, 3H) 2.13 (s, 3H) 3.22-3.28 (m, 2H) 3.96-4.05 (m, 2H) 4.60-4.66 (m, 1H) 4.71-4.77 (m, 1H) 5.17 (s, 1H) 6.62 (d, J=2.20 Hz, 1H) 6.77 (d, J=7.03 Hz, 1H) 7.07 (dd, J=8.13, 1.98 Hz, 1H) 7.11 (d, J=1.76 Hz, 1H) 7.17 (dd, J=9.23, 2.20 Hz, 1H) 7.29-7.32 (m, 1H) 7.34 (d, J=7.91 Hz, 1H) 7.58 (dd, J=8.35, 2.20 Hz, 1H) 7.74 (d, J=1.76 Hz, 1H) 7.77 (d, J=8.79 Hz, 1H) 8.06 (d, J=9.23 Hz, 1H) 8.68 (t, J=6.15 Hz, 1H); LC MS (610 (M+H).

Example 64

N-(3-Acetylamino-benzyl)-2-(1-amino-isoquinolin-6-ylamino)-2-(3-ethoxy-4-fluoro-phenyl)-acetamide trifluoroacetic acid salt

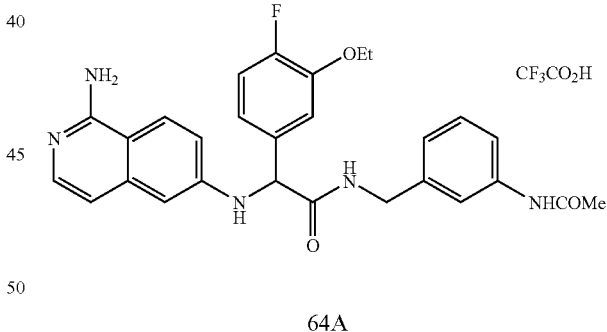

64A

5-Bromo-2-fluorophenol

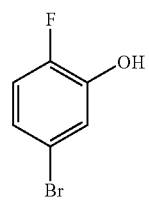

To a solution of 2,2,6,6-tetramethyl piperidine (5.6 mL, 33.2 mmol) in THF at −20° C. was added n-BuLi (1.6 M in hexanes, 18.8 mL, 30 mmol). The mixture was stirred at −20° C. for 10 min before it was cooled to −78° C. 1-Bromo-4-fluorobenzene (2.95 mL, 27 mmol) was added over 10 min and the mixture was stirred at −78° C. for 2.0 h before trimethyl borate (6.0 mL, 54 mmol) was added. The mixture was stirred at −78° C. for 30 min and then at rt for 2.0 h. After it was cooled back to 0° C., glacial acetic acid (4.86 mL, 81 mmol) was added and stirred for 30 min, followed by addition of 30% $H_2O_2$ (4.86 mL, 81 mmol). The mixture was stirred at rt for 24 h., quenched by addition of $MnO_2$ (40 mg). After stirring at rt for 30 min., the cloudy solution was filtered through a pad of wet Celite® and extracted with EtOAc. The EtOAc layer was washed with aquous $NaHSO_3$, brine and dried over $Na_2SO_4$. The crude residue was purified by flash column chromatography (EtOAc:hexanes=1:5) to give 4.4 g (85%) of 64A as a liquid. $^1$H NMR (400 MHz, $CDCl_3$) δ ppm 5.39 (s, 1H) 6.90-6.98 (m, 2H) 7.14 (dd, J=8.13, 1.98 Hz, 1H).

64B

4-Bromo-2-ethoxy-1-fluorobenzene

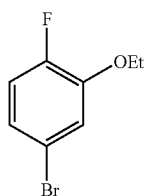

To a solution of 64A (4.4 g, 23 mmol) and $K_2CO_3$ (6.4 g, 46 mmol) in DMF (30 mL) was added ethyl iodide (2.49 mL, 31 mmol) at rt. The mixture was heated at 50° C. for 2.0 h. After cooled to rt, it was diluted with ether, washed with water and brine, dried over $MgSO_4$. The crude residue was purified by flash column chromatography (EtOAc:hexanes=1:5) to give 3.86 g (77%) of 64B as viscous oil. $^1$H NMR (400 MHz, $CDCl_3$) δ ppm 1.47 (m, 3H) 4.00 (m, 2H) 6.96-7.08 (m, 3H).

64C

3-Ethoxy-4-fluorophenylboronic acid

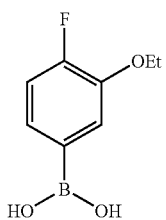

To a solution of 64B (3.86 g, 17.6 mmol) in THF (60 mL) at −78° C. was added n-BuLi (1.6 M in hexanes, 14.3 mL, 22.8 mmol). The mixture was stirred at −78° C. for 40 min before trimethyl borate (3.63 mL, 33 mmol) was added. The reaction was left stirring from −78° C. to rt over 4 h. It was quenched with 1.0 N HCl (40 mL), extracted with EtOAc, washed with brine and dried over $Na_2SO_4$. After evaporation of the solvent, the crude solid product was triturated with EtOAc/hexanes (1:4). After filtration, 64C (2.2 g, 69% yield) was collected as a white solid. $^1$H NMR (400 MHz, $CDCl_3$) δ ppm 1.42 (t, J=7.03 Hz, 3H) 4.11 (q, J=7.03 Hz, 2H) 7.03 (dd, J=11.42, 8.35 Hz, 1H) 7.18-7.29 (m, 2H) 7.35 (d, J=7.91 Hz, 1H).

64D 2-(1-di-tert-Butoxycarbonylaminoisoquinolin-6-ylamino)-2-(3-ethoxy-4-fluorophenyl)acetic acid

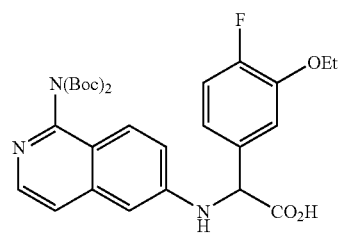

A mixture of 64C (43 mg, 0.23 mmol), Intermediate 1 (72 mg, 0.2 mmol) and glyoxylic acid monohydrate (21 mg, 0.23 mmol) in 1,2-dichloroethane (0.8 mL) was heated at 100° C. for 5 min. in a Microwave Reactor. The crude product was purified by flash column chromatography ($CH_2Cl_2$: MeOH=100:15) to give 36 mg (32%) of 64D as a solid. $^1$H NMR (400 MHz, Methanol-$d_4$) δ ppm 1.26 (s, 18H) 4.08 (dd, J=12.30, 7.03 Hz, 2H) 4.98 (s, 1H) 6.61 (d, J=2.20 Hz, 1H) 7.03 (s, 1H) 7.13 (s, 1H) 7.25 (s, 2H) 7.38 (d, J=6.15 Hz, 1H) 7.61 (d, J=9.23 Hz, 1H) 7.99 (d, J=6.15 Hz, 1H); LC MS 556 (M+H).

64E

Example 64 was prepared according to the general coupling-deprotection using 64D and commercial N-(3-(aminomethyl)phenyl)acetamide HCl salt. $^1$H NMR (400 MHz, Methanol-$d_4$) δ ppm 1.36 (t, J=7.03 Hz, 3H) 2.08 (s, 3H) 4.01 (q, J=7.03 Hz, 2H) 4.36 (d, J=5.71 Hz, 2H) 5.11 (s, 1H) 6.63 (d, J=2.20 Hz, 1H) 6.76 (d, J=7.03 Hz, 1H) 6.90 (d, J=7.91 Hz, 1H) 7.08 (d, J=8.35 Hz, 2H) 7.13-7.22 (m, 3H) 7.28-7.35 (m, 2H) 7.43 (s, 1H) 8.07 (d, J=9.23 Hz, 1H) 8.87 (t, J=5.93 Hz, 1H); LC MS 502 (M+H).

Example 65

N-(5-Acetylamino-2-ethanesulfonyl-benzyl)-2-(1-amino-isoquinolin-6-ylamino)-2-(3-ethoxy-4-fluorophenyl)-acetamide trifluoroacetic acid salt

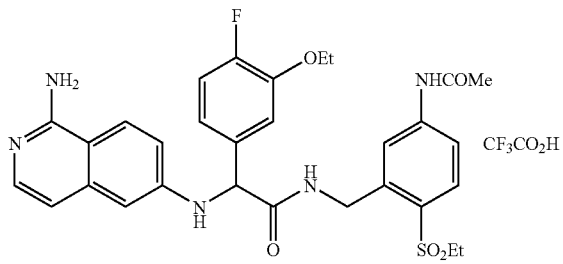

Example 65 was prepared according to the general coupling-deprotection using 64D and Intermediate 9. $^1$H NMR (400 MHz, Methanol-$d_4$) δ ppm 1.16 (t, J=7.25 Hz, 3H) 1.35

(t, J=7.03 Hz, 3H) 2.12 (s, 3H) 3.22-3.29 (m, 2H) 3.95-4.05 (m, 2H) 4.60-4.66 (m, 1H) 4.71-4.77 (m, 1H) 5.15 (s, 1H) 6.60 (d, J=2.20 Hz, 1H) 6.75 (d, J=7.03 Hz, 1H) 7.07 (d, J=7.91 Hz, 2H) 7.15 (d, J=9.23 Hz, 2H) 7.29 (d, J=7.03 Hz, 1H) 7.58 (dd, J=8.57, 1.98 Hz, 1H) 7.71 (d, J=2.20 Hz, 1H) 7.76 (d, J=8.79 Hz, 1H) 8.05 (d, J=9.23 Hz, 1H) 8.67 (t, J=5.93 Hz, 1H); LC MS 594 (M+H).

Example 66

2-(1-Amino-isoquinolin-6-ylamino)-N-(2-cyclopropanesulfonyl-benzyl)-2-(3-ethoxy-4-fluoro-phenyl)-acetamide trifluoroacetic acid salt

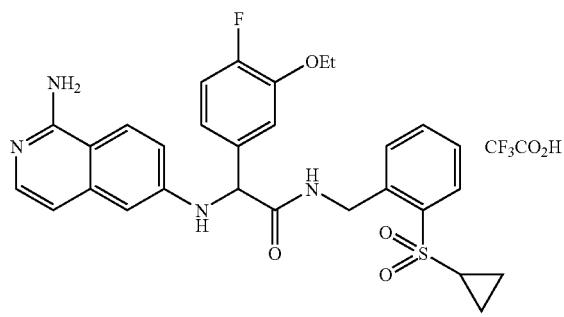

Example 66 was prepared according to the general coupling-deprotection using 64D and Intermediate 7. $^1$H NMR (400 MHz, Methanol-$d_4$) δ ppm 0.96-1.04 (m, 2H) 1.10-1.22 (m, 2H) 1.36 (t, J=7.03 Hz, 3H) 2.80-2.86 (m, 1H) 4.03 (qd, J=7.10, 4.61 Hz, 2H) 4.80 (d, J=5.71 Hz, 1H) 5.18 (s, 1H) 6.65 (d, J=2.20 Hz, 1H) 6.79 (d, J=7.03 Hz, 1H) 7.07-7.12 (m, 2H) 7.15-7.23 (m, 2H) 7.32 (d, J=7.03 Hz, 1H) 7.37 (d, J=7.47 Hz, 1H) 7.41-7.51 (m, 2H) 7.80-7.83 (m, 1H) 8.07 (d, J=9.23 Hz, 1H) 8.70 (t, J=5.93 Hz, 1H); LC MS 549 (M+H).

Example 67

N-(3-Acetylamino-benzyl)-2-(1-amino-isoquinolin-6-ylamino)-2-(2,5-dimethoxy-phenyl)-acetamide trifluoroacetic acid salt

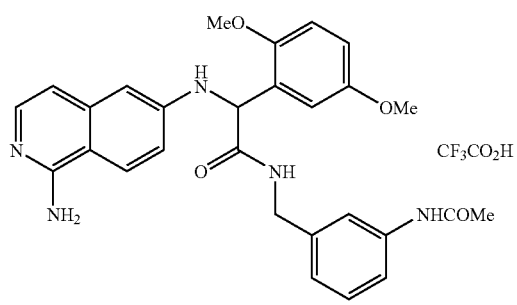

67A 2-(1-di-tert-Butoxycarbonylaminoisoquinolin-6-ylamino)-2-(2,5-dimethoxyphenyl)acetic acid

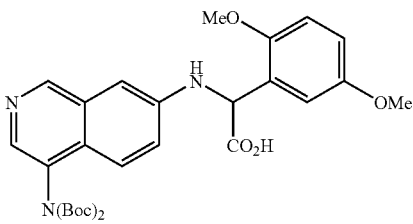

A mixture of 2,5-dimethoxyphenylboronic acid (29 mg, 0.16 mmol), Intermediate 1 (50 mg, 014 mmol) and glyoxylic acid monohydrate (15 mg, 0.16 mmol) in 1,2-dichloroethane (0.7 mL) was heated at 100° C. for 5 min in a Microwave Reactor. The crude product was purified by flash column chromatography (CH$_2$Cl$_2$:MeOH=100:15) to give 26 mg (33%) of 67A as a solid. $^1$H NMR (400 MHz, Methanol-$d_4$) δ ppm 1.26 (s, 18H) 3.66 (s, 3H) 3.92 (s, 3H) 5.44 (s, 1H) 6.70 (d, J=1.76 Hz, 1H) 6.78 (dd, J=9.01, 2.86 Hz, 1H) 6.95 (d, J=9.23 Hz, 1H) 7.06 (d, J=2.64 Hz, 1H) 7.17 (dd, J=9.23, 2.20 Hz, 1H) 7.35 (d, J=5.71 Hz, 1H) 7.56 (d, J=9.23 Hz, 1H) 7.98 (d, J=6.15 Hz, 1H); LC MS 554 (M+H).

67B

Example 67 was prepared according to the general coupling-deprotection using 67A and commercial N-(3-(aminomethyl)phenyl)acetamide HCl salt. $^1$H NMR (400 MHz, Methanol-$d_4$) δ ppm 2.08 (s, 3H) 3.66 (s, 3H) 3.82 (s, 3H) 4.32-4.43 (m, 2H) 5.55 (s, 1H) 6.64 (d, J=1.76 Hz, 1H) 6.77 (d, J=7.03 Hz, 1H) 6.85-6.89 (m, 1H) 6.90 (d, J=7.91 Hz, 1H) 6.95-7.00 (m, 2H) 7.12-7.19 (m, 2H) 7.28 (d, J=7.03 Hz, 1H) 7.34 (d, J=8.35 Hz, 1H) 7.43 (s, 1H) 8.04 (d, J=9.23 Hz, 1H); LC MS 500 (M+H).

Example 68

N-(5-Acetylamino-2-ethanesulfonyl-benzyl)-2-(1-amino-isoquinolin-6-ylamino)-2-(2,5-dimethoxy-phenyl)-acetamide trifluoroacetic acid salt

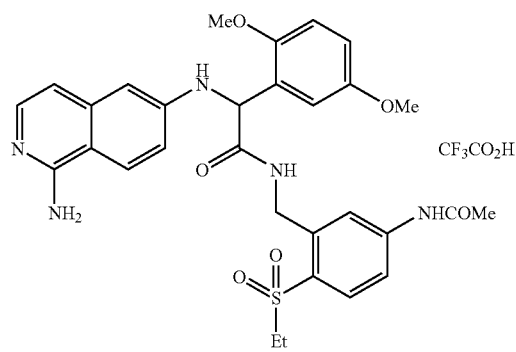

Example 68 was prepared according to the general coupling-deprotection using 67A and Intermediate 9. $^1$H NMR (400 MHz, Methanol-$d_4$) δ ppm 1.17 (t, J=7.47 Hz, 3H) 2.12

(s, 3H) 3.24 (q, J=7.18 Hz, 2H) 3.62-3.66 (s, 3H) 3.82-3.86 (s, 3H) 4.67 (dd, J=6.15, 3.52 Hz, 2H) 5.52 (s, 1H) 6.57 (d, J=2.20 Hz, 1H) 6.73 (d, J=7.03 Hz, 1H) 6.85 (td, J=8.57, 3.08 Hz, 2H) 6.95 (d, J=8.79 Hz, 1H) 7.12 (dd, J=9.23, 2.64 Hz, 1H) 7.27 (d, J=7.03 Hz, 1H) 7.64-7.69 (m, 1H) 7.72-7.80 (m, 2H) 8.02 (d, J=9.23 Hz, 1H) 8.25 (t, J=6.37 Hz, 1H); LC MS 592 (M+H).

Example 69

N-(3-Acetylamino-benzyl)-2-(1-amino-isoquinolin-6-ylamino)-2-(4-fluoro-3-methoxy-phenyl)-acetamide trifluoroacetic acid salt

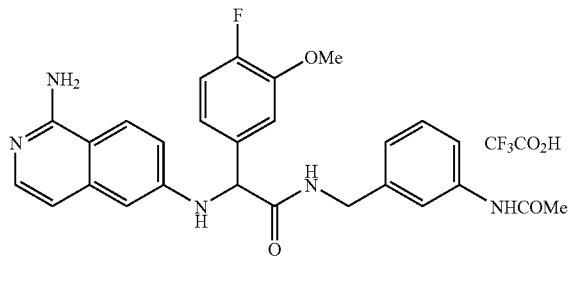

69A

4-Bromo-2-methoxy-1-fluorobenzene

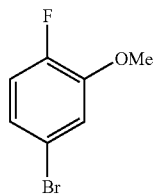

To a solution of 64A (3.3 g, 17.3 mmol) and $K_2CO_3$ (4.78 g, 34.6 mmol) in DMF (20 mL) was added methyl iodide (1.46 mL, 23.4 mmol) at rt. The mixture was heated at 40° C. for 2.0 h. After cooled to rt, it was diluted with ether, washed with water and brine, dried over $MgSO_4$. The crude residue was purified by flash column chromatography (EtOAc:hexanes=1:6) to give 2.74 g (77%) of 69A as viscous oil. $^1$H NMR (400 MHz, CDCl$_3$) δ ppm 3.89 (s, 3H), 6.95-7.00 (m, 3H).

69B

3-Methoxy-4-fluorophenylboronic acid

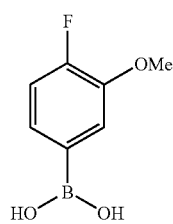

To a solution of 69A (2.7 g, 13.1 mmol) in THF (25 mL) at −78° C. was added n-BuLi (1.6 M in hexanes, 11.0 mL, 17.7 mmol). The mixture was stirred at −78° C. for 40 min before trimethyl borate (2.7 mL, 24.3 mmol) was added. The reaction was left stirring from −78° C. to rt over 18 h. It was quenched with 1.0 N HCl (40 mL), extracted with EtOAc, washed with brine and dried over $Na_2SO_4$. After evaporation of the solvent, the crude solid product was triturated with EtOAc/hexanes (1:4). After filtration, 69B (0.75 g, 35% yield) was collected as a white solid. $^1$H NMR (400 MHz, Methanol-d$_4$) δ ppm 3.86 (s, 3H) 7.03-7.45 (m, 3H).

69C 2-(1-di-tert-Butoxycarbonylaminoisoquinolin-6-ylamino)-2-(4-fluoro-3-methoxyphenyl)acetic acid

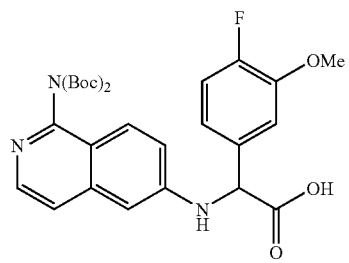

A mixture of 69B (39 mg, 0.23 mmol), Intermediate 1 (72 mg, 0.2 mmol) and glyoxylic acid monohydrate (21 mg, 0.23 mmol) in 1,2-dichloroethane (0.8 mL) was heated at 85° C. for 8 min in a Microwave Reactor. The crude product was purified by flash column chromatography (CH$_2$Cl$_2$: MeOH=100:15) to give 54 mg (50%) of 69C as a solid. $^1$H NMR (400 MHz, Methanol-d$_4$) δ ppm 1.27 (s, 18H) 3.83 (s, 3H) 4.97 (s, 1H) 6.61 (d, J=2.20 Hz, 1H) 7.00 (dd, J=10.99, 8.35 Hz, 1H) 7.12 (ddd, J=8.24, 4.28, 1.98 Hz, 1H) 7.23 (dd, J=9.23, 2.20 Hz, 1H) 7.32 (dd, J=8.35, 2.20 Hz, 1H) 7.38 (d, J=5.71 Hz, 1H) 7.61 (d, J=9.23 Hz, 1H) 7.99 (d, J=6.15 Hz, 1H); LC MS 542 (M+H).

69D

Example 69 was prepared according to the general coupling-deprotection using 69C and commercial N-(3-(aminomethyl)phenyl)acetamide HCl salt. $^1$H NMR (400 MHz, Methanol-d$_4$) δ ppm 6 ppm 2.08 (s, 3H) 3.81 (s, 3H) 4.34-4.39 (m, 2H) 5.12 (s, 1H) 6.64 (d, J=2.20 Hz, 1H) 6.77 (d, J=7.03 Hz, 1H) 6.90 (d, J=7.47 Hz, 1H) 7.08-7.19 (m, 4H) 7.24 (d, J=8.79 Hz, 1H) 7.28-7.34 (m, 2H) 7.42 (s, 1H) 8.07 (d, J=9.23 Hz, 1H) 8.9 (br, 1H) LS MS 488 (M+H).

Example 70

N-(5-Amino-2-ethanesulfonyl-benzyl)-2-(1-amino-isoquinolin-6-ylamino)-2-(4-fluoro-3-methoxy-phenyl)-acetamide trifluoroacetic acid salt

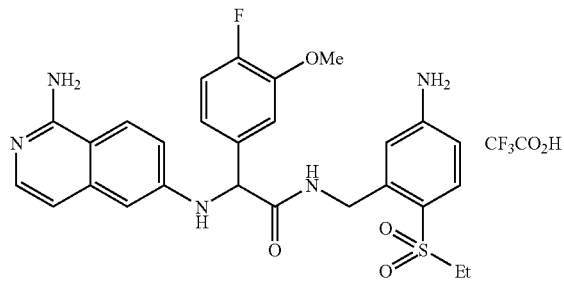

Example 70 was prepared according to the general coupling-deprotection using 69C and Intermediate 9. The acetamide was hydrolyzed to the aniline during the deprotection step. $^1$H NMR (400 MHz, Methanol-d$_4$) δ ppm 1.13 (t, J=7.47 Hz, 3H) 3.11 (q, J=7.47 Hz, 2H) 3.81 (s, 3H) 4.56 (d, J=5.71 Hz, 2H) 5.14 (s, 1H) 6.55-6.58 (m, 1H) 6.58-6.64 (m, 3H) 6.81 (d, J=7.03 Hz, 1H) 7.05-7.12 (m, 3H) 7.15-7.19 (m, 2H) 7.20 (d, J=2.20 Hz, 1H) 7.31 (d, J=7.03 Hz, 1H) 7.48 (d, J=8.35 Hz, 1H) 8.07 (d, J=9.23 Hz, 1H) 8.48 (s, 1H). LS-MS 538 (M+H).

Example 71

N-(3-Acetylamino-benzyl)-2-(4-aminomethyl-phenylamino)-2-(3-ethoxy-4-isopropoxy-phenyl)-acetamide trifluoroacetic acid salt

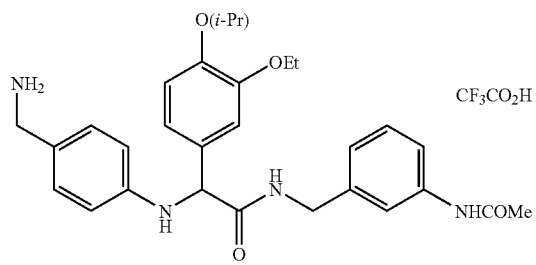

71A 2-(4-((tert-Butoxycarbonyl)methyl)phenylamino)-2-(3-ethoxy-4-isopropoxyphenyl)acetic acid

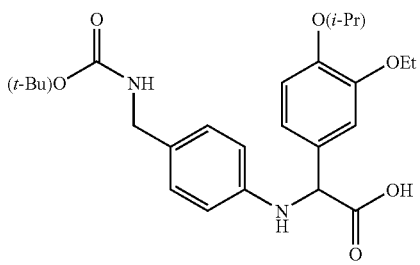

A solution of Intermediate 2E (112 mg, 0.5 mmol), tert-butyl 4-aminobenzylcarbamate (111 mg, 0.5 mmol) and glyoxylic acid monohydrate (46.1 mg, 0.5 mmol) in toluene (4.0 mL) was heated at 55° C. for 15 min. and then at rt for 18 h. Solvent was removed and the crude was purified by column chromatography (CH$_2$Cl$_2$:MeOH=25:1) to give 173 mg (74%) of 71A as a solid. $^1$H NMR (400 MHz, Methanol-d$_4$) δ ppm 1.27 (d, J=6.15 Hz, 6H) 1.35 (t, J=7.03 Hz, 3H) 1.42 (s, 9H) 4.01 (d, J=1.76 Hz, 1H) 4.03 (d, J=4.39 Hz, 3H) 4.43-4.49 (m, 1H) 6.57 (d, J=8.35 Hz, 2H) 6.87 (d, J=8.35 Hz, 1H) 6.98 (d, J=8.79 Hz, 2H) 7.02 (dd, J=8.35, 2.20 Hz, 1H) 7.11 (d, J=1.76 Hz, 1H) LC MS 500 (M+H).

71B

Example 71 was prepared according to the general coupling-deprotection using 71A and commercial N-(3-(aminomethyl)phenyl)acetamide HCl salt. $^1$H NMR (400 MHz, Methanol-d$_4$) δ ppm 1.29 (s, 6H) 1.36 (s, 3H) 2.12 (s, 3H) 3.91-3.97 (m, 1H) 3.99-4.04 (m, 1H) 4.14 (s, 2H) 4.29-4.38 (m, 2H) 4.52-4.59 (m, 1H) 5.28 (s, 1H) 6.84 (d, J=7.47 Hz, 1H) 6.91-7.01 (m, 2H) 7.09 (s, 1H) 7.15 (t, J=7.91 Hz, 1H) 7.35 (d, J=7.91 Hz, 1H) 7.40-7.48 (m, 3H) 7.56 (d, J=8.35 Hz, 2H); LC MS 488 (M−NH$_3$).

Example 72

2-(1-Amino-isoquinolin-6-ylamino)-2-(3-ethoxy-4-isopropoxy-phenyl)-N-[3-(propane-2-sulfonyl)-pyridin-2-ylmethyl]-acetamide trifluoroacetic acid salt

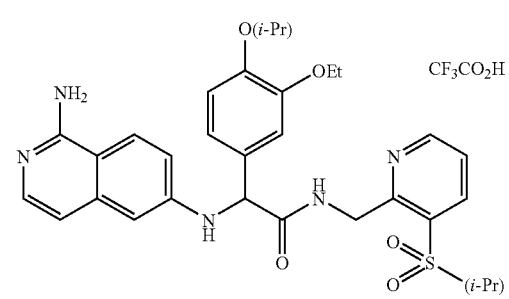

72A

3-Fluoro-pyridin-1-ol

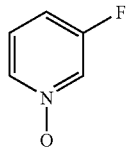

To a solution of 3-fluoropyridine (4.7 g, 48.4 mmol) in $CH_2Cl_2$ and 30% $H_2O_2$ (10 mL, 104 mmol) at rt was added methyl trioxorhenium (25 mg, 0.1 mmol). The mixture was stirred at rt for 20 h before manganese dioxide (25 mg) was added and stirred for an additional 1.0 h. It was extracted with $CH_2Cl_2$ (5×100 mL), dried over $Na_2SO_4$. After evaporation of solvent, 72A (4.5 g, 90%) was obtained as a white solid. $^1$H NMR (400 MHz, DMSO-$d_6$) δ ppm 7.29-7.40 (m, 1H) 7.40-7.54 (m, 1H) 8.08-8.21 (m, 1H) 8.46-8.56 (m, 1H).

72B

3-Fluoropicolinonitrile

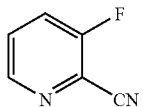

To 72A (4.4 g, 39 mmol) in $CH_2Cl_2$ (150 mL) was added trimethylsilyl cyanide (8.3 mL, 62 mmol). The mixture was heated at reflux for 6 h. Additional trimethylsilyl cyanide (16 mL) was added and refluxed for additional 10 h. After cooled to rt, the reaction was quenched by addition of 100 mL of sat. $NaHCO_3$. The organic layer was collected and dried over $Na_2SO_4$. The crude product was purified by column chromatography (EtOAc:hexanes=6:9) to give 72B (2.5 g) as a solid. $^1$H NMR (400 MHz, $CDCl_3$) δ ppm 8.57 (m, 1H), 7.61 (m, 2H).

72C

3-(Isopropylthio)picolinonitrile

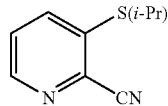

To a solution of 72B (246 mg, 2.0 mmol) in DMF (5.0 mL) was added $K_2CO_3$ (484 mg, 3.5 mmol) and propane-2-thiol (0.33 mL, 3.5 mmol). The reaction was heated at 40° C. for 18 h. The mixture was diluted with EtOAc, washed with water and brine, dried over $Na_2SO_4$. After evaporation of solvent, 72C (300 mg) was obtained as viscous oil. It was used for next step without further purification. $^1$H NMR (400 MHz, $CDCl_3$) δ ppm 1.36 (d, J=6.59 Hz, 6H) 3.45-3.70 (m, 1H) 7.43 (dd, J=8.13, 4.61 Hz, 1H) 8.42-8.66 (m, 1H).

72D

(3-(Isopropylthio)pyridin-2-yl)methanamine HCl salt

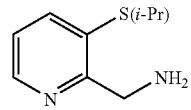

To 72C (250 mg, 1.4 mmol) in MeOH (8.0 mL) was added 4.0 N HCl in dioxane (1.0 mL) and 10% Pd/C (125 mg). The mixture was hydrogenated at 60 psi for 18 h. After filtration and evaporation of solvent, 72D (310 mg) was obtained as HCl salt. $^1$H NMR (400 MHz, Methanol-$d_4$) δ ppm 1.34 (d, J=6.59 Hz, 6H) 3.53-3.63 (m, 1H) 4.40 (s, 2H) 7.50 (dd, J=7.91, 4.83 Hz, 1H) 8.06 (d, J=7.91 Hz, 1H) 8.53 (d, J=4.83 Hz, 1H).

72E tert-Butyl (3-(isopropylthio)pyridin-2-yl)methylcarbamate

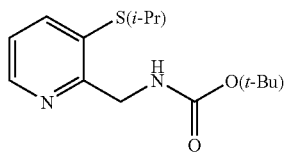

To a solution of 72D (100 mg, 0.39 mmol) in MeOH (2.0 mL) was added di-tert-butyl dicarbonate (1.0 M in $CH_2Cl_2$, 0.49 mL, 0.49 mmol). The mixture was stirred at rt for 6 h. After removal of solvent, 72E (300 mg) was obtained. $^1$H NMR (400 MHz, $CDCl_3$) δ ppm 1.28 (d, J=6.59 Hz, 6H) 1.46 (s, 9H) 3.35 (dt, J=13.18, 6.59 Hz, 1H) 4.56 (d, J=3.95 Hz, 2H) 6.10 (s, 1H) 7.16 (dd, J=7.47, 4.83 Hz, 1H) 7.68 (d, J=7.47 Hz, 1H) 8.38 (dd, J=4.83, 1.76 Hz, 1H).

72F tert-Butyl (3-(isopropylsulfonyl)pyridin-2-yl)methylcarbamate

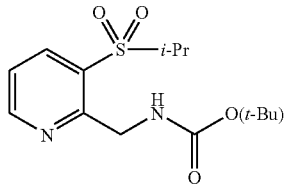

To a solution of 72E (560 mg, 1.98 mmol) and 1-tosyl-1H-imidazole (1.1 g, 4.96 mmol) in MeOH (15 mL) at 0° C. was added 30% $H_2O_2$ (0.95 mL, 9.9 mmol) and 1.0 N NaOH (4.36 mL, 4.36 mmol). After it was stirred at rt for 2.0 h, MeOH was removed under reduced pressure. The crude was extracted with EtOAc, washed with brine and dried over $Na_2SO_4$ and purified by column chromatography to give 560 mg (90%) of 72F as a viscous oil. $^1$H NMR (400 MHz, $CDCl_3$) δ ppm 1.31

(d, J=7.03 Hz, 6H) 1.40-1.46 (m, 9H) 4.80 (d, J=5.71 Hz, 2H) 5.85 (s, 1H) 7.41 (dd, J=7.91, 4.83 Hz, 1H) 8.23 (dd, J=7.91, 1.76 Hz, 1H) 8.77 (dd, J=4.83, 1.76 Hz, 1H).

72G (3-Iisopropylsulfonyl)pyridin-2-yl)methanamine HCl salt

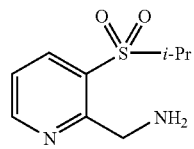

To a solution of 72F (770 mg, 2.5 mmol) in EtOAc (5.0 mL) was added 4.0 N HCl in dioxane (12.3 mL, 49 mmol). The mixture was stirred at rt for 45 min. After removal of solvent, white solid product 72G was obtained as HCl salt. $^1$H NMR (400 MHz, Methanol-$d_4$) δ ppm 1.30 (d, J=6.59 Hz, 6H) 3.49 (t, J=6.59 Hz, 1H) 4.72 (s, 2H) 7.70 (dd, J=7.91, 4.83 Hz, 1H) 8.37 (dd, J=7.91, 1.76 Hz, 1H) 8.92 (dd, J=4.83, 1.76 Hz, 1H); LC-MS 215 (M+H).

72H

Example 72 was prepared according to the general coupling-deprotection using Intermediate 2 and 72G. $^1$H NMR (400 MHz, Methanol-$d_4$) δ ppm 1.22 (dd, J=7.03, 2.64 Hz, 6H) 1.28 (d, J=5.71 Hz, 6H) 1.37 (t, J=6.81 Hz, 3H) 3.58-3.65 (m, 1H) 4.04 (q, J=7.03 Hz, 2H) 4.48-4.55 (m, 1H) 5.16 (s, 1H) 6.74 (d, J=2.20 Hz, 1H) 6.85 (d, J=7.03 Hz, 1H) 6.95 (d, J=8.35 Hz, 1H) 7.09 (dd, J=8.35, 2.20 Hz, 1H) 7.16 (d, J=2.20 Hz, 1H) 7.19 (dd, J=9.23, 2.20 Hz, 1H) 7.32 (d, J=7.03 Hz, 1H) 7.51 (dd, J=8.13, 4.61 Hz, 1H) 8.07 (d, J=9.23 Hz, 1H) 8.22-8.25 (m, 1H) 8.70 (dd, J=4.83, 1.76 Hz, 1H).

Example 73

N-(5-Acetylamino-2-ethanesulfonyl-benzyl)-2-(1-amino-isoquinolin-6-ylamino)-2-(5-ethoxy-2-fluoro-phenyl)-acetamide trifluoroacetic acid salt

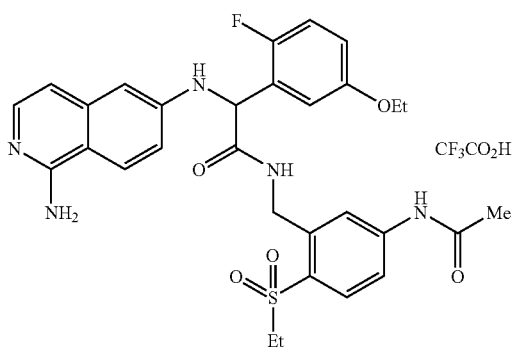

73A 2-(1-di-tert-Butoxycarbonylaminoisoquinolin-6-ylamino)-2-(5-ethoxy-2-fluorophenyl)acetic acid

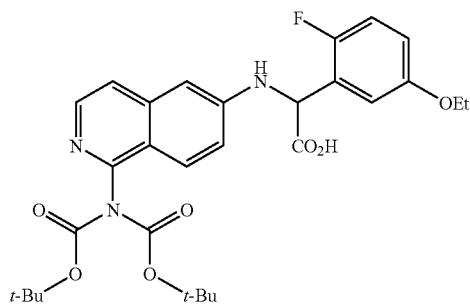

A mixture of 5-ethoxy-2-fluorophenylboronic acid (43 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography ($CH_2Cl_2$:MeOH=100:15) to give 28 mg (25%) of 73A as a solid. $^1$H NMR (400 MHz, Methanol-$d_4$) δ ppm 1.14 (s, 18H) 1.19 (t, J=6.81 Hz, 3H) 3.83 (q, J=7.03 Hz, 2H) 5.39 (s, 1H) 6.59 (d, J=2.20 Hz, 1H) 6.70-6.77 (m, 1H) 6.89-7.00 (m, 2H) 7.16 (dd, J=9.23, 2.20 Hz, 1H) 7.33 (d, J=5.71 Hz, 1H) 7.52 (d, J=9.23 Hz, 1H) 7.85 (s, 1H) 7.91 (d, J=6.15 Hz, 1H); LC MS 556 (M+H).

73B

Example 73 was prepared according to the general coupling-deprotection using 73A and Intermediate 9. $^1$H NMR (400 MHz, Methanol-$d_4$) δ ppm 1.09 (t, J=7.25 Hz, 3H) 1.23 (t, J=7.03 Hz, 3H) 2.05 (s, 3H) 3.13-3.22 (m, 2H) 3.73-3.89 (m, 2H) 4.55-4.71 (m, 2H) 5.37 (s, 1H) 6.58 (d, J=2.20 Hz, 1H) 6.71 (d, J=7.03 Hz, 1H) 6.77-6.85 (m, 2H) 6.95-7.05 (m, 1H) 7.09 (dd, J=9.01, 2.42 Hz, 1H) 7.23 (d, J=7.03 Hz, 1H) 7.51-7.66 (m, 1H) 7.69 (d, J=8.79 Hz, 2H) 7.99 (d, J=9.23 Hz, 1H) 8.56 (t, J=6.15 Hz, 1H); LC MS 594 (M+H).

Example 74

N-(3-Acetylamino-benzyl)-2-(1-amino-isoquinolin-6-ylamino)-2-(5-ethoxy-2-fluoro-3-hydroxy-phenyl)-acetamide trifluoroacetic acid salt

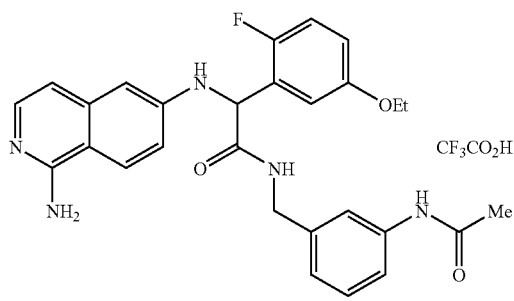

74A

5-Ethoxy-2-fluorophenol

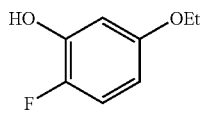

To 4-ethoxy-1-fluorobenzene (1.0 g, 7.1 mmol) in THF (8.0 mL) was added freshly distilled N,N,N',N'',N''-pentamethyldiethylenetriamine (0.8 mL) and 1.6 M n-butyllithium in hexane (5.13 ml, 8.2 mmol) at −78° C. After stirred at −60° C. for 1 h, trimethylborate (0.52 mL, 4.6 mmol) was introduced at −78° C. and the solution was warmed up to rt for 2 h. The reaction was quenched by acetic acid (1.5 ml) at 0° C. After 15 min, 30% hydrogen peroxide (1.2 ml) was introduced and the mixture was stirred from 0° C. to rt overnight. The mixture was extracted by EtOAc (3×30 mL). The combined organic layer was washed by brine, dried over $MgSO_4$, and concentrated. The crude product was purified by column chromatography to give 1.0 g colorless oil of 74A. $^1$H NMR (400 MHz, $CDCl_3$) δ ppm 1.39 (t, J=6.81 Hz, 3 H) 3.96 (q, J=7.03 Hz, 2H) 5.30 (d, J=2.20 Hz, 1H) 6.28-6.43 (m, 1H) 6.55 (dd, J=7.47, 3.08 Hz, 1H) 6.90-7.01 (m, 1H).

74B tert-Butyl(5-ethoxy-2-fluorophenoxy)dimethylsilane

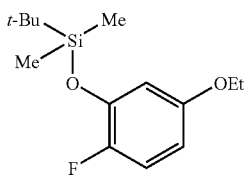

To 74A (1.0 g, 6.4 mmol) in DMF (20 mL) was added imidazole (0.6 g, 8.8 mmol) and t-butyl chlorodimethylsilane (2.0 g, 12.8 mmol) and the mixture was stirred at rt overnight. The reaction was diluted by EtOAc (100 mL) and washed by water (100 mL) and brine (50 mL). The organic layer was dried over $MgSO_4$ and concentrated. The crude product was purified by column chromatography to give 1.15 g of 74B (67% yield). $^1$H NMR (400 MHz, $CDCl_3$) δ ppm 0.19 (s, 6H) 1.00 (s, 9H) 1.39 (t, J=6.81 Hz, 3H) 3.95 (q, J=7.03 Hz, 2H) 6.37-6.44 (m, 1H) 6.46 (dd, J=7.03, 3.08 Hz, 1H) 6.78-7.06 (m, 1H).

74C

3-(tert-Butyldimethylsilyloxy)-5-ethoxy-2-fluorophenylboronic acid

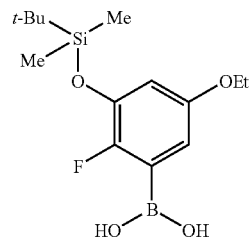

To 74B (110 mg, 0.4 mmol) in THF (1.5 mL) was added freshly distilled N,N,N',N'',N''-pentamethyldiethylenetriamine (0.2 mL) and 1.6 M n-butyllithium in hexane (0.5 mL, 0.8 mmol) at −78° C. After stirred at −35° C. for 1.5 h, trimethylborate (0.23 mL, 2.0 mmol) was introduced at −78° C., the solution was warmed up to rt overnight. The reaction was quenched by 1.0 N HCl (1.5 mL). After 30 min, the mixture was extracted by EtOAc (3×15 mL). The combined organic layer was washed by brine, dried over $MgSO_4$, and concentrated. The crude product was purified by column chromatography to give 90 mg white solid of 74C (72% yield). $^1$H NMR (400 MHz, Methanol-$d_4$) δ ppm 0.19 (s, 6H) 1.00 (s, 9H) 1.39 (t, J=7.03 Hz, 3H) 4.00 (q, J=7.03 Hz, 2H) 5.17 (d, J=6.59 Hz, 2H) 6.59 (dd, J=7.47, 3.08 Hz, 1H) 6.86 (t, J=3.52 Hz, 1H).

74D

2-(1-(tert-Butoxycarbonyl)isoquinolin-6-ylamino)-2-(5-ethoxy-2-fluoro-3-hydroxyphenyl)acetic acid

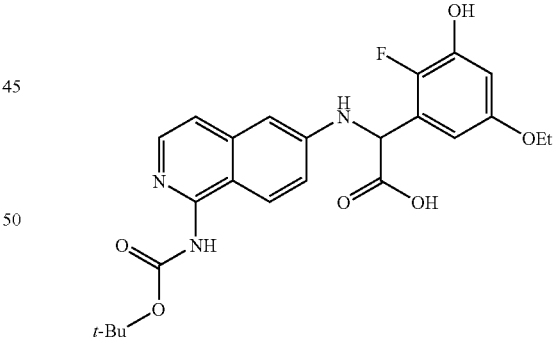

A mixture 74C, Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography ($CH_2Cl_2$:MeOH=100:15) to give 28 mg (25%) of 74D as a solid. $^1$H NMR (400 MHz, Methanol-$d_4$) δ ppm 0.92 (s, 9H) 1.22 (t, J=7.03 Hz, 3H) 3.82 (q, J=7.03 Hz, 2H) 5.45 (s, 1H) 6.36 (dd, J=6.59, 3.08 Hz, 1H) 6.48-6.53 (m, 1H) 6.60 (d, J=2.20 Hz, 1H) 6.74 (d, J=7.03 Hz, 1H) 7.11 (d, J=2.64 Hz, 1H) 7.22 (d, J=7.03 Hz, 1H) 7.99 (d, J=9.23 Hz, 1H).

74E

Example 74 was prepared according to the general coupling-deprotection using 74D and commercial N-(3-(aminomethyl)phenyl)acetamide HCl salt. ¹H NMR (400 MHz, Methanol-d₄) δ ppm 1.21 (t, J=7.03 Hz, 3H) 2.00 (s, 3H) 3.67-3.88 (m, 2H) 4.30 (d, J=5.27 Hz, 2H) 5.34 (s, 1H) 6.30-6.42 (m, 2H) 6.62 (d, J=2.20 Hz, 1H) 6.74 (d, J=7.03 Hz, 1H) 6.87 (d, J=7.47 Hz, 1H) 7.05-7.31 (m, 4H) 7.38 (s, 1H) 8.00 (d, J=9.23 Hz, 1H) 8.72 (t, J=6.15 Hz, 1H); LC MS 518 (M+H).

Example 75

N-(3-Acetylamino-benzyl)-2-(1-amino-isoquinolin-6-ylamino)-2-(5-ethoxy-2-fluoro-phenyl)-acetamide trifluoroacetic acid salt

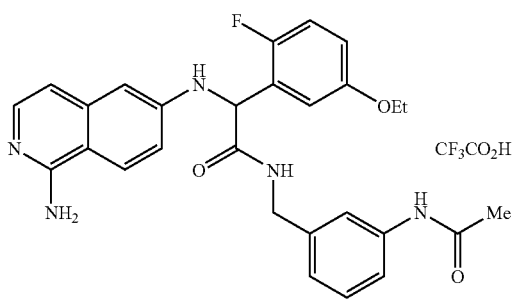

Example 75 was prepared according to the general coupling-deprotection using 73A and commercial N-(3-(aminomethyl)phenyl)acetamide HCl salt. ¹H NMR (400 MHz, Methanol-d₄) δ ppm 1.23 (t, J=6.81 Hz, 3H) 1.99 (s, 3H) 3.74-3.92 (m, 2H) 4.30 (dd, J=5.71, 2.64 Hz, 2H) 5.36 (s, 1H) 6.62 (d, J=2.20 Hz, 1H) 6.73 (d, J=7.03 Hz, 1H) 6.77-6.93 (m, 3H) 7.00 (t, J=9.23 Hz, 1H) 7.04-7.14 (m, 2H) 7.21-7.32 (m, 2H) 7.38 (s, 1H) 8.00 (d, J=9.23 Hz, 1H) 8.77 (t, J=5.93 Hz, 1H); LC MS 502 (M+H).

Example 76

2-(1-Amino-isoquinolin-6-ylamino)-N-(2-cyclopropanesulfonyl-benzyl)-2-(5-ethoxy-2-fluoro-phenyl)-acetamide trifluoroacetic acid salt

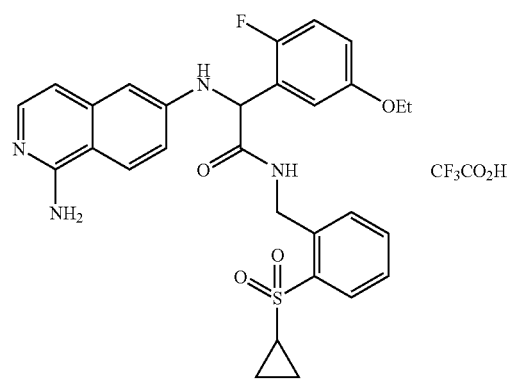

Example 76 was prepared according to the general coupling-deprotection using 73A and Intermediate 7. ¹H NMR (400 MHz, Methanol-d₄) δ ppm 0.90-0.98 (m, 2H) 1.01-1.15 (m, 2H) 1.24 (t, J=7.03 Hz, 3H) 2.75-2.84 (m, 1H) 3.76-3.91 (m, 2H) 4.68-4.88 (m, 2H) 6.62 (d, J=2.20 Hz, 1H) 6.74 (d, J=7.03 Hz, 1H) 6.78-6.89 (m, 2H) 7.01 (t, J=9.23 Hz, 1H) 7.10 (dd, J=9.23, 2.64 Hz, 1H) 7.25 (d, J=7.03 Hz, 1H) 7.34-7.49 (m, 3H) 7.71-7.77 (m, 1H) 8.00 (d, J=9.23 Hz, 2H) 8.60 (t, J=6.15 Hz, 1H); LC MS 549 (M+H).

Example 77

N-(3-Acetylamino-benzyl)-2-(1-amino-isoquinolin-6-ylamino)-2-(2-chloro-5-methoxy-phenyl)-acetamide trifluoroacetic acid salt

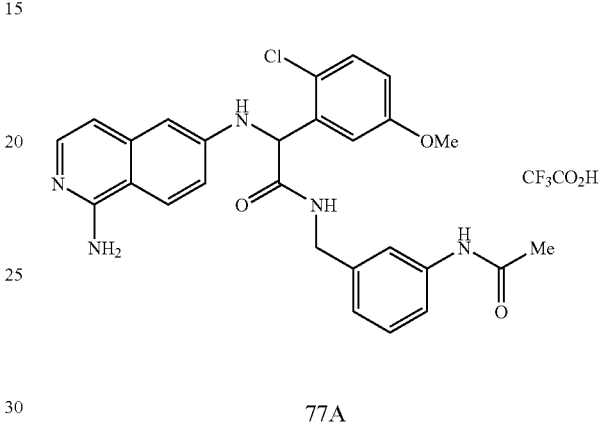

77A 2-(1-di-tert-Butoxycarbonylaminoisoquinolin-6-ylamino)-2-(2-chloro-5-methoxyphenyl)acetic acid

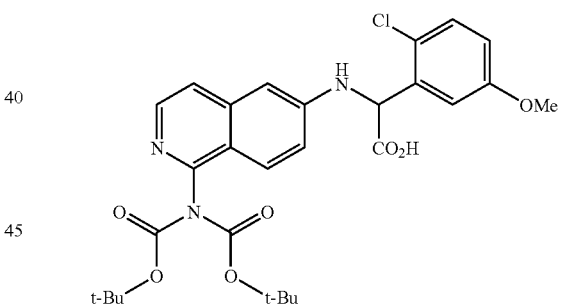

A mixture of 2-chloro-5-methoxyhenylboronic acid (43 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH₂Cl₂:MeOH=100:15) to give 28 mg (25%) of 77A as a solid. ¹H NMR (400 MHz, Methanol-d₄) δ ppm 1.16 (s, 18H) 3.24 (s, 3H) 5.55 (s, 1H) 6.57 (d, J=2.20 Hz, 1H) 6.75-6.84 (m, 2H) 7.00 (d, J=3.08 Hz, 1H) 7.10-7.20 (m, 1H) 7.27 (d, J=9.23 Hz, 1H) 7.32 (d, J=5.27 Hz, 1H) 7.54 (d, J=9.23 Hz, 1H) 7.93 (d, J=6.15 Hz, 1H); LC MS 558 (M+H).

77B

Example 77 was prepared according to the general coupling-deprotection using 77A and commercial N-(3-(aminomethyl)phenyl)acetamide HCl salt. ¹H NMR (400 MHz, Methanol-d$_4$) δ ppm 2.00 (s, 3H) 3.61 (s, 3H) 4.33 (d, J=5.71 Hz, 2H) 5.47 (s, 1H) 6.60 (d, J=2.20 Hz, 1H) 6.74 (d, J=7.03 Hz, 1H) 6.84 (dd, J=8.79, 3.08 Hz, 1H) 6.89 (d, J=7.47 Hz, 1H) 6.94 (d, J=2.64 Hz, 1H) 7.06-7.14 (m, 2H) 7.22-7.31 (m, 3H) 7.42 (s, 1H) 8.00 (d, J=9.23 Hz, 1H) 8.76 (t, J=5.93 Hz, 1H); LC MS 504 (M+H).

Example 78

N-(5-Acetylamino-2-ethanesulfonyl-benzyl)-2-(1-amino-isoquinolin-6-ylamino)-2-(2-chloro-5-methoxy-phenyl)-acetamide trifluoroacetic acid salt

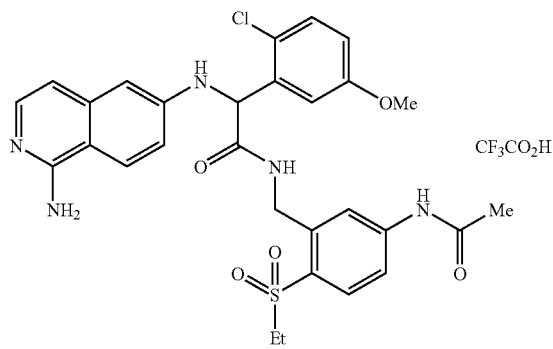

Example 78 was prepared according to the general coupling-deprotection using 77A and Intermediate 9. $^1$H NMR (400 MHz, Methanol-d$_4$) δ ppm 1.09 (t, J=7.47 Hz, 3H) 2.05 (s, 3H) 3.14-3.21 (m, 2H) 3.59 (s, 3H) 4.63 (t, J=5.05 Hz, 2H) 5.47 (s, 1H) 6.56 (d, J=2.20 Hz, 1H) 6.70 (d, J=7.03 Hz, 1H) 6.80-6.86 (m, 2H) 7.07 (dd, J=9.23, 2.20 Hz, 1H) 7.22 (d, J=7.03 Hz, 1H) 7.28 (d, J=8.35 Hz, 1H) 7.54 (dd, J=8.35, 2.20 Hz, 1H) 7.69 (d, J=8.79 Hz, 1H) 7.76 (d, J=2.20 Hz, 1H) 7.99 (d, J=9.23 Hz, 1H) 8.52 (t, J=5.93 Hz, 1H); LC MS 596 (M+H).

Example 79

N-(3-Acetylamino-benzyl)-2-(1-amino-isoquinolin-6-ylamino)-2-(4-chloro-3-methoxy-phenyl)-acetamide trifluoroacetic acid salt

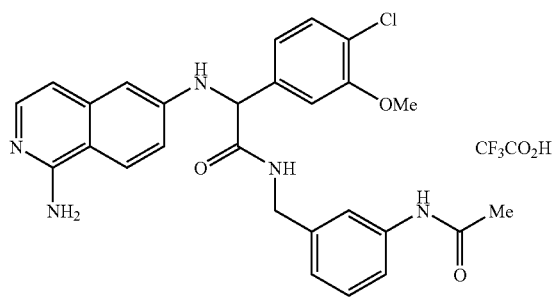

79A

4-Chloro-3-methoxyphenylboronic acid

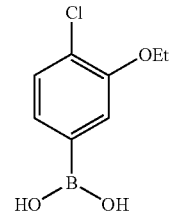

To 4-bromo-1-chloro-2-methoxybenzene (2.2 g, 9.9 mmol) in toluene/THF (16/6 mL) at −78° C. was added n-butyl lithium (8.7 mL, 1.6 M in hexane, 14 mmol) dropwise. The reaction was stirred at −78° C. for 30 min., then trimethylborate (2.2 mL, 19.8 mmol) was added. The reaction was allowed to warm to rt and stirred overnight and then quenched with 1 M HCl (15 mL). The organic layer was separated and dried over sodium sulfate. The solvent was removed and the crude product was purified by flash column chromatography to give 79A (1.2 g, 65% yield) as a white solid. $^1$H NMR (400 MHz, Methanol-d$_4$) δ ppm 3.87 (m, 3H) 7.11 (d, J=7.83 Hz, 1H) 7.20 (s, 1H) 7.29 (d, J=7.83 Hz, 1H).

79B 2-(1-di-tert-Butoxycarbonylaminoisoquinolin-6-ylamino)-2-(4-chloro-3-methoxyphenyl)acetic acid

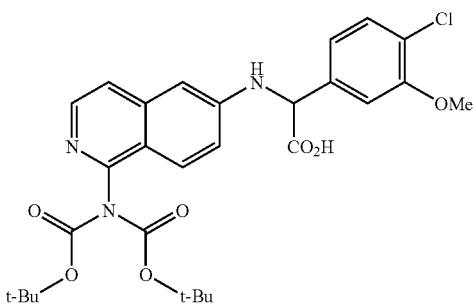

A mixture of 79A (43 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 56 mg (50%) of 79B as a solid. $^1$H NMR (400 MHz, Methanol-d$_4$) δ ppm 1.18 (s, 18H) 3.78 (s, 3H) 6.56 (d, J=2.20 Hz, 1H) 7.05 (d, J=8.35 Hz, 1H) 7.17 (dd, J=8.79, 2.20 Hz, 1H) 7.20-7.25 (m, 3H) 7.32 (d, J=5.71 Hz, 1H) 7.53 (d, J=9.23 Hz, 1H) 7.92 (d, J=5.71 Hz, 1H); LC MS 558 (M+H).

79C

Example 79 was prepared according to the general coupling-deprotection using 79B and commercial N-(3-(aminomethyl)phenyl)acetamide HCl salt. $^1$H NMR (400 MHz, Methanol-d₄) δ ppm 1.99 (s, 3H) 3.73 (s, 3H) 4.28 (d, J=5.27 Hz, 2H) 5.04 (s, 1H) 6.56 (d, J=2.20 Hz, 1H) 6.70 (d, J=7.03 Hz, 1H) 6.81 (d, J=7.03 Hz, 1H) 7.00 (dd, J=8.13, 1.98 Hz, 1H) 7.05-7.12 (m, 3H) 7.20-7.30 (m, 3H) 7.34 (s, 1H) 7.99 (d, J=9.23 Hz, 1H) 8.78 (t, J=5.71 Hz, 1H); LC MS 504 (M+H).

Example 80

2-(1-Amino-isoquinolin-6-ylamino)-2-(4-chloro-3-methoxy-phenyl)-N-(2-cyclopropanesulfonyl-benzyl)-acetamide trifluoroacetic acid salt

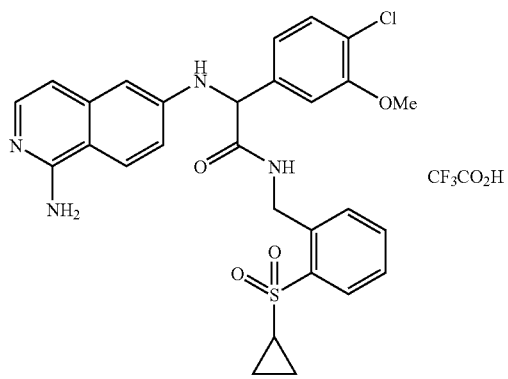

Example 80 was prepared according to the general coupling-deprotection using 79B and Intermediate 7. ¹H NMR (400 MHz, Methanol-d₄) δ ppm 0.86-0.97 (m, 2H) 1.00-1.18 (m, 2H) 2.64-2.81 (m, 1H) 3.75 (s, 3H) 4.64-4.89 (m, 2H) 5.11 (s, 1H) 6.57 (d, J=2.64 Hz, 1H) 6.72 (d, J=7.03 Hz, 1H) 7.00 (dd, J=8.13, 1.98 Hz, 1H) 7.06-7.14 (m, 2H) 7.20-7.31 (m, 3H) 7.31-7.44 (m, 2H) 7.73 (d, J=9.23 Hz, 1H) 7.99 (d, J=9.23 Hz, 1H) 8.58 (t, J=6.15 Hz, 1H); LC MS 551 (M+H).

Example 81

N-(5-Acetylamino-2-ethanesulfonyl-benzyl)-2-(1-amino-isoquinolin-6-ylamino)-2-(4-chloro-3-methoxy-phenyl)-acetamide trifluoroacetic acid salt

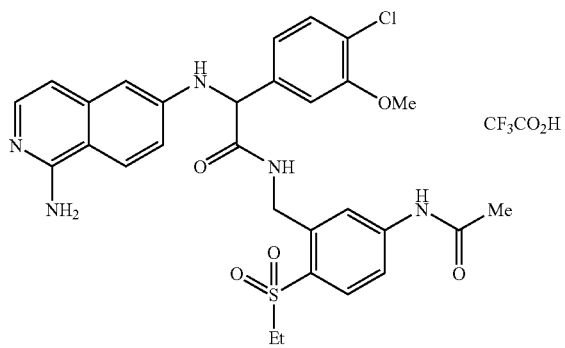

Example 81 was prepared according to the general coupling-deprotection using 79B and Intermediate 9. ¹H NMR (400 MHz, Methanol-d₄) δ ppm 1.07 (t, J=7.25 Hz, 3H) 2.03 (s, 3H) 3.11-3.32 (m, 2H) 3.73 (s, 3H) 4.47-4.70 (m, 2H) 5.08 (s, 1H) 6.52 (d, J=2.64 Hz, 1H) 6.68 (d, J=7.03 Hz, 1H) 6.98 (dd, J=8.13, 1.98 Hz, 1H) 7.04-7.12 (m, 2H) 7.21 (d, J=7.03 Hz, 1H) 7.26 (d, J=8.35 Hz, 1H) 7.47 (dd, J=8.79, 2.20 Hz, 1H) 7.62-7.72 (m, 2H) 7.97 (d, J=9.23 Hz, 1H) 8.58 (t, J=6.15 Hz, 1H); LC MS 596 (M+H).

Example 82

N-(3-Acetylamino-benzyl)-2-(1-amino-isoquinolin-6-ylamino)-2-(2-fluoro-5-methoxy-phenyl)-acetamide trifluoroacetic acid salt

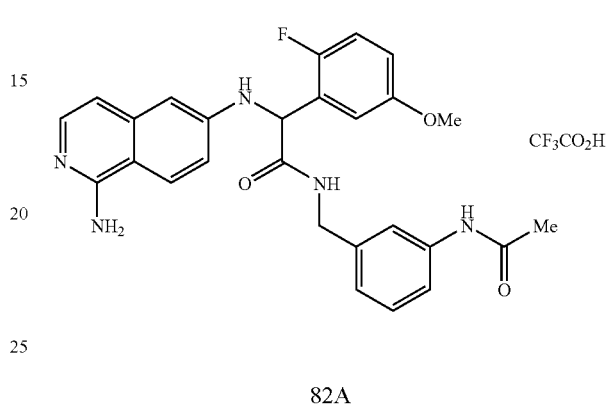

82A 2-(1-di-tert-Butoxycarbonylaminoisoquinolin-6-ylamino)-2-(3-ethoxy-4-fluorophenyl)acetic acid

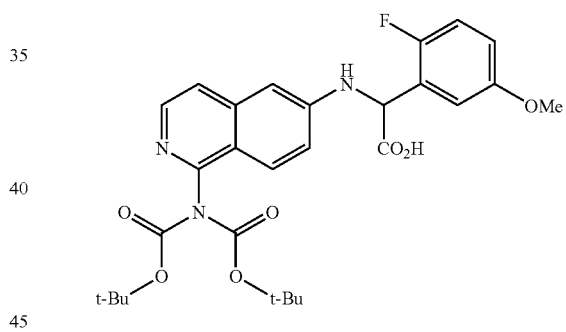

A mixture of 2-fluoro-5-methoxyphenylboronic acid (38 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH₂Cl₂:MeOH=100:15) to give 27 mg (25%) of 82A as a solid. ¹H NMR (400 MHz, Methanol-d₄) δ ppm 1.17 (s, 18H) 3.63 (s, 3H) 5.43 (s, 1H) 6.62 (d, J=2.20 Hz, 1H) 6.74-6.91 (m, 2H) 6.93-7.04 (m, 2H) 7.18 (dd, J=9.23, 2.20 Hz, 1H) 7.36 (d, J=5.71 Hz, 1H) 7.54 (d, J=9.23 Hz, 1H) 7.94 (d, J=5.71 Hz, 1H); LC MS 542 (M+H).

82B

Example 82 was prepared according to the general coupling-deprotection using 82A and commercial N-(3-(aminomethyl)phenyl)acetamide HCl salt. ¹H NMR (400 MHz, Methanol-d₄) δ ppm 1.98 (s, 3H) 3.61 (s, 3H) 4.29 (d, J=5.71 Hz, 2H) 5.36 (s, 1H) 6.61 (d, J=2.20 Hz, 1H) 6.72 (d, J=7.47 Hz, 1H) 6.78-6.88 (m, 2H) 6.92 (dd, J=5.71, 3.08 Hz, 1H)

7.00 (t, J=9.23 Hz, 1H) 7.04-7.12 (m, 2H) 7.19-7.29 (m, 2H) 7.37 (s, 1H) 7.99 (d, J=9.23 Hz, 1H) 8.78 (t, J=5.93 Hz, 1H); LC MS 488 (M+H).

Example 83

2-(1-Amino-isoquinolin-6-ylamino)-N-(2-cyclopropanesulfonyl-benzyl)-2-(2-fluoro-5-methoxy-phenyl)-acetamide trifluoroacetic acid salt

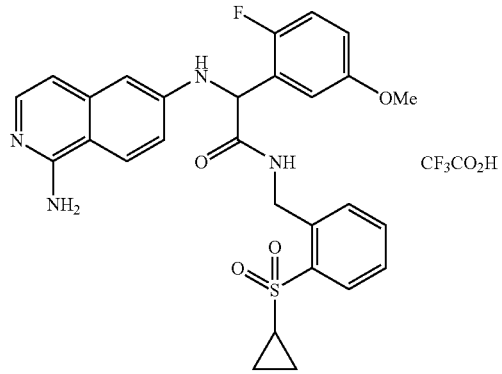

Example 83 was prepared according to the general coupling-deprotection using 82A and Intermediate 7. $^1$H NMR (400 MHz, Methanol-$d_4$) δ ppm 0.88-0.97 (m, 2H) 0.99-1.15 (m, 2H) 2.64-2.95 (m, 1H) 3.62 (s, 3H) 4.66-4.91 (m, 2H) 5.39 (s, 1H) 6.61 (d, J=2.20 Hz, 1H) 6.73 (d, J=7.03 Hz, 1H) 6.80-6.86 (m, 1H) 6.89 (dd, J=5.71, 3.08 Hz, 1H) 7.02 (t, J=9.23 Hz, 1H) 7.09 (dd, J=9.01, 2.42 Hz, 1H) 7.24 (d, J=7.03 Hz, 1H) 7.33-7.40 (m, 2H) 7.44 (t, J=6.81 Hz, 1H) 7.70-7.75 (m, 1H) 8.00 (d, J=9.23 Hz, 1H) 8.60 (t, J=5.93 Hz, 1H); LC MS 535 (M+H).

Example 84

N-(5-Acetylamino-2-ethanesulfonyl-benzyl)-2-(1-amino-isoquinolin-6-ylamino)-2-(2-fluoro-5-methoxy-phenyl)-acetamide trifluoroacetic acid salt

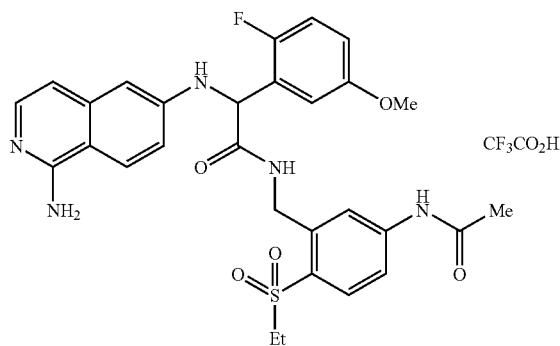

Example 84 was prepared according to the general coupling-deprotection using 82A and Intermediate 9. $^1$H NMR (400 MHz, Methanol-$d_4$) δ ppm 1.08 (t, J=7.47 Hz, 3H) 2.03 (s, 3H) 3.11-3.21 (m, 2H) 3.60 (s, 3H) 4.51-4.71 (m, 2H) 5.37 (s, 1H) 6.56 (d, J=2.20 Hz, 1H) 6.69 (d, J=7.03 Hz, 1H) 6.77-6.86 (m, 2H) 7.00 (t, J=9.01 Hz, 1H) 7.08 (dd, J=9.23, 2.20 Hz, 1H) 7.21 (d, J=7.03 Hz, 1H) 7.53 (dd, J=8.79, 2.20 Hz, 1H) 7.65-7.71 (m, 2H) 7.98 (d, J=9.23 Hz, 1H) 8.57 (t, J=5.93 Hz, 1H); LC MS 580 (M+H).

Example 85

N-(3-Acetylamino-benzyl)-2-(1-amino-isoquinolin-6-ylamino)-2-(2-fluoro-5-propoxy-phenyl)-acetamide trifluoroacetic acid salt

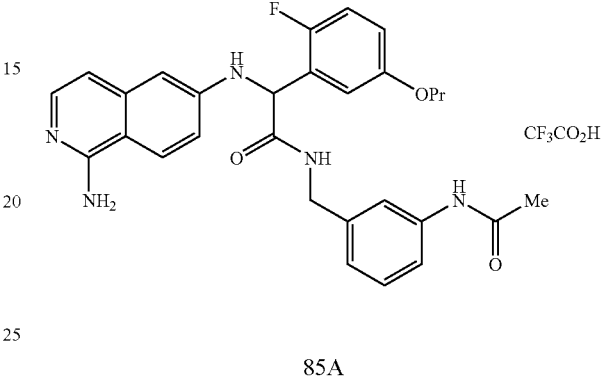

85A 2-(1-di-tert-Butoxycarbonylaminoisoquinolin-6-ylamino)-2-(2-fluoro-5-propoxyphenyl)acetic acid

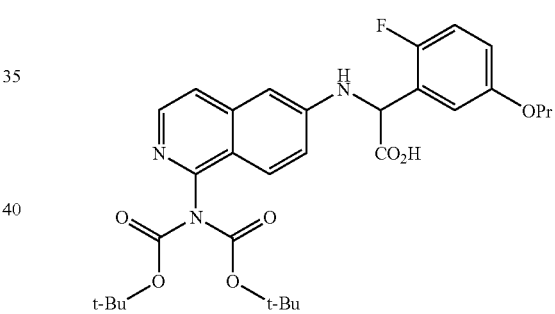

A mixture of 2-fluoro-5-propoxyphenylboronic acid (45 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 29 mg (25%) of 85A as a solid. $^1$H NMR (400 MHz, Methanol-$d_4$) δ ppm 0.87 (t, J=7.25 Hz, 3H) 1.17 (s, 18H) 1.61 (q, J=6.59 Hz, 2H) 3.74 (t, J=6.37 Hz, 2H) 5.25 (s, 1H) 6.58 (d, J=1.76 Hz, 1H) 6.66-6.77 (m, 1H) 6.90-7.01 (m, 2H) 7.14 (dd, J=9.01, 1.98 Hz, 1H) 7.31 (d, J=6.15 Hz, 1H) 7.52 (d, J=9.23 Hz, 1H) 7.92 (d, J=5.71 Hz, 1H); LC MS 570 (M+H).

85B

Example 85 was prepared according to the general coupling-deprotection using 85A and commercial N-(3-(aminomethyl)phenyl)acetamide HCl salt. $^1$H NMR (400 MHz, Methanol-$d_4$) δ ppm 0.89 (t, J=7.47 Hz, 3H) 1.55-1.71 (m, 2H) 1.98 (s, 3H) 3.66-3.77 (m, 2H) 4.25-4.35 (m, 2H) 5.35 (s, 1H) 6.61 (d, J=2.20 Hz, 1H) 6.71 (d, J=7.03 Hz, 1H) 6.77-

6.83 (m, 1H) 6.85 (d, J=7.91 Hz, 1H) 6.89 (dd, J=5.71, 3.08 Hz, 1H) 6.99 (t, J=9.23 Hz, 1H) 7.03-7.12 (m, 2H) 7.19-7.29 (m, 2H) 7.37 (s, 1H) 7.99 (d, J=9.23 Hz, 1H) 8.78 (t, J=5.93 Hz, 1H); LC MS 516 (M+H).

Example 86

N-(5-Acetylamino-2-ethanesulfonyl-benzyl)-2-(1-amino-isoquinolin-6-ylamino)-2-(2-fluoro-5-propoxy-phenyl)-acetamide trifluoroacetic acid salt

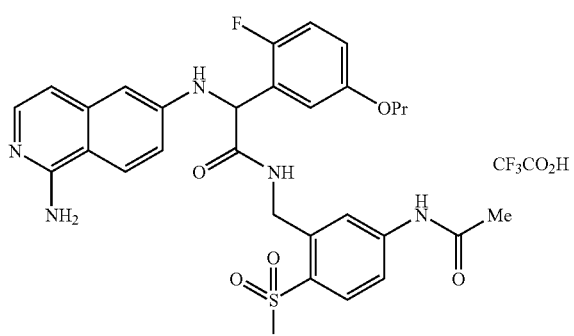

Example 86 was prepared according to the general coupling-deprotection using 85A and Intermediate 9. $^1$H NMR (400 MHz, Methanol-$d_4$) δ ppm 0.83-0.95 (m, 3H) 0.98-1.13 (m, 3H) 1.55-1.70 (m, 2H) 2.03 (s, 3H) 3.10-3.10 (m, 2H) 3.60-3.79 (m, 2H) 4.52-4.71 (m, 2H) 5.36 (s, 1H) 6.57 (d, J=2.20 Hz, 1H) 6.69 (d, J=7.47 Hz, 1H) 6.76-6.84 (m, 2H) 6.94-7.03 (m, 1H) 7.07 (dd, J=9.23, 2.20 Hz, 1H) 7.21 (d, J=7.47 Hz, 1H) 7.53-7.59 (m, 1H) 7.68 (d, J=8.79 Hz, 2H) 7.94-8.01 (m, 1H) 8.56 (t, J=5.93 Hz, 1H); LC MS 608 (M+H).

Example 87

N-(3-Acetylamino-benzyl)-2-(1-amino-isoquinolin-6-ylamino)-2-(2-fluoro-5-methyl-phenyl)-acetamide trifluoroacetic acid salt

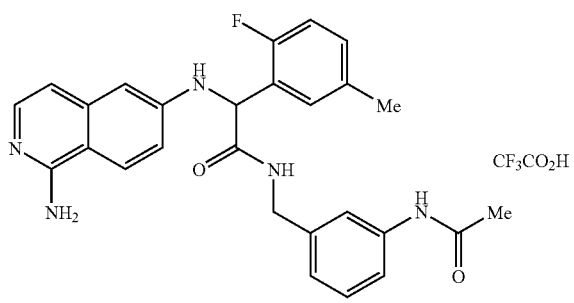

87A 2-(1-di-tert-Butoxycarbonylaminoisoquinolin-6-ylamino)-2-(2-fluoro-5-methylphenyl)acetic acid

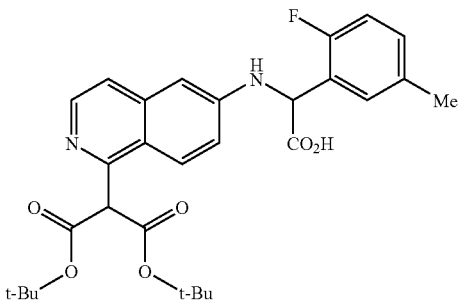

A mixture of 2-fluoro-5-methylphenylboronic acid (34 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min. in a Microwave Reactor. The crude product was purified by flash column chromatography (CH$_2$Cl$_2$:MeOH=100:15) to give 52 mg (50%) of 87A as a solid. $^1$H NMR (400 MHz, Methanol-$d_4$) δ ppm 1.18 (s, 18H) 2.19 (s, 3H) 5.44 (s, 1H) 6.62 (d, J=2.20 Hz, 1H) 6.93-7.00 (m, 1H) 7.03-7.09 (m, 1H) 7.19 (dd, J=9.23, 2.20 Hz, 1-H) 7.22-7.27 (m, 1H) 7.37 (d, J=5.71 Hz, 1H) 7.55 (d, J=9.23 Hz, 1H) 7.95 (d, J=5.71 Hz, 1H); LC MS 526 (M+H).

87B

Example 87 was prepared according to the general coupling-deprotection using 87A and commercial N-(3-(aminomethyl)phenyl)acetamide HCl salt. $^1$H NMR (400 MHz, Methanol-$d_4$) δ ppm 1.98 (s, 3H) 2.18 (s, 3H) 4.29 (d, J=6.15 Hz, 2H) 5.35 (s, 1H) 6.60 (d, J=2.20 Hz, 1H) 6.72 (d, J=7.03 Hz, 1H) 6.84 (d, J=7.47 Hz, 1H) 6.92-7.01 (m, 1H) 7.04-7.12 (m, 3H) 7.16-7.28 (m, 3H) 7.38 (s, 1H) 7.98 (d, J=9.23 Hz, 1H) 8.76 (t, J=5.93 Hz, 1H); LC MS 472 (M+H).

Example 88

N-(5-Acetylamino-2-ethanesulfonyl-benzyl)-2-(1-amino-isoquinolin-6-ylamino)-2-(2-fluoro-5-methylphenyl)-acetamide trifluoroacetic acid salt

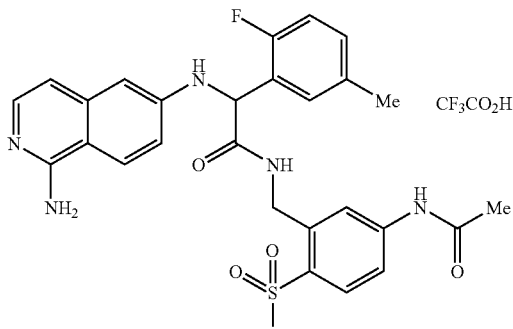

Example 88 was prepared according to the general coupling-deprotection using 87A and Intermediate 9. $^1$H NMR (400 MHz, Methanol-d$_4$) δ ppm 1.08 (t, J=7.47 Hz, 3H) 2.04 (s, 3H) 2.17 (s, 3H) 3.14 (s, 2H) 4.61 (t, J=5.27 Hz, 2H) 5.35 (s, 1H) 6.55 (d, J=2.20 Hz, 1H) 6.68 (d, J=7.03 Hz, 1H) 6.89-7.01 (m, 1H) 7.05-7.16 (m, 3H) 7.21 (d, J=7.03 Hz, 1H) 7.53 (dd, J=8.57, 1.98 Hz, 1H) 7.67 (d, J=8.79 Hz, 1H) 7.73 (d, J=1.76 Hz, 1H) 7.97 (d, J=9.23 Hz, 1H) 8.56 (t, J=5.93 Hz, 1H); LC MS 564 (M+H).

Example 89

N-(3-Acetylamino-benzyl)-2-(1-amino-isoquinolin-6-ylamino)-2-(5-ethyl-2-fluoro-phenyl)-acetamide trifluoroacetic acid salt

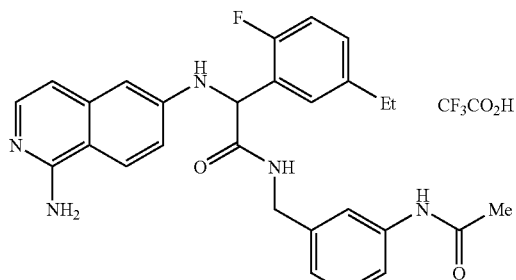

89A 1-(3-Bromo-4-fluorophenyl)ethanol

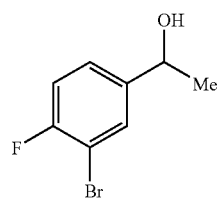

To a solution of 3-bromo-4-fluoroacetophenone (10 g, 46 mmol) in THF (100 mL) and methanol (1.0 mL) was added sodium borohydride (2.1 g, 55.5 mmol). The mixture was heated up to 70° C. for 1 h, then cooled down to rt. The reaction was quenched by 100 ml of 1N HCl solution and extracted by EtOAc (3×100 mL). The combined organic layer was washed by brine, dried over MgSO$_4$, and concentrated. The crude product was purified by column chromatography to give 9.8 g of 89A (97% yield). $^1$H NMR (400 MHz, CDCl$_3$) δ ppm 1.48 (d, J=6.15 Hz, 3H) 7.24-7.33 (m, 1H) 7.59 (dd, J=6.59, 2.20 Hz, 1H).

89B

2-Bromo-4-ethyl-1-fluorobenzene

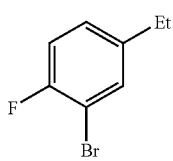

To 89A (9.8 g, 45 mmol) in trifluoroacetic acid (20 mL) was added triethylsilane (14.3 mL, 90 mmol). After stirring at 50° C. for 6 h, the reaction was quenched by 100 mL of saturated NaHCO$_3$ solution and extracted by diethyl ether (3×). The combined organic layer was washed by brine, dried by MgSO$_4$, and concentrated. The crude residual was distilled at 200° C. to give 89B (85% purity). $^1$H NMR (400 MHz, CDCl$_3$) δ ppm 1.22 (t, J=7.69 Hz, 3H) 2.60 (q, J=7.47 Hz, 2H) 7.02 (t, J=8.57 Hz, 1H) 7.06-7.12 (m, 1H) 7.37 (dd, J=6.59, 2.20 Hz, 1H).

89C

5-Ethyl-2-fluorophenylboronic acid

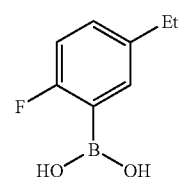

To 89B (550 mg, 2.3 mmol) in THF (10 mL) was added 1.6 M n-butyllithium in hexane (2.2 ml, 3.5 mmol) at −78° C. After stirred for 1 h, trimethylborate (0.52 mL, 4.6 mmol) was introduced at −78° C. The reaction mixture was warmed up to room temperature overnight. It was then quenched by 1.0 N HCl (10 mL) and extracted by EtOAc (3×30 mL). The combined organic layer was washed by brine, dried over MgSO$_4$, and concentrated. The crude product was purified by column chromatography to give 255 mg white solid of 89C. $^1$H NMR (400 MHz, Methanol-d$_4$) δ ppm 1.15-1.27 (m, 3H) 2.61 (q, J=7.76 Hz, 2H) 6.94 (t, J=8.57 Hz, 1H) 7.17-7.27 (m, 2H).

89D 2-(1-di-tert-Butoxycarbonylaminoisoquinolin-6-ylamino)-2-(5-ethyl-2-fluoro-phenyl)acetic acid

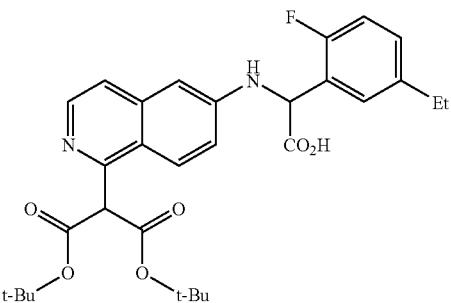

A mixture of 89C (36 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH$_2$Cl$_2$:MeOH=100:15) to give 54 mg (51% yield) of 89D as a solid. $^1$H NMR (400 MHz, Methanol-d$_4$) δ ppm 1.05 (t, J=7.47 Hz, 3H) 1.16 (s, 18H) 2.48 (q, J=7.62 Hz, 2H) 5.44 (s, 1H) 6.61 (d, J=2.20 Hz, 1H) 6.93-7.00 (m, 1H) 7.03-7.10 (m, 1H) 7.18 (dd, J=9.23, 2.20 Hz, 1H) 7.25 (dd, J=7.03, 2.20 Hz, 1H) 7.35 (d, J=5.71 Hz, 1H) 7.54 (d, J=9.23 Hz, 1H) 7.93 (d, J=6.15 Hz, 1H) LC MS 540 (M+H).

89E

Example 89 was prepared according to the general coupling-deprotection using 89D and commercial N-(3-(aminomethyl)phenyl)acetamide HCl salt. ¹H NMR (400 MHz, Methanol-d₄) δ ppm 1.07 (t, J=7.69 Hz, 3H) 1.94-2.06 (m, 3H) 2.49 (q, J=7.76 Hz, 2H) 4.30 (d, J=6.15 Hz, 2H) 5.36 (s, 1H) 6.62 (d, J=2.20 Hz, 1H) 6.73 (d, J=7.03 Hz, 1H) 6.85 (d, J=7.47 Hz, 1H) 6.95-7.02 (m, 1H) 7.04-7.16 (m, 3H) 7.19-7.30 (m, 3H) 7.40 (s, 1H) 7.99 (d, J=9.23 Hz, 1H) 8.78 (t, J=5.93 Hz, 1H); LC MS 486 (M+H).

Example 90

N-(5-Acetylamino-2-ethanesulfonyl-benzyl)-2-(1-amino-isoquinolin-6-ylamino)-2-(5-ethyl-2-fluoro-phenyl)-acetamide trifluoroacetic acid salt

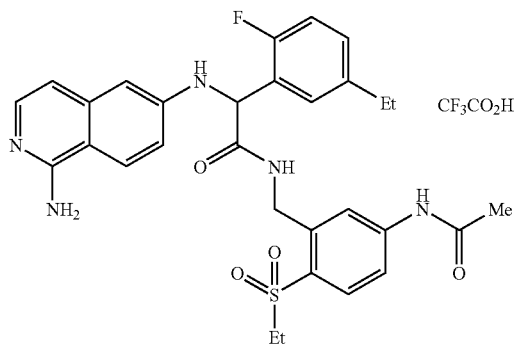

Example 90 was prepared according to the general coupling-deprotection using 89D and Intermediate 9. ¹H NMR (400 MHz, Methanol-d₄) δ ppm 1.01-1.10 (m, 6H) 2.04 (s, 3H) 2.46 (q, J=7.47 Hz, 2H) 3.11-3.21 (m, 2H) 4.61 (d, J=6.15 Hz, 2H) 5.35 (s, 1H) 6.56 (d, J=2.20 Hz, 1H) 6.69 (d, J=7.03 Hz, 1H) 6.98 (t, J=9.67 Hz, 1H) 7.04-7.15 (m, 3H) 7.22 (d, J=7.03 Hz, 1H) 7.55 (dd, J=8.79, 2.20 Hz, 1H) 7.67 (d, J=8.35 Hz, 1H) 7.73 (d, J=2.20 Hz, 1H) 7.98 (d, J=8.79 Hz, 1H) 8.56 (t, J=6.15 Hz, 1H); LC MS 578 (M+H).

Example 91

N-(3-Acetylamino-benzyl)-2-(1-amino-isoquinolin-6-ylamino)-2-(4-chloro-3-ethyl-phenyl)-acetamide trifluoroacetic acid salt

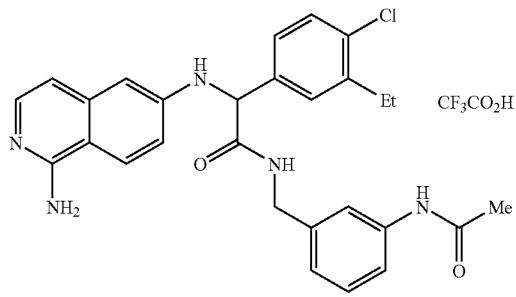

91A 2-(1-di-tert-Butoxycarbonylaminoisoquinolin-6-ylamino)-2-(4-chloro-3-ethyl-phenyl)acetic acid

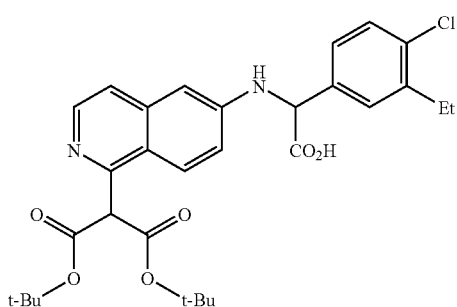

A mixture of 4-chloro-3-ethylphenylboronic acid (38 mg, 0.23 mmol), Intermediate 1 (72 mg, 0.2 mmol) and glyoxylic acid monohydrate (21 mg, 0.23 mmol) in acetonitrile (0.7 mL) and DMF (0.07 mL) was heated at 85° C. for 30 min in a Microwave Reactor. The crude product was purified by flash column chromatography (CH₂Cl₂:MeOH=100:15) to give 54 mg (50%) of 91A as a solid. ¹H NMR (400 MHz, Methanol-d₄) δ ppm 1.07 (t, J=7.69 Hz, 3H) 1.16 (s, 18H) 2.63 (q, J=7.47 Hz, 2H) 5.11 (s, 1H) 6.56 (d, J=2.20 Hz, 1H) 7.18 (dd, J=9.23, 2.20 Hz, 1H) 7.21-7.24 (m, 1H) 7.26-7.33 (m, 2H) 7.40 (d, J=2.20 Hz, 1H) 7.53 (d, J=9.23 Hz, 1H) 7.91 (d, J=5.71 Hz, 1H); LC MS 556 (M+H).

91B

Example 91 was prepared according to the general coupling-deprotection using 91A and commercial N-(3-(aminomethyl)phenyl)acetamide HCl salt. ¹H NMR (400 MHz, Methanol-d₄) δ ppm 1.09 (t, J=7.69 Hz, 3H) 1.99 (s, 3H) 2.62-2.73 (m, 2H) 4.27 (d, J=5.71 Hz, 2H) 5.03 (s, 1H) 6.54 (d, J=2.20 Hz, 1H) 6.68 (d, J=7.03 Hz, 1H) 6.79 (d, J=7.47 Hz, 1H) 7.02-7.12 (m, 2H) 7.19-7.30 (m, 4H) 7.35 (d, J=3.08 Hz, 2H) 7.98 (d, J=9.23 Hz, 1H) 8.79 (t, J=5.71 Hz, 1H); LC MS 502 (M+H).

Example 92

N-(5-Acetylamino-2-ethanesulfonyl-benzyl)-2-(1-amino-isoquinolin-6-ylamino)-2-(4-chloro-3-ethyl-phenyl)-acetamide trifluoroacetic acid salt

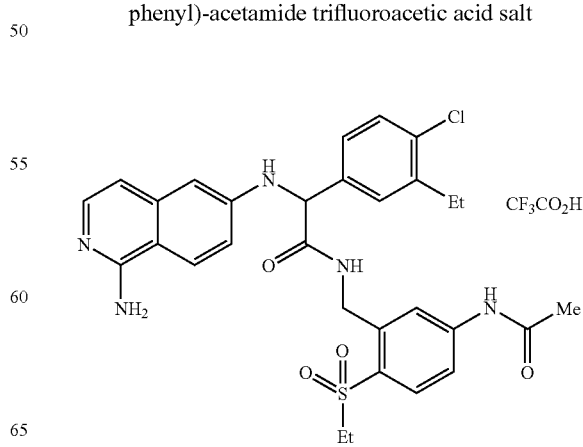

Example 92 was prepared according to the general coupling-deprotection using 91A and Intermediate 9. ¹H NMR (400 MHz, Methanol-d₄) δ ppm 1.02-1.14 (m, 6H) 2.03 (s, 3H) 2.63 (q, J=7.47 Hz, 2H) 3.11-3.21 (m, 2H) 4.46-4.69 (m, 2H) 5.06 (s, 1H) 6.50 (d, J=2.20 Hz, 1H) 6.66 (d, J=7.03 Hz, 1H) 7.07 (dd, J=9.23, 2.20 Hz, 1H) 7.17-7.33 (m, 4H) 7.49 (dd, J=8.79, 2.20 Hz, 1H) 7.62-7.72 (m, 2H) 7.96 (d, J=9.23 Hz, 1H) 8.58 (t, J=5.93 Hz, 1H); LC MS 594 (M+H).

Example 93

2-(1-Amino-isoquinolin-6-ylamino)-N-(2-cyclobutanesulfonyl-benzyl)-2-(3-ethoxy-4-fluoro-phenyl)-N-methyl-acetamide trifluoroacetic acid salt

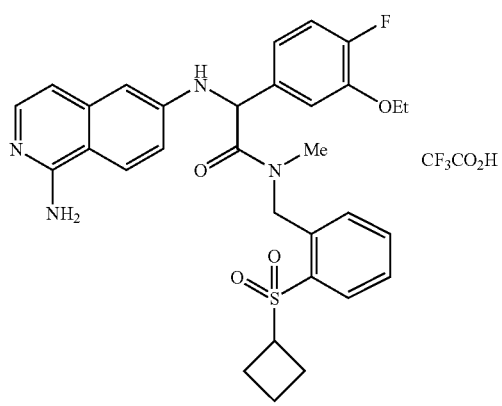

Example 93 was prepared according to the general coupling-deprotection using 64D and Intermediate 12. ¹H NMR (400 MHz, Methanol-d₄) δ ppm a mixture of two rotomers: 1.30 (m, 3H) 1.90-2.41 (m, 6H) 2.96 and 3.11 (s, 3H) 3.90-4.10 (m, 3H) 4.76 (m, 1H), 5.04-5.19 (m, 2H) 5.53 and 5.72 (s, 1H) 6.60-7.41 (m, 11H) 7.83-8.00 (m, 2H); LC MS 577 (M+H).

Example 94

2-(1-Amino-isoquinolin-6-ylamino)-N-(2-cyclobutanesulfonyl-benzyl)-2-(5-ethoxy-2-fluoro-phenyl)-N-methyl-acetamide trifluoroacetic acid salt

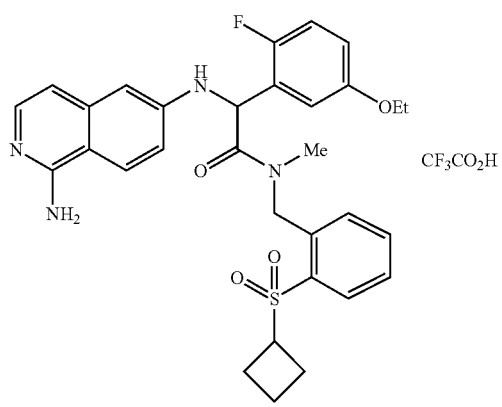

Example 94 was prepared according to the general coupling-deprotection using 73A and Intermediate 12. ¹H NMR (400 MHz, Methanol-d₄) δ ppm a mixture of two rotomers: 1.25 (m, 3H) 1.90-2.42 (m, 6H) 2.93 and 3.05 (s, 3H) 3.83-4.11 (m, 3H) 4.49-5.12 (m, 2H) 5.82-5.95 (s, 1H) 6.62-7.43 (m, 10H) 7.79-7.86 (m, 1H) 7.94-8.01 (m, 1H) LC MS 577) M+H).

Example 95

2-(1-Amino-isoquinolin-6-ylamino)-2-(4-chloro-3-ethoxy-phenyl)-N-(2-cyclobutanesulfonyl-benzyl)-N-methyl-acetamide trifluoroacetic acid salt

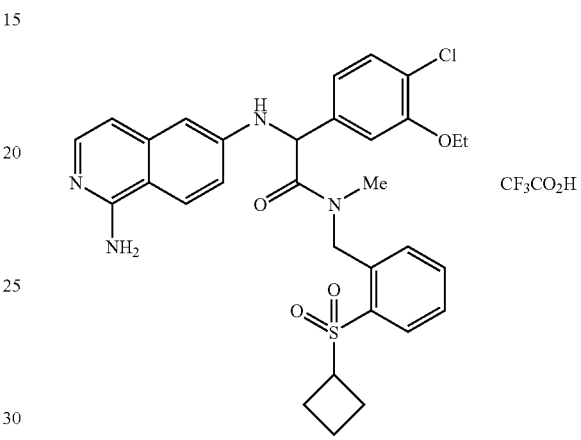

Example 95 was prepared according to the general coupling-deprotection using Intermediate 15 and Intermediate 12. ¹H NMR (400 MHz, Methanol-d₄) δ ppm a mixture of two rotomers: 1.32 (m, 3H) 1.90-2.42 (m, 6H) 2.97 and 3.12 (s, 3H) 4.02 (m, 2H) 5.05-5.18 (s, 1H) 5.55 and 5.74 (s, 1H) 6.61-7.37 (m, 10H) 7.83-8.00 (m, 2H); LC MS 593 (M+H).

Example 96

2-(1-Amino-isoquinolin-6-ylamino)-N-(3-difluoromethyl-benzyl)-2-(3-ethoxy-4-isopropoxy-phenyl)-acetamide trifluoroacetic acid salt

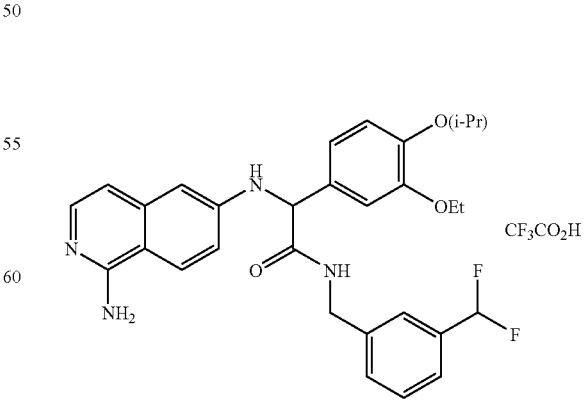

96A

3-(Difluoromethyl)benzonitrile

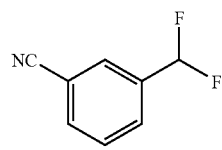

To a solution of 3-nitrobenzaldehyde (262 mg, 2.0 mmol) in dichloromethane (10 mL) was added (diethylamino)sulfur trifluoride (DAST, 0.31 mL, 2.4 mmol) at rt. After stirring for two hrs, the reaction was quenched by 10 mL of saturated NaHCO$_3$ solution, and extracted by dichloromethane (2×10 mL), the combined organic layer was washed by brine, dried by MgSO$_4$, and concentrated. The crude product was purified by column chromatography to give 200 mg (65% yield) colorless liquid of 96A. $^1$H NMR (400 MHz, CDCl$_3$) δ ppm 6.68 (t, J=56.03 Hz, 1H) 7.61 (t, J=7.69 Hz, 1H) 7.73-7.85 (m, 3H).

96B

(3-(Difluoromethyl)phenyl)methanamine

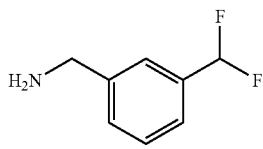

To a solution of 96A (200 mg, 1.3 mmol) in methanol (5 mL) was added 10% Pd/C (50 mg) and 4.0 N HCl in dioxane (0.4 mL, 1.6 mmol). The mixture was stirred under hydrogen balloon at room temperature for 2 h and filtrated. The filtration was concentrated to a white solid of 96B as HCl salt (250 mg, 100% yield). $^1$H NMR (400 MHz, Methanol-d$_4$) δ ppm 4.08 (s, 2H) 6.71 (t, J=56.03 Hz, 1H) 7.45-7.53 (m, 3H) 7.57 (s, 1H).

96C

Example 96 was prepared according to the general coupling-deprotection using 96B and Intermediate 2. $^1$H NMR (400 MHz, Methanol-d$_4$) δ ppm 1.30 (d, J=6.15 Hz, 6H) 1.36 (t, J=7.03 Hz, 3H) 3.96-4.03 (m, J=7.03, 7.03, 6.81, 1.98 Hz, 2H) 4.36-4.41 (m, 1H) 4.49-4.56 (m, 2H) 5.07 (s, 1H) 6.66 (d, J=2.20 Hz, 1H) 6.80 (d, J=7.03 Hz, 1H) 6.95-6.98 (m, 1H) 7.05-7.11 (m, 2H) 7.19 (dd, J=9.23, 2.64 Hz, 1H) 7.26-7.38 (m, 6H) 8.08 (d, J=9.23 Hz, 1H) 8.90 (t, J=6.15 Hz, 1H); LC MS 535 (M+H).

Example 97

2-(1-Amino-isoquinolin-6-ylamino)-2-(3,4-dimethoxy-phenyl)-N-(3-methyl-benzyl)-acetamide trifluoroacetic acid salt

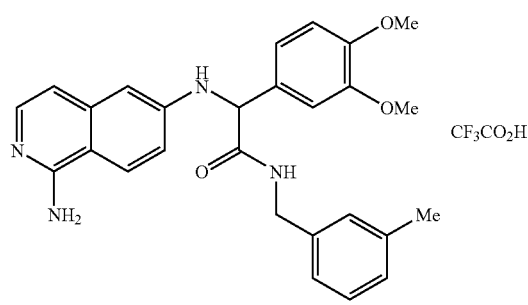

Example 97 was prepared according to the general coupling-deprotection using Intermediate 4 and commercial m-tolylmethanamine. $^1$H NMR (400 MHz, Methanol-d$_4$) δ ppm 2.06 (s, 3H) 3.69 (s, 3H) 3.74 (s, 3H) 4.18-4.24 (m, 1H) 4.30-4.36 (m, 1H) 4.99 (s, 1H) 6.58 (d, J=1.76 Hz, 1H) 6.71 (d, J=7.47 Hz, 1H) 6.75 (s, 1H) 6.83-6.91 (m, 3H) 6.98-7.04 (m, 3H) 7.11 (dd, J=9.23, 1.76 Hz, 1H) 7.24 (d, J=7.03 Hz, 1H) 7.99 (d, J=9.23 Hz, 1H) 8.70 (t, J=5.93 Hz, 1H); LC MS 457 (M+H).

Example 98

(R)-3-[2-(1-Amino-isoquinolin-6-ylamino)-2-(5-ethoxy-2-fluoro-phenyl)-acetylamino]-3-(2-isopropylsulfanyl-5-methoxycarbonylamino-phenyl)-propionic acid methyl ester trifluoroacetic acid salt

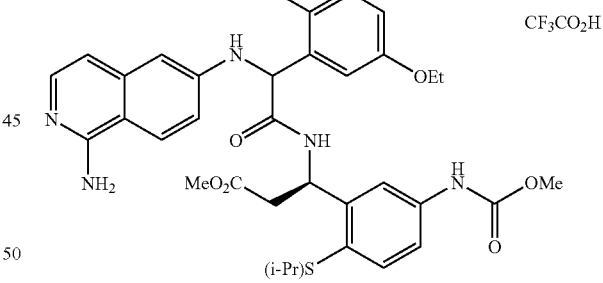

98A (S,E)-N-(2-(Isopropylthio)-5-nitrobenzylidene)-4-methylbenzenesulfinamide

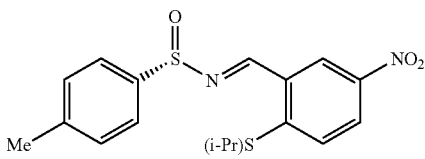

To 2-(isopropylthio)-5-nitrobenzaldehyde (234 mg, 1.0 mmol) and (S)-(+)-p-toluenesulfinamide (161 mg, 1.0 mmol)

in CH$_2$Cl$_2$ (10 mL) was added Ti(OEt)$_4$ (25% tech, 0.54 mL). The mixture was heated at 75° C. for 3.0 h. TLC indicated a clean reaction. Solvent was removed and the residue was redissolved in EtOAc, under stirring sat. Na$_2$SO$_4$ solution was added and the slurry was stirred at rt for 30 min before it was filtered through a pad of Celite®. The filtrate was extracted with EtOAc, washed with brine and dried over Na$_2$SO$_4$. After evaporation of solvent, 98A (320 mg, 88% yield) was obtained as a solid used for next step without further purification. $^1$H NMR (400 MHz, CDCl$_3$) δ ppm 1.34 (d, J=6.59 Hz, 6H) 2.34 (s, 3H) 3.51-3.61 (m, 1H) 7.27 (d, J=7.91 Hz, 2H) 7.45 (d, J=8.79 Hz, 1H) 7.59 (d, J=8.35 Hz, 2H) 8.14 (dd, J=8.79, 2.64 Hz, 1H) 8.69 (d, J=2.64 Hz, 1H) 9.17 (s, 1H).

98B (R)-Methyl 3-(2-(isopropylthio)-5-nitrophenyl)-3-((S)-4-methylphenylsulfinamido)propanoate

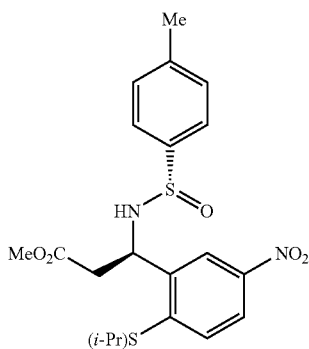

To a solution of sodium bis(trimethylsilyl)amide (1.0 M in THF, 0.82 mL) in Et$_2$O at –78° C. was added methyl acetate (0.065 mL, 0.82 mmol). After stirring for 30 min at –78° C., a solution of 98A (150 mg, 0.41 mmol) in a mixture of Et$_2$O (1.0 m) and THF (1.0 mL) was slowly added. The mixture was stirred for 30 min before it was quenched by addition of sat. ammonium chloride solution at –78° C. After it warmed up to rt, it was diluted with EtOAc, washed with brine, dried over Na$_2$SO$_4$. After column purification (EtOAc:hexanes=1:2), 98B (318 mg, 90% yield) was obtained as viscous oil). $^1$H NMR (400 MHz, CDCl$_3$) δ ppm 1.42 (m, 6H) 2.42 (s, 3H) 2.84-2.93 (m, 2H) 3.63 (s, 3H) 5.34 (s, 1H) 7.32 (d, J=7.91 Hz, 2H) 7.40 (d, J=7.91 Hz, 1H) 7.46 (d, J=8.79 Hz, 1H) 7.60 (d, J=7.91 Hz, 2H) 8.10 (dd, J=8.57, 2.42 Hz, 1H) 8.36 (d, J=2.64 Hz, 1H); LC MS 437 (M+H).

98C (R)-Methyl 3-amino-3-(2-(isopropylthio)-5-nitrophenyl)propanoate

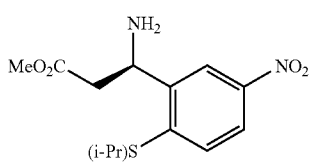

A solution of 98B (550 mg, 1.3 mmol) in methanol (5.0 mL) was treated with TFA (0.28 mL, 3.78 mmol) at 0° C. for 2.0 h and at rt for 1.0 h. After removal of solvent, the crude was diluted with diethyl ether and washed with 3.0 N HCl (3×4.0 mL). The ether layer was discarded and the aqueous was made basic by addition of 1.0 N NaOH (15 mL). The aqueous was extracted with EtOAc and dried over Na$_2$SO$_4$. After evaporation of solvent 98C (220 mg, 58% yield) was obtained as viscous oil. It was used for next step without further purification. $^1$H NMR (400 MHz, CDCl$_3$) δ ppm 1.39 (m, 6H) 2.59 (dd, J=16.70, 9.67 Hz, 1H) 2.71-2.81 (m, 1H) 3.56-3.64 (m, 1H) 3.71 (s, 3H) 4.06-4.17 (m, 1H) 4.87 (dd, J=9.67, 3.08 Hz, 1H) 7.36 (d, J=8.79 Hz, 1H) 8.05 (dd, J=8.79, 2.20 Hz, 1H) 8.46 (d, J=2.64 Hz, 1H).

98D (R)-Methyl 3-(tert-butoxycarbonyl)-3-(2-(isopropylthio)-5-nitrophenyl)propanoate

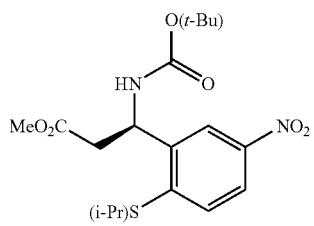

A solution of 98C (220 mg, 0.74 mmol) in THF (2.0 mL) was treated with a solution of di-tert-butyldicarbonate (1.0 M in THF, 1.3 mL, 1.3 mmol) and triethyl amine (0.13 ml, 0.93 mmol) at rt for 4.0 h. It was diluted with EtOAc, washed with 1.0 N HCl and brine, dried over Na$_2$SO$_4$. After evaporation of solvent, 98D (230 mg, 82% yield) was obtained as viscous oil used for the next step without further purification. $^1$H NMR (400 MHz, CDCl$_3$) δ ppm 1.44 (m, 15H) 2.84 (d, J=3.95 Hz, 2H) 3.58-3.67 (m, 4H) 5.39 (s, 1H) 5.91 (d, J=1.76 Hz, 1H) 7.38 (d, J=8.79 Hz, 1H) 8.04 (dd, J=8.57, 2.42 Hz, 1H) 8.19 (d, J=2.64 Hz, 1H).

98E (R)-Methyl 3-(tert-butoxycarbonyl)-3-(2-(isopropylthio)-5-(methoxycarbonyl)phenyl)propanoate

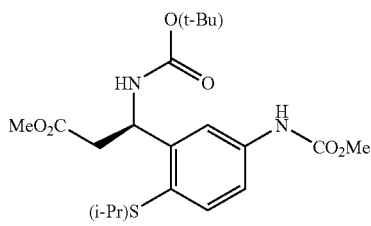

A solution of 98D (230 mg, 0.63 mmol) in methanol was hydrogenated with a hydrogen balloon over 10% Pd/C (50 mg) for 2.0 h. After evaporation of solvent, the crude was dissolved in pyridine (2.0 mL) and treated with methyl chloroformate (0.085 mL, 1.1 mmol) at 0° C. for 30 min and then at rt for 2.0 h. It was diluted with EtOAc, washed with 5.0 N HCl, brine and dried over Na$_2$SO$_4$. After evaporation of solvent and column purification (EtOAc:hexanes=1:2), 98E (210 mg, 80% yield) was obtained as a viscous oil. $^1$H NMR (400 MHz, CDCl$_3$) δ ppm 1.25-1.31 (m, 6H) 1.41 (s, 9H) 2.85

(d, J=4.83 Hz, 2H) 3.28-3.38 (m, 1H) 3.61 (s, 3H) 3.77 (s, 3H) 6.67 (s, 1H) 7.24 (s, 1H) 7.42 (s, 2H).

98F (R)-Methyl 3-amino-3-(2-(isopropylthio)-5-(methoxycarbonyl)phenyl)propanoate

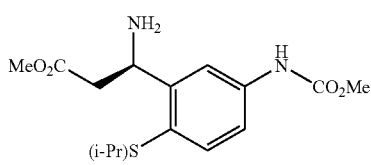

A solution of 98E (210 mg, 0.49 mmol) in EtOAc (2.5 mL) was treated with 4.0 N HCl in dioxane (2.5 mL, 10 mmol) at rt for 4.0 h. After evaporation of solvent, 98F was obtained as white solid used for next step without further purification. $^1$H NMR (400 MHz, Methanol-$d_4$) δ ppm 1.18 (d, J=6.59 Hz, 6H) 2.93 (dd, J=16.92, 5.49 Hz, 1H) 3.11 (dd, J=17.14, 8.35 Hz, 1H) 3.18-3.28 (m, 1H) 3.64 (s, 3H) 3.66 (s, 3H) 5.42 (dd, J=8.35, 5.27 Hz, 1H) 7.48 (s, 2H) 7.63 (s, 1H); LC MS 327 (M+H).

98G

Example 98 was prepared according to the general coupling-deprotection using 73A and 98F. $^1$H NMR (400 MHz, Methanol-$d_4$) δ ppm 1.07-1.14 (m, 6H) 1.18-1.24 (m, 3H) 2.58-2.80 (m, 2H) 3.22-3.30 (m, 1H) 3.32 and 3.53 (s, 3H) 3.57 and 3.64 (s, 3H) 3.74-3.93 (m, 2H) 5.24 and 5.35 (s, 1H) 5.88-6.02 (m, 1H) 6.55 (dd, J=23.95, 1.98 Hz, 1H) 6.66-7.38 (m, 8H) 7.90-8.09 (m, 1H) 8.80 (dd, J=23.29, 8.35 Hz, 1H); LC MS 664 (M+H).

Example 99

2-(1-Amino-isoquinolin-6-ylamino)-N-[(R)-1-(2-ethanesulfonyl-phenyl)-ethyl]-2-(3-ethoxy-4-isobutyl-phenyl)-acetamide trifluoroacetic acid salt

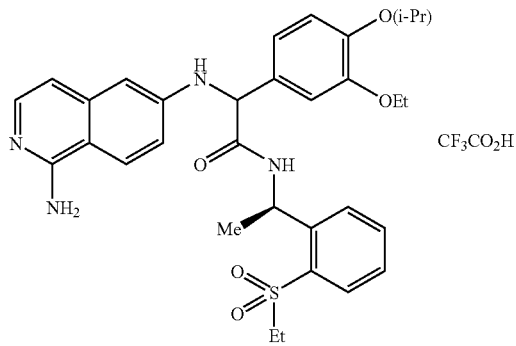

99A 2-((R)-1-Pivalamidoethyl)benzenesulfinic acid

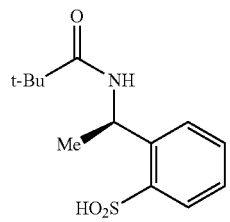

99A was prepared in 45% yield according to a literature procedure (*J. Chem. Soc. Perkin Trans.* 1993, 1585). $^1$H NMR (400 MHz, CDCl$_3$) δ ppm 1.13 (s, 9H) 1.54 (d, J=6.59 Hz, 3H) 6.09-6.16 (m, 1H) 7.34 (t, J=7.69 Hz, 2H) 7.43-7.49 (m, 1H) 7.57 (d, J=7.47 Hz, 1H).

99B

Sodium 2-((R)-1-pivalamidoethyl)benzenesulfinate

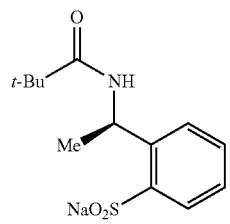

To a solution of 99A (160 mg, 0.59 mmol) in MeOH (4.0 mL) was added 1.0 N NaOH (0.65 mL, 0.65 mmol). The mixture was stirred at rt for 2.0 h. MeOH was removed and the residue was suspended in H$_2$O and lyophilized to give 99B as a white solid. $^1$H NMR (400 MHz, DMSO-$d_6$) δ ppm 1.07 (s, 9H) 1.45 (d, J=7.03 Hz, 3H) 5.27-5.35 (m, 1H) 7.14-7.24 (m, 3H) 7.73 (d, J=7.47 Hz, 1H) 8.98 (d, J=8.35 Hz, 1H).

99C (R)-N-(1-(2-(Ethylsulfonyl)phenyl)ethyl)pivalamide

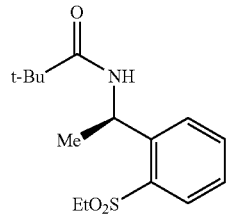

A mixture of 99B (150 mg, 0.51 mmol) and ethyl iodide (0.056 mL, 0.69 mmol) in DMF (2.0 mL) was heated at 40° C. for 1.0 h. It was diluted with EtOAc, washed with brine and dried over Na$_2$SO$_4$. After evap[oration of solvent, 99C (120 mg) was obtained and used for next step without further purification. ¹H NMR (400 MHz, CDCl₃) δ ppm 1.15 (s, 9H) 1.25-1.30 (m, 3H) 1.41-1.44 (m, 3H) 3.53-3.63 (m, 2H) 5.43-5.52 (m, 1H) 6.38 (d, J=5.71 Hz, 1H) 7.30-7.36 (m, 1H) 7.42-7.48 (m, 1H) 7.52 (d, J=7.47 Hz, 1H) 7.89 (d, J=6.59 Hz, 1H).

99D (R)-1-(2-(Ethylsulfonyl)phenyl)ethanamine

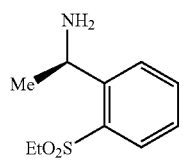

A mixture of 99C (120 mg) and conc. HCl (5.0 mL) was heated at 128° C. for 10 h. After evaporation of solvent, the crude was purified by a prep HPLC to give 99D (96 mg) as a TFA salt. ¹H NMR (400 MHz, Methanol-d₄) δ ppm 1.27 (t, J=7.25 Hz, 3H) 1.69 (d, J=7.03 Hz, 3H) 5.38 (q, J=6.88 Hz, 1H) 7.68 (ddd, J=8.02, 5.38, 2.86 Hz, 1H) 7.83-7.88 (m, 2H) 8.06 (d, J=7.91 Hz, 1H); LC MS 214 (M+H).

99E

Example 99 was prepared according to the general coupling-deprotection using Intermediate 2 and 99D. ¹H NMR (400 MHz, Methanol-d₄) δ ppm 1.14 (m, 12H) 3.49-4.50 (m, 5H), 5.07 and 5.09 (s, 1H), 6.60-8.07 (m, 11H) 8.97-9.12 (m, 1H); LC MS 591 (M+H).

Example 100

(R)-3-[2-(1-Amino-isoquinolin-6-ylamino)-2-(3,4-dimethoxy-phenyl)-acetylamino]-3-(2-isopropylsulfanyl-5-methoxycarbonylamino-phenyl)-propionic acid methyl ester trifluoroacetic acid salt

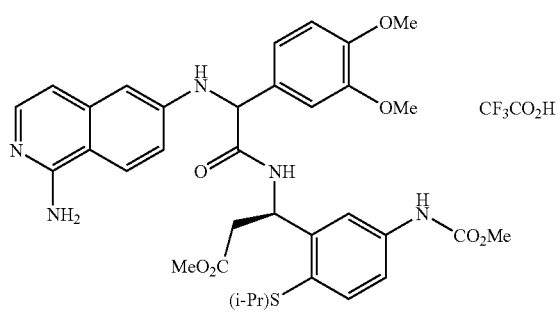

Example 100 was prepared according to the general coupling-deprotection using Intermediate 4 and 98F. ¹H NMR (400 MHz, Methanol-d₄) δ ppm 1.20 (m, 6H) 2.74 (d, J=4.83 Hz, 1H) 2.77 (m, 2H) 3.35 (m, 1H) 3.66 (s, 3H) 3.79 (s, 3H) 3.82 (s, 3H) 4.99 (s, 1H) 5.98-6.02 (m, 1H) 6.59 (s, 1H) 6.83 (d, J=7.47 Hz, 1H) 6.93 (d, J=7.91 Hz, 1H) 7.04-7.08 (m, 4H) 7.11 (s, 1H) 7.16 (d, J=9.23 Hz, 1H) 7.29 (d, J=7.03 Hz, 1H) 7.33 (d, J=8.35 Hz, 1H) 8.06 (d, J=9.23 Hz, 1H); LC MS 662 (M+H).

Example 101

2-(1-Amino-isoquinolin-6-ylamino)-2-(3-ethoxy-4-isobutyl-phenyl)-N-(3-methyl-benzyl)-acetamide trifluoroacetic acid salt

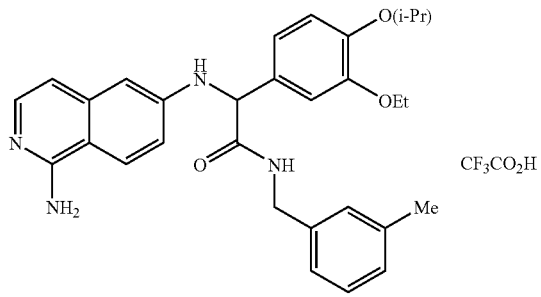

Example 101 was prepared according to the general coupling-deprotection using Intermediate 2 and commercial m-tolylmethanamine. ¹H NMR (400 MHz, Methanol-d₄) δ ppm 1.18 (d, J=5.71 Hz, 6-H) 1.25 (t, J=7.03 Hz, 3H) 2.05 (s, 3H) 3.87 (q, J=7.03 Hz, 2H) 4.14-4.36 (m, 2H) 4.36-4.48 (m, 1H) 4.94 (s, 1H) 6.55 (d, J=1.76 Hz, 1H) 6.68 (d, J=7.03 Hz, 1H) 6.76 (s, 1H) 6.79-6.91 (m, 3H) 6.93-7.01 (m, 3H) 7.07 (dd, J=9.23, 2.20 Hz, 1H) 7.21 (d, J=7.03 Hz, 1H) 7.97 (d, J=9.23 Hz, 1H) 8.68 (t, J=6.15 Hz, 1H); LC MS 497 (M+H).

Example 102

(R)-3-[2-(1-Amino-isoquinolin-6-ylamino)-2-(5-ethoxy-2-fluoro-phenyl)-acetylamino]-3-(2-isopropylsulfanyl-5-methoxycarbonylamino-phenyl)-propionic acid trifluoroacetic acid salt

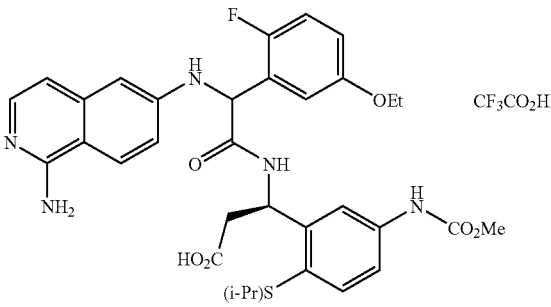

Example 102 was prepared from Example 98 by hydrolysis of the methyl ester as described in procedure 5E. ¹H NMR (400 MHz, Methanol-d₄) δ ppm 1.19 (m, 6H) 1.31 (m, 3H) 2.69-2.80 (m, 1H) 3.65 and 3.74 (s, 3H) 3.83-3.94 (m, 2H) 5.38 and 5.46 (s, 1H) 6.00 (m, 1H) 6.64-7.41 (m, 9H) 8.03-8.09 (m, 2H) LC MS 650 (M+H).

Example 103

(R)-3-[(R)-2-(1-Amino-isoquinolin-6-ylamino)-2-(3,4-dimethoxy-phenyl)-acetylamino]-3-(2-isopropyl-sulfanyl-5-methoxycarbonylamino-phenyl)-propionic acid trifluoroacetic acid salt

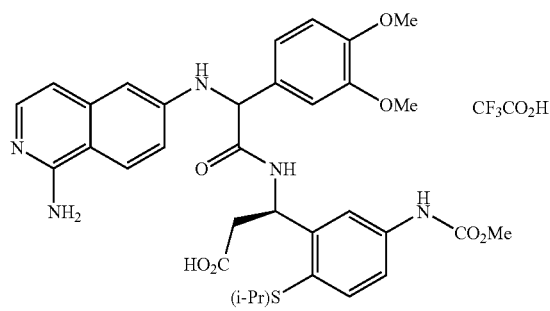

Example 103 was prepared from Example 100 by hydrolysis of the methyl ester as described in procedure 5E. The enantiomer was separated from the diastereomers by prep HPLC. $^1$H NMR-(400 MHz, Methanol-$d_4$) δ ppm 1.20 (m, 6H) 2.74 (m, 1H) 3.66 (s, 3H) 3.80 (s, 3H) 3.82 (s, 3H) 4.99 (s, 1H) 6.00 (dd, J=9.67, 4.83 Hz, 1H) 6.59 (s, 1H) 6.83 (d, J=7.47 Hz, 1H) 6.93 (d, J=7.91 Hz, 1H) 7.04-7.08 (m, 4H) 7.10-7.18 (m, 2H) 7.29 (d, J=7.03 Hz, 1H) 7.33 (d, J=8.35 Hz, 1H) 8.02-8.08 (m, 2H); LCMS 648(M+H).

Example 104

2-(1-Amino-isoquinolin-6-ylamino)-2-(3-ethoxy-4-isopropoxy-phenyl)-N-(3-fluoromethyl-benzyl)-acetamide trifluoroacetic acid salt

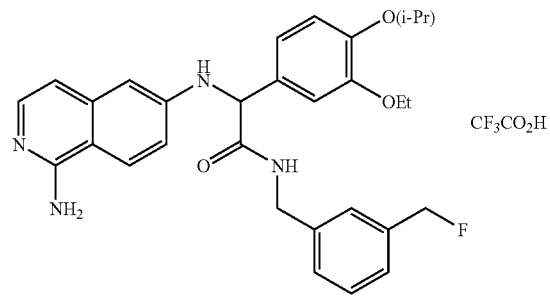

104A 3-(Fluoromethyl)benzonitrile

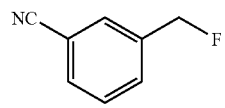

To a solution of 3-hydroxybenzonitrile (133 mg, 1.0 mmol) in dichloromethane (5.0 mL) was added (diethylamino)sulfur trifluoride (DAST, 0.26 mL, 2.0 mmol) at rt. After stirring for two hours, the reaction was quenched by 5 mL of saturated NaHCO$_3$ solution, and extracted by dichloromethane (2×5 mL). The combined organic layer was washed by brine, dried over MgSO$_4$, and concentrated. The crude product was purified by column chromatography to give 80 mg (59% yield) colorless liquid of 104A. $^1$H NMR (400 MHz, CDCl$_3$) δ ppm 5.42 (d, J=47.02 Hz, 2H) 7.53 (t, J=7.69 Hz, 1H) 7.59-7.63 (m, 1H) 7.64-7.70 (m, 2H).

104B (3-(Fluoromethyl)phenyl)methanamine

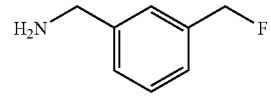

To 104A (110 mg, 0.82 mmol) in THF (2.5 mL) was added 1.0 M borane THF complex solution (2.4 mL, 2.4 mmol) at 0° C. The mixture was stirred from 0° C. to rt for 2 h before it was quenched by addition of 2.5 mL of 1.0 N HCl solution and 2.5 mL of MeOH. The mixture was stirred at rt overnight, extracted by EtOAc, washed by saturated NaHCO$_3$ solution and brine. The organic layer was dried by MgSO$_4$, and concentrated. The crude product was purified by HPLC to give 76 mg (37% yield) white solid of 104B as trifluoroacetic acid salt. $^1$H NMR (400 MHz, Methanol-$d_4$) δ ppm 4.01 (s, 2H) 5.28 (d, J=47.46 Hz, 2H) 7.24-7.49 (m, 4H).

104C

Example 104 was prepared according to the general coupling-deprotection using Intermediate 2 and 104B. $^1$H NMR (400 MHz, Methanol-$d_4$) δ ppm 1.21 (d, J=5.71 Hz, 6H) 1.27 (t, J=7.03 Hz, 3H) 3.87-3.94 (m, 2H) 4.24-4.31 (m, 1H) 4.37-4.47 (m, 2H) 4.98 (s, 1H) 5.04 (s, 1H) 5.16 (s, 1H) 6.58 (d, J=2.20 Hz, 1H) 6.71 (d, J=7.03 Hz, 1H) 6.86-6.89 (m, 1H) 6.97-7.00 (m, 1H) 7.01 (s, 2H) 7.05-7.16 (m, 4H) 7.23 (d, J=7.47 Hz, 1H) 7.99 (d, J=9.23 Hz, 1H) 8.77 (t, J=6.15 Hz, 1H); LC MS 517 (M+H).

Example 105

2-(1-Amino-isoquinolin-6-ylamino)-N-(2-cyclobutanesulfonyl-benzyl)-2-(5-ethoxy-2-fluoro-4-methoxy-phenyl)-N-methyl-acetamide trifluoroacetic acid salt

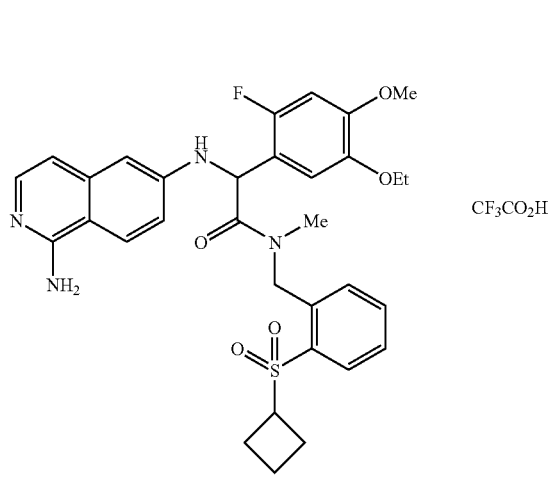

105A

4-Fluoro-2-methoxyphenyl acetate

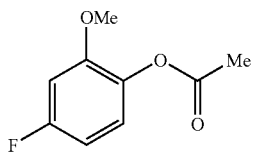

To a solution of 4-fluoro-2-methoxyphenol (569 mg, 4.0 mmol) and pyridine (0.56 mL, 7.0 mmol) in $CH_2Cl_2$ (8.0 mL) at 0° C. was added acetyl chloride (0.33 mL, 4.6 mmol). The mixture was stirred at rt for 2.0 h and then diluted with EtOAc and washed with 4.0 N HCl. The organic layer was washed with brine and dried over $Na_2SO_4$. After evaporation of solvent, 105A (680 mg, 92% yield) was obtained as a solid used for the next step without further purification. $^1$H NMR (400 MHz, CDCl$_3$) δ ppm 2.29 (s, 3H) 3.79 (s, 3H) 6.62 (m, 1H) 6.68 (dd, J=10.33, 2.86 Hz, 1H) 6.95 (dd, J=8.79, 5.71 Hz, 1H).

105B

4-Fluoro-5-iodo-2-methoxyphenyl acetate

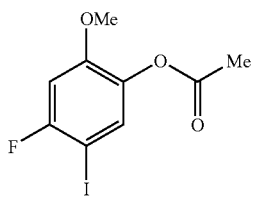

To a solution of 105A (850 mg, 4.6 mmol) in $CH_2Cl_2$ (5.0 mL) was added ICl (1.0 M in $CH_2Cl_2$, 10.2 mL, 10.2 mmol). The mixture was stirred at 50° C. for 4 h and then at rt for 18 h. The reaction was quenched by a sat. solution of NaHCO$_3$. After extraction with $CH_2Cl_2$, the organic layer was washed with a solution of $Na_2S_2O_3$, brine and dried over $Na_2SO_4$. After evaporation of solvent, the crude was purified by column chromatography (EtOAc:hexanes=1:4) to give 105B (1.22 g, 80% yield) as a solid. $^1$H NMR (400 MHz, CDCl$_3$) δ ppm 2.29 (s, 3H) 3.81 (s, 3H) 6.73 (d, J=9.23 Hz, 1H) 7.35 (d, J=6.59 Hz, 1H).

105C

4-Fluoro-5-iodo-2-methoxyphenol

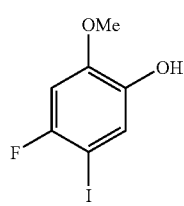

To a solution of 105B (680 mg, 2.19 mmol) in THF (3.0 mL) and MeOH (1.0 mL) was added 1.0 N NaOH (2.74 mL, 2.74 mmol). The reaction was stirred at rt for 2.0 h before it was acidified by addition of 5% citric acid. The mixture was extracted with EtOAc, washed with brine and dried over $Na_2SO_4$. After evaporation of solvent, 105C (586 mg, 100% yield) was obtained as a solid and used for next step without further purification. $^1$H NMR (400 MHz, CDCl$_3$) δ ppm 3.85 (s, 3H) 6.62 (d, J=8.79 Hz, 1H) 7.21 (d, J=6.15 Hz, 1H).

105D

1-Ethoxy-4-fluoro-5-iodo-2-methoxybenzene

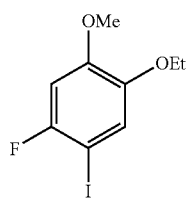

A mixture of 105C (580 mg, 2.16 mmol), ethyl iodide (0.23 mL, 2.92 mmol) and $K_2CO_3$ (598 mg, 4.32 mmol) in DMF (5.0 mL) was heated at 40° C. for 3.0 h. It was diluted with diethyl ether, washed with brine and dried over $Na_2SO_4$. After evaporation of solvent, the crude was purified by a column chromatography (EtOAc:hexanes=1:5) to give 105D (540 mg, 85% yield) as a white solid. $^1$H NMR (400 MHz, CDCl$_3$) δ ppm 1.42 (t, J=7.03 Hz, 3H) 3.82 (s, 3H) 4.01 (q, J=7.03 Hz, 2H) 6.64 (d, J=9.23 Hz, 1H) 7.09 (d, J=6.15 Hz, 1H).

105E

5-Ethoxy-2-fluoro-4-methoxyphenylboronic acid

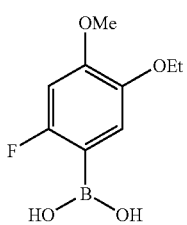

To a solution of 105D (324 mg, 1.1 mmol) in THF (5 mL) at −78° C., n-BuLi (1.6 M in hexanes, 1.40 mL, 2.2 mmol) was slowly added. The reaction mixture was stirred at −78° C. for 20 min, followed by addition of trimethyl borate (0.31 mL, 2.8 mmol). The mixture was stirred at −78° C. for 3.0 h and then warm up to rt over 18 h. It was quenched by addition of 1.0 N HCl (2.0 mL). After extraction with EtOAc, washing with a solution of $Na_2S_2O_3$, brine and drying over $Na_2SO_4$, the crude was purified by chromatography to give 105E (210 mg, 80% yield) as a white solid. $^1$H NMR (400 MHz, Methanol-d$_4$) δ ppm 1.36 (t, J=6.81 Hz, 3H) 3.86 (s, 3H) 4.00 (q, J=7.03 Hz, 2H) 6.72 (d, J=10.11 Hz, 1H) 6.89 (d, J=5.27 Hz, 1H).

105F 2-(1-di-tert-Butoxycarbonylaminoisoquinolin-6-ylamino)-2-(5-ethoxy-2-fluoro-4-methoxyphenyl)acetic acid

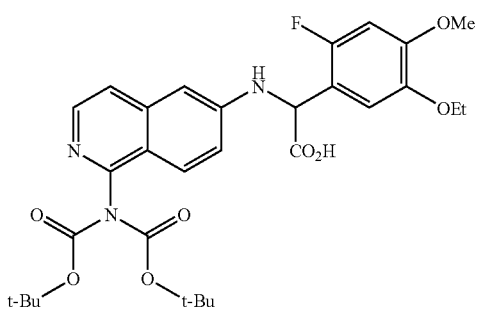

A mixture of 105E (118 mg, 0.55 mmol), Intermediate 1 (180 mg, 0.5 mmol) and glyoxylic acid monohydrate (51 mg, 0.55 mmol) in acetonitrile (1.3 mL) and DMF (0.13 mL) was heated at 85° C. for 25 min in a microwave oven. After removing solvent, the crude was purified by chromatography eluting with $CH_2Cl_2$:MeOH=100:20 to give 105F (190 mg, 65% yield) as a yellow solid. $^1$H NMR (400 MHz, acetonitrile-$d_3$) δ ppm 1.91 (m, 21H) 3.76 (s, 3H) 3.92 (dd, J=10.11, 7.03 Hz, 2H) 5.45 (s, 1H) 6.70 (d, J=2.20 Hz, 1H) 6.79 (d, J=11.86 Hz, 1H) 6.92 (d, J=7.03 Hz, 1H) 7.17 (dd, J=9.01, 2.42 Hz, 1H) 7.38 (d, J=5.27 Hz, 1H) 7.63 (d, J=8.79 Hz, 1H) 8.08 (d, J=5.71 Hz, 1H); LC MS 586 (M+H).

105G

Example 105 was prepared according to the general coupling-deprotection using 105F and Intermediate 12. $^1$H NMR (400 MHz, Methanol-$d_4$) δ ppm a mixture of two rotamers: 1.28 (m, 3H) 1.91-2.70 (m, 5H) 2.92 and 3.06 (s, 3H) 3.59 and 3.76 (s, 3H) 3.88-4.10 (m, 3H) 5.08 and 5.12 (s, 1H) 6.74-7.40 (m, 9H), 7.83-8.00 (m, 2H); LC MS 607 (M+H).

Example 106

2-(1-Amino-isoquinolin-6-ylamino)-2-(3-ethoxy-4-isopropoxy-phenyl)-N-(3-isopropylsulfanyl-pyridin-2-ylmethyl)-acetamide trifluoroacetic acid salt

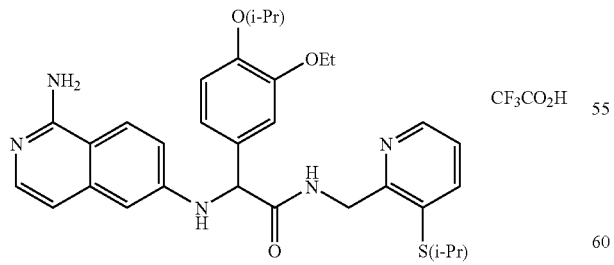

Example 106 was prepared according to the general coupling-deprotection using Intermediate 2 and 72D. $^1$H NMR (400 MHz, Methanol-$d_4$) δ ppm 1.15 (d, J=6.59 Hz, 6H) 1.20 (d, J=5.71 Hz, 6H) 1.28 (t, J=6.81 Hz, 3H) 3.30-3.39 (m, 1H) 3.95 (q, J=7.03 Hz, 2H) 4.38-4.46 (m, 1H) 4.55 (d, J=18.02 Hz, 1H) 5.07 (s, 1H) 6.64 (d, J=2.20 Hz, 1H) 6.77 (d, J=7.03 Hz, 1H) 6.86 (d, J=8.35 Hz, 1H) 6.98 (dd, J=8.35, 2.20 Hz, 1H) 7.06 (d, J=2.20 Hz, 1H) 7.11 (dd, J=9.23, 2.20 Hz, 1H) 7.21-7.26 (m, 2H) 7.79 (d, J=7.91 Hz, 1H) 7.99 (d, J=9.23 Hz, 1H) 8.24 (d, J=4.83 Hz, 1H); LC MS 546 (M+H).

Example 107

2-(1-Amino-isoquinolin-6-ylamino)-2-(5-ethoxy-2-fluoro-phenyl)-N-(3-isopropylsulfanyl-pyridin-2-ylmethyl)-acetamide trifluoroacetic acid salt

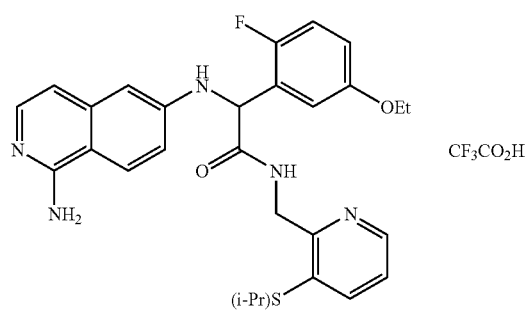

Example 107 was prepared according to the general coupling-deprotection using 73A and 72D. $^1$H NMR (400 MHz, Methanol-$d_4$) δ ppm 1.17 (d, J=7.03 Hz, 6H) 1.25 (t, J=7.03 Hz, 3H) 3.32-3.42 (m, 1H) 3.88 (q, J=6.74 Hz, 2H) 4.49-4.57 (m, 1H) 4.59-4.65 (m, 1H) 5.46 (s, 1H) 6.70 (d, J=2.20 Hz, 1H) 6.77-6.83 (m, 2H) 6.96-7.03 (m, 2H) 7.12 (dd, J=9.23, 2.64 Hz, 1H) 7.21-7.27 (m, 2H) 7.80 (d, J=6.59 Hz, 1H) 8.01 (d, J=9.23 Hz, 1H) 8.25 (dd, J=4.83, 1.76 Hz, 1H); LC MS 506(M+H).

Example 108

N-(3-Acetylamino-benzyl)-2-(4-aminomethyl-phenylamino)-2-(4-chloro-3-methoxy-phenyl)-acetamide trifluoroacetic acid salt

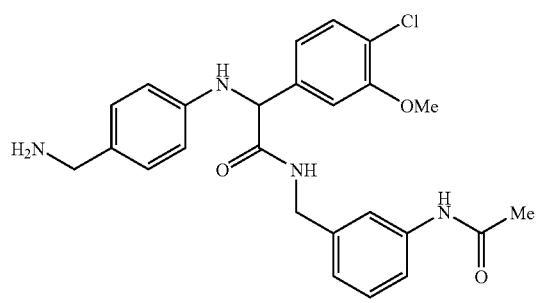

108A 2-(4-((tert-butoxycarbonyl)methyl)phenylamino)-2-(4-chloro-3-methoxyphenyl)acetic acid

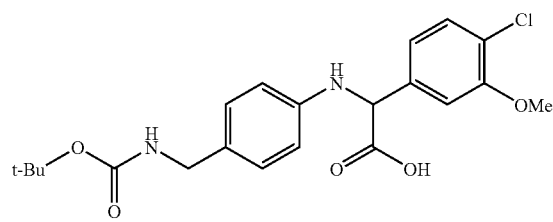

A mixture of 79A (102 mg, 0.55 mmol), (4-amino-benzyl)-carbamic acid tert-butyl ester (111 mg, 0.5 mmol) and glyoxylic acid monohydrate (51 mg, 0.55 mmol) in toluene (5 mL) and MeOH (0.4 mL) was heated at 55° C. for 5.0 h. After removing solvent, the crude was purified by chromatography eluting with $CH_2Cl_2$:MeOH=100:10 to give 108A (39 mg, 18% yield) as a yellow solid. $^1H$ NMR (400 MHz, Methanol-$d_4$) δ ppm 1.33 (s, 9H) 3.75 (s, 3H) 3.97 (s, 2H) 5.02 (s, 1H) 6.58 (d, J=8.56 Hz, 2H) 6.96 (m, 3H) 7.10 (d, J=1.96 Hz, 1H) 7.22 (d, J=8.07 Hz, 1H).

108B

Example 108 was prepared according to the general coupling-deprotection using 108A and commercial N-(3-(aminomethyl)phenyl)acetamide HCl salt. $^1H$ NMR (400 MHz, Methanol-$d_4$) δ ppm 2.02 (s, 3H) 3.71 (s, 3H) 3.85 (s, 2H) 4.26 (d, J=5.62 Hz, 2H) 4.87 (s, 1H) 6.62 (d, J=8.56 Hz, 2H) 6.80 (d, J=7.34 Hz, 1H) 6.96 (dd, J=8.07, 1.96 Hz, 1H) 7.09 (m, 4H) 7.23 (d, J=8.07 Hz, 2H) 7.34 (s, 1H) 8.68 (m, 1H); LC MS 467 (M+H).

Example 109

2-(1-Amino-isoquinolin-6-ylamino)-2-(3-ethoxy-4-isopropoxy-phenyl)-N-pyridin-2-ylmethyl-acetamide trifluoroacetic acid salt

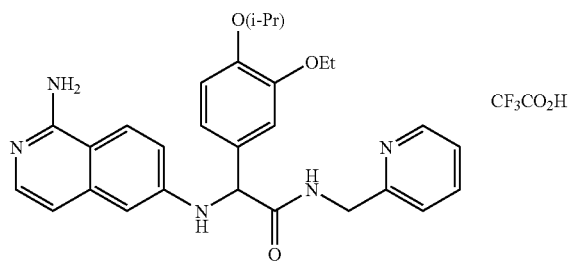

Example 109 was prepared according to the general coupling-deprotection using Intermediate 2 and commercial pyridin-2-ylmethanamine HCl salt. $^1H$ NMR (400 MHz, Methanol-$d_4$) δ ppm 1.23 (d, J=6.11 Hz, 6H) 1.30 (t, J=7.09 Hz, 3H) 3.97 (q, J=7.09 Hz, 2H) 4.48 (m, 3H) 5.09 (s, 1H) 6.65 (d, J=2.20 Hz, 1H) 6.79 (d, J=7.09 Hz, 1H) 6.91 (d, J=8.31 Hz, 1H) 7.03 (m, 1H) 7.07 (d, J=2.20 Hz, 1H) 7.14 (m, 2H) 7.30 (m, 2H) 7.73 (m, 1H) 8.02 (d, J=9.29 Hz, 1H) 8.42 (d, J=4.40 Hz, 1H); LC MS 486 (M+H).

Example 110

(R)-3-[2-(1-Amino-isoquinolin-6-ylamino)-2-(3-ethoxy-4-isopropoxy-phenyl)-acetylamino]-3-(3-amino-phenyl)-propionic acid trifluoroacetic acid salt

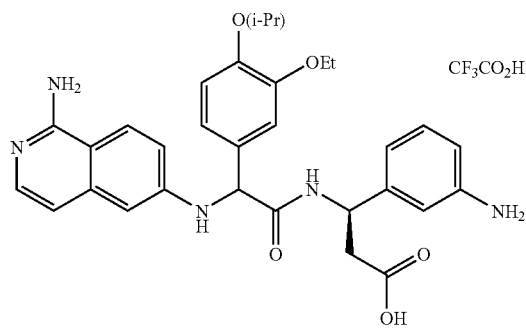

Example 110 was prepared according to the general coupling-deprotection using Intermediate 2 and 60B followed by hydrolysis of the ethyl ester as described in procedure 5E. $^1H$ NMR (400 MHz, Methanol-$d_4$) δ ppm 1.33 (m, 9H) 2.86 (m, 2H) 3.98 (m, 2H) 4.51 (m, 1H) 5.07 (s, 1H) 5.36 (m, 1H) 6.64 (d, J=17.36 Hz, 1H) 6.87 (m, 2H) 7.04 (m, 3H) 7.18 (m, 3H) 7.33 (m, 1H) 7.48 (d, J=4.89 Hz, 1H) 8.06 (m, 1H) 8.97 (t, J=8.19 Hz, 1H); LC MS 558 (M+H).

Example 111

(R)-3-(3-Acetylamino-phenyl)-3-[2-(1-amino-isoquinolin-6-ylamino)-2-(3,4-dimethoxy-phenyl)-acetylamino]-propionic acid trifluoroacetic acid salt

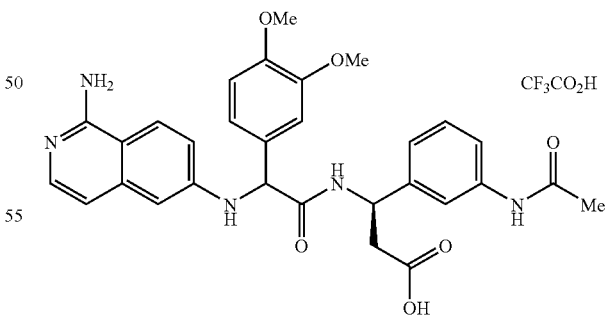

Example 111 was prepared according to the general coupling-deprotection using Intermediate 4 and 60E followed by hydrolysis of the methyl ester as in procedure 5E. $^1H$ NMR (400 MHz, Methanol-$d_4$) δ ppm 2.74 (m, 2H) 3.71 (m, 6H) 4.97 (m, 1H) 5.27 (m, J=9.41, 5.01 Hz, 1H) 6.50 (m, 1H) 6.70 (m, 2H) 6.85 (d, J=8.31 Hz, 1H) 7.01 (m, 4H) 7.24 (m, 3H) 7.96 (m, 1H) 8.74 (d, J=8.31 Hz, 1H); LC MS 558 (M+H).

Example 112

(R)-3-[2-(1-Amino-isoquinolin-6-ylamino)-2-(3-ethoxy-4-isopropoxy-phenyl)-acetylamino]-3-(2-fluoro-phenyl)-propionic acid methyl ester trifluoroacetic acid salt

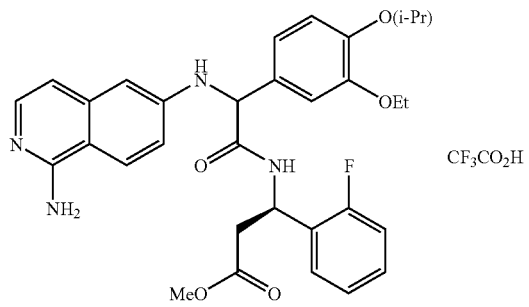

Example 112 was prepared according to the general coupling-deprotection using Intermediate 2 and commercial (R)-methyl 3-amino-3-(2-fluorophenyl)propanoate HCl salt. $^1$H NMR (400 MHz, Methanol-$d_4$) δ ppm 1.27 (m, 9H) 2.77 (m, 2H) 3.37 (m, 3H) 3.94 (m, 2H) 4.45 (m, 1H) 4.99 (s, 1H) 5.52 (m, J=4.16 Hz, 1H) 6.54 (s, 1H) 6.82 (m, 3H) 7.03 (m, 5H) 7.28 (m, 2H) 7.99 (t, J=9.66 Hz, 1H) 8.79 (m, 1H); LC MS 575 (M+H).

Example 113

(R)-3-[2-(1-Amino-isoquinolin-6-ylamino)-2-(3,4-dimethoxy-phenyl)-acetylamino]-3-(2-fluoro-phenyl)-propionic acid methyl ester trifluoroacetic acid salt

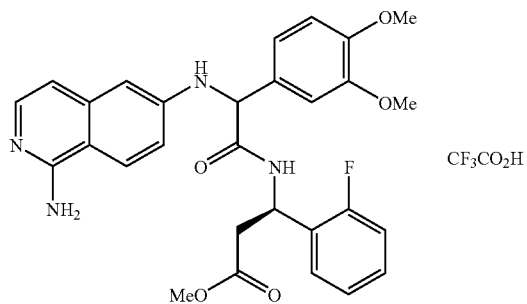

Example 113 was prepared according to the general coupling-deprotection using Intermediate 4 and commercial (R)-methyl 3-amino-3-(2-fluorophenyl)propanoate HCl salt. $^1$H NMR (400 MHz, Methanol-$d_4$) δ ppm 2.84 (m, 2H) 3.77 (m, 9H) 5.08 (d, J=2.93 Hz, 1H) 5.61 (dd, J=9.29, 5.38 Hz, 1H) 6.64 (dd, J=17.36, 2.20 Hz, 1H) 6.90 (m, 4H) 7.13 (m, 4H) 7.37 (m, 2H) 8.07 (dd, J=10.52, 9.54 Hz, 1H); LC MS 533 (M+H).

Example 114

(R)-3-[2-(1-Amino-isoquinolin-6-ylamino)-2-(3,4-dimethoxy-phenyl)-acetylamino]-3-(2-fluoro-phenyl)-propionic acid trifluoroacetic acid salt

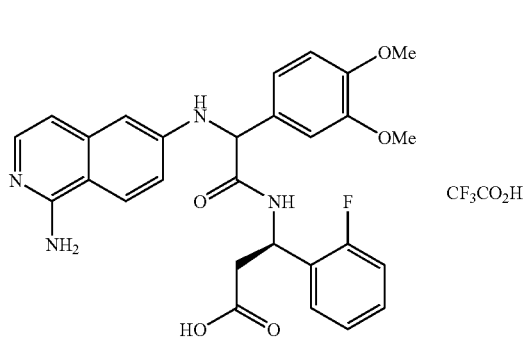

Example 114 was prepared by hydrolysis of Example 113 using LiOH in aqueous THF. $^1$H NMR (400 MHz, Methanol-$d_4$) δ ppm 2.73 (m, 2H) 3.73 (m, 6H) 5.02 (d, J=12.72 Hz, 1H) 5.52 (m, 1H) 6.56 (m, 1H) 6.82 (m, 4H) 7.05 (m, 4H) 7.25 (m, 2H) 7.98 (t, J=9.66 Hz, 1H) 8.79 (d, J=36.44 Hz, 1H); LC MS 519 (M+H).

Example 115

(R)-3-[2-(1-Amino-isoquinolin-6-ylamino)-2-(3-ethoxy-4-isopropoxy-phenyl)-acetylamino]-3-(2-fluoro-phenyl)-propionic acid trifluoroacetic acid salt

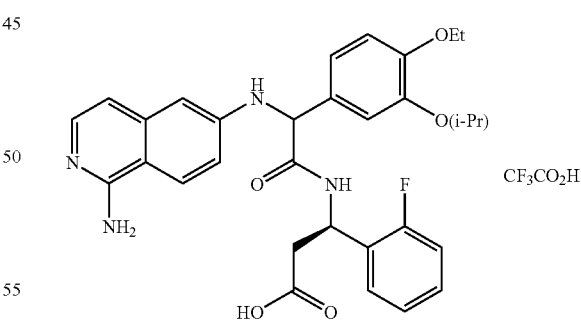

Example 115 was prepared by hydrolysis of Example 112 using LiOH in aqueous THF. $^1$H NMR (400 MHz, Methanol-$d_4$) δ ppm 1.25 (m, 9H) 2.71 (m, 2H) 3.90 (m, 2H) 4.44 (m, 1H) 5.00 (d, J=6.85 Hz, 1H) 5.51 (m, 1H) 6.56 (m, 1H) 6.82 (m, 4H) 7.03 (m, 4H) 7.25 (m, 2H) 7.97 (dd, J=9.29, 5.62 Hz, 1H); LC MS 561 (M+H).

Example 116

(R)-3-[2-(1-Amino-isoquinolin-6-ylamino)-2-(3-ethoxy-4-isopropoxy-phenyl)-acetylamino]-3-[2-(propane-2-sulfonyl)-phenyl]-propionic acid methyl ester trifluoroacetic acid salt

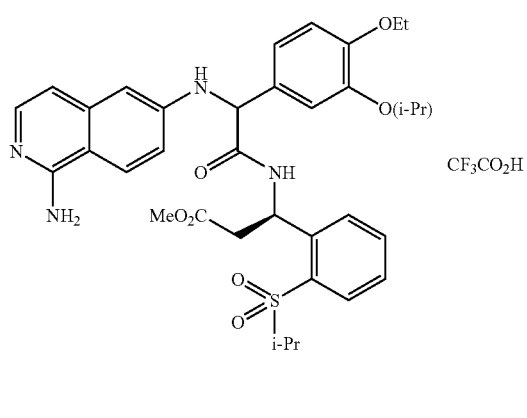

116A 2-(Isopropylthio)benzaldehyde

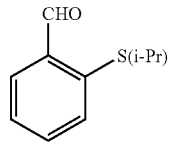

To 2-fluorobenzaldehyde (2.0 g, 16.1 mmol) and 2-thiopropane (1.65 mL, 17.7 mmol) in DMF (6 mL) was added potassium carbonate (2.45 g, 17.7 mmol). The reaction mixture was stirred overnight at 70° C. After cooling, the crude reaction mixture was filtered over Celite® and washed with ethyl acetate. The combined filtrate and washings was concentrated. The residue was redissolved in ethyl acetate and washed with water (3×) and then dried over sodium sulfate. The crude mixture was purified by flash column chromatography to give 1.7 g of yellow oil product 116A (60% total yield). $^1$H NMR (400 MHz, CDCl$_3$) δ ppm 1.32 (d, J=6.85 Hz, 6H) 3.41 (m, 1H) 7.35 (d, J=4.40 Hz, 1H) 7.51 (m, 2H) 7.87 (d, J=7.34 Hz, 1H) 10.53 (s, 1H).

116B tert-Butyl 3-(2-(isopropylthio)phenyl)acrylate

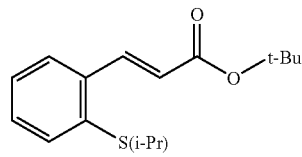

To tert-butyldiethylphosphonoacetate (0.52 mL, 2.2 mmol) in THF (1.5 mL) at 0° C. was added sodium hydride (95%, 0.056 g, 2.2 mmol) and stirred for 30 min. To this mixture was added 116A (0.2 g, 1.1 mmol) in THF (1.5 mL) and allowed to warm to rt and stirred overnight. The reaction was quenched with sat. ammonium chloride and then extracted with ether, washed with brine and dried over sodium sulfate. The solvent was removed and the crude product was purified by flash column chromatography to give 0.28 g of colorless oil 116B (92%). $^1$H NMR (400 MHz, CDCl$_3$) δ ppm 1.20 (d, J=6.85 Hz, 6H) 1.47 (s, 9H) 3.22 (m, 1H) 6.23 (d, J=15.89 Hz, 1H) 7.21 (m, 2H) 7.42 (dd, J=7.58, 1.47 Hz, 1H) 7.52 (dd, J=7.46, 1.59 Hz, 1H) 8.20 (d, J=15.90 Hz, 1H).

116C (R)-tert-butyl 3-(benzyl((S)-1-phenylethyl)amino)-3-(2-(isopropylthio)phenyl)propanoate

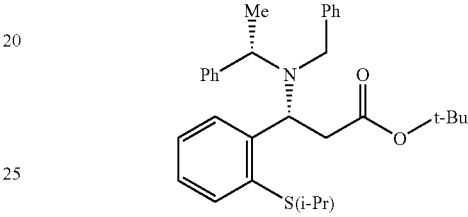

To (S)-(−)-N-benzyl-1-phenylethylamine (0.4 mL, 1.9 mmol) in THF at −78° C. was added n-butyl lithium (1.18 mL, 1.6 M in hexanes, 1.9 mmol) dropwise. The reaction was stirred at −78° C. for 30 min., then 116B (0.28 g, 1.0 mmol) in THF was added slowly. The reaction was stirred at −78° C. for 2 h. The reaction was quenched with sat. ammonium chloride and stirred overnight at rt. The aqueous layer was extracted with ethyl acetate (2×). The combined organic extracts was washed with brine and dried over sodium sulfate. The solvent was removed and the crude product was purified by flash column chromatography to give 0.41 g of colorless oil 116C (84%). $^1$H NMR (400 MHz, CDCl$_3$) δ ppm 1.10 (m, 9H) 1.17 (m, 6H) 1.28 (d, J=6.85 Hz, 3H) 2.26 (dd, J=14.18, 10.03 Hz, 1H) 2.57 (dd, J=14.06, 5.75 Hz, 1H) 3.40 (m, 1H) 3.67 (s, 2H) 3.86 (d, J=6.85 Hz, 1H) 4.95 (dd, J=10.03, 5.62 Hz, 1H) 7.12 (m, 10H) 7.35 (m, 3H) 7.52 (m, 1H).

116D (R)-tert-butyl 3-(benzyl((S)-1-phenylethyl)amino)-3-(2-(isopropylsulfonyl)phenyl)propanoate

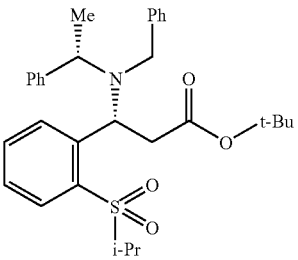

To 116C (0.14 g, 0.28 mmol) in methanol (2 mL) was added Oxone® (0.53 g, 0.86 mmol) in water (1.5 mL) and stirred at rt overnight. The reaction was quenched with 5% NaHSO$_3$ and then neutralized with 1 M NaOH. The organic solvent was evaporated and the aqueous layer was extracted with dichloromethane (3×). The combined extracts were washed with brine and dried over sodium sulfate. The solvent was removed and the crude residue was purified by flash column chromatography to give 0.13 g of white solid product 116D (87% yield). $^1$H NMR (400 MHz, Methanol-d$_4$) δ ppm 1.06 (d, J=6.60 Hz, 3H) 1.27 (d, J=11.74 Hz, 12H) 1.45 (d, J=6.85 Hz, 3H) 2.24 (dd, J=16.14, 3.91 Hz, 1H) 2.60 (m, 1H) 3.44 (m, 1H) 3.79 (s, 2H) 3.96 (m, 1H) 5.50 (m, 1H) 7.10 (m, 6H) 7.21 (m, 4H) 7.43 (t, J=7.21 Hz, 2H) 7.65 (t, J=7.09 Hz, 1H) 7.91 (dd, J=12.72, 8.07 Hz, 2H).

116E (R)-tert-Butyl-3-amino-3-(2-(isopropylsulfonyl)phenyl)propanoate

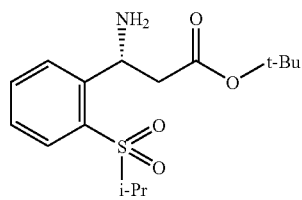

To 116D (0.12 g, 0.23 mmol) in methanol (10 mL) and acetic acid (0.1 mL) under nitrogen was added 20% Pd(OH)$_2$ (0.12 g) and then a balloon filled with hydrogen gas was introduced. The reaction was stirred for 4 h at rt. The catalyst was filtered off and the filtrate was concentrated. The residue was dissolved in methanol and a base resin (Supelco Diaion WA21J resin, 0.5 g) was added. The mixture was stirred for 1 h and then filtered and concentrated to give 0.07 g (89% yield) of 116E. $^1$H NMR (400 MHz, Methanol-d$_4$) δ ppm 1.17 (m, 6H) 1.27 (m, 9H) 2.73 (m, 2H) 3.60 (m, 1H) 5.01 (t, J=7.34 Hz, 1H) 7.45 (m, 1H) 7.69 (m, 2H) 7.88 (dd, J=7.95, 1.10 Hz, 1H).

116F

Example 116 was prepared according to the general coupling-deprotection using Intermediate 2 and 116E. $^1$H NMR (400 MHz, Methanol-d$_4$) δ ppm 1.22 (m, 15H) 2.75 (m, 2H) 3.28 (m, 3H) 3.87 (dd, J=22.01, 6.85 Hz, 1H) 3.99 (q, J=7.09 Hz, 1H) 4.11 (dd, J=8.31, 6.85 Hz, 1H) 4.47 (m, 1H) 4.98 (d, J=7.09 Hz, 1H) 5.91 (m, 1H) 6.58 (dd, J=34.24, 2.20 Hz, 1H) 6.93 (m, 5H) 7.09 (m, 1H) 7.26 (m, 1H) 7.41 (m, 1H) 7.70 (dd, J=18.83, 0.98 Hz, 1H) 7.82 (m, 1H) 8.01 (dd, J=19.56, 9.05 Hz, 1H) 9.05 (dd, J=25.80, 7.21 Hz, 1H); LC MS 663 (M+H).

Example 117

(R)-3-[2-(1-Amino-isoquinolin-6-ylamino)-2-(3-ethoxy-4-isopropoxy-phenyl)-acetylamino]-3-[2-(propane-2-sulfonyl)-phenyl]-propionic acid trifluoroacetic acid salt

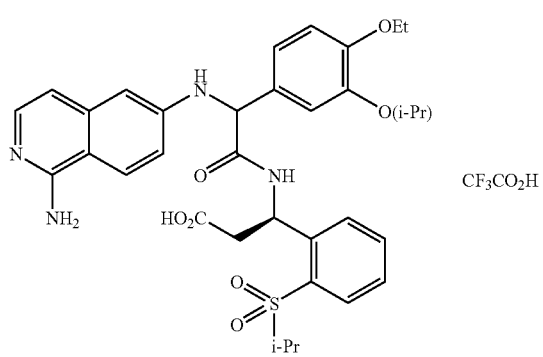

Example 117 was prepared by hydrolysis of Example 116 in a procedure similar to that of procedure 5E. $^1$H NMR (400 MHz, Methanol-d$_4$) δ ppm 1.24 (m, 15H) 2.72 (m, 2H) 3.90 (m, 2H) 4.13 (m, 1H) 4.46 (m, 1H) 5.01 (d, J=21.27 Hz, 1H) 5.87 (m, 1H) 6.59 (dd, J=23.48, 2.20 Hz, 1H) 6.92 (m, 5H) 7.09 (m, 1H) 7.25 (m, 1H) 7.40 (m, 1H) 7.68 (m, 1H) 7.82 (m, 1H) 8.00 (dd, J=18.71, 9.17 Hz, 1H) 9.09 (dd, J=23.48, 6.85 Hz, 1H); LC MS 649 (M+H).

Example 118

{(3-Acetylamino-benzyl)-[2-(1-amino-isoquinolin-6-ylamino)-2-(3-ethoxy-4-isopropoxy-phenyl)-acetyl]-amino}-acetic acid ethyl ester trifluoroacetic acid salt

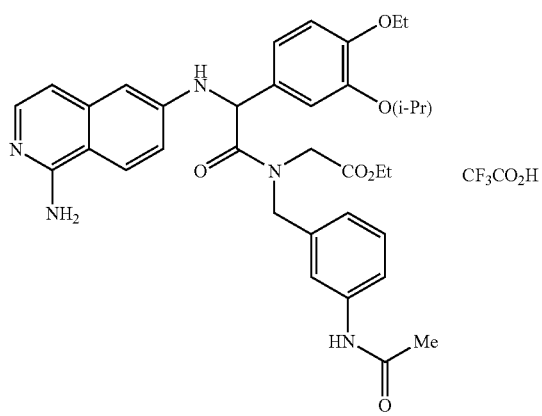

118A

Ethyl 2-(3-acetamidobenzylamino)acetate

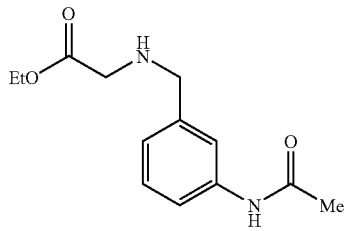

To 3-acetamide benzylamine (0.15 g, 0.75 mmol) in DMF was added potassium carbonate (0.52 g, 3.75 mmol) and ethyl 2-bromoacetate (0.086 mL, 0.78 mmol). The reaction mixture was stirred for 90 min at rt. The reaction was diluted in ethyl acetate and washed with water (3×) and then dried over sodium sulfate. The crude mixture was purified by flash column chromatography to give 0.06 g of 118A (32% total yield). $^1$H NMR (400 MHz, CDCl$_3$) δ ppm 1.25 (t, J=7.21 Hz, 3H) 2.11 (s, 3H) 3.34 (d, J=4.65 Hz, 2H) 3.74 (s, 2H) 4.17 (q, J=7.09 Hz, 2H) 7.07 (d, J=7.83 Hz, 1H) 7.26 (t, J=7.83 Hz, 1H) 7.46 (d, J=8.07 Hz, 1H) 7.50 (s, 1H).

118B

Example 118 was prepared according to the general coupling-deprotection using Intermediate 2 and 118A. $^1$H NMR (400 MHz, Methanol-d$_4$) δ ppm 1.24 (m, 12H) 2.03 (d, J=3.91 Hz, 3H) 4.01 (m, 6H) 4.52 (m, 3H) 5.48 (d, J=61.13 Hz, 1H) 6.88 (m, 7-H) 7.23 (m, 4H) 7.98 (m, 1H) 9.73 (d, J=11.25 Hz, 1H); LC MS 628 (M+H).

Example 119

{(3-Acetylamino-benzyl)-[2-(1-amino-isoquinolin-6-ylamino)-2-(3-ethoxy-4-isopropoxy-phenyl)-acetyl]-amino}-acetic acid trifluoroacetic acid salt

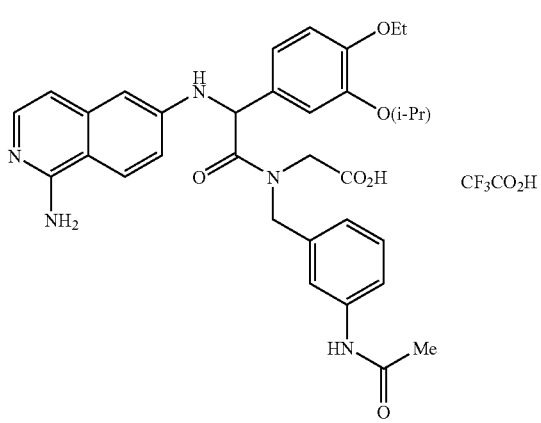

Example 119 was prepared by hydrolysis of Example 118 in a procedure similar to that of procedure 5E. $^1$H NMR (400 MHz, Methanol-d$_4$) δ ppm 1.27 (m, 9H) 2.03 (d, J=1.47 Hz, 3H) 3.98 (m, 5H) 4.44 (m, 2H) 5.44 (d, J=81.92 Hz, 1H) 6.89 (m, 7H) 7.23 (m, 4H) 7.97 (m, 1H); LC MS 600 (M+H).

Example 120

2-(1-Amino-isoquinolin-6-ylamino)-2-(3-ethoxy-4-isopropoxy-phenyl)-N-{1-[2-(propane-2-sulfonyl)-phenyl]-ethyl}-acetamide trifluoroacetic acid salt

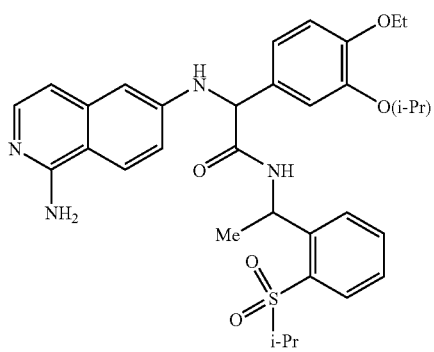

120A 1-(2-(Isopropylthio)phenyl)ethanone

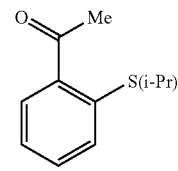

To 1-(2-fluorophenyl)ethanone (1.0 g, 7.2 mmol) and 2-thiopropane (1.3 mL, 14.4 mmol) in DMF (4 mL) was added potassium carbonate (2.0 g, 14.4 mmol). The reaction mixture was stirred overnight at 50° C. After cooling, the crude reaction mixture was diluted in ethyl acetate and washed with water (3×) and then dried over sodium sulfate. The solvent was removed and the residue dried under high vacuum to give 1.4 g product 120A (>99% yield). $^1$H NMR (400 MHz, CDCl$_3$) δ ppm 1.29 (dd, J=15.90, 6.60 Hz, 6H) 2.59 (s, 3H) 3.44 (m, 1H) 7.19 (m, 1H) 7.40 (m, 2H) 7.64 (dd, J=7.70, 1.34 Hz, 1H).

120B 1-(2-(Isopropylsulfonyl)phenyl)ethanone

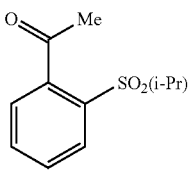

To 120A (0.5 g, 2.6 mmol) in methanol (5 mL) was added Oxone® (4.7 g, 7.7 mmol) in water (5 mL) and stirred at room temperature for 3 h. The reaction was quenched with 5% NaHSO$_3$ and then neutralized with 1 M NaOH. The organic

120C 1-(2-(Isopropylsulfonyl)phenyl)ethanol

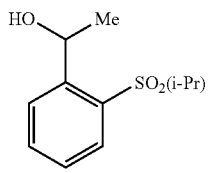

To 120B (0.09 g, 0.38 mmol) in methanol (2 mL) was added sodium borohydride (0.07 g, 1.9 mmol). The reaction was quenched with water after 10 min of stirring at rt. The product was extracted with ethyl acetate (3×) and then dried over sodium sulfate. The solvent was removed and place under high vacuum to give 0.08 g of 120C (90% yield). $^1$H NMR (400 MHz, CDCl$_3$) δ ppm 1.11 (d, J=6.85 Hz, 3H) 1.29 (d, J=6.85 Hz, 3H) 1.40 (m, 3H) 3.35 (m, 1H) 5.57 (q, J=6.20 Hz, 1H) 7.43 (m, 1H) 7.67 (m, 1H) 7.83 (m, 2H).

120D 1-(2-(Isopropylsulfonyl)phenyl)ethyl diphenyl phosphate

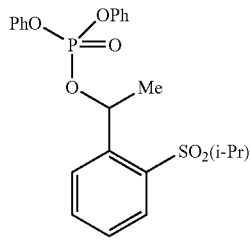

To 120C (0.14 g, 0.61 mmol) in toluene was added diphenylphosphoryl azide (0.25 g, 0.92 mmol) and the reaction was cooled to 0° C. 1,8-Diazabicyclo[5.4.0]undec-7-ene (0.14 mL, 0.92 mmol) was added and the reaction was allowed to warm to rt and stirred for 2 h. The reaction was quenched with water and then 10% citric acid. The aqueous layer was extracted with ethyl acetate (3×) and the combined extracts were washed with brine and dried over sodium sulfate. The solvent was removed and the crude product was purified by flash column chromatography to give 0.1 g of 120D. $^1$H NMR (400 MHz, CDCl$_3$) δ ppm 0.95 (d, J=6.60 Hz, 3H) 1.27 (d, J=6.85 Hz, 3H) 1.57 (dd, J=6.24, 1.10 Hz, 3H) 3.47 (m, 1H) 6.44 (m, 1H) 6.98 (m, 2H) 7.17 (m, 6H) 7.35 (t, J=7.95 Hz, 2H) 7.49 (m, 1H) 7.64 (m, 1H) 7.70 (m, 1H) 7.81 (dd, J=8.07, 1.22 Hz, 1H).

120E 1-(1-Azidoethyl)-2-(isopropylsulfonyl)benzene

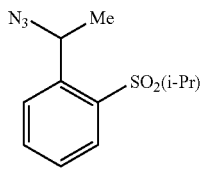

To 120D (0.11 g, 0.22 mmol) in DMF (10 mL) was added sodium azide (0.049 g, 0.75 mmol). The reaction was stirred for 24 h at 60° C. After cooling, the crude reaction mixture was diluted in ethyl acetate and washed with water (3×) and then dried over sodium sulfate. The solvent was removed and the residue was purified by flash column chromatography to give 0.031 g of 120E (56% yield). $^1$H NMR (400 MHz, CDCl$_3$) δ ppm 1.17 (d, J=6.60 Hz, 3H) 1.26 (d, J=6.85 Hz, 3H) 1.49 (d, J=6.60 Hz, 3H) 3.32 (m, 1H) 5.67 (q, J=6.68 Hz, 1H) 7.52 (m, 1H) 7.74 (m, 2H) 7.92 (d, J=7.83 Hz, 1H).

120F 1-(2-(Isopropylsulfonyl)phenyl)ethanamine hydrochloride

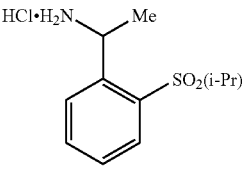

To 120E (0.031 g, 0.12 mmol) in methanol (5 mL) and hydrochloric acid (0.05 mL) under nitrogen was added 10% Pd/C (0.02 g) and then a balloon filled with hydrogen gas was introduced. The reaction was stirred for 1 h at rt. The catalyst was filtered off and washed with methanol. The combined filtrate and washings were concentrated and dried under high vacuum to give 0.03 g of 120F (>99%). $^1$H NMR (400 MHz, Methanol-d$_4$) δ ppm 1.24 (dd, J=14.31, 6.72 Hz, 6H) 1.63 (d, J=6.85 Hz, 3H) 3.35 (m, 1H) 5.31 (q, J=6.60 Hz, 1H) 7.64 (m, 1H) 7.81 (m, 2H) 7.99 (d, J=9.05 Hz, 1H).

120G

Example 120 was prepared according to the general coupling-deprotection using Intermediate 2 and 120F. $^1$H NMR (400 MHz, Methanol-d$_4$) δ ppm 0.92 (dd, J=13.21, 6.60 Hz, 3H) 1.31 (m, 15H) 3.93 (m, 3H) 4.46 (m, 1H) 5.04 (d, J=2.20 Hz, 1H) 5.55 (m, 1H) 6.65 (m, 2H) 7.00 (m, 5H) 7.27 (m, 2H) 7.65 (m, 2H) 7.99 (dd, J=22.62, 9.17 Hz, 1H) 8.94 (dd, J=54.29, 6.60 Hz, 1H); LC MS 605 (M+H).

Example 121

N-(2-(Methylsulfonyl)benzyl)-2-(1-aminoisoquinolin-6-ylamino)-2-(3-vinylphenyl)acetamide trifluoroacetic acid salt

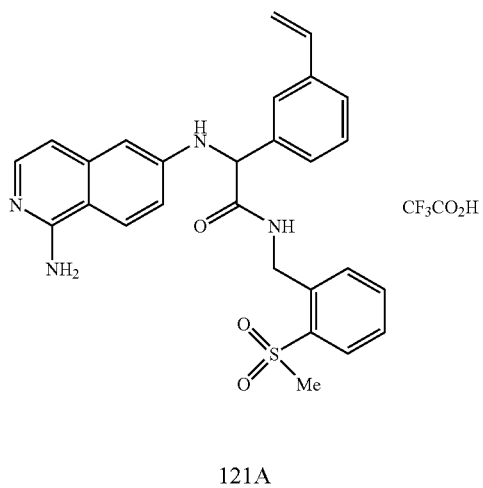

121A

Methyl 2-(3-bromophenyl)acetate

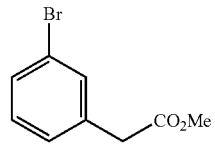

A mixture of 3-bromophenylacetic acid (5.29 g, 24.6 mmol) and concentrated sulfuric acid (100 μL) in anhydrous methanol (40 mL) was refluxed overnight and then concentrated in vacuo. The residue was partitioned between ethyl acetate and saturated sodium bicarbonate solution. The organic layer was washed with saturated sodium bicarbonate solution, saturated sodium chloride solution, dried (MgSO$_4$) and concentrated in vacuo to give 121A (5.82 g, 100%) as pale yellow oil. LC-MS m/z: 228.18 (M+H)$^+$.

121B

Methyl 2-bromo-2-(3-bromophenyl)acetate

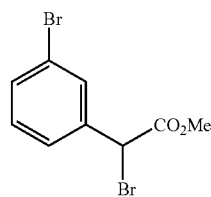

A mixture of 121A (2.28 g, 10.0 mmol) and N-bromosuccinimide (1.96 g, 11.0 mmol) in carbon tetrachloride (20 mL) was deoxygenated with a flow of nitrogen for 5 min. 2,2'-Azobisisobutyronitrile (82 mg, 0.5 mmol) was added and the mixture was refluxed for 18 h. Hexanes was added to the cooled mixture, and the resulting solid was filtered and washed with hexanes. The filtrate was concentrated on a rotary evaporator and then chromatographed (silica gel, step gradient from 100% hexanes to 5% ethyl acetate in hexanes) to give 121B (1.3 g, 42%) as clear oil. LC-MS m/z: 309.1 (M+H)$^+$.

121C

Methyl 2-(1-(di-tert-butoxycarbonylamino)isoquinolin-6-ylamino)-2-(3-bromophenyl)acetate

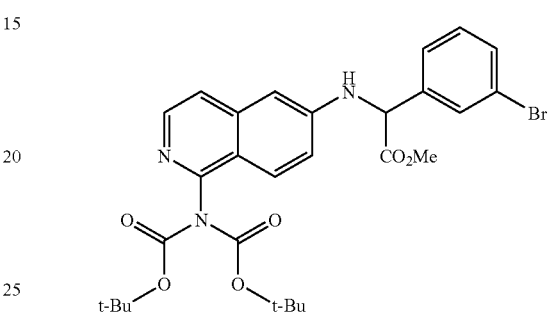

A mixture of 121B (404 mg, 1.31 mmol), Intermediate 1 (238 mg, 0.66 mmol), and 2,6-lutidine (0.60 mL, 5.17 mmol) in dimethylformamide (3 mL), was heated in a pressure tube at 55° C. for 3 days. The mixture was concentrated in vacuo and the residue was partitioned between ethyl acetate and saturated sodium bicarbonate solution. The organic layer was washed with water, saturated sodium chloride solution, dried (MgSO$_4$), and concentrated. Chromatography (silica gel, 30% ethyl acetate in hexanes) gave 121C (263 mg, 68%) as yellow oil which solidified upon standing. LC-MS m/z: 586.2 (M+H)$^+$.

121D 2-(1-(di-tert-butoxycarbonylamino)isoquinolin-6-ylamino)-2-(3-bromophenyl)acetic acid

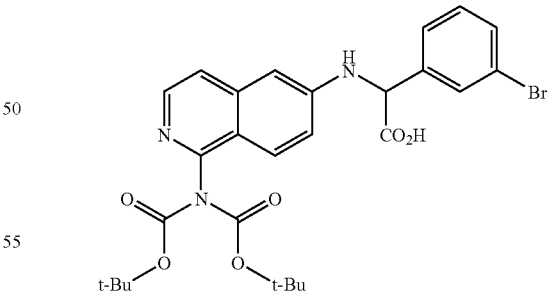

A mixture of 121C (600 mg, 1.03 mmol) and lithium hydroxide monohydrate (86 mg, 2.05 mmol) in THF (4 mL), water (4 mL), and methanol (1 mL) was stirred at rt for 1 h. The mixture was concentrated in vacuo, and the residue was partitioned between ethyl acetate and 1N hydrochloric acid solution. The organic layer was washed with saturated ammonium chloride solution, water, saturated sodium chloride solution, dried (MgSO$_4$), and concentrated to give 121D (547 mg, 93%) as yellow solid. LC-MS m/z: 572.1 (M+H)$^+$.

121E

N-(2-(methylsulfonyl)benzyl)-2-(3-bromophenyl)-2-(1-(di-tert-butoxycarbonylamino)isoquinolin-6-ylamino)acetamide

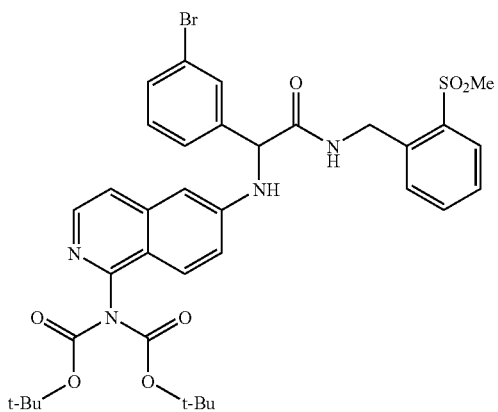

To a mixture of 121D (547 mg, 0.96 mmol) and Intermediate 6 (340 mg, 1.54 mmol) in dimethylformamide (3 mL) and dichloromethane (20 mL), diisopropylethylamine (0.55 mL, 3.15 mmol), 1-(3-dimethylaminopropyl)-3-ethylcarbodiimide hydrochloride (392 mg, 2.04 mmol) and 1-hydroxy-7-azabenzotriazole (278 mg, 2.04 mmol) were added. The reaction mixture was stirred at rt overnight. The solvent was evaporated and ice water was added. The resulting solid was filtered and washed with water. The solid was purified by silica gel chromatography (100% chloroform, followed by 10% methanol in chloroform). The product fractions were combined and triturated with hexanes, filtered, and washed with hexanes to afford 121E (614 mg, 81%) as yellow solid. LC-MS m/z: 739.1 (M+H)$^+$.

121F

N-(2-(Methylsulfonyl)benzyl)-2-(1-(di-tert-butoxycarbonylamino)isoquinolin-6-ylamino)-2-(3-vinylphenyl)acetamide

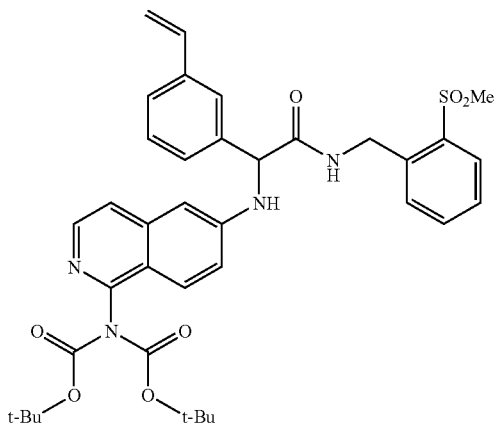

A suspension of 121E (150 mg, 0.2 mmol), potassium carbonate (40 mg, 0.28 mmol) and 2,4,6-trivinylcyclotriboroxane pyridine complex (80 mg, 0.22 mmol in ethyleneglycol dimethyl ether (2 mL) and water (0.5 mL) in pressure tube was deoxygenated with a nitrogen flow for 3 min.

Tetrakis(triphenylphosphine)palladium(0) (10 mg, 0.009 mmol) was added. The mixture was heated at 90° C. for 1 h. The reaction mixture was chromatographed (silica gel, 10% methanol in chloroform) to give 121F (124 mg, 89%). LC-MS m/z: 687.3 (M+H)$^+$.

21G

Example 121: A solution of 121F (35 mg, 0.05 mmol) in ethyl acetate (1.5 mL) and 4N hydrogen chloride in dioxane (1.5 mL) was stirred overnight at rt. The solvent was evaporated and the crude material was purified by reversed-phase HPLC to afford Example 121 (15 mg, 49%) as a white amorphous solid. LC-MS m/z: 487.3 (M+H)$^+$. $^1$H NMR (400 MHz, CD$_3$OD) δ 8.81 (t, 0.5H), 8.07 (d, 1H), 7.90 (m, 1H), 7.61 (m, 1H), 7.45-7.44 (m, 7H), 7.19 (dd, 1H), 6.80 (dd, 1H), 6.63 (dd, 1H), 6.66 (d, 1H), 5.81 (d, 1H), 5.28 (d, 1H), 5.21 (s, 1H), 4.88-4.77 (m, 2H), 3.15 (s, 3H).

Example 122

N-(2-(Methylsulfonyl)benzyl)-2-(1-aminoisoquinolin-6-ylamino)-2-(3-ethylphenyl)acetamide trifluoroacetic acid salt

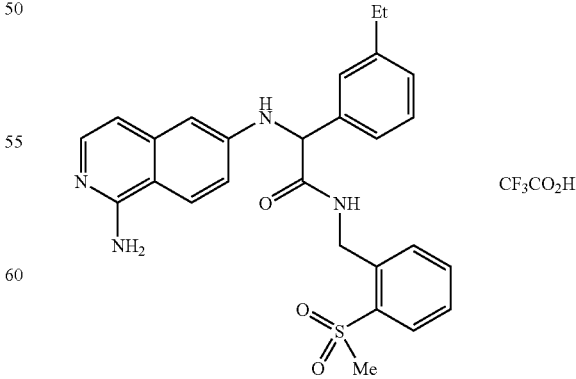

122A

N-(2-(Methylsulfonyl)benzyl)-2-(1-(di-tert-butoxy-carbonylamino)isoquinolin-6-ylamino)-2-(3-ethylphenyl)acetamide

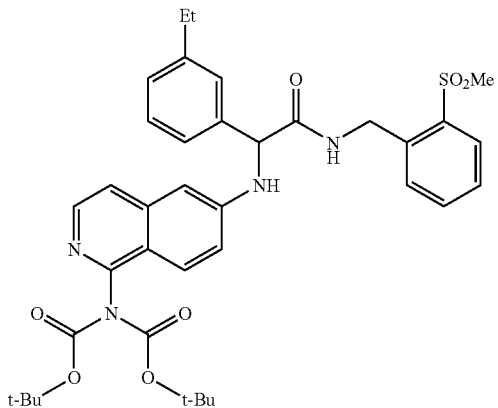

To a solution of 121F (50 mg, 0.07 mmol) in methanol (2 mL), 10% palladium on carbon (23 mg) was added. The reaction flask was evacuated, flushed with nitrogen (3×), and then stirred under hydrogen (65 psi) for 2 h. The reaction mixture was filtered and concentrated to afford crude 122A which was used as is in the next step. LC-MS m/z: 689.2 (M+H)$^+$.

122B

Example 122: A solution of 122A in ethyl acetate (1.5 mL) and 4N hydrogen chloride in dioxane (1.5 mL) was stirred overnight at rt. The solvent was evaporated and the crude material was purified by reversed-phase HPLC to afford Example 122 (17 mg, 39%, 2 steps) as a white amorphous solid. LC-MS m/z: 489.3 (M+H)$^+$. $^1$H NMR (400 MHz, CD$_3$OD) δ 8.87 (t, 0.75H), 8.07 (d, 1H), 7.45 (m, 2H), 7.37-7.29 (m, 5H), 7.23-7.16 (m, 2H), 6.78 (d, 1H), 6.65 (d, 1H), 5.17 (s, 1H), 4.87-4.67 (m, 2H), 3.14 (s, 3H), 2.64 (q, 2H), 1.21 (t, 3H).

Example 123

N-(3-(Benzenesulfonamide)-2-(1-aminoisoquinolin-6-ylamino)-2-(3-ethylphenyl)acetamide trifluoroacetic acid salt

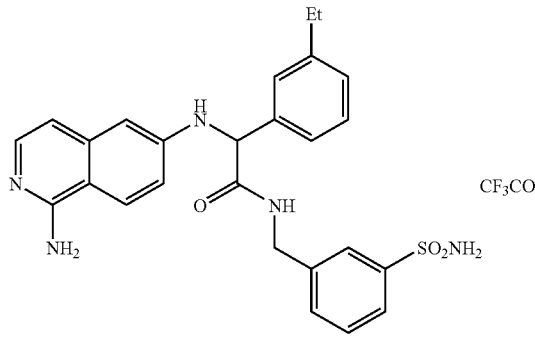

123A

N-(3-(Menzenesulfonamide)-2-(3-bromophenyl)-2-(1-(di-tert-butoxycarbonylamino)isoquinolin-6-ylamino)acetamide

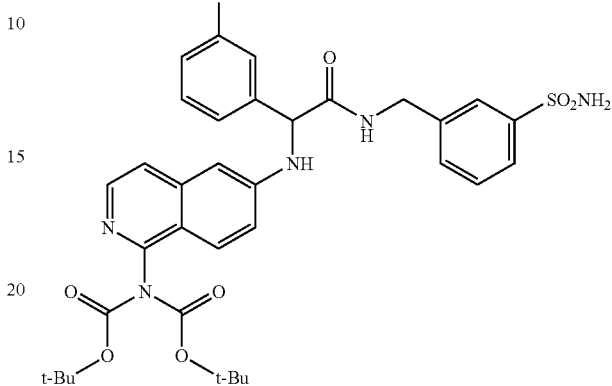

To a mixture of 121D (299 mg, 0.51 mmol) and Intermediate 5 (170 mg, 0.76 mmol) in dimethylformamide (2 mL) and dichloromethane (10 mL), diisopropylethylamine (0.267 mL, 1.53 mmol), 1-(3-dimethylaminopropyl)-3-ethylcarbodiimide hydrochloride (196 mg, 1.02 mmol) and 1-hydroxy-7-azabenzotriazole (139 mg, 1.02 mmol) were added. The reaction mixture was stirred at 4 h. The solvent was evaporated and ice water was added. The resulting solid was filtered and washed with water. The solid was purified by silica gel chromatography (100% chloroform, followed by 10% methanol in chloroform). The product fractions were combined to afford 123A (0.33 g, 88%) as a yellow foam. LC-MS m/z: 740.1 (M+H)$^+$.

123B

N-(3-(Benzenesulfonamide)-2-(1-(di-tert-butoxycarbonylamino)isoquinolin-6-ylamino)-2-(3-vinylphenyl)acetamide

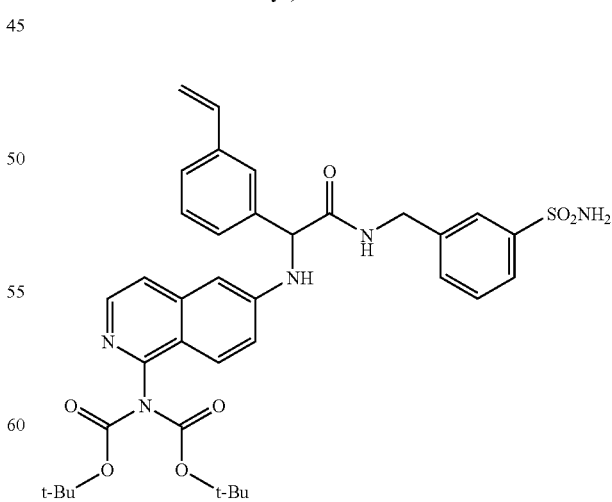

A suspension of 123A (74 mg, 0.1 mmol), potassium carbonate (20 mg, 0.14 mmol) and 2,4,6-trivinylcyclotriboroxane pyridine complex (40 mg, 0.11 mmol in ethyleneglycol dimethyl ether (2 mL) and water (0.5 mL) in pressure tube was deoxygenated under a flow of nitrogen for 3 min. Tetrakis(triphenylphosphine)palladium(0) (5.5 mg, 0.005 mmol) was added. The mixture was heated at 90° C. for 1 h. The reaction mixture was chromatographed (silica gel, 10% methanol in chloroform) to give 123B (40 mg, 60%). LC-MS m/z: 688.2 (M+H)$^+$.

123C

N-(3-(Benzenesulfonamide)-2-(1-(di-tert-butoxycarbonylamino)isoquinolin-6-ylamino)-2-(3-ethylphenyl)acetamide

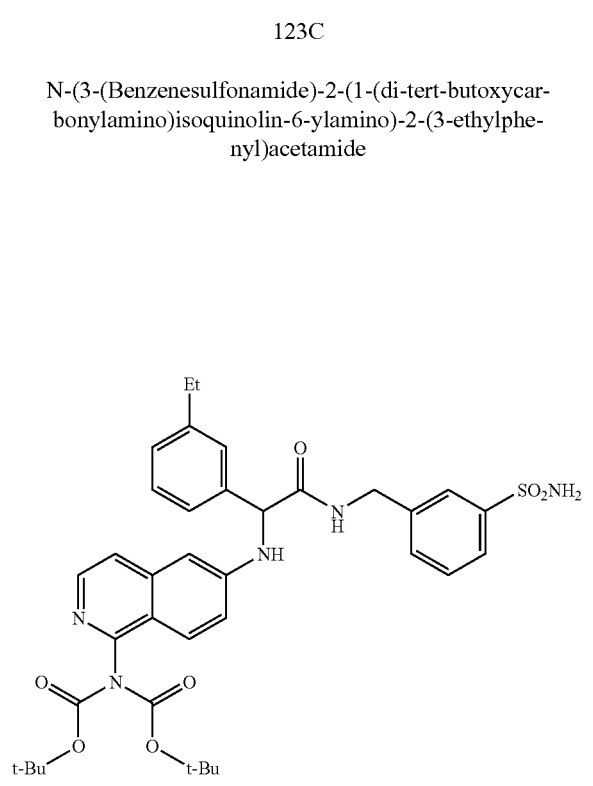

To a solution of 123B (40 mg, 0.06 mmol) in methanol (4 mL), 10% palladium on carbon (23 mg) was added. The reaction flask was evacuated, flushed with nitrogen (3×), and then stirred under hydrogen (60 psi) for 1 h. The reaction mixture was filtered, concentrated to afford crude 123C which was used as is in the next step. LC-MS m/z: 690.3 (M+H)$^+$.

123D

Example 123: A solution of 123C in ethyl acetate (1.5 mL), 4N hydrogen chloride in dioxane (1.5 mL) was stirred overnight at rt. The solvent was evaporated and the crude material was purified by reversed-phase HPLC to afford Example 123 (16 mg, 46%, 2 steps) as a white amorphous solid. LC-MS m/z: 490.3 (M+H)$^+$. $^1$H NMR (400 MHz, CD$_3$OD) δ 8.98 (t, 0.75H), 8.07 (d, 1H), 7.80 (m, 1H), 7.75 (m, 1H), 7.38-7.30 (m, 6H), 7.22-7.16 (m, 2H), 6.80 (d, 1H), 6.5 (d, 1H), 5.14 (s, 1H), 4.47 (d, 2H), 2.65 (q, 2H), 1.27 (t, 3H).

Example 124

N-(2-(Methylsulfonyl)benzyl)-2-(1-aminoisoquinolin-6-ylamino)-2-(3-methoxyphenyl)acetamide trifluoroacetic acid salt

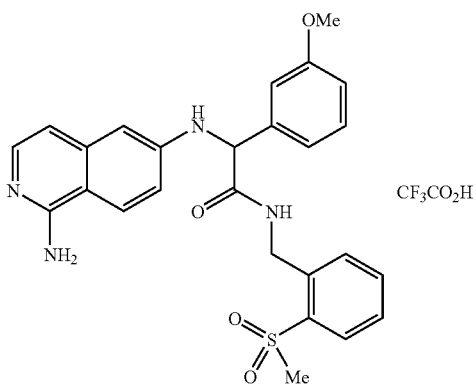

124A 2-(1-(di-tert-butoxycarbonylamino)isoquinolin-6-ylamino)-2-(3-methoxyphenyl)acetic acid

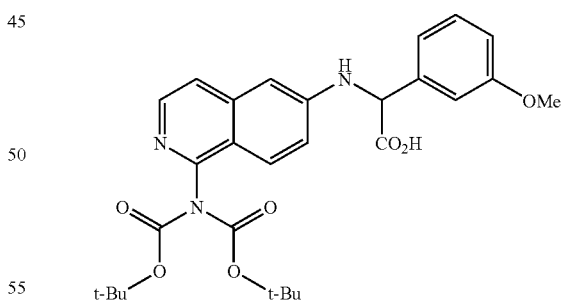

A mixture of 3-methoxyphenylboronic acid (76 mg, 0.5 mmol), Intermediate 1 (90 mg, 0.25 mmol), and glyoxylic acid (0.23 mg, 0.25 mmol) in DCE (1.3 mL), was heated in a pressure tube at 60° C. for 5 h. The mixture was chromatographed (silica gel, 10% methanol in chloroform) to give 124A (72 mg, 56%). LC-MS m/z: 524.3 (M+H)$^+$.

124B

N-(2-(Methylsulfonyl)benzyl)-2-(1-(di-tert-butoxy-carbonylamino)isoquinolin-6-ylamino)-2-(3-methoxyphenyl)acetamide

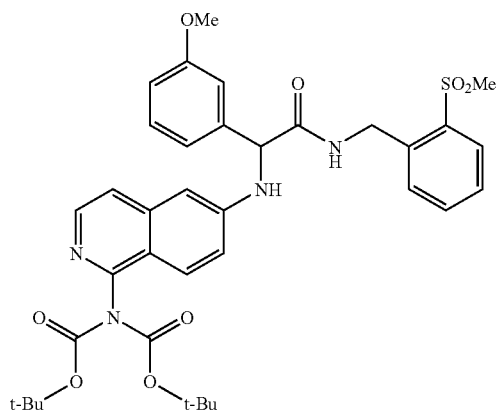

To a mixture of 124A (36 mg, 0.07 mmol) and Intermediate 6 (27 mg, 0.12 mmol) in dimethylformamide (0.2 mL) and dichloromethane (1 mL), diisopropylethylamine (0.05 mL, 0.28 mmol), 1-(3-dimethylaminopropyl)-3-ethylcarbodiimide hydrochloride (34 mg, 0.18 mmol) and 1-hydroxy-7-azabenzotriazole (24 mg, 0.18 mmol) were added. The reaction mixture was stirred at RT for 6 h. The solvent was concentrated in vacuo. The residue was purified by silica gel chromatography (10% to 100% ethyl acetate in hexanes to give 124B. LC-MS m/z: 691.3 (M+H)$^+$.

124C

Example 124: A solution of 124B in ethyl acetate (1 mL) and 4N hydrogen chloride in dioxane (1 mL) was stirred overnight at RT. The solvent was evaporated and the crude material was purified by reversed-phase HPLC to afford Example 124 (30 mg, 71%, 2 steps) as a pale yellow amorphous solid. LC-MS m/z: 491.3 (M+H)$^+$. $^1$H NMR (400 MHz, CD$_3$OD) δ 8.78 (t, 0.75H), 8.06 (d, 1H), 7.91 (dd, 1H), 7.45 (m, 2H), 7.31 (m, 3H), 7.22 (dd, 1H), 7.11 (m, 2H), 6.92 (dd, 1H), 6.76 (d, 1H), 6.5 (d, 1H), 5.19 (s, 1H), 4.89-4.68 (m, 2H), 3.77 (s, 3H), 3.15 (s, 3H).

Example 125

N-(3-(Benzenesulfonamide)-2-(1-aminoisoquinolin-6-ylamino)-2-(3-methoxyphenyl)acetamide trifluoroacetic acid salt

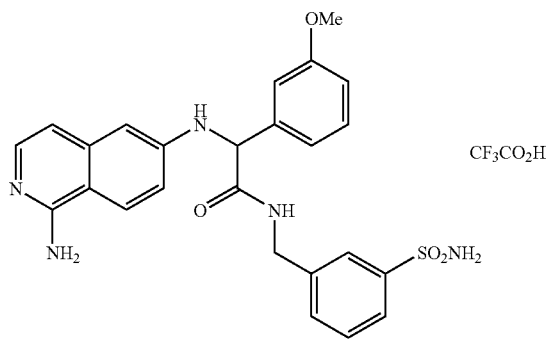

125A

N-(3-(Benzenesulfonamide)-2-(1-(di-tert-butoxycarbonylamino)isoquinolin-6-ylamino)-2-(3-methoxyphenyl)acetamide

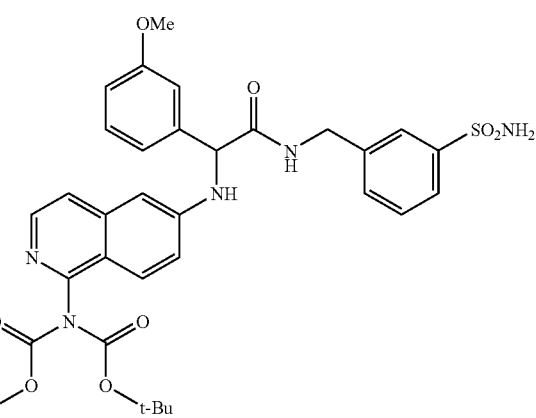

To a mixture of 124A (36 mg, 0.07 mmol) and Intermediate 5 (27 mg, 0.12 mmol) in dimethylformamide (0.2 mL) and dichloromethane (1 mL), diisopropylethylamine (0.04 mL, 0.23 mmol), 1-(3-dimethylaminopropyl)-3-ethylcarbodiimide hydrochloride (34 mg, 0.18 mmol) and 1-hydroxy-7-azabenzotriazole (22 mg, 0.16 mmol) were added. The reaction mixture was stirred at rt for 6 h. The solvent was concentrated in vacuo. The residue was purified by silica gel chromatography (10% to 100% ethyl acetate in hexanes to give 125A. LC-MS m/z: 692.3 (M+H)$^+$.

125B

Example 125: A solution of 125A in ethyl acetate (1 mL) and 4N hydrogen chloride in dioxane (1 mL) was stirred overnight at rt. The solvent was evaporated and the crude material was purified by reversed-phase HPLC to afford Example 125 (17 mg, 40%, 2steps) as a pale yellow amorphous solid. LC-MS m/z: 492.3 (M+H)$^+$. $^1$H NMR (400 MHz, CD$_3$OD) δ 9.0 (t, 0.5H), 8.07 (dd, 1H), 7.78 (dd, 1H), 7.74 (m, 1H), 7.39-7.29 (m, 4H), 7.19-7.11 (m, 3H), 6.91 (dd, 1H), 6.80 (dd, 1H), 6.65 (d, 1H), 5.15 (s, 1H), 4.46 (d, 2H), 3.77 (s, 3H).

Example 126

N-(2-(Methylsulfonyl)benzyl)-2-(1-aminoisoquinolin-6-ylamino)-2-(3-methylthiophenyl)acetamide trifluoroacetic acid salt

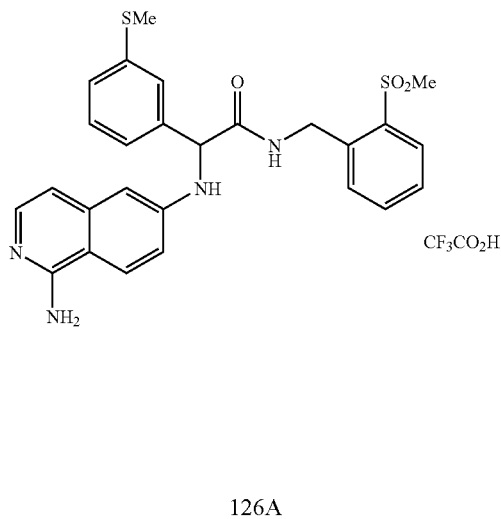

126A 2-(1-(di-tert-butoxycarbonylamino)isoquinolin-6-ylamino)-2-(3-methylthiophenyl)acetic acid

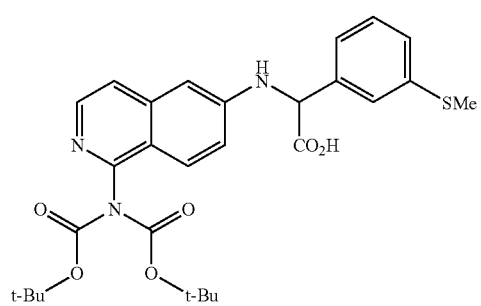

A mixture of 3-methylthiophenylboronic acid (84 mg, 0.5 mmol), Intermediate 1 (90 mg, 0.25 mmol), and glyoxylic acid (0.23 mg, 0.25 mmol) in DCE (1.25 mL), was heated in a pressure tube at 60° C. for 6 h. The mixture was chromatographed (silica gel, 10% methanol in chloroform) to give 126A (86 mg, 69%). LC-MS m/z: 540.3 (M+H)$^+$.

126B

N-(2-(Methylsulfonyl)benzyl)-2-(1-(di-tert-butoxycarbonylamino)isoquinolin-6-ylamino)-2-(3-methylthiophenyl)acetamide To a mixture of 126A (43 mg, 0.08 mmol) and Intermediate 6 (27 mg, 0.12 mmol) in dimethylformamide (0.2 mL) and dichloromethane (1 mL), diisopropylethylamine (0.03 mL, 0.17 mmol), 1-(3-dimethylaminopropyl)-3-ethylcarbodiimide hydrochloride (31 mg, 0.16 mmol) and 1-hydroxy-7-azabenzotriazole (22 mg, 0.16 mmol) were added. The reaction mixture was stirred at RT overnight. The solvent was concentrated in vacuo. Water was added to the residue and the solid was filtered. The solid was purified by silica gel chromatography (30% to 100% ethyl acetate in hexanes) to give 126B (28 mg, 50%). LC-MS m/z: 707.2 (M+H)$^+$.

126C

Example 126: A solution of 126B in ethyl acetate (1 mL) and 4N hydrogen chloride in dioxane (1 mL) was stirred overnight at rt. The solvent was evaporated and the crude material was purified by reversed-phase HPLC to afford Example 126 (22 mg, 89%) as an off white amorphous solid. LC-MS m/z: 491.3 (M+H)$^+$. $^1$H NMR (400 MHz, CD$_3$OD) δ 8.80 (t, 0.5H), 8.07 (d, 1H), 7.91 (dd, 1H), 7.51-7.42 (m, 3H), 7.42-7.31 (m, 4H), 7.29-7.24 (m, 1H), 7.19 (dd, 1H), 6.89 (d, 1H), 6.66 (d, 1H), 5.19 (s, 1H), 4.90-4.69 (m, 2H), 3.15 (s, 3H), 2.45 (s, 3H).

Example 127

N-(3-(Benzenesulfonamide)-2-(1-aminoisoquinolin-6-ylamino)-2-(3-methylthiophenyl)acetamide trifluoroacetic acid salt

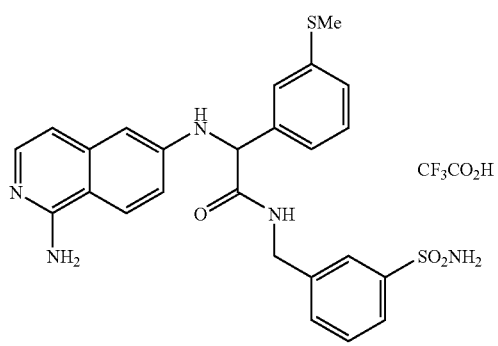

127A

N-(3-(Benzenesulfonamide)-2-(1-(di-tert-butoxycarbonylamino)isoquinolin-6-ylamino)-2-(3-methylthiophenyl)acetamide

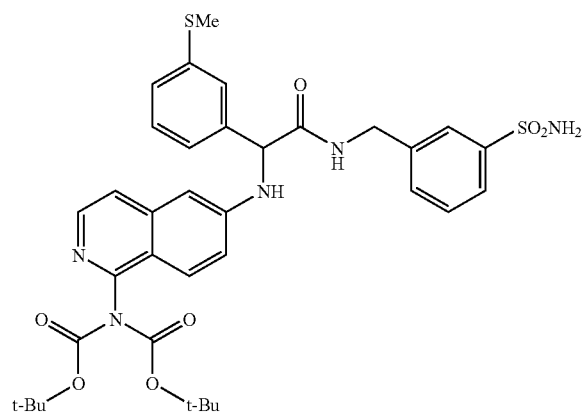

To a mixture of 126A (43 mg, 0.08 mmol) and Intermediate 5 (27 mg, 0.12 mmol) in dimethylformamide (0.2 mL) and dichloromethane (1 mL), diisopropylethylamine (0.03 mL, 0.17 mmol), 1-(3-dimethylaminopropyl)-3-ethylcarbodiimide hydrochloride (31 mg, 0.16 mmol) and 1-hydroxy-7-azabenzotriazole (22 mg, 0.16 mmol), were added. The reaction mixture was stirred at rt overnight. The solvent was concentrated in vacuo. Water was added to the residue and the solid was filtered. The solid was purified by silica gel chromatography (30% to 100% ethyl acetate in hexanes) to give 127A (28 mg, 50%). LC-MS m/z: 708.2 (M+H)$^+$.

127B

Example 127: A solution of 127A in ethyl acetate (1 mL) and 4N hydrogen chloride in dioxane (1 mL) was stirred overnight at RT. The solvent was evaporated and the crude material was purified by reversed-phase HPLC to afford Example 127 (19 mg, 76%) as a pale yellow amorphous solid. LC-MS m/z: 508.3 (M+H)$^+$. $^1$H NMR (400 MHz, CD$_3$OD) δ 9.0 (t, 0.5H), 8.07 (d, 1H), 7.79 (bs, 1H), 7.75 (m, 1H), 7.44 (bs, 1H), 7.39-7.30 (m, 6H), 7.26 (m, 1H), 7.19 (dd, 1H), 6.80 (d, 1H), 6.64 (dd, 1H), 5.15 (s, 1H), 4.47 (d, 2H), 2.46 (s, 3H).

Example 128

N-(2-(Methylsulfonyl)benzyl)-2-(1-aminoisoquinolin-6-ylamino)-2-(3-allylphenyl)acetamide trifluoroacetic acid salt

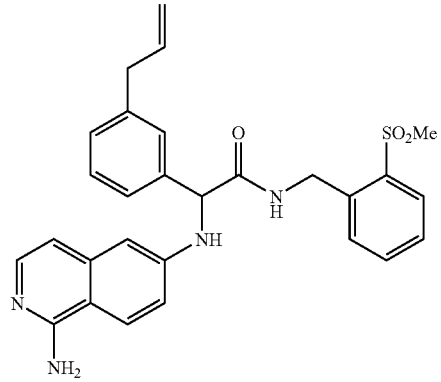

128A

N-(2-(Methylsulfonyl)benzyl)-2-(1-(di-tert-butoxycarbonylamino)isoquinolin-6-ylamino)-2-(3-allylphenyl)acetamide

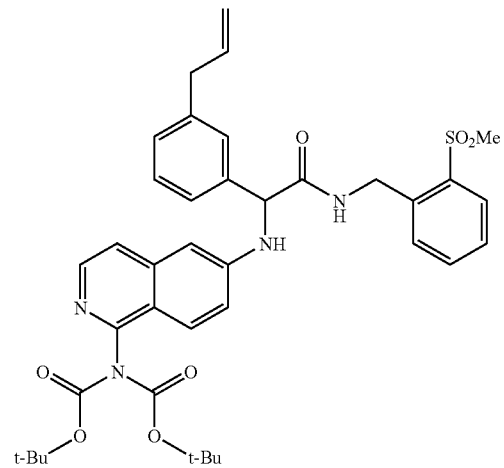

A suspension of 121E (569 mg, 0.5 mmol), and allyl tributyltin (0.155 mL, 0.22 mmol) in toluene (3 mL) in a pressure tube was deoxygenated under a flow of nitrogen. Tetrakis(triphenylphosphine)palladium(0) (29 mg, 0.025 mmol) was added. The mixture was heated at 100° C. overnight. The reaction mixture was chromatographed (silica gel, gradient 30% to 100% ethyl acetate in hexanes) to give 128A (225 mg, 64%). LC-MS m/z: 701.3 (M+H)$^+$.

128B

Example 128: A solution of 128A (36 mg, 0.05 mmol) in ethyl acetate (1.5 mL) and 4N hydrogen chloride in dioxane (1.5 mL) was stirred overnight at rt. The solvent was evaporated and the crude material was purified by reversed-phase HPLC to afford Example 128 (10 mg, 32%) as a white amorphous solid. LC-MS m/z: 501.3 (M+H)+. $^1$H NMR (400 MHz, CD$_3$OD) δ 8.81 (t, 1H), 8.07 (d, 1H), 7.90 (m, 1H), 7.49-7.44 (m, 2H), 7.38-7.33 (m, 5H), 7.19-7.17 (m, 2H), 6.80 (d, 1H), 6.65 (d, 1H), 5.93 (m, 1H), 5.17 (s, 1H), 5.04 (m, 2H), 4.88-4.68 (m, 2H), 3.31-3.34 (2d, 2H), 3.15 (s.3H).

Example 129

N-(2-(Methylsulfonyl)benzyl)-2-(1-aminoisoquinolin-6-ylamino)-2-(3-propylphenyl)acetamide trifluoroacetic acid salt

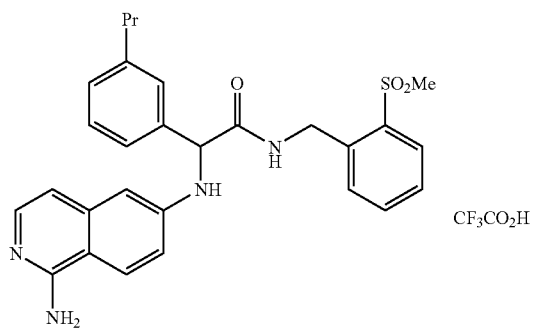

129A

N-(2-(Methylsulfonyl)benzyl)-2-(1-(di-tert-butoxycarbonylamino)isoquinolin-6-ylamino)-2-(3-propylphenyl)acetamide

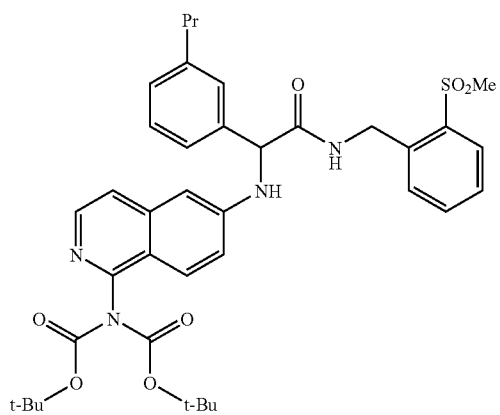

To a solution of 128A (40 mg, 0.057 mmol) in methanol (5 mL), 10% palladium on carbon (24 mg) was added. The reaction flask was evacuated, flushed with nitrogen (3×), and then stirred under hydrogen (60 psi) for 1.2 h. The reaction mixture was filtered and concentrated to afford crude 129A which was used as is in the next step. LC-MS m/z: 703.3 (M+H)+.

129B

Example 129: A solution of 129A in ethyl acetate (1.5 mL) and 4N hydrogen chloride in dioxane (1.5 mL) was stirred overnight at rt. The solvent was evaporated and the crude material was purified by reversed-phase HPLC to afford Example 129 (10 mg, 28%, 2 steps) as a white amorphous solid. LC-MS m/z: 503.3 (M+H)+. $^1$H NMR (400 MHz, CD$_3$OD) δ 8.75 (t, 1H), 8.07 (d, 1H), 7.91 (m, 1H), 7.48-7.42 (m, 2H), 7.36-7.29 (m, 5H), 7.20-7.17 (m, 2H), 6.79 (d, 1H), 6.65 (d, 1H), 5.16 (s, 1H), 4.88-4.67 (m, 2H), 3.14 (s, 3H), 2.59 (t, 2H), 1.60 (m, 2H), 0.91 (t, 3H).

Example 130

N-(2-(Methylsulfonyl)benzyl)-2-(1-aminoisoquinolin-6-ylamino)-2-(3-(p)prop-1-en-2-yl)phenyl)acetamide trifluoroacetic acid salt

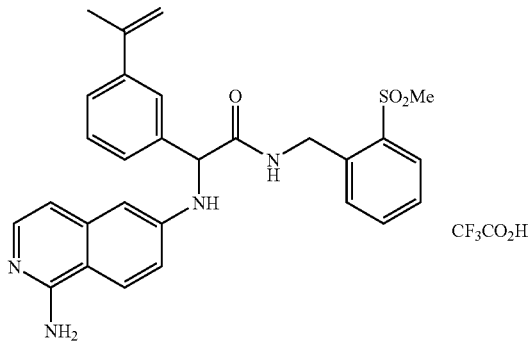

130A

N-(2-(Methylsulfonyl)benzyl)-2-(1-(di-tert-butoxycarbonylamino)isoquinolin-6-ylamino)-2-(3-(prop-1-en-2-yl)phenyl)acetamide

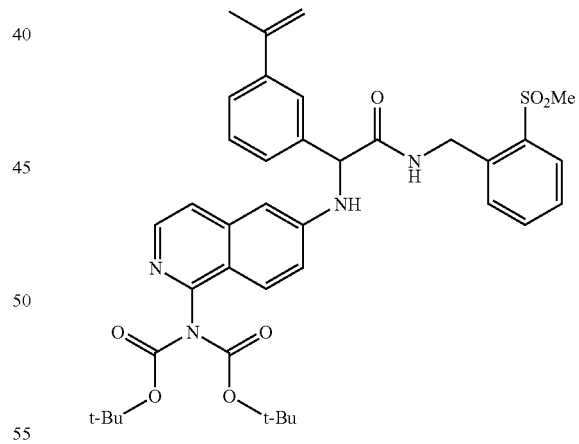

Isopropenyl magnesium bromide (5 mL 0.5M solution, 2.5 mmol) was added dropwise to a stirring solution of trimethyl borate (0.84 mL, 7.5 mmol) in THF (3 mL). The cloudy solution was stirred at rt for 2 h, cooled to 0° C. and treated with 1N aqueous hydrochloric acid (3 mL) dropwise. After 15 min the solution was extracted with 3×25 mL diethyl ether. The organic layer was washed with saturated sodium chloride solution, dried (MgSO$_4$) and concentrated in vacuo to give prop-1-en-2-ylboronic acid as a white solid (340 mg, >100%). A suspension of 121E(165 mg, 0.22 mmol), prop-1-en-2-ylboronic acid (60 mg, 0.7 mmol) and potassium carbonate (156 mg, 1.13 mmol) in a mixture of ethyleneglycol dimethylether (2 mL) and water (0.22 mL) in a pressure tube was deoxygenated under a flow of nitrogen. Dichloro[1,1'-bis(diphenylphosphino) ferrocene] palladium(II) dichloromethane adduct (18 mg, 0.025 mmol) was added. The mixture was heated at 90° C. for 1.2 h. The reaction mixture was chromatographed (silica gel, gradient from 30% to 100% ethyl acetate in hexanes) to give 130A (125 mg, 80%). LC-MS m/z: 701.4 (M+H)$^+$.

130B

Example 130: A solution of 130A (40 mg, 0.057 mmol) in ethyl acetate (1 mL) and 4N hydrogen chloride in dioxane (1 mL) was stirred overnight at rt. The solvent was evaporated and the crude material was purified by reversed-phase HPLC to afford Example 130 (5 mg, 14%) as a beige amorphous solid. LC-MS m/z: 501.4 (M+H)$^+$. $^1$H NMR (400 MHz, CD$_3$OD) δ 8.80 (t, 0.75H), 8.08 (d, 1H), 7.91 (m, 1H), 7.46 (m, 1H), 7.51-7.31 (m, 7H), 7.19 (m, 1H), 6.81 (d, 1H), 6.67 (m, 1H), 5.38 (s, 1H), 5.21-5.11 (m, 2H), 4.88-4.73 (m, 2H), 3.15 (s, 3H), 2.13 (s,3H).

Example 131

N-(2-(Methylsulfonyl)benzyl)-2-(1-aminoisoquinolin-6-ylamino)-2-(3-isopropylphenyl)acetamide trifluoroacetic acid salt

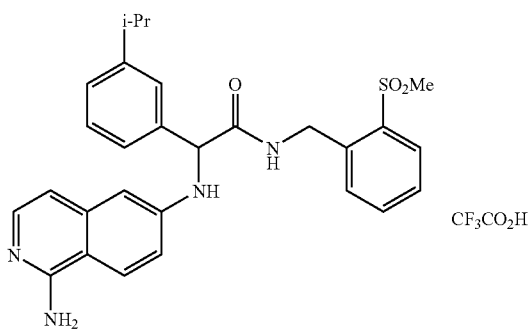

131A

N-(2-(Methylsulfonyl)benzyl)-2-(1-(di-tert-butoxycarbonylamino)isoquinolin-6-ylamino)-2-(3-isopropylphenyl)acetamide

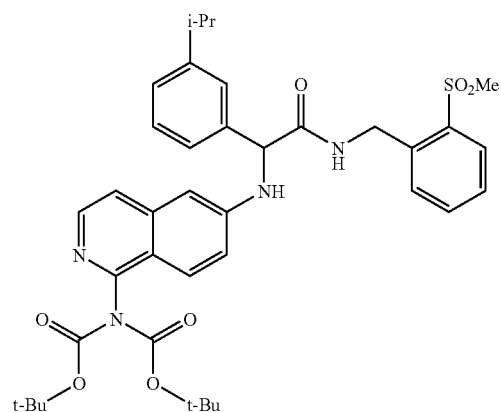

To a solution of 130A (40 mg, 0.057 mmol) in methanol (5 mL), 10% palladium on carbon (28 mg) was added. The reaction flask was evacuated, flushed with nitrogen (3×), and then stirred under hydrogen (60 psi) for 2 h. The reaction mixture was filtered, concentrated to afford crude 131A which was used as is in the next step. LC-MS m/z: 703.4 (M+H)$^+$.

131B

Example 131: A solution of 131A in ethyl acetate (1 mL) and 4N hydrogen chloride in dioxane (1 mL) was stirred overnight at rt. The solvent was evaporated and the crude material was purified by reversed-phase HPLC to afford Example 131 (24 mg, 69%, 2 steps) as a pale pink amorphous solid. LC-MS m/z: 503.4 (M+H)$^+$. $^1$H NMR (400 MHz, CD$_3$OD) 8.07 (d, 1H), 7.91 (m, 1H), 7.47-7.44 (m, 2H), 7.39 (bs, 1H), 7.34-7.29 (m, 4H), 7.26 (m, 1H), 7.19 (dd, 1H), 6.80 (d, 1H), 6.65 (d, 1H), 5.16 (s, 1H), 4.90-4.69 (m, 2H), 3.14 (s, 3H), 2.90 (m, 1H), 1.22 (d, 6H).

Example 132

N-(2-(Methylsulfonyl)benzyl)-2-(1-aminoisoquinolin-6-ylamino)-2-(3-cyclopropylphenyl)acetamide trifluoroacetic acid salt and Example 133

N-(2-(Methylsulfonyl)benzyl)-2-(1-aminoisoquinolin-6-ylamino)-2-(3-bromophenyl)acetamide trifluoroacetic acid salt

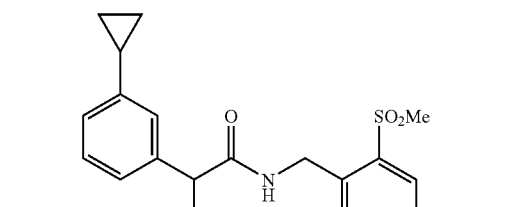

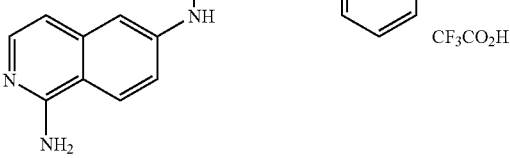

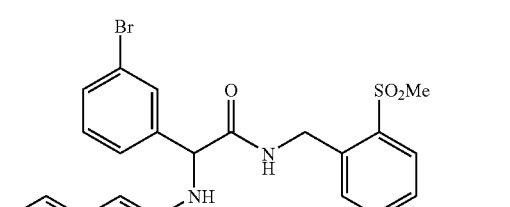

132A

N-(2-(Methylsulfonyl)benzyl)-2-(1-(di-tert-butoxy-carbonylamino)isoquinolin-6-ylamino)-2-(3-cyclopropylphenyl)acetamide

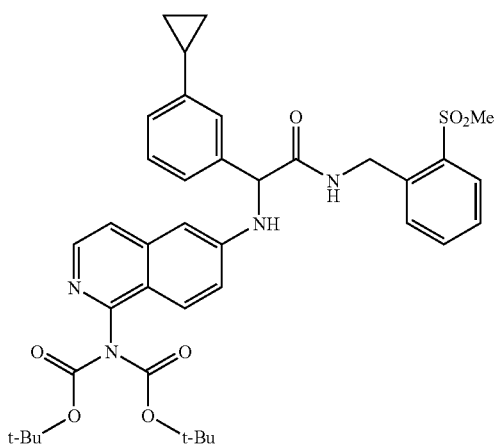

A suspension of 121E (111 mg, 0.15 mmol), cyclopropylboronic acid (40 mg, 0.71 mmol), and potassium carbonate (104 mg, 0.75 mmol) in a mixture of ethyleneglycol dimethylether (1.3 mL) and water (0.15 mL) in a pressure tube was deoxygenated under a flow of nitrogen. Dichloro[1,1'-bis(diphenylphosphino) ferrocene] palladium(II) dichloromethane adduct (12 mg, 0.016 mmol) was added. The mixture was heated at 90° C. for 3 h. The reaction mixture was chromatographed (silica gel, gradient from 10% to 100% ethyl acetate in hexanes) to give a 1:2 mixture of 132A and 121E (30 mg). LC-MS m/z: 701.3, 741.1 (M+H)$^+$.

132B

Example 132 and Example 133: To a mixture of 132A and 121E (40 mg, 0.057 mmol) in ethyl acetate (1 mL) was added 4 N hydrogen chloride in dioxane (1 mL). The mixture was stirred overnight at rt. The solvent was evaporated and the crude material was purified by reversed-phase HPLC to afford Example 132 (6 mg, 7%) and Example 133 (14 mg, 14%) as white amorphous solids. Example 132: LC-MS m/z: 501.4 (M+H)$^+$. $^1$H NMR (400 MHz, CD$_3$OD) δ 8.74 (t, 0.75H), 8.07 (d, 1H), 7.92 (dd, 1H), 7.49-7.45 (m, 2H), 7.34-7.24 (m, 5H), 7.19 (dd, 1H), 7.08 (m, 1H), 6.80 (d, 1H), 6.65 (d, 1H), 5.14 (s, 1H), 4.88-4.68 (m, 2H), 3.15 (s, 3H), 1.91 (m, 1H), 0.96 (m, 2H), 0.67 (m, 2H). Example 133: LC-MS m/z: 539.2 (M+H)$^+$. $^1$H NMR (400 MHz, CD$_3$OD) δ 8.84 (t, 0.1H), 8.08 (d, 1H), 7.92 (dd, 1H), 7.72 (m, 1H), 7.54-7.44 (m, 4H), 7.35-7.31 (m, 3H), 7.17 (dd, 1H), 6.80 (d, 1H), 6.66 (d, 1H), 5.23 (s, 1H), 4.89-4.70 (m, 2H), 3.17 (s, 3H)

Example 134

N-(3-(Cyclopropylsulfonyl)benzyl)-2-(1-aminophthalazin-6-ylamino)-2-(3-ethoxy-4-isopropoxyphenyl)acetamide trifluoroacetic acid salt

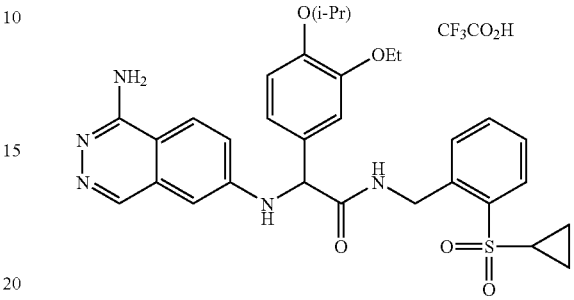

134A

4-Bromo-N-diethylbenzamide

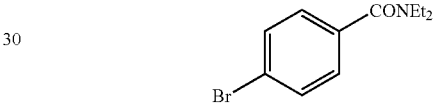

Oxalyl chloride (3.5 mL, 40.1 mmol) was added dropwise to a solution of 4-bromobenzoic acid (4.08 g, 20.3 mmol) and dimethyl formamide (0.04 mL) in anhydrous DCE (50 mL) at 0° C. The mixture was stirred for 2 h at rt, concentrated in vacuo and coevaporated with toluene twice. The residue was dissolved in anhydrous DCE (25 mL) and cooled in an ice bath. Diethyl amine (5 mL, 48.3 mmol) in DCE (25 mL) was added dropwise. The reaction was stirred overnight and then concentrated in vacuo. The residue was treated with 1N hydrochloric acid solution and extracted twice with dichloromethane. The organic layer was washed with water and saturated sodium chloride solution, dried (MgSO$_4$), and concentrated in vacuo to give 134A (4.87 g, 94%) as a pink solid. LC-MS m/z: 588.19 (M+H)$^+$.

134B

4-Bromo-N,N-diethyl-2-formylbenzamide

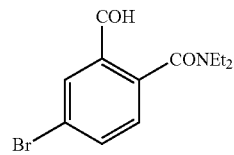

An oven dried round bottom flask was charged with anhydrous THF (20 mL) and 2,2,6,6-tetramethyl piperidine (0.68 mL, 4.0 mmol). The mixture was cooled in an ice bath and 1.46 M n-butyl lithium in hexane (2.8 mL, 4.09 mmol) was added dropwise over 5 min. After 10 min, the solution was cooled to −78° C. and a solution of 134A (512 mg, 2.0 mmol) in anhydrous THF (2 mL) was added quickly down the side of flask to precool the solution. After 1 h at −78° C. dimethyl formamide (0.5 mL, 6.38 mmol) was added dropwise and the mixture was stirred at −78° C. for 20 min and at RT for 30 min. Water was added dropwise followed by ethyl acetate. The mixture was extracted twice with ethyl acetate. The organic layer was washed with water, saturated sodium chloride solution, dried (MgSO$_4$) and concentrated in vacuo to give 134B (0.256 g, 45%) as yellow oil. LC-MS m/z: 286.16 (M+H)$^+$.

134C

5-Bromo-3-hydroxyisobenzofuran-1(3H)-one

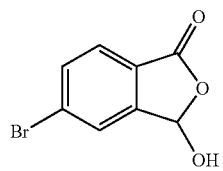

A solution of 134B (1.15 g, 4.05 mmol) in 6N hydrochloric acid (20 mL), was heated at 105° C. overnight. After cooling, the reaction mixture was extracted with ethyl acetate (4×50 mL). The combined organic layers were washed with water, saturated sodium chloride solution, dried (MgSO$_4$), and concentrated to give 134C (904 mg, 97%) as a beige solid. LC-MS m/z: 228.91 (M−H).

134D

6-Bromophthalazin-1(2H)-one

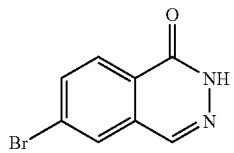

134C (954 mg, 4.17 mmol) was suspended in isopropyl alcohol (10 mL). The solution was heated at 90° C. for 1.5 h. Hydrazine monohydrate (0.4 mL, 8.25 mmol) was added in 4 increments. The resulting suspension was filtered and washed with isopropyl alcohol to give 134D (813 mg, 87%) as a beige solid. LC-MS m/z: 227.12 (M+H)$^+$.

134E

6-Bromo-1-chlorophthalazine

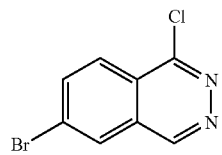

A suspension of 134D (315 mg, 1.4 mmol) and phosphorus oxychloride (2 mL) was heated at 110° C. for 1 h. The reaction mixture was cooled to rt and the solvent was evaporated in vacuo. The residue was cooled in an ice bath and cold water and 1N NaOH solution were added until the mixture was basic. The yellow solid was filtered and washed with water to afford 134E (295 mg, 87%). LC-MS m/z: 245.13 (M+H)$^+$.

134F

6-Bromophthalazin-1-amine

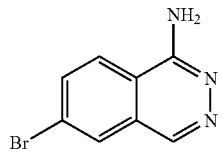

A solution of 134E (200 mg, 0.83 mmol) in saturated ammonia solution in ethylene glycol (3 mL) was heated to 130° C. overnight in a pressure tube. The reaction mixture was concentrated and the residue was chromatographed (silica gel, chloroform, 5% methanol in chloroform) to give 134F (164 mg, 89%). LC-MS m/z: 226.2 (M+H)$^+$.

134G

6-Bromo-1-(N,N-di-tert-butoxycarbonylamino)phthalazine—

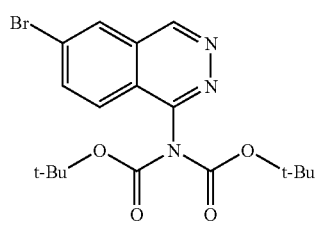

A solution of 134F (130 mg, 0.58 mmol), 4-dimethylaminopyridine (4 mg, 0.03 mmol) and di-tert-butyl dicarbonate (382 mg, 1.75 mmol) in acetonitrile (5 mL) was stirred overnight at rt. The solvent was evaporated and the crude material was purified by silica gel chromatography (0-50% ethyl acetate in hexane) to afford 134G (100 mg, 41%) as a yellow solid. $^1$H NMR (400 MHz, CD$_3$OD) δ 9.45 (s, 1H), 8.21 (d, 1H), 8.04 (dd, 1H), 7.85 (d, 1H), 1.32 (s, 18H).

134H

Methyl 2-(1-(di-tert-butoxycarbonylamino)phthalazin-6-ylamino)-2-(3-ethoxy-4-isopropoxyphenyl)acetate

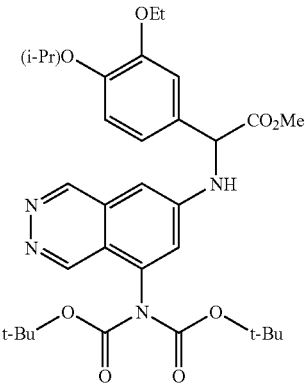

A suspension of 134G (100 mg, 0.24 mmol), Intermediate 13B (63 mg, 0.24 mmol), cesium carbonate (285 mg, 0.87 mmol) and rac-2,2'-bis(diphenylphosphino)-1,1'-binaphthyl (8 mg, 0.013 mmol) and toluene (3 mL) in pressure tube was deoxygenated under a flow of nitrogen for 5 min. Tris(dibenzylideneacetone)dipalladium(0) (5 mg, 0.005 mmol) was added. The mixture was heated at 100° C. overnight. The reaction mixture was purified by preparative LC-MS to afford to afford 134H (39 mg, 27%). LC-MS m/z: 611.3 (M+H)$^+$.

134I 2-(1-(di-tert-butoxycarbonylamino)phthalazin-6-ylamino)-2-(3-ethoxy-4-isopropoxyphenyl)acetic acid

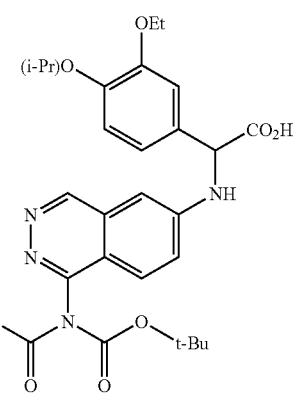

A mixture of 134H (39 mg, 0.063 mmol) and lithium hydroxide monohydrate (5.4 mg, 0.13 mmol) in THF (1 mL) and water (1 mL) was stirred at rt for 2 h. Additional lithium hydroxide monohydrate (2.7 mg, 0.06 mmol) was added and the mixture was stirred for 1 h. The mixture was concentrated in vacuo, and the residue was partitioned between ethyl acetate and 1N hydrochloric acid solution. The organic layer was dried (MgSO$_4$), and concentrated to give 134I (40 mg, 100%) as a yellow glass. LC-MS m/z: 597.3 (M+H)$^+$.

134J

N-(3-(Cyclopropylsulfonyl)benzyl)-2-(1-(di-tert-butoxycarbonylamino) phthalazin-6-ylamino)-2-(3-ethoxy-4-isopropoxyphenyl)acetamide

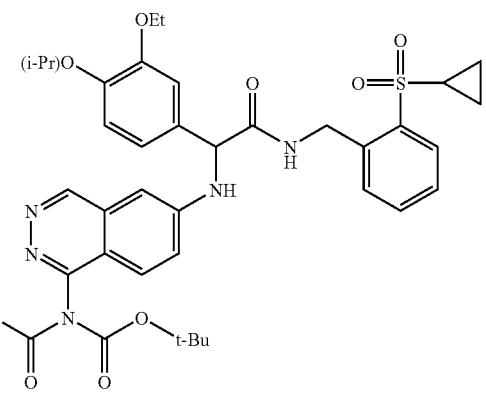

To a solution of 134I (30 mg, 0.05 mmol) in dimethylformamide (0.5 mL) was added diisopropylethylamine (0.025 mL, 0.15 mmol), Intermediate 7 (24 mg, 0.069 mmol), and benzotriazol-1-yloxy-tris(dimethylamino)phosphonium hexafluorophosphate (33 mg, 0.075 mmol). The reaction mixture was stirred at rt for 0.5 h. The solvent was evaporated and the residue was purified by reversed-phase HPLC to afford 134J. LC-MS m/z: 790.3 (M+H)$^+$.

134K

Example 134: A solution of 134J in ethyl acetate (1 mL) and 4N hydrogen chloride in dioxane (1 mL) was stirred overnight at rt. The solvent was evaporated and the crude material was purified by reversed-phase HPLC to afford Example 134 (2.5 mg, 7%, 2steps) as a white amorphous solid. LC-MS m/z: 590.3 (M+H)$^+$. $^1$H NMR (400 MHz, CD$_3$OD δ): 8.59 (t, 1H), 8.38 (s, 1H), 8.16 (d, 1H), 7.81 (d, 1H), 7.49 (m, 2H), 7.39 (m, 2H), 7.08 (s, 1H), 7.05 (d, 1H), 6.97 (d, 1H), 6.85 (s, 1H), 5.15 (s, 1H), 4.88-4.74 (m, 2H), 4.54 (m, 1H), 3.99 (m, 2H), 2.80 (m, 1H), 1.37 (t, 3H), 1.30 (d, 6H), 1.21 (m, 1H), 1.13 (m, 1H), 1.00 (m, 2H).

Example 135

N-(2-(Cyclopropylsulfonyl)benzyl)-2-(3-aminoisoquinolin-6-ylamino)-2-(3-ethoxy-4-isopropoxyphenyl)acetamide trifluoroacetic acid salt

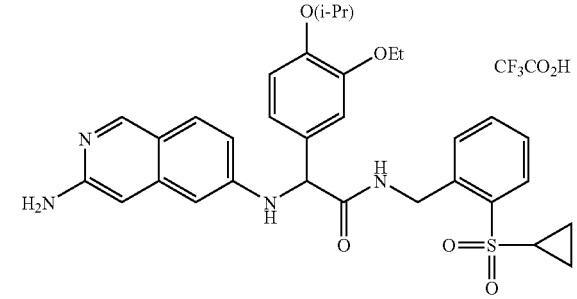

135A 2-(Bromomethyl)-4-nitrobenzonitrile

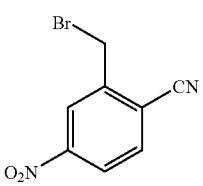

A suspension of 2-methyl-4-nitrobenzonitrile (0.872 g, 5.28 mmol) and N-bromosuccinimide (1.16 g, 6.52 mmol, recrystallized from water) in carbon tetrachloride (25 mL) was irradiated with a sun lamp for 16 h. The reaction mixture was concentrated under reduced pressure and the residue was purified by chromatography on silica gel (gradient from 0 to 15% ethyl acetate in hexanes) to afford 135A (0.610 g, 48%). $^1$H NMR (400 MHz, CDCl$_3$, δ): 8.44 (d, J=2.2 Hz, 1H), 8.29 (dxd, J=8.3 Hz, 1H), 7.90 (d, J=8.3 Hz, 1H), 4.70 (s, 2H).

135B 2-(Cyanomethyl)-4-nitrobenzonitrile

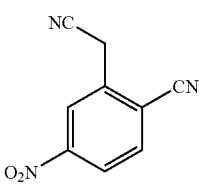

To a solution of sodium cyanide (99.5 mg, 2.03 mmol) in water (0.5 mL) at 0° C. was added carefully sulfuric acid (0.95 mL, diluted 10% w/w with water). Caution: this reaction generates hydrogen cyanide and must be performed in a fume hood with good ventilation. A solution of 135A (48 mg, 0.2 mmol) in acetonitrile (2 mL) was added all at once. The reaction was heated to 80° C. for 4 h, adding additional crystals of sodium cyanide several times to raise the pH to ~9. The reaction mixture was extracted three times with methylene chloride and the combined organics were washed with water and brine, dried (MgSO$_4$), and concentrated under reduced pressure. The residue was purified by silica gel chromatography (gradient of 0 to 30% ethyl acetate in hexanes) to give 135B (20 mg, 53%). $^1$H NMR (400 MHz, CDCl$_3$, δ): 8.55 (d, J=1.8 Hz, 1H), 8.37 (dxd, J=8.4, 2.2 Hz, 1H), 7.96 (d, J=8.4 Hz, 1H), 4.14 (s, 2H).

135C

N-(1-Bromo-6-nitroisoquinolin-3-yl)acetamide

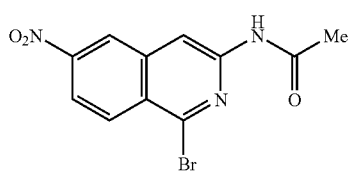

Hydrogen bromide in acetic acid (1.5 mL, 33% solution) was added to 135B (54 mg, 0.29 mmol). After six hours, the reaction mixture was concentrated under reduced pressure. The residual orange solid was triturated with a sodium acetate solution (144 mg in 11 mL water), filtered, washed with water, and coevaporated with methanol and dichloromethane to give 135C (71 mg, 89%) as a yellow solid. LC-MS m/z: 310.2 (M+H)$^+$.

135D

N-(6-Aminoisoquinolin-3-yl)acetamide

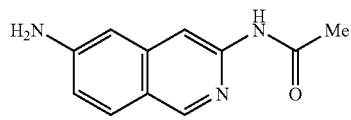

A suspension of 135C (70 mg, 0.23 mmol) and 10% palladium/carbon (20 mg) in ethanol (6 mL) was hydrogenated (50 psi) for 3 h. Methanol and hydrogen chloride (0.5 mL, 4 N solution in dioxanes) were added to dissolve the product. The solution was filtered and concentrated under reduced pressure to give 135D (57 mg, 100%) as a yellow solid. LC-MS m/z: 202.3 (M+H)$^+$.

135E

Methyl 2-(3-acetamidoisoquinolin-6-ylamino)-2-(3-ethoxy-4-isopropoxyphenyl)acetate

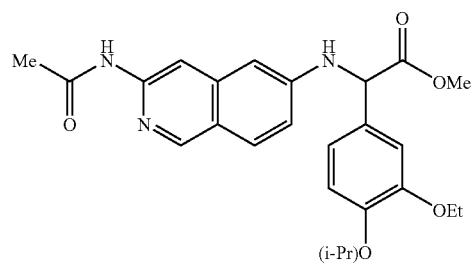

A solution of 135D (53 mg, 0.23 mmol) and methyl 2-chloro-2-(3-ethoxy-4-isopropoxyphenyl)acetate (66 mg, 0.23 mmol, see WO 2004/072101 for synthesis), and N,N-diisopropylethylamine (0.1 mL) in dimethylformamide (2 mL) was heated at 90° C. for 5 h. The reaction mixture was concentrated and the residue was purified by chromatography on silica gel (gradient from 0 to 100% ethyl acetate in hexanes) to give 135E (22 mg, 21%) as a red glass. LC-MS m/z: 452.3 (M+H)$^+$.

135F 2-(3-acetamidoisoquinolin-6-ylamino)-2-(3-ethoxy-4-isopropoxyphenyl)acetic acid

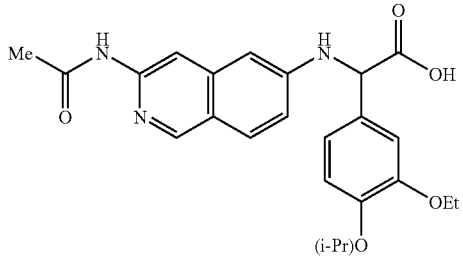

Lithium hydroxide solution (0.1 mL of 500 mg LiOH in 10 mL water) was added to a solution of 135E (22 mg, 0.049 mmol) in tetrahydrofuran (1 mL) and water (1 mL). After 1.5 h, an additional aliquot of lithium hydroxide solution (0.1 mL) was added. After an additional 1 h, the reaction was concentrated under reduced pressure. The residue was partitioned between ethyl acetate and hydrochloric acid (1 N). The organic layer was dried (MgSO$_4$) and concentrated under reduced pressure to give 135F (21 mg, 100%) as a yellow film. LC-MS m/z: 438.3 (M+H)$^+$.

135G

Example 135: A solution of 1-35F (21 mg, 0.048 mmol), Intermediate 7 (24 mg, 0.098 mmol), and DIEA (0.025 mL, 0.14 mmol) in DMF (0.5 mL) was treated with BOP (32 mg, 0.072 mmol). The reaction mixture was stirred overnight at rt and then concentrated under reduced pressure. The residue was purified by reverse phase HPLC to afford 4 mg of acetylated product. This material was dissolved in methanol (several mL) and treated with sodium hydroxide (0.020 g) and lithium hydroxide solution (0.1 mL of 0.5 g lithium hydroxide in 10 mL water). The reaction mixture was refluxed overnight and then concentrated under reduced pressure. The residue was purified by reverse phase HPLC to afford Example 135 (1.4 mg, 5%) as a yellow amorphous solid. LC-MS m/z: 589.3 (M+H)$^+$.

Example 136

N-(2-(Cyclopropylsulfonyl)benzyl)-2-(1-amino-8-fluoroisoquinolin-6-ylamino)-2-(3-ethoxy-4-isopropoxyphenyl)acetamide trifluoroacetic acid salt

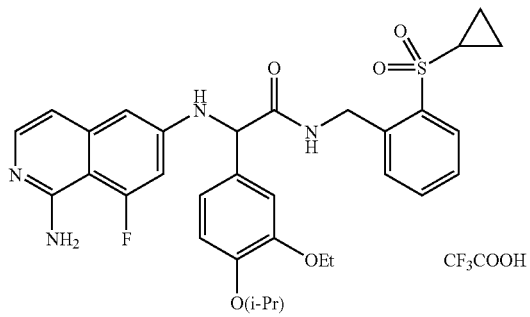

136A (E)-methyl 3-(3-amino-5-fluorophenyl)acrylate

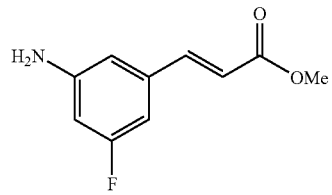

A mixture of 1-fluoro-3-iodo-5-nitrobenzene (1.145 g, 4.29 mmol), sodium acetate (0.430 g, 5.24 mmol), palladium (II) acetate (1.7 mg, 0.0076 mmol), methyl acrylate (0.425 mL, 4.71 mmol), and 1-methyl-2-pyrrolidinone (11 mL) under argon was degassed with three freeze/pump/thaw cycles. The reaction mixture was heated to 130° C. for 35 min and then at 100° C. for 14 h. The reaction mixture was diluted with water and saturated sodium bicarbonate solution and extracted three times with diethyl ether. The combined organic extracts were washed with saturated sodium bicarbonate solution, hydrochloric acid (1N), and brine, dried (MgSO$_4$), and concentrated under reduced pressure. The residue was suspended in a mixture of ethanol (12 mL), water (2.5 mL), and acetic acid (1.25 mmol) and heated to reflux. Iron powder (0.519 g, 9.28 mmol) was added portionwise over 30 min, and reflux was continued for an additional 30 min. The reaction mixture was concentrated under reduced pressure. The residue was partitioned between ethyl acetate and sodium bicarbonate solution and filtered through a glass fibre filter to remove a fine grey precipitate. The aqueous phase was extracted with ethyl acetate (3×) and the organic phase was dried (MgSO$_4$) and concentrated under reduced pressure to give 136A (0.328 g, 74%) as a pale yellow solid. LC-MS m/z: 196.2 (M+H)$^+$.

136B (E)-Methyl 3-(3-(dibenzylamino)-5-fluorophenyl)acrylate

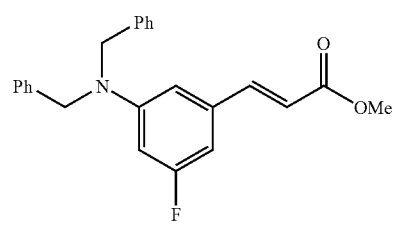

Benzyl bromide (0.440 mL, 3.70 mmol) was added to a solution of 136A (0.328 g, 1.68 mmol) and DIEA (0.880 mL) in acetonitrile (5 mL). The reaction mixture was heated at 60° C. for 14 h and then concentrated under reduced pressure. The residual solid was triturated twice with diethyl ether, dissolved in dichloromethane, and extracted with hydrochloric acid (1N) and saturated sodium bicarbonate solution. The organic layer was dried (MgSO$_4$) and concentrated under reduced pressure. The residue was purified by silica gel chromatography (gradient from 0 to 15% ethyl acetate in hexanes) to give 136B (0.468 g, 74%) as a white solid. LC-MS m/z: 376.5 (M+H)$^+$.

136C

(E)-3-(3-(Dibenzylamino)-5-fluorophenyl)acrylic acid

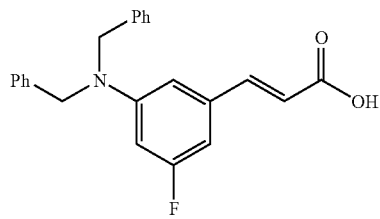

Sodium hydroxide (2 mL, 2 mmol, 1.00 N solution) was added to a solution of 136B (0.467 g, 1.24 mmol) in tetrahydrofuran (2 mL) and methanol (1 mL). The reaction was heated at 80° C. for 1 h. Hydrochloric acid (1 N) was added and the reaction mixture was extracted with ethyl acetate (2×). The combined organic layers were dried (MgSO$_4$) and concentrated under reduced pressure to give 136C (0.411 g, 91%) as a pale yellow solid. LC-MS m/z: 362.4 (M+H)$^+$.

136D

6-(Dibenzylamino)-8-fluoroisoquinolin-1(2H)-one

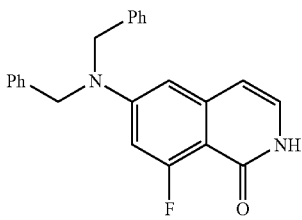

A solution of ethyl chloroformate (0.421 mL, 4.4 mmol) in acetone (10 mL) was added dropwise to a suspension of 136C (1.46 g, 4.0 mmol) in a mixture of acetone (50 mL) and triethylamine (1.25 mL, 9.0 mmol) at 0° C. The reaction mixture was stirred for 45 min and then a solution of sodium azide (0.478 g 7.4 mmol) in water (14 mL) was added dropwise over 1 h. After an additional 1 h, the reaction was warmed to rt, poured into water, and extracted with dichloromethane (3×). The combined organic layers were washed with water and brine, dried (MgSO$_4$), and concentrated under reduced pressure to give a yellow solid (1.5 g). (Caution: this acyl azide intermediate is potentially explosive and should be handled in small quantities behind a safety shield.) A portion of this solid (0.488 g) was dissolved in a mixture of dichloromethane (1 mL) and phenyl ether (3 mL) and added slowly dropwise to a refluxing mixture of phenyl ether (3 mL) and tributylamine (0.8 mL). Reflux was continued for an additional 1 h, after which the majority of the solvent was removed in vacuo. The residue was cooled to rt and a mixture of hexanes and diethyl ether was added. The solid was collected by filtration and washed with hexanes to give 136D (0.245 g, 46%) as an off-white solid. LC-MS m/z: 359.4 (M+H)$^+$.

136E

$N^6,N^6$-Dibenzyl-8-fluoroisoquinoline-1,6-diamine

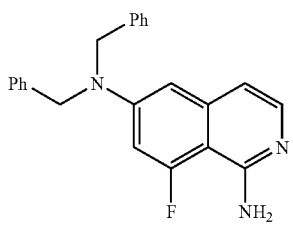

A mixture of 136D (0.284 g, 0.792 mmol) and phosphorous oxychloride (3 mL) was heated at 100° C. for 1 h. The reaction mixture was concentrated under reduced pressure, and ice was added, followed by sodium hydroxide (1N solution) until the pH was basic. The resulting solid was collected by filtration, washed with water, and dried in vacuo to give a chloride intermediate (0.33 g) as a yellow solid. A portion of this solid (0.100 g) was treated with a saturated solution of ammonia in ethylene glycol (4 mL) at 130° C. in a glass pressure tube overnight. The reaction mixture was concentrated under reduced pressure and the residue was purified by silica gel chromatography (5% methanol/dichloromethane) to give 136E (55 mg, 64%) as a brown solid. LC-MS m/z: 358.4 (M+H)$^+$.

136F

$N^6,N^6$-Dibenzyl-$N^1,N^1$-di-tert-butoxycarbonyl-8-fluoroisoquinoline-1,6-diamine

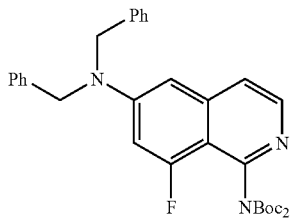

Di-tert-butyl dicarbonate (58 mg, 0.266 mmol) was added to a suspension of 136E (21 mg, 0.059 mmol) and DMAP (5 mg, 0.041 mmol) in acetonitrile (2 mL). The reaction mixture was stirred overnight at rt and then concentrated under reduced pressure. The residue was purified by silica gel chromatography (gradient from 0 to 30% ethyl acetate in hexanes) to afford 136F (23 mg, 70%) as a clear glass. LC-MS m/z: 558.3 (M+H)$^+$.

136G

N¹,N¹-Di-tert-butoxycarbonyl-8-fluoroisoquinoline-1,6-diamine

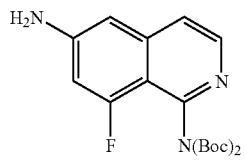

A mixture of 136F (77 mg, 0.14 mmol), 20% palladium(II) hydroxide on carbon (94 mg) and ethanol (20 mL) was hydrogenated (55 psi) for 4 h. The reaction mixture was filtered and concentrated under reduced pressure to give 136G (47 mg, 90%) as a yellow solid. LC-MS m/z: 378.3 (M+H)⁺.

136H (1-Di-tert-butoxycarbonylamino-8-fluoro-isoquinolin-6-ylamino)-(3-ethoxy-4-isopropoxy-phenyl)-acetic acid methyl ester

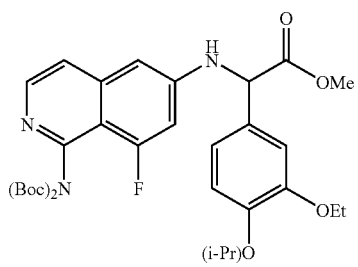

A solution of 136G (66 mg, 0.18 mmol) and methyl 2-chloro-2-(3-ethoxy-4-isopropoxyphenyl)acetate (52 mg, 0.18 mmol, see WO 2004/072101 for synthesis), and N,N-diisopropylethylamine (0.059 mL, 0.34 mmol) in dimethylformamide (2 mL) was heated at 90° C. overnight. The reaction mixture was concentrated and the residue was purified by chromatography on silica gel to give 136H (40 mg, 35%). LC-MS m/z: 628.3 (M+H)⁺.

136I (1-Di-tert-butoxycarbonylamino-8-fluoro-isoquinolin-6-ylamino)-(3-ethoxy-4-isopropoxy-phenyl)-acetic acid

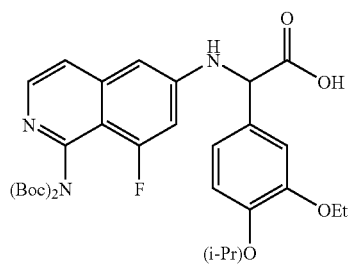

Lithium hydroxide solution (0.2 mL of 500 mg LiOH in 9.5 mL water) was added to a solution of 136H (40 mg, 0.064 mmol) in tetrahydrofuran (1 mL) and water (1 mL). After 1 h, the reaction was concentrated under reduced pressure. The residue was partitioned between dichloromethane and water and acidified with hydrochloric acid (1 N). The organic layer was dried (MgSO₄) and concentrated under reduced pressure to give 136I (36 mg, 92%) as a yellow glass. LC-MS m/z: 614.3 (M+H)⁺.

136J

Example 136: A solution of 136I (24 mg, 0.039 mmol), Intermediate 7 (19 mg, 0.077 mmol), and DIEA (0.020 mL, 0.11 mmol) in DMF (0.5 mL) was treated with BOP (16 mg, 0.059 mmol). The reaction mixture was stirred overnight at rt and then concentrated under reduced pressure. The residue was triturated with water and then purified by silica gel chromatography (gradient from 0 to 100% ethyl acetate in hexanes) to afford 5 mg of di-Boc protected product. This material was dissolved in ethyl acetate (1 mL) and treated with hydrogen chloride (1 mL, 4 N solution in dioxane). The reaction mixture was stirred overnight at rt and then concentrated under reduced pressure. The residue was purified by reverse phase HPLC to afford Example 136 (3.0 mg, 11%) as a white solid. LC-MS m/z: 607.3 (M+H)⁺.

Example 137

N-(5-Acetylamino-2-ethanesulfonyl-benzyl)-2-(1-amino-8-fluoro-isoquinolin-6-ylamino)-2-(3-ethoxy-phenyl)-acetamide trifluoroacetic acid salt

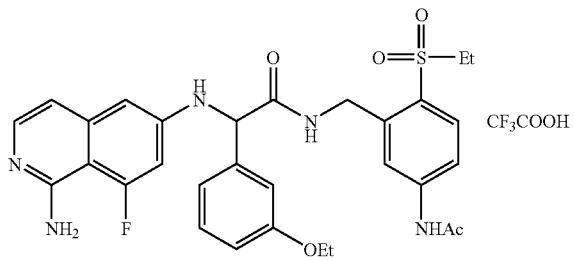

137A 2-(1-Di-tert-butoxycarbonylamino-8-fluoroisoquinolin-6-ylamino)-2-(3-ethoxyphenyl)acetic acid

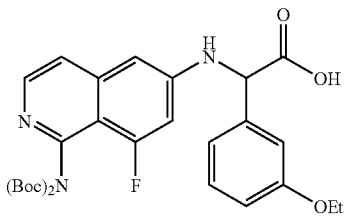

A mixture of 136G (40 mg, 0.11 mmol), 3-ethoxyphenylboronic acid (25 mg, 0.15 mmol) and glyoxylic acid monohydrate (15 mg, 0.16 mmol) in 1,2-dichloroethane (1 mL) was heated at 100° C. for 10 min in a microwave reactor. The crude product was purified by reverse phase HPLC to give 137A (22 mg, 36%) as a solid. LC-MS m/z: 556.2 (M+H)⁺.

137B

Example 137: Using the general coupling-deprotection procedure, 137A (22 mg, 0.033 mmol) was coupled with Intermediate 9 (22 mg, 0.085 mmol) and subsequently deprotected to give Example 137 (12 mg, 52%) as a yellow solid. LC-MS m/z: 594.2 (M+H)$^+$.

Example 138

N-(5-Acetylamino-2-ethanesulfonyl-benzyl)-2-(1-amino-8-fluoro-isoquinolin-6-ylamino)-2-(3-ethoxy-phenyl)-N-methyl-acetamide trifluoroacetic acid salt

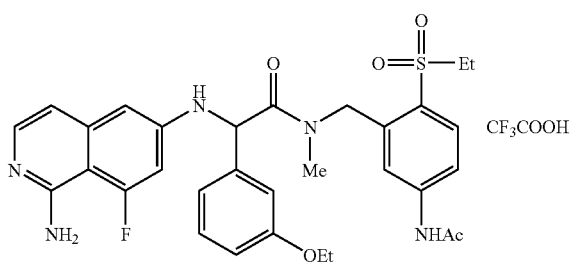

Using the general coupling-deprotection procedure, 137A (60 mg, 0.11 mmol) was coupled with Intermediate 10 (39 mg, 0.14 mmol) and subsequently deprotected to give Example 138 (21 mg, 30%) as a yellow solid. LC-MS m/z: 608.0 (M+H)$^+$.

Example 139

2-(1-Amino-8-fluoro-isoquinolin-6-ylamino)-N-(2-cyclobutanesulfonyl-benzyl)-2-(3-methoxy-phenyl)-N-methyl-acetamide trifluoroacetic acid salt

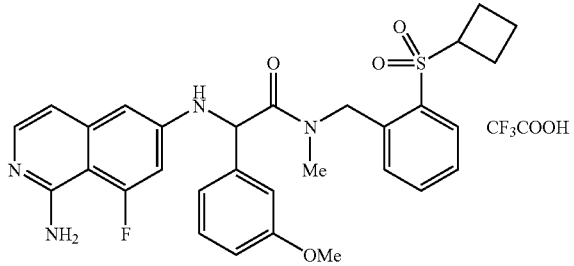

139A 2-(1-Di-tert-butoxycarbonylamino-8-fluoroisoquino-lin-6-ylamino)-2-(3-methoxyphenyl)acetic acid

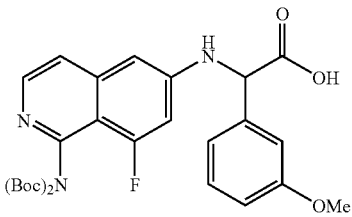

A mixture of 136G (106 mg, 0.28 mmol), 3-methoxyphenylboronic acid (52 mg, 0.34 mmol) and glyoxylic acid monohydrate (31 mg, 0.34 mmol) in 1,2-dichloroethane (2 mL) was heated at 100° C. for 10 min in a microwave reactor. The crude product was purified by silica gel chromatography (gradient from 0 to 20% methanol in dichloromethane) to give 139A (40 mg, 26%) as a solid. LC-MS m/z: 542.0 (M+H)$^+$.

139B

Example 139: Using the general coupling-deprotection procedure, 139A (25 mg, 0.046 mmol) was coupled with Intermediate 12 (17 mg, 0.062 mmol) and subsequently deprotected to give Example 139 (15 mg, 48%) as a yellow solid. LC-MS m/z: 563.1 (M+H)$^+$.

Example 140

2-(1-Amino-8-fluoro-isoquinolin-6-ylamino)-N-(2-cyclobutanesulfonyl-benzyl)-2-(3-methoxy-phenyl)-acetamide trifluoroacetic acid salt

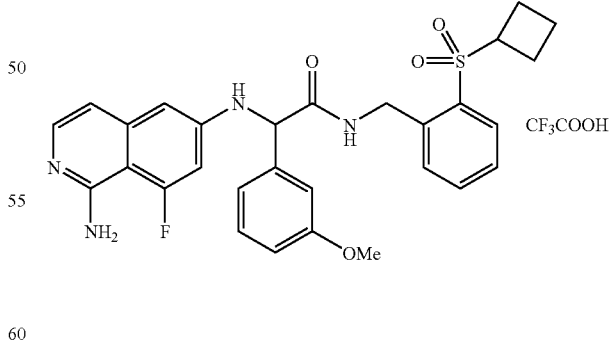

Using the general coupling-deprotection procedure, 139A (25 mg, 0.046 mmol) was coupled with Intermediate 11 (17 mg, 0.065 mmol) and subsequently deprotected to give Example 140 (19 mg, 62%) as a yellow solid. LC-MS m/z: 549.1 (M+H)$^+$.

Example 141

N-(5-Acetylamino-2-ethanesulfonyl-benzyl)-2-(1-amino-8-fluoro-isoquinolin-6-ylamino)-2-(3-methoxy-phenyl)-N-methyl-acetamide trifluoroacetic acid salt

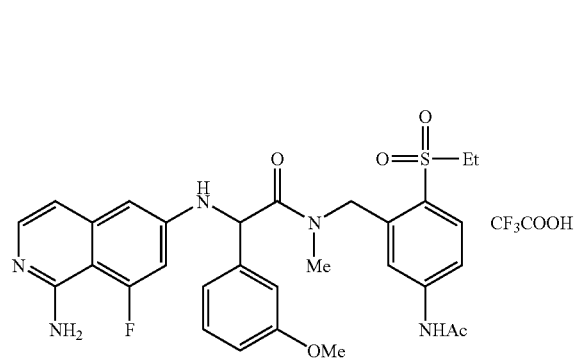

Using the general coupling-deprotection procedure, 139A (26 mg, 0.048 mmol) was coupled with Intermediate 10 (17 mg, 0.063 mmol) and subsequently deprotected to give Example 141 (8 mg, 28%) as a yellow solid. LC-MS m/z: 594.0 (M+H)$^+$.

Example 142

2-(1-Amino-phthalazin-6-ylamino)-N-(2-cyclobutanesulfonyl-benzyl)-2-(3-ethoxy-4-isopropoxy-phenyl)-N-methyl-acetamide trifluoroacetic acid salt

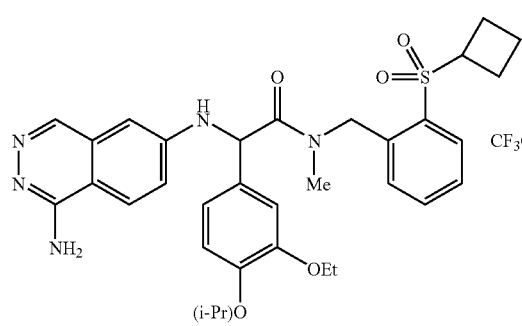

Using the general coupling-deprotection procedure, 134I (45 mg, 0.075 mmol) was coupled with Intermediate 12 (27 mg, 0.098 mmol) and subsequently deprotected to give Example 142 (12 mg, 22%) as a yellow solid. LC-MS m/z: 618.1 (M+H)$^+$.

Example 143

2-(1-Amino-phthalazin-6-ylamino)-N-(2-cyclobutanesulfonyl-benzyl)-2-(3-ethoxy-4-isopropoxy-phenyl)-acetamide trifluoroacetic acid salt

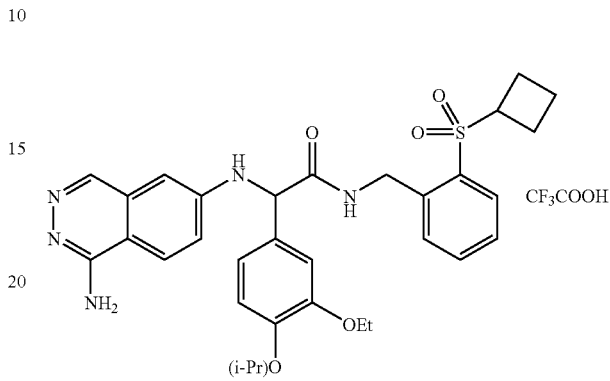

Using the general coupling-deprotection procedure, 134I (45 mg, 0.075 mmol) was coupled with Intermediate 11 (26 mg, 0.10 mmol) and subsequently deprotected to give Example 143 (12 mg, 22%) as a yellow solid. LC-MS m/z: 604.2 (M+H)$^+$.

Example 144

2-(1-Amino-phthalazin-6-ylamino)-N-(2-cyclopropanesulfonyl-benzyl)-2-(3-ethoxy-4-isopropoxy-phenyl)-N-methyl-acetamide trifluoroacetic acid salt

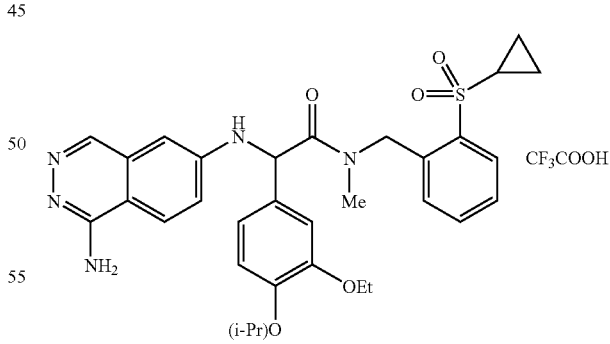

Using the general coupling-deprotection procedure, 134 (54 mg, 0.091 mmol) was coupled with Intermediate 8 (31 mg, 0.12 mmol) and subsequently deprotected to give Example 144 (25 mg, 38%) as a solid. LC-MS m/z: 604.1 (M+H)$^+$.

Example 145

2-(1-Amino-phthalazin-6-ylamino)-N-(2-cyclopropanesulfonyl-benzyl)-2-(4-fluoro-3-methoxy-phenyl)-N-methyl-acetamide trifluoroacetic acid salt

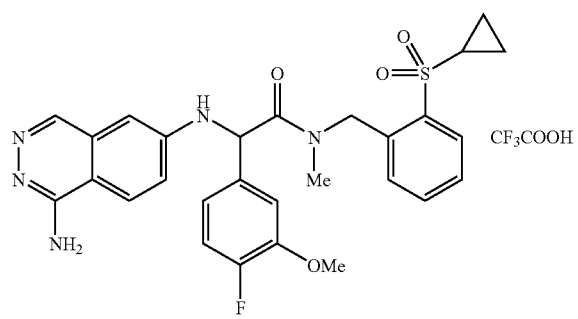

145A

Methyl 2-amino-2-(4-fluoro-3-methoxyphenyl)acetate

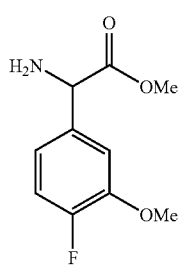

Trimethylsilyl cyanide (2 mL, 15 mmol) was added dropwise to a solution of 4-fluoro-3-methoxybenzaldehyde (1.54 g, 10 mmol) and ammonia (7 N) in methanol (40 mL) at 0° C. The reaction mixture was stirred at rt overnight and then concentrated under reduced pressure. The residue was dissolved in methanol (2 mL), cooled to 0° C., and hydrogen chloride saturated methanol (15 mL) was added. The reaction mixture was heated at reflux overnight, cooled, and then diluted with water and ethyl acetate. The aqueous layer was adjusted to pH 8 with NaOH, and extracted repeatedly with ethyl acetate. The organic extracts were combined, dried (MgSO$_4$), and concentrated under reduced pressure. The residue was purified by silica gel chromatography (10% methanol, 90% chloroform) to afford 145A (0.179 g, 8.4%) as a solid. LC-MS m/z: 197.1 (M−NH$_2$)$^+$.

145B

Methyl 2-(1-(di-tert-butoxycarbonyl)phthalazin-6-ylamino)-2-(4-fluoro-3-methoxyphenyl)acetate

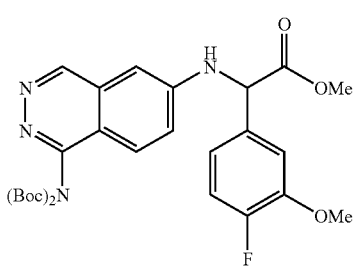

Using the procedure for preparation of compound 134H, 134G (74 mg, 0.17 mmol) was coupled with 145A (60 mg, 0.28 mmol) to give 145B (46 mg, 47%) as a yellow glass. LC-MS m/z: 557.2 (M+H)$^+$.

145C 2-(1-(Di-tert-butoxycarbonyl)phthalazin-6-ylamino)-2-(4-fluoro-3-methoxyphenyl)acetic acid

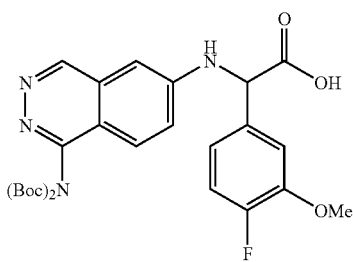

Using the procedure for preparation of compound 134I, 145B (46 mg, 0.083 mmol) was hydrolyzed to give 145C (30 mg, 67%) as a solid. LC-MS m/z: 543.2 (M+H)$^+$.

145D

Example 145: Using the general coupling-deprotection procedure, 145C (30 mg, 0.055 mmol) was coupled with Intermediate 8 (19 mg, 0.073 mmol) and subsequently deprotected to give Example 145 (8 mg, 22%) as a white solid. LC-MS m/z: 550.2 (M+H)$^+$.

Example 146

N-(5-Acetylamino-2-ethanesulfonyl-benzyl)-2-(1-amino-isoquinolin-6-ylamino)-2-(3-ethoxy-phenyl)-acetamide trifluoroacetic acid salt

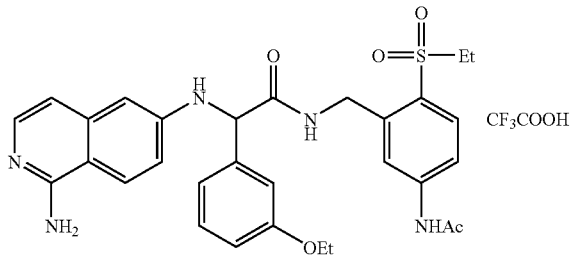

Using the general coupling-deprotection procedure, Intermediate 16 (54 mg, 0.10 mmol) was coupled with Intermediate 9 (33 mg, 0.13 mmol) and subsequently deprotected to give Example 146 (37 mg, 54%) as a yellow solid. LC-MS m/z: 576.2 (M+H)$^+$.

Example 147

N-(5-Acetylamino-2-ethanesulfonyl-benzyl)-2-(1-amino-isoquinolin-6-ylamino)-2-(3-methoxy-phenyl)-acetamide trifluoroacetic acid salt

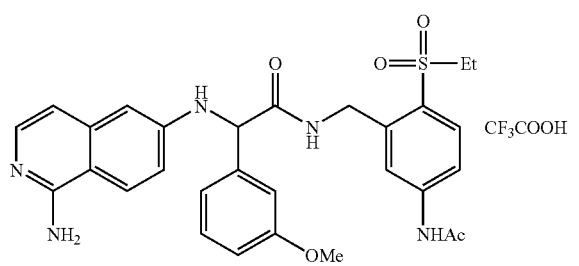

Using the general coupling-deprotection procedure, 124A (27 mg, 0.051 mmol) was coupled with Intermediate 9 (17 mg, 0.066 mmol) and subsequently deprotected to give Example 147 (23 mg, 66%) as a beige solid. LC-MS m/z: 562.2 (M+H)$^+$.

Example 148

N-(5-Acetylamino-2-ethanesulfonyl-benzyl)-2-(1-amino-isoquinolin-6-ylamino)-2-(3-ethyl-phenyl)-acetamide trifluoroacetic acid salt

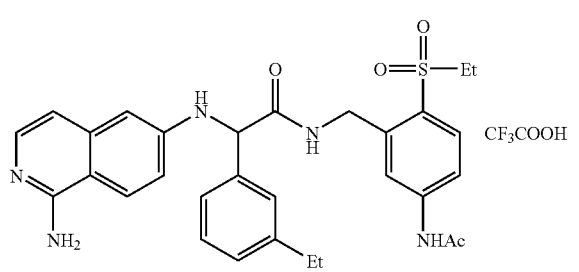

148A 2-(1-(Di-tert-butoxycarbonyl)isoquinolin-6-ylamino)-2-(3-vinylphenyl)acetic acid

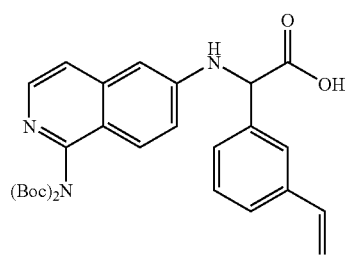

Using the procedure for preparation of Intermediate 16, Intermediate 1 (108 mg, 0.300 mmol) was reacted with 3-vinylboronic acid (59 mg, 0.40 mmol) and glyoxylic acid monohydrate (38 mg, 0.41 mmol) to give Example 148A (60 mg, 38%) as a solid. LC-MS m/z: 520.3 (M+H)$^+$.

148B

Example 148: Using the general coupling-deprotection procedure, 148A (26 mg, 0.050 mmol) was coupled with Intermediate 9 (17 mg, 0.066 mmol). Prior to deprotection, the material was dissolved in methanol (5 mL) and hydrogenated (60 psi) over 10% palladium/carbon (19 mg) for 2.5 h. The solution was filtered and concentrated under reduced pressure. This material was deprotected according to the general procedure to give Example 148 (23 mg, 68%) as a beige solid. LC-MS m/z: 560.2 (M+H)$^+$.

Example 149

N-(5-Acetylamino-2-ethanesulfonyl-benzyl)-2-(1-amino-isoquinolin-6-ylamino)-2-(3-methyl-phenyl)-acetamide trifluoroacetic acid salt

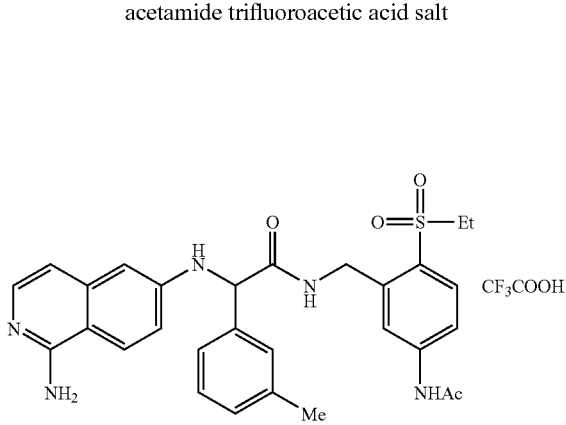

149A 2-(1-(Di-tert-butoxycarbonyl)isoquinolin-6-ylamino)-2-(3-methylphenyl)acetic acid

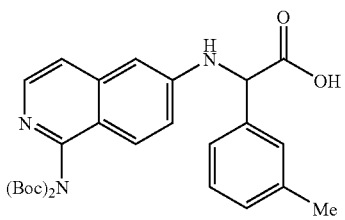

Using the procedure for preparation of Intermediate 16, Intermediate 1 (108 mg, 0.300 mmol) was reacted with 3-methylboronic acid (49 mg, 0.36 mmol) and glyoxylic acid monohydrate (41 mg, 0.44 mmol) to give Example 149A (65 mg, 43%) as a solid. LC-MS m/z: 508.3 (M+H)$^+$.

149B

Example 149: Using the general coupling-deprotection procedure, 149A (26 mg, 0.051 mmol) was coupled with Intermediate 9 (17 mg, 0.066 mmol) and subsequently deprotected to give Example 149 as a beige solid. LC-MS m/z: 546.2 (M+H)$^+$.

Example 150

N-(2-(cyclopropylsulfonyl)benzyl)-2-(1-aminoisoquinolin-6-ylamino)-2-(3-methoxyphenyl)acetamide trifluoroacetic acid salt

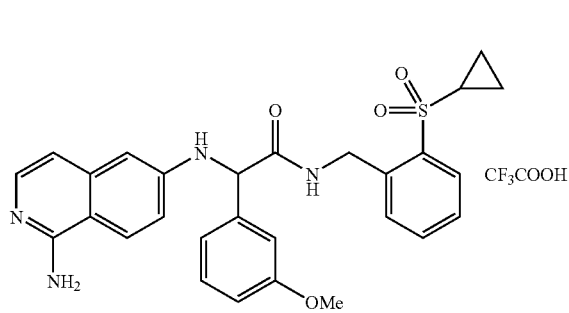

Using the general coupling-deprotection procedure, 124A (27 mg, 0.052 mmol) was coupled with Intermediate 7 (17 mg, 0.069 mmol) and subsequently deprotected to give Example 150 (22 mg, 67%) as a yellow solid. LC-MS m/z: 517.2 (M+H)$^+$.

Example 151

N-(2-(cyclopropylsulfonyl)benzyl)-2-(1-aminoisoquinolin-6-ylamino)-2-(3-ethylphenyl)acetamide trifluoroacetic acid salt

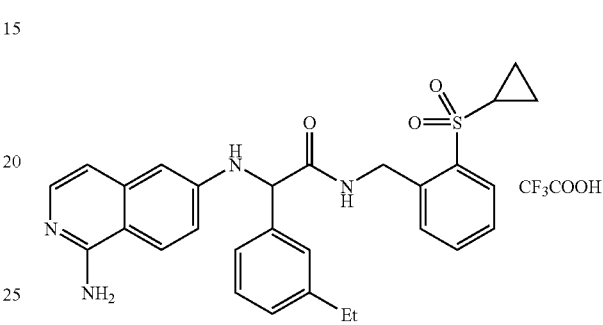

Using the coupling-hydrogenation-deprotection procedure described for Example 148, 148A (26 mg, 0.050 mmol) was coupled with Intermediate 7 (17 mg, 0.069 mmol) and subsequently hydrogenated and deprotected to give Example 151 (13 mg, 41%) as a solid. LC-MS m/z: 515.2 (M+H)$^+$.

Example 152

N-(2-(cyclopropylsulfonyl)benzyl)-2-(1-aminoisoquinolin-6-ylamino)-2-(3-methylphenyl)acetamide trifluoroacetic acid salt

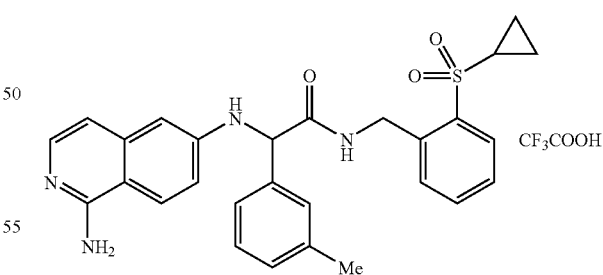

Using the general coupling-deprotection procedure, 149A (29 mg, 0.057 mmol) was coupled with Intermediate 7 (17 mg, 0.069 mmol) and subsequently deprotected to give Example 152 (29 mg, 83%) as a yellow solid. LC-MS m/z: 501.2 (M+H)$^+$.

Example 153

N-(2-(cyclopropylsulfonyl)benzyl)-2-(1-aminoiso-quinolin-6-ylamino)-2-(3-ethoxyphenyl)acetamide trifluoroacetic acid salt

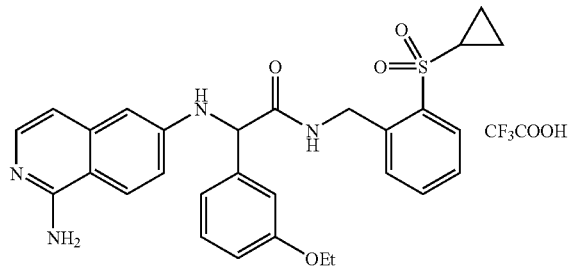

Using the general coupling-deprotection procedure, Intermediate 16 (27 mg, 0.050 mmol) was coupled with Intermediate 7 (17 mg, 0.069 mmol) and subsequently deprotected to give Example 153 (12 mg, 37%) as a yellow solid. LC-MS m/z: 531.2 (M+H)$^+$.

Example 154

N-(3-Acetylamino-benzyl)-2-(1-amino-isoquinolin-6-ylamino)-2-(3-ethoxy-phenyl)-acetamide trifluoroacetic acid salt

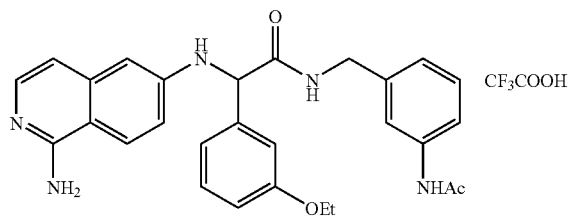

Using the general coupling-deprotection procedure, Intermediate 16 (27 mg, 0.050 mmol) was coupled with N-(3-(aminomethyl)phenyl)acetamide (18 mg, 0.11 mmol) and subsequently deprotected to give Example 154 (9 mg, 30%) as a solid. LC-MS m/z: 484.3 (M+H)$^+$.

Example 155

N-(5-Acetylamino-2-ethanesulfonyl-benzyl)-2-(1-amino-isoquinolin-6-ylamino)-2-(3-bromo-phenyl)-acetamide trifluoroacetic acid salt

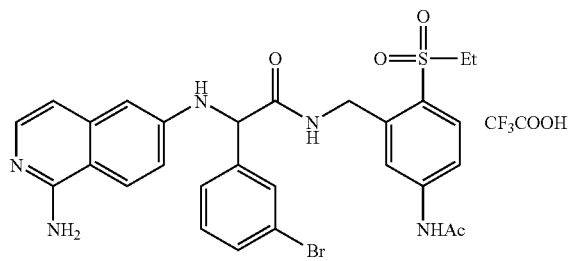

Using the general coupling-deprotection procedure, 121D (30 mg, 0.052 mmol) was coupled with Intermediate 9 (17 mg, 0.066 mmol) and subsequently deprotected to give Example 155 (6 mg, 16%) as a beige solid. LC-MS m/z: 610.1, 612.1 (M+H)$^+$.

Example 156

2-(1-Amino-isoquinolin-6-ylamino)-2-(3-bromo-phenyl)-N-(2-cyclopropanesulfonyl-benzyl)-acetamide trifluoroacetic acid salt

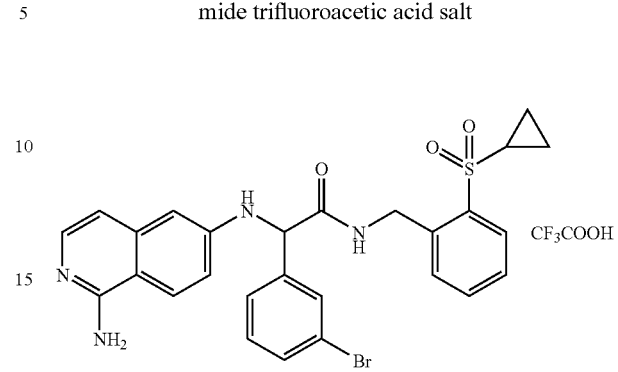

Using the general coupling-deprotection procedure, 121D (30 mg, 0.052 mmol) was coupled with Intermediate 7 (17 mg, 0.069 mmol) and subsequently deprotected to give Example 156 (4 mg, 11%) as a white solid. LC-MS m/z: 565.0, 567.0 (M+H)$^+$.

Example 157

N-(5-Acetylamino-2-ethanesulfonyl-benzyl)-2-(1-amino-isoquinolin-6-ylamino)-2-(3-chlorophenyl)-acetamide trifluoroacetic acid salt

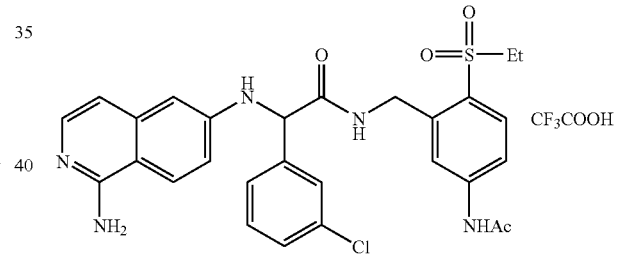

157A 2-(1-(Di-tert-butoxycarbonyl)isoquinolin-6-ylamino)-2-(3-chlorophenyl)acetic acid

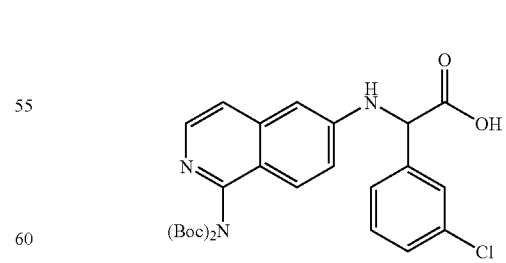

Using the procedure for preparation of Intermediate 16, Intermediate 1 (108 mg, 0.300 mmol) was reacted with 3-chloroboronic acid (56 mg, 0.36 mmol) and glyoxylic acid monohydrate (36 mg, 0.39 mmol) to give 157A (42 mg, 26%) as a solid. LC-MS m/z: 528.2 (M+H)$^+$.

Example 157

Example 157: Using the general coupling-deprotection procedure, 157A (20 mg, 0.038 mmol) was coupled with Intermediate 9 (18 mg, 0.070 mmol) and subsequently deprotected to give Example 157 (16 mg, 62%) as a beige solid. LC-MS m/z: 566.1, 568.1 (M+H)+.

Example 158

2-(1-Amino-isoquinolin-6-ylamino)-2-(3-chlorophenyl)-N-(2-cyclopropanesulfonyl-benzyl)-acetamide trifluoroacetic acid salt

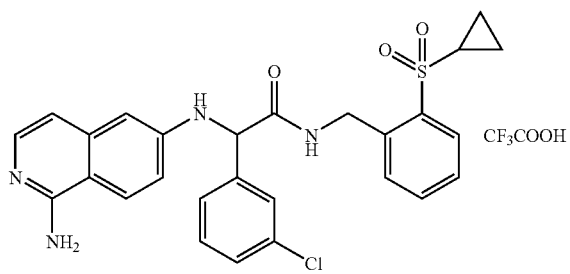

Using the general coupling-deprotection procedure, 157A (20 mg, 0.038 mmol) was coupled with Intermediate 7 (16 mg, 0.076 mmol) and subsequently deprotected to give Example 158 (13 mg, 54%) as a yellow solid. LC-MS m/z: 521.1, 523.1 (M+H)+.

Example 159

2-(1-Amino-isoquinolin-6-ylamino)-2-(3-cyclopropylphenyl)-N-(2-cyclopropanesulfonyl-benzyl)-acetamide trifluoroacetic acid salt

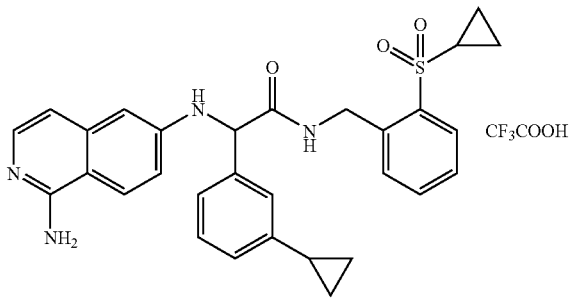

159A (1-Di-tert-Butoxycarbonylamino-isoquinolin-6-ylamino)-(3-cyclopropyl-phenyl)-acetic acid methyl ester

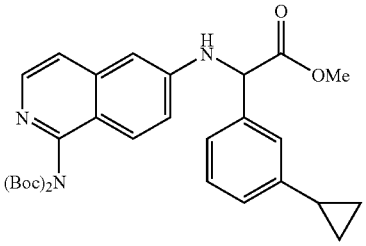

A mixture of 121C (100 mg, 0.17 mmol), cyclopropylboronic acid (30 mg, 0.35 mmol), potassium phosphate (150 mg), toluene (2 mL), and water (0.050 mL) was degassed by bubbling N$_2$ through the suspension. Tricyclohexylphosphine (14 mg) and palladium (II) acetate (7 mg) was added and the reaction was heated overnight at 90° C. and then concentrated under reduced pressure. The residue was purified by silica gel chromatography (gradient from 0 to 20% methanol in dichloromethane) to give a 2:1 mixture of 159A and 121C (33 mg, 24%) as a clear glass. LC-MS m/z: 548.3 (M+H)+.

159B (1-Di-tert-Butoxycarbonylamino-isoquinolin-6-ylamino)-(3-cyclopropyl-phenyl)-acetic acid

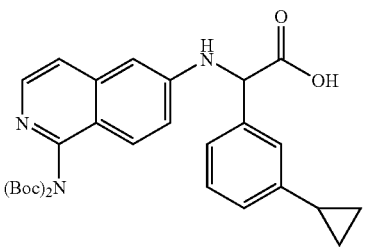

Ester 159A (63 mg, 0.1 mmol, 1:1 mixture of 159A and 121C) was hydrolyzed according to the procedure for 121D to give a 1:1 mixture 159B and 121D as a solid. LC-MS m/z: 534 (M+H)+.

159C

Example 159: Using the general coupling-deprotection procedure, 159B (30 mg, 0.05 mmol, 1:1 mixture of 159B and 121D) was coupled with Intermediate 7 (24 mg, 0.11 mmol) and subsequently deprotected to give Example 159 (8 mg) as a beige solid. LC-MS m/z: 527.2 (M+H)+.

Example 160

N-(5-Acetylamino-2-ethanesulfonyl-benzyl)-2-(1-amino-isoquinolin-6-ylamino)-2-(3-cyclopropylphenyl)-acetamide trifluoroacetic acid salt

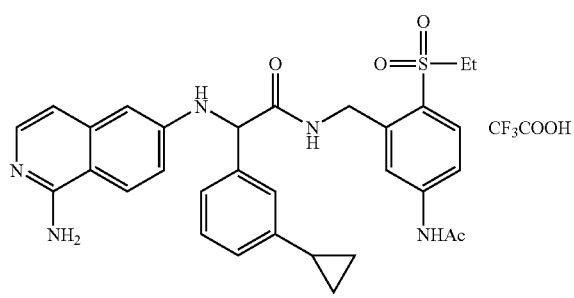

Using the general coupling-deprotection procedure, 159B (30 mg, 0.05 mmol, 1:1 mixture of 159B and 121D) was coupled with Intermediate 9 (24 mg, 0.094 mmol) and subsequently deprotected to give Example 160 (5 mg) as a beige solid. LC-MS m/z: 572.2 (M+H)+.

Example 161

N-(5-Acetylamino-2-ethanesulfonyl-benzyl)-2-(4-aminomethyl-3-methyl-phenylamino)-2-(3-ethoxyphenyl)-acetamide trifluoroacetic acid salt

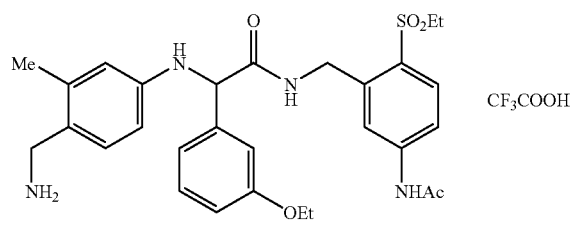

161A (2-Methyl-4-nitro-benzyl)-carbamic acid tert-butyl ester

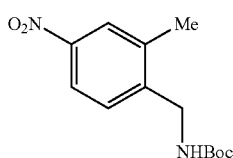

Borane (1.5 mL, 1.5 mmol, 1M solution in tetrahydrofuran) was added dropwise to a solution of 2-methyl-4-nitrobenzonitrile (0.155 g, 0.957 mmol) and trimethylborate (1.0 mL, 8.97 mmol) in tetrahydrofuran (5 mL). After 24 h at rt, additional borane solution (1.5 mL) was added and the reaction mixture was heated at 60° C. for 3.5 h. Methanol was added dropwise at 0° C., and the reaction was concentrated under reduced pressure. The residue was dissolved in tetrahydrofuran (3 mL) and treated with di-tert-butyl dicarbonate (0.240 mL, 1.04 mmol). After 6 h at rt, the reaction mixture was diluted with ethyl acetate and washed with sodium bicarbonate solution and brine, dried (MgSO4), and concentrated under reduced pressure. The residue was purified by silica gel chromatography (gradient from 0 to 20% ethyl acetate in hexanes) to give 161A (0.183 g, 72%) as a colorless oil which solidified on standing. LC-MS m/z: 555 (2M+Na)+.

161B (4-Amino-2-methyl-benzyl)-carbamic acid tert-butyl ester

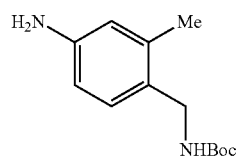

A solution of 161A (0.306 g, 1.15 mmol) in ethanol (3 mL) was hydrogenated (1 atm) over 10% palladium on carbon (15 mg) for 4 h. The reaction mixture was filtered and concentrated under reduced pressure to give 161B (0.276 g, 100%) as a colorless oil. LC-MS m/z: 181.1 (M+H-t-Bu)+.

161C 2-(4-((tert-butoxycarbonylamino)methyl)-3-methylphenylamino)-2-(3-ethoxyphenyl)acetic acid

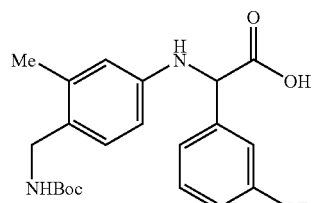

Using the procedure for preparation of Intermediate 16, 161B (172 mg, 0.728 mmol) was reacted with 3-ethoxyboronic acid (0.147 g, 0.886 mmol) and glyoxylic acid monohydrate (81 mg, 0.88 mmol) to give 161C (140 mg, 46%) as a yellow oil. LC-MS m/z: 415.2 (M+H)+.

161D

Example 161: Using the general coupling-deprotection procedure, 161C (34.3 mg, 0.083 mmol) was coupled with Intermediate 9 (13.3 mg, 0.051 mmol) and subsequently deprotected (using 50% trifluoroacetic acid in dichloromethane (1 mL), instead of hydrogen chloride in dioxane/ethyl acetate) to give Example 161 (15.7 mg, 45%) as a yellow solid. LC-MS m/z: 536.2 (M–NH2)+.

Example 162

N-(5-Acetylamino-2-ethanesulfonyl-benzyl)-2-(4-aminomethyl-phenylamino)-2-(3-ethoxyphenyl)-acetamide trifluoroacetic acid salt

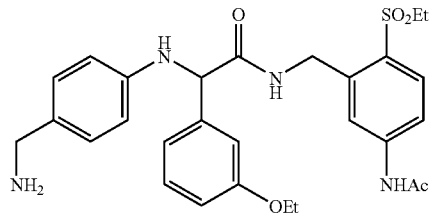

162A 2-(4-((tert-butoxycarbonylamino)methyl)phenylamino)-2-(3-ethoxyphenyl)acetic acid

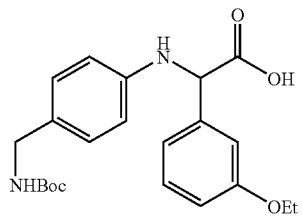

Using the procedure for preparation of Intermediate 16, 4-(N-Boc)-aminomethylaniline (111 mg, 0.500 mmol) was reacted with 3-ethoxyboronic acid (0.125 g, 0.75 mmol) and glyoxylic acid monohydrate (55 mg, 0.60 mmol) to give 162A (134 mg, 67%) as an orange oil. LC-MS m/z: 401.3 (M+H)$^+$.

162B

Example 162: Using the general coupling-deprotection procedure, 162A (60 mg, 0.15 mmol) was coupled with Intermediate 9 (50 mg, 0.195 mmol) and subsequently deprotected to give Example 162 (45 mg, 61%) as a beige solid. LC-MS m/z: 522.2 (M−NH$_2$)$^+$.

Example 163

N-(5-Acetylamino-2-ethanesulfonyl-benzyl)-2-(4-aminomethyl-3-fluorophenylamino)-2-(3-ethoxyphenyl)-acetamide trifluoroacetic acid salt

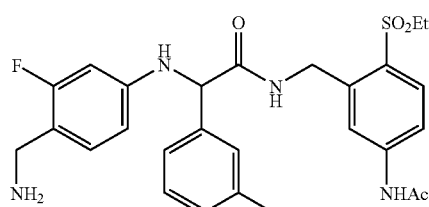

163A (4-Amino-2-fluoro-benzyl)-carbamic acid tert-butyl ester

A solution of 2-fluoro-4-nitrobenzonitrile (0.541 g, 2.43 mmol) in methanol (20 mL) and hydrochloric acid (3 mL, 6 N) was hydrogenated (55 psi) over 10% palladium on carbon (164 mg) overnight. The reaction mixture was filtered and concentrated under reduced pressure. The residue was dissolved in tetrahydrofuran (5 mL) and treated with 2-(tert-butoxycarbonyloxyimino)-2-phenylacetonitrile (0.517 mg, 2.10 mmol) and triethylamine (0.6 mL, 4.3 mmol). After 16 h at rt, the reaction mixture was diluted with dichloromethane and washed with sodium bicarbonate solution and brine, dried (MgSO$_4$), and concentrated under reduced pressure. The residue was purified by silica gel chromatography (gradient from 0 to 50% ethyl acetate in hexanes) to give 1-63A- (0.287 g, 60%) as a colorless oil which solidified on standing.

163B 2-(4-((tert-butoxycarbonylamino)methyl)-3-fluorophenylamino)-2-(3-ethoxyphenyl)acetic acid

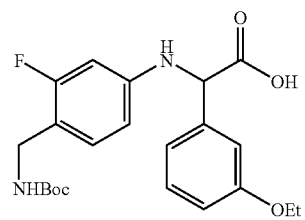

Using the procedure for preparation of Intermediate 16, 163A (120 mg, 0.500 mmol) was reacted with 3-ethoxyboronic acid (0.125 g, 0.75 mmol) and glyoxylic acid monohydrate (55 mg, 0.60 mmol) to give 163B (134 mg, 64%). LC-MS m/z: 419.3 (M+H)$^+$.

163C

Example 163: Using the general coupling-deprotection procedure, 163B (63 mg, 0.15 mmol) was coupled with Intermediate 9 (50 mg, 0.195 mmol) and subsequently deprotected to give Example 163 (36 mg, 36%) as a beige solid. LC-MS m/z: 540.2 (M−NH$_2$)$^+$.

Example 164

N-(5-Acetylamino-2-ethanesulfonyl-benzyl)-2-(4-aminomethyl-3-chlorophenylamino)-2-(3-ethoxyphenyl)-acetamide trifluoroacetic acid salt

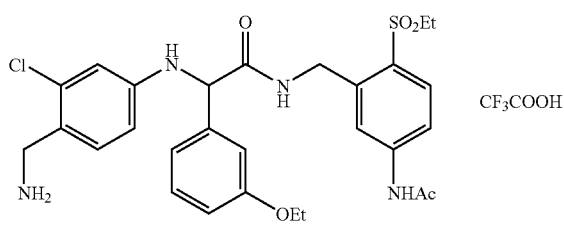

164A (4-Amino-2-chloro-benzyl)-carbamic acid tert-butyl ester

Borane (9 mL, 9 mmol, 1M solution in tetrahydrofuran) was added dropwise to a solution of 4-amino-2-chlorobenzonitrile (0.500 g, 3.28 mmol) in tetrahydrofuran (3 mL) at 0° C. After 2 h at rt, hydrochloric acid (6N) was added slowly dropwise at 0° C., and the reaction was concentrated under reduced pressure. The residue was dissolved in tetrahydrofuran (5 mL) and treated with 2-(tert-butoxycarbonyloxyimino)-2-phenylacetonitrile (0.517 mg, 2.10 mmol). After 16 h at rt, the reaction mixture was diluted with dichloromethane and washed with sodium bicarbonate solution and brine, dried (MgSO$_4$), and concentrated under reduced pressure. The residue was purified by silica gel chromatography (gradient from 0 to 50% ethyl acetate in hexanes) to give 164A (0.427 g, 51%) as a yellow oil which solidified on standing.

164B 2-(4-(((tert-butoxycarbonylamino)methyl)-3-chlorophenylamino)-2-(3-ethoxyphenyl)acetic acid

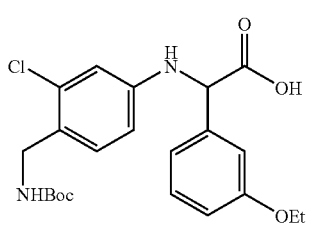

Using the procedure for preparation of Intermediate 16, 164A (128 mg, 0.500 mmol) was reacted with 3-ethoxyboronic acid (0.125 g, 0.75 mmol) and glyoxylic acid monohydrate (55 mg, 0.60 mmol) to give 164B. LC-MS m/z: 435.3 (M+H)$^+$.

164C

Example 164: Using the general coupling-deprotection procedure, 164B (32 mg, 0.074 mmol) was coupled with Intermediate 9 (25 mg, 0.098 mmol) and subsequently deprotected to give Example 164 (22 mg, 43%) as a beige solid. LC-MS m/z: 557.1, 559.1 (M–NH$_2$)$^+$.

Example 165

N-(5-Acetylamino-2-ethanesulfonyl-benzyl)-2-(6-aminomethyl-pyridin-3-ylamino)-2-(3-ethoxyphenyl)-acetamide trifluoroacetic acid salt

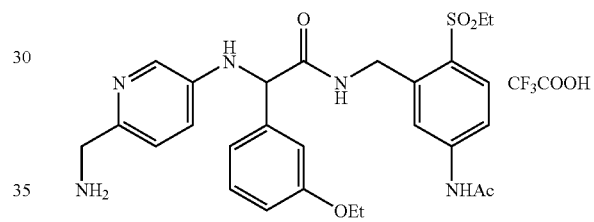

165A (6-Cyanopyridin-3-ylamino)-(3-ethoxy-phenyl)-acetic acid

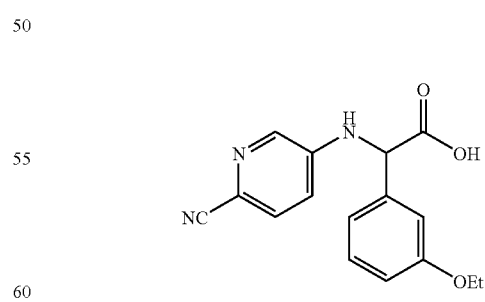

Using the procedure for preparation of Intermediate 16, 5-amino-2-cyanopyridine (60 mg, 0.500 mmol) was reacted with 3-ethoxyboronic acid (83 mg, 0.50 mmol) and glyoxylic acid monohydrate (55 mg, 0.60 mmol) to give 165A (32 mg, 21%). LC-MS m/z: 298.3 (M+H)$^+$.

165B

N-(5-Acetylamino-2-ethanesulfonyl-benzyl)-2-(6-cyanopyridin-3-ylamino)-2-(3-ethoxyphenyl)-acetamide

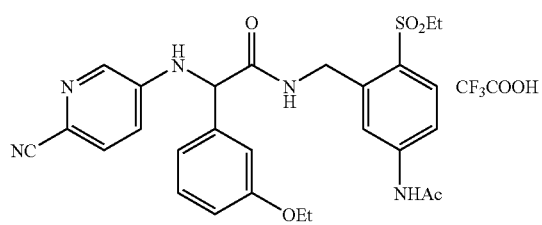

Using the general coupling-deprotection procedure, 165A (32 mg, 0.11 mmol) was coupled with Intermediate 9 (37 mg, 0.14 mmol). The acidic deprotection step was omitted, to give 165B (40 mg, 68%) as a white solid. LC-MS m/z: 536.1 (M+H)$^+$.

165C

Example 165: A solution of 165B (0.040 g, 0.075 mmol) in methanol (several mL) was hydrogenated (50 psi) over Raney nickel for 7 h. The reaction mixture was filtered and concentrated under reduced pressure. The residue was purified by reverse phase HPLC to give Example 165 (25 mg, 51%) as a white solid. LC-MS m/z: 540.2 (M+H)$^+$.

Example 166

N-(5-Acetylamino-2-ethanesulfonylbenzyl)-2-(1-amino-7-fluoro-isoquinolin-6-ylamino)-2-(3-ethoxyphenyl)-N-methyl-acetamide trifluoroacetic acid salt

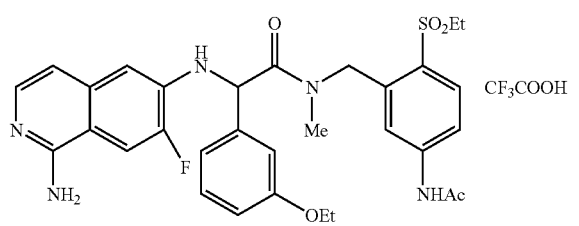

166A

Ethyl 3-(dibenzylamino)-4-fluorobenzoate

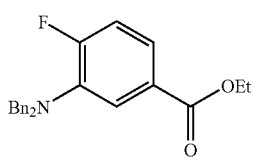

A solution of ethyl-3-amino-4-fluorobenzoate (4.58 g, 25 mmol), benzyl bromide (7 mL, 59 mmol), and DIEA (15 mL, 86 mmol) in acetonitrile (50 mL) was heated at reflux overnight. An additional portion of benzyl bromide (0.5 mL) was added and the reflux was continued 8 h. The reaction mixture was concentrated under reduced pressure and the residue purified by silica gel chromatography (gradient from 0 to 10% ethyl acetate in hexanes) to give 166A (7.4 g, 81%) as a clear oil that solidified on standing.

166B (3-(dibenzylamino)-4-fluorophenyl)methanol

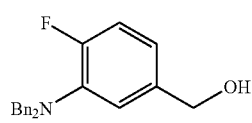

Lithium aluminum hydride (2.5 mL, 1M solution in tetrahydrofuran, 2.5 mmol) was added dropwise to a solution of 166A (0.916 g, 2.52 mmol) in tetrahydrofuran (10 mL) at 0° C. The reaction mixture was then heated at 80° C. for 1.5 h. The mixture was cooled to 0° C. and water (~1 mL) was added dropwise, followed by 1 N NaOH (~1 mL). The mixture was filtered, the filtrate was concentrated under reduced pressure, and the residue purified by silica gel chromatography (gradient from 0 to 30% ethyl acetate in hexanes) to give 166B (0.9 g, 100%). LC-MS m/z: 322.2 (M+H)$^+$.

166C 3-(dibenzylamino)-4-fluorobenzaldehyde

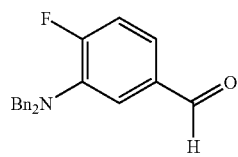

Manganese(IV) oxide (2.3 g, 30 mmol) was added to a solution of 166B (1.4 g, 4.4 mmol) in tetrahydrofuran (35 mL). After two hours, an additional portion of manganese (IV) oxide (2.3 g) was added. After three hours, the reaction mixture was filtered and concentrated under reduced pressure. The residue was purified by silica gel chromatography (gradient from 0 to 30% ethyl acetate in hexanes) to give 166C (0.94 g, 68%) together with recovered 166B (0.32 g).

166D (E)-ethyl 3-(3-(dibenzylamino)-4-fluorophenyl)acrylate

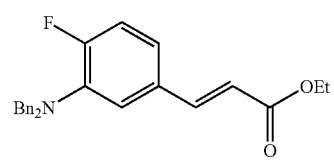

Sodium hydride (16 mg, 60% dispersion in oil, 0.4 mmol) was added to a solution of 166C (111 mg, 0.35 mmol) and diethyl phosphoric acid ethyl ester (94 mg, 0.42 mmol) in tetrahydrofuran (2.5 mL). The reaction mixture was heated at 60° C. for 2 h. The reaction was then diluted with ethyl acetate and washed successively with 5% potassium hydrogen sulfate solution, saturated sodium bicarbonate, water, and brine. The organic layer was dried (MgSO$_4$) and concentrated under reduced pressure to give 166D (0.122 g, 89%) as an oil that solidified on standing. LC-MS m/z: 390.2 (M+H)$^+$.

166E (E)-3-(3-(dibenzylamino)-4-fluorophenyl)acrylic acid

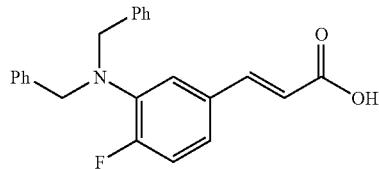

Using a procedure similar to that described for 136C, 166D (0.500 g, 1.28 mmol) was hydrolyzed to give 166E (0.5 g, 100%) as a white solid. LC-MS m/z: 362.2 (M+H)$^+$.

166F 6-(Dibenzylamino)-7-fluoroisoquinolin-1(2H)-one

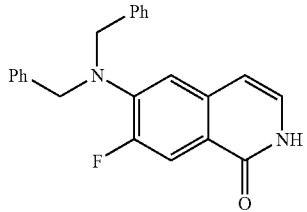

Using a procedure similar to that described for 136D, 166E (0.500 g, 1.38 mmol) was converted to an acyl azide and then cyclized to give 166F (0.22 g, 56%) as an off-white solid. LC-MS m/z: 359.2 (M+H)$^+$.

166G

N$^6$,N$^6$-dibenzyl-7-fluoroisoquinoline-1,6-diamine

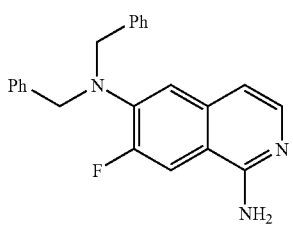

Using a procedure similar to that described for 136E, 166F (0.22 g, 0.61 mmol) was chlorinated and then reacted with ammonia to give 166G as a solid. LC-MS m/z: 358.3 (M+H)$^+$.

166H

N$^6$,N$^6$-Dibenzyl-N$^1$,N$^1$-di-tert-butoxycarbonyl-7-fluoroisoquinoline-1,6-diamine

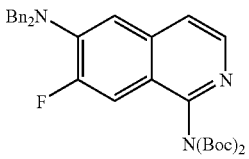

A mixture of 166G (50 mg, 0.14 mmol), di-tert-butyl dicarbonate (277 mg, 1.27 mmol), and 4-dimethylaminopyridine (6 mg, 0.049 mmol) was heated to 130° C. for 15 min. The mixture was concentrated in vacuo, and the residue was purified by silica gel chromatography (gradient from 0 to 500% ethyl acetate in hexanes) to afford 166H (60 mg, 77%) as a solid. LC-MS m/z: 558.2 (M+H)$^+$.

166I

N$^1$,N$^1$-Di-tert-butoxycarbonyl-7-fluoroisoquinoline-1,6-diamine

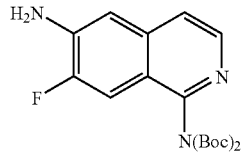

A mixture of 166H (123 mg, 0.22 mmol), palladium(II) hydroxide on carbon (138 mg, Degussa type) and ethanol (10 mL) was hydrogenated (55 psi) for 6 h. The reaction mixture was filtered and concentrated under reduced pressure to give 166I (80 mg, 96%) as a white solid. LC-MS m/z: 378.3 (M+H)$^+$.

166J (1-Di-tert-butoxycarbonylamino-7-fluoro-isoquinolin-6-ylamino)-(3-ethoxy-phenyl)-acetic acid

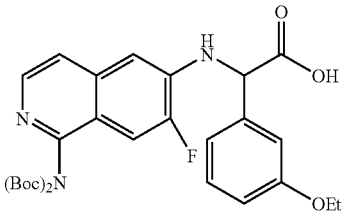

Using the procedure for preparation of Intermediate 16, 166I (38 mg, 0.10 mmol) was reacted with 3-ethoxyboronic acid (11 mg, 0.30 mmol) and glyoxylic acid monohydrate (22 mg, 0.24 mmol) to give 166J (10 mg, 18%). LC-MS m/z: 556.2 (M+H)$^+$.

166K

Example 166: Using the general coupling-deprotection procedure, 166J (10 mg, 0.018 mmol) was coupled with Intermediate 10 (10 mg, 0.037 mmol) and subsequently deprotected to give Example 166 (5 mg, 38%) as a solid. LC-MS m/z: 608.2 (M+H)$^+$.

Example 167

2-(1-Amino-7-fluoroisoquinolin-6-ylamino)-N-(2-cyclopropanesulfonylbenzyl)-2-(3-ethoxy-4-isopropoxyphenyl)-acetamide trifluoroacetic acid salt

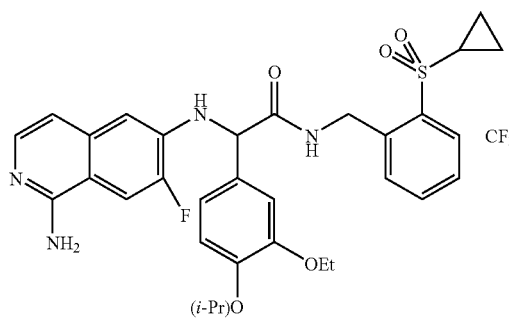

167A (1-Di-tert-butoxycarbonylamino-7-fluoro-isoquinolin-6-ylamino)-(3-ethoxy-4-isopropoxyphenyl)-acetic acid

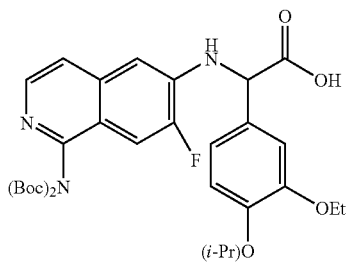

Using the procedure for preparation of Intermediate 16, 166I (32 mg, 0.085 mmol) was reacted with 3-ethoxy-4-isopropoxyboronic acid (28 mg, 0.125 mmol) and glyoxylic acid monohydrate (12 mg, 0.13 mmol) to give 167A (32 mg, 61%). LC-MS m/z: 614.2 (M+H)$^+$.

167B

Example 167: Using the general coupling-deprotection procedure, 167A (32 mg, 0.052 mmol) was coupled with Intermediate 7 (26 mg, 0.10 mmol) and subsequently deprotected to give Example 167 (15 mg, 40%) as a solid. LC-MS m/z: 607.2 (M+H)$^+$.

Example 168

3-{[(5-Acetylamino-2-ethanesulfonylbenzylcarbamoyl)-(3-ethoxyphenyl)methyl]amino}benzamide trifluoroacetic acid salt

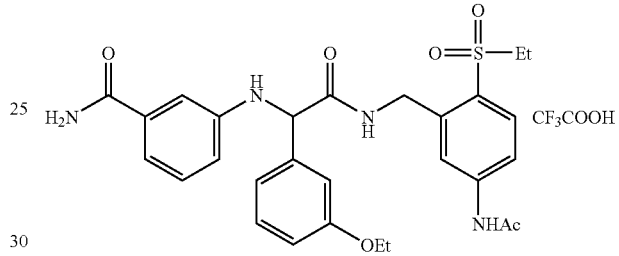

168A (3-Carbamoyl-phenylamino)-(3-ethoxy-phenyl)-acetic acid

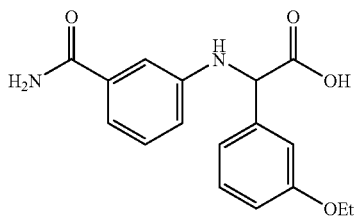

Using the procedure for preparation of Intermediate 16, 3-aminobenzamide (68 mg, 0.50 mmol) was reacted with 3-ethoxyboronic acid (83 mg, 0.50 mmol) and glyoxylic acid monohydrate (55 mg, 0.60 mmol) to give 168A (15 mg, 10%) as a white solid. LC-MS m/z: 315.3 (M+H)$^+$.

168B

Example 168: Using the general coupling-deprotection procedure, 168A (15 mg, 0.048 mmol) was coupled with Intermediate 9 (16 mg, 0.064 mmol) to give Example 168 (20 mg, 62%) as a white solid. LC-MS m/z: 553.2 (M+H)$^+$.

Example 169

N-(5-Acetylamino-2-ethanesulfonylbenzyl)-2-(1-aminoisoquinolin-6-ylamino)-2-(3-ethoxyphenyl)-N-methyl-acetamide trifluoroacetic acid salt

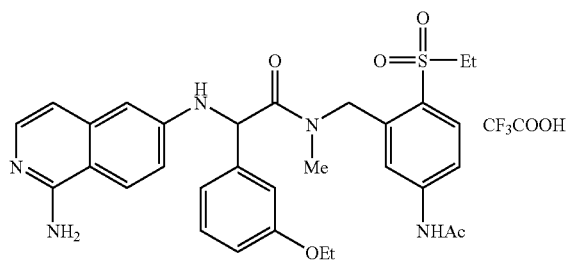

Using the general coupling-deprotection procedure, Intermediate 16 (20 mg, 0.056 mmol) was coupled with Intermediate 10 (20 mg, 0.074 mmol) and subsequently deprotected to give Example 169 (8 mg, 20%) as a white solid. LC-MS m/z: 590.2 (M+H)$^+$.

Example 170

N-(2-Ethylbenzyl)-2-(1-aminoisoquinolin-6-ylamino)-2-(3-ethoxy-4-isopropoxyphenyl)acetamide trifluoroacetic acid salt

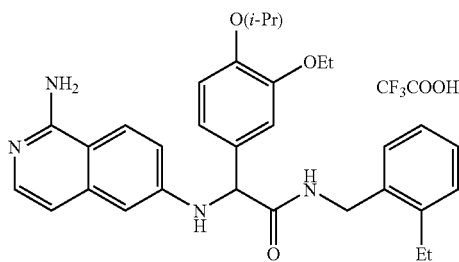

170A

2-Ethylbenzylamine hydrochloride salt

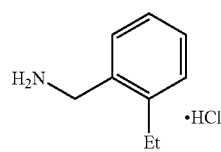

To 2-ethylbenzonitrile (250 mg, 1.91 mmol) in methanol (19 mL) was added 4 M HCl in dioxane (0.57 mL, 2.3 mmol) followed by 10% Pd/C (150 mg). The mixture was hydrogenated (using a hydrogen balloon) for 2 days. The reaction was filtered through Celite® and concentrated to provide 170A as a yellow solid (299 mg, 92%). LC-MS: 136.1 (M+H)$^+$.

170B

Example 170 (10 mg) was prepared from Intermediate 2 (20 mg) and 170A (7.0 mg) following the general coupling/deprotection procedure in 58% overall yield. $^1$H NMR (400 MHz, CD$_3$OD) δ ppm 1.09 (t, J=7.47 Hz, 3H) 1.30 (d, J=6.15 Hz, 6H) 1.37 (t, J=6.81 Hz, 3H) 2.54 (q, J=7.62 Hz, 2H) 4.01 (q, J=7.03 Hz, 2H) 4.47 (m, 3H) 5.09 (s, 1H) 6.68 (d, J=2.64 Hz, 1H) 6.80 (d, J=7.03 Hz, 1H) 6.96 (d, J=7.91 Hz, 1H) 7.12 (m, 7H) 7.32 (d, J=7.03 Hz, 1H) 8.08 (d, J=9.23 Hz, 1H) 8.63 (s, 1H). LC-MS: 513.41 (M+H)$^+$.

Example 171

N-(2-(Trifluoromethoxy)benzyl)-2-(1-aminoisoquinolin-6-ylamino)-2-(3-ethoxy-4-isopropoxyphenyl)acetamide trifluoroacetic acid salt

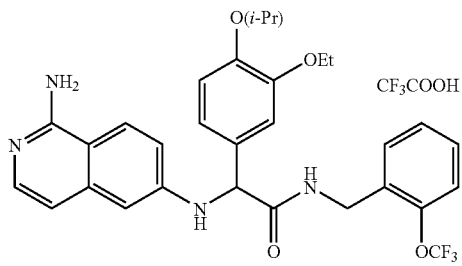

Example 171 (5.6 mg) was prepared from Intermediate 2 (12 mg) and commercially available 2-trifluoromethoxybenzylamine (4.6 mg) following the general coupling/deprotection procedure in 50% overall yield. $^1$H NMR (400 MHz, CD$_3$OD) δ ppm 1.30 (d, J=6.15 Hz, 6H) 1.37 (t, J=7.03 Hz, 3H) 4.02 (q, J=7.03 Hz, 2H) 4.41 (m, 1H) 4.54 (m, 2H) 5.10 (s, 1H) 6.69 (d, J=1.76 Hz, 1H) 6.83 (d, J=7.47 Hz, 1H) 6.97 (d, J=7.91 Hz, 1H) 7.08 (m, 1H) 7.13 (m, 3H) 7.20 (m, 2H) 7.31 (m, 2H) 8.08 (d, J=9.23 Hz, 1H) 8.74 (s, 1H). LC-MS: 569.36 (M+H)$^+$.

Example 172

N-(2-Nitrobenzyl)-2-(1-aminoisoquinolin-6-ylamino)-2-(3-ethoxy-4-isopropoxyphenyl)acetamide trifluoroacetic acid salt

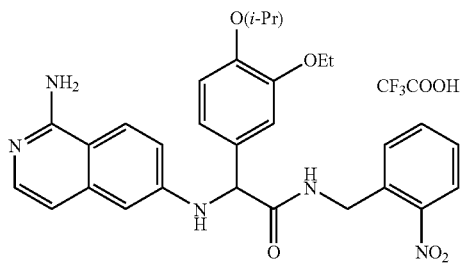

Example 172 (12 mg) was prepared from Intermediate 2 (30 mg) and commercially available 2-nitrobenzylamine (13 mg) following the general coupling/deprotection procedure in 38% overall yield. LC-MS: 530.09 (M+H)$^+$

Example 173

N-(2-(Phenylsulfonyl)benzyl)-2-(1-aminoisoquinolin-6-ylamino)-2-(3-ethoxy-4-isopropoxyphenyl)acetamide trifluoroacetic acid salt

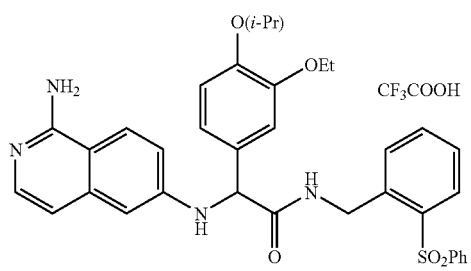

173A 2-(Phenylsulfonyl)benzonitrile

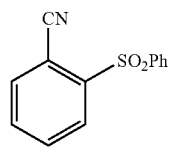

A mixture of 2-fluorobenzonitrile (1.0 mL, 9.1 mmol) and benzenethiol (1.0 mL, 9.7 mmol) was stirred at 80° C. overnight. The reaction was cooled to rt then concentrated. The residue was dissolved in CH$_2$Cl$_2$ (20 mL) and cooled to 0° C. MCPBA (~75%, 4.40 g, 19.1 mmol) was added and the whole was stirred (0° C. to rt) for 2 h. The reaction was diluted with CH$_2$Cl$_2$ and was washed with water then brine. The organic layer was concentrated then purified via silica gel chromatography eluting with 0-30% ethyl acetate/hexane to provide 173A (2.14 g, 90%). LC-MS: 244.11 (M+H)$^+$

173B 2-(Phenylsulfonyl)benzylamine

To 173A (487 mg, 2.00 mmol) in methanol (10 mL) was added a 4M solution of HCl in dioxane (0.57 mL, 2.3 mmol) followed by 10% Pd/C (150 mg). The mixture was hydrogenated at 30 psi for 4 h. The reaction was filtered, concentrated and dissolved in ethyl acetate. The solution was washed with saturated aqueous NaHCO$_3$. After separation, the organic layer was concentrated to provide 173B (350 mg, 71%). LC-MS: 248.1 (M+H)$^+$.

173C

Example 173 (10 mg) was prepared from Intermediate 2 (18 mg) and amine 173B (25 mg) following the general coupling/deprotection procedure in 54% overall yield. LC-MS: 625.35 (M+H)$^+$.

Example 174

N-(2-(Phenyl)benzyl)-2-(1-aminoisoquinolin-6-ylamino)-2-(3-ethoxy-4-isopropoxyphenyl)acetamide trifluoroacetic acid salt

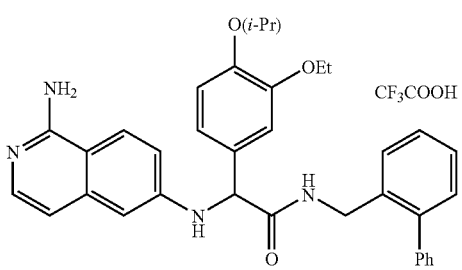

Example 174 (9 mg) was prepared from Intermediate 2 (18 mg) and commercially available 2-phenylbenzylamine (9.2 mg) following the general coupling/deprotection procedure in 54% overall yield. $^1$H NMR-(400 MHz, CD$_3$OD) δ ppm 1.20 (m, 6H) 1.28 (m, 3H) 3.90 (m, 2H) 4.19 (m, 2H) 4.44 (m, 1H) 4.95 (m, 1H) 6.56 (m, 1H) 6.72 (m, 1H) 6.87 (m, 1H) 6.94 (m, 1H) 7.00 (m, 1H) 7.16 (m, 12H) 7.98 (d, J=9.23 Hz, 1H) 8.39 (s, 1H). LC-MS: 561.39 (M+H)$^+$.

Example 175

N-(2-(o-Tolyl)benzyl)-2-(1-aminoisoquinolin-6-ylamino)-2-(3-ethoxy-4-isopropoxyphenyl)acetamide trifluoroacetic acid salt

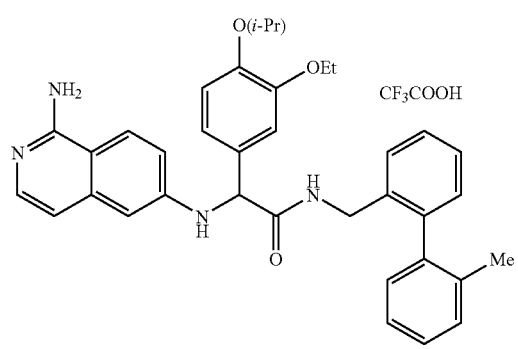

175A 2-(o-Tolyl)benzonitrile

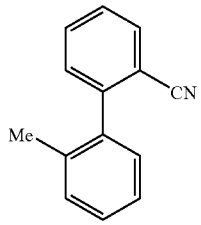

2-Cyanophenyl boronic acid (676 mg, 4.60 mmol), 2-bromotoluene (342 mg, 2.0 mmol), 3M aqueous sodium carbonate (3 mL), and toluene (18 mL) were combined in a tube. The mixture was degassed with argon for 3 min, when palladium tetrakistriphenylphosphine (230 mg, 0.20 mmol) was added. The tube was sealed and heated to 100° C. overnight. The reaction was cooled to rt, then concentrated and purified via silica gel chromatography eluting with 0-10% ethyl acetate/hexanes to provide 175A (113 mg). LC-MS: 194.12 (M+H)$^+$

175B 2-(o-Tolyl)benzylamine trifluoroacetic acid salt

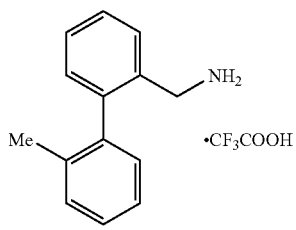

To 175A (113 mg, 0.59 mmol) in THF (5 mL) was added a 1M THF solution of BH$_3$.THF (3.0 mL, 3.0 mmol) and the reaction was heated to reflux for 1 h. After cooling to rt, 1M HCl (5 mL) was added, and the reaction was heated to reflux for 10 min. The reaction was cooled to rt, concentrated and purified via preparative HPLC eluting with MeOH/water/TFA to provide 175B (135 mg).

175C

Example 175 (3.7 mg) was prepared from Intermediate 2 (30 mg) and 175B (37 mg) following the general coupling/deprotection procedure in 0.5% overall yield. LC-MS: 575.4 (M+H)$^+$.

Example 176

N-(2-(2-Trifluoromethyl)benzyl)-2-(1-aminoisoquinolin-6-ylamino)-2-(3-ethoxy-4-isopropoxyphenyl)acetamide trifluoroacetic acid salt

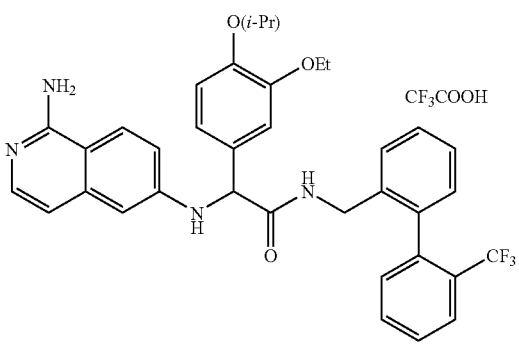

176A 2-(2-Trifluoromethyl)benzonitrile

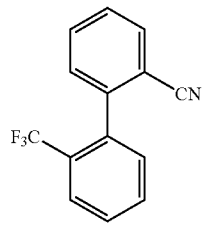

2-Trifluoromethyl phenylboronic acid (380 mg, 2.00 mmol), 2-bromobenzonitrile (182 mg, 1.0 mmol), potassium carbonate (552 mg, 4.00 mmol), dichlorobis(chloro-tert-butylphosphine) palladium (Omniphos Catalysts, Inc.) (54 mg, 0.10 mmol) and methanol (2 mL) were combined in a tube. The tube was sealed and heated to 80° C. for 1 h. The reaction was cooled to rt, then filtered, concentrated and purified via silica gel chromatography eluting with 0-20% ethyl acetate/hexanes to provide 176A (230 mg). LC-MS: 248.03 (M+H)$^+$

176B 2-(2-Trifluoromethyl)benzylamine trifluoroacetic acid salt

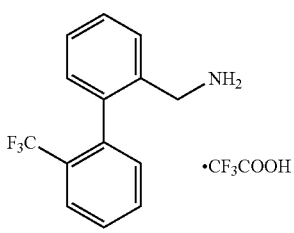

To 176A (110 mg, 0.45 mmol) in THF (5 mL) was added a 1M THF solution of BH$_3$.THF (2.0 mL, 2.0 mmol) and the reaction was refluxed for 1 h. After cooling to rt, 1M HCl (5 mL) was added, and the mixture was heated to reflux for 10 min. The reaction was cooled to rt, concentrated and purified via preparative HPLC (eluting with acetonitrile/water/TFA) to provide 176B (110 mg). LC-MS: 253.09 (M+H)⁺

176C

Example 176 (7.7 mg) was prepared from Intermediate 2 (24 mg) and 176B (37 mg) following the general coupling/ deprotection procedure in 26% overall yield. LC-MS: 629.30 (M+H)⁺.

Example 177

N-(2-(m-Tolyl)benzyl)-2-(1-aminoisoquinolin-6-ylamino)-2-(3-ethoxy-4-isopropoxyphenyl)acetamide trifluoroacetic acid salt

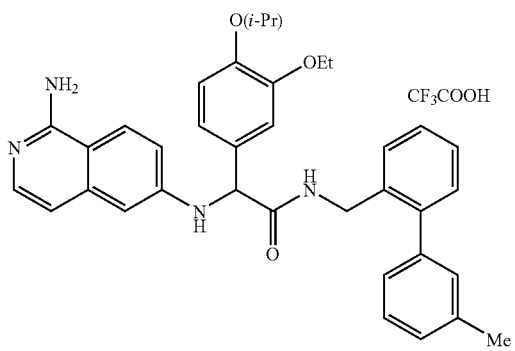

177A 2-(m-Tolyl)benzonitrile

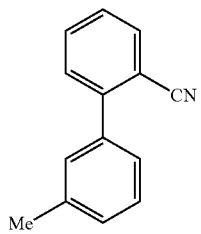

3-Methyl phenylboronic acid (163 mg, 1.20 mmol), 2-bromobenzonitrile (182 mg, 1.00 mmol), 2M aqueous sodium carbonate (2 mL, 4.00 mmol), dichlorobis(chloro-tert-butylphosphine) palladium (Omniphos Catalysts, Inc.) (180 mg, 0.16 mmol) and toluene (6 mL) were combined in a tube. The mixture was degassed with nitrogen for 2 min, then the tube was sealed and heated to 100° C. for 72 h. The reaction was cooled to rt, diluted with ethyl acetate, washed with water and brine, then dried (Na₂SO₄), filtered and concentrated. The residue was purified via silica gel chromatography eluting with 0-10% ethyl acetate/hexanes to provide 177A (156 mg). LC-MS: 194.08 (M+H)⁺

177B 2-(m-Tolyl)benzylamine trifluoroacetic acid salt

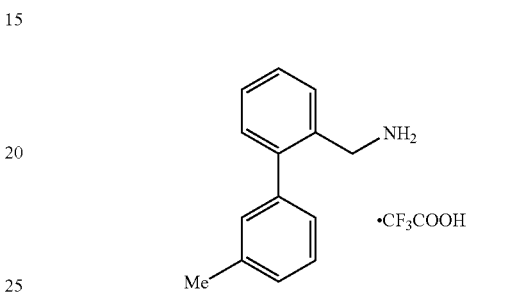

To 177A (156 mg, 0.81 mmol) in THF (6 mL) was added a 1M THF solution of BH₃.THF (6.0 mL, 6.0 mmol) and the solution was refluxed for 2 h. The reaction was cooled to rt, 1M HCl (5 mL) was added, and the mixture was heated to reflux for 30 min. The reaction was cooled to rt, concentrated and purified via preparative HPLC (eluting with MeOH/water/TFA) to provide 177B (160 mg). LC-MS: 197.18 (M+H)⁺

177C

Example 177 (2.5 mg) was prepared from Intermediate 2 (20 mg) and 177B (20 mg) following the general coupling/ deprotection procedure in 11% overall yield. LC-MS: 575.38 (M+H)⁺.

Example 178

N-(2-((2,5-Dimethyl)phenyl)benzyl)-2-(1-aminoisoquinolin-6-ylamino)-2-(3-ethoxy-4-isopropoxyphenyl)acetamide trifluoroacetic acid salt

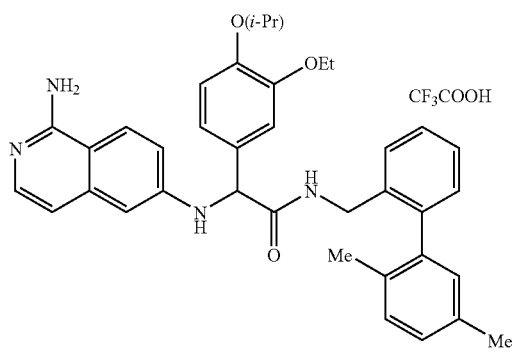

178A

2-((2,5-Dimethyl)phenyl)benzonitrile

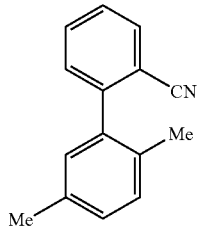

2,5-Dimethyl phenylboronic acid (90 mg, 0.60 mmol), 2-bromobenzonitrile (91 mg, 0.50 mmol), 2M sodium carbonate (1.0 mL, 2.00 mmol), palladium tetrakistriphenylphosphine (58 mg, 0.05 mmol) and toluene (3 mL) were combined in a tube. The mixture was degassed with nitrogen for 2 min, then was sealed and heated to 85° C. overnight. The reaction was cooled to rt, diluted with ethyl acetate, washed with water and brine, then dried ($Na_2SO_4$), filtered and concentrated. The residue was purified via silica gel chromatography eluting with 0-5% ethyl acetate/hexanes to provide 178A (103 mg). LC-MS: 208.17 $(M+H)^+$.

178B

2-((2,5-Dimethyl)phenyl)benzylamine trifluoroacetic acid salt

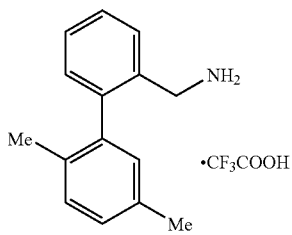

To 178A (104 mg, 0.50 mmol) in THF (3 mL) was added a 2M THF solution of $BH_3 \cdot Me_2S$ (1.0 mL, 2.0 mmol) and the reaction was refluxed for 1 h. The solution was cooled to rt, 1M HCl (1 mL) was added, and the reaction was heated to reflux for 10 min. The mixture was cooled to rt, concentrated and purified via preparative HPLC (eluting with MeOH/water/TFA) to provide 178B (110 mg). LC-MS: 212.20 $(M+H)^+$.

78C

Example 178: To Intermediate 3 (22 mg) in DMF (2 mL) was added EDC (16 mg), HOAT (6 mg), 178B (32 mg) and DIPEA (30 μL) and the reaction was heated to 60° C. in a sealed vial for 2 h then at rt overnight. The reaction was diluted with ethyl acetate and brine. The layers were separated and the organic layer was concentrated and purified via preparative HPLC (eluting with /MeOH/water/TFA) to provide Example 178 (12 mg). LC-MS: 589.44 $(M+H)^+$.

Example 179

N-(2-(Methylthio)benzyl)-2-(1-aminoisoquinolin-6-ylamino)-2-(3-ethoxy-4-isopropoxyphenyl)acetamide trifluoroacetic acid salt

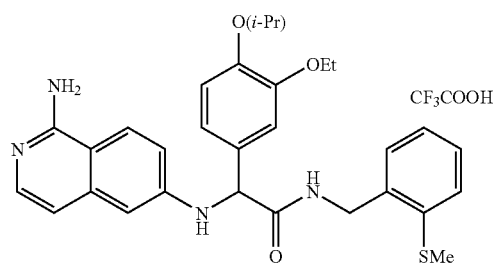

Example 179 (5.7 mg) was prepared from Intermediate 2 (15 mg) and commercially available 2-(methylthio)benzylamine (4.8 mg) following the general coupling/deprotection procedure in 42% overall yield. $^1$H NMR (400 MHz, $CD_3OD$) δ ppm 1.30 (d, J=6.15 Hz, 6H) 1.38 (t, J=7.03 Hz, 3H) 2.39 (s, 3H) 4.03 (q, J=7.03 Hz, 2H) 4.49 (m, 3H) 5.11 (s, 1H) 6.70 (d, J=2.20 Hz, 1H) 6.83 (d, J=7.03 Hz, 1H) 7.03 (m, 4H) 7.13 (d, J=2.20 Hz, 1H) 7.21 (m, 3H) 7.33 (d, J=7.03 Hz, 1H) 8.08 (d, J=9.23 Hz, 1H) 8.61 (s, 1H). LC-MS: 531.37 $(M+H)^+$.

Example 180

N-(2-(2,2,2-trifluoroethylthio)benzyl)-2-(1-aminoisoquinolin-6-ylamino)-2-(3-ethoxy-4-isopropoxyphenyl)acetamide trifluoroacetic acid salt

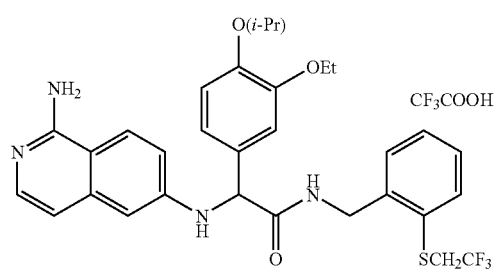

180A

2-(2,2,2-Trifluoroethylthio)benzoic acid

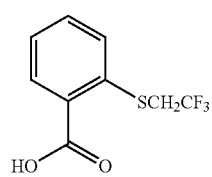

To methyl 2-(2,2,2-trifluoroethylthio)benzoate (250 mg, 1.00 mmol) in THF (5 mL) at 0° C. was added 1M LiOH (1 mL), followed by additional 1M LiOH (1 mL) 1 h later. The reaction was stirred at rt overnight. The reaction was concentrated, diluted with water (10 mL), and the pH was adjusted to pH 3 with 1N HCl. The resulting solid was filtered and dried to provide 180A (212 mg).

180B 2-(2,2,2-Trifluoroethylthio)benzamide

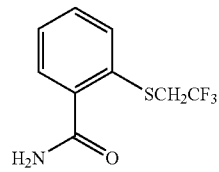

To 2-(2,2,2-trifluoroethylthio)benzoic acid (118 mg, 0.50 mmol) in DMF (5 mL) were added EDC (115 mg, 0.60 mmol) and HOBT (81 mg, 0.60 mmol) and the reaction was stirred for 2 h at rt then cooled to 0° C. Ammonium hydroxide (28%, 0.22 mL, 1.50 mmol) was added, the ice bath was removed, and the reaction was stirred at rt overnight. The reaction was concentrated and purified via preparative HPLC to provide 180B (69 mg). LC-MS: 236.14 (M+H)$^+$

180C (2-(2,2,2-Trifluoroethylthio)phenyl)methanamine trifluoroacetic acid salt

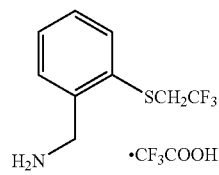

To 180B (69 mg, 0.29 mmol) in THF (5 mL) was added a 1M THF solution of BH$_3$.THF (1.5 mL, 1.5 mmol) and the reaction was refluxed for 5 h. After cooling to rt, 1M HCl (2 mL) was added, and the mixture was heated to reflux for 1 h. The reaction was cooled to rt, concentrated and purified via preparative HPLC to provide 180C (59 mg). LC-MS: 221.18 (M+H)$^+$.

180D

Example 180 (4 mg) was prepared from Intermediate 2 (15 mg) and 180C (7.5 mg) following the general coupling/deprotection procedure in 22% overall yield. LC-MS: 599.41 (M+H)$^+$.

Example 181

N-(3-Cyanobenzyl)-2-(1-aminoisoquinolin-6-ylamino)-2-(3-ethoxy-4-isopropoxyphenyl)acetamide trifluoroacetic acid salt

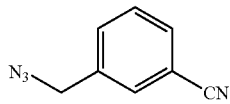

181A 3-(Azidomethyl)benzonitrile

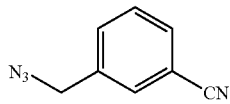

To a solution of 3-(hydroxymethyl)benzonitrile (1.00 g, 7.50 mmol) in THF (75 mL) at 0° C. was added DPPA (2.04 mL, 9.00 mmol) followed by DBU (1.23 mL, 8.25 mmol). After stirring at rt overnight, reaction was concentrated and purified via silica gel chromatography eluting with 30% ethyl acetate/hexanes to provide 181A (1.60 g) as a clear oil.

181B 3-(Aminomethyl)benzonitrile hydrochloride

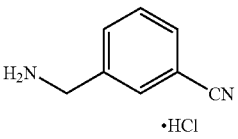

To 181A (25 mg, 1.58 mmol) in THF (8 mL) and water (2 mL) was added polymer-bound triphenylphospine (0.79 g, ca. 2.37 mmol) and the reaction was heated to 60° C. for 2 h. After cooling to rt, the reaction was filtered and concentrated. The resulting residue was dissolved in acetonitrile, and treated with 4M HCl/dioxane (0.79 mL). The mixture was concentrated, diluted with diethyl ether, and filtered to provide 181B (165 mg) as a white solid.

181C

Example 181: To Intermediate 3 (15 mg, 0.035 mmol) in DMF (1 mL) was added EDC (10.5 mg, 0.055 mmol), HOAT (6 mg, 0.044 mmol), DIPEA (40 μL, 0.23 mmol), and 181B (15 mg, 0.089 mol) and the reaction was heated to 60° C. in a sealed vial for 2.5 h. After cooling to rt overnight, the reaction was purified via preparative HPLC (MeOH/water/TFA). The major peak was collected and concentrated, then lyophilized (acetonitrile/water) overnight to provide Example 181 (11.5 mg) as a yellow solid. LC-MS: 510.33 (M+H)⁺.

Example 182

N-(3-(1H-imidazol-4-yl)benzyl)-2-(1-aminoisoquinolin-6-ylamino)-2-(3-ethoxy-4-isopropoxyphenyl)acetamide trifluoroacetic acid salt

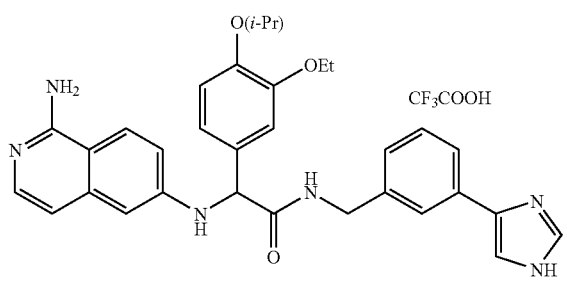

182A 3-(1-Trityl-1H-imidazol-4-yl)benzonitrile

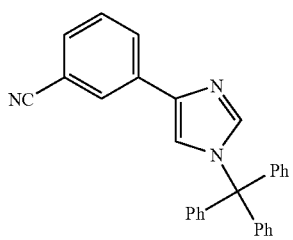

To 3-cyanoboronic acid (100 mg, 0.68 mmol) in DMF (2 mL) in a tube was added 4-iodo-1-trityl-1H-imidazole (247 mg, 0.57 mmol), 2M aqueous sodium carbonate (1.7 mL, 3.42 mmol), Pd₂(dba)₃ (21 mg, 0.023 mmol), and triphenylphosphine (9 mg, 0.034 mmol) and the reaction was degassed with nitrogen for 5 min. The tube was sealed and heated to 80° C. for 6 h, then cooled to rt. The mixture was filtered through Celite® and washed with ethyl acetate then concentrated. The resulting residue was purified via silica gel chromatography eluting with 10-30% ethyl acetate/hexanes to provide 182A (46 mg).

182B (3-(1H-Imidazol-4-yl)phenyl)methanamine dihydrochloride

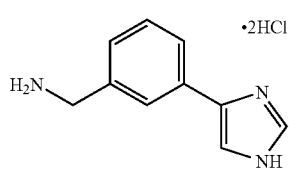

To 182A (46 mg, 0.11 mmol) in EtOH (2 mL) was added Pd/C (cat.) and 4M HCl/dioxane (70 μL) and the whole was hydrogenated at 60 psi overnight. The reaction was filtered through Celite® and concentrated to provide a mixture of 182B and triphenylmethane (ca. 30 mg). This mixture was taken onto the next step crude.

182C

Example 182 (8 mg) was prepared from Intermediate 2 (20 mg) and 182B (30 mg) following the general coupling/deprotection procedure in 29% overall yield. LC-MS: 551.30 (M+H)⁺.

Example 183

N-(2-(Methyl)benzyl)-2-(1-aminoisoquinolin-6-ylamino)-2-(3-ethoxy-4-isopropoxyphenyl)acetamide trifluoroacetic acid salt

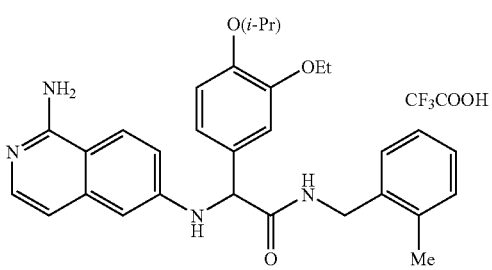

Example 183 (7.3 mg) was prepared from Intermediate 2 (15 mg) and commercially available 2-(methyl)benzylamine (7.2 mg) following the general coupling/deprotection procedure in 59% overall yield. ¹H NMR (400 MHz, CD₃OD) δ ppm 1.30 (d, J=6.15 Hz, 6H) 1.38 (t, J=7.03 Hz, 3H) 2.39 (s, 3H) 4.03 (q, J=7.03 Hz, 2H) 4.49 (m, 3H) 5.11 (s, 1H) 6.70 (d, J=2.20 Hz, 1H) 6.83 (d, J=7.03 Hz, 1H) 7.03 (m, 4H) 7.13 (d, J=2.20 Hz, 1H) 7.21 (m, 3H) 7.33 (d, J=7.03 Hz, 1H) 8.08 (d, J=9.23 Hz, 1H) 8.61 (s, 1H). LC-MS: 499.3 (M+H)⁺.

Example 184

N-(2-(Trifluoromethyl)benzyl)-2-(1-aminoisoquinolin-6-ylamino)-2-(3-ethoxy-4-isopropoxyphenyl)acetamide trifluoroacetic acid salt

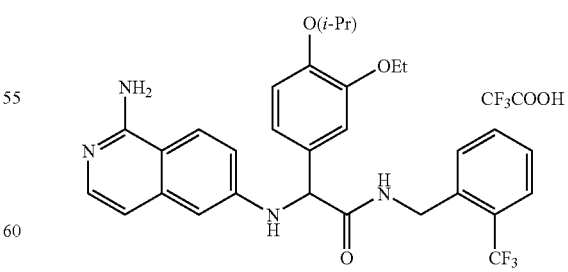

Example 184 (6.9 mg) was prepared from Intermediate 2 (18 mg) and commercially available 2-(trifluoromethyl)benzylamine (16 mg) following the general coupling/deprotection procedure in 42% overall yield. LC-MS: 553.3 (M+H)⁺.

Example 185

N-(2-(Ethoxy)benzyl)-2-(1-aminoisoquinolin-6-ylamino)-2-(3-ethoxy-4-isopropoxyphenyl)acetamide trifluoroacetic acid salt

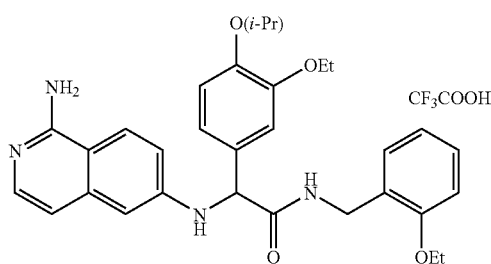

Example 185 (6.9 mg) was prepared from Intermediate 2 (18 mg) and commercially available 2-(ethoxy)benzylamine (14 mg) following the general coupling/deprotection procedure in 36% overall yield. LC-MS: 529.4 (M+H)$^+$.

Example 186

N-(2-(Methoxy)benzyl)-2-(1-aminoisoquinolin-6-ylamino)-2-(3-ethoxy-4-isopropoxyphenyl)acetamide trifluoroacetic acid salt

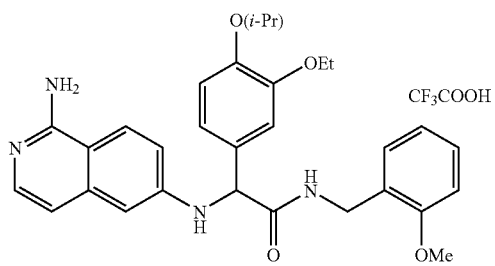

Example 186 (7.2 mg) was prepared from Intermediate 2 (15 mg) and commercially available 2-(methoxy)benzylamine (27 mg) following the general coupling/deprotection procedure in 46% overall yield. $^1$H NMR (400 MHz, CD$_3$OD) δ ppm 1.30 (d, J=6.15 Hz, 6H) 1.38 (t, J=7.03 Hz, 3H) 2.39 (s, 3H) 4.03 (q, J=7.03 Hz, 2H) 4.45 (m, 3H) 5.11 (m, 1H) 6.70 (d, J=2.20 Hz, 1H) 6.83 (d, J=7.03 Hz, 1H) 7.03 (m, 4H) 7.13 (d, J=2.20 Hz, 1H) 7.21 (m, 3H) 7.33 (d, J=7.03 Hz, 1H) 8.08 (d, J=9.23 Hz, 1H) 8.61 (s, 1H). LC-MS: 515.4 (M+H)$^+$.

Example 187

N-(2-(Isopropoxy)benzyl)-2-(1-aminoisoquinolin-6-ylamino)-2-(3-ethoxy-4-isopropoxyphenyl)acetamide trifluoroacetic acid salt

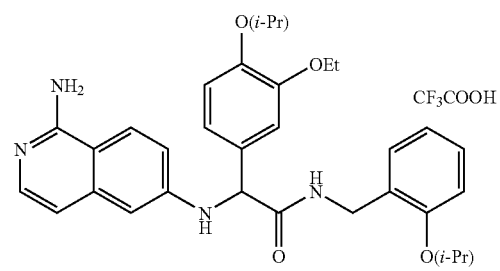

Example 187 (7.6 mg) was prepared from Intermediate 2 (15 mg) and commercially available 2-(isopropoxy)benzylamine (33 mg) following the general coupling/deprotection procedure in 46% overall yield. $^1$H NMR (400 MHz, CD$_3$OD) δ ppm 1.18 (d, J=6.15 Hz, 3H) 1.23 (d, J=5.71 Hz, 3H) 1.29 (d, J=6.15 Hz, 6H) 1.35 (t, J=7.03 Hz, 3H) 3.97 (m, 2H) 4.39 (m, 2H) 4.52 (m, 2H) 5.08 (s, 1H) 6.68 (d, J=2.20 Hz, 1H) 6.73 (t, J=7.47 Hz, 1H) 6.81 (d, J=7.03 Hz, 1H) 6.87 (d, J=8.35 Hz, 1H) 6.95 (d, J=7.91 Hz, 1H) 7.05 (m, 3H) 7.17 (m, 2H) 7.32 (d, J=7.03 Hz, 1H) 8.08 (d, J=9.23 Hz, 1H) 8.35 (s, 1H). LC-MS: 543.5 (M+H)$^+$.

Example 188

N-(2-Propoxybenzyl)-2-(1-aminoisoquinolin-6-ylamino)-2-(3-ethoxy-4-isopropoxyphenyl)acetamide trifluoroacetic acid salt

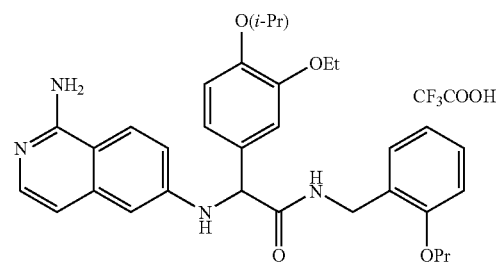

188A (2-Propoxyphenyl)methanamine trifluoroacetic acid salt

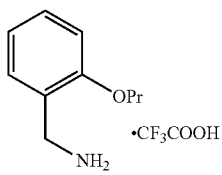

To commercially available 2-propoxybenzonitrile (161 mg, 1.00 mmol) in THF (5 mL) was added a 1M THF solution of BH$_3$.THF (4.00 mL, 4.00 mmol). After heating at reflux for 1 h, the reaction was cooled to rt and 1N HCl (4 mL) was slowly added. The reaction was heated to reflux for 30 min, then cooled to rt and concentrated. The resulting residue was purified via preparative HPLC eluting with MeOH/water/TFA to provide 188A (130 mg) as a white solid. LC-MS: 331.21 (2M+H)$^+$.

188B

Example 188 (2.1 mg) was prepared from Intermediate 2 (10 mg) and 188A (30 mg) following the general coupling/deprotection procedure in 19% overall yield. LC-MS: 543.3 (M+H)$^+$.

Example 189

N-(2-Isobutoxybenzyl)-2-(1-aminoisoquinolin-6-ylamino)-2-(3-ethoxy-4-isopropoxyphenyl)acetamide trifluoroacetic acid salt

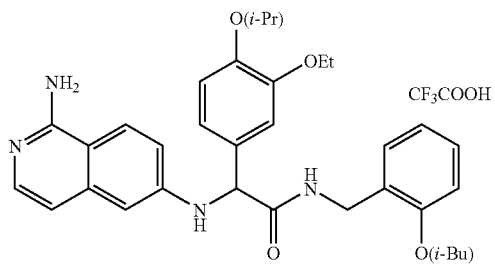

189A

2-Isobutoxybenzonitrile

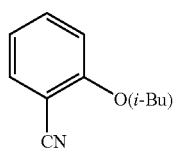

To 2-hydroxybenzonitrile (60 mg, 0.50 mmol) in DMF (5 mL) in a tube was added 1-bromo-2-methylpropane (140 mg, 1.0 mmol) and potassium carbonate (276 mg, 2.0 mmol). The tube was sealed and heated to 95° C. overnight. After cooling to rt, the reaction was diluted with ethyl acetate, washed with brine, then dried (Na$_2$SO$_4$), filtered and concentrated. The residue was purified via silica gel chromatography eluting with 0-10% ethyl acetate/hexanes to provide 189A (78 mg). LC-MS: 176.18 (M+H)$^+$.

189B (2-Isobutoxyphenyl)methanamine trifluoroacetic acid salt

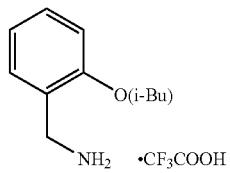

189B was prepared from 189A in 100% yield following a procedure analogous to that used in the preparation of 188A.

189C

Example 189 (3.6 mg) was prepared from Intermediate 2 (24 mg) and 189B (24 mg) following the general coupling/deprotection procedure in 13% overall yield. LC-MS: 557.36 (M+H)$^+$.

Example 190

N-(2-(Pentan-3-yloxy)benzyl)-2-(1-aminoisoquinolin-6-ylamino)-2-(3-ethoxy-4-isopropoxyphenyl)acetamide trifluoroacetic acid salt

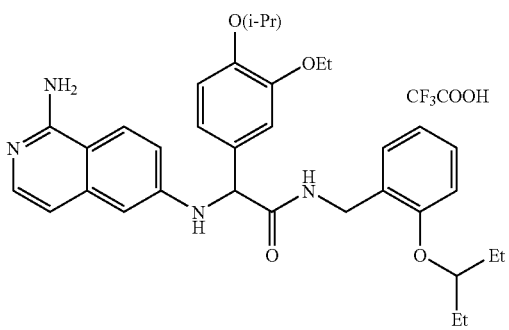

190A (2-(Pentan-3-yloxy)phenyl)methanamine trifluoroacetic acid salt

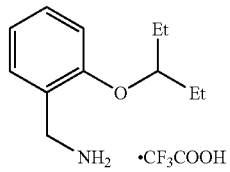

190A was prepared from 2-hydroxybenzonitrile in two steps (23% overall yield) following procedures analogous to those used in the preparation of 189B. LC-MS: 194.19 (M+H)$^+$.

190B

Example 190: To Intermediate 3 (20 mg) in DMF (1 mL) was added EDC (18 mg), HOAT (6 mg), 190A (15 mg) and DIPEA (40 µL) and the reaction was heated to 60° C. in a sealed vial for 2 h. After cooling to rt, the reaction was concentrated and purified via preparative HPLC (eluting with /MeOH/water/TFA) to provide Example 190 (6.5 mg). LC-MS: 571.38 (M+H)$^+$.

Example 191

N-(2-(Cyclopropylmethoxy)benzyl)-2-(1-aminoisoquinolin-6-ylamino)-2-(3-ethoxy-4-isopropoxyphenyl)acetamide trifluoroacetic acid salt

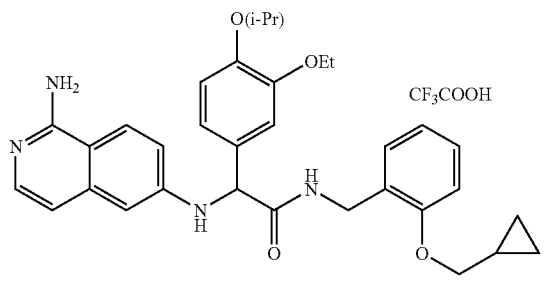

191a 2-(Cyclopropylmethoxy)benzonitrile

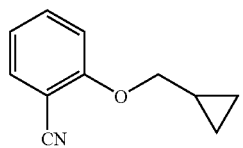

To 2-hydroxybenzonitrile (119 mg, 1.0 mmol) in acetonitrile (6 mL) was added (chloromethyl)cyclopropane (130 mg, 1.4 mmol) and potassium carbonate (540 mg, 4.0 mmol), and the reaction was heated to 75° C. overnight. After cooling to rt, the reaction was filtered and concentrated. The residue was purified via preparative HPLC eluting with MeOH/water/TFA to provide 191A (15 mg). LC-MS: 178.21 (M+H)$^+$.

191B (2-(Cyclopropylmethoxy)phenyl)methanamine trifluoroacetic acid salt

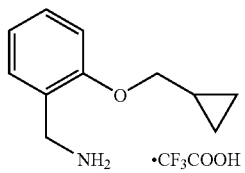

191B was prepared from 191A in 48% yield following a procedure analogous to that used in the preparation of 188A.

194C

Example 191 (2.9 mg) was prepared from Intermediate 2 (18 mg) and 191B (11 mg) following the general coupling/deprotection procedure in 14% overall yield. LC-MS: 555.36 (M+H)$^+$.

Example 192

N-(2-Isopropoxy-3-methylbenzyl)-2-(1-aminoisoquinolin-6-ylamino)-2-(3-ethoxy-4-isopropoxyphenyl)acetamide trifluoroacetic acid salt

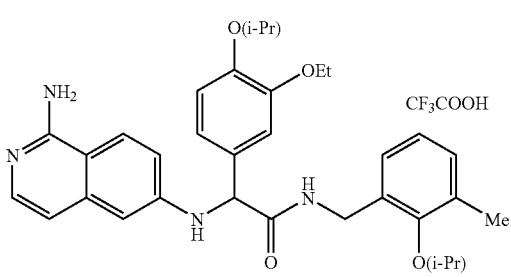

192A

2-Isopropoxy-3-methylbenzaldehyde

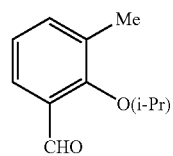

To 2-hydroxy-3-methylbenzaldehyde (680 mg, 5.0 mmol) in DMF (10 mL) was added 2-iodopropane (1.70 g, 10.0 mmol) and potassium carbonate (1.04 g, 7.5 mmol), and the reaction was heated to 50° C. for 72 h. After cooling to rt, the reaction was diluted with ethyl acetate, washed with water (3×50 mL) and brine (1×50 mL), then dried (Na$_2$SO$_4$), filtered and concentrated. The residue was purified via silica gel chromatography eluting with 0-10% ethyl acetate/hexanes to provide 192A (840 mg). LC-MS: 201.14 (M+Na)$^+$.

192B (2-Isopropoxy-3-methylphenyl)methanol

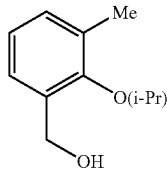

To 192A (159 mg, 0.9 mmol) in MeOH (5 mL) at 0° C. was added sodium borohydride (38 mg, 1.0 mmol). The ice bath was removed and the reaction was stirred for 30 min at rt. The reaction was then concentrated, diluted with ethyl acetate, washed with brine, then the organic layer was dried (Na$_2$SO$_4$), filtered and concentrated. The residue was purified via silica gel chromatography eluting with 0-30% ethyl acetate/hexanes to provide 192B (136 mg). LC-MS: 203.15 (M+Na)$^+$.

192C 1-(Azidomethyl)-2-isopropoxy-3-methylbenzene

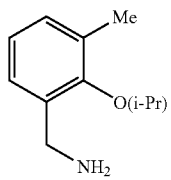

To 192B (131 mg, 0.73 mmol) in THF (3 mL) at 0° C. was added DPPA (240 mg, 0.87 mmol) in THF (0.5 mL) followed by DBU (134 mg, 0.88 mmol) in THF (0.5 mL). The ice bath was removed and the reaction was stirred overnight. The reaction was then concentrated and purified via preparative HPLC eluting with MeOH/water/TFA to provide 192C (38 mg).

192D (2-Isopropoxy-3-methylphenyl)methanamine trifluoroacetic acid salt

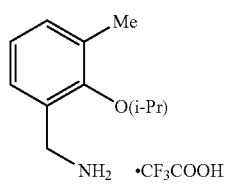

To 192C (15 mg, 0.073 mmol) in THF (2 mL) and water (1 mL) was added polymer-bound triphenylphosphine (50 mg, ~3.2 mmol/g, ca. 0.16 mmol). The reaction was heated to 60° C. for 1 h, then filtered and concentrated. The residue was purified via preparative HPLC eluting with MeOH/water/TFA to provide 192D (6 mg). LC-MS: 359.22 (2M+H)$^+$.

192E

Example 192 (4.5 mg) was prepared from Intermediate 2 (12 mg) and 192D (6 mg) following the general coupling/deprotection procedure in 34% overall yield. LC-MS: 557.3 (M+H)$^+$.

Example 193

N-(3-Chloro-2-isopropoxybenzyl)-2-(1-aminoisoquinolin-6-ylamino)-2-(3-ethoxy-4-isopropoxyphenyl)acetamide trifluoroacetic acid salt

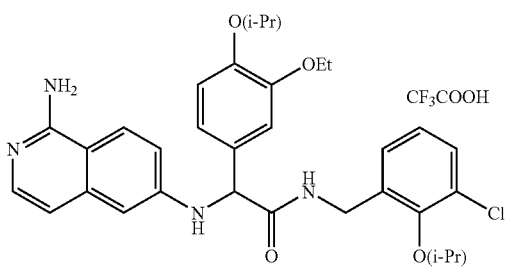

193A

3-Chloro-2-hydroxybenzonitrile Trifluoroacetic acid salt

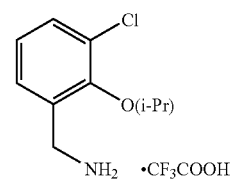

193A was prepared from 3-chloro-2-hydroxybenzaldehyde in four steps (6% overall yield) following procedures analogous to those used in the preparation of 192D. LC-MS: 193.21 (M+H)$^+$.

193B

Example 193: To Intermediate 3 (13 mg, 0.03 mmol) in DMF (1.5 mL) was added EDC (10 mg, 0.05 mmol), HOAT (3 mg, 0.02 mmol), DIPEA (20 µL, 0.11 mmol), and 193A (5 mg, 0.025 mmol) and the reaction was heated to 60° C. in a sealed vial for 4 h. After cooling to rt, the reaction was diluted with ethyl acetate and brine. The layers were separated and the organic layer was concentrated and purified via preparative HPLC (eluting with /MeOH/water/TFA) to provide Example 193 (7 mg). LC-MS: 577.37 (M+H)$^+$.

Example 194

N-(2-(2-Methylprop-1-enyl)benzyl)-2-(1-aminoisoquinolin-6-ylamino)-2-(3-ethoxy-4-isopropoxyphenyl)acetamide trifluoroacetic acid salt

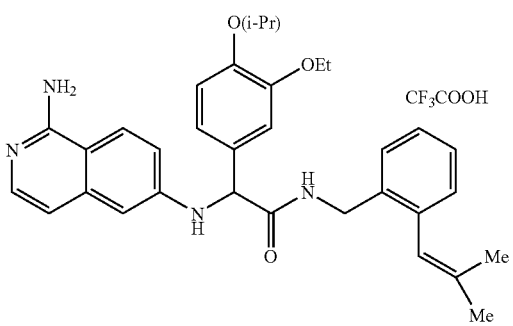

194A 2-(2-Methylprop-1-enyl)benzonitrile

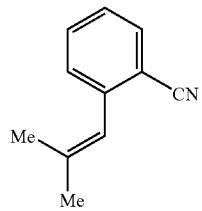

To isopropyl triphenylphosphonium iodide (2.41 g, 5.60 mmol) in THF (5 mL) at 0° C. was added 1M potassium tert-butoxide in THF (5.87 mL, 5.87 mmol). After stirring for 20 min, 2-cyanobenzaldehyde (500 mg, 3.81 mmol) in THF (5.4 mL) was added. After stirring for 30 min at 0° C., the reaction was quenched with saturated aqueous ammonium chloride. Ethyl acetate was added and the layers were separated. The organic layer was washed with water and brine, then dried (MgSO$_4$), filtered and concentrated. The resulting residue was purified via silica gel chromatography (0-50% ethyl acetate/hexanes) to provide 194A (211 mg).

194B (2-(2-Methylprop-1-enyl)phenyl)methanamine hydrochloride

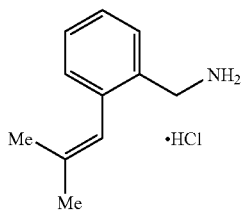

To 194A (100 mg, 0.64 mmol) in THF (6 mL) at 0° C. was added 1M LAH in THF (1.5 mL, 1.50 mmol). After 15 min, the ice bath was removed and the reaction was warmed to rt. After a total of 2 h, the reaction was slowly quenched with water (0.10 mL) in THF (1 mL), then stirred for 5 min. 15% NaOH (0.3 mL) was added, then after 5 min water (0.3 mL) in THF (1 mL) was added. The mixture was stirred for 5 min then filtered through Celite®, washing with THF, then concentrated. The resulting residue was diluted with diethyl ether and 4M HCl/dioxane (0.20 mL) was added. The resulting solid was filtered to provide 194B (45 mg) as a grey solid.

194C

Example 194 (9 mg) was prepared from Intermediate 2 (20 mg) and 194B (13 mg) following the general coupling/deprotection procedure in 41% overall yield. LC-MS: 539.33 (M+H)$^+$.

Example 195

N-(2-Isobutylbenzyl)-2-(1-aminoisoquinolin-6-ylamino)-2-(3-ethoxy-4-isopropoxyphenyl)acetamide trifluoroacetic acid salt

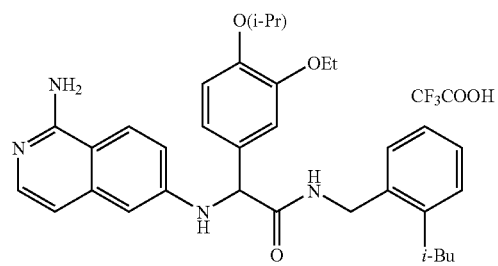

195A (2-Isobutylphenyl)methanamine hydrochloride

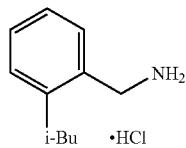

A solution of 194A (40 mg, 0.25 mmol) in MeOH (2 mL) was hydrogenated at 60 psi overnight in the presence of Pd(OH)$_2$/C (cat.) and 4M HCl/dioxane (0.26 mL). The mixture was filtered through Celite® and concentrated to provide 195A (35 mg) as a white solid. LC-MS: 164.11 (M+H)$^+$

195B

Example 195 (9 mg) was prepared from Intermediate 2 (20 mg) and 195A (13 mg) following the general coupling/deprotection procedure in 41% overall yield. LC-MS: 541.36 (M+H)$^+$.

Example 196

N-(2-(Ethylsulfonyl)benzyl)-2-(1-aminoisoquinolin-6-ylamino)-2-(3-ethoxy-4-isopropoxyphenyl)acetamide trifluoroacetic acid salt

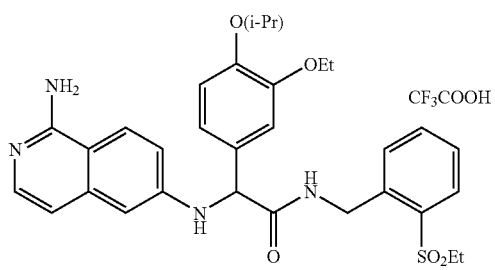

196A 2-(Ethylthio)benzonitrile

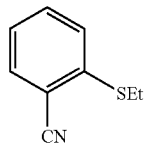

To 2-bromobenzonitrile (250 mg, 1.37 mmol) in THF (8 mL) at −78° C. was added a 1.9M solution of n-BuLi in hexanes (0.80 mL, 1.5 mmol). After stirring at the same temperature for 10 min, diethyl disulfide was added and the reaction was stirred for 15 min. The reaction was quenched with saturated aqueous ammonium chloride and was allowed to warm to rt. Ethyl acetate and water were added and the layers were separated. The organic layer was washed with brine then was dried (MgSO$_4$), filtered and concentrated to provide 196A as a yellow oil (193 mg, 87%). LC-MS: 329.25 (2M+H)$^+$.

196B 2-(Ethylsulfonyl)benzonitrile

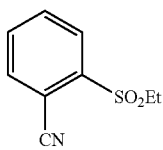

To 196A (193 mg, 1.18 mmol) in CH$_2$Cl$_2$ was added 75% MCPBA (817 mg, 3.55 mmol). After stirring at rt for 30 min, the reaction was diluted with CH$_2$Cl$_2$ and saturated aqueous NaHCO$_3$. The layers were separated and the organic layer was washed with saturated aqueous NaHCO$_3$ and brine, dried (MgSO$_4$), filtered then concentrated. The resulting residue was purified via preparative HPLC (MeOH/H$_2$O/TFA) to provide 196B (130 mg, 56%) as a yellow oil. LC-MS: 218.1 (M+23)$^+$.

196C (2-(Ethylsulfonyl)benzylamine

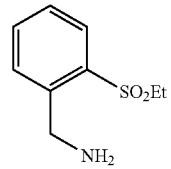

To 196B (120 mg, 0.615 mmol) in methanol (10 mL), conc. HCl (100 mg) was added followed by 10% Pd/C (10 mg). The mixture was hydrogenated using a hydrogen balloon for 16 h. The mixture was filtered, concentrated and dissolved in ethyl acetate. The solution was washed with saturated aqueous NaHCO$_3$ then brine. After separation, the organic layer was dried (Na$_2$SO$_4$), filtered, concentrated, and purified via silica get chromatography eluting with 10-40% ethyl acetate/hexanes to provide recovered starting material, 196B (38 mg), and 196C (18 mg, 21%, BORSM).

196D

Example 196 (10 mg) was prepared from Intermediate 2 (18 mg) and amine 196C (18 mg) following the general coupling/deprotection procedure in 49% overall yield. $^1$H NMR (400 MHz, CD$_3$OD) δ ppm 1.17 (t, J=7.47 Hz, 3H) 1.29 (d, J=6.15 Hz, 6H) 1.36 (t, J=7.03 Hz, 3H) 3.26 (q, J=7.18 Hz, 2H) 4.01 (m, 2 H) 4.53 (m, 1H) 4.74 (m, 2H) 5.09 (s, 1H) 6.64 (d, J=2.20 Hz, 1H) 6.80 (d, J=7.03 Hz, 1H) 6.96 (d, J=7.91 Hz, 1H) 7.05 (m, 2H) 7.18 (dd, J=9.23, 2.64 Hz, 1H) 7.34 (m, 2H) 7.48 (m, 2H) 7.86 (m, 1H) 8.07 (d, J=9.23 Hz, 1H) 8.65 (s, 1H). LC-MS: 577.4 (M+H)$^+$.

Example 197

N-(2-(Isopropylthio)benzyl)-2-(1-aminoisoquinolin-6-ylamino)-2-(3-ethoxy-4-isopropoxyphenyl)acetamide trifluoroacetic acid salt

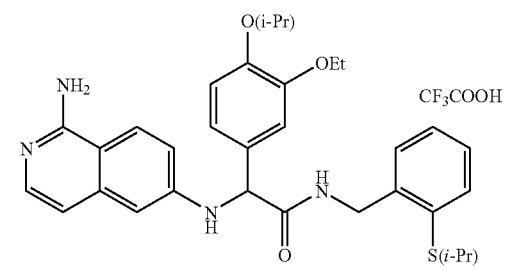

197A 2-(Isopropylthio)benzonitrile

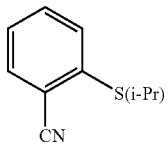

To 2-fluorobenzonitrile (605 mg, 5.00 mmol) in DMF (5 mL) in a tube was added sodium carbonate (2.12 g, 20.0 mmol) and propane-2-thiol (0.93 mL, 10.0 mmol). The tube was sealed and the reaction was heated to 80° C. overnight. After cooling to rt, the reaction was diluted with ethyl acetate and water. The layers were separated and the organic layer was washed with water and brine, then dried ($Na_2SO_4$), filtered and concentrated to provide 197A (780 mg). LC-MS: 200.00 $(M+Na)^+$.

197B (2-(Isopropylthio)phenyl)methanamine hydrochloride

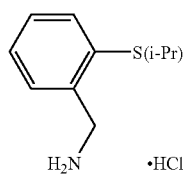

To 197A (354 mg, 2.00 mmol) in THF (4 mL) was added a 1M THF solution of $BH_3$.THF (5.0 mL, 5.0 mmol). After heating at reflux for 2 h, the reaction was cooled to rt and 1 N HCl (5 mL) was slowly added. The reaction was heated to reflux for 10 min, then cooled to rt and concentrated. The resulting residue was purified via preparative HPLCeluting with MeOH/water/TFA to provide 197B (500 mg) as a white solid. LC-MS: 182.05 $(M+H)^+$.

197C

Example 197 (2.6 mg) was prepared from Intermediate 2 (18 mg) and 197B (30 mg) following the general coupling/deprotection procedure in 13% overall yield. LC-MS: 559.24 $(M+H)^+$.

Example 198

N-(2-(Isopropylsulfonyl)benzyl)-2-(1-aminoisoquinolin-6-ylamino)-2-(3-ethoxy-4-isopropoxyphenyl)acetamide trifluoroacetic acid salt

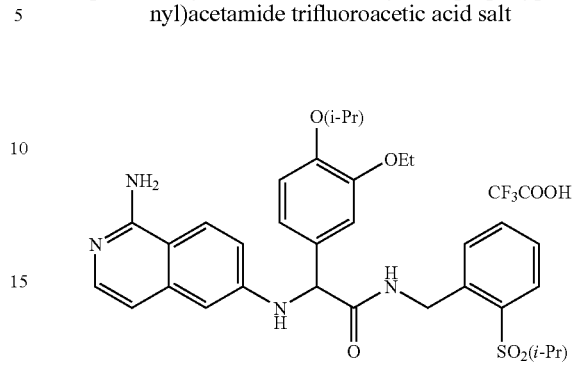

Example 198 (14 mg) was prepared from Intermediate 2 (24 mg) and Intermediate 14 (20 mg) following the general coupling/deprotection procedure in 60% overall yield. $^1$H NMR (400 MHz, $CD_3OD$) δ ppm 1.18 (d, J=7.03 Hz, 3H) 1.23 (d, J=6.59 Hz, 3H) 1.29 (t, J=6.81 Hz, 6H) 1.36 (t, J=7.03 Hz, 3H) 3.45 (m, 1H) 3.99 (m, 2H) 4.53 (m, 1H) 4.74 (m, 2H) 5.09 (s, 1H) 6.64 (d, J=2.20 Hz, 1H) 6.80 (d, J=7.03 Hz, 1H) 6.96 (d, J=7.91 Hz, 1H) 7.05 (m, 2H) 7.18 (dd, J=9.23, 2.20 Hz, 1H) 7.35 (m, 2H) 7.48 (m, 2H) 7.84 (m, 1H) 8.07 (d, J=9.23 Hz, 1H) 8.61 (t, J=6.15 Hz, 1H). LC-MS: 591.43 $(M+H)^+$.

Example 199

N-(2-(Isobutylsulfonyl)benzyl)-2-(1-aminoisoquinolin-6-ylamino)-2-(3-ethoxy-4-isopropoxyphenyl) acetamide trifluoroacetic acid salt

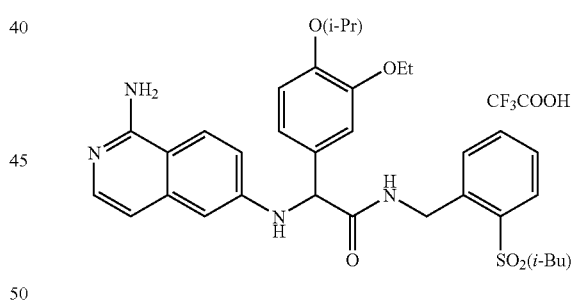

199A 2-(Isobutylsulfonyl)benzylamine hydrochloride salt

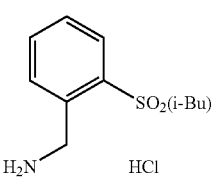

199A (173 mg) was prepared in three steps from 2-bromobenzonitrile (550 mg) and diisobutyl disulfide in 23% overall yield following procedures analogous to those used in the preparation of Intermediate 14. LC-MS: 224.20 (M+H)⁺.

199B

Example 199 (8 mg) was prepared from Intermediate 2 (24 mg) and amine 199A (21 mg) following the general coupling/deprotection procedure in 28% overall yield. $^1$H NMR (400 MHz, CD$_3$OD) δ ppm 1.01 (dd, J=6.59, 4.83 Hz, 6H) 1.30 (d, J=6.15 Hz, 6H) 1.36 (t, J=6.81 Hz, 3H) 2.17 (m, 1H) 3.19 (d, J=6.59 Hz, 2H) 4.00 (m, 2H) 4.53 (m, 1H) 4.74 (m, 2H) 5.10 (s, 1H) 6.65 (d, J=2.20 Hz, 1H) 6.80 (d, J=7.03 Hz, 1H) 6.97 (d, J=7.91 Hz, 1H) 7.05 (m, 2H) 7.18 (dd, J=9.23, 2.20 Hz, 1H) 7.33 (d, J=7.03 Hz, 2H) 7.46 (m, 2H) 7.89 (m, 1H) 8.07 (d, J=9.23 Hz, 1H). LC-MS: 605.4 (M+H)⁺.

Example 200

N-(2-(Propylsulfonyl)benzyl)-2-(1-aminoisoquinolin-6-ylamino)-2-(3-ethoxy-4-isopropoxyphenyl)acetamide trifluoroacetic acid salt

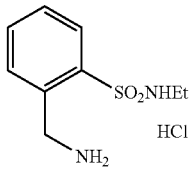

200A 2-(Propyl)benzylamine hydrochloride salt

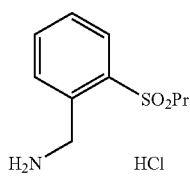

200A was prepared in three steps from 2-bromobenzonitrile and di-n-propyl disulfide following procedures analogous to those used in the preparation of Intermediate 14. LC-MS: 210.21 (M+H)⁺.

200B

Example 200 (9 mg) was prepared from Intermediate 2 (18 mg) and 200A (8 mg) following the general coupling/deprotection procedure in 43% overall yield. LC-MS: 591.45 (M+H)⁺.

Example 201

2-(1-Amino-isoquinolin-6-ylamino)-2-(3-ethoxy-4-isopropoxy-phenyl)-N-(2-ethylsulfamoyl-benzyl)-acetamide trifluoroacetic acid salt

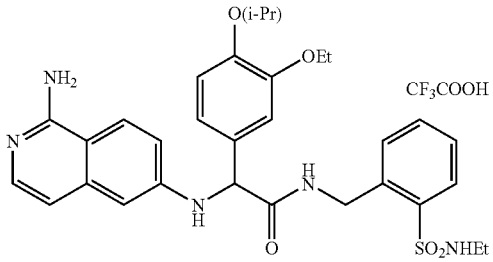

201A 2-(Aminomethyl)-N-ethylbenzenesulfonamide hydrochloride salt

To 2-cyanobenzene-1-sulfonyl chloride (201 mg, 1.00 mmol) in THF (10 mL), a 2M THF solution of ethylamine (5.0 mL, 10.0 mmol) was added. After stirring for 30 min, the reaction was concentrated then purified via preparative HPLC eluting with MeOH/H$_2$O/TFA to provide 2-cyano-N-ethyl-benzenesulfonamide (105 mg). The product was dissolved in MeOH (8 mL), conc. HCl (70 mg) was added, and the whole was hydrogenated at 30 psi for 3 h. The reaction was filtered and dried (Na$_2$SO$_4$) to provide 201A (123 mg, 49%). LC-MS: 215.1 (M+H)⁺.

201B

Example 201 (7 mg) was prepared from Intermediate 2 (18 mg) and 201A (13 mg) following the general coupling/deprotection procedure in 33% overall yield. $^1$H NMR (400 MHz, CD$_3$OD) δ ppm 0.98 (t, J=7.03 Hz, 3H) 1.29 (d, J=6.15 Hz, 6H) 1.36 (t, J=7.03 Hz, 3H) 2.79 (q, J=7.47 Hz, 2H) 3.98 (m, 2H) 4.52 (m, 1H) 4.78 (m, 2H) 5.08 (s, 1H) 6.64 (d, J=2.20 Hz, 1H) 6.78 (d, J=7.47 Hz, 1H) 6.96 (d, J=7.91 Hz, 1H) 7.05 (m, J=10.55, 2.64 Hz, 2H) 7.18 (dd, J=9.23, 2.20 Hz, 1H) 7.32 (d, J=7.03 Hz, 2H) 7.40 (m, 2H) 7.82 (m, 1H) 8.07 (d, J=9.23 Hz, 1H) 8.64 (t, J=6.15 Hz, 1H). LC-MS: 592.5 (M+H)⁺.

Example 202

2-(1-Amino-isoquinolin-6-ylamino)-N-(2-dimethylsulfamoyl-benzyl)-2-(3-ethoxy-4-isopropoxy-phenyl)-acetamide trifluoroacetic acid salt

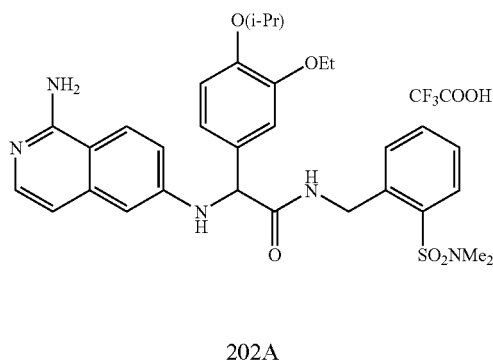

202A

2-Cyano-N,N-dimethylbenzenesulfonamide

To dimethylamine hydrochloride salt (1.01 g, 12.4 mmol) in water (5 mL), triethylamine (1.70 mL, 12.4 mmol) was added and followed by 2-cyanobenzene-1-sulfonyl chloride (500 mg, 2.47 mmol) and THF (1 mL). The reaction was stirred overnight and was then diluted with ethyl acetate and water. The layers were separated and the organic layer was washed with water and brine, then dried (MgSO$_4$), filtered and concentrated to provide 202A (335 mg, 65%) as a solid. LC-MS: 211.1 (M+H)$^+$.

202B 2-(Aminomethyl)-N,N-dimethylbenzenesulfonamide trifluoroacetic acid salt

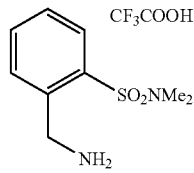

To 202A (335 mg, 1.60 mmol) in MeOH (8 mL), 10% Pd/C (170 mg) was added and followed by 4M solution of HCl in dioxane (1.6 mL, 6.40 mmol) and the whole was hydrogenated at 60 psi overnight. The reaction was filtered through Celite® and concentrated. The resulting residue was dissolved in EtOAc and water and the layers were separated. The organic layer was dried (MgSO$_4$) and concentrated to provide the starting material, 202A (135 mg). The aqueous layer was concentrated and purified via preparative HPLC (MeOH/H$_2$O/TFA) to provide 202B (99 mg, 32% BORSM). LC-MS: 215.1 (M+H)$^+$.

202C

Example 202 (7.9 mg) was prepared from Intermediate 2 (18.0 mg) and 202B (16.0 mg) following the general coupling/deprotection procedure in 45% overall yield. $^1$H NMR (400 MHz, CD$_3$OD) δ ppm 1.29 (m, 6H) 1.37 (t, J=6.81 Hz, 3H) 2.74 (s, 6H) 4.02 (m, 2H) 4.54 (m, 1H) 4.76 (m, 2H) 5.11 (s, 1H) 6.66 (d, J=2.20 Hz, 1H) 6.81 (d, J=6.59 Hz, 1H) 6.98 (d, J=8.35 Hz, 1H) 7.08 (m, 2H) 7.19 (dd, J=9.23, 2.20 Hz, 1H) 7.31 (m, 2H) 7.43 (m, 2H) 7.76 (m, 1H) 8.08 (d, J=9.23 Hz, 1H) 8.54 (s, 1H). LC-MS: 592.50 (M+H)$^+$.

Example 203

2-(1-Amino-isoquinolin-6-ylamino)-N-(2-cyclopropylsulfamoyl-benzyl)-2-(3-ethoxy-4-isopropoxy-phenyl)-acetamide trifluoroacetic acid salt

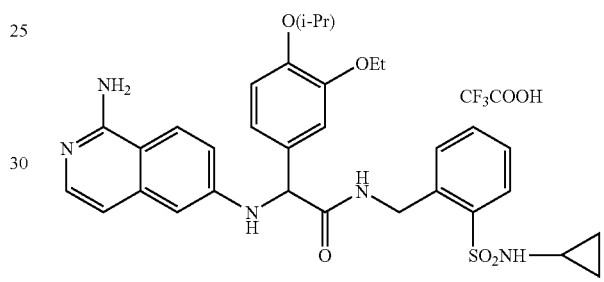

203A 2-(Aminomethyl)-N-cyclopropylbenzenesulfonamide hydrochloride salt

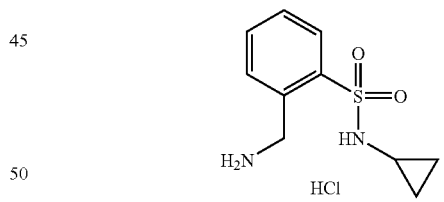

202A (100 mg) was prepared in two steps from commercially available 2-cyanobenzene-1-sulfonyl chloride (201 mg) and cyclopropanamine in 34% overall yield following a procedure analogous to that used in the preparation of 2-(aminomethyl)-N-ethylbenzenesulfonamide hydrochloride salt.

203B

Example 203 (9.0 mg) was prepared from Intermediate 2 (18.0 mg) and 203A (16.0 mg) following the general coupling/deprotection procedure in 42% overall yield. $^1$H NMR (400 MHz, CD$_3$OD) δ ppm 0.28 (m, 4H) 1.20 (d, J=6.15 Hz, 6H) 1.27 (t, J=7.03 Hz, 3H) 2.05 (m, 1H) 3.89 (m, 2H) 4.43 (m, 1H) 4.69 (m, 2H) 5.00 (s, 1H) 6.56 (d, J=2.20 Hz, 1H) 6.71 (d, J=7.03 Hz, 1H) 6.87 (d, J=7.91 Hz, 1H) 6.97 (m, 2H)

7.09 (dd, J=9.01, 2.42 Hz, 1H) 7.22 (dd, J=10.55, 7.03 Hz, 2H) 7.32 (m, 2H) 7.80 (m, 1H) 7.98 (d, J=9.23 Hz, 1H). LC-MS: 604.5 (M+H)$^+$.

Example 204

2-(1-Amino-isoquinolin-6-ylamino)-N-(2-cyclohexylsulfamoyl-benzyl)-2-(3-ethoxy-4-isopropoxyphenyl)-acetamide trifluoroacetic acid salt

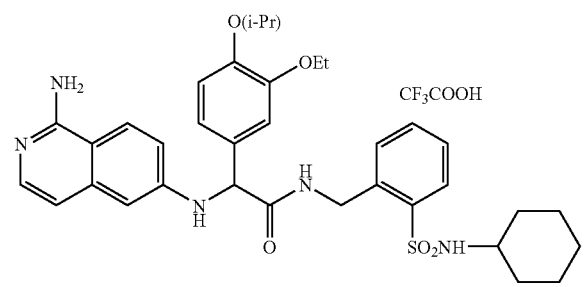

204A 2-(Aminomethyl)-N-cyclohexylbenzenesulfonamide hydrochloride salt

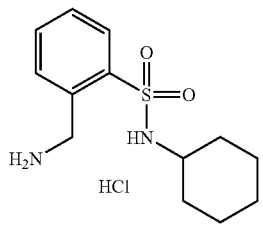

204A (127 mg) was prepared in two steps from commercially available 2-cyanobenzene-1-sulfonyl chloride (201 mg) and cyclohexanamine in 42% overall yield following a procedure analogous to that used in the preparation of 2-(aminomethyl)-N-ethylbenzenesulfonamide hydrochloride salt. LC-MS: 269.3 (M+H)$^+$.

204B

Example 204 (7.3 mg) was prepared from Intermediate 2 (18 mg) and 204A (22 mg) following the general coupling/deprotection procedure in 31% overall yield. LC-MS: 646.4 (M+H)$^+$.

Example 205

2-(1-Amino-isoquinolin-6-ylamino)-2-(3-ethoxy-4-isopropoxy-phenyl)-N-(2-isopropylsulfamoyl-benzyl)-acetamide trifluoroacetic acid salt

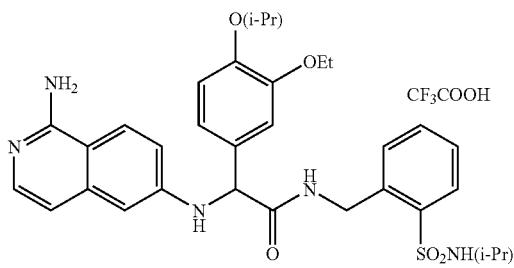

205A 2-(Aminomethyl)-N-isopropylbenzenesulfonamide hydrochloride salt

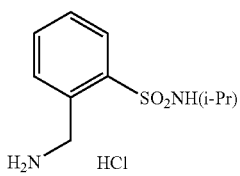

205A (188 mg) was prepared in two steps from commercially available 2-cyanobenzene-1-sulfonyl chloride (300 mg) and propan-2-amine in 47% overall yield following a procedure analogous to that used in the preparation of 2-(aminomethyl)-N-ethylbenzenesulfonamide hydrochloride salt. LC-MS: 229.26 (M+H)$^+$.

205B

Example 205 (9.0 mg) was prepared from Intermediate 2 (18 mg) and 205A (14 mg) following the general coupling/deprotection procedure in 50% overall yield. $^1$H NMR (400 MHz, CD$_3$OD) δ ppm 0.88 (dd, J=6.59, 3.95 Hz, 6H) 1.20 (d, J=6.15 Hz, 6H) 1.27 (t, J=7.03 Hz, 3H) 3.18 (m, 1H) 3.89 (m, 2H) 4.43 (m, 1H) 4.72 (m, 2H) 4.99 (s, 1H) 6.56 (d, J=2.20 Hz, 1H) 6.71 (d, J=7.03 Hz, 1H) 6.87 (d, J=7.91 Hz, 1H) 6.97 (m, 2H) 7.09 (dd, J=9.23, 2.20 Hz, 1H) 7.26 (m, 4H) 7.77 (m, 1H) 7.98 (d, J=9.23 Hz, 1H) 8.53 (s, 1H). LC-MS: 606.5 (M+H)$^+$.

Example 206

N-(2-(Morpholinosulfonyl)benzyl)-2-(1-aminoisoquinolin-6-ylamino)-2-(3-ethoxy-4-isopropoxyphenyl)acetamide trifluoroacetic acid salt

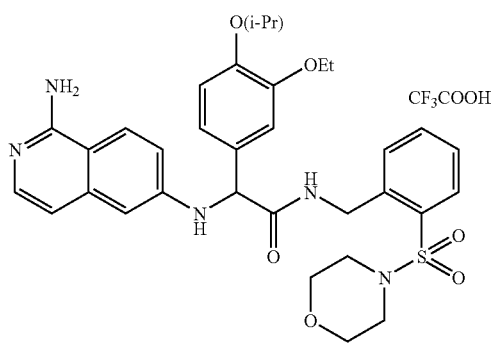

206A (2-(Morpholinosulfonyl)phenyl)methanamine hydrochloride salt

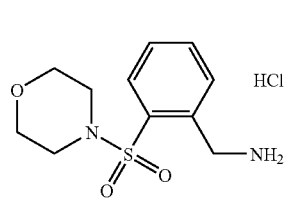

206A (233 mg) was prepared in two steps from commercially available 2-cyanobenzene-1-sulfonyl chloride (201 mg) and morpholine in 91% overall yield following a procedure analogous to that used in the preparation of 2-(aminomethyl)-N-ethylbenzenesulfonamide hydrochloride salt.

206B

Example 206 (5.8 mg) was prepared from Intermediate 2 (16 mg) and 206A (12 mg) following the general coupling/deprotection procedure in 35% overall yield. $^1$H NMR (400 MHz, CD$_3$OD) δ ppm 1.30 (d, J=6.15 Hz, 6H) 1.37 (t, J=7.03 Hz, 3H) 3.06 (m, 4H) 3.66 (t, J=4.61 Hz, 4H) 4.02 (m, 2H) 4.54 (m, 1H) 4.74 (m, 2H) 5.12 (s, 1H) 6.67 (d, J=2.20 Hz, 1H) 6.81 (d, J=7.03 Hz, 1H) 6.98 (d, J=7.91 Hz, 1H) 7.09 (m, 2H) 7.19 (dd, J=9.23, 2.20 Hz, 1H) 7.31 (m, 2H) 7.43 (m, 2H) 7.80 (m, 1H) 8.08 (d, J=9.23 Hz, 1H) 8.59 (t, J=6.15 Hz, 1H). LC-MS: 634.5 (M+H)$^+$.

Example 207

N-(2-(Piperidin-1-ylsulfonyl)benzyl)-2-(1-aminoisoquinolin-6-ylamino)-2-(3-ethoxy-4-isopropoxyphenyl)acetamide trifluoroacetic acid salt

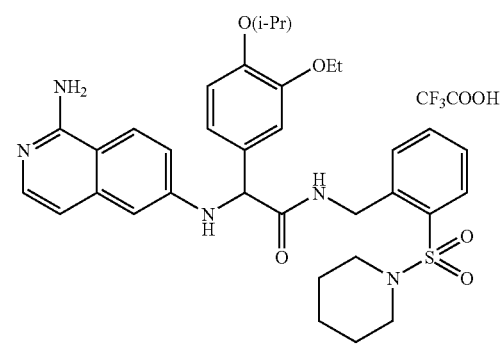

207A (2-(Piperidin-1-ylsulfonyl)phenyl)methanamine hydrochloride salt

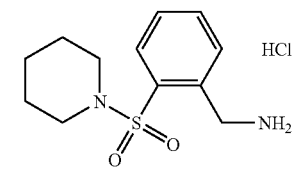

207A (255 mg) was prepared in two steps from commercially available 2-cyanobenzene-1-sulfonyl chloride (201 mg) and piperidine in 88% overall yield following a procedure analogous to that used in the preparation of 2-(aminomethyl)-N-ethylbenzenesulfonamide hydrochloride salt.

207B

Example 207 (4.5 mg) was prepared from Intermediate 2 (16 mg) and 207A (12 mg) following the general coupling/deprotection procedure in 23% overall yield. $^1$H NMR (400 MHz, CD$_3$OD) δ ppm 1.30 (d, J=6.15 Hz, 6H) 1.37 (t, J=6.81 Hz, 3H) 1.53 (m, 6H) 3.07 (m, 4H) 4.01 (m, 2H) 4.53 (m, 1H) 4.77 (m, 2H) 5.11 (s, 1H) 6.66 (d, J=2.20 Hz, 1H) 6.81 (d, J=7.03 Hz, 1H) 6.97 (d, J=8.35 Hz, 1H) 7.08 (m, 2H) 7.19 (dd, J=9.23, 2.20 Hz, 1H) 7.29 (m, 1H) 7.33 (d, J=7.03 Hz, 1H) 7.41 (m, 2H) 7.77 (m, 1H) 8.07 (d, J=9.23 Hz, 1H) 8.54 (s, 1H). LC-MS: 632.5 (M+H)$^+$.

Example 208

(R)-N-(2-(Piperidin-1-ylsulfonyl)benzyl)-2-(1-aminoisoquinolin-6-ylamino)-2-(3-ethoxy-4-isopropoxyphenyl)acetamide trifluoroacetic acid salt and

Example 209

(S)-N-(2-(Piperidin-1-ylsulfonyl)benzyl)-2-(1-aminoisoquinolin-6-ylamino)-2-(3-ethoxy-4-isopropoxyphenyl)acetamide trifluoroacetic acid salt

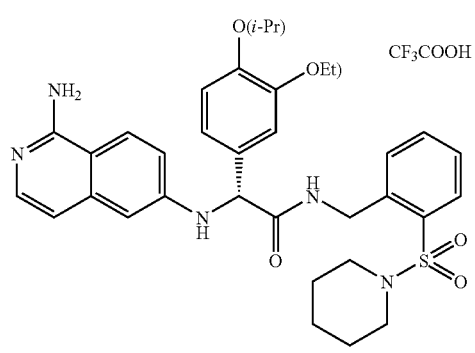

208

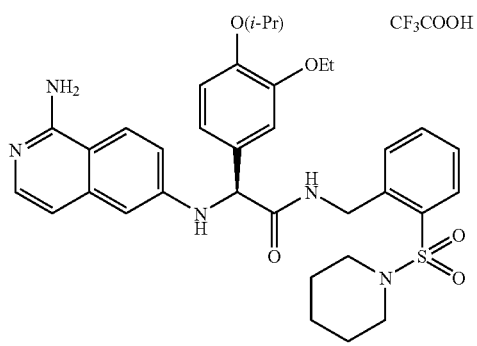

209

Example 207 (70 mg) was dissolved in isopropanol and the enantiomers were separated on a Chiralpak® AD column eluting with 75% heptane, 25% isopropanol, 0.1% DEA which eluted Example 208 (free base), followed by Example 209 (free base). Both products were repurified via preparative HPLC (MeOH/water/TFA) then lyophilized (acetonitrile/water) overnight to provide Example 208 (26.0 mg) [LC-MS: 632.38 (M+H)$^+$], and Example 209 (23.8 mg). [LC-MS: 632.38 (M+H)$^+$].

Example 210

N-(2-(4-(Trifluoromethyl)piperidin-1-ylsulfonyl)benzyl)-2-(1-aminoisoquinolin-6-ylamino)-2-(3-ethoxy-4-isopropoxyphenyl)acetamide trifluoroacetic acid salt

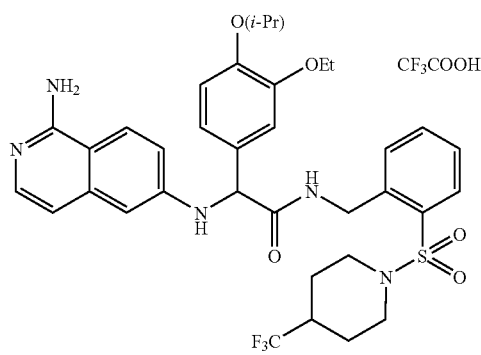

210A (2-(4-(Trifluoromethyl)piperidin-1-ylsulfonyl)phenyl)methanamine hydrochloride

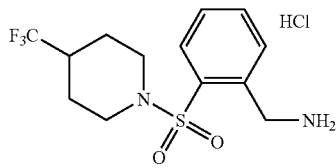

To 2-cyanobenzene-1-sulfonyl chloride (201 mg, 1.00 mmol) in THF (5 mL), triethylamine (0.84 mL, 6.00 mmol) and 4-trifluoromethylpiperidine hydrochloride (284 mg, 1.50 mmol) were added. After stirring for 2 h, the reaction was concentrated and diluted with ethyl acetate and washed with water. After drying (Na$_2$SO$_4$), filtering, and concentrating, the residue was purified via silica gel chromatography eluting with 45% ethyl acetate/hexanes to provide 2-(4-(trifluoromethyl)piperidin-1-ylsulfonyl)benzonitrile [95 mg, LC-MS: 319.19 (M+H)$^+$]. The product (52 mg) was dissolved in MeOH (5 mL), conc. HCl (25.0 mg) was added, and the whole was hydrogenated at 50 psi overnight. The reaction was concentrated and purified via preparative HPLC (CH$_3$CN/water/TFA) to provide 210A. LC-MS: 323.21 (M+H)$^+$.

210B

Example 210 (24 mg) was prepared from Intermediate 2 (20 mg) and 210A (18 mg) following the general coupling/deprotection procedure in 32% overall yield. LC-MS: 700.50 (M+H)$^+$.

Example 211

N-(2-(4,4-difluoropiperidin-1-ylsulfonyl)benzyl)-2-(1-aminoisoquinolin-6-ylamino)-2-(3-ethoxy-4-isopropoxyphenyl)acetamide trifluoroacetic acid salt

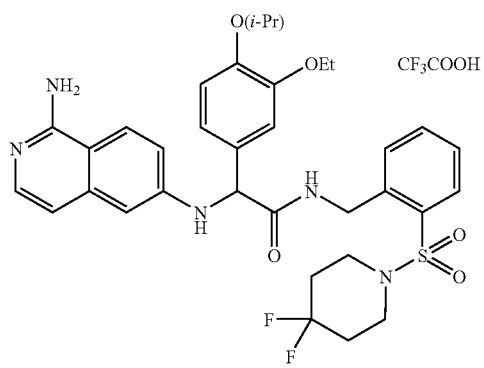

211A (2-(4,4-Difluoropiperidin-1-ylsulfonyl)phenyl)methanamine hydrochloride

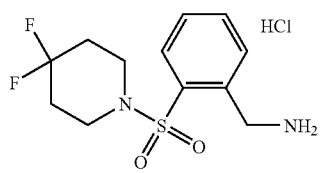

(2-(4,4-Difluoropiperidin-1-ylsulfonyl)phenyl)methanamine hydrochloride (81 mg) was prepared in two steps from commercially available 2-cyanobenzene-1-sulfonyl chloride (201 mg) and 4,4-difluoropiperidine (316 mg) in 25% overall yield following a procedure analogous to that used in the preparation 210A. LC-MS: 291.19 (M+H)$^+$.

211B

Example 211 (13.2 mg) was prepared from Intermediate 2 (30 mg) and 211A (32 mg) following the general coupling/deprotection procedure in 33% overall yield. LC-MS: 668.45 (M+H)$^+$.

Example 212

N-(2-(Pyrrolidine-1-carbonyl)benzyl)-2-(1-aminoisoquinolin-6-ylamino)-2-(3-ethoxy-4-isopropoxyphenyl)acetamide trifluoroacetic acid salt

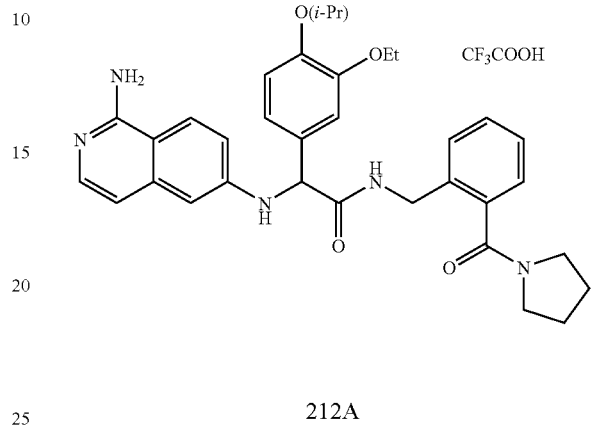

212A 2-(Pyrrolidine-1-carbonyl)benzonitrile

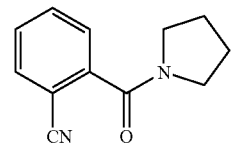

To 2-cyanobenzoic acid (294 mmol) in acetonitrile (2 mL) were added EDC (460 mg, 2.40 mmol), HOAT (37 mg, 0.27 mmol), and DIPEA (0.70 mL, 4.00 mmol) and pyrrolidine (170 mg, 2.40 mmol) and the reaction was stirred at rt overnight. The reaction was concentrated and purified via silica gel chromatography (0-70% ethyl acetate/hexanes) to provide 212A (65 mg). LC-MS: 201.24 (M+H)$^+$.

212B (2-(Aminomethyl)phenyl)(pyrrolidin-1-yl)methanone trifluoroacetic acid salt

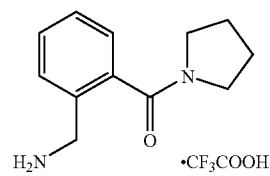

To 212A (65 mg) in MeOH (5 mL) was added Raney-Ni (slurry in water, cat. amount) and the reaction was hydrogenated at 60 psi for 22 h. The reaction was filtered, concentrated, and purified via preparative HPLC to provide 212B (60 mg). LC-MS: 205.27 (M+H)$^+$.

212C

Example 212 (8.4 mg) was prepared from Intermediate 2 (24 mg) and 212B (20 mg) following the general coupling/deprotection procedure in 30% overall yield. LC-MS: 582.48 (M+H)⁺.

Example 213

N-(2-(Piperidine-1-carbonyl)benzyl)-2-(1-aminoisoquinolin-6-ylamino)-2-(3-ethoxy-4-isopropoxyphenyl)acetamide trifluoroacetic acid salt

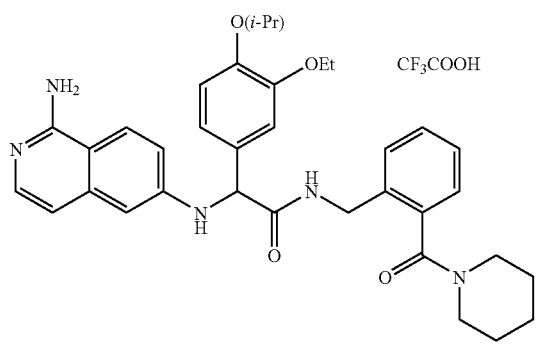

213A (2-(Aminomethyl)phenyl)(piperidin-1-yl)methanone trifluoroacetic acid salt

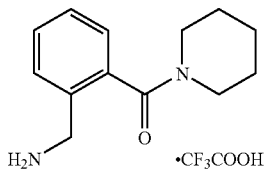

213A (49 mg) was prepared in two steps from 2-cyanobenzoic acid and piperidine in 7% overall yield following procedures analogous to those used in the preparation of 212B (with the exception that HOBT was used instead of HOAT in the first step). LC-MS: 219.3 (M+H)⁺.

213B

Example 213 (15.7 mg) was prepared from Intermediate 2 (50 mg) and 213A (22 mg) following the general coupling/deprotection procedure in 28% overall yield. LC-MS: 596.43 (M+H)⁺.

Example 214

2-((2-(1-Aminoisoquinolin-6-ylamino)-2-(3-ethoxyisopropoxy-phenyl)acetamido)methyl)-N,N-dimethylbenzamide trifluoroacetic acid salt

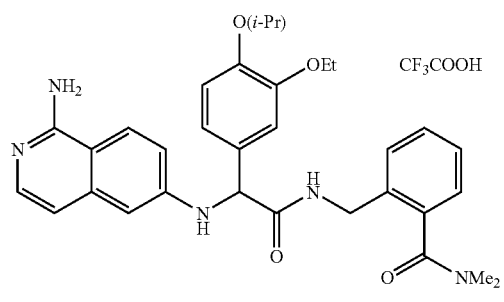

214A 2-(Aminomethyl)-N,N-dimethylbenzamide trifluoroacetic acid salt

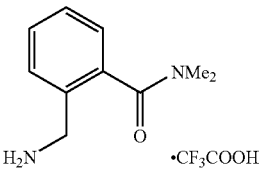

214A (82 mg) was prepared in two steps from 2-cyanobenzoic acid and dimethylamine hydrochloride in 36% overall yield following procedures analogous to those used in the preparation of 212B. LC-MS: 179.13 (M+H)⁺.

214B

Example 214 (35.6 mg) was prepared from Intermediate 2 (72 mg) and 214A (57 mg) following the general coupling/deprotection procedure in 45% overall yield. LC-MS: 556.45 (M+H)⁺.

Example 215

2-((2-(1-Aminoisoquinolin-6-ylamino)-2-(3-ethoxy-4-isopropoxyphenyl)acetamido)methyl)-N-ethylbenzamide trifluoroacetic acid salt

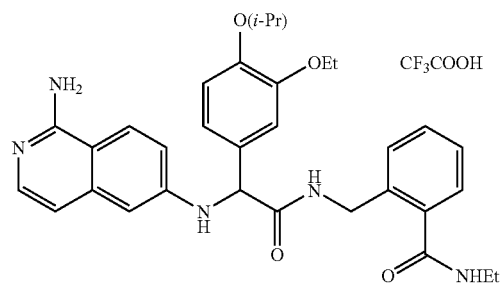

215A

N-Ethyl-2-(hydroxymethyl)benzamide

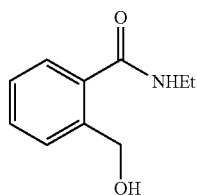

To ethylamine hydrochloride (162 mg, 2.00 mmol) in methylene chloride (4 mL) at 0° C. was added 1M trimethylaluminum in hexane (1.0 mL, 1.0 mmol). The ice bath was removed, and after stirring for 20 min, isobenzofuran-1(3H)-one (268 mg, 2.0 mmol) in methylene chloride (3 mL) was added. The mixture was stirred at rt for 2 h, then was heated to 40° C. for 4 h, then at 35° C. overnight. After cooling to rt, the reaction was diluted with ethyl acetate and water. The layers were separated and the organic layer was washed with brine, then dried ($Na_2SO_4$), filtered and concentrated. The residue was purified via silica gel chromatography eluting with 0-80% ethyl acetate/hexanes to provide 215A (245 mg). LC-MS: 180.18 $(M+H)^+$.

215B 2-(Azidomethyl)-N-ethylbenzamide

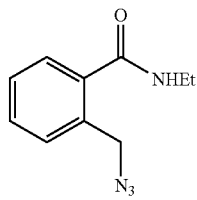

To 215A (89 mg, 0.50 mmol) in THF (2 mL) at 0° C. was added DPPA (165 mg, 0.60 mmol) in THF (0.5 mL) followed by DBU (92 mg, 0.60 mmol) in THF (0.5 mL). The ice bath was removed and the reaction was stirred overnight. The reaction was then concentrated and purified via silica gel chromatography to provide 215B (71 mg).

215C 2-(Aminomethyl)-N-ethylbenzamide trifluoroacetic acid salt

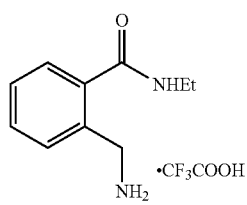

To 215B (40 mg, 0.20 mmol) in THF (2 mL) and water (0.5 mL) was added triphenylphosphine (polymer-bound, ~3.2 mmol/g) (200 mg, ca. 0.60 mmol). The reaction was heated to 50° C. for 1 h, then filtered and concentrated. The residue was purified via preparative HPLC eluting with MeOH/water/TFA to provide 215C (10 mg). LC-MS: 179.22 $(M+H)^+$.

215D

Example 215: To Intermediate 3 (14 mg) in DMF (1 mL) was added EDC (13 mg), HOAT (5 mg), 215C (10 mg) and DIPEA (30 µL) and the reaction was heated to 60° C. in a sealed vial for 2 h then stirred at rt overnight. The reaction was concentrated and purified via preparative HPLC (eluting with /MeOH/water/TFA) to provide Example 215 (4.0 mg). LC-MS: 556.35 $(M+H)^+$.

Example 216

2-((2-(1-Aminoisoquinolin-6-ylamino)-2-(3-ethoxy-4-isopropoxyphenyl)acetamido)methyl)-N-isopropylbenzamide trifluoroacetic acid salt

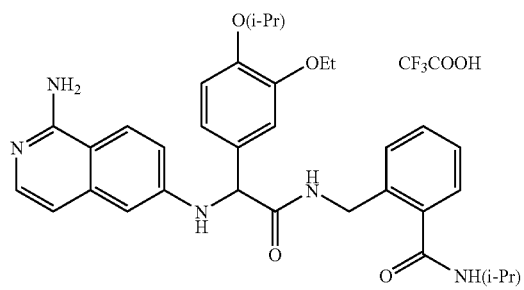

216A 2-(Aminomethyl)-N-isopropylbenzamide trifluoroacetic acid salt

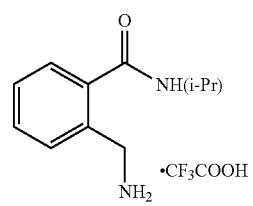

216A was prepared from isobenzofuran-1(3H)-one and isopropylamine in three steps (9% overall yield) following procedures analogous to those used in the preparation of 2-(aminomethyl)-N-ethylbenzamide trifluoroacetic acid salt. LC-MS: 193.21 $(M+H)^+$.

216B

Example 216: To Intermediate 3 (19 mg) in DMF (2 mL) was added EDC (16 mg), HOAT (6 mg), 216A (27 mg) and DIPEA (30 µL) and the reaction was heated to 60° C. in a sealed vial for 2 h. After cooling to rt, the reaction was diluted with ethyl acetate and brine. The layers were separated and the organic layer was concentrated and purified via preparative HPLC (eluting with /MeOH/water/TFA) to provide Example 216 (12.2 mg). LC-MS: 570.43 (M+H)⁺.

Example 217

2-((2-(1-Aminoisoquinolin-6-ylamino)-2-(3-ethoxy-4-isopropoxyphenyl)-acetamido)methyl)-N-methyl-benzamide trifluoroacetic acid salt

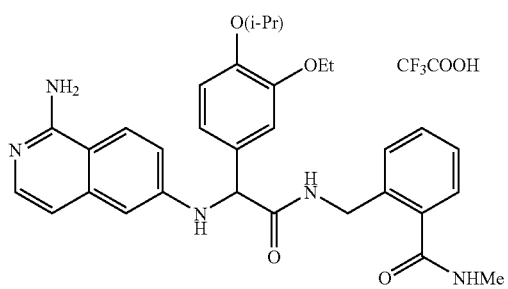

217A 2-(Aminomethyl)-N-methylbenzamide trifluoroacetic acid salt

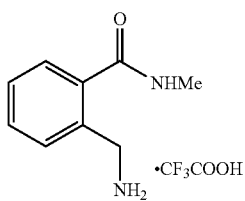

217A was prepared from isobenzofuran-1(3H)-one and methylamine hydrochloride in three steps following procedures analogous to those used in the preparation of 2-(aminomethyl)-N-ethylbenzamide trifluoroacetic acid salt. LC-MS: 165.21 (M+H)⁺.

217B

Example 217: To Intermediate 3 (18 mg) in DMF (1 mL) was added EDC (16.5 mg), HOAT (5.4 mg), 217A (24 mg) and DIPEA (30 µL) and the reaction was heated to 60° C. in a sealed vial for 2 h. After cooling to rt, the reaction was diluted with ethyl acetate and brine. The layers were separated and the organic layer was concentrated and purified via preparative HPLC (eluting with /MeOH/water/TFA) to provide Example 217 (6.0 mg). LC-MS: 542.33 (M+H)⁺.

Example 218

N-(2-(tert-Butylsulfonyl)benzyl)-2-(1-aminoisoquinolin-6-ylamino)-2-(3-ethoxy-4-isopropoxyphenyl)acetamide trifluoroacetic acid salt

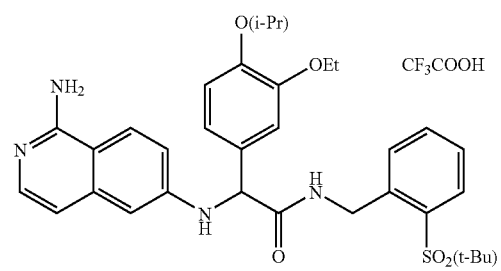

218A 2-(tert-Butylsulfonyl)benzonitrile

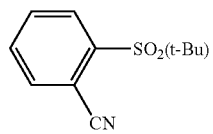

To 2-fluorobenzonitrile (0.45 mL, 4.13 mmol) in DMF (20 mL) was added sodium-2-methyl-2-propanethiolate (90%, 617 mg, 4.96 mmol). After stirring for 5 min at rt, the reaction was diluted with ethyl acetate and water. The layers were separated and the organic layer was washed with 1N HCl (3×), water (3×) and brine (1×). The organic layer was then dried (MgSO₄), filtered and concentrated. The resulting residue was dissolved in CH₂Cl₂ (20 mL) and MCPBA (~75%, 3.30 g, ca. 14.0 mmol) was added. After stirring at rt for 3 h, 1 N NaOH was added and the mixture was stirred for 10 min. The layers were separated and the organic layer was washed with 1N NaOH (3×) and brine (1×), then was dried (MgSO₄), filtered and concentrated to provide 218A (812 mg) as a white solid.

218B (2-(tert-Butylsulfonyl)phenyl)methanamine hydrochloride

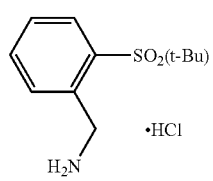

To 218A (400 mg, 1.79 mmol) in refluxing THF (18 mL), a 2M THF solution of BH₃.SMe₂ (2.70 mL, 5.37 mmol) was added. After heating at reflux for 2 h, the reaction was cooled to rt and 6M HCl (1.00 mL) was slowly added. The reaction was heated to reflux for 30 min, then cooled to rt, concentrated and azeotroped (3×) with THF/MeOH on a rotary evaporator. The resulting residue was diluted with THF and filtered to provide 218B (285 mg) as a white solid. LC-MS: 228.13 (M+H)+.

218C

Example 218 (5 mg) was prepared from Intermediate 3 (15 mg) and 218B (11 mg) following the general coupling/deprotection procedure in 33% overall yield. LC-MS: 605.27 (M+H)+.

Example 219

N-(2-(Cyclopropylsulfonyl)benzyl)-2-(1-aminoisoquinolin-6-ylamino)-2-(3-ethoxy-4-isopropoxyphenyl)acetamide trifluoroacetic acid salt

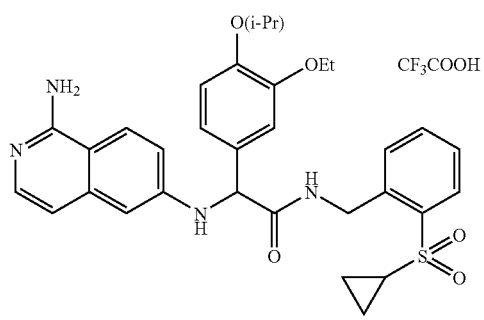

Example 219 (183 mg) was prepared from Intermediate 2 (282 mg) and Intermediate 7 (115 mg) following the general coupling/deprotection procedure in 66% overall yield. $^1$H NMR (400 MHz, CD$_3$OD) δ ppm 1.10 (m, 4H) 1.29 (t, J=6.59 Hz, 6H) 1.36 (t, J=7.03 Hz, 3H) 2.81 (m, 1H) 4.00 (m, 2H) 4.53 (m, 1H) 4.85 (m, 2H) 5.11 (s, 1H) 6.66 (d, J=2.20 Hz, 1H) 6.81 (d, J=7.03 Hz, 1H) 6.96 (d, J=8.35 Hz, 1H) 7.06 (m, 2H) 7.18 (dd, J=9.23, 2.64 Hz, 1H) 7.35 (m, 2H) 7.46 (m, 2H) 7.81 (m, 1H) 8.08 (d, J=9.23 Hz, 1H) 8.63 (t, J=6.15 Hz, 1H). LC-MS: 589.40 (M+H)+.

Example 220

(R)-N-(2-(Cyclopropylsulfonyl)benzyl)-2-(1-aminoisoquinolin-6-ylamino)-2-(3-ethoxy-4-isopropoxyphenyl)acetamide trifluoroacetic acid salt and Example 221

(S)-N-(2-(Cyclopropylsulfonyl)benzyl)-2-(1-aminoisoquinolin-6-ylamino)-2-(3-ethoxy-4-isopropoxyphenyl)acetamide trifluoroacetic acid salt

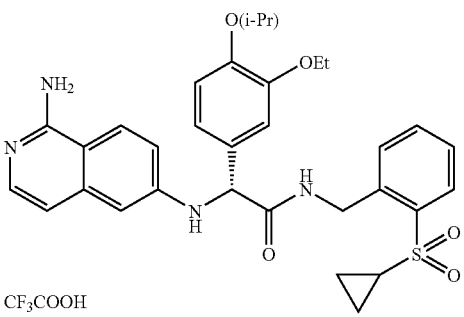

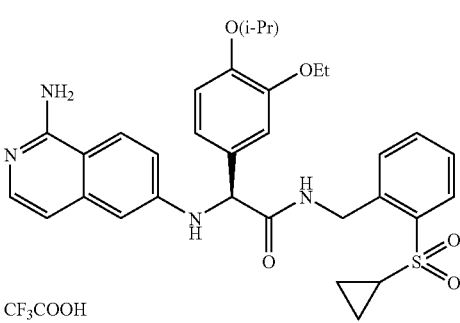

Example 219 (160 mg) was dissolved in MeOH (13 mL), EtOH (3 mL) and heptane (12 mL) and the enantiomers were separated on a Chiralpak® AD column eluting with 70% heptane, 30% 1:1 MeOH/EtOH, 0.1% DEA which eluted Example 220 (free base), followed by Example 221 (free base). Both products were repurified via preparative HPLC (MeOH/water/TFA) then lyophilized (acetonitrile/water) overnight to provide Example 221 (35.2 mg) [LC-MS: 589.45 (M+H)+], and Example 220 (40.0 mg) [LC-MS: 589.46 (M+H)+].

Example 222

N-(2-(Cyclopropylsulfonyl)benzyl)-2-(1-aminoisoquinolin-6-ylamino)-2-(3-ethoxy-4-isopropoxyphenyl)-N-methylacetamide trifluoroacetic acid salt

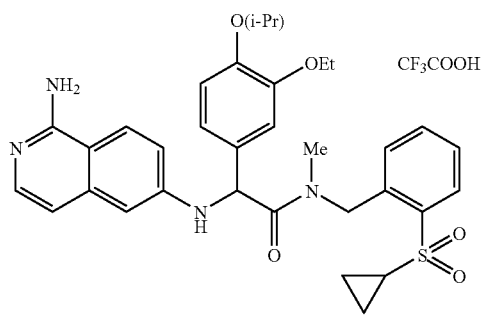

Example 222 (183 mg) was prepared from Intermediate 2 (100 mg) and Intermediate 8 (58 mg) following the general coupling/deprotection procedure in 48% overall yield. LC-MS: 603.44 (M+H)$^+$.

Example 223

(S)-N-(2-(Cyclopropylsulfonyl)benzyl)-2-(1-aminoisoquinolin-6-ylamino)-2-(3-ethoxy-4-isopropoxyphenyl)-N-methylacetamide trifluoroacetic acid salt and

Example 224

(R)-N-(2-(Cyclopropylsulfonyl)benzyl)-2-(1-aminoisoquinolin-6-ylamino)-2-(3-ethoxy-4-isopropoxyphenyl)-N-methylacetamide trifluoroacetic acid salt

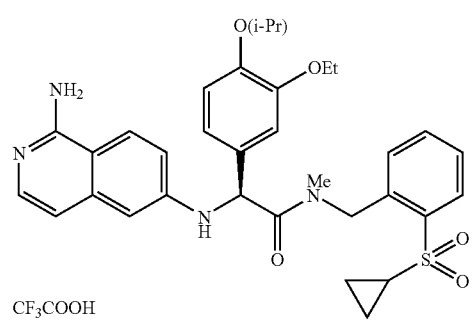

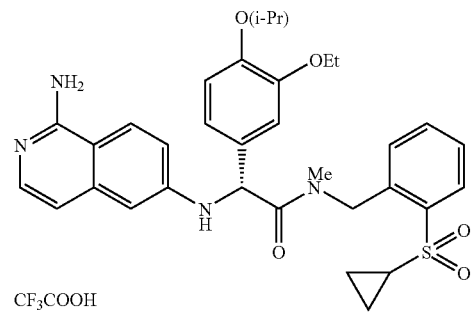

Example 222 (75 mg) was dissolved in isopropyl alcohol and the enantiomers were separated on a Chiralpak® AD column eluting with 40% heptane, 60% isopropyl alcohol, 0.1% DEA which eluted Example 223 (free base), followed by Example 224 (free base). Both products were repurified via preparative HPLC (MeOH/water/TFA) then lyophilized (acetonitrile/water) overnight to provide Example 223 (31.0 mg) [LC-MS: 603.43 (M+H)$^+$], and Example 224 (21.0 mg) [LC-MS: 603.42 (M+H)$^+$].

Example 225

N-(2-(Cyclopropylthio)benzyl)-2-(1-aminoisoquinolin-6-ylamino)-2-(3-ethoxy-4-isopropoxyphenyl)acetamide trifluoroacetic acid salt

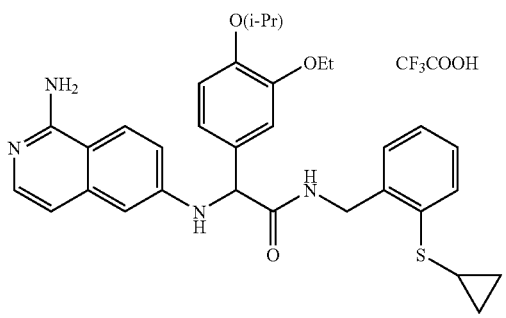

225A

2-(Cyclopropylthio)benzonitrile

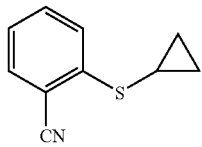

To 2,2'-dithio-bis(benzonitrile) (obtained from Sumitomo Seika) (3.00 g, 11.2 mmol) in THF (56 mL) at −78° C., a 0.5 M THF solution of cyclopropyl magnesium bromide (224 mL, 111.9 mmol) was added via addition funnel. After 10 min, the reaction was quenched with saturated aqueous ammonium chloride (200 mL). After warming to rt, the reaction was diluted with water and ethyl acetate and the layers were separated. The organic layer was washed with water and brine, dried (MgSO$_4$), filtered and concentrated. The resulting residue was purified via silica gel chromatography eluting with 15% ethyl acetate/hexane to provide 225A as a yellow oil (2.20 g). LC-MS: 176.02 (M+H)$^+$.

225B

(2-(Cyclopropylthio)phenyl)methanamine hydrochloride

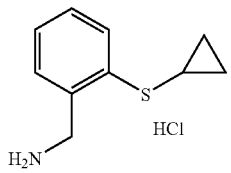

To 225A (100 mg, 0.57 mmol) in refluxing THF (6 mL), a 2M THF solution of BH$_3$.SMe$_2$ (1.7 mL, 1.71 mmol) was added. After heating at reflux for 1 h, the reaction was cooled to rt and 4M HCl (0.51 mL) was slowly added. The reaction was heated to reflux for 1 h, then cooled to rt, concentrated and azeotroped (3×) with THF/MeOH on a rotary evaporator. The resulting residue was taken up in THF and filtered to provide 225B (83 mg) as a yellow solid. LC-MS: 180.14 (M+H)$^+$.

225C

Example 225 (8 mg) was prepared from Intermediate 2 (20 mg) and 225B (14 mg) following the general coupling/deprotection procedure in 35% overall yield. LC-MS: 557.24 (M+H)$^+$.

Example 226

2-(1-Amino-isoquinolin-6-ylamino)-N-[2-(benzyl-methyl-sulfamoyl)-benzyl]-2-(3-ethoxy-4-isopropoxy-phenyl)-acetamide trifluoroacetic acid salt

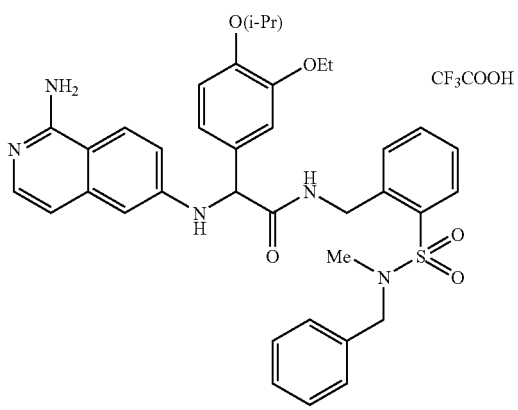

226A

N-Benzyl-2-cyano-N-methylbenzenesulfonamide

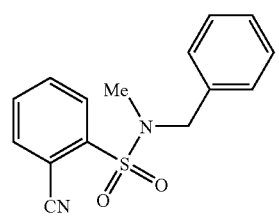

To N-methyl-N-benzyl amine (363 mg, 3.00 mmol) in THF (5 mL), triethylamine (505 mg, 5.00 mmol) was added followed by a solution of 2-cyanobenzene-1-sulfonyl chloride (201 mg, 1.00 mmol) in THF (5 mL). The reaction mixture was stirred at rt for 30 min. After filtering, the mixture was concentrated and purified via silica gel chromatography (eluting with 30% ethyl acetate/hexane) to provide 226A (120 mg, 42%). LC-MS: 287.22 (M+H)$^+$.

226B

2-(Aminomethyl)-N-benzyl-N-methylbenzenesulfonamide hydrochloride salt

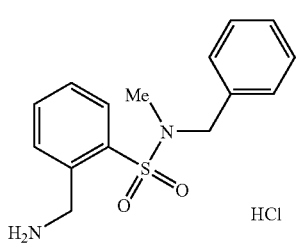

226A (50 mg, 0.175 mmol) was dissolved in MeOH (10 mL), conc. HCl (100 mg) was added, and the whole solution was hydrogenated at 50 psi overnight. The mixture was filtered and dried (Na$_2$SO$_4$) to provide 226B (46 mg, 79%). LC-MS: 291.25 (M+H)$^+$.

226C

Example 226 (4.76 mg) was prepared from Intermediate 2 (15 mg) and 226B (10 mg) following the general coupling/deprotection procedure in 29% overall yield. LC-MS: 668.6 (M+H)$^+$.

Example 227

N-(2-(Cyclopentylsulfonyl)benzyl)-2-(1-aminoisoquinolin-6-ylamino)-2-(3-ethoxy-4-isopropoxyphenyl)acetamide trifluoroacetic acid salt

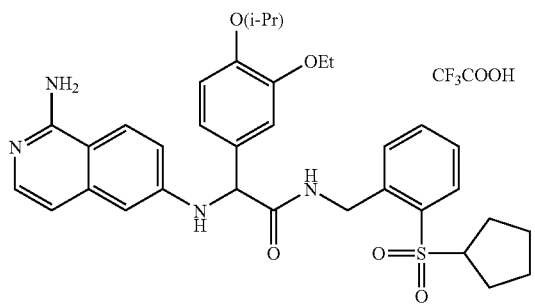

227A (2-(Cyclopentylsulfonyl)phenyl)methanamine hydrochloride salt

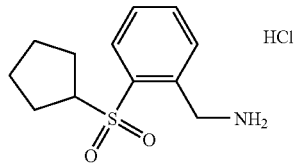

227A was prepared in three steps from 2,2'-dithio-bis(benzonitrile) (57% overall yield) following procedures analogous to those used in the preparation of (2-(cyclopropylsulfonyl)phenyl)methanamine hydrochloride salt. LC-MS: 240.2 (M+H)$^+$.

227B

Example 227 (5.4 mg) was prepared from Intermediate 2 (18 mg) and 227A (21 mg) following the general coupling/deprotection procedure in 30% overall yield. $^1$H NMR (400 MHz, CD$_3$OD) δ ppm 1.30 (d, J=6.15 Hz, 6H) 1.37 (t, J=7.03 Hz, 3H) 1.85 (m, 4H) 3.23 (m, 4H) 4.01 (m, 2H) 4.53 (m, 1H) 4.77 (m, 2H) 5.10 (s, 1H) 6.66 (d, J=2.20 Hz, 1H) 6.81 (d, J=7.47 Hz, 1H) 6.97 (d, J=8.35 Hz, 1H) 7.07 (m, 2H) 7.18 (dd, J=9.23, 2.20 Hz, 1H) 7.30 (m, 2H) 7.41 (m, 2H) 7.79 (m, 1H) 8.07 (d, J=9.23 Hz, 1H) 8.53 (t, J=6.15 Hz, 1H). LC-MS: 617.50 (M+H)$^+$.

Example 228

N-(2-Morpholinobenzyl)-2-(1-aminoisoquinolin-6-ylamino)-2-(3-ethoxy-4-isopropoxyphenyl)acetamide trifluoroacetic acid salt

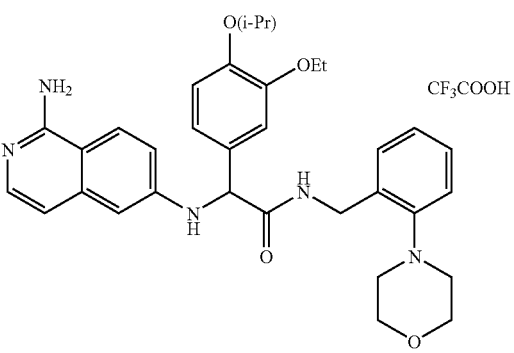

Example 228 (6.3 mg) was prepared from Intermediate 2 (18 mg) and commercially available 2-morpholinobenzylamine (14 mg) following the general coupling/deprotection procedure in 37% overall yield. $^1$H NMR (400 MHz, CD$_3$OD) δ ppm 1.29 (d, J=6.15 Hz, 6H) 1.35 (t, J=6.81 Hz, 3H) 2.90 (m, 4H) 3.78 (t, J=4.39 Hz, 4H) 3.96 (dd, J=7.03, 3.52 Hz, 2H) 4.53 (m, 3H) 5.11 (s, 1H) 6.67 (d, J=2.20 Hz, 1H) 6.80 (d, J=7.03 Hz, 1H) 6.95 (d, J=7.91 Hz, 1H) 7.12 (m, 8H) 8.09 (d, J=9.23 Hz, 1H). LC-MS: 570.50 (M+H)$^+$.

Example 229

N-(2-(Piperidin-1-yl)benzyl)-2-(1-aminoisoquinolin-6-ylamino)-2-(3-ethoxy-4-isopropoxyphenyl)acetamide trifluoroacetic acid salt

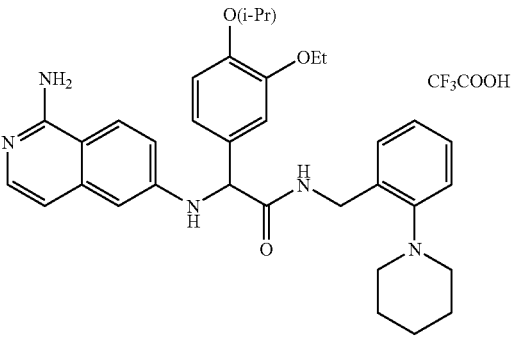

Example 229 (5 mg) was prepared from Intermediate 2 (18 mg) and commercially available 2-piperidinobenzylamine (14 mg) following the general coupling/deprotection procedure in 25% overall yield. $^1$H NMR (400 MHz, CD$_3$OD) δ ppm 1.27 (d, J=6.11 Hz, 6H) 1.32 (t, J=6.97 Hz, 3H) 2.05 (br. s., 2H) 3.51 (br. s., 2H) 3.87 (m, 2H) 4.51 (m, 2H) 4.51 (m, 1H) 5.16 (s, 1H) 6.59 (d, J=2.20 Hz, 1H) 6.67 (d, J=7.09 Hz, 1H) 6.93 (d, J=8.80 Hz, 1H) 7.01 (m, 2H) 7.20 (dd, J=9.17, 2.32 Hz, 1H) 7.32 (d, J=7.09 Hz, 1H) 7.54 (m, 3H) 7.67 (d, J=8.07 Hz, 1H) 8.10 (d, J=9.29 Hz, 1H). LC-MS: 568.50 (M+H)$^+$.

Example 230

N-(2-(2-Methylpiperidin-1-yl)benzyl)-2-(1-aminoisoquinolin-6-ylamino)-2-(3-ethoxy-4-isopropoxyphenyl)acetamide trifluoroacetic acid salt

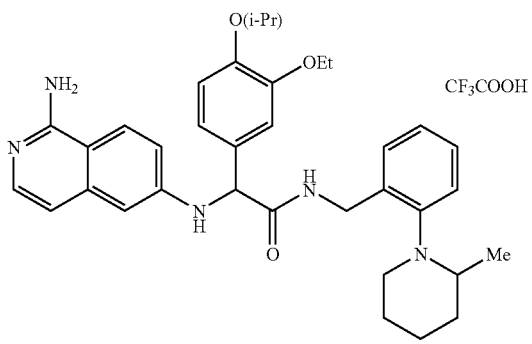

Example 230 (9.3 mg) was prepared as a mixture of diastereomers from Intermediate 2 (18 mg) and commercially available (ART-CHEM) (2-(2-methylpiperidin-1-yl)phenyl)methanamine (14 mg) following the general coupling/deprotection procedure in 55% overall yield. LC-MS 582.38 (M+H)+.

Example 231

N-(2-(3-Methylpiperidin-1-yl)benzyl)-2-(1-aminoisoquinolin-6-ylamino)-2-(3-ethoxy-4-isopropoxyphenyl)acetamide trifluoroacetic acid salt

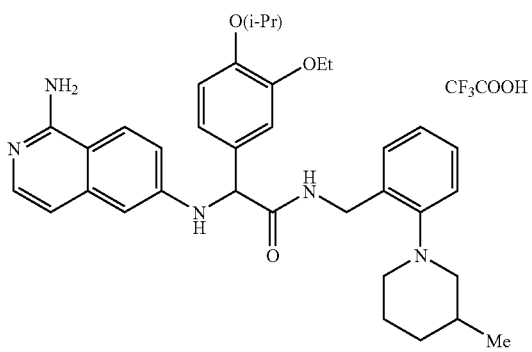

Example 231 (5 mg) was prepared as a mixture of diastereomers from Intermediate 2 (18 mg) and commercially available (ART-CHEM) (2-(3-methylpiperidin-1-yl)phenyl)methanamine (14.0 mg) following the general coupling/deprotection procedure in 30% overall yield. LC-MS: 582.37 (M+H)+.

Example 232

N-(2-(3,5-Dimethyl-1H-pyrazol-1-yl)benzyl)-2-(1-aminoisoquinolin-6-ylamino)-2-(3-ethoxy-4-isopropoxyphenyl)acetamide trifluoroacetic acid salt

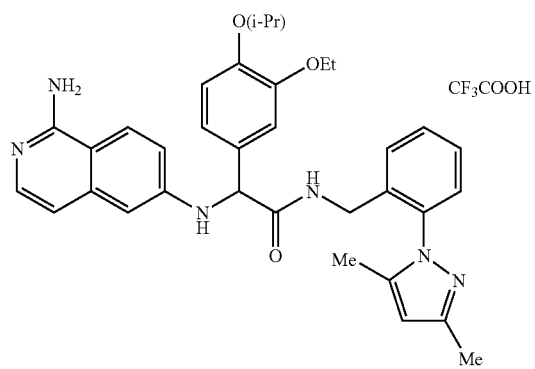

Example 232 (4.2 mg) was prepared from Intermediate 2 (15 mg) and commercially available (ART-CHEM) (2-(3,5-dimethyl-1H-pyrazol-1-yl)phenyl)methanamine hydrochloride (10 mg) following the general coupling/deprotection procedure in 29% overall yield. LC-MS: 579.44 (M+H)+.

Example 233

N-(2-(3,5-Diethyl-1H-pyrazol-1-yl)benzyl)-2-(1-aminoisoquinolin-6-ylamino)-2-(3-ethoxy-4-isopropoxyphenyl)acetamide Trifluoroacetic Acid Salt

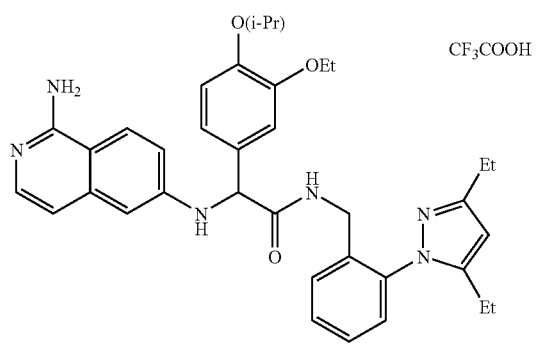

233A

N-(3-Aminobenzyl)-2,2,2-trifluoroacetamide

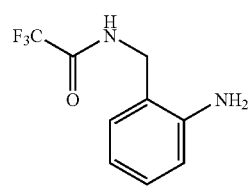

2-Aminobenzylamine (1.5 Kg, 12.28 mol) was charged to 1.5 L tBME and slurried. Heptanes (13.5 L) were charged to bring the solvent ratio to 10% v/v tBME/heptanes. Ethyl trifluoroacetate (1.6 L, 1.9 Kg, 13.5 mol) was added slowly to the reaction at 25±5° C. over 27 min. Visually this reaction went from a gray or off-white slurry to a bright white slurry of fine crystals. The reaction was stirred for 1 h at ambient temperature. The product was filtered and washed with 1.2 L of heptanes then dried by drawing nitrogen through the wet cake overnight to provide 233A (2255 g).

233B

N-(2-(3,5-Diethyl-1H-pyrazol-1-yl)benzyl)-2,2,2-trifluoroacetamide

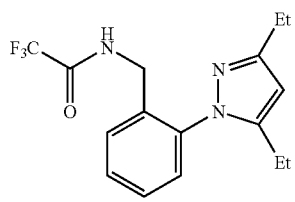

To N-(3-aminobenzyl)-2,2,2-trifluoroacetamide (1.00 g, 4.60 mmol) in conc. HCl (9.2 mL) at 0° C. was added sodium nitrite (481 mg, 6.97 mmol) in cold water (4 mL), dropwise. After stirring at the same temperature for 30 min, tin (II) chloride dihydrate (3.11 g, 13.8 mmol) in cold conc. HCl (4.5 mL) was slowly added and the ice bath was removed. After stirring for 45 min, 2,4-heptadione (1.18 g, 9.20 mmol) and acetonitrile (1 mL) were added. After 1 h, the reaction was filtered through Celite® washing with ethyl acetate and methylene chloride then concentrated. The residue was dissolved in ethyl acetate and washed with water (2×) and brine (1×). The aqueous layer was back-extracted with ethyl acetate, and the combined organic layers were dried (MgSO$_4$), filtered and concentrated. The resulting residue was purified via silica gel chromatography eluting with 0-50% ethyl acetate/hexanes to provide 233B (280 mg) as a yellow oil. LC-MS: 326.09 (M+H)$^+$.

233C (2-(3,5-Diethyl-1H-pyrazol-1-yl)phenyl)methanamine

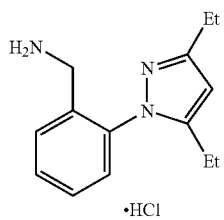

To 233B (140 mg, 0.43 mmol) in MeOH (2 mL) and water (0.30 mL) was added potassium carbonate (297 mg, 2.15 mmol) and the reaction was heated to 80° C. for 2 h. After cooling to rt, the reaction was concentrated and the residue was partioned between ethyl acetate and water. The aqueous layer was back-extracted with ethyl acetate (4×), and the combined organic layers were dried (MgSO$_4$), filtered and concentrated. The residue was diluted with diethyl ether and 4M HCl/dioxane (180 μL) was added. The resulting solid was filtered, and the hygroscopic solid was collected by dissolving in MeOH and concentrating to provide 233C (99 mg) as a yellow oil.

233D

Example 233 (8 mg) was prepared from Intermediate 2 (20 mg) and 233C (18 mg) following the general coupling/deprotection procedure in 29% overall yield. LC-MS: 607.40 (M+H)$^+$.

Example 234

N-(2-(3,5-Dimethyl-1H-pyrazol-1-yl)-5-hydroxybenzyl)-2-(1-aminoisoquinolin-6-ylamino)-2-(3,4-dimethoxyphenyl)acetamide Trifluoroacetic Acid Salt

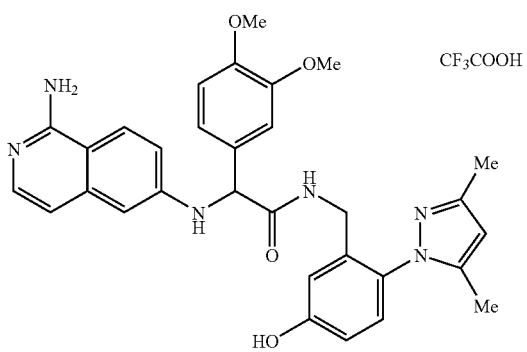

234A

Methyl 2-(3,5-dimethyl-1H-pyrazol-1-yl)-5-methoxybenzoate

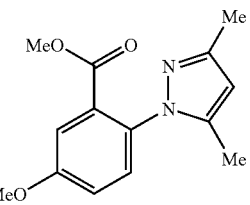

To 2-amino-5-methoxy benzoic acid (1.00 g, 5.99 mmol) in conc. HCl (12 mL) at 0° C. was added sodium nitrite (496 mg, 7.19 mmol) in cold water (5 mL), dropwise. After stirring at the same temperature for 30 min, tin (II) chloride dihydrate (4.05 g, 18.0 mmol) in cold conc. HCl (6 mL) was slowly added and the ice bath was removed. After stirring for 45 min, 2,4-pentadione (1.23 mL, 12.0 mmol) was added, and after an additional 30 min, acetonitrile (3 mL) was added. After 2 h, the reaction was concentrated, diluted with methylene chloride, and filtered through Celite® washing with ethyl acetate and methylene chloride. The solution was concentrated and purified via silica gel chromatography eluting with 10% MeOH/CH$_2$Cl$_2$ to yield a brown solid [6.6 g, LC-MS: 246.98 (M+H)$^+$]. The solid was dissolved in MeOH (50 mL), cooled to 0° C., and thionyl chloride (1.31 mL) was added. After stirring overnight with warming to rt, the reaction was heated

234B (2-(3,5-Dimethyl-1H-pyrazol-1-yl)-5-methoxyphenyl)methanol

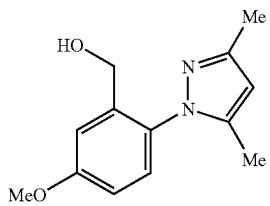

To 234A (450 mg, 1.73 mmol) in THF (17 mL) at 0° C. was added 1M LAH in THF (3.8 mL, 3.80 mmol). After ca. 5 min, the reaction was slowly quenched with water (0.14 mL) in THF (1 mL), then stirred for 5 min. 15% NaOH (0.4 mL) was added, then after 5 min water (0.4 mL) in THF (1 mL) was added. The mixture was stirred for 5 min then filtered through Celite®, washing with THF and ethyl acetate. Concentrating provided 234B (393 mg) as a yellow solid. LC-MS: 233.05 (M+H)+.

234C 1-(2-(Azidomethyl)-4-methoxyphenyl)-3,5-dimethyl-1H-pyrazole

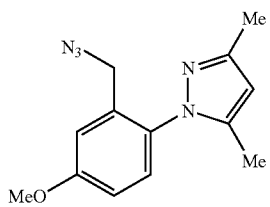

To 234B (393 mg, 1.70 mmol) in toluene (5 mL) at 0° C. was added DPPA (0.44 mL, 2.04 mmol) followed by DBU (0.28 mL, 1.87 mmol). The ice bath was removed and the reaction was stirred overnight. The reaction was then diluted with water and ethyl acetate, and the layers were separated. The organic layer was washed with water and 1 N HCl, then dried (MgSO4), filtered and concentrated to provide 234C (325 mg) as a yellow oil. LC-MS: 258.01 (M+H)+.

234D (2-(3,5-Dimethyl-1H-pyrazol-1-yl)-5-methoxyphenyl)methanamine

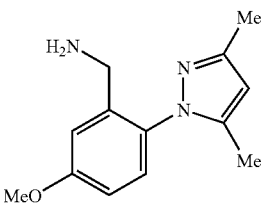

To 234C (325 mg, 1.26 mmol) in THF (13 mL) at 0° C. was added 1M LAH in THF (1.5 mL, 1.50 mmol). After 45 min, the reaction was slowly quenched with water (0.2 mL) in THF (1 mL), then stirred for 5 min. 15% NaOH (0.3 mL) was added, then after 5 min water (0.3 mL) in THF (1 mL) was added. The mixture was stirred for 5 min then filtered through Celite®, washing with THF and ethyl acetate. Concentrating provided 234D (240 mg) as a yellow oil. LC-MS: 232.05 (M+H)+.

234E 3-(Aminomethyl)-4-(3,5-dimethyl-1H-pyrazol-1-yl)phenol

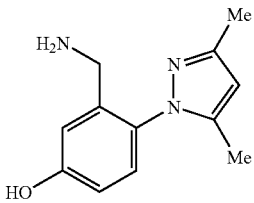

To 234D (240 mg, 1.04 mmol) in methylene chloride (2.6 mL) at −78° C. was added 1M boron tribromide in methylene chloride (2.6 mL, 2.6 mmol). The cold bath was removed and the reaction was stirred for 2 h, then placed in freezer overnight. The reaction was then brought to rt, stirred for 1.5 h then concentrated, diluted with THF and filtered to provide a solid. The solid was dissolved in water and washed with diethyl ether (3×). The aqueous layer was basified with 1 N NaOH, then extracted with diethyl ether/ethyl acetate (3×). The solution was dried (MgSO4), filtered and concentrated to provide 234E (80 mg) as a white solid. LC-MS: 218.15 (M+H)+.

234F

Example 234 (5.0 mg) was prepared from Intermediate 4 (20 mg) and 234E (16 mg) following the general coupling/deprotection procedure in 18% overall yield. $^1$H NMR (400 MHz, CD$_3$OD) δ ppm 2.02 (s, 3H), 2.19 (s, 3H), 3.80 (s, 3H), 3.83 (s, 3H), 3.89-4.07 (m, 2H), 5.06 (s, 1H), 6.04 (s, 1H), 6.70 (dd, J=18.68, 2.42 Hz, 2H), 6.76 (dd, J=8.35, 2.64 Hz, 1H), 6.86 (d, J=7.03 Hz, 1H), 6.96 (d, J=8.35 Hz, 1H), 7.02-7.12 (m, 4H), 7.19 (dd, J=9.23, 2.20 Hz, 1H), 7.32 (d, J=7.03 Hz, 1H), 8.09 (d, J=9.23 Hz, 1H); LC-MS: 553.14 (M+H)+.

Example 235

N-(2-(3,5-Dimethyl-1H-pyrazol-1-yl)-5-hydroxybenzyl)-2-(1-aminoisoquinolin-6-ylamino)-2-(3-ethoxy-4-isopropoxyphenyl)acetamide Trifluoroacetic Acid Salt

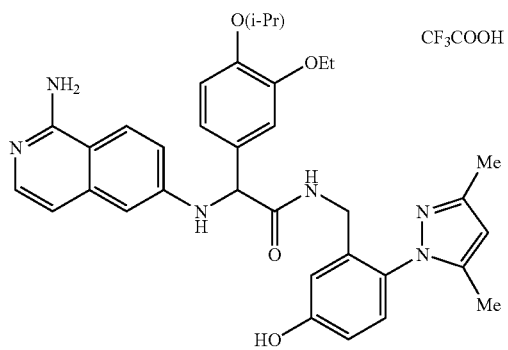

Example 235 (7.5 mg) was prepared from Intermediate 2 (20 mg) and 234E (15 mg) following the general coupling/deprotection procedure in 27% overall yield. LC-MS: 595.21 (M+H)⁺.

Example 236

N-(2-(3,5-Bis(trifluoromethyl)-1H-pyrazol-1-yl)benzyl)-2-(1-aminoisoquinolin-6-ylamino)-2-(3-ethoxy-4-isopropoxyphenyl)acetamide Trifluoroacetic Acid Salt

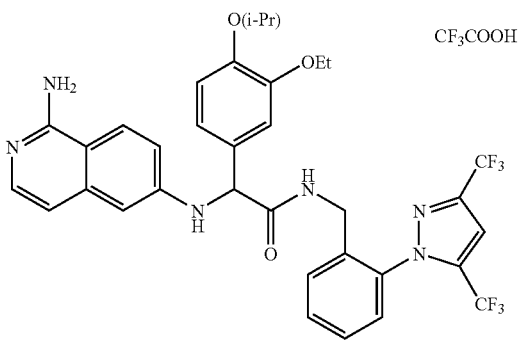

236A (2-(3,5-bis(trifluoromethyl)-1H-pyrazol-1-yl)phenyl)methanamine hydrochloride

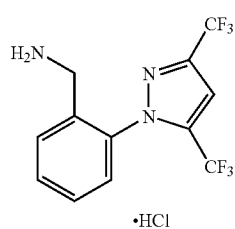

236A was prepared from N-(3-aminobenzyl)-2,2,2-trifluoroacetamide in three steps (including HCl salt formation) in 42% overall yield following procedures analogous to those used in the preparation of 233C.

236B

Example 236: To Intermediate 3 (15 mg, 0.035 mmol) in DMF (1 mL) was added EDC (10 mg, 0.055 mmol), HOAT (6 mg, 0.044 mmol), DIPEA (40 μL, 0.23 mmol) and 236A (32 mg, 0.093 mmol) and the reaction was heated to 60° C. in a sealed vial for 2.5 h. After cooling to rt overnight, the reaction was purified via preparative HPLC (MeOH/water/TFA). The major peak was collected and concentrated, then lyophilized (acetonitrile/water) overnight to provide Example 236 (13.8 mg) as a yellow solid. LC-MS: 687.34 (M+H)⁺.

Example 237

N-(2-(1H-1,2,4-Triazol-1-yl)benzyl)-2-(1-aminoisoquinolin-6-ylamino)-2-(3-ethoxy-4-isopropoxyphenyl)acetamide trifluoroacetic acid salt

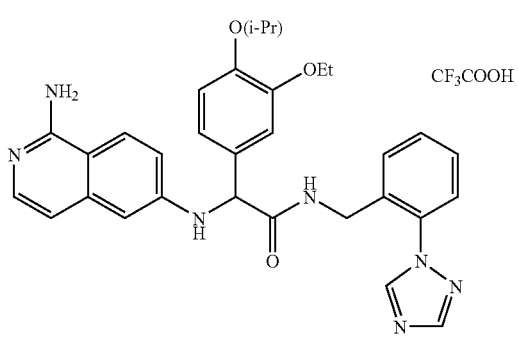

Example 237 (12 mg) was prepared from Intermediate 2 (18 mg) and commercially available (ART-CHEM) (2-(1H-1,2,4-triazol-1-yl)phenyl)methanamine (13 mg) following the general coupling/deprotection procedure in 72% overall yield. LC-MS: 552.49 (M+H)⁺.

Example 238

N-(2-(N-Methylaminosulfonyl)benzyl)-2-(1-aminoisoquinolin-6-ylamino)-2-(3-ethoxy-4-isopropoxyphenyl)acetamide trifluoroacetic acid salt

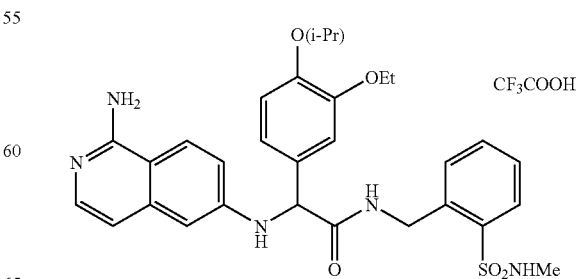

238A

N-tert-Butyl-2-cyano-N-methylbenzenesulfonamide

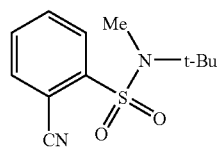

To N-tert-butylmethylamine (1.50 mL, 12.0 mmol) in THF (7.5 mL) was added triethylamine (500 mg, 4.94 mmol) followed by a solution of 2-cyanobenzene-1-sulfonyl chloride (600 mg, 3.00 mmol) in THF (3 mL). The reaction mixture was stirred at rt for 30 min. After filtering, the reaction was concentrated and purified via silica gel chromatography (eluting with 25% ethyl acetate/hexane) to provide 238A (150 mg, 20%). LC-MS: 275.19 (M+Na)$^+$.

238B

2-(Aminomethyl)-N-tert-butyl-N-methylbenzenesulfonamide hydrochloride salt

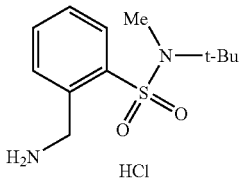

Compound 238A (51 mg, 0.202) was dissolved in MeOH (5 mL), conc. HCl (35 mg) and 10% Pd/C (cat.) were added, and the mixture was hydrogenated at 60 psi for 72 h. The reaction was filtered, concentrated and purified via preparative HPLC eluting with MeOH/water/TFA to provide 238B (17 mg, 42%) and recovered 238A (16 mg, 31%).

238C

Example 238 (5.2 mg) was prepared from Intermediate 2 (16 mg) and 238B (16.mg) following the general coupling/deprotection procedure in 33% overall yield (the tert-butyl group was removed in the deprotection step). LC-MS: 578.4 (M+H)$^+$.

Example 239

N-(2-(Azepan-1-ylsulfonyl)benzyl)-2-(1-aminoisoquinolin-6-ylamino)-2-(3-ethoxy-4-isopropoxyphenyl)acetamide trifluoroacetic acid salt

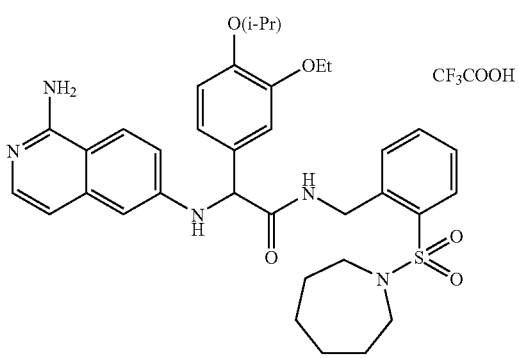

239A

(2-(Azepan-1-ylsulfonyl)phenyl)methanamine hydrochloride salt

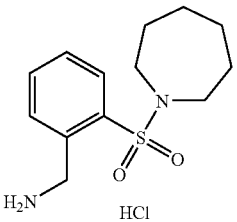

A (125 mg) was prepared in two steps from 2-cyanobenzene-1-sulfonyl chloride (100 mg) and azepane in 82% overall yield following procedures analogous to those used in the preparation of 2-(aminomethyl)-N-tert-butyl-N-methylbenzenesulfonamide hydrochloride salt. LC-MS: 269.25 (M+H)$^+$.

239B

Example 239 (5.5 mg) was prepared from Intermediate 2 (13 mg) and 239A (12 mg) following the general coupling/deprotection procedure in 39% overall yield. LC-MS: 646.6 (M+H)$^+$.

Example 240

N-(2-(Pyrrolidin-1-ylsulfonyl)benzyl)-2-(1-aminoisoquinolin-6-ylamino)-2-(3-ethoxy-4-isopropoxyphenyl)acetamide trifluoroacetic acid salt

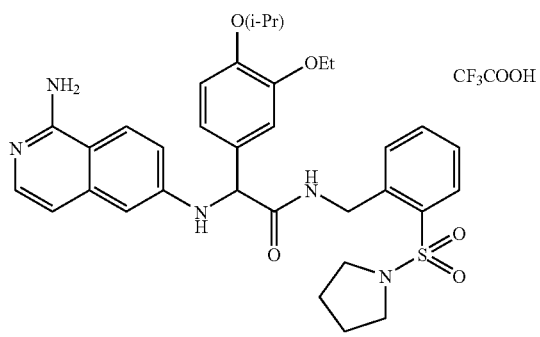

240A (2-(Pyrrolidin-1-ylsulfonyl)phenyl)methanamine trifluoroacetic acid salt

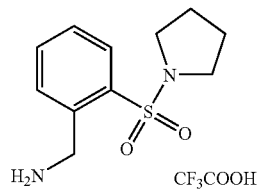

240A (210 mg) was prepared in two steps from 2-cyanobenzene-1-sulfonyl chloride (260 mg) and pyrrolidine in 40% overall yield following procedures analogous to those used in the preparation 2-(aminomethyl)-N-tert-butyl-N-methylbenzenesulfonamide hydrochloride salt followed by purification via preparative HPLC (MeOH/water/TFA). LC-MS: 241.27 (M+H)$^+$.

240B

Example 240 (4.6 mg) was prepared from Intermediate 2 (13 mg) and amine 240A (16 mg) following the general coupling/deprotection procedure in 34% overall yield. $^1$H NMR (400 MHz, CD$_3$OD) δ ppm 1.30 (d, J=6.15 Hz, 6H) 1.37 (t, J=7.03 Hz, 3H) 1.85 (m, 4H) 3.22 (m, 4H) 4.00 (m, 2H) 4.53 (m, 1H) 4.76 (m, 2H) 5.10 (s, 1H) 6.66 (d, J=2.20 Hz, 1H) 6.81 (d, J=7.47 Hz, 1H) 6.97 (d, J=8.35 Hz, 1H) 7.07 (m, 2H) 7.18 (dd, J=9.23, 2.20 Hz, 1H) 7.30 (m, 2H) 7.41 (m, 2H) 7.79 (m, 1H) 8.07 (d, J=9.23 Hz, 1H) 8.54 (m, 1H). LC-MS: 618.5 (M+H)$^+$.

Example 241

N-(2-(Thiomorpholinosulfonyl)benzyl)-2-(1-aminoisoquinolin-6-ylamino)-2-(3-ethoxy-4-isopropoxyphenyl)acetamide trifluoroacetic acid salt

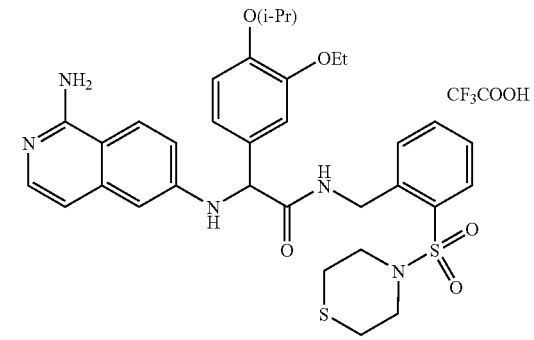

241A 2-(Thiomorpholinosulfonyl)benzonitrile

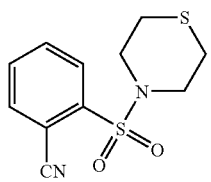

To thiomorpholine (206 mg, 1.99 mmol) in THF (10 mL), triethylamine (300 mg, 2.96 mmol) was added and followed by a solution of 2-cyanobenzene-1-sulfonyl chloride (100 mg, 0.496 mmol). The reaction mixture was stirred at rt for 20 min. After filtering, the reaction was concentrated and purified via silica gel chromatography (eluting with 0-30% ethyl acetate/hexane) to provide 241A (78 mg, 58%). LC-MS: 269.2 (M+H)$^+$.

241B (2-(Thiomorpholinosulfonyl)phenyl)methanamine Hydrochloric Acid Salt

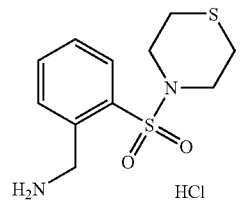

To 241A (74 mg, 0.276 mmol) in THF (3 mL) was added 2M BH$_3$·SMe$_2$ in THF (0.10 mL, 1.05 mmol). After heating at reflux for 1 h, the reaction was cooled to rt and 6M HCl (0.20 mL) was added. The reaction mixture was heated to reflux for 30 min, then cooled to rt, concentrated and purified via preparative HPLC (MeOH/water/TFA) to provide 241B (79 mg, 75%). LC-MS: 273.19 (M+H)⁺.

241C

Example 241 (5.3 mg) was prepared from Intermediate 2 (13 mg) and amine 241B (16 mg) following the general coupling/deprotection procedure in 37% overall yield. $^1$H NMR (500 MHz, CD$_3$OD) δ ppm 1.31 (d, J=6.05 Hz, 6H) 1.37 (t, J=6.87 Hz, 3H) 2.64 (dd, J=6.05, 3.85 Hz, 4H) 3.42 (m, 4H) 4.02 (m, 2H) 4.54 (m, 1H) 4.73 (m, 2H) 5.12 (s, 1H) 6.68 (d, J=2.20 Hz, 1H) 6.83 (d, J=7.15 Hz, 1H) 6.98 (d, J=8.25 Hz, 1H) 7.09 (m, 2H) 7.20 (dd, J=8.80, 2.20 Hz, 1H) 7.27 (m, 1H) 7.33 (d, J=7.15 Hz, 1H) 7.42 (m, 2H) 7.79 (m, 1H) 8.08 (d, J=8.80 Hz, 1H) 8.60 (s, 1H). LC-MS: 650.5 (M+H)⁺.

Example 242

N-(2-(4-Methylpiperazin-1-ylsulfonyl)benzyl)-2-(1-aminoisoquinolin-6-ylamino)-2-(3-ethoxy-4-isopropoxyphenyl)acetamide trifluoroacetic acid salt

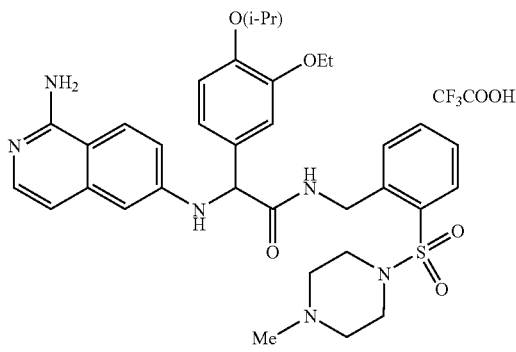

242A (2-(4-Methylpiperazin-1-ylsulfonyl)phenyl)methanamine Hydrochloric Acid Salt

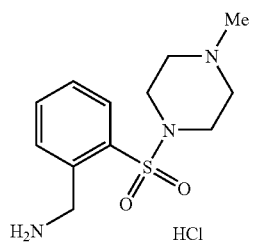

242A was prepared in two steps from 2-cyanobenzene-1-sulfonyl chloride and 1-methylpiperazine in 34% overall yield following procedures analogous to those used in the preparation of 2-(aminomethyl)-N-tert-butyl-N-methylbenzenesulfonamide hydrochloride salt. LC-MS: 270.25 (M+H)⁺

242B

Example 242 (5.7 mg) was prepared from Intermediate 2 (13 mg) and 242A (21 mg) following the general coupling/deprotection procedure in 40% overall yield. LC-MS: 647.6 (M+H)⁺.

Example 243

N-(5-Acetylamino-2-ethanesulfonyl-benzyl)-2-(1-amino-isoquinolin-6-ylamino)-2-(3-ethoxy-4-isopropoxy-phenyl)-acetamide trifluoroacetic acid salt

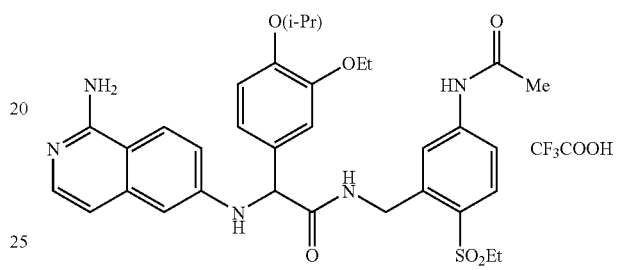

Example 243 (33 mg) was prepared from Intermediate 2 (135 mg) and Intermediate 9 (85 mg) following the general coupling/deprotection procedure in 20% overall yield. $^1$H NMR (400 MHz, CD$_3$OD) δ ppm 1.07 (t, J=7.25 Hz, 3H) 1.19 (d, J=6.15 Hz, 6H) 1.26 (t, J=7.03 Hz, 3H) 2.03 (s, 3H) 3.14 (q, J=7.47 Hz, 2H) 3.87 (m, 2H) 4.42 (m, 1H) 4.59 (m, 2H) 4.98 (s, 1H) 6.50 (d, J=2.20 Hz, 1H) 6.66 (d, J=7.03 Hz, 1H) 6.85 (d, J=7.91 Hz, 1H) 6.94 (m, 2H) 7.07 (dd, J=9.23, 2.20 Hz, 1H) 7.20 (d, J=7.03 Hz, 1H) 7.55 (dd, J=8.79, 2.20 Hz, 1H) 7.65 (m, 2H) 7.96 (d, J=9.23 Hz, 1H) 8.48 (m, 1H). LC-MS: 634.52 (M+H)⁺.

Example 244

N-(5-Acetylamino-2-ethanesulfonyl-benzyl)-2-(1-amino-isoquinolin-6-ylamino)-2-(3,4-dimethoxy-phenyl)-acetamide

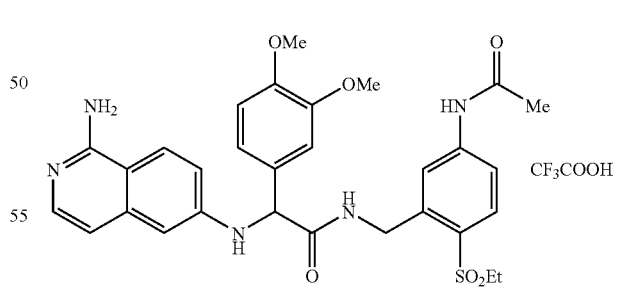

Example 244 (10 mg) was prepared from Intermediate 4 (44 mg) and Intermediate 9 (33 mg) following the general coupling/deprotection procedure in 18% overall yield. $^1$H NMR (400 MHz, CD$_3$OD) δ ppm 1.07 (t, J=7.25 Hz, 3H) 3.14 (q, J=7.47 Hz, 2H) 3.69 (s, 3H) 3.72 (s, 3H) 4.59 (m, 2H) 5.00 (s, 1H) 6.51 (d, J=2.20 Hz, 1H) 6.66 (d, J=7.03 Hz, 1H) 6.85 (d, J=8.35 Hz, 1H) 6.97 (m, 2H) 7.07 (dd, J=9.23, 2.20 Hz, 1H) 7.20 (d, J=7.03 Hz, 1H) 7.51 (dd, J=8.35, 2.20 Hz, 1H)

7.61 (d, J=1.76 Hz, 1H) 7.67 (d, J=8.79 Hz, 1H) 7.96 (d, J=9.23 Hz, 1H) 8.49 (t, J=5.93 Hz, 1H). LC-MS: 592.44 (M+H)$^+$.

Example 245

(R)-N-(5-Acetylamino-2-ethanesulfonyl-benzyl)-2-(1-amino-isoquinolin-6-ylamino)-2-(3,4-dimethoxyphenyl)-acetamide trifluoroacetic acid salt and

Example 246

(S)-N-(5-Acetylamino-2-ethanesulfonyl-benzyl)-2-(1-amino-isoquinolin-6-ylamino)-2-(3,4-dimethoxyphenyl)-acetamide trifluoroacetic acid salt

245

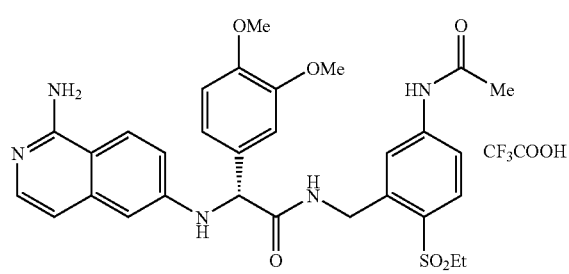

246

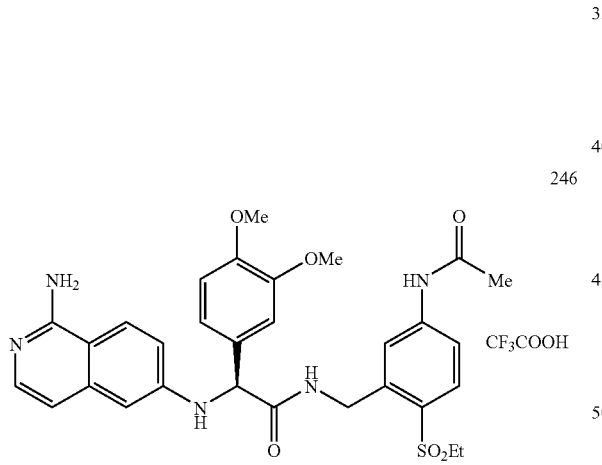

Example 244 (260 mg) was dissolved in isopropanol and the enantiomers were separated on a Chiralpak® AD column eluting with 70% heptane, 30% 1:1 MeOH/EtOH, 0.1% DEA which eluted Example 245 (free base), followed by Example 246 (free base). Both products were repurified via preparative HPLC (MeOH/water/TFA) then lyophilized (acetonitrile/water) overnight to provide Example 245 (22.5 mg) [LC-MS: 592.34 (M+H)$^+$], and Example 246 (24.8 mg) [LC-MS: 592.31 (M+H)$^+$].

Example 247

N-(5-Acetylamino-2-ethanesulfonyl-benzyl)-2-(1-amino-isoquinolin-6-ylamino)-2-(3,4-dimethoxyphenyl)-N-Me-acetamide trifluoroacetic acid salt

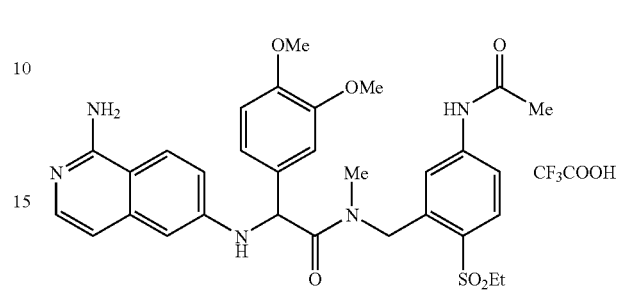

Example 247 (3.1 mg) was prepared from Intermediate 4 (16 mg) and Intermediate 10 (11 mg) following the general coupling/deprotection procedure in 16% overall yield. LC-MS: 606.30 (M+H)$^+$.

Example 248

N-(2-(Ethylsulfonyl)-5-N-aminosulfonylaminobenzyl)-2-(1-aminoisoquinolin-6-ylamino)-2-(3-ethoxy-4-isopropoxyphenyl)acetamide trifluoroacetic acid salt

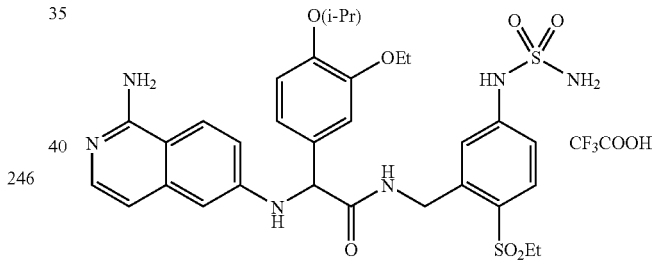

248A

5-Amino-2-(ethylsulfonyl)benzonitrile

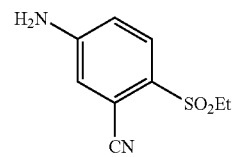

To Intermediate 9B (200 mg, 0.833 mmol) in acetic acid (3.0 mL) was added Fe (233 mg, 4.16 mmol). The reaction mixture was heated to 100° C. for 1 h. After cooling to rt, the product was extracted with ethyl acetate, and the organic layer was washed with water, then concentrated and azeotroped with toluene to provide 248A (163 mg, 93%) as a tan solid. LC-MS: 209.2 (M–H)$^-$.

248B

[(3-Cyano-4-ethylsulfonylphenylamino)sulfonyl] carbamic acid phenylmethyl ester

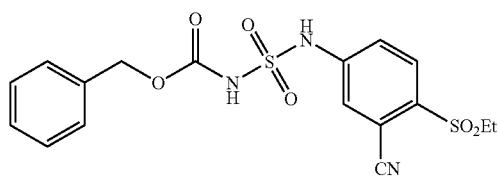

To 248A (163 mg, 0.776 mmol) in $CH_2Cl_2$ (7 mL) was added benzyl chlorosulfonylcarbamate (25A) (232 mg, 0.932 mmol). After stirring at rt for 3 h, the reaction was concentrated, taken up in ethyl acetate, and washed with saturated aqueous $NaHCO_3$ and brine, then dried ($MgSO_4$), filtered and concentrated to provide 248B (275 mg, 84%) as a yellow film. LC-MS: 422.1 $(M-H)^-$.

248C

2-Ethylsulfonyl-5-(aminosulfonyl)amino benzylamine hydrochloride

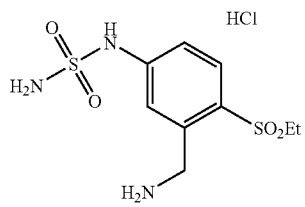

To 248B (275 mg, 0.650 mmol) in MeOH (5 mL), 10% Pd/C (20.0 mg) was added. The mixture was hydrogenated at 50 psi for 48 h. The reaction was concentrated to provide an off-white solid (219 mg) which contained a mixture of 2-ethylsulfonyl-5-aminobenzylamine [LC-MS: 215.27 $(M+H)^+$] and 248C, 2-ethylsulfonyl-5-(aminosulfonyl)amino benzylamine [LC-MS: 294.24 $(M+H)^+$].

248D

Example 248: A mixture of Intermediate 2 (44 mg, 0.062 mmol), EDC (24.0 mg, 0.13 mmol), HOAT (8.4 mg, 0.062 mmol), DIPEA (54 µL, 0.31 mmol) and a mixture of 2-ethylsulfonyl-5-aminobenzylamine and 248C, 2-ethylsulfonyl-5-(aminosulfonyl)amino benzylamine (61 mg) in $CH_2Cl_2$ (1 mL) and DMF (100 µL) was stirred at overnight. The reaction was concentrated and purified via preparative HPLC (MeOH/$H_2O$/TFA) to provide two products: the first to elute was N-(2-(ethylsulfonyl)-5-N-aminosulfonylaminobenzyl)-2-(1-bis(tert-butyl)carbonylaminoisoquinolin-6-ylamino)-2-(3-ethoxy-4-isopropoxyphenyl)acetamide trifluoroacetic acid salt [13 mg, LC-MS: 871.65 $(M+H)^+$] followed by N-(2-(ethylsulfonyl)-5-N-aminobenzyl)-2-(1-bis(tert-butyl)carbonylaminoisoquinolin-6-ylamino)-2-(3-ethoxy-4-isopropoxyphenyl)acetamide trifluoroacetic acid salt [40 mg, LC-MS: 792.65 $(M+H)^+$]. The minor product was dissolved in ethyl acetate (0.50 mL) and was treated with 4 M HCl in dioxane (0.50 mL) and was stirred at rt overnight. The reaction was concentrated and purified via preparative HPLC (MeOH/$H_2O$/TFA) to provide Example 248 (1.2 mg) as a clear film. $^1$H NMR (400 MHz, $CD_3OD$) δ ppm 1.06 (t, J=7.25 Hz, 3H) 1.19 (d, J=6.15 Hz, 6H) 1.26 (t, J=7.03 Hz, 3H) 3.14 (q, J=7.47 Hz, 2H) 3.86 (m, 2H) 4.42 (m, 1H) 4.59 (m, 2H) 4.98 (s, 1H) 6.50 (d, J=2.20 Hz, 1H) 6.66 (d, J=7.03 Hz, 1H) 6.85 (d, J=7.91 Hz, 1H) 6.94 (m, 2H) 7.07 (dd, J=9.23, 2.20 Hz, 1H) 7.20 (d, J=7.03 Hz, 1H) 7.55 (dd, J=8.79, 2.20 Hz, 1H) 7.65 (m, 2H) 7.96 (d, J=9.23 Hz, 1H) 8.48 (t, J=6.15 Hz, 1H). LC-MS: 671.48 $(M+H)^+$.

Example 249

N-(5-Acetylamino-2-morpholino-benzyl)-2-(1-amino-isoquinolin-6-ylamino)-2-(3-ethoxy-4-isopropoxyphenyl)-acetamide

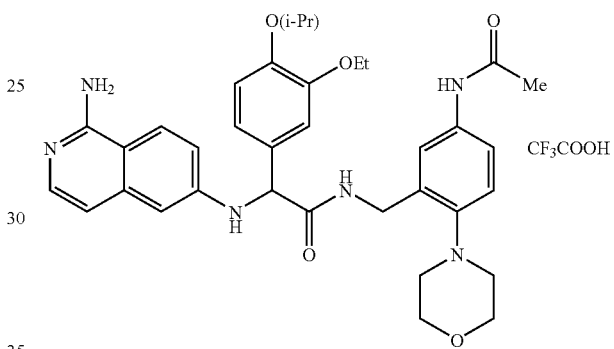

249A

2-Morpholino-5-nitrobenzonitrile

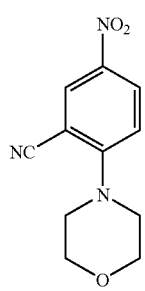

To 2-fluoro-5-nitrobenzonitrile (1.00 g, 6.02 mmol) in acetonitrile (60 mL) was added morpholine (525 µL, 6.02 mmol) and the reaction was stirred at rt for 1.5 h, then heated to 60° C. Since the reaction was progressing slowly, additional morpholine (100 µL) was added and the reaction was heated to 80° C. for 30 min. The reaction was cooled to rt, concentrated, diluted with MeOH and filtered to provide a yellow solid. The filtrate was concentrated, diluted with MeOH, filtered and combined with the first lot to provide 249A (1.35 g total) as a yellow solid.

249B

N-(3-Cyano-4-morpholinophenyl)acetamide

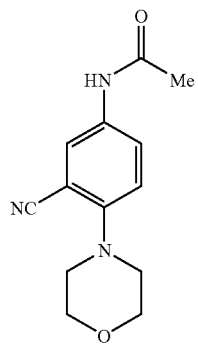

To 249A (900 mg, 3.86 mmol) in acetic anhydride (9 mL) was added iron (1.08 g, 19.3 mmol) and the reaction was heated to 100° C. for 2 h. The mixture was cooled to rt and poured over ice. When the ice melted, the product was extracted with ethyl acetate (2×). The layers were separated and the organic layer was washed with water (3×), saturated aqueous NaHCO$_3$ (3×) and brine (1×), then dried (MgSO$_4$), filtered and concentrated to provide a yellow solid (200 mg) which contained a 2:1 mixture of 249B and the diacylated by-product.

249C

N-(3-(Aminomethyl)-4-morpholinophenyl)acetamide trifluoroacetic acid salt

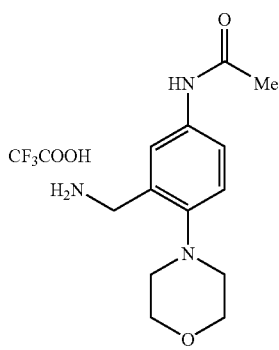

249B (200 mg, 0.816 mmol) was dissolved in MeOH (4 mL) and was hydrogenated at 60 psi in the presence of Raney Ni (cat) for 2 d. The mixture was filtered through Celite® and concentrated, and the resulting oil was purified via preparative chromatography eluting with MeOH/water/TFA to provide 249C (108 mg) as a clear oil. LC-MS: 250.10 (M+H)$^+$.

249D

Example 249 (5.2 mg) was prepared from Intermediate 2 (15 mg) and 249C (20 mg) following the general coupling/deprotection procedure in 25% overall yield. LC-MS: 627.28 (M+H)$^+$.

Example 250

N-(2-(Cyclopropylsulfonyl)benzyl)-2-(1-aminoisoquinolin-6-ylamino)-2-(3,4-dimethoxyphenyl)acetamide trifluoroacetic acid salt

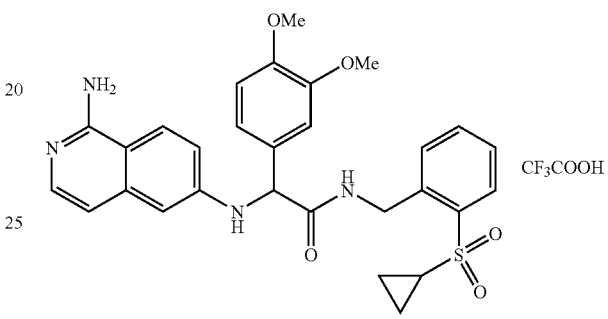

Example 250 (19 mg) was prepared from Intermediate 4 (33 mg) and Intermediate 7 (23 mg) following the general coupling/deprotection procedure in 48% overall yield. $^1$H NMR (400 MHz, CD$_3$OD) δ ppm 1.09 (m, 4H) 2.80 (m, 1H) 3.78 (s, 3H) 3.82 (s, 3H) 4.85 (m, 2H) 5.12 (s, 1H) 6.65 (d, J=1.76 Hz, 1H) 6.80 (d, J=7.03 Hz, 1H) 6.96 (m, 1H) 7.09 (m, 2H) 7.18 (dd, J=9.23, 2.64 Hz, 1H) 7.34 (m, 2H) 7.46 (m, 2H) 7.80 (m, 1H) 8.07 (d, J=9.23 Hz, 1H) 8.64 (t, J=5.93 Hz, 1H). LC-MS: 547.4 (M+H)$^+$.

Example 251

N-(2-(Cyclopropylsulfonyl)benzyl)-2-(1-aminoisoquinolin-6-ylamino)-2-(4-chloro-3-ethoxyphenyl)acetamide trifluoroacetic acid salt

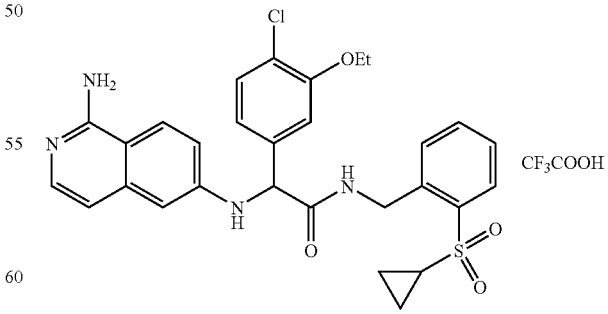

Example 252 (12 mg) was prepared from Intermediate 15 (25 mg) and Intermediate 7 (15 mg) following the general coupling/deprotection procedure in 41% overall yield. LC-MS: 604.95 (M+H)$^+$.

Example 252

N-(2-(Cyclobutylsulfonyl)benzyl)-2-(1-aminoisoquinolin-6-ylamino)-2-(3-ethoxy-4-isopropoxyphenyl)acetamide trifluoroacetic acid salt

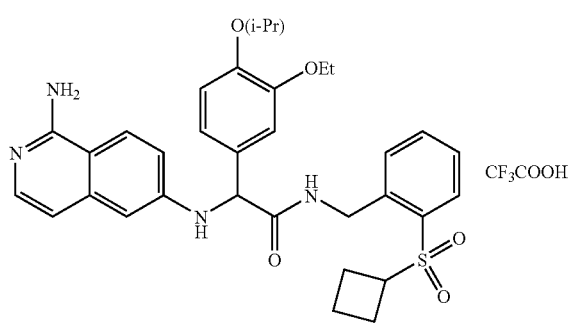

Example 252 (32 mg) was prepared from Intermediate 2 (60 mg) and Intermediate 11 (45 mg) following the general coupling/deprotection procedure in 45% overall yield. LC-MS: 603.04 (M+H)$^+$.

Example 253

(R)-N-(2-(Cyclobutylsulfonyl)benzyl)-2-(1-aminoisoquinolin-6-ylamino)-2-(3-ethoxy-4-isopropoxyphenyl)acetamide trifluoroacetic acid salt and

Example 254

(S)-N-(2-(Cyclobutylsulfonyl)benzyl)-2-(1-aminoisoquinolin-6-ylamino)-2-(3-ethoxy-4-isopropoxyphenyl)acetamide trifluoroacetic acid salt

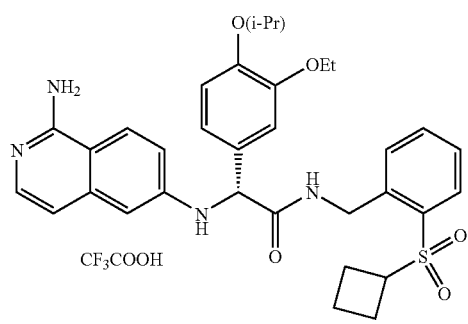

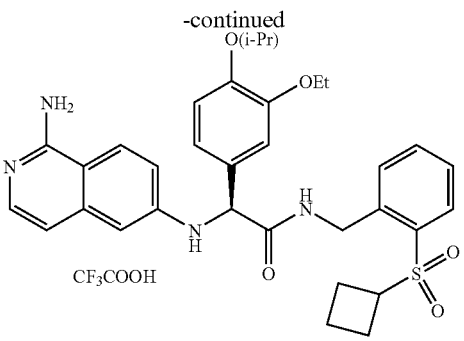

Example 252 (46 mg) was dissolved in isopropanol, heptane and DEA and the enantiomers were separated on a Chiralpak® AD column eluting with 60% heptane, 40% isopropanol, 0.1% DEA which eluted Example 253 (free base), followed by Example 254 (free base). Both products were separately dissolved in acetonitrile (~1 mL) and TFA (~10 μL) was added. The solutions were concentrated then dissolved in acetonitrile/water and lyophilized overnight to provide Example 253 (20 mg) [LC-MS: 603.24 (M+H)$^+$], and Example 254 (20 mg) [LC-MS: 603.24 (M+H)$^+$].

Example 255

N-(2-(Cyclobutylsulfonyl)benzyl)-2-(1-aminoisoquinolin-6-ylamino)-2-(3-ethoxy-4-isopropoxyphenyl)-N-methylacetamide trifluoroacetic acid salt

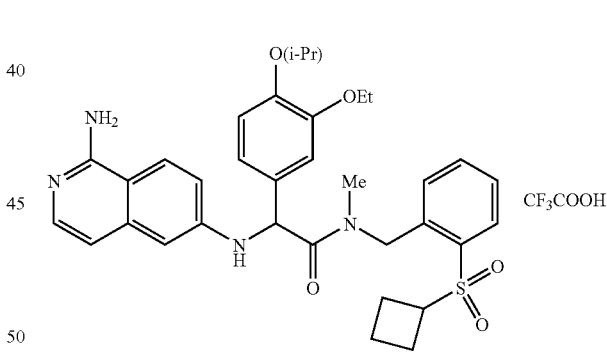

Example 255 (32 mg) was prepared from Intermediate 2 (30 mg) and Intermediate 12 (20 mg) following the general coupling/deprotection procedure in 23% overall yield. $^1$H NMR (400 MHz, CD$_3$OD) δ ppm 1.29 (d, J=6.15 Hz, 6H), 1.35 (t, J=7.03 Hz, 3H), 1.85-2.00 (m, 2H), 2.00-2.20 (m, 2H), 2.26-2.60 (m, 2H), 3.91-4.04 (m, 2H), 4.08-4.20 (m, 1H), 4.47-4.58 (m, 1H), 4.74 (m, 2H), 5.10 (s, 1H), 6.64 (d, J=2.20 Hz, 1H), 6.79 (d, J=7.03 Hz, 1H), 6.95-6.98 (m, 1H), 7.01-7.10 (m, 2H), 7.17 (dd, J=9.23, 2.20 Hz, 1H), 7.28-7.39 (m, 2H), 7.39-7.52 (m, 2H), 7.82 (dd, J=7.69, 1.54 Hz, 1H), 8.07 (d, J=9.23 Hz, 1H), 8.63 (t, J=5.93 Hz, 1H); LC-MS: 617.27 (M+H)$^+$.

Example 256

(R)-N-(2-(Cyclobutylsulfonyl)benzyl)-2-(1-aminoisoquinolin-6-ylamino)-2-(3-ethoxy-4-isopropoxyphenyl)-N-methylacetamide trifluoroacetic acid salt and

Example 257

(S)-N-(2-(Cyclobutylsulfonyl)benzyl)-2-(1-aminoisoquinolin-6-ylamino)-2-(3-ethoxy-4-isopropoxyphenyl)-N-methylacetamide trifluoroacetic acid salt trifluoroacetic acid salt

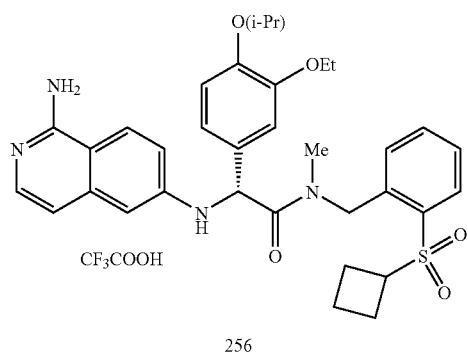

256

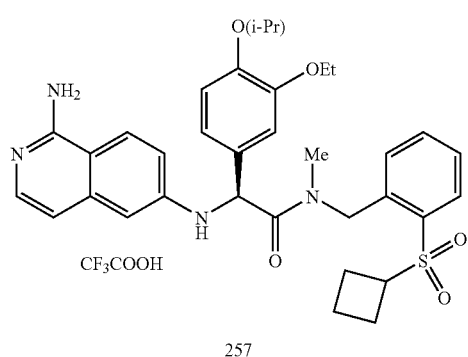

257

Example 255 (55 mg) was dissolved in MeOH and the enantiomers were separated on a Chiralpak® AD column eluting with 50% heptane, 50% 1:1 MeOH/EtOH, 0.1% DEA which eluted Example 256 (free base), followed by Example 257 (free base). Both products were separately dissolved in acetonitrile (0.5 mL) and TFA (~5 µL) was added. The solutions were concentrated then dissolved in acetonitrile/water and lyophilized overnight to provide Example 256 (23 mg) [LC-MS: 617.19 (M+H)$^+$], and Example 257 (23 mg) [LC-MS: 617.17 (M+H)$^+$].

Example 258

N-(2-(Cyclopropylsulfonyl)benzyl)-2-(1-amino-5-methylisoquinolin-6-ylamino)-2-(3-ethoxy-4-isopropoxyphenyl)acetamide trifluoroacetic acid salt

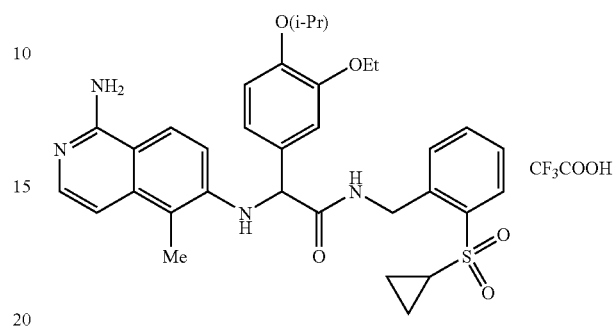

258A

5-Bromo-6-Amino-1-di-tert-butoxycarbonylaminoisoquinoline

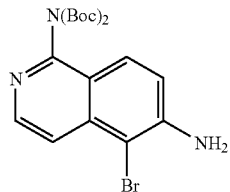

To Intermediate 1 (250 mg, 0.696 mmol) in CH$_2$Cl$_2$ (7 mL), NBS (124 mg, 0.697 mmol) was added. After stirring for 10 min, the reaction was concentrated and purified via silica gel chromatography eluting with 30-50% ethyl acetate/hexane to provide 258A (350 mg) as a pale yellow solid. LC-MS: 438 (M+H)$^+$.

258B

5-Methyl-6-Amino-1-di-tert-butoxycarbonylaminoisoquinoline trifluoroacetic acid salt

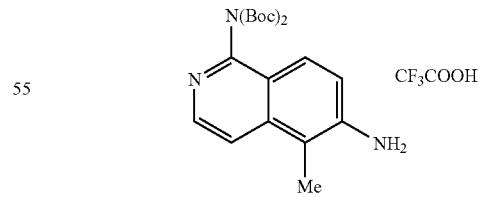

258A (150 mg, 0.343 mmol) and PdCl$_2$(PPh$_3$)$_2$ were placed in a tube and the solids were degassed with nitrogen for 5 min. DMF (1.5 mL) and tetramethyltin (141 mL, 1.02 mmol) were added and the mixture was degassed with nitrogen for 2 min. The tube was sealed and the reaction mixture was heated to 110° C. overnight then cooled to rt. The mixture was loaded onto a silica gel column and was eluted with 100% hexanes followed by 30-50% ethyl acetate/hexane. The isolated product was purified via preparative chromatography (MeOH/water/TFA) to provide 258B (91 mg, 57%) as a yellow film. LC-MS: 374.30 (M+H)+.

258C

Benzyl 2-(1-di-tert-butoxycarbonylamino-5-methyl-isoquinolin-6-ylamino)-2-(3-ethoxy-4-isopropoxyphenyl)acetate trifluoroacetic acid salt

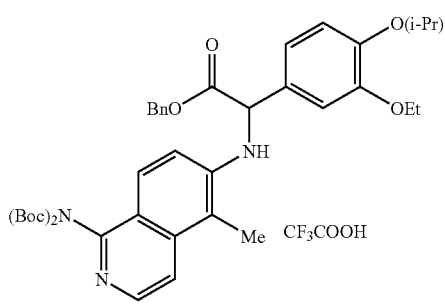

To a mixture of chloro-(3-ethoxy-4-isopropoxy-phenyl)-acetic acid benzyl ester ((WO 2004072101) (131 mg, 0.361 mmol) and 258B (91 mg, 0.244 mmol) in acetonitrile (2.4 mL) in a tube, DIPEA (167 µL, 0.959 mmol) and TBAB (15 mg, 0.047 mmol) were added. The tube was sealed and the reaction mixture was heated to 80° C. overnight. After cooling to rt, the reaction was concentrated and purified via preparative chromatography (MeOH/water/TFA) to provide benzyl 2-(3-ethoxy-4-isopropoxyphenyl)-2-hydroxyacetate (50 mg) followed by 258C (43 mg, 26%) as a yellow oil. LC-MS: 700.64 (M+H)+.

258D 2-(1-Di-tert-butoxycarbonylamino-5-methylisoquinolin-6-ylamino)-2-(3-ethoxy-4-isopropoxyphenyl)acetic acid trifluoroacetic acid salt

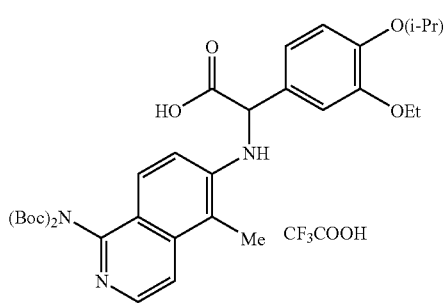

258C (43 mg, 0.062 mmol) in methanol (1 mL) was hydrogenated with a hydrogen balloon in the presence of 10% Pd/C (10 mg) for 1.5 h. Filtration through Celite® and concentration gave compound 258D as a yellow oil (32 mg, 73%). LC-MS: 610.57 (M+H)+.

258E

Example 259 (5.1 mg) was prepared from acid 258D (16 mg) and Intermediate 7 (11 mg) following the general coupling/deprotection procedure in 35% overall yield. $^1$H NMR (400 MHz, CD$_3$OD) δ ppm 1.09 (m, 4H) 1.29 (d, J=6.15 Hz, 6H) 1.34 (t, J=7.03 Hz, 3H) 2.44 (s, 3H) 2.77 (m, 1H) 3.99 (q, J=7.03 Hz, 2H) 4.52 (m, 1H) 4.87 (m, 2H) 5.28 (s, 1H) 6.95 (m, 2H) 7.06 (m, 2H) 7.27 (m, 2H) 7.39 (d, J=7.47 Hz, 1H) 7.47 (m, 2H) 7.82 (m, 1H) 7.99 (d, J=9.23 Hz, 1H) 8.53 (s, 1H). LC-MS: 603.24 (M+H)+.

Example 259

N-(2-(Cyclopropylsulfonyl)benzyl)-2-(1-amino-5-methylisoquinolin-6-ylamino)-2-(3-ethoxy-4-isopropoxyphenyl)-N-methylacetamide trifluoroacetic acid salt

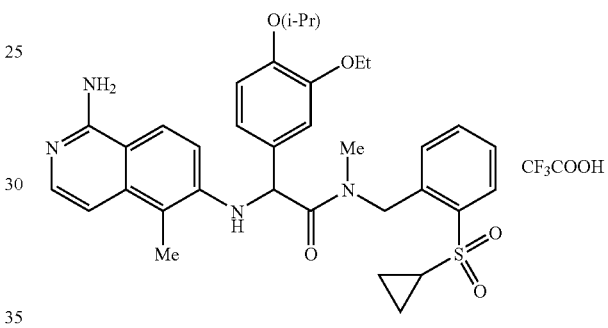

Example 259 (6 mg) was prepared from acid 258D (20 mg) and Intermediate 8 (17 mg) following the general coupling/deprotection procedure in 25% overall yield. LC-MS: 617.37 (M+H)+.

Example 260

N-(5-Acetylamino-2-ethanesulfonyl-benzyl)-2-(1-amino-5-methylisoquinolin-6-ylamino)-2-(3-ethoxy-4-isopropoxyphenyl)-N-Me-acetamide trifluoroacetic acid salt

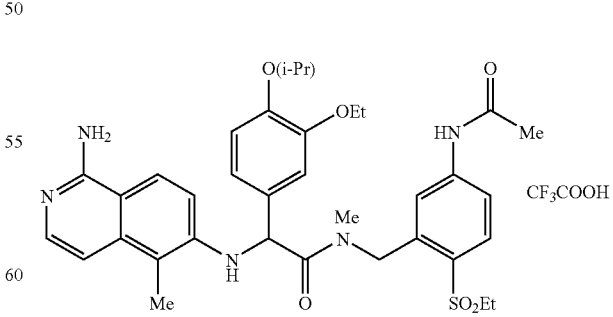

Example 260 (6 mg) was prepared from 258D (20 mg) and Intermediate 10 (18 mg) following the general coupling/deprotection procedure in 23% overall yield. LC-MS: 662.40 (M+H)+.

Example 261

N-(2-(Cyclopropylsulfonyl)benzyl)-2-(1-amino-5-fluoroisoquinolin-6-ylamino)-2-(3-ethoxy-4-isopropoxyphenyl)acetamide Trifluoroacetic Acid Salt

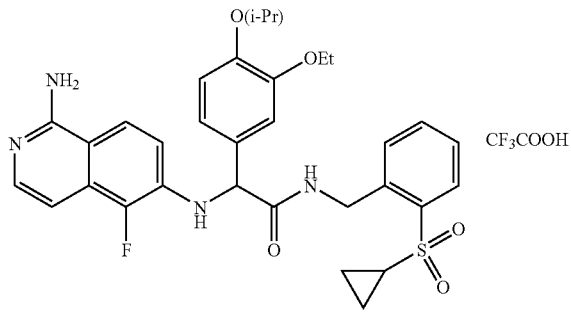

261A

5-Fluoro-6-Amino-1-di-tert-butoxycarbonylaminoisoquinoline

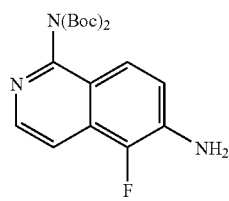

To Intermediate 1 (300 mg, 0.836 mg) in acetonitrile (15 mL), Selectfluor™ (296 mg, 0.836 mmol) was added. After stirring for 1 h at rt, the reaction was concentrated and purified via silica gel chromatography eluting with 20-50% ethyl acetate/hexane to provide 261A [88 mg, 28%, LC-MS: 378.33 (M+H)$^+$] as a yellow oil followed by the starting material, 6-amino-1-di-tert-butoxycarbonylaminoisoquinoline (100 mg, 33%).

261B

Benzyl 2-(1-di-tert-butoxycarbonylamino-5-fluoroisoquinolin-6-ylamino)-2-(3-ethoxy-4-isopropoxyphenyl)acetate Trifluoroacetic Acid Salt

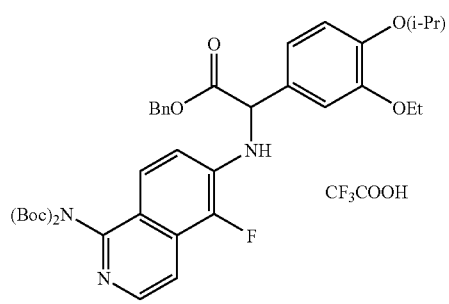

To a mixture of chloro-(3-ethoxy-4-isopropoxy-phenyl)-acetic acid benzyl ester (WO 2004072101) (102 mg, 0.281 mmol) and 261A (88 mg, 0.23 mmol) in acetonitrile (2.3 mL) in a tube, DIPEA (160 µl, 0.919 mmol) was added. The tube was sealed and the reaction mixture was heated to 80° C. for 16 h. After cooling to rt, the reaction was concentrated and purified via preparative chromatography (MeOH/water/TFA) to provide starting material, 261A (15.0 mg, 17%) and 261B (88 mg, 47%) as a yellow oil. LC-MS: 704.22 (M+H)$^+$.

261C 2-(1-Di-tert-butoxycarbonylamino-5-fluoroisoquinolin-6-ylamino)-2-(3-ethoxy-4-isopropoxyphenyl) acetic acid Trifluoroacetic Acid Salt

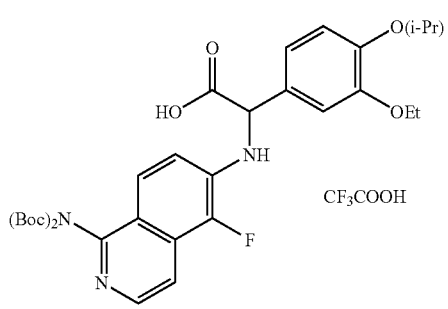

261B (88 mg, 0.11 mmol) in methanol (2 mL) was hydrogenated with a hydrogen balloon in the presence of 10% Pd/C (20 mg) for 1.5 h. Filtration through Celite® and concentration gave compound 261C as a yellow glass (77 mg, 98%). LC-MS: 614.17 (M+H)$^+$.

261D

Example 261 (9.9 mg) was prepared from acid 261C (28 mg) and Intermediate 7 (19 mg) following the general coupling/deprotection procedure in 36% overall yield. $^1$H NMR (400 MHz, CD$_3$OD) δ ppm 1.10 (m, 4H) 1.29 (d, J=5.71 Hz, 6H) 1.35 (t, J=7.03 Hz, 3H) 2.79 (m, 1H) 4.00 (m, 2H) 4.52 (m, 1H) 4.86 (m, 2H) 5.30 (s, 1H) 6.96 (d, J=7.91 Hz, 1H) 7.07 (m, 3H) 7.12 (m, 1H) 7.31 (m, 1H) 7.46 (m, 3H) 7.83 (m, 1H) 7.96 (d, J=8.79 Hz, 1H) 8.56 (m, 1H). LC-MS: 607.05 (M+H)$^+$.

Example 262

N-(2-(Cyclobutylsulfonyl)benzyl)-2-(1-amino-4-methylisoquinolin-6-ylamino)-2-(3-ethoxy-4-isopropoxyphenyl)-N-methylacetamide Trifluoroacetic Acid Salt

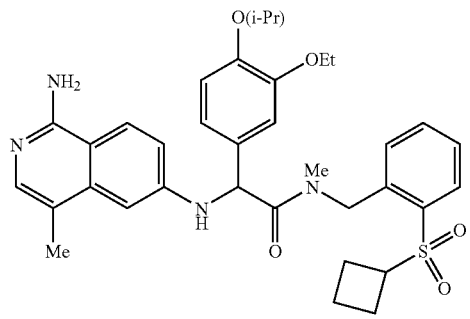

262A

N,N-Dibenzyl-3-bromobenzenamine

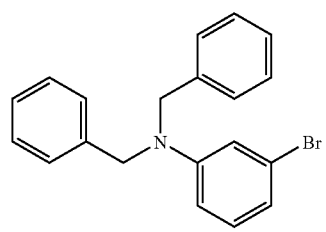

To 3-bromoaniline (5.00 g, 29.1 mmol) in acetonitrile (145 mL) was added DIPEA (5.1 mL, 87.2 mmol) and benzyl bromide (7.6 mL, 63.9 mmol) and the reaction was heated to 60° C. overnight. After cooling to rt, the reaction was concentrated and purified via silica gel chromatography eluting with 100% hexanes–10% ethyl acetate/hexanes to provide 262A (3.85 g) as a yellow oil. LC-MS: 353.92 (M+H)$^+$.

262B

Methyl 3-(3-(dibenzylamino)phenyl)but-2-enoate

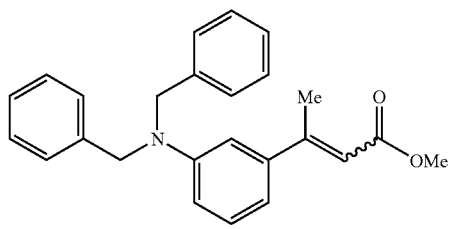

To 262A (3.00 g, 8.52 mmol) in triethylamine (5 mL) in a tube was added methyl crotonate (1.8 mL, 17.0 mmol) and the solution was degassed for 5 min with nitrogen. Palladium (II) acetate (96.0 mg, 0.43 mmol) and tri(o-tolyl) phosphine (259 mg, 0.85 mmol) were added and degassing was continued for another 5 min. The tube was sealed and the reaction was heated to 100° C. for 4 h. After cooling to rt, the reaction was diluted with ethyl acetate, filtered through Celite®, concentrated, and purified via silica gel chromatography (eluting with 10% ethyl acetate/hexanes) to provide 262B (1.80 g) as a yellow oil. LC-MS: 372.18 (M+H)$^+$.

262C 3-(3-(Dibenzylamino)phenyl)but-2-enoic acid

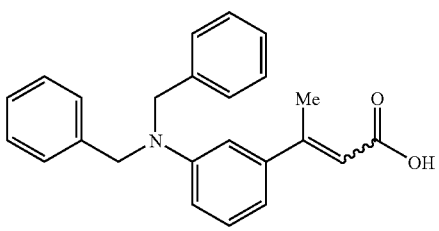

To 262B (1.8 g, 4.85 mmol) in THF (48 mL) and MeOH (24 mL) was added 1N NaOH (19.4 mL). The reaction was heated to 80° C. for 2.5 h then cooled to rt. The volatiles were removed under reduced pressure, and the remaining solution was cooled to 0° C. and acidified to pH 1 with 1 N HCl. The solution was extracted with ethyl acetate, dried (MgSO$_4$), filtered and concentrated to provide 262C (1.6 g) as a yellow oil. LC-MS: 358.24 (M+H)$^+$.

262D

1-Azido-3-(3-(dibenzylamino)phenyl)but-2-en-1-one

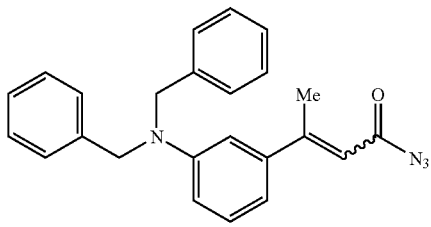

To 262C (800 mg, 2.24 mmol) in acetone (2 mL) at 0° C. was added triethylamine (375 µL, 2.69 mmol) and ethylchloroformate (278 µL, 2.91 mmol). After stirring for 30 min, sodium azide (218 mg, 3.36 mmol) in water (1 mL) was added dropwise. The ice bath was removed and the reaction was stirred for 1 h. The reaction was poured over ice, and when ice melted, the acetone was removed under reduced pressure. The resulting solution was extracted with ethyl acetate, then dried, filtered and concentrated to provide 262D (714 mg) as a yellow oil. LC-MS: 383.09 (M+H)$^+$.

262E 6-(Dibenzylamino)-4-methylisoquinolin-1(2H)-one

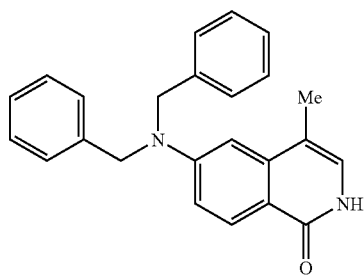

A solution of 262D (431 mg, 1.13 mmol) in CH$_2$Cl$_2$ (2 mL) was added via addition funnel to diphenylether (2 mL) and tributylamine (323 mL, 1.36 mmol) at 240° C. The CH$_2$Cl$_2$ was allowed to evaporate and the reaction was heated at 240° C. for 2 h. After cooling to rt, hexane was added and the resulting solid was filtered to provide 262E (244 mg) as a yellow solid. LC-MS: 355.20 (M+H)$^+$.

262F

N,N-Dibenzyl-1-chloro-4-methylisoquinolin-6-amine trifluoroacetc acid salt

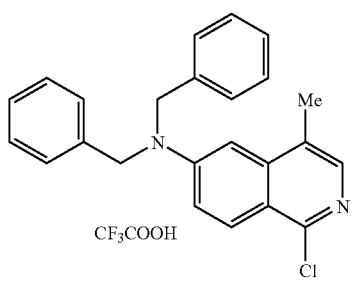

262E (475 mg, 1.34 mmol) was diluted with phosphorous (III) oxychloride (10 mL) and the reaction was heated to reflux for 1 h. After cooling to rt, the reaction was concentrated and purified via flash chromatography (eluting with 30% ethyl acetate/hexanes –100% ethyl acetate –10% MeOH/ethyl acetate) followed by preparative HPLC (MeOH/water/TFA) to provide 262F (385 mg) as a brown solid. LC-MS: 373.13 (M+H)$^+$.

262G

4-Methylisoquinoline-1,6-diamine

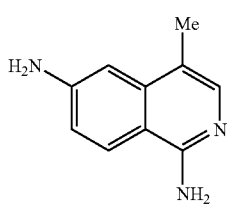

262F (295 mg, 0.79 mmol), copper (I) oxide (11 mg, 0.79 mmol) and a –12M solution of ammonia in ethylene glycol (2.6 mL) were combined in a sealed tube and the whole was heated to 130° C. for 62 h. After cooling to rt, the ammonia was removed under reduced pressure and the reaction was diluted with ethyl acetate, and washed with water and brine. The aqueous layer was back-extracted with ethyl acetate and the combined organic layers were dried (MgSO$_4$), filtered and concentrated. The resulting residue was dissolved in MeOH and TFA (10 µL) was added. The reaction was concentrated and purified via flash chromatography eluting with 10% MeOH/CH$_2$Cl$_2$ to provide 262G (306 mg) as a brown solid. LC-MS: 354.01 (M+H)$^+$.

262H

4-Me-amino-1-di-tert-butoxycarbonylaminoisoquinoline hydrochloride

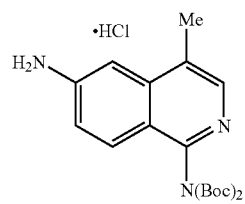

A mixture of 262G (150 mg, 0.42 mmol) and di-tert-butyl dicarbonate (324.0 mg, 1.49 mmol) was heated to 130° C. for 30 min. After cooling to rt, the residue was purified via silica gel chromatography eluting with 30% ethyl acetate/hexanes to provide a yellow foam (128 mg) [LC-MS: 554.1 (M+H)$^+$]. The foam was dissolved in EtOH (2 mL), Pd(OH)$_2$/C (ca. 10 mg) and 4 M HCl/dioxane (0.23 mL) were added, and the mixture was hydrogenated at 50 psi overnight. The reaction was filtered through Celite® and concentrated to provide 262H (84 mg) as a yellow film. LC-MS: 374.13 (M+H)$^+$.

262I

Benzyl 2-(1-di-tert-butoxycarbonylamino-4-methyl-isoquinolin-6-ylamino)-2-(3-ethoxy-4-isopropoxyphenyl)acetate

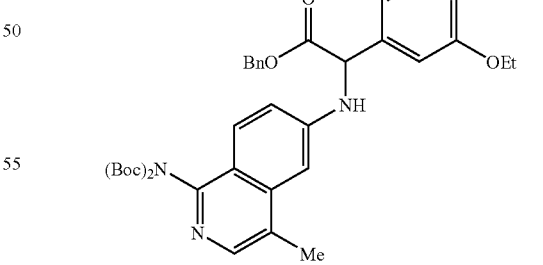

To a mixture of chloro-(3-ethoxy-4-isopropoxy-phenyl)-acetic acid benzyl ester (WO 2004072101) (68 mg, 0.187 mmol) and 262H (83 mg, 0.187 mmol) in acetonitrile (2.0 mL) in a tube, DIPEA (130 g, 0.748 mmol) was added. The tube was sealed and the reaction mixture was heated to 80° C. overnight. After cooling to rt, the reaction was concentrated and purified via silica gel chromatography (50% ethyl acetate/hexanes) to provide starting material, 262H (18.0 mg) and 262I (33 mg) as a yellow oil. LC-MS: 700.42 (M+H)⁺.

262J

Benzyl 2-(1-di-tert-butoxycarbonylamino-4-methyl-isoquinolin-6-ylamino)-2-(3-ethoxy-4-isopropoxyphenyl)acetic acid

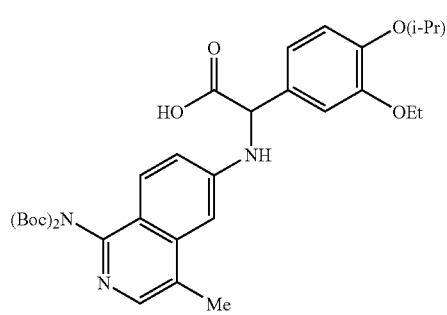

Compound 262I (33 mg, 0.047 mmol) in methanol (2 mL) was hydrogenated with a hydrogen balloon in the presence of 10% Pd/C (ca. 10 mg) for 3 h. Filtration through Celite® and concentration provided compound 262J (23 mg). LC-MS: 610.11 (M+H)⁺

262K

Example 262 (10 mg) was prepared from 262J (23 mg) and Intermediate 12 (26 mg) following the general coupling/deprotection procedure in 29% overall yield. LC-MS: 631.1 (M+H)⁺.

Example 263

N-(2-(Cyclobutylsulfonyl)benzyl)-2-(1-amino-7-methylisoquinolin-6-ylamino)-2-(3-ethoxy-4-isopropoxyphenyl)-N-methylacetamide Trifluoroacetic Acid Salt

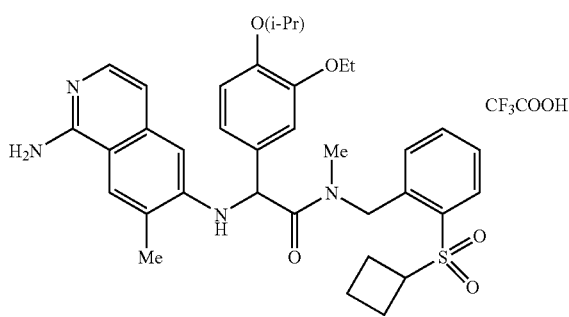

263A

N,N-Dibenzyl-5-bromo-2-methylbenzenamine

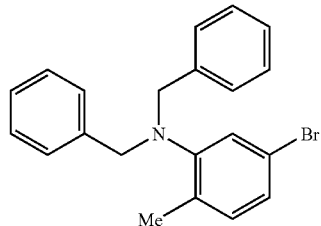

To 5-bromo-2-methylaniline (5.00 g, 27.0 mmol) in acetonitrile (135 mL) was added DIPEA (14 mL, 81.1 mmol) and benzyl bromide (7.0 mL, 59.4 mmol) and the reaction was heated to 65° C. overnight. After cooling to rt, the reaction was concentrated and purified via silica gel chromatography eluting with 5% ethyl acetate/hexanes to provide 263A (6.10 g) as a yellow oil.

263B (E)-Methyl 3-(3-(dibenzylamino)-4-methylphenyl) acrylate

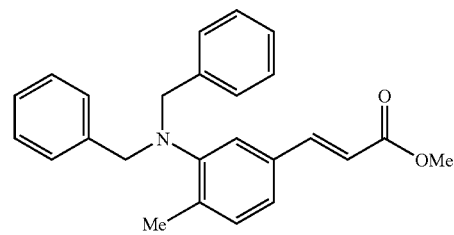

To 263A (3.00 g, 8.20 mmol) in triethylamine (4.8 mL) in a tube was added methyl acrylate (1.5 mL, 16.4 mmol) and the solution was degassed for 5 min with nitrogen. Palladium (II) acetate (92.0 mg, 0.41 mmol) and tri(o-tolyl) phosphine (250 mg, 0.82 mmol) were added and degassing was continued for another 5 min. The tube was sealed and the reaction was heated to 100° C. for 5.5 h. After cooling to rt, the reaction was diluted with ethyl acetate, filtered through Celite®, concentrated, and purified via silica gel chromatography (eluting with 5-10% ethyl acetate/hexanes) to provide 263B (2.8 g) as a clear oil. LC-MS: 372.11 (M+H)⁺.

263C (E)-3-(3-(dibenzylamino)-4-methylphenyl)acrylic acid

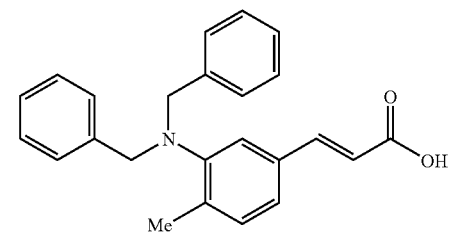

To 263B (2.8 g, 7.55 mmol) in THF (76 mL) and MeOH (38 mL) was added 1N NaOH (30 mL). The reaction was heated to 80° C. for 1.25 h then cooled to rt. The volatiles were removed under reduced pressure, and the remaining solution was cooled to 0° C. and acidified to pH 1 with 1 N HCl. The solution was extracted with ethyl acetate, dried (MgSO$_4$), filtered and concentrated to provide 263C (2.59 g) as a yellow solid. LC-MS: 358.11 (M+H)$^+$.

263D

Benzyl 2-(1-di-tert-butoxycarbonylamino-7-methyl-isoquinolin-6-ylamino)-2-(3-ethoxy-4-isopropoxyphenyl)acetic acid

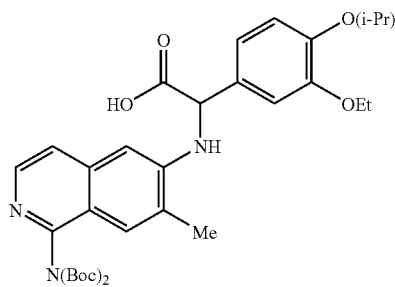

263D was prepared in 7 steps from 263C following procedures analogous to those used to prepare 262J. LC-MS: 610.15 (M+H)$^+$.

263E

Example 263 (3.0 mg) was prepared from 263D (20 mg) and Intermediate 12 (15 mg) following the general coupling/deprotection procedure in 29% overall yield. LC-MS: 631.1 (M+H)$^+$.

Example 264

N-Benzyl-2-(3-ethoxy-4-isopropoxyphenyl)-2-(isoquinolin-6-ylamino)acetamide Trifluoroacetic Acid Salt

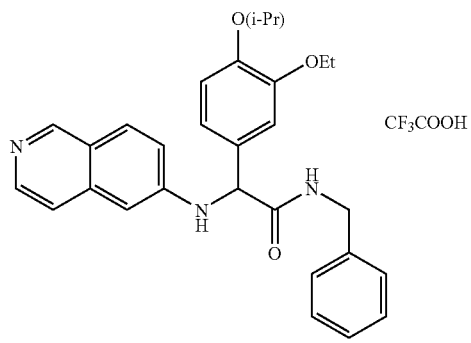

A mixture of Intermediate 13 (24 mg, 0.063 mmol), benzylamine (13 mg, 0.12 mmol), EDC (23 mg, 0.12 mmol), HOAT (2.5 mg, 0.018 mmol), and DIPEA (24 mg, 0.18 mmol) in CH$_2$Cl$_2$/DMF (2 mL, 4:1) was stirred at rt overnight. The reaction was concentrated and purified via preparative HPLC (MeOH/H$_2$O/TFA) to provide Example 264 (21 mg, 71%) as a yellow solid. $^1$H NMR (400 MHz, d$_6$-DMSO) δ ppm 1.22 (d, J=6.15 Hz, 6H) 1.30 (t, J=7.03 Hz, 3H) 3.97 (q, J=6.88 Hz, 2H) 4.31 (m, 2H) 4.47 (m, 1H) 5.26 (m, 1H) 6.78 (s, 1H) 6.94 (d, J=8.35 Hz, 1H) 7.03 (m, 1H) 7.19 (m, 5H) 7.59 (d, J=8.35 Hz, 1H) 7.76 (d, J=7.03 Hz, 1H) 8.08 (d, J=9.23 Hz, 1H) 8.23 (m, 2H) 8.90 (s, 1H) 9.20 (s, 1H). LC-MS: 470.38 (M+H)$^+$.

Example 265

2-(3-Ethoxy-4-isopropoxyphenyl)-2-(isoquinolin-6-ylamino)-N-(2-phenylpropan-2-yl)acetamide Trifluoroacetic Acid Salt

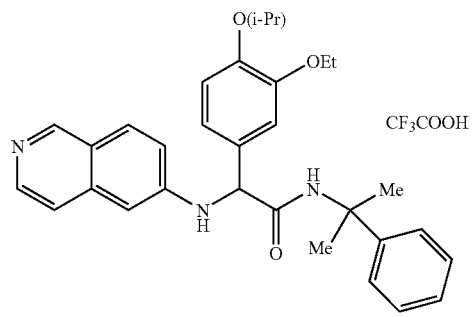

A mixture of Intermediate 13 (23 mg, 0.060 mmol), 2-phenylpropan-2-amine (11 mg, 0.078 mmol), EDC (23 mg, 0.12 mmol), HOAT (2.5 mg, 0.018 mmol), and DIPEA (24 mg, 0.18 mmol) in CH$_2$Cl$_2$/DMF (2 mL, 4:1) was stirred at rt overnight. The reaction was concentrated and purified via preparative HPLC (MeOH/H$_2$O/TFA) to provide Example 265 (18 mg, 60%) as a yellow solid. $^1$H NMR (400 MHz, CD$_3$OD) δ ppm 1.27 (m, 6H) 1.39 (m, 3H) 1.55 (m, 3H) 1.71 (s, 3H) 4.03 (q, J=6.74 Hz, 2H) 4.56 (m, 1H) 5.21 (s, 1H) 6.85 (s, 1H) 7.01 (d, J=8.79 Hz, 1H) 7.13 (m, 7H) 7.46 (dd, J=9.23, 2.20 Hz, 1H) 7.80 (d, J=6.59 Hz, 1H) 8.07 (m, 2H) 8.44 (s, 1H) 9.05 (s, 1H). LC-MS: 498.41 (M+H)$^+$.

Example 266

2-(3-Ethoxy-4-isopropoxyphenyl)-2-(isoquinolin-6-ylamino)-N-((R)-1-phenylethyl)acetamide Trifluoroacetic Acid Salt

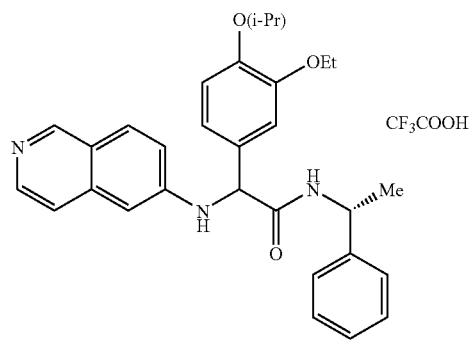

A mixture of Intermediate 13 (23 mg, 0.060 mmol), (R)-α-methylbenzylamine (15.0 mg, 0.12 mmol), EDC (23 mg, 0.12 mmol), HOAT (2.5 mg, 0.01-8 mmol), and DIPEA (24 mg, 0.18 mmol) in CH$_2$Cl$_2$/DMF (2 mL, 4:1) was stirred at rt overnight. The reaction was concentrated and purified via preparative HPLC (MeOH/H$_2$O/TFA) to provide Example 266 (28 mg, 97%) as a yellow solid. LC-MS: 484.44 (M+H)$^+$.

Examples 267-274 were prepared as part of a library, from Intermediate 13 and amines or amine hydrochloric acid salts that were either commercially available or prepared as described in the previous examples. The following coupling procedure was used: To an individual well of a 48-position MiniBlock® XT reactor was added 100 µL of a 0.25 M solution of the amine in dimethylformamide (DMF) (0.025 mmol, 1.25 eq); 25 µL of a 1.0 M solution of 1-hydroxybenzotriazole in DMF (0.025 mmol, 1.25 eq); 100 µL of a 0.25 M solution of N-(3-dimethylaminopropyl)-N'-ethylcarbodiimide hydrochloride (0.025 mmol, 1.25 eq); 100 µL of DCE; and 40 µL of a 0.50 M solution of Intermediate 13 (0.020 mmol, 1.0 eq) in DMF and N-ethyldiisopropylamine (0.060 mmol, 3.0 eq). The reactor was agitated for 3 h at 50° C., then cooled to rt. The crude product was diluted with methanol to a total volume of 1 mL, then purified by standard preparative HPLC-MS (H$_2$O/MeOH/0.1% TFA, gradient 35-90% MeOH over 12 min, 20×100 mm 5 µm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA).

Table 1 exemplifies these Examples with their substituents and LC-MS data.

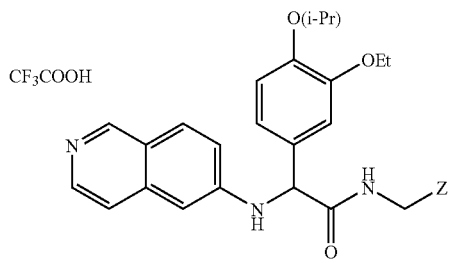

TABLE 1

| Example # | Name | Z | LC-MS: (M + H)$^+$ |
|---|---|---|---|
| 267 | 2-(3-ethoxy-4-isopropoxyphenyl)-2-(isoquinolin-6-ylamino)-N-(pyridin-2-ylmethyl)acetamide trifluoroacetic acid salt | | 471.090 |
| 268 | N-(3-Acetylamino-benzyl)-2-(3-ethoxy-4-isopropoxy-phenyl)-2-(isoquinolin-6-ylamino)-acetamide trifluoroacetic acid salt | | 527.200 |
| 269 | N-(2-(methylsulfonyl)benzyl)-2-(3-ethoxy-4-isopropoxyphenyl)-2-(isoquinolin-6-ylamino)acetamide trifluoroacetic acid salt | | 548.060 |
| 270 | N-(2-(piperidin-1-yl)benzyl)-2-(3-ethoxy-4-isopropoxyphenyl)-2-(isoquinolin-6-ylamino)acetamide trifluoroacetic acid salt | | 553.190 |
| 271 | 2-(3-Ethoxy-4-isopropoxy-phenyl)-2-(isoquinolin-6-ylamino)-N-(2-sulfamoyl-benzyl)-acetamide trifluoroacetic acid salt | | 549.070 |
| 272 | N-(4-chloro-2-fluorobenzyl)-2-(3-ethoxy-4-isopropoxyphenyl)-2-(isoquinolin-6-ylamino)acetamide trifluoroacetic acid salt | | 522.030 |

TABLE 1-continued

| Example # | Name | Z | LC-MS: (M + H)+ |
|---|---|---|---|
| 273 | N-(2-(trifluoromethylthio)benzyl)-2-(3-ethoxy-4-isopropoxyphenyl)-2-(isoquinolin-6-ylamino)acetamide trifluoroacetic acid salt | 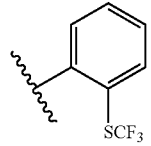 | 570.240 |
| 274 | N-(4-hydroxy-3-methoxybenzyl)-2-(3-ethoxy-4-isopropoxyphenyl)-2-(isoquinolin-6-ylamino)acetamide trifluoroacetic-acid salt | 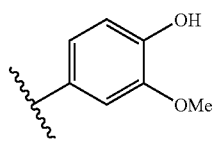 | 516.290 |

Example 275

N-(5-Acetamido-2-(ethylsulfonyl)benzyl)-2-(1-aminoisoquinolin-6-ylamino)-2-(3,5-diethoxyphenyl)acetamide trifluoroacetic acid salt

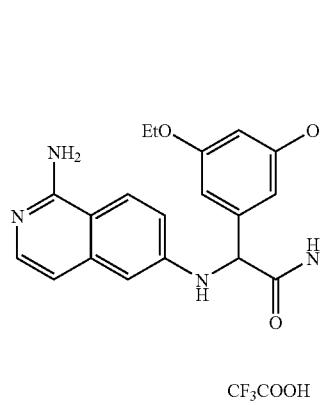

CF$_3$COOH

275A 3,5-Diethoxybenzaldehyde

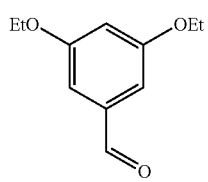

A mixture of 3,5-dihydroxybenzaldehyde (1.38 g, 10 mmol), ethyl iodide (2.00 mL, 25 mmol), and potassium carbonate (3.45 g, 25 mmol) in acetonitrile (10 mL) was stirred at 80° C. overnight. TLC showed starting material and monoalkylated product, so additional ethyl iodide (0.5 mL, 6.2 mmol) was added and heating continued for 7 h. The reaction mixture was concentrated in vacuo. The residue was partitioned between dichloro-methane and water, and the organic extract was then concentrated in vacuo. The residual material was purified by silica gel chromatography (gradient from 0 to 30% EtOAc in hexanes) to give 275A (1.3 g, 67%) as a pale yellow solid. $^1$H NMR (400 MHz, CDCl$_3$) δ ppm 1.43 (t, J=6.81 Hz, 6H) 4.07 (q, J=7.03 Hz, 4H) 6.69 (t, J=1.98 Hz, 1H) 6.99 (d, J=2.64 Hz, 2H) 9.89 (s, 1H).

275B 2-(3,5-Diethoxyphenyl)-2-hydroxyacetonitrile

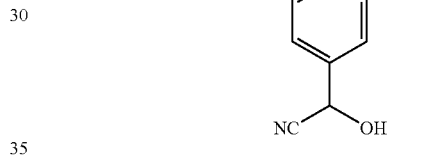

Sodium hydrogen sulfite (2.09 g, 20 mmol) was added to a solution of aldehyde 275A (1.3 g, 6.7 mmol) in EtOAc (15 mL). Water (5 mL) was then added, followed by potassium cyanide (1.32 g, 20 mmol). The resulting clear solution was stirred at rt for 48 h. The reaction mixture was diluted with water and extracted with ethyl acetate. The organic layers were dried and concentrated in vacuo. The residue was purified by silica gel chromatography (gradient from 0 to 30% EtOAc in hexanes) to give 275B (1.07 g, 72%) as a white solid. $^1$H NMR (400 MHz, CDCl$_3$) δ ppm 1.41 (t, J=7.03 Hz, 6H) 4.03 (q, J=7.03 Hz, 4H) 5.45 (d, J=7.47 Hz, 1H) 6.48 (t, J=2.20 Hz, 1H) 6.64 (d, J=2.20 Hz, 2H).

275C

Methyl 2-(3,5-diethoxyphenyl)-2-hydroxyacetate

A solution of cyanohydrin 275B (1.04 g, 4.84 mmol) in ether (25 mL) was cooled to 0° C. Methanol (1.03 mL, 24 mmol) was added, followed by hydrogen chloride (4 N solution in dioxane, 7 mL). The reaction mixture was placed in a refrigerator for one week. The reaction mixture was filtered, to give a white solid (1.61 g). The solid (0.78 g) was dissolved in dichloromethane (5 mL) and water (5 mL) and stirred for 1 h. The aqueous layer was extracted with dichloromethane. The organic extracts were dried and concentrated to give 275C (0.73 g, 93%) as a clear oil. $^1$H NMR (400 MHz, CDCl$_3$) δ ppm 1.40 (t, J=7.03 Hz, 6H) 3.40 (d, J=5.71 Hz, 1H) 3.77 (s, 3H) 4.01 (q, J=7.03 Hz, 4H) 5.08 (d, J=5.71 Hz, 1H) 6.41 (t, J=2.20 Hz, 1H) 6.55 (d, J=2.20 Hz, 2H).

275D

Methyl 2-(3,5-diethoxyphenyl)-2-(methylsulfonyloxy)acetate

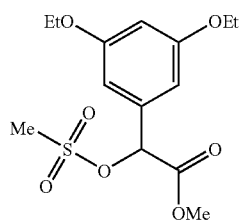

Methanesulfonyl chloride (0.148 mL, 1.91 mmol) was added slowly dropwise to a solution of 275C (0.35 g, 1.38 mmol) and TEA (0.288 mL, 2.07 mmol) in dichloromethane (10 mL). The reaction was stirred at rt until tlc indicated completion. It was diluted with EtOAc, and washed with cold hydrochloric acid (0.1 N), water, and then brine. The organic layers were dried and concentrated in vacuo to give 275D (0.43 g, 94%) as a white solid. $^1$H NMR (400 MHz, CDCl$_3$) δ ppm 1.41 (t, J=6.81 Hz, 6H) 3.07 (s, 3H) 3.78 (s, 3H) 4.01 (q, J=7.03 Hz, 4H) 5.82 (s, 1H) 6.47 (t, J=2.20 Hz, 1H) 6.56 (d, J=2.20 Hz, 2H).

275E

Methyl 2-(1-di-tert-butoxycarbonylaminoisoquinolin-6-ylamino)-2-(3,5-diethoxyphenyl)acetate

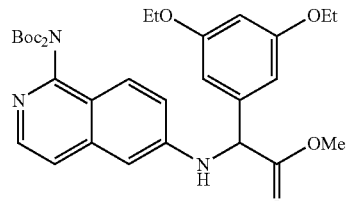

A solution of mesylate 275D (0.087 g, 0.26 mmol), Intermediate 1 (108 mg, 0.300 mmol), and DIEA (0.080 mL, 0.46 mmol) in DMF was stirred at 90° C. overnight. The reaction mixture was concentrated and the residue was purified by chromatography on silica gel (gradient from 20 to 50% EtOAc in hexanes) to give 275E (32 mg, 21%). $^1$H NMR (400 MHz, CDCl$_3$) δ ppm 1.31 (s, 18H) 1.39 (t, J=7.03 Hz, 6H) 3.78 (s, 3H) 4.00 (q, J=7.03 Hz, 4H) 5.08 (d, J=5.27 Hz, 1H) 5.51 (d, J=5.27 Hz, 1H) 6.41 (t, J=1.98 Hz, 1H) 6.53 (d, J=1.76 Hz, 1H) 6.66 (d, J=1.76 Hz, 2H) 7.02 (dd, J=9.01, 1.98 Hz, 1H) 7.29 (d, J=6.15 Hz, 1H) 7.71 (d, J=9.23 Hz, 1H) 8.18 (d, J=5.71 Hz, 1H).

275F 2-(1-Di-tert-butoxycarbonylaminoisoquinolin-6-ylamino)-2-(3,5-diethoxyphenyl)acetic acid

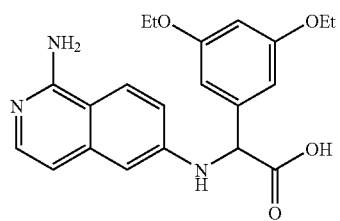

Using a procedure similar to that used to prepare Intermediate 13, 275E (32 mg, 0.054 mmol) was hydrolyzed to give 275F (39 mg, 100%) as an off-white solid. LC-MS: 582.2 (M+H)$^+$.

275G

Example 275 (20 mg, 41%, white solid) was prepared from 275F (39 mg, 0.067 mmol) and Intermediate 9 (22 mg, 0.085 mmol) using the general coupling-deprotection procedure. $^1$H NMR (400 MHz, CD$_3$OD) δ ppm 1.16 (t, J=7.25 Hz, 3H) 1.33 (t, J=6.81 Hz, 6H) 2.12 (s, 3H) 3.22 (q, J=7.47 Hz, 2H) 3.88-4.02 (m, 4H) 4.61-4.77 (m, J=12.96, 5.93 Hz, 2H) 5.09 (s, 1H) 6.40 (t, J=2.20 Hz, 1H) 6.58-6.64 (m, 3H) 6.75 (d, J=7.47 Hz, 1H) 7.16 (dd, J=9.01, 1.98 Hz, 1H) 7.29 (d, J=7.47 Hz, 1H) 7.62-7.68 (m, 1H) 7.71 (d, J=1.32 Hz, 1H) 7.77 (d, J=8.79 Hz, 1H) 8.04 (d, J=9.23 Hz, 1H) 8.58 (t, J=6.15 Hz, 1H); LC-MS: 620.2 (M+H)$^+$.

Example 276

Ethyl 3-((2-(1-aminoisoquinolin-6-ylamino)-2-(5-ethoxy-2-fluorophenyl)acetamido)methyl)-4-(ethylsulfonyl)phenylcarbamate trifluoroacetic acid salt

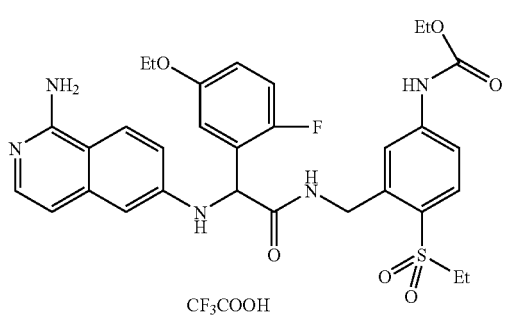

276A

5-Amino-2-(ethylsulfonyl)benzonitrile

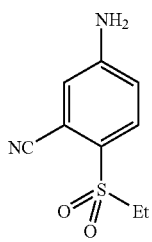

Iron powder (1.67 g, 29.9 mmol) was added portionwise over 1.5 h to a suspension of Intermediate 9B (0.95 g, 4.0 mmol) in a mixture of acetic acid (3 mL), ethanol (26 mL), and water (5 mL) at 115° C. The reaction was cooled to rt, filtered through glass fibre filter paper, neutralized with saturated sodium bicarbonate, and extracted with ethyl acetate (4×). The combined organics were washed with brine, dried, and concentrated in vacuo. The residue was purified by silica gel chromatography to give 276A (0.312 g, 38%), along with recovered starting material (0.737 g). $^1$H NMR (400 MHz, CDCl$_3$) δ ppm 1.31 (t, J=7.47 Hz, 3H) 3.31 (q, J=7.18 Hz, 2H) 4.47 (s, 2H) 6.89 (dd, J=8.79, 2.64 Hz, 1H) 7.04 (d, J=2.64 Hz, 1H) 7.86 (d, J=8.35 Hz, 1H).

276B

Ethyl 3-(aminomethyl)-4-(ethylsulfonyl)phenylcarbamate

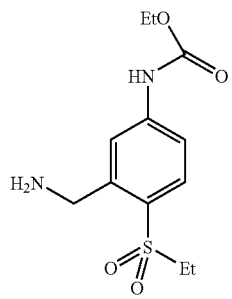

Ethyl chloroformate (0.077 mL, 0.8 mmol) was added dropwise to a solution of 276A (84 mg, 0.4 mmol) in pyridine (0.5 mL) at 0° C. The reaction mixture was warmed to rt, stirred for 30 min, and then stored overnight in a refrigerator. The solvent was removed in vacuo and the residue was triturated with water. This solid was hydrogenated (55 psi) over Raney nickel in MeOH overnight. The solution was filtered and concentrated in vacuo to give 276B (36 mg, 31%). $^1$H NMR (400 MHz, CD$_3$OD) δ ppm 1.25 (t, J=7.47 Hz, 3H) 1.32 (t, J=7.03 Hz, 3H) 3.24-3.33 (m, 2H) 4.23 (q, J=7.03 Hz, 2H) 4.33 (s, 2H) 7.72 (d, J=8.35 Hz, 1H) 7.85 (s, 1H) 7.92 (d, J=8.79 Hz, 1H).

276C

Example 276 (38 mg, 52%, yellow solid) was prepared from 276B (35 mg, 0.13 mmol) and 73A (56 mg, 0.1 μmol) using the general coupling-deprotection procedure. $^1$H NMR (400 MHz, CD$_3$OD) δ ppm 1.18 (t, J=7.25 Hz, 3H) 1.32 (t, J=6.81 Hz, 3H) 3.19-3.30 (m, 2H) 3.74 (s, 3H) 3.79-4.02 (m, 2H) 4.58-4.81 (m, 2H) 5.46 (s, 1H) 6.66 (s, 1H) 6.78 (d, J=7.03 Hz, 1H) 6.83-6.96 (m, 2H) 7.09 (t, J=9.01 Hz, 1H) 7.18 (d, J=9.23 Hz, 1H) 7.31 (d, J=7.03 Hz, 1H) 7.51 (d, J=8.79 Hz, 1H) 7.65 (s, 1H) 7.75 (d, J=8.35 Hz, 1H) 8.08 (d, J=9.23 Hz, 1H) 8.73 (t, J=5.93 Hz, 1H) 9.64 (s, 1H); LC-MS: 610.2 (M+H)$^+$.

Example 277

Isopropyl 3-((2-(1-aminoisoquinolin-6-ylamino)-2-(5-ethoxy-2-fluorophenyl)acetamido)methyl)-4-(ethylsulfonyl)phenylcarbamate trifluoroacetic acid salt

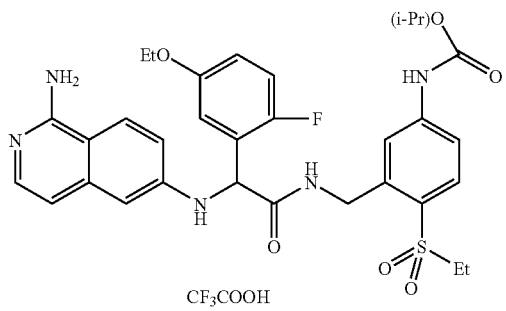

277A

Isopropyl 3-(aminomethyl)-4-(ethylsulfonyl)phenylcarbamate

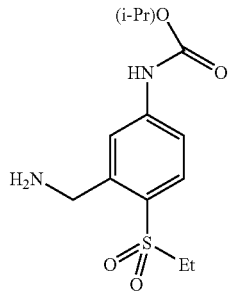

Using a procedure analogous to that used to prepare 276B, isopropyl chloroformate (0.8 mL, 0.8 mmol, 1M solution in toluene) was reacted with 276A (84 mg, 0.4 mmol) followed by hydrogenation to give 277A (20 mg, 17%). LC-MS: 301.3 (M+H)$^+$.

277B

Example 277 (21 mg, 55%, yellow solid) was prepared from 277A (20 mg, 0.067 mmol) and 73A (28 mg, 0.050 mmol) using the general coupling-deprotection procedure. $^1$H NMR (400 MHz, CD$_3$OD) δ ppm 1.17 (t, J=7.47 Hz, 3H) 1.27-1.36 (m, 9H) 3.25 (q, J=7.32 Hz, 2H) 3.77-3.95 (m, 2H) 4.64-4.78 (m, 1H) 4.91-4.99 (m, 2H) 5.47 (s, 1H) 6.67 (d, J=2.20 Hz, 1H) 6.79 (d, J=7.47 Hz, 1H) 6.84-6.92 (m, 2H)

7.08 (t, J=9.45 Hz, 1H) 7.18 (dd, J=9.23, 2.20 Hz, 1H) 7.31 (d, J=7.03 Hz, 1H) 7.51 (dd, J=8.35, 2.20 Hz, 1H) 7.68 (d, J=2.20 Hz, 1H) 7.74 (d, J=8.79 Hz, 1H) 8.08 (d, J=9.23 Hz, 1H) 8.67 (t, J=6.15 Hz, 1H) 9.59 (s, 1H); LC-MS: 638.2 (M+H)+.

Example 278

Isobutyl 3-((2-(1-aminoisoquinolin-6-ylamino)-2-(5-ethoxy-2-fluorophenyl)acetamido)methyl)-4-(ethyl-sulfonyl)phenylcarbamate trifluoroacetic acid salt

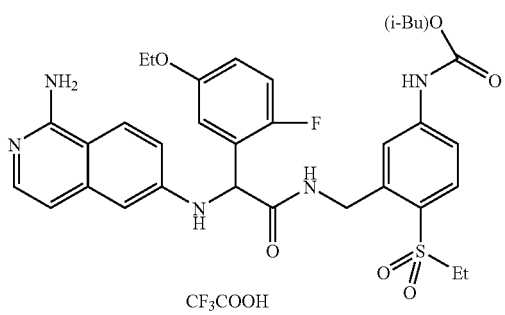

278A

Isobutyl 3-(aminomethyl)-4-(ethylsulfonyl)phenylcarbamate

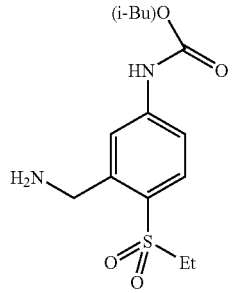

Using a procedure analogous to that used to prepare 276B, isobutyl chloroformate (0.104 mL, 0.8 mmol) was reacted with 276A (84 mg, 0.4 mmol) followed by hydrogenation to give 278A (80 mg, 64%). LC-MS: 315.3 (M+H)+.

278B

Example 278 (21 mg, 55%, yellow solid) was prepared from 278A (20 mg, 0.067 mmol) and 73A (28 mg, 0.050 mmol) using the general coupling-deprotection procedure. $^1$H NMR (400 MHz, CD$_3$OD) δ ppm 0.95-0.98 (m, 3H) 0.99 (s, 3H) 1.17 (t, J=7.47 Hz, 3H) 1.30 (t, J=7.03 Hz, 3H) 1.97 (dq, J=13.40, 6.59 Hz, 1H) 3.26 (q, J=7.18 Hz, 2H) 3.78-3.96 (m, 4H) 4.64-4.79 (m, 2H) 5.43-5.50 (m, 1H) 6.67 (d, J=2.20 Hz, 1H) 6.77 (d, J=7.03 Hz, 1H) 6.82-6.95 (m, 2H) 7.08 (t, J=9.23 Hz, 1H) 7.16 (dd, J=9.01, 2.42 Hz, 1H) 7.30 (d, J=7.03 Hz, 1H) 7.52 (dd, J=8.79, 2.20 Hz, 1H) 7.69 (s, 1H) 7.74 (d, J=8.79 Hz, 1H) 8.06 (d, J=9.23 Hz, 1H) 8.70 (t, J=5.93 Hz, 1H) 9.65 (s, 1H); LC-MS: 638.2 (M+H)+.

Example 279

N-(3-((2-(1-Aminoisoquinolin-6-ylamino)-2-(5-ethoxy-2-fluorophenyl)acetamido)methyl)-4-(ethyl-sulfonyl)phenyl)pentanamide trifluoroacetic acid salt

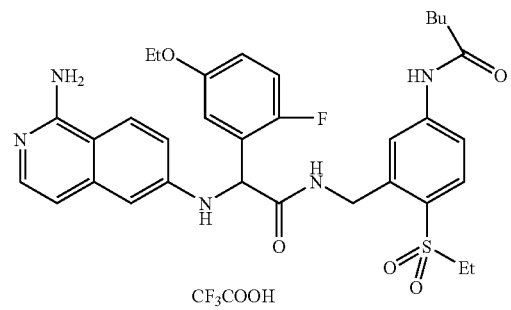

279A

N-(3-(Aminomethyl)-4-(ethylsulfonyl)phenyl)pentanamide

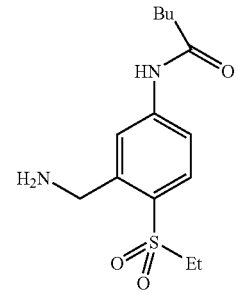

Using a procedure analogous to that used to prepare 276B, butyryl chloride (0.083 mL, 0.8 mmol) was reacted with 276A (84 mg, 0.4 mmol) followed by hydrogenation to give 279A (36 mg, 32%). LC-MS: 285.3 (M+H)+.

279B

Example 279 (21 mg, 39%, yellow solid) was prepared from 279A (36 mg, 0.13 mmol) and 73A (56 mg, 0.10 mmol) using the general coupling-deprotection procedure. $^1$H NMR (400 MHz, CD$_3$OD) δ ppm 0.99 (t, J=7.47 Hz, 3H) 1.17 (t, J=7.25 Hz, 3H) 1.30 (t, J=7.03 Hz, 3H) 1.71 (tq, J=7.47 Hz, 1H) 2.36 (t, J=7.47 Hz, 2H) 3.26 (q, J=7.32 Hz, 2H) 3.35 (s, 1H) 3.81-3.94 (m, 2H) 4.69-4.75 (m, J=5.71 Hz, 2H) 5.47 (s, 1H) 6.67 (d, J=1.76 Hz, 1H) 6.78 (d, J=7.47 Hz, 1H) 6.85-6.93 (m, 2H) 7.08 (t, J=9.23 Hz, 1H) 7.17 (dd, J=9.23, 2.20 Hz, 1H) 7.31 (d, J=7.03 Hz, 1H) 7.67 (dd, J=8.57, 1.98 Hz, 1H) 7.78 (d, J=8.10 Hz, 1H) 7.85 (d, J=2.20 Hz, 1H) 8.07 (d, J=9.23 Hz, 1H) 8.68 (t, J=5.93 Hz, 1H); LC-MS: 622.2 (M+H)+.

Example 280

(R)-3-((R)-2-(1-Aminoisoquinolin-6-ylamino)-2-(5-ethoxy-2-fluoro-4-methylphenyl)acetamido)-3-(2-(isopropylsulfonyl)phenyl)propanoic acid trifluoroacetic acid salt

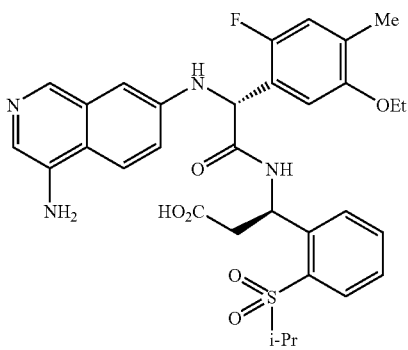

280A

Bis(4-fluoro-2-methylphenyl) carbonate

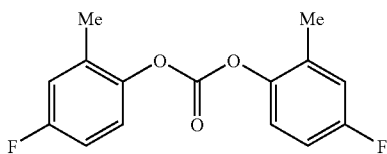

To a solution of 4-fluoro-2-methylphenol (3.8 g, 30.2 mmol) in toluene (8.0 mL) was added pyridine (5.3 mL) and phosgene (1.9M in toluene, 8.0 mL) at 0° C. The mixture was stirred for 2 h at rt before it was quenched by water and extracted with EtOAc. The combined organic layer was washed with brine, dried over MgSO$_4$ and concentrated to give a white solid product 280A. $^1$H NMR (400 MHz, CDCl$_3$) δ ppm 2.30 (s, 6H) 6.87-7.05 (m, 4H) 7.15 (dd, J=8.79, 4.83 Hz, 2H).

280B

Bis(4-fluoro-5-iodo-2-methylphenyl)carbonate

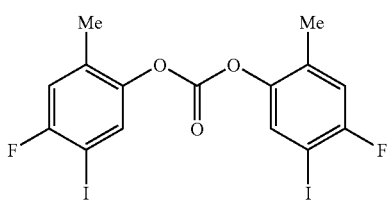

To 280A (2.3 g, 8.3 mmol) in trifluoroacetic acid (25 mL) was added N-iodosuccinimide (7.4 g). The mixture was stirred at rt for a week before it was poured into ice and extracted with EtOAc/hexanes (1:1). The organic layer was washed with saturated Na$_2$S$_2$O$_3$, NaHCO$_3$, brine and dried over MgSO$_4$. Evaporation of the solvent gave 280B (4.2 g, 95% yield) as a solid. $^1$H NMR (400 MHz, CDCl$_3$) δ ppm 2.27 (s, 6H) 6.99 (d, J=8.35 Hz, 2H) 7.56 (d, J=5.27 Hz, 2H).

280C

4-Fluoro-5-iodo-2-methylphenol

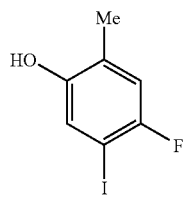

To 280B (4.2 g, 7.9 mmol) in methanol (20 mL) was added NaOH (0.63 g as a 50% aqueous solution) at 0° C. After TLC (10% EtOAc/hexanes) indicated the reaction was complete (2 h at 0° C.), the mixture was diluted with EtOAc, and washed with water and brine. The organic layer was dried over MgSO$_4$ and concentrated. The crude product was purified by silica gel chromatography to give 280C (3.36 g, 84% yield) as a solid. $^1$H NMR (400 MHz, CDCl$_3$) δ ppm 2.19 (s, 3H) 4.87 (s, 1H) 6.83 (d, J=8.35 Hz, 1H) 7.10 (d, J=5.27 Hz, 1H).

280D

1-Ethoxy-4-fluoro-5-iodo-2-methylbenzene

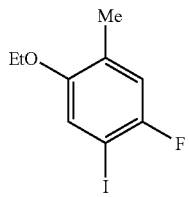

To a solution of 280C (759 mg, 3 mmol) in acetone (7.0 mL) was added K$_2$CO$_3$ (1.24 g) and iodoethane (0.73 mL). The mixture was stirred at rt overnight. After TLC(10% EtOAc/hexanes) indicated the reaction was complete, the mixture was diluted with diethyl ether, washed with water and brine. The organic layer was dried over MgSO$_4$ and concentrated. The crude product was purified by silica gel column chromatography to give 280D as a colorless oil (484 mg, 63% yield). $^1$H NMR (400 MHz, CDCl$_3$) δ ppm 1.38-1.47 (m, 3H) 2.18 (s, 3H) 3.98 (t, J=7.03 Hz, 2H) 6.86 (d, J=7.91 Hz, 1H) 7.06 (d, J=4.83 Hz, 1H).

280E

5-Ethoxy-2-fluoro-4-methylphenylboronic acid

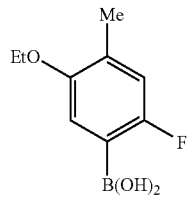

To 280D (240 mg, 0.85 mmol) in THF (3.0 mL) was added n-BuLi (1.6M in hexanes, 0.69 mL) at −78° C. After stirring for 10 min, trimethyl borate (0.19 mL) was introduced. The mixture was stirred from −78° C. to rt for 3 h before it was quenched by 1N HCl and extracted with ethyl acetate. The organic extracts were washed with saturated $Na_2S_2O_3$, brine and dried over $MgSO_4$. Evaporation of the solvent gave product 280E (130 mg, 77% yield) as a solid. $^1$H NMR (400 MHz, $CDCl_3$) δ ppm 1.39 (t, J=7.03 Hz, 3H) 2.19 (s, 3H) 4.00 (q, J=6.74 Hz, 2H) 6.78-6.86 (m, 2H).

280F

2-(1-(bis(tert-Butoxycarbonyl)amino)isoquinolin-6-ylamino)-2-(5-ethoxy-2-fluoro-4-methylphenyl)acetic acid

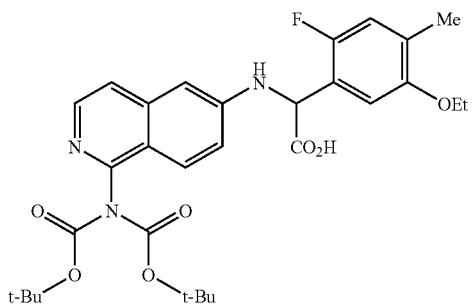

A mixture of 280E (48 mg, 0.24 mmol), Intermediate 1 (72 mg, 0.2 mmol) and glyoxylic acid monohydrate (22 mg, 0.24 mmol) in acetonitrile (0.4 mL) and DMF (0.04 mL) was heated at 100° C. for 30 min in a Microwave Reactor. The crude product was purified by silica gel chromatography ($CH_2Cl_2$:MeOH=100:15) to give 280F (70 mg, 61% yield) as a solid. $^1$H NMR (400 MHz, Methanol-$d_4$) δ ppm 1.25-1.36 (m, 21H) 2.16-2.17 (m, 3H) 3.90-4.00 (m, 2H) 5.48-5.54 (m, 1H) 6.73 (d, J=2.20 Hz, 1H) 6.96 (d, J=2.64 Hz, 1H) 6.97 (s, 1H) 7.29 (dd, J=9.23, 2.20 Hz, 1H) 7.46 (d, J=5.71 Hz, 1H) 7.64 (d, J=9.23 Hz, 1H) 7.97 (s, 1H) 8.04 (d, J=5.71 Hz, 1H), LC-MS 570 (M+1).

280G

Example 280 was prepared according to the general coupling-deprotection using 280F and 116E followed by hydrolysis of the ester. $^1$H NMR (400 MHz, Methanol-$d_4$) δ ppm 1.05-1.51 (m, 9H) 2.19 (s, 3H) 3.10-3.25 (m, 3H) 3.55-3.89 (m, 2H) 5.66 (s, 1H) 5.93-6.06 (m, 1H) 6.69-6.73 (m, 2H) 6.95-7.03 (m, 2H) 7.13-7.19 (m, 2H) 7.33-7.41 (m, 2H) 7.46 (t, J=7.03 Hz, 1H) 7.89 (d, J=7.91 Hz, 1H) 8.11 (d, J=8.79 Hz, 1H); LC-MS 623 (M+H).

Example 281

(R)-3-((R)-2-(1-Aminoisoquinolin-6-ylamino)-2-(5-ethyl-2-fluoro-4-methoxyphenyl)acetamido)-3-(2-(isopropylsulfonyl)phenyl)propanoic acid trifluoroacetic acid salt

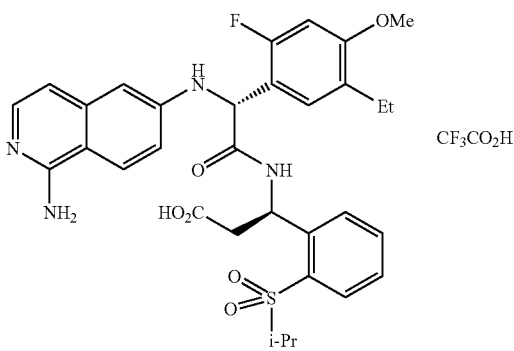

281A

5-Ethyl-2-fluorophenol

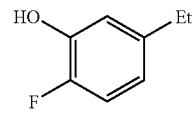

To a solution of 1-ethyl-4-fluorobenzene (7.2 g, 58 mmol) in THF (30 mL) and N,N,N',N'',N'''-pentamethyldiethylenetriamine (3.0 mL) was added n-BuLi (1.6M in hexane, 42 mL) at −78° C. After 1 h stirring, trimethyl borate (13 mL) was added. The mixture was stirred from −78° C. to rt overnight. It was quenched by acetic acid (5.0 mL) and hydrogen peroxide solution (30% in water) at 0° C. The mixture was stirred for 2 h before extracted with EtOAc. The organic extracts were washed with brine, dried over $MgSO_4$ and concentrate to give 281A (7.6 g, 94% yield) as an oil. $^1$H NMR (400 MHz, $CDCl_3$) δ ppm 1.19 (t, J=7.69 Hz, 3H) 2.56 (q, J=7.62 Hz, 2H) 6.60-6.71 (m, 1H) 6.83 (dd, J=8.79, 2.20 Hz, 1H) 6.95 (dd, J=10.55, 8.35 Hz, 1H).

281B tert-Butyl(5-ethyl-2-fluorophenoxy)dimethylsilane

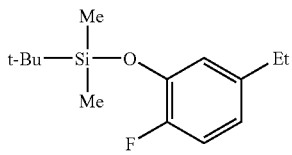

To 281A (3.75 g, 26.8 mmol) in DMF (20 mL) was added tert-butyldimethylsilyl chloride (6.1 g) and imidazole (2.6 g). The mixture was stirred at rt for overnight. It was then diluted with EtOAc/hexanes (1:4) and washed with water and brine. The organic extracts were dried and concentrated. The crude product was purified by silica gel column chromatography to give 281B (4.46 g, 66% yield) as an oil. $^1$H NMR (400 MHz, CDCl$_3$) δ ppm 0.21 (s, 6H) 0.99 (s, 9H) 1.18 (t, J=7.69 Hz, 3H) 2.54 (q, J=7.76 Hz, 2H) 6.64-6.76 (m, 2H) 6.93 (dd, J=10.55, 8.35 Hz, 1H).

281C 3-(tert-Butyldimethylsilyloxy)-5-ethyl-2-fluorobenzaldehyde

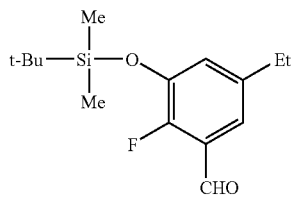

To 281B (625 mg, 2.46 mmol) in THF (10 mL) and N,N,N',N'',N''-pentamethyldiethylenetriamine (0.77 mL) was added n-BuLi (1.6M in hexane, 1.77 mL) at −78° C. After stirring for 45 min at −35° C., DMF (0.94 mL) was added at −78° C. and the reaction was slowly warmed up to rt. The mixture was stirred at rt for 1 h, diluted with EtOAc. The organic extracts were washed with saturated NaHCO$_3$, brine and dried. The crude product was purified by silica gel column chromatography to give 281C (615 mg, 89% yield) as an oil. $^1$H NMR (400 MHz, CDCl$_3$) δ ppm 0.21 (s, 6H) 1.01 (s, 9H) 1.21 (t, J=7.47 Hz, 3H) 2.59 (q, J=7.47 Hz, 2H) 6.99 (dd, J=7.91, 2.20 Hz, 1H) 7.21-7.27 (m, 1H) 10.30 (s, 1H).

281D

5-Ethyl-2-fluoro-3-methoxybenzaldehyde

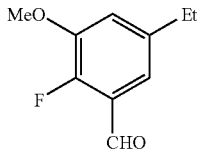

To 281C (244 mg, 0.87 mmol) in DMF (2.0 mL) was added potassium fluoride (100 mg) and iodomethane (0.13 mL). The mixture was stirred at rt overnight. It was diluted with EtOAc and the organic extracts were washed with brine and dried. The crude product was purified by silica gel column chromatography to give 281D (158 mg, 100% yield) as an oil. $^1$H NMR (400 MHz, CDCl$_3$) (ppm 1.23 (t, J=7.47 Hz, 3H) 2.64 (q, J=7.62 Hz, 2H) 3.92 (s, 3H) 7.02 (dd, J=8.13, 1.98 Hz, 1H) 7.23 (dd, J=5.27, 2.20 Hz, 1H) 10.35 (s, 1H).

281E 2-(5-Ethyl-2-fluoro-3-methoxyphenyl)-2-hydroxyacetonitrile

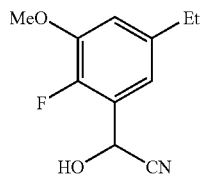

To 281D (630 mg, 3.46 mmol) in ethyl acetate (10 mL) was added a solution of KCN (676 mg) and NaHSO$_3$ (1.08 g) dissolved in H$_2$O (10 mL). It was left stirring overnight before extracted with ethyl acetate (2×50 mL). The combined organic extracts were dried and concentrated. The crude product was purified by silica gel column chromatography to give 281E (685 mg, 92% yield) as an oil. $^1$H NMR (400 MHz, CDCl$_3$) (ppm 1.23 (t, J=7.47 Hz, 3H) 2.64 (q, J=7.62 Hz, 2H) 3.89 (s, 3H) 5.76 (s, 1H) 6.86 (dd, J=7.91, 2.20 Hz, 1H) 6.98 (dd, J=5.93, 1.98 Hz, 1H).

281F

Methyl 2-(5-ethyl-2-fluoro-3-methoxyphenyl)-2-hydroxyacetate

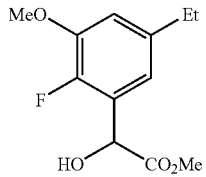

To 281E (630 mg, 2.93 mmol) in anhydrous diethyl ether (10 mL) at 0° C. was added MeOH (1.2 mL) and 4.0 N HCl in dioxane (2.9 mL). The mixture was stirred at 0° C. for 30 min and then at rt over night. Solvent was removed to give methyl 2-(3-methoxy-5-ethyl-2-fluorophenyl)-2-hydroxyacetimidate HCl salt. To this salt in CH$_2$Cl$_2$ (5.0 mL) was added H$_2$O (8.0 mL). The mixture was stirred at rt for 30 min, then extracted with CH$_2$Cl$_2$ (2×50 mL). The combined organic extracts were dried and concentrated. The crude was purified by silica gel column chromatography to give 281F (632 mg, 89% yield) as a viscous oil. $^1$H NMR (400 MHz, CDCl$_3$) δ ppm 1.21 (t, J=7.69 Hz, 3H) 2.59 (q, J=7.47 Hz, 2H) 3.76 (s, 3H) 3.87 (s, 3H) 5.38 (s, 1H) 6.65-6.85 (m, 2H).

281G

Methyl 2-(1-(bis(tert-butoxycarbonyl)amino)iso-quinolin-6-ylamino)-2-(5-ethyl-2-fluoro-3-methoxyphenyl)acetate

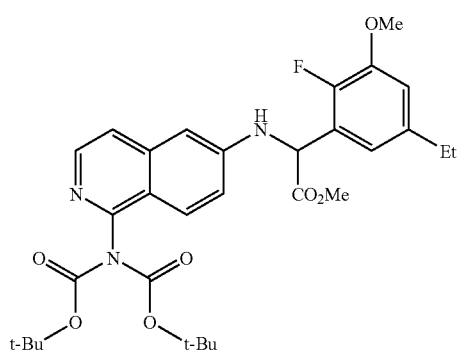

To 281F (257 mg, 1.06 mmol) in CH$_2$Cl$_2$ (5.0 mL) at 0° C. was added trifluoromethanesulfonic anhydride (0.2 mL) and 2,6-lutidine (0.19 mL). The mixture was stirred for 15 min before Intermediate 1 (343 mg, 0.57 mmol) and 2,6-lutidine (0.37 mL) in CH$_2$Cl$_2$ (2.0 mL) was added. The reaction was left stirring from 0° C. to rt for 3.0 h. It was diluted with ethyl acetate, washed with 0.5 N HCl (3×20 mL). The organic extract was dried and concentrated. A silica gel column chromatography purification gave product 281G (520 mg, 84% yield). $^1$H NMR (400 MHz, CDCl$_3$) δ ppm 1.17 (t, J=7.47 Hz, 3H) 1.27 (s, 18H) 2.58 (q, J=7.62 Hz, 2H) 3.76 (s, 3H) 3.87 (s, 3H) 5.62 (s, 1H) 6.72 (d, J=2.20 Hz, 1H) 6.85-6.93 (m, 2H) 7.07 (d, J=7.91 Hz, 1H) 7.28 (dd, J=9.23, 2.64 Hz, 1H) 7.46 (d, J=5.71 Hz, 1H) 7.64 (d, J=8.79 Hz, 1H) 8.05 (d, J=5.71 Hz, 1H). LC-MS 584 (M+H).

281H 2-(1-(bis(tert-Butoxycarbonyl)amino)isoquinolin-6-ylamino)-2-(5-ethyl-2-fluoro-3-methoxyphenyl)acetic acid

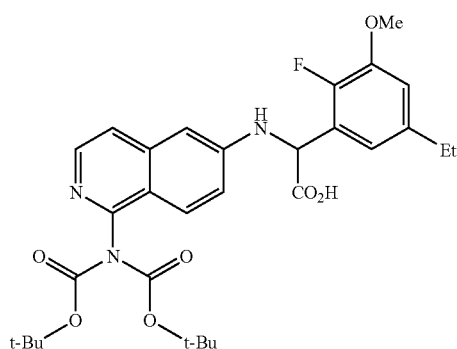

281G (77 mg, 0.13 mmol) was hydrolyzed with NaOH (1.0 N, 0.19 mL, 0.19 mmol) in THF (0.6 mL) and MeOH (0.3 mL) at rt for 2 h. After acidification with 5% KHSO$_4$, it was extracted with ethyl acetate (2×30 mL). The organic extract was dried and concentrated to give a solid product 281H (64 mg, 84% yield). LC-MS 570 (M+H)$^+$.

281I

Example 281 was prepared according to the general coupling-deprotection using 281H and 116E followed by hydrolysis of the ester. $^1$H NMR (400 MHz, Methanol-d$_4$) δ ppm 1.05-1.11 (m, 6H) 1.44 (d, J=6.59 Hz, 3H) 2.46-2.57 (m, 2H) 2.69-2.91 (m, 2H) 3.89 (s, 3H) 4.16-4.32 (m, 1H) 5.42 (s, 1H) 5.95-6.06 (m, 1H) 6.66-6.74 (m, 2H) 6.93-7.00 (m, 2H) 7.17 (d, J=7.91 Hz, 2H) 7.32-7.40 (m, 2H) 7.45 (t, J=7.69 Hz, 1H) 7.89 (d, J=7.47 Hz, 1H) 8.10 (d, J=9.23 Hz, 1H); LC-MS 623 (M+H).

Example 282

(R)-3-((R)-2-(1-Aminoisoquinolin-6-ylamino)-2-(5-chloro-2-fluorophenyl)acetamido)-3-(2-(isopropylsulfonyl)-5-(methoxycarbonylamino)phenyl)propanoic acid trifluoroacetic acid salt

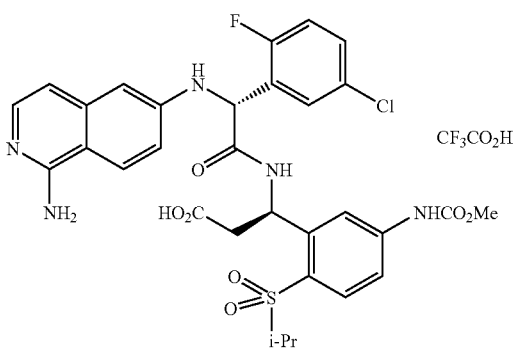

282A 2-(2-Fluoro-5-chlorophenyl)-2-hydroxyacetonitrile

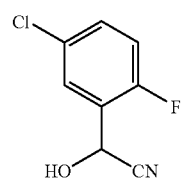

To 2-fluoro-5-chloro-benzaldehyde (12.7 g, 17 mmol) in ethyl acetate (50 mL) was added a solution of KCN (3.3 g) and NaHSO$_3$ (5.3 g) dissolved in H$_2$O (25 mL). It was left stirring overnight before extracted with ethyl acetate (3×50 mL). The combined organic extracts were dried and concentrated. The crude product was purified by silica gel column chromatography to give 282A (3.1 g, 99% yield) as an oil.

282B

Methyl 2-(5-chloro-2-fluorophenyl)-2-hydroxyacetate

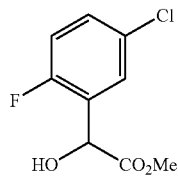

To 282A (640 mg, 3.48 mmol) in anhydrous diethyl ether (15 mL) at 0° C. was added MeOH (1.4 mL) and 4.0 N HCl in dioxane (3.5 mL). The mixture was stirred at 0° C. for 30 min and then at rt for 4 h. The solvent was removed to give methyl 2-(5-chloro-2-fluorophenyl)-2-hydroxyacetimidate HCl salt. To this salt in $CH_2Cl_2$ (10 mL) was added $H_2O$ (10 mL). The mixture was stirred at rt for 30 min, then extracted with $CH_2Cl_2$ (2×50 mL). The combined organic extracts were dried and concentrated. The crude product was purified by silica gel column chromatography to give 282B (610 mg, 80% yield) as a viscous oil. $^1$H NMR (400 MHz, $CDCl_3$) δ ppm 3.55 (d, J=4.83 Hz, 1H) 3.80 (s, 3H) 5.38 (d, J=4.83 Hz, 1H) 7.03 (t, J=9.23 Hz, 1H) 7.27-7.31 (m, 1H) 7.39 (dd, J=6.15, 2.64 Hz, 1H).

282C

Methyl 2-(1-(bis(tert-butoxycarbonyl)amino)isoquinolin-6-ylamino)-2-(5-chloro-2-fluorophenyl)acetate

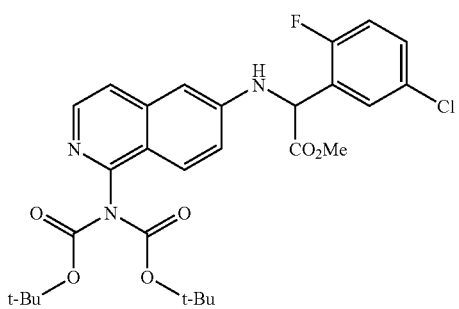

To 282B (320 mg, 1.47 mmol) in $CH_2Cl_2$ (5.0 mL) at 0° C. was added trifluoromethanesulfonic anhydride (0.27 mL) and 2,6-lutidine (0.26 mL). The mixture was stirred for 15 min before Intermediate 1 (475 mg, 1.32 mmol) and 2,6-lutidine (0.51 mL) in $CH_2Cl_2$ (2.0 mL) were added. The reaction was left stirring from 0° C. to rt for 3.0 h. It was diluted with ethyl acetate, washed with 0.5 N HCl (3×20 mL). The organic extract was dried and concentrated. A silica gel column chromatography purification gave product 282C (447 mg, 60% yield). $^1$H NMR (400 MHz, $CDCl_3$) δ ppm 1.16 (s, 18H) 3.67 (s, 3H) 5.58 (s, 1H) 6.63 (d, J=2.20 Hz, 1 H) 7.10 (t, J=9.23 Hz, 1H) 7.19 (dd, J=9.01, 2.42 Hz, 1H) 7.22-7.30 (m, 1H) 7.37 (d, J=5.71 Hz, 1H) 7.44 (d, J=2.64 Hz, 1H) 7.56 (d, J=9.23 Hz, 1H) 7.95 (d, J=5.71 Hz, 1H); LC-MS 560 (M+H).

282D 2-(1-(bis(tert-Butoxycarbonyl)amino)isoquinolin-6-ylamino)-2-(5-chloro-2-fluorophenyl)acetic acid

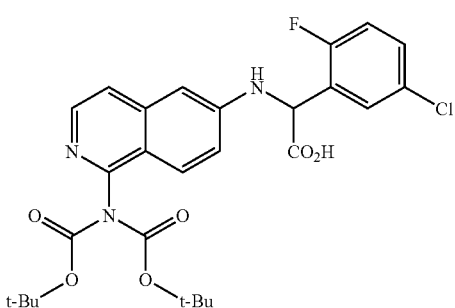

282C (440 mg, 0.79 mmol) was hydrolyzed with NaOH (1.0 N, 0.95 mL, 0.95 mmol) in THF (4 mL) and MeOH (0.5 mL) at rt for 2 h. After acidification with 5% $KHSO_4$, it was extracted with ethyl acetate (2×30 mL). The organic extract was dried and concentrated to give a solid product 282D (400 mg, 93% yield). $^1$H NMR (400 MHz, Methanol-$d_4$) δ ppm 1.29 (s, 18H) 5.62 (s, 1H) 6.77 (d, J=1.76 Hz, 1H) 7.22 (t, J=9.23 Hz, 1H) 7.33-7.40 (m, 2H) 7.54-7.59 (m, 2H) 7.73 (d, J=9.23 Hz, 1H) 8.07 (d, J=6.15 Hz, 1H); LC-MS 546 $(M+H)^+$.

282E (R)-Methyl 3-(tert-butoxycarbonylamino)-3-(2-(isopropylsulfonyl)-5-(methoxycarbonylamino)phenyl)propanoate

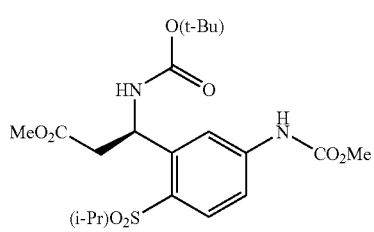

To 98E (1.5 g, 3.4 mmol) in EtOH (15 mL) at rt was added Oxone® (4.2 g, 6.8 mmol) in $H_2O$ (40 mL). The mixture was stirred at rt over night. EtOH was removed in vaccuo. The residue was suspended in EtOAc and washed with water, $Na_2S_2O_3$ and brine. The organic layer was dried over $Na_2SO_4$. After evaporation of solvent, the crude was purified by silica gel column chromatography eluting with gradient EtOAc in hexanes to give 282E as a white solid (1.5 g, 93% yield). $^1$H NMR (400 MHz, $CDCl_3$) δ ppm 1.14 (d, J=7.03 Hz, 3H) 1.18 (d, J=7.05 Hz, 3H) 1.36 (s, 9H) 1.47 (d, J=6.59 Hz, 3H) 2.83-2.90 (m, 1H) 2.93-3.00 (m, 1H) 3.81 (s, 3H) 3.86 (s, 1H) 4.11 (m, 2H) 5.57-5.65 (m, 1H) 6.18 (s, 1H) 6.96 (s, 1H) 7.51 (d, J=2.20 Hz, 1H) 7.62 (d, J=7.91 Hz, 1H) 7.90 (d, J=8.79 Hz, 1H); LC-MS 473 (M+H).

282F (R)-Methyl 3-amino-3-(2-(isopropylsulfonyl)-5-(methoxycarbonylamino)phenyl)propanoate hydrochloride

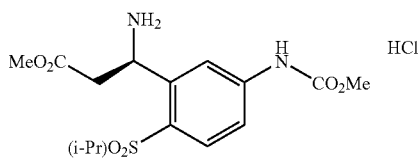

To 282E (1.35 g, 2.86 mmol) in EtOAc (10 mL) was added 4.0 N HCl in dioxane (15 mL, 60 mmol). The mixture was stirred at rt for 3.0 h. Solvent was removed in vaccuo to give 282F as a white solid (1.1 g, 99% yield). $^1$H NMR (500 MHz, Methanol-$d_4$) δ ppm 1.11-1.15 (m, 6H) 1.31 (d, J=7.15 Hz, 3H) 3.04-3.11 (m, 1H) 3.15-3.20 (m, 1H) 3.50 (ddd, J=13.61, 6.74, 6.60 Hz, 1H) 3.70 (s, 3H) 4.05 (q, J=7.15 Hz, 2H) 5.44 (t, J=7.42 Hz, 1H) 7.51 (d, J=10.45 Hz, 1H) 7.85 (d, J=8.80 Hz, 1H) 7.99 (s, 1H), LC-MS 373 (M+H).

282G

Example 282 was prepared according to the general coupling-deprotection using 282D and 282F followed by hydrolysis of the ester. $^1$H NMR (400 MHz, Methanol-$d_4$) δ ppm 1.13 (d, J=6.59 Hz, 3H) 1.43 (d, J=6.59 Hz, 3H) 2.71-2.93 (m, 2H) 3.66 (s, 3H) 4.13-4.30 (m, 1H) 5.39 (s, 1H) 5.85-6.00 (m, 1H) 6.64 (d, J=2.20 Hz, 1H) 6.88 (d, J=7.03 Hz, 1H) 7.16 (dd, J=9.23, 2.20 Hz, 1H) 7.18-7.28 (m, 2H) 7.30-7.35 (m, 2H) 7.37-7.44 (m, 1H) 7.54 (d, J=1.76 Hz, 1H) 7.76 (d, J=8.79 Hz, 1H) 8.11 (d, J=8.79 Hz, 1H); LC-MS 786 (M+H).

Example 283

(R)-3-((R)-2-(1-Aminoisoquinolin-6-ylamino)-2-(3-(difluoromethoxy)phenyl)acetamido)-3-(2-(isopropylsulfonyl)-5-(methoxycarbonylamino)phenyl)propanoic acid trifluoroacetic acid salt

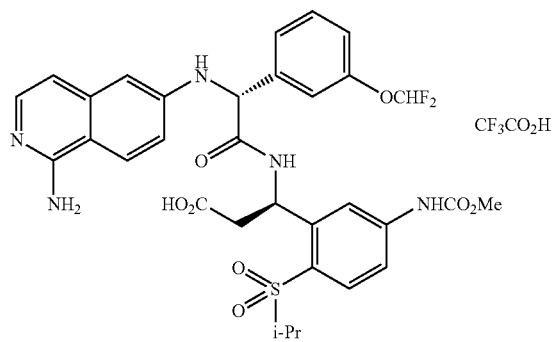

283A 2-(3-Difluoromethoxyphenyl)-2-hydroxyacetonitrile

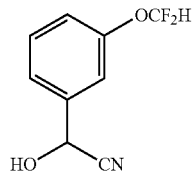

To 3-difluoromethoxybenzaldehyde (1.77 g, 10 mmol) in ethyl acetate (25 mL) was added a solution of KCN (2.0 g) and NaHSO$_3$ (3.2 g) dissolved in H$_2$O (25 mL). It was left stirring overnight before it was extracted with ethyl acetate (2×50 mL). The combined organic extracts were dried and concentrated. The crude product was purified by silica gel column chromatography to give 283A (1.85 g, 92% yield) as an oil. $^1$H NMR (400 MHz, CDCl$_3$) δ ppm 5.66 (s, 1H) 6.86 (t, J=73.82 Hz, 1H) 7.18 (dd, J=7.91, 2.20 Hz, 1H) 7.31 (s, 1H) 7.36-7.42 (m, 1H) 7.47 (t, J=7.91 Hz, 1H).

283B

Methyl 2-(3-difluoromethoxyphenyl)-2-hydroxyacetate

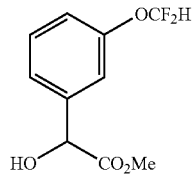

To 283A (1.83 g, 9.2 mmol) in anhydrous CH$_2$Cl$_2$ (30 mL) at 0 (C was added MeOH (2.24 mL) and 4.0 N HCl in dioxane (9.2 mL). The mixture was stirred at 0 (C for 30 min and then at rt for 4.0 h. Solvent was removed to give methyl 2-(3-(difluoromethoxy)-phenyl)-2-hydroxyacetimidate HCl salt. To this salt in CH$_2$Cl$_2$ (10 mL) was added H$_2$O (10 mL). The mixture was stirred at rt for 30 min, then extracted with CH$_2$Cl$_2$ (2×50 mL). The combined organic extracts were dried and concentrated. The crude product was purified by silica gel column chromatography to give 283B (700 mg, 33% yield) as a viscous oil. $^1$H NMR (400 MHz, CDCl$_3$) δ ppm 3.70 (s, 3H) 5.22 (s, 1H) 6.82 (t, J=74.04 Hz, 1H) 7.09 (dd, J=7.91, 2.20 Hz, 1H) 7.23 (s, 1H) 7.28-7.34 (m, 1H) 7.38 (t, J=7.91 Hz, 1H).

283C

Methyl 2-(1-(bis(tert-butoxycarbonyl)amino)iso-quinolin-6-ylamino)-2-(3-(difluoromethoxy)phenyl) acetate

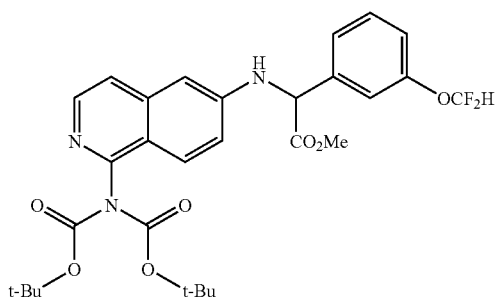

To 283B (650 mg, 2.8 mmol) in $CH_2Cl_2$ (10 mL) at 0° C. was added trifluoromethanesulfonic anhydride (0.52 mL) and 2,6-lutidine (0.49 mL). The mixture was stirred for 15 min before Intermediate 1 (1.0 g, 2.8 mmol) and 2,6-lutidine (0.97 mL) in $CH_2Cl_2$ (5.0 mL) were added. The reaction was left stirring from 0° C. to rt for 3.0 h. It was diluted with ethyl acetate, and washed with 0.5 N HCl (3×20 mL). The organic extract was dried and concentrated. A silica gel column chromatography purification gave 283C (680 mg, 42% yield). $^1$H NMR (400 MHz, $CDCl_3$) δ ppm 1.27 (s, 18H) 3.76 (s, 3H) 5.44 (s, 1H) 6.56-7.03 (m, 2H) 7.10-7.14 (m, 1H) 7.31 (dd, J=9.23, 2.20 Hz, 1H) 7.35 (s, 1H) 7.41-7.47 (m, 3H) 7.65 (d, J=9.23 Hz, 1H) 8.04 (d, J=6.15 Hz, 1H); LC-MS 574 (M+H).

283D 2-(1-(bis(tert-Butoxycarbonyl)amino)isoquinolin-6-ylamino)-2-(3-(difluoromethoxy)phenyl)acetic acid

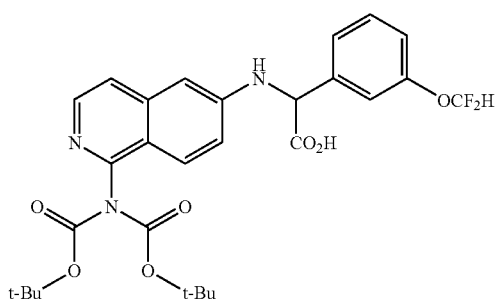

283C (680 mg, 1.2 mmol) was hydrolyzed with NaOH (1.0 N, 1.42 mL, 1.42 mmol) in THF (6 mL) and MeOH (0.5 mL) at rt for 3 h. After acidification with 5% $KHSO_4$, it was extracted with ethyl acetate (2×30 mL). The organic extract was dried and concentrated to give a solid product 283D (650 mg, 96% yield). $^1$H NMR (400 MHz, Methanol-$d_4$) (ppm 1.26 (s, 18H) 4.99 (s, 1H) 6.58 (d, J=2.20 Hz, 1H) 6.79 (t, J=74.26 Hz, 1H) 7.01 (dd, J=8.13, 2.42 Hz, 1H) 7.25 (dd, J=8.79, 2.20 Hz, 1H) 7.31-7.40 (m, 3H) 7.47 (d, J=7.91 Hz, 1H) 7.61 (d, J=9.23 Hz, 1H) 7.99 (d, J=5.71 Hz, 1H). LC-MS 560 (M+H).

283E

Example 283 was prepared according to the general coupling-deprotection using 282F and 283D followed by hydrolysis of the ester. $^1$H NMR (400 MHz, Methanol-$d_4$) δ ppm 1.10 (d, J=6.59 Hz, 3H) 1.42 (d, J=6.59 Hz, 3H) 2.67-2.93 (m, 2H) 3.69 (s, 3H) 4.12-4.31 (m, 1H) 5.09 (s, 1H) 5.83-5.98 (m, 1H) 6.58 (s, 1H) 6.63-7.02 (m, 2H) 7.10-7.15 (m, 1H) 7.15-7.23 (m, 2H) 7.28 (s, 1H) 7.31 (d, J=7.03 Hz, 1H) 7.35-7.43 (m, 2H) 7.45 (d, J=1.76 Hz, 1H) 7.72 (d, J=8.79 Hz, 1H) 8.09 (d, J=9.23 Hz, 1H); LC-MS 686 (M+H).

Example 284

(R)-3-((R)-2-(1-Aminoisoquinolin-6-ylamino)-2-(3-chlorophenyl)acetamido)-3-(2-(isopropylsulfonyl)-5-(methoxycarbonylamino)phenyl)propanoic acid

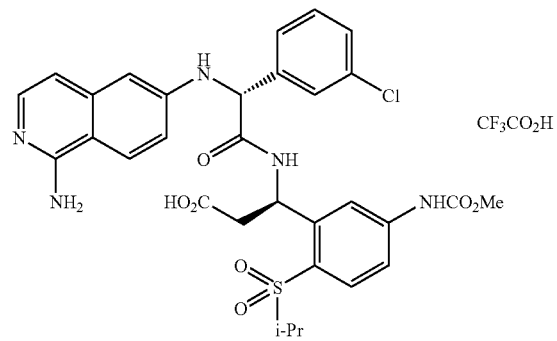

284A 2-(1-(bis(tert-Butoxycarbonyl)amino)isoquinolin-6-ylamino)-2-(3-chlorophenyl)acetic acid 284A was prepared in procedures similar to that of 282D following steps 282A to 282D starting from 3-chlorobenzaldehyde. $^1$H NMR (400 MHz, Methanol-$d_4$) δ ppm 1.27 (s, 18H) 5.29 (s, 1H) 6.67 (d, J=1.76 Hz, 1H) 7.27-7.40 (m, 3H) 7.44 (d, J=6.15 Hz, 1H) 7.53 (d, J=7.47 Hz, 1H) 7.61 (s, 1H) 7.65 (d, J=9.23 Hz, 1H) 8.03 (d, J=5.71 Hz, 1H); LC-MS 530 (M+1)

284B

Example 284 was prepared according to the general coupling-deprotection using 282F and 284A followed by hydrolysis of the ester. $^1$H NMR (400 MHz, Methanol-$d_4$) δ ppm 0.98 (d, J=6.59 Hz, 3H) 1.30 (d, J=7.03 Hz, 3H) 2.58-2.80 (m, 2H) 3.58 (s, 3H)-4.03-4.15 (m, 1H) 4.99 (s, 1H) 5.75-5.83 (m, 1H) 6.47 (s, 1H) 6.71 (d, J=7.03 Hz, 1H) 7.04 (dd, J=9.23, 2.20 Hz, 1H) 7.10 (dd, J=8.79, 2.20 Hz, 1H) 7.19 (d, J=7.03 Hz, 1H) 7.21-7.25 (m, 2H) 7.31-7.38 (m, 3H) 7.61 (d, J=8.35 Hz, 1H) 7.96 (d, J=9.23 Hz, 1H); LC-MS 654 (M+H).

Example 285

Methyl 3-((2-(3-carbamoylphenylamino)-2-(3,4-dimethoxyphenyl)acetamido)methyl)-4-(isopropylsulfonyl)phenylcarbamate

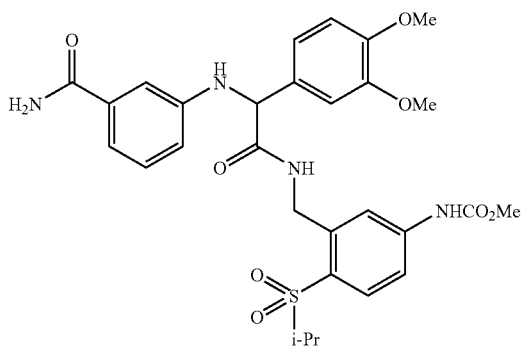

285A 2-(3-Carbamoylphenylamino)-2-(3,4-dimethoxyphenyl)acetic acid

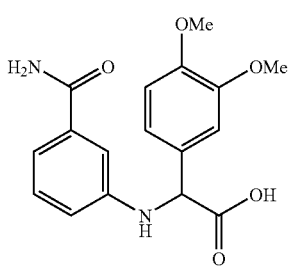

A mixture of 3-aminobenzamide (204 mg, 1.5 mmol), 3,4-dimethoxyphenylboronic acid (273 mg, 1.5 mmol) and glyoxylic acid monohydrate (138 mg, 1.5 mmol) in acetonitrile (8.0 mL) and DMF (0.8 mL) was heated at 55° C. for 4.0 h and then stirred at rt for 18 h. The precipitate formed was collected by filtration and washed with ethyl acetate to give 285A (390 mg, 78% yield) after drying. $^1$H NMR (400 MHz, DMSO-$d_6$) δ ppm 7.03-7.19 (m, 5H) 6.91 (d, J=9.0 Hz, 1H) 6.81 (d, J=8.00 Hz, 1H) 5.05 (s, 1H) 3.83 (s, 3H) 3.72 (s, 3H). LC-MS 331 (M+H).

285B

5-Amino-2-(isopropylsulfonyl)benzonitrile

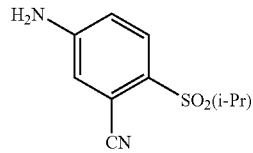

2-(Isopropylsulfonyl)-5-nitrobenzonitrile (127 mg, prepared in a procedure similar to that of Intermediate 9B in place of ethanethiol with 2-thiopropane) was hydrogenated with 10% Pd/C in MeOH under 60 psi over night. Pd/C was removed by filtration. The filtrate was concentrated to give 285B (114 mg). $^1$H NMR (400 MHz, Methanol-$d_4$) δ ppm 1.27 (d, J=6.59 Hz, 6H) 3.40 (dt, J=13.62, 6.81 Hz, 1H) 6.90 (dd, J=8.79, 2.64 Hz, 1H) 7.07 (d, J=2.20 Hz, 1H) 7.67 (d, J=8.79 Hz, 1H).

285C

Methyl 3-cyano-4-(isopropylsulfonyl)phenylcarbamate

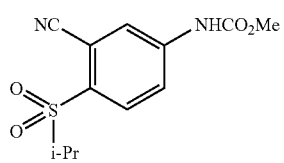

To 285B (63 mg, 0.28 mmol) in pyridine (2.0 mL) at 0° C. was added methyl chloroformate (0.1 mL, 1.4 mmol). The mixture was stirred at rt for 1.0 h before it was quenched with 1.0 N HCl and extracted with EtOAc. The organic extract was dried and concentrated. A silica gel column chromatography purification gave 285C (79 mg, 100% yield). $^1$H NMR (400 MHz, Methanol-$d_4$) ppm 1.31 (d, J=6.59 Hz, 6H) 3.42-3.52 (m, 1H) 7.80 (dd, J=8.79, 2.20 Hz, 1H) 7.92-7.99 (m, 2H) 8.10 (d, J=2.20 Hz, 1H).

285D

Methyl 3-(aminomethyl)-4-(isopropylsulfonyl)phenylcarbamate

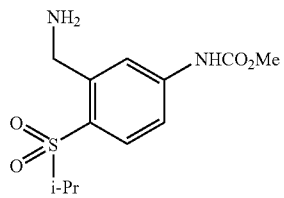

285C (77 mg) in THF (5.0 mL) was hydrogenated with Raney-Ni under 50 psi over night. Raney-Ni was removed by filtration. The filtrate was concentrated to give 285D as a white solid (45 mg, 80% yield). $^1$H NMR (400 MHz, Methanol-d$_4$) ppm 1.24 (d, J=6.59 Hz, 6H) 3.32-3.41 (m, 1H) 3.76 (s, 3H) 4.03 (s, 2H) 7.61-7.68 (m, 2H) 7.81 (d, J=8.79 Hz, 1H).

285E

Example 285 was prepared according to the general coupling-deprotection using 285A and 285D. $^1$H NMR (400 MHz, Methanol-d$_4$) ppm 1.07-1.13 (m, 6H) 3.66 (s, 3H) 3.67 (s, 3H) 3.71 (s, 3H) 4.59 (d, J=5.71 Hz, 2H) 4.83 (s, 1H) 6.76 (ddd, J=6.04, 2.97, 2.86 Hz, 1H) 6.81 (d, J=8.79 Hz, 1H) 6.91-6.96 (m, 2 H) 7.07-7.14 (m, 3H) 7.44-7.50 (m, 2H) 7.67 (d, J=9.67 Hz, 1H) 8.59 (t, J=6.15 Hz, 1H) 9.48 (s, 1H), LC-MS 599 (M+H).

Example 286

(R)-3-((R)-2-(3-Carbamoylphenylamino)-2-(3,4-dimethoxyphenyl)acetamido)-3-(2-(isopropylsulfonyl)-5-(methoxycarbonylamino)phenyl)propanoic acid

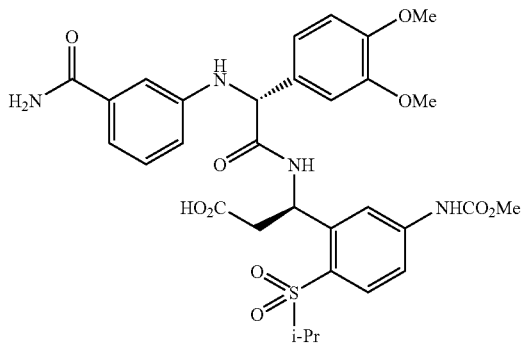

Example 286 was prepared according to the general coupling-deprotection using 285A and 282F followed by hydrolysis of the ester. $^1$H NMR (400 MHz, Methanol-d$_4$) δ ppm 1.11 (d, J=6.59 Hz, 3H) 1.43 (d, J=7.03 Hz, 3H) 2.67-2.83 (m, 2H) 3.73 (s, 3H) 3.78 (s, 3H) 3.81 (s, 3H) 4.16-4.31 (m, 1H) 4.84 (s, 1H) 5.86-5.97 (m, 1H) 6.73 (d, J=7.91 Hz, 1H) 6.87-6.90 (m, 1H) 6.95-7.03 (m, 2H) 7.09-7.21 (m, 3H) 7.29 (dd, J=8.79, 2.20 Hz, 1H) 7.33 (s, 1H) 7.73 (d, J=8.35 Hz, 1H); LC-MS 657 (M+H).

Example 287

2-(1-Aminoisoquinolin-6-ylamino)-N-(3-(3,3-dimethylureido)benzyl)-2-(3-ethoxyphenyl)acetamide trifluoroacetic acid salt

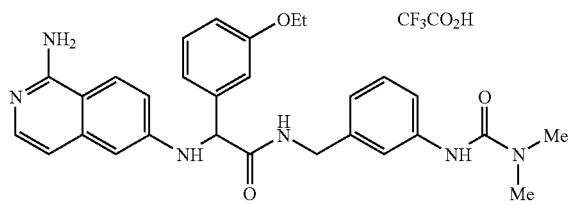

287A 3-(3-Cyanophenyl)-1,1-dimethylurea

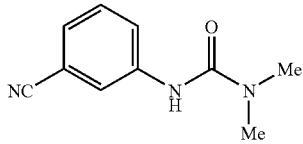

To 3-cyanophenyl isocanate (720 mg, 5 mmol) in 5 mL CH$_2$Cl$_2$, was added Et$_3$N (1 g, 10 mmol) and dimethylamine hydrochloride (490 mg, 6 mmol) at rt. The mixture was stirred overnight. CH$_2$Cl$_2$ (20 mL) was added, washed with brine (20 ml), and dried (Na$_2$SO$_4$). Purified by ISCO (0-60% EtOAc/Hex) to provide 287A (855 mg) as a light yellow solid. $^1$H NMR (400 MHz, CD$_3$OD) δ ppm 3.01 (s, 6H) 6.84 (s, 1H) 7.19-7.28 (m, 1H) 7.31 (t, J=7.91 Hz, 1H) 7.61 (d, J=8.35 Hz, 1H) 7.75 (s, 1H); LC-MS 190.20 (M+H).

287B 3-(3-(Aminomethyl)phenyl)-1,1-dimethylurea

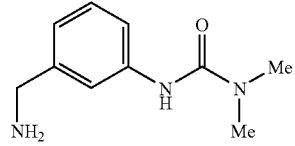

To 287A (95 mg, 0.5 mmol) in MeOH (10 mL) was added 10% Pd/C (ca. 50 mg), and the whole was hydrogenated at 60 psi for 6 h. The reaction was filtered and concentrated and dried to provide 287B (93 mg) as a white solid. LC-MS 194.48 (M+H).

287C

Example 287 was prepared according to the general coupling-deprotection using Intermediate 16 and 287B. $^1$H NMR (400 MHz, CD$_3$OD) δ ppm 1.34 (t, J=7.03 Hz, 3H) 2.98 (s, 6H) 3.98 (q, J=7.03 Hz, 2H) 4.29-4.41 (m, 2H) 5.12 (s, 1H) 6.63 (s, 1H) 6.75 (d, J=7.03 Hz, 1H) 6.82 (d, J=7.47 Hz, 1H) 6.84-6.91 (m, 1H) 7.08-7.17 (m, 4H) 7.18-7.23 (m, 2H) 7.24-7.31 (m, 2H) 8.04 (d, J=8.79 Hz, 1H). LC-MS 513.5 (M+H).

Example 288

2-(1-Aminoisoquinolin-6-ylamino)-2-(3-ethoxyphenyl)-N-(3-(3-ethyl-3-methylureido)benzyl)acetamide trifluoroacetic acid salt

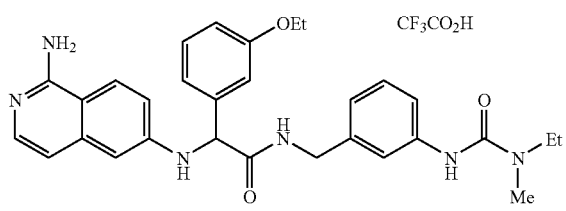

288A 3-(3-Cyanophenyl)-1-ethyl-1-methylurea

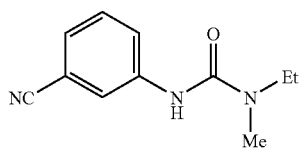

288A was prepared from 3-cyanophenyl isocanate in 90% yield following a procedure analogous to that used in the preparation of 287A. $^1$H NMR (400 MHz, CDCl$_3$) δ ppm 1.17 (t, J=7.25 Hz, 3H) 2.99 (s, 3H) 3.40 (q, J=7.32 Hz, 2H) 6.83 (s, 1H) 7.25 (t, J=7.25 Hz, 1H) 7.32 (t, J=7.91 Hz, 1H) 7.61 (d, J=8.35 Hz, 1H) 7.78 (s, 1H). LC-MS 204.43 (M+H).

288B 3-(3-(Aminomethyl)phenyl)-1-ethyl-1-methylurea

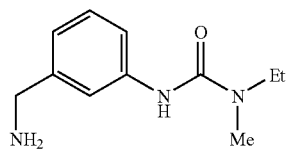

To 288A (273 mg, 1.35 mmol) in 15 mL THF, was added Raney-Ni (ca 50 mg), and the whole was hydrogenated at 60 psi for 5 h. The reaction was filtered and concentrated and purified by prep HPLC to provide 288B (158 mg) as a white solid. $^1$H NMR (400 MHz, CD$_3$OD) δ ppm 1.16 (t, J=7.25 Hz, 3H) 3.00 (s, 3H) 3.42 (q, J=7.18 Hz, 2H) 4.03 (s, 2H) 7.10 (d, J=7.03 Hz, 1H) 7.26-7.43 (m, 2H) 7.49 (s, 1H). LC-MS 208.44 (M+H).

288C

Example 288

Example 288 was prepared according to the general coupling-deprotection using Intermediate 16 and 288B. $^1$H NMR (400 MHz, CD$_3$OD) δ ppm 1.14 (t, J=7.25 Hz, 3H) 1.34 (t, J=7.03 Hz, 3H) 2.97 (s, 3H) 3.39 (q, J=7.18 Hz, 2H) 3.97-4.07 (m, 2H) 4.28-4.43 (m, 2H) 5.12 (s, 1H) 6.64 (d, J=2.20 Hz, 1H) 6.76 (d, J=7.03 Hz, 1H) 6.82 (d, J=7.91 Hz, 1H) 6.88 (dd, J=7.91, 2.20 Hz, 1H) 7.07-7.13 (m, 3H) 7.15 (dd, J=9.23, 2.20 Hz, 1H) 7.19-7.25 (m, 2H) 7.25-7.31 (m, 2H) 8.04 (d, J=9.23 Hz, 1H). LC-MS 527.45 (M+H).

Example 289

N-(3-((2-(1-Aminoisoquinolin-6-ylamino)-2-(3-ethoxyphenyl)acetamido)methyl)phenyl)pyrrolidine-1-carboxamide trifluoroacetic acid salt

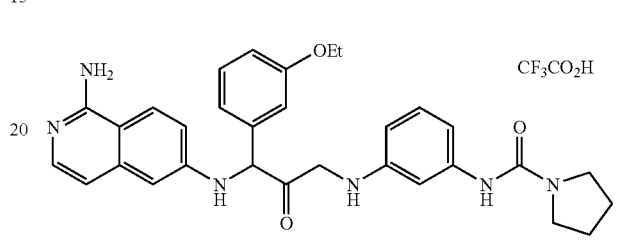

289A

N-(3-Cyanophenyl)pyrrolidine-1-carboxamide

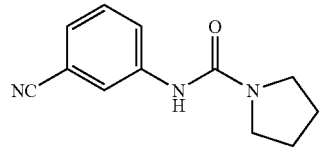

289A was prepared from 3-cyanophenyl isocanate in 63% yield following a procedure analogous to that used in the preparation of 287A. $^1$H NMR (400 MHz, CDCl$_3$) δ ppm 1.91-2.10 (m, 4H) 3.46 (t, J=6.81 Hz, 4H) 6.30 (s, 1H) 6.30 (s, 1H) 7.24-7.30 (m, 1H) 7.35 (t, J=8.13 Hz, 1H) 7.64 (d, J=8.35 Hz, 1H) 7.79 (s, 1H). LC-MS 216.35 (M+H).

289B

N-(3-(Aminomethyl)phenyl)pyrrolidine-1-carboxamide

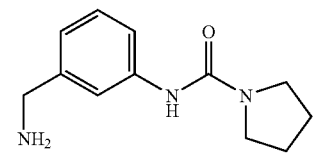

289B was prepared from 289A in 90% yield following a procedure analogous to that used in the preparation of 288B. $^1$H NMR (400 MHz, CD$_3$OD) δ ppm 1.95 (t, J=6.59 Hz, 4H) 3.45 (t, J=6.81 Hz, 4H) 4.04 (s, 2H) 7.09 (d, J=7.47 Hz, 1H) 7.32 (t, J=7.91 Hz, 1H) 7.36-7.42 (m, 1H) 7.55 (s, 1H). LC-MS 220.45 (M+H).

289C

Example 289 was prepared according to the general coupling-deprotection using Intermediate 16 and 289B. $^1$H NMR (400 MHz, CD$_3$OD) δ ppm 1.35 (t, J=7.03 Hz, 3H) 1.89-2.03 (m, 4H) 3.41 (t, J=6.59 Hz, 4H) 3.98-4.06 (m, 2H) 4.28-4.45 (m, 2H) 5.11 (s, 1H) 6.64 (d, J=2.20 Hz, 1H) 6.76 (d, J=7.03 Hz, 1 H) 6.82 (d, J=7.47 Hz, 1H) 6.88 (dd, J=8.35, 1.76 Hz, 1H) 7.06-7.14 (m, 3H) 7.16 (dd, J=9.23, 2.20 Hz, 1H) 7.23-7.33 (m, 4H) 8.05 (d, J=9.23 Hz, 1H). LC-MS 539.46 (M+H).

Example 290

2-(1-Aminoisoquinolin-6-ylamino)-2-(4-chloro-3-ethoxyphenyl)-N-(5-(3,3-dimethylureido)-2-(isopropylsulfonyl)benzyl)acetamide trifluoroacetic acid salt

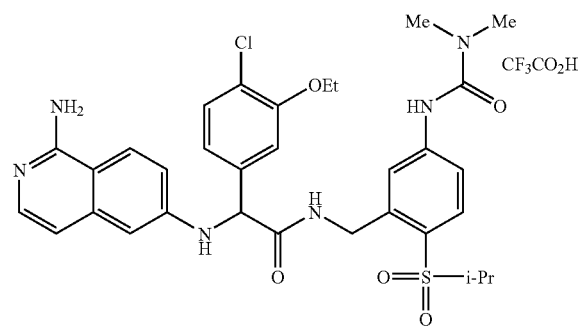

290A

5-Amino-2-(isopropylsulfonyl)benzonitrile

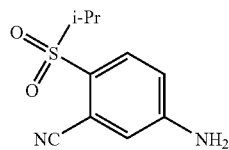

Using the procedures analogous to those described for preparation of Intermediate 9A, Intermediate 9B, and 276A, 2-fluoro-5-nitrobenzonitrile and isopropanethiol were converted to 290A.

290B 3-(3-Cyano-4-(isopropylsulfonyl)phenyl)-1,1-dimethylurea

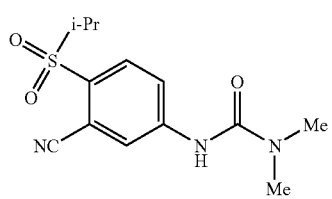

290A (25 mg, 0.11 mmol) was dissolved in 2 mL pyridine. Dimethyl carbamyl chloride (0.025 ml, 0.3 mmol) was added at rt, and the solution was stirred at rt overnight. Concentrated and purified by ISCO (0-80% EtOAc/Hex) to provide 290B (12.8 mg) as a white solid. $^1$H NMR (400 MHz, CDCl$_3$) δ ppm 1.26 (d, J=7.03 Hz, 6H) 3.01 (s, 6H) 3.33-3.54 (m, 1H) 7.30 (s, 1H) 7.67-7.80 (m, 1H) 7.80-7.91 (m, 1H) 8.00 (d, J=2.20 Hz, 1H). LC-MS 296.37 (M+H).

290C 3-(3-(Aminomethyl)-4-(isopropylsulfonyl)phenyl)-1,1-dimethylurea

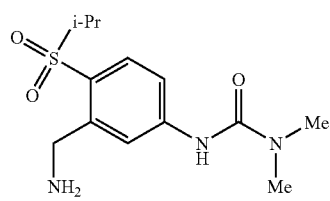

To 290B (13 mg, 0.044 mmol) in 2 mL THF was added Raney-Ni (ca 5 mg), and the whole was hydrogenated at 60 psi for 4 h. The reaction was filtered and concentrated to provide 290C (13 mg, 100%) as a colorless solid. LC-MS 300.38 (M+H).

290D

Example 290 was prepared according to the general coupling-deprotection using Intermediate 15 and 290C. $^1$H NMR (400 MHz, CD$_3$OD) δ ppm 1.17 (d, J=6.59 Hz, 3H) 1.21 (d, J=7.03 Hz, 3H) 1.37 (q, J=7.32 Hz, 3H) 3.02 (s, 6H) 3.33-3.47 (m, 1H) 3.93-4.11 (m, 2H) 4.56-4.81 (m, 2H) 5.18 (s, 1H) 6.63 (d, J=2.20 Hz, 1H) 6.79 (d, J=7.47 Hz, 1H) 7.08 (dd, J=8.13, 1.98 Hz, 1H) 7.11-7.20 (m, 2H) 7.30 (d, J=7.03 Hz, 1H) 7.35 (d, J=7.91 Hz, 1H) 7.49 (dd, J=8.35, 2.20 Hz, 1H) 7.57 (d, J=2.20 Hz, 1H) 7.69 (d, J=8.79 Hz, 1H) 8.00 (d, J=9.23 Hz, 1H). LC-MS 653.48 (M+H).

Example 291

N-(3-((2-(1-Aminoisoquinolin-6-ylamino)-2-(4-chloro-3-ethoxyphenyl)acetamido)methyl)-4-(isopropylsulfonyl)phenyl)pyrrolidine-1-carboxamide trifluoroacetic acid salt

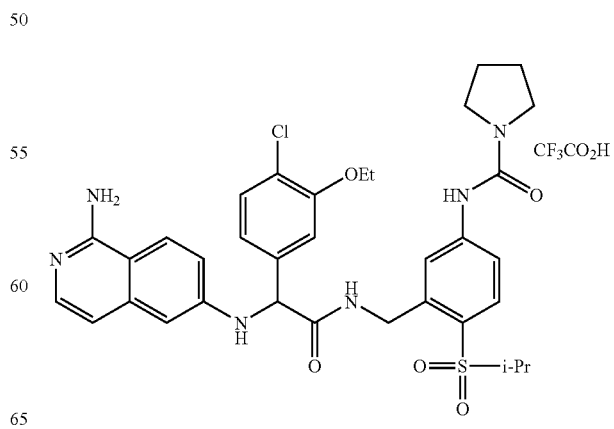

291A

N-(3-Cyano-4-(isopropylsulfonyl)phenyl)pyrrolidine-1-carboxamide

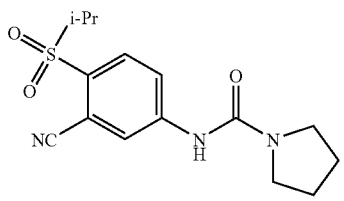

290A (35 mg, 0156 mmol) was dissolved in 2 mL CH$_2$Cl$_2$. NaHCO$_3$ (126 mg, 1.5 mmol) was added, followed by phosgene (0.2 ml, 0.38 mmol) at 0° C. Stirred at rt for 2 h, filtered and concentrated, dried. The residue was dissolved in 2 mL CH$_2$Cl$_2$, Et$_3$N (65 mg, 0.64 mmol) was added, followed by pyrrolidine (22 mg, 0.3 mmol) at 0° C., stirred rt for 2 h, purified by ISCO (0-80% EtOAc/Hex) to provide 291A (40 mg) as a white solid. $^1$H NMR (400 MHz, CDCl$_3$) δ ppm 1.29 (d, J=6.59 Hz, 6H) 1.95 (s, 4H) 3.39-3.53 (m, 5H) 7.28 (s, 1H) 7.85 (s, 2H) 8.13 (s, 1H). LC-MS 322.34 (M+H).

291B

N-(3-(Aminomethyl)-4-(isopropylsulfonyl)phenyl)pyrrolidine-1-carboxamide

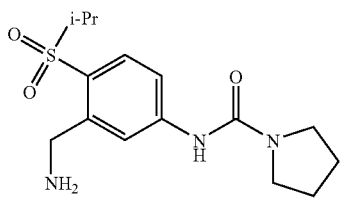

291B was prepared from 291A in 94% yield following a procedure analogous to that used in the preparation of 290C. $^1$H NMR (400 MHz, CDCl$_3$) δ ppm 1.20 (d, J=6.59 Hz, 6H) 1.93 (m, 4H) 3.29-3.37 (m, 1H) 3.39-3.49 (m, 4H) 3.94 (s, 2H) 7.56-7.62 (m, 1H) 7.64 (d, J=2.20 Hz, 1H) 7.73 (d, J=8.79 Hz, 1H). LC-MS 326.37 (M+H).

291C

Example 291 was prepared according to the general coupling-deprotection using Intermediate 15 and 291B. $^1$H NMR (400 MHz, CDCl$_3$) δ ppm 1.09 (d, J=7.03 Hz, 3H) 1.13 (d, J=6.59 Hz, 3H) 1.29 (t, J=7.03 Hz, 3H) 1.90 (s, 4H) 3.26-3.33 (m, 1H) 3.36 (t, J=6.81 Hz, 4H) 3.82-4.05 (m, 2H) 4.48-4.73 (m, 2H) 5.08 (s, 1H) 6.54 (d, J=1.76 Hz, 1H) 6.70 (d, J=7.03 Hz, 1H) 6.98 (dd, J=8.13, 1.98 Hz, 1H) 7.02-7.11 (m, 2H) 7.21 (d, J=7.03 Hz, 1H) 7.26 (d, J=8.35 Hz, 1H) 7.47 (d, J=9.23 Hz, 1H) 7.52 (t, J=2.42 Hz, 1H) 7.61 (d, J=8.79 Hz, 1H) 7.97 (d, J=9.23 Hz, 1H). LC-MS 679.38 (M+H).

Example 292

N-(3-((2-(1-Aminoisoquinolin-6-ylamino)-2-(4-chloro-3-ethoxyphenyl)acetamido)methyl)phenyl)pyrrolidine-1-carboxamide trifluoroacetic acid salt

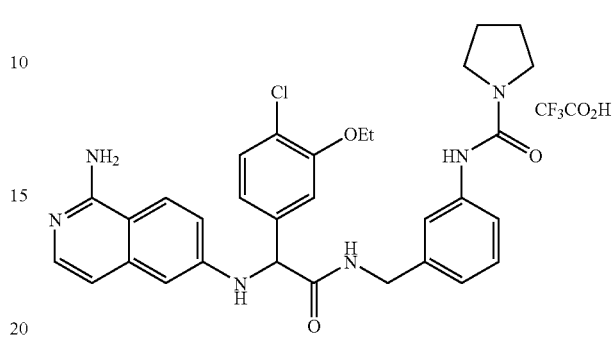

Example 292 was prepared according to the general coupling-deprotection using Intermediate 15 and 289B. $^1$H NMR (400 MHz, CDCl$_3$) δ ppm 1.37 (t, J=7.03 Hz, 3H) 1.88-2.03 (m, 4H) 3.36-3.46 (m, 4H) 4.03 (q, J=7.03 Hz, 2H) 4.31-4.45 (m, 2H) 5.13 (s, 1H) 6.65 (d, J=2.20 Hz, 1H) 6.78 (d, J=7.03 Hz, 1H) 6.83 (d, J=7.47 Hz, 1H) 7.09 (dd, J=8.13, 1.98 Hz, 1H) 7.11-7.14 (m, 1H) 7.16 (dd, J=9.23, 2.20 Hz, 1H) 7.19 (d, J=1.76 Hz, 1H) 7.24-7.27 (m, 2H) 7.29 (d, J=7.03 Hz, 1H) 7.33-7.37 (m, 1H) 8.06 (d, J=9.23 Hz, 1H). LC-MS 573.27 (M+H).

Example 293

N-(3-((2-(1-Aminoisoquinolin-6-ylamino)-2-(3-ethoxyphenyl)acetamido)methyl)phenyl)azetidine-1-carboxamide trifluoroacetic acid salt

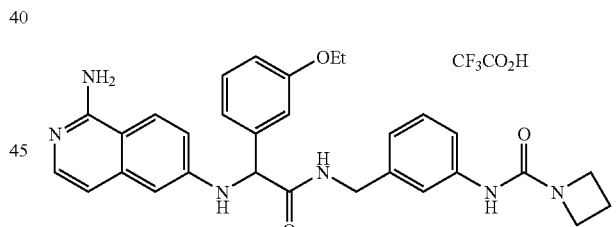

293A

N-(3-Cyanophenyl)azetidine-1-carboxamide

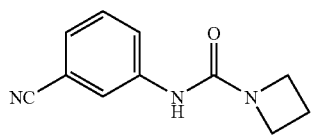

293A was prepared from 3-cyanophenyl isocanate in 94% yield following a procedure analogous to that used in the preparation of 287A. $^1$H NMR (400 MHz, CDCl$_3$) δ ppm 2.21-2.44 (m, 2H) 3.97-4.16 (m, 4H) 6.11 (s, 1H) 7.21-7.29

(m, 1H) 7.34 (t, J=7.91 Hz, 1H) 7.62 (d, J=8.35 Hz, 1H) 7.75 (s, 1H). LC-MS 202.34 (M+H).

293B

N-(3-(Aminomethyl)phenyl)azetidine-1-carboxamide

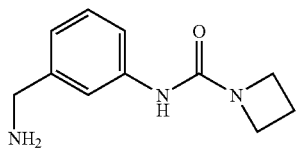

293B was prepared from 293A in 59% yield following a procedure analogous to that used in the preparation of 288B. $^1$H NMR (400 MHz, CD$_3$OD) δ ppm 2.30 (t, J=7.69 Hz, 2H) 4.07 (m, 6H) 7.07 (d, J=5.71 Hz, 1H) 7.28-7.35 (m, 2H) 7.63 (s, 1H). LC-MS 206.37 (M+H).

293C

Example 293 was prepared according to the general coupling-deprotection procedure using Intermediate 16 and 293B. $^1$H NMR (400 MHz, CD$_3$OD) δ ppm 1.35 (t, J=7.03 Hz, 3H) 2.20-2.36 (m, 2H) 3.97-4.06 (m, 6H) 4.25-4.48 (m, 2H) 5.10 (s, 1H) 6.63 (d, J=2.20 Hz, 1H) 6.74 (d, J=7.03 Hz, 1H) 6.78-6.83 (m, 1H) 6.89 (dd, J=8.35, 1.76 Hz, 1H) 7.06-7.12 (m, 3H) 7.16 (dd, J=9.01, 2.42 Hz, 1H) 7.23-7.32 (m, 4H) 8.05 (d, J=9.23 Hz, 1H). LC-MS 525.29 (M+H).

Example 294

2-(1-Aminoisoquinolin-6-ylamino)-N-(5-(3,3-dimethylureido)-2-(isopropylsulfonyl)benzyl)-2-(5-ethoxy-2-fluorophenyl)acetamide trifluoroacetic acid salt

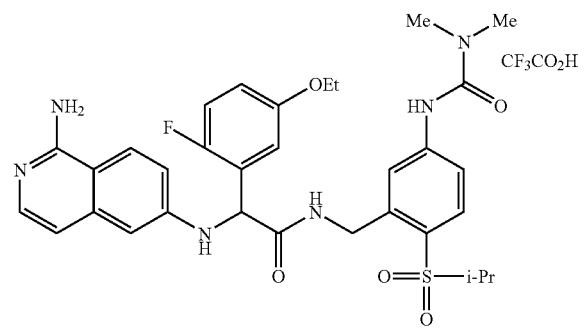

Example 294 was prepared according to the general coupling-deprotection using 73A and 290C. $^1$H NMR (400 MHz, CD$_3$OD) δ ppm 1.17 (d, J=7.03 Hz, 3H) 1.20 (d, J=7.03 Hz, 3H) 1.27-1.35 (m, 3H) 3.01 (s, 6H) 3.37-3.47 (m, 1H) 3.82-3.95 (m, 2H) 4.69 (dd, J=13.40, 5.93 Hz, 2H) 5.45 (s, 1H) 6.66 (d, J=2.20 Hz, 1H) 6.78 (d, J=7.03 Hz, 1H) 6.85-6.91 (m, 1H) 6.92 (dd, J=5.71, 3.08 Hz, 1H) 7.08 (t, J=9.23 Hz, 1H) 7.14 (dd, J=9.23, 2.20 Hz, 1H) 7.30 (d, J=7.47 Hz, 1H) 7.52 (dd, J=8.79, 2.20 Hz, 1H) 7.62 (d, J=2.20 Hz, 1H) 7.67 (d, J=8.79 Hz, 1H) 8.05 (d, J=9.23 Hz, 1H). LC-MS 637.38 (M+H).

Example 295

N-(3-((2-(1-Aminoisoquinolin-6-ylamino)-2-(3-ethoxyphenyl)acetamido)methyl)phenyl)thiazolidine-3-carboxamide trifluoroacetic acid salt

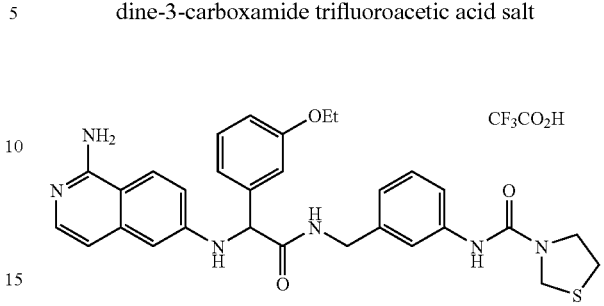

295A

N-(3-Cyanophenyl)thiazolidine-3-carboxamide

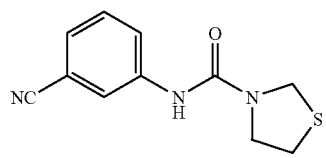

295A was prepared from 3-cyanophenyl isocanate in 87% yield following a procedure analogous to that used in the preparation of 287A. $^1$H NMR (400 MHz, CDCl$_3$) δ ppm 3.13 (t, J=6.37 Hz, 2H) 3.83 (t, J=6.37 Hz, 2H) 4.60 (s, 2H) 7.32 (d, J=3.08 Hz, 1H) 7.32-7.35 (m, 1H) 7.39 (t, J=7.91 Hz, 1H) 7.70 (d, J=7.91 Hz, 1H) 7.81 (s, 1H). LC-MS 234.25 (M+H).

295B

N-(3-(Aminomethyl)phenyl)thiazolidine-3-carboxamide

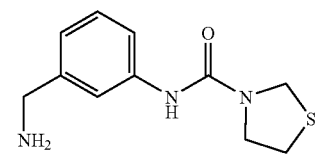

295A (200 mg, 0.86 mmol) was dissolved in 5 mL THF, BH$_3$ (4 mL, 1M in THF, 4 mmol) was added, and the whole mixture was refluxed for 2 h, then was cooled down, HCl (5 mL, 1N) was added, the mixture was stirred 1 h. It was concentrated and purified by prep HPLC to provide 295B (220 mg) as a white solid. $^1$H NMR (400 MHz, CD$_3$OD) δ ppm 3.11 (t, J=6.37 Hz, 2H) 3.78 (t, J=6.37 Hz, 2H) 4.01-4.12 (m, 2H) 4.57 (s, 2H) 7.05-7.21 (m, 1H) 7.28-7.43 (m, 2H) 7.58 (s, 1H). LC-MS 238.3 (M+H).

295C

Example 295 was prepared according to the general coupling-deprotection using Intermediate 16 and 295B. $^1$H NMR (400 MHz, CD$_3$OD) δ ppm 1.35 (t, J=6.81 Hz, 3H) 3.09 (t, J=6.15 Hz, 2H) 3.71-3.75 (m, 2H) 4.00 (q, J=7.03 Hz, 2H) 4.36 (dd, J=7.91, 6.15 Hz, 2H) 4.52 (d, J=2.20 Hz, 2H) 5.10 (s, 1H) 6.64 (d, J=2.20 Hz, 1H) 6.77 (d, J=7.03 Hz, 1H) 6.85 (d, J=7.47 Hz, 1H) 6.89 (dd, J=8.13, 2.42 Hz, 1H) 7.11 (dd, J=13.62, 5.71 Hz, 3H) 7.17 (dd, J=9.23, 2.20 Hz, 1H) 7.22-7.27 (m, 2H) 7.29 (s, 1H) 7.31 (s, 1H) 8.06 (d, J=9.23 Hz, 1H). LC-MS 557.30 (M+H).

Example 296

(R)-2-(1-Aminoisoquinolin-6-ylamino)-2-(3,4-dimethoxyphenyl)-N-(5-(3,3-dimethylureido)-2-(isopropylsulfonyl)benzyl)acetamide trifluoroacetic acid salt

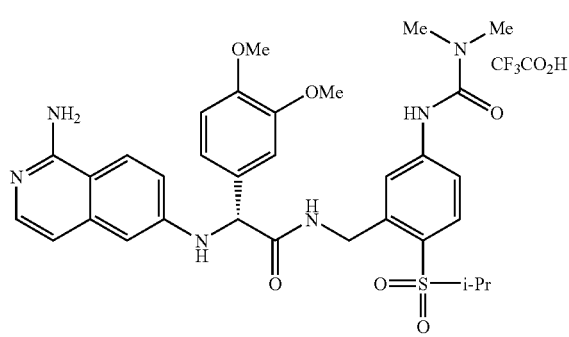

296A (R)-2-(1-Di-tert-butoxycarbonylaminoisoquinolin-6-ylamino)-2-(3,4-dimethoxyphenyl)acetic acid

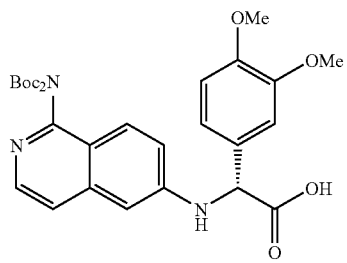

Intermediate 4 (10.5 g) was dissolved in 240 mL solvent (MeOH/TFA/DEA, 100/0.1/0.05), and injected onto a Chiralpak AD column, eluted with CO$_2$/(MeOH/TFA/DEA, 100/ 0.1/0.05) (75/25). The first peak was collected. With 8 L solution in hand, Et$_3$N (4 mL) was added, and the whole was concentrated. The residue was mixed with CH$_2$Cl$_2$ (200 mL) and filtered, dried to provide 296A (2.8 g).

296B (R)-2-(1-Aminoisoquinolin-6-ylamino)-2-(3,4-dimethoxyphenyl)acetic acid

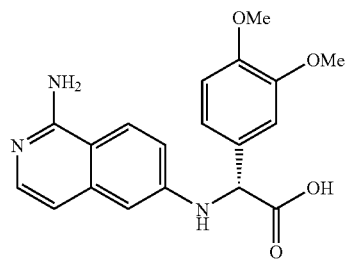

Concentrated hydrochloric acid was added dropwise to a solution of 296A (366 mg, 1.04 mmol) in THF (10 mL), until a clear solution was obtained. The reaction mixture was concentrated and dried to provide 296B (402 mg) as a yellow solid. LC-MS 354.2 (M+H).

296C

Example 296

296B (20 mg, 0.051 mmol), 290C (18.5 mg, 0.055 mmol), BOP (40 mg, 0.09 mmol) and Et$_3$N (50 mg, 0.5 mmol) were mixed in DMF (2 mL), stirred at rt for 2 h and purified by preparative HPLC to provide Example 296 (28.3 mg) as a white solid. $^1$H NMR (400 MHz, CD$_3$OD) δ ppm 1.13 (d, J=7.03 Hz, 3H) 1.16 (d, J=6.59 Hz, 3H) 3.00 (s, 6H) 3.33-3.43 (m, 1H) 3.74 (s, 3H) 3.79 (s, 3H) 4.65-4.69 (m, 2H) 5.11 (s, 1H) 6.60 (d, J=2.20 Hz, 1H) 6.74 (d, J=7.03 Hz, 1H) 6.92 (d, J=8.79 Hz, 1H) 7.02 (dd, J=9.01, 2.42 Hz, 1H) 7.05-7.11 (m, 2H) 7.26 (d, J=7.03 Hz, 1H) 7.49 (dd, J=8.79, 2.20 Hz, 1H) 7.56 (d, J=2.20 Hz, 1H) 7.66 (d, J=8.79 Hz, 1H) 7.95 (d, J=9.23 Hz, 1H). LC-MS 635.32 (M+H).

Example 297

2-(1-Aminoisoquinolin-6-ylamino)-2-(3-ethoxyphenyl)-N-(3-(3-isopropyl-3-methylureido)benzyl)acetamide trifluoroacetic acid salt

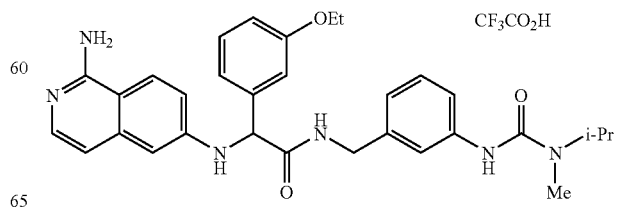

297A 3-(3-Cyanophenyl)-1-isopropyl-1-methylurea

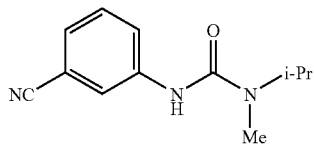

297A was prepared from 3-cyanophenyl isocanate in 89% yield following a procedure analogous to that used in the preparation of 287A. ¹H NMR (400 MHz, CDCl₃) δ ppm 1.16 (d, J=6.59 Hz, 6H) 2.86 (s, 3H) 4.50-4.63 (m, 1H) 6.66 (s, 1H) 7.25-7.29 (m, 1H) 7.35 (t, J=7.91 Hz, 1H) 7.60-7.65 (m, 1H) 7.79 (s, 1H). LC-MS 218.14 (M+H).

297B 3-(3-(Aminomethyl)phenyl)-1-isopropyl-1-methylurea

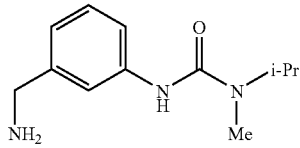

297B was prepared from 297A in 80% yield following a procedure analogous to that used in the preparation of 295B. ¹H NMR (400 MHz, CD₃OD) δ ppm 1.1-8 (d, J=7.03 Hz, 6H) 2.87 (s, 3H) 4.05 (s, 2H) 4.48-4.59 (m, 1H) 7.09 (d, J=6.59 Hz, 1H) 7.29-7.36 (m, 2H) 7.52 (s, 1H). LC-MS 222.26 (M+H).

297C

Example 297 was prepared according to the general coupling-deprotection using Intermediate 16 and 297B. ¹H NMR (400 MHz, CD₃OD) δ ppm 1.14 (s, 3H) 1.35 (t, J=7.03 Hz, 3H) 2.83 (s, 3H) 3.99 (q, J=7.03 Hz, 2H) 4.35 (dd, J=14.28-5.93 Hz, 2H) 4.45-4.5.5 (m, 1H) 5.12 (s, 1H) 6.65 (d, J=2.20 Hz, 1H) 6.77 (d, J=7.03 Hz, 1H) 6.82 (d, J=7.91 Hz, 1H) 6.88 (dd, J=8.35, 1.76 Hz, 1H) 7.07-7.14 (m, 3H) 7.16 (dd, J=9.23, 2.20 Hz, 1H) 7.19-7.32 (m, 4H) 8.05 (d, J=9.23 Hz, 1H). LC-MS 541.35 (M+H).

Example 298

(3S)—N-(3-((2-(1-Aminoisoquinolin-6-ylamino)-2-(4-chloro-3-ethoxyphenyl)acetamido)methyl)phenyl)-3-hydroxypyrrolidine-1-carboxamide trifluoroacetic acid salt

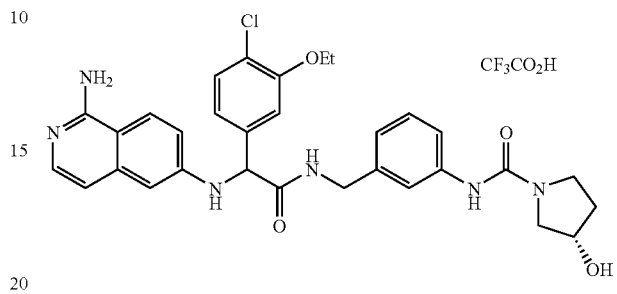

298A 2-(1-Aminoisoquinolin-6-ylamino)-2-(4-chloro-3-ethoxyphenyl)acetic acid

Intermediate 15 (350 mg, 0.61 mmol) was dissolved in EtOAc (12 mL). HCl (12 mL, 4N in dioxane) was added dropwise and the whole was stirred at rt overnight. The reaction mixture was concentrated and dried to provide 298A (250 mg) as a yellow solid. LC-MS 372.1 (M+H).

298B (3S)—N-(3-Cyanophenyl)-3-hydroxypyrrolidine-1-carboxamide

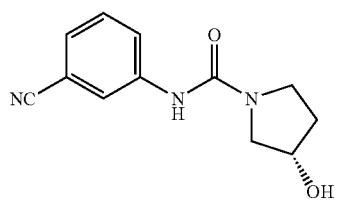

298B was prepared from 3-cyanophenyl isocanate in 75% yield following a procedure analogous to that used in the preparation of 287A. ¹H NMR (400 MHz, CD₃OD) δ ppm 1.93-2.02 (m, 1H) 2.02-2.14 (m, 1H) 3.42-3.49 (m, 1 H)

3.52-3.64 (m, 4-H) 4.45 (s, 1H) 7.30-7.35 (m, 1H) 7.70 (d, J=8.35 Hz, 1H) 7.88 (d, J=2.20 Hz, 1H). LC-MS 232.12 (M+H).

298C (3S)—N-(3-(Aminomethyl)phenyl)-3-hydroxypyrrolidine-1-carboxamide

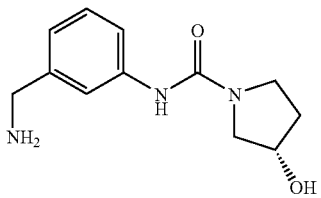

298C was prepared from 298B in 77% yield following a procedure analogous to that used in the preparation of 295B. $^1$H NMR (400 MHz, CD$_3$OD) δ ppm 1.93-2.02 (m, 1H) 2.03-2.14 (m, 1H) 3.43-3.51 (m, 1H) 3.52-3.64 (m, 4H) 4.06 (s, 2H) 4.46 (s, 1H) 7.10 (d, J=6.59 Hz, 1H) 7.30-7.38 (m, 2H) 7.59 (s, 1H). LC-MS 236.3 (M+H).

298D

Example 298 was prepared according to the general coupling procedure using 298A and 298C. 298A (19 mg, 0.047 mmol), 298C (20 mg, 0.057 mmol), EDCI (20 mg, 0.1 mmol), HOAt (2 mg, 0.015 mmol), and DIEA (0.06 mL, 0.345 mmol) were mixed in DMF (2 mL). The whole was stirred for 2 h at 60° C. Purification through preparative HPLC provided Example 298 (13 mg) as a white solid. $^1$H NMR (400 MHz, CD$_3$OD) δ ppm 1.38 (t, J=7.25 Hz, 3H) 1.93-2.02 (m, 1H) 2.02-2.16 (m, 1H) 3.39-3.46 (m, 1H) 3.50-3.61 (m, 4H) 4.03 (q, J=7.03 Hz, 2H) 4.36 (t, J=5.71 Hz, 2H) 4.43-4.49 (m, 1H) 5.11-5.35 (m, 1H) 6.63-6.71 (m, 1H) 6.78 (d, J=7.03 Hz, 1H) 6.80-6.86 (m, 1H) 7.06-7.22 (m, 4H) 7.23-7.39 (m, 4H) 8.06 (d, J=9.23 Hz, 1H). LC-MS 589.35 (M+H).

Example 299

(3R)—N-(3-((2-(1-Aminoisoquinolin-6-ylamino)-2-(4-chloro-3-ethoxyphenyl)acetamido)methyl)phenyl)-3-hydroxypyrrolidine-1-carboxamide trifluoroacetic acid salt

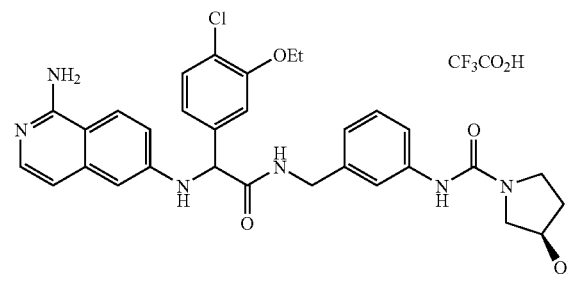

299A (3R)—N-(3-Cyanophenyl)-3-hydroxypyrrolidine-1-carboxamide

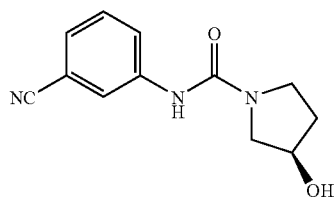

299A was prepared from 3-cyanophenyl isocanate in 84% yield following a procedure analogous to that used in the preparation of 287A. $^1$H NMR (400 MHz, CD$_3$OD) δ ppm 1.93-2.02 (m, 1H) 2.02-2.14 (m, 1H) 3.42-3.49 (m, 1H) 3.53-3.62 (m, 4H) 4.42-4.49 (m, 1H) 7.30-7.34 (m, 1H) 7.41 (t, J=7.91 Hz, 1H) 7.70 (d, J=8.35 Hz, 1H) 7.88 (d, J=2.20 Hz, 1H). LC-MS 232.14 (M+H).

299B (3R)—N-(3-(aminomethyl)phenyl)-3-hydroxypyrrolidine-1-carboxamide

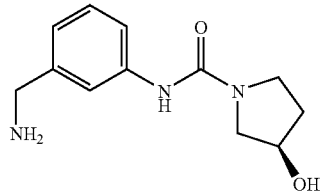

299B was prepared from 299A in 77% yield following a procedure analogous to that used in the preparation of 295B. $^1$H NMR (400 MHz, CD$_3$OD) δ ppm 1.94-2.02 (m, 1H) 2.02-2.14 (m, 1H) 3.43-3.49 (m, 1H) 3.53-3.63 (m, 4H) 4.05 (s, 2H) 4.44-4.48 (m, 1H) 7.10 (d, J=6.59 Hz, 1H) 7.30-7.38 (m, 2H) 7.58 (s, 1H). LC-MS 236.3 (M+H).

299C

Example 299 was prepared according to the general coupling procedure analogous to that used in the preparation of Example 298 by using 298A and 299B. $^1$H NMR (400 MHz, CD$_3$OD) δ ppm 1.37 (t, J=7.03 Hz, 3H) 1.92-2.02 (m, 1H) 2.02-2.13 (m, 1H) 3.39-3.47 (m, 1H) 3.49-3.62 (m, 4H) 4.03 (q, J=7.03 Hz, 2H) 4.32-4.39 (m, 2H) 4.43-4.48 (m, 1H) 5.14 (s, 1H) 6.64 (d, J=2.20 Hz, 1-H) 6.77 (d, J=7.03 Hz, 1H) 6.83 (d, J=7.47 Hz, 1H) 7.06-7.18 (m, 3H) 7.19 (d, J=2.20 Hz, 1H) 7.23-7.32 (m, 3H) 7.33-7.38 (m, 1H) 8.02-8.09 (m, 1H). LC-MS 589.37 (M+H).

Example 300

3-(1-(3,4-Dimethoxyphenyl)-2-(5-(3,3-dimethylureido)-2-(isopropylsulfonyl)benzylamino)-2-oxoethylamino)benzamide trifluoroacetic acid salt

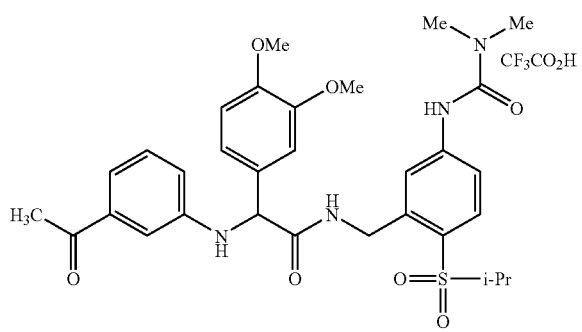

285A (24 mg, 0.05 mmol), 290C (18 mg, 0.054 mmol), BOP reagent (26 mg, 0.06 mmol), and Et$_3$N (31 mg, 0.3 mmol) were mixed in DMF (1 mL) and the whole mixture was stirred at rt for 1 h. Purification through preparative HPLC provided Example 300 (13 mg) of white solid. $^1$H NMR (400 MHz, CD$_3$OD) δ ppm 1.17 (d, J=3.95 Hz, 3H) 1.19 (d, J=3.52 Hz, 3H) 3.01 (s, 6H) 3.34-3.44 (m, 1H) 3.73 (s, 3H) 3.78 (s, 3H) 4.67 (s, 2H) 4.88 (s, 1H) 6.76-6.81 (m, 1H) 6.86-6.91 (m, 1H) 6.99-7.04 (m, 2H) 7.11-7.19 (m, 3H) 7.48 (d, J=2.20 Hz, 1H) 7.53 (dd, J=8.79, 2.20 Hz, 1H) 7.73 (d, J=8.79 Hz, 1H). LC-MS 612.3 (M+H).

UTILITY

The compounds of the present invention are inhibitors of factor VIIa and/or plasma kallirein and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders (or conditions)" as used herein includes arterial or venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

It is noted that thrombosis includes vessel occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant or antithrombotic effect of compounds of the present invention is believed to be due to inhibition of serine proteases involved in the coagulation cascade, more specifically, inhibition of the coagulation factors: factor VIIa, factor IXa, factor Xa, factor XIa, thrombin, and/or plasma kallikrein.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

The effectiveness of compounds of the present invention as inhibitors of the coagulation factors VIIa, IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M.

In general, preferred compounds of the present invention, such as the particular compounds disclosed in the above examples, have been identified to be active and exhibit $K_i$'s of equal to or less than 15 µM in the Factor VIIa assay, thereby demonstrating the utility of the compounds of the present invention as especially effective inhibitors of coagulation Factor VIIa. More preferred compounds have $K_i$'s of equal to or less than 1 µM, preferably equal to or less than 0.5 µM, more preferably equal to or less than 0.2 µM, even more preferably equal to or less than 0.1 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, compounds tested in the Factor XIa assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. In general, compounds tested in the plasma kallikrein assay are considered to be active if they exhibit a $K_i$ of equal to or less than 15 µM.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$$(v_o-v_s)/v_s=I/(K_i(1+S/K_m))\text{ for a competitive inhibitor with one binding site; or}$$

$$v_s/v_o=A+((B-A)/1+((IC_{50}/(I)^n)))\text{ and}$$

$$K_i=IC_{50}/(1+S/K_m)\text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J. Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-Venous (AV) Shunt Thrombosis Model:

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The compounds of the present invention can be administered alone or in combination with one or more additional therapeutic agents. These other agents include, but are not limited to, other anti-coagulant or coagulation inhibitory agents, anti-platelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVANOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granular-content secretion of platelets. Such agents include, but are not limited to, the various known non-steroidal antiinflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA), and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR1) antagonists (e.g., SCH-530348, SCH-203099, SCH-529153 and SCH-205831), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, prasugrel, and AZD-6140, and pharmaceutically acceptable salts or prodrugs thereof. Clopidogrel is an even more preferred agent. Ticlopidine and clopidogrel are also preferred compounds since they are known to be more gentle than aspirin on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin AT-1 receptor antagonists (e.g., irbestatin, losartan, valsartan); ET-A receptor antagonists (e.g., sitaxsentan, atrsentan and compounds disclosed in U.S. Pat. Nos. 5,612, 359 and 6,043,265); Dual ET-A/AT-1 antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Cholesterol/lipid lowering agents for use in combination with the compounds of the present invention include HMG-CoA reductase inhibitors (lovastatin, simvastatin, pravastatin, fluvastatin, atorvsatatin, rosuvastatin, and other statins), sequestrants (cholestyramine and colestipol), nicotonic acid, fenofibric acid derivatives (gemfibrozil, clofibrat, fenofibrate and benzafibrate), and probucol.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of plasma kallikrein, thrombin, factor VIIa, IXa, Xa and/or XIa. Such compounds may be provided in a commercial kit, for example, for use in pharmaceutical research involving plasma kallikrein, thrombin, factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving plasma kallikrein, thrombin, factor VIIa, IXa, Xa, and/or XIa. For example, the presence of plasma kallikrein, thrombin, factor VIIa, IXa, Xa and/or XIa in an unknown sample could be determined by addition of the relevant chromogenic substrate, for example, S2288 for factor VIIa, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.001 to 20 mg/kg/day. Intravenously, the most preferred doses will range from about 0.1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anticoagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:
1. A compound of Formula (III):

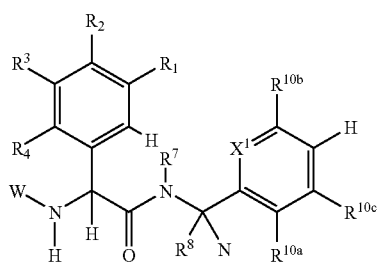

(III)

or a stereoisomer or a pharmaceutically acceptable salt thereof, wherein:
W is

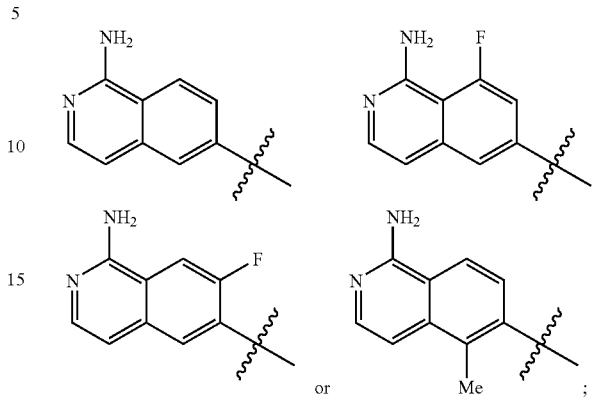

$X^1$ is CH or N;
$R^1$ is Cl, Br, Me, Et, OMe, OEt, $OCHF_2$, or cyclopropyl;
$R^2$ is H, F, Cl, OMe, O(i-Pr), or $OCHF_2$;
$R^3$ is H or OMe;
$R^4$ is H, F, Cl, or OMe;
$R^7$ is H, Me, —$CH_2CO_2H$, or —$CH_2CO_2(C_{1-4}$ alkyl);
$R^8$ is H, Me, $CO_2H$, $CO_2(C_{1-4}$ alkyl), —$CH_2CO_2H$, or —$CH_2CO_2(C_{1-4}$ alkyl);
$R^{10a}$ is F, $O(C_{1-4}$ alkyl), $CONR^cR^d$, —$S(C_{1-4}$ alkyl), —$SO_2(C_{1-4}$ alkyl), —$SO_2$-cyclopropyl, —$SO_2$-cyclobutyl, —$SO_2$-cyclopentyl, —$SO_2$-(pyrrolidin-1-yl), —$SO_2$-(piperid-1-yl), —$SO_2$-(azepan-1-yl), —$SO_2NR^cR^d$, —$SO_2NH$-cyclopropyl, morpholin-4-yl, 3,5-dimethyl-pyrazol-1-yl, or 3,5-diethyl-pyrazol-1-yl;
$R^{10b}$ is OH, $NH_2$, —$NHCO(C_{1-4}$ alkyl), —$NHCO_2(C_{1-4}$ alkyl), —$NHSO_2NH_2$, —$SO_2NH_2$, or —$NHCONR^cR^d$;
$R^{10c}$ is H, Cl, or Me;
$R^c$ and $R^d$ are, independently at each occurrence, H or $C_{1-4}$ alkyl;
alternatively, $R^c$ and $R^d$, when attached to the same nitrogen atom, combine to form a 4- to 5-membered heterocycle comprising: carbon atoms and 0-2 additional heteroatoms selected from N, O, and $S(O)_p$; wherein said heterocycle is substituted with 0-2 $R^g$; and
$R^g$ is, independently at each occurrence, =O, F, Cl, Br, $CF_3$, OH, or $C_{1-4}$ alkyl.

2. A compound according to claim 1, wherein:
W is

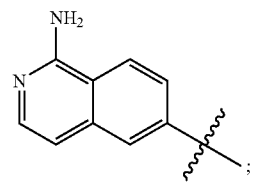

$X^1$ is CH;
$R^7$ is H, Me, or —$CH_2CO_2H$;
$R^8$ is H, Me, $CO_2H$, —$CH_2CO_2H$, or —$CH_2CO_2Me$;
$R^{10a}$ is F, O(i-Pr), —$CONMe_2$, —CO-(pyrrolidin-1-yl), —CO-(piperid-1-yl), —S(i-Pr), —$SO_2Et$, —$SO_2Pr$, —$SO_2$(i-Pr), —$SO_2$(t-Bu), —$SO_2$-cyclopropyl, —$SO_2$-cyclobutyl, —$SO_2$-cyclopentyl, —$SO_2$—(pyrrolidin-1-yl), —$SO_2$— (piperid-1-yl), —$SO_2$-(azepan-1-yl), —SO$_2$NHMe, —SO$_2$NMe$_2$, —SO$_2$NHEt, —SO$_2$NH(i-Pr), —SO$_2$NH-cyclopropyl, morpholin-4-yl, 3,5-dimethyl-pyrazol-1-yl, or 3,5-diethyl-pyrazol-1-yl;

R$^{10b}$ is OH, NH$_2$, —NHCOMe, —NHCOPr, —NHCO$_2$Me, —NHCO$_2$Et, —NHCO$_2$(i-Pr), —NHCO$_2$(i-Bu), —NHSO$_2$NH$_2$, —SO$_2$NH$_2$, —NHCON(Me)$_2$, —NHCON(Me)(Et), —NHCON(Me)(i-Pr),

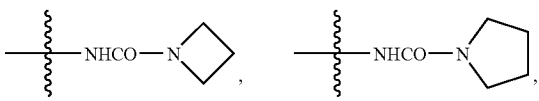

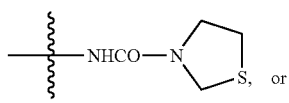

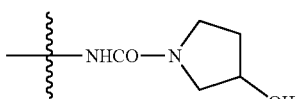

and
R$^{10c}$ is H.

3. A method for treating a thromboembolic disorder, comprising: administering to a patient in need thereof a therapeutically effective amount of a compound of claim 1.

4. A method according to claim 3, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

5. A method according to claim 3, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

6. A pharmaceutical composition, comprising: a pharmaceutically acceptable carrier and a therapeutically effective amount of a compound of claim 1.

7. A pharmaceutical composition, comprising: a pharmaceutically acceptable carrier and a therapeutically effective amount of a compound of claim 2.

8. A compound according to claim 1, wherein the compound is of Formula (IIIa):

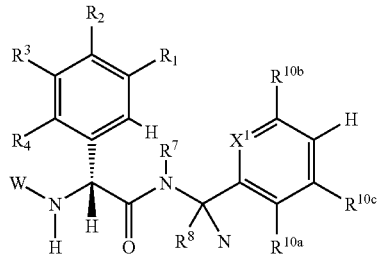

or a pharmaceutically acceptable salt thereof.

9. A pharmaceutical composition, comprising: a pharmaceutically acceptable carrier and a therapeutically effective amount of a compound of claim 8.

10. A compound according to claim 1, wherein the compound is selected from the group consisting of:

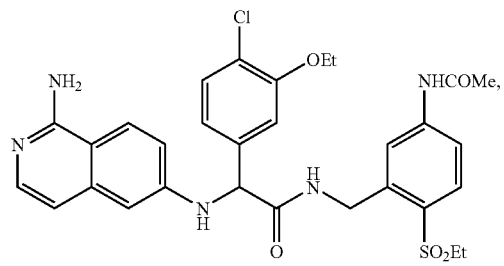

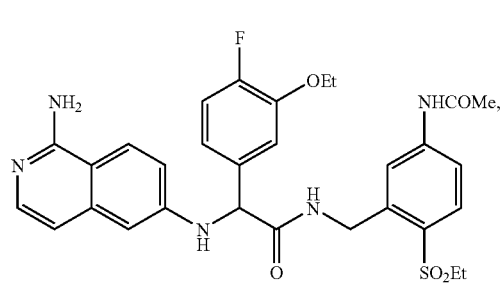

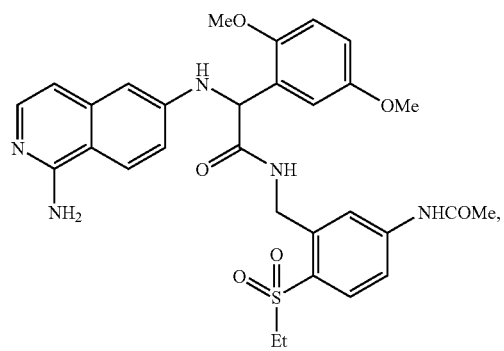

393
-continued
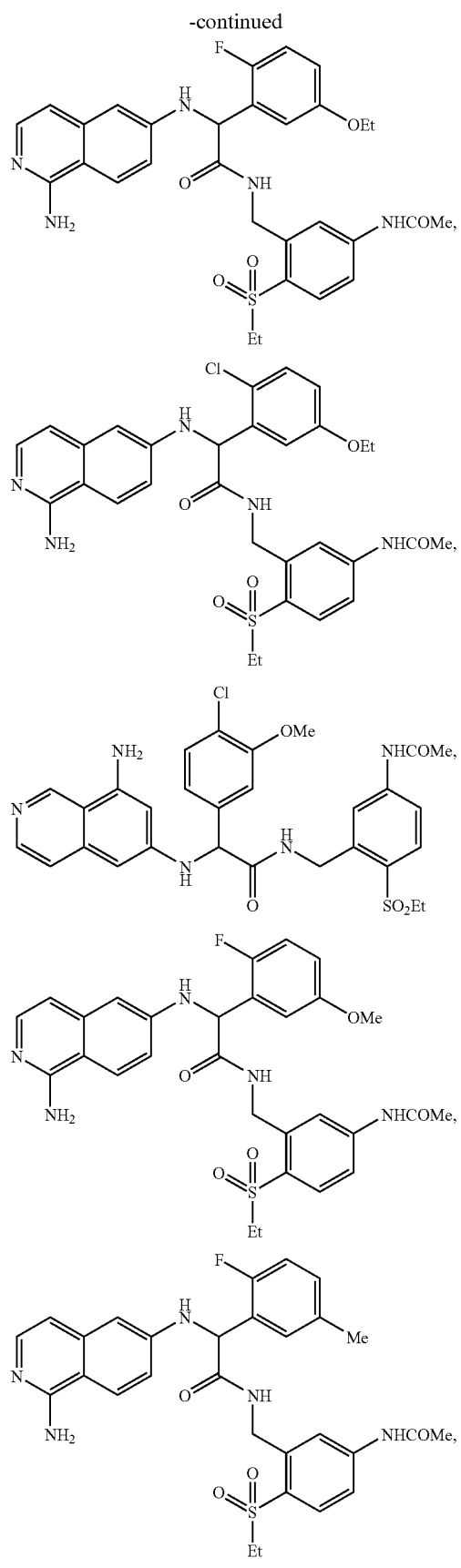
394
-continued
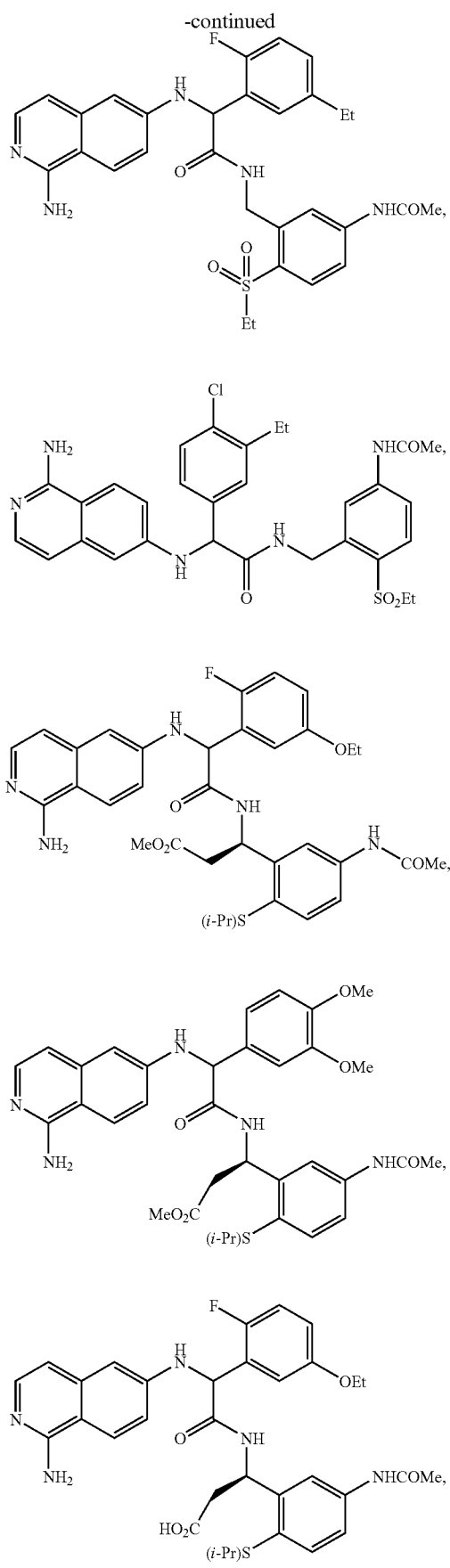

-continued
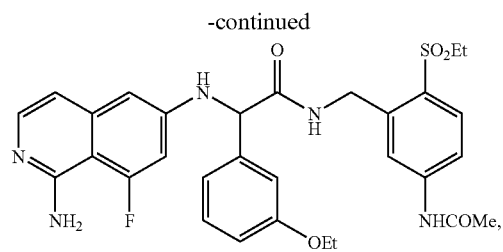
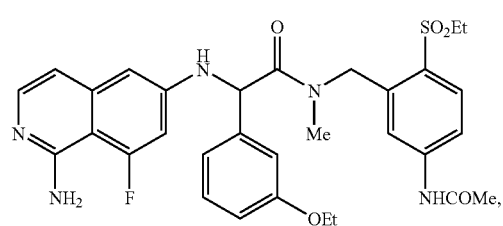
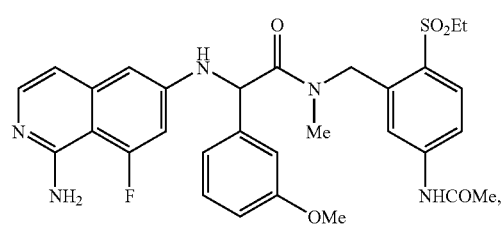
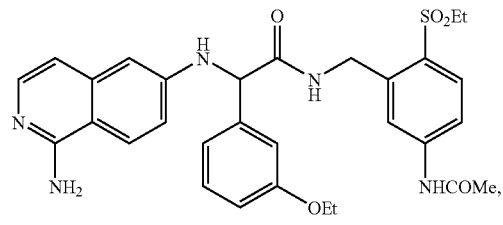
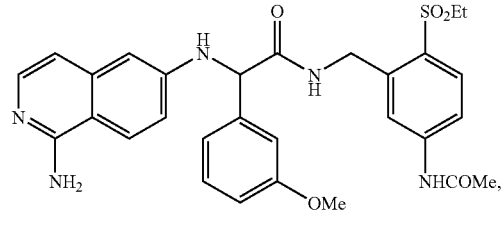
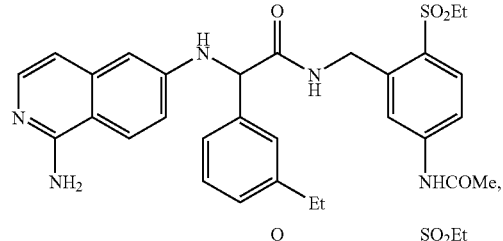
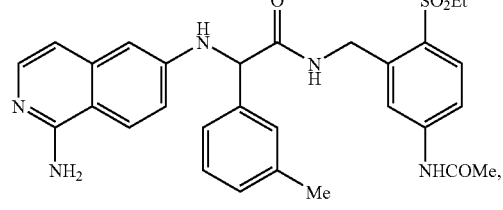
-continued
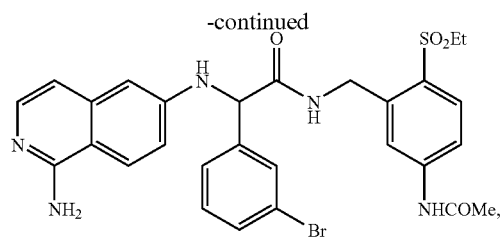
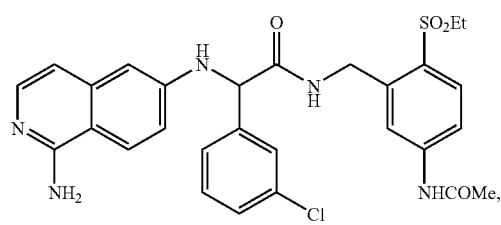
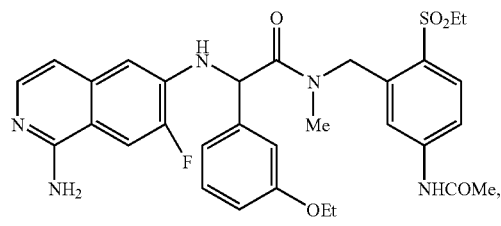
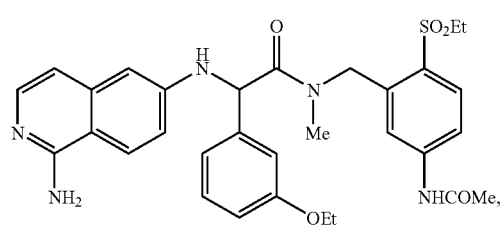
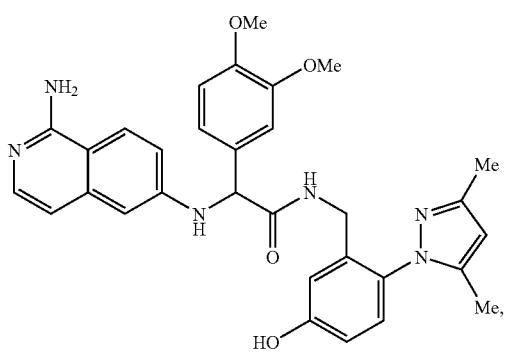

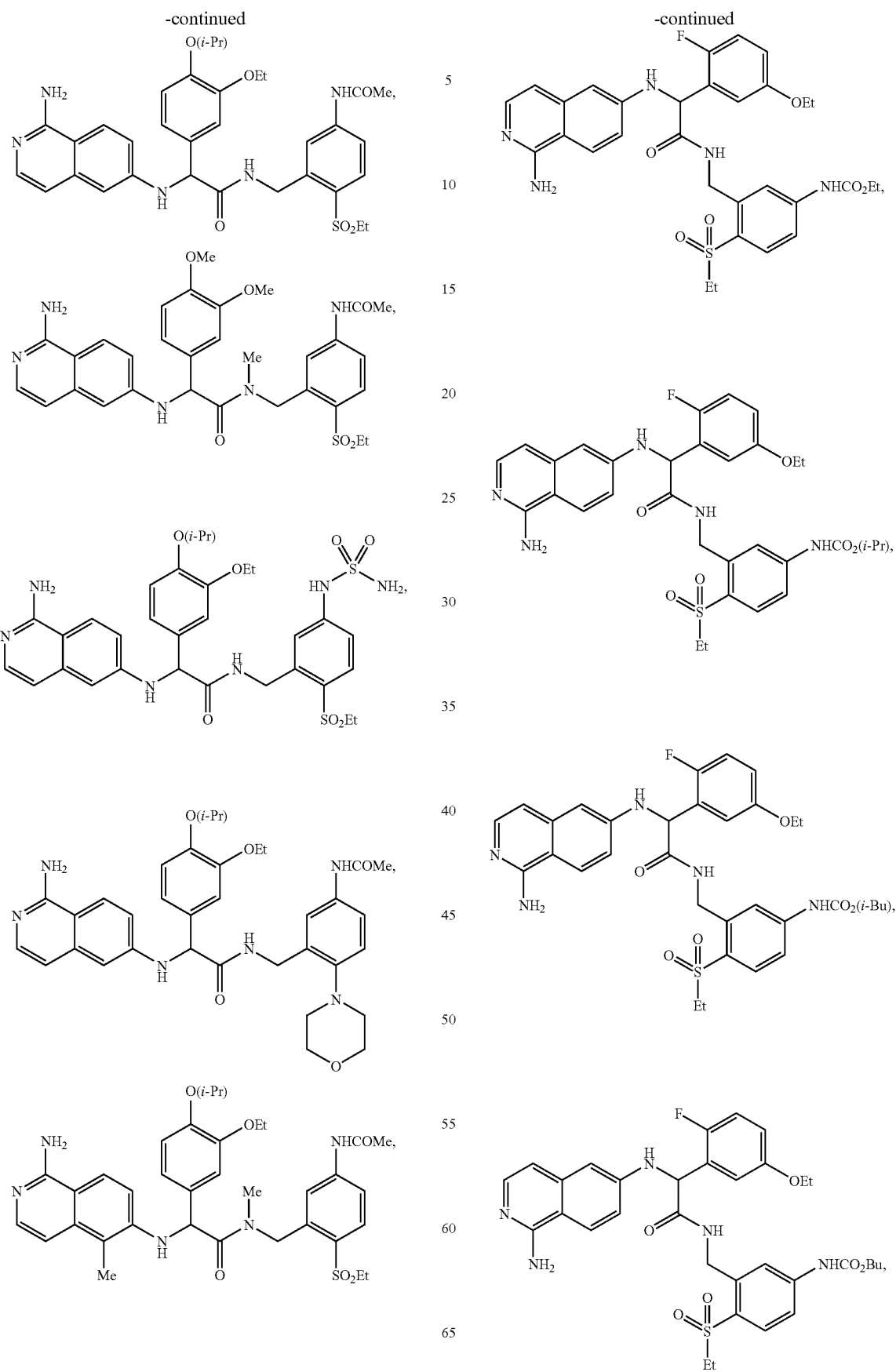

-continued
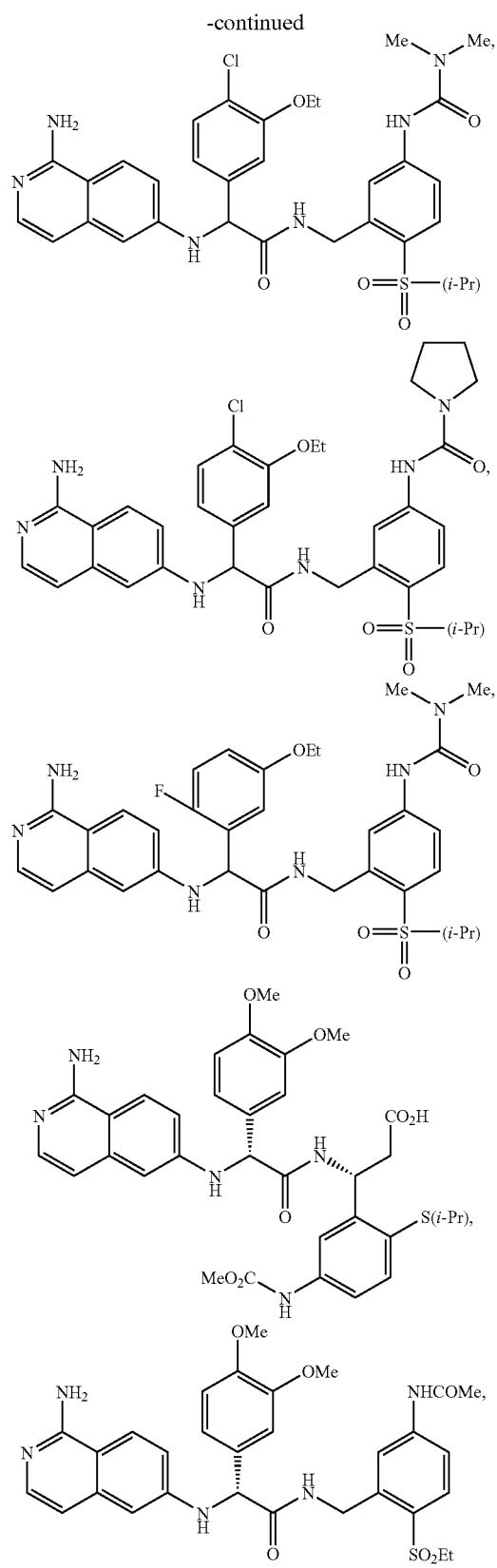
-continued
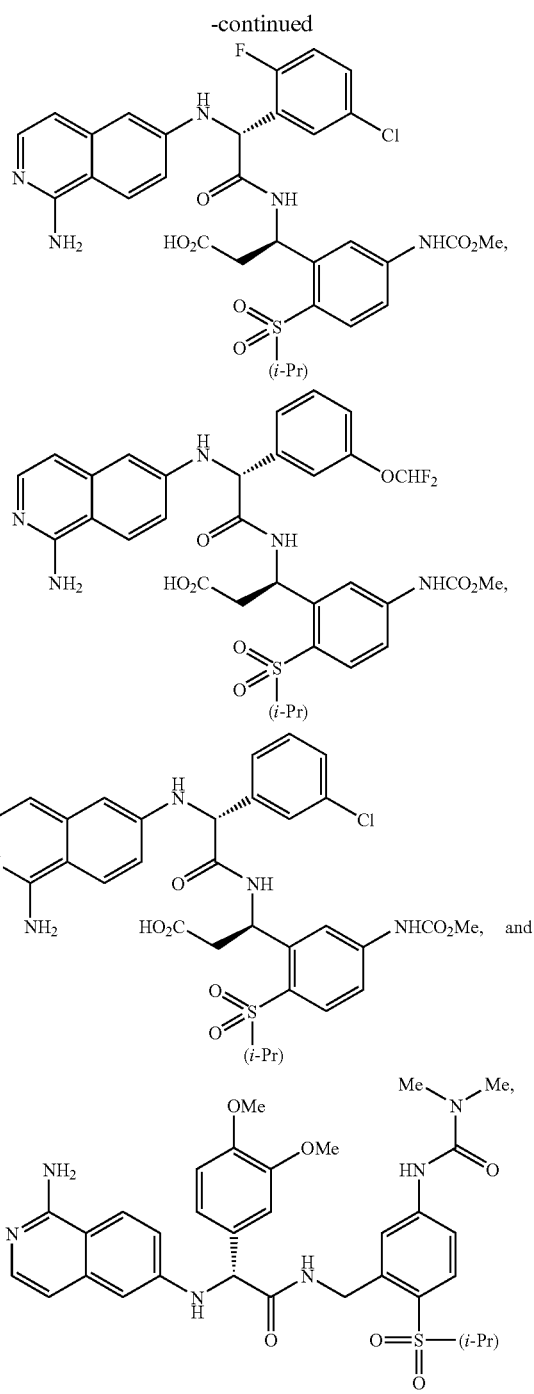
or a stereoisomer or a pharmaceutically acceptable salt thereof.
11. A pharmaceutical composition, comprising: a pharmaceutically acceptable carrier and a therapeutically effective amount of a compound of claim 10.
* * * * *

UNITED STATES PATENT AND TRADEMARK OFFICE
CERTIFICATE OF CORRECTION

PATENT NO. : 7,456,195 B2
APPLICATION NO. : 11/472845
DATED : November 25, 2008
INVENTOR(S) : Xiaojun Zhang et al.

It is certified that error appears in the above-identified patent and that said Letters Patent is hereby corrected as shown below:

COLUMN 392:

Line 10 (approx.) " 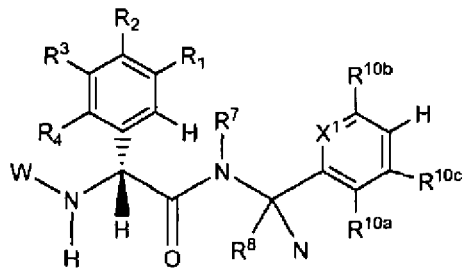 " should read

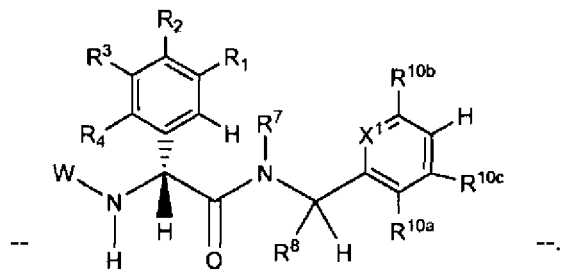

-- --.

COLUMN 394:

Line 35 (approx.) " 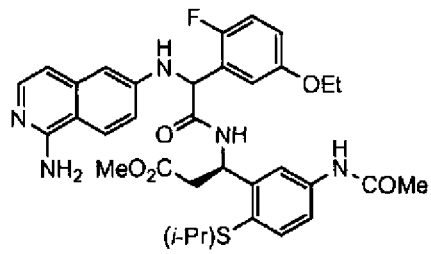 " should read

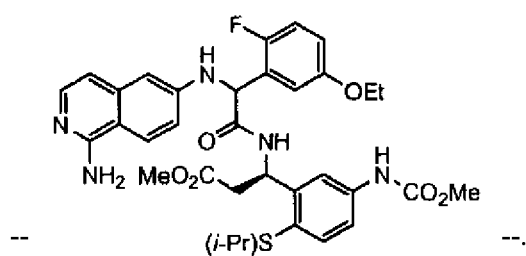

-- --.

UNITED STATES PATENT AND TRADEMARK OFFICE
CERTIFICATE OF CORRECTION

PATENT NO. : 7,456,195 B2
APPLICATION NO. : 11/472845
DATED : November 25, 2008
INVENTOR(S) : Xiaojun Zhang et al.

It is certified that error appears in the above-identified patent and that said Letters Patent is hereby corrected as shown below:

COLUMN 394:

Line 45 (approx.) " 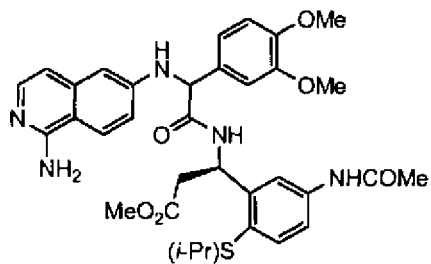 " should read

-- 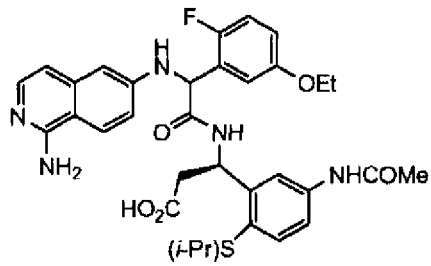 --.

COLUMN 394:

Line 60 (approx.) " " should read

UNITED STATES PATENT AND TRADEMARK OFFICE
CERTIFICATE OF CORRECTION

PATENT NO.        : 7,456,195 B2
APPLICATION NO.   : 11/472845
DATED             : November 25, 2008
INVENTOR(S)       : Xiaojun Zhang et al.

It is certified that error appears in the above-identified patent and that said Letters Patent is hereby corrected as shown below:

-- 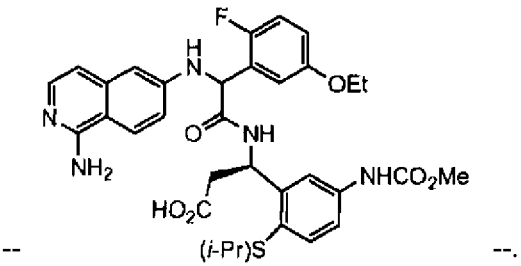 --.

Signed and Sealed this

Twelfth Day of May, 2009

JOHN DOLL
*Acting Director of the United States Patent and Trademark Office*